US006773908B1

(12) United States Patent
Paul et al.

(10) Patent No.: US 6,773,908 B1
(45) **Date of Patent: *Aug. 10, 2004**

(54) PROTEINS ENCODED BY POLYNUCLEIC ACIDS OF PORCINE REPRODUCTIVE AND RESPIRATORY SYNDROME VIRUS (PRRSV)

(75) Inventors: Prem S. Paul, Ames, IA (US); Yanjin Zhang, San Antonio, TX (US)

(73) Assignee: Iowa State University Research Foundation, Inc., Ames, IA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/601,326

(22) PCT Filed: Feb. 8, 1999

(86) PCT No.: PCT/US99/02630

§ 371 (c)(1),
(2), (4) Date: Sep. 25, 2000

(87) PCT Pub. No.: WO99/39582

PCT Pub. Date: Aug. 12, 1999

Related U.S. Application Data

(63) Continuation-in-part of application No. 09/019,793, filed on Feb. 6, 1998, now Pat. No. 6,380,376, which is a continuation-in-part of application No. 08/478,316, filed on Jun. 7, 1995, now Pat. No. 6,251,397, which is a continuation-in-part of application No. 08/301,435, filed on Sep. 1, 1994, now Pat. No. 6,592,873, which is a continuation-in-part of application No. 08/131,625, filed on Oct. 5, 1993, now Pat. No. 5,695,766, which is a continuation-in-part of application No. 07/969,071, filed on Oct. 30, 1992, now abandoned.

(51) Int. Cl.$^{7}$ ............................ C12N 7/00; C12N 7/01; C07H 21/04; A61K 39/12

(52) U.S. Cl. ................................ 435/235.1; 536/23.72; 424/204.1

(58) Field of Search ................... 435/235.1; 424/204.1; 536/23.72

(56) References Cited

U.S. PATENT DOCUMENTS

| | | | | |
|---|---|---|---|---|
| 5,213,795 | A | 5/1993 | Carlson et al. | |
| 5,419,907 | A | 5/1995 | Paul et al. | |
| 5,476,778 | A | 12/1995 | Chladek et al. | |
| 5,510,258 | A | 4/1996 | Sanderson et al. | |
| 5,587,164 | A | 12/1996 | Sanderson et al. | |
| 5,597,721 | A | 1/1997 | Brun et al. | |
| 5,620,691 | A | 4/1997 | Wensvoort et al. | |
| 5,674,500 | A | 10/1997 | Peeters et al. | |
| 5,677,429 | A | 10/1997 | Benfield | |
| 5,683,865 | A | 11/1997 | Collins et al. | |
| 5,695,766 | A | 12/1997 | Paul et al. | |
| 5,698,203 | A | 12/1997 | Visser et al. | |
| 5,789,388 | A | 8/1998 | Visser et al. | |
| 5,840,563 | A | 11/1998 | Chladek et al. | |
| 5,846,805 | A | 12/1998 | Collins et al. | |
| 5,858,729 | A | 1/1999 | Van Woensel et al. | |
| 5,866,401 | A | 2/1999 | Hesse | |
| 5,888,513 | A | 3/1999 | Plana Duran et al. | |
| 5,910,310 | A | 6/1999 | Heinen et al. | |
| 5,925,359 | A | 7/1999 | Van Woensel et al. | |
| 5,976,537 | A | 11/1999 | Mengeling et al. | |
| 5,989,563 | A | 11/1999 | Chladek et al. | |
| 5,998,601 | A | 12/1999 | Murtaugh et al. | |
| 6,001,370 | A | 12/1999 | Burch et al. | |
| 6,015,663 | A | 1/2000 | Wesley et al. | |
| 6,251,397 | B1 * | 6/2001 | Paul et al. | 424/186.1 |

FOREIGN PATENT DOCUMENTS

| | | |
|---|---|---|
| CA | 2076744 | 2/1993 |
| EP | 0 595 436 A2 | 5/1994 |
| EP | 0 595 436 | 5/1994 |
| GB | 2282811 | 4/1995 |
| WO | WO 92/21375 | 12/1992 |
| WO | WO 93/03760 | 3/1993 |
| WO | WO 93/06211 | 4/1993 |
| WO | WO 93/07898 | 4/1993 |
| WO | WO 94/18311 | 8/1994 |
| WO | WO 95/31550 | 11/1995 |
| WO | WO 96/04010 | 2/1996 |
| WO | WO 96/06619 | 3/1996 |
| WO | WO 96/40932 | 12/1996 |

OTHER PUBLICATIONS

Plana Duran et al., Virus Genes, 14/1:19–29, 1997.*

Kwang et al., Research in Veterinary Science 67/2:199–201, 1999.*

V. Kapur, et al., Journal of General Virology, vol. 77, pp. 1271 to 1276, "Genetic Variation in Porcine Reproductive and Respiratory Syndrome Virus Isolates in the Midwestern United States", 1996.

Meng, X.–J., et al., *Phylogenetic analyses of the putative M (ORF 6) and N (ORF 7) genes of porcine reproductive and respiratory syndrome virus (PRRSV)*: implication for the existence of two genotypes of PRRSV in the U.S.A. and Europe, Arch Virol (1995) 140: 745–755, Austria.

Meng, Xiang–Jin, et al., *Sequence comparison of open reading frames 2 to 5 of low and high virulence United States isolates of porcine reproductive and respiratory syndrome virus*, Journal of General Virology (1995), 76, 3181–3188, Great Britain.

(List continued on next page.)

*Primary Examiner*—James Housel
*Assistant Examiner*—Zachariah Lucas
(74) *Attorney, Agent, or Firm*—Burns Doane Swecker & Mathis LLP

(57) ABSTRACT

The present invention provides an isolated DNA sequence encoding, for example, at least one polypeptide selected from the group consisting of proteins encoded by one or more open reading frames (ORF's) of an Iowa strain of porcine reproductive and respiratory syndrome virus (PRRSV), specifically ISU-55, and the polypeptides encoded by the isolated DNA sequences. The present invention also concerns a vaccine comprising an effective amount of such a protein; methods of producing antibodies which specifically bind to such a protein; and methods of protecting a pig against a PRRSV, and treating a pig infected by a PRRSV.

27 Claims, 109 Drawing Sheets

OTHER PUBLICATIONS

P.W. Blackburn et al., "Use of Human Influenza Vaccine to Protect Against Blue–Eared Pig Disease", Veterinary Record, Jul. 6, 1991, p. 19, British Veterinary Assoc., London, UK.

M.J. Meredith, Review Paper on "Blue Ear" Disease/Mystery Pig Disease/S.I.R.S./ P.R.R.S./P.E.A.R.S., Mar. 4, 1992, Pig Disease Information Centre, Cambridge, UK.

R.W. Wills et al., "Transmission of PRRS Virus by Contact vs Airborne Exposures", Final Report of a grant, 1995, pp. 103–108, National Pork Producers Council, Des Moines, Iowa.

Abstract Nos. 218–222, p. 43, Abstracts of Conf. of Research Workers in Animal Diseases, Chicago, IL (1993).

"'Mystery Pig Disease' Studies Needed", Animal Pharm., vol. 215, p. 12, publ. date: Nov. 2, 1990, Theta Reports, New York, NY.

"Mystery Virus in German Pig Herds", Animal Pharm., vol. 220, p. 8, publ. date: Jan. 25, 1991, Theta Reports, New York, NY.

"'Mystery Pig Disease' Still Unidentified", Animal Pharm., vol. 223, p. 3, publ. date: Mar. 8, 1991, Theta Reports, New York, NY.

"Dutch Team Isolates Mystery Pig Disease Agent", Animal Pharm., vol. 230, p. 21, publ. date: Jun. 21, 1991, Theta Reports, New York, NY.

"Dutch Scientists Confirm Porcine Reproductive and Respiratory Syndrome (PRRS) Agent is a Virus", Animal Pharm., vol. 238, p. 6, publ. date: Oct. 25, 1991, Theta Reports, New York, NY.

"Cyanamid Reports on Isolation of Porcine Reproductive and Respiratory Syndrome (PRRS) Virus", Animal Pharm., vol. 238, p. 20, publ. date: Oct. 25, 1991, Theta Reports, New York, NY.

"Pig Disease Mystery Solved by FRG Scientists", Animal Pharm., vol. 240, p. 7, publ. date: Nov. 22, 1991, Theta Reports, New York, NY.

"Bayer Prepare Cuts Mortality in PRRS Herds", Animal Pharm., vol. 240, p. 22, publ. date: Nov. 22, 1991, Theta Reports, New York, NY.

"Porcine Epidemic and Respiratory Syndrome (PEARS) Virus Isolated in France", Animal Pharm., vol. 244, p. 7, publ. date: Jan. 24, 1992, Theta Reports, New York, NY.

"No Immediate Prospect of a Porcine Epidemic and Respiratory Syndrome (PEARS) Vaccine", Animal Pharm., vol. 244, p. 25, publ. date: Jan. 24, 1992, Theta Reports, New York, NY.

"US Market for Animal Health Products," Animal Pharm., vol. 247, Supplement, publ. date: Mar. 6, 1992, Theta Reports, New York, NY.

"Porcine Reproductive and Respiratory Syndrome (PRRS) Antibody Test Developed in France", Animal Pharm., vol. 253, p. 5, publ. date: Jun. 5, 1992, Theta Reports, New York, NY.

"IDEXX to Develop Porcine Reproductive and Respiratory Syndrome (PRRS) Diagnostic", Animal Pharm., vol. 257, p. 20, publ. date: Jul. 31, 1992, Theta Reports, New York, NY.

"PRRS widespread in US herds", Animal Pharm., publ. date: Nov. 13, 1992, p. 11, vol. 264, Theta Reports, New York, NY.

"Porcine Reproductive and Respiratory Syndrome (PRRS) Virus Identified in Japan", Animal Pharm., vol. 283, p. 11, publ. date: Aug. 27, 1993, Theta Reports, New York, NY.

"Porcine Reproductive and Respiratory Syndrome (PRRS): an Appraisal of Current Research", Animal Pharm., vol. 284, p. 20, publ. date: Sep. 10, 1993, Theta Reports, New York, NY.

Bautista et al., "Comparison of Swine Alveolar Macrophages and Cell Line 2621 for the Detection of SIRS Virus and its Antibody", Amer. Assoc. of Swine Practitioners Newsletter, 1992, p. 32, vol. 4, No. 4, American Assoc. of Swine Veterinarians, Perry, 1A.

Bautista et al., "Serologic survey for Lelystad and VR–2332 strains of porcine respiratory and reproductive syndrome (PRRS) virus in US swine herds", J. Vet. Diagn. Invest., 1993, pp. 612–614, vol. 5, American Assoc. of Vet. Lab. Diagnosticians, Columbia, MO.

Bautista et al., "Comparison of porcine alveolar macrophages and CL 2621 for the detection of porcine reproductive and respiratory syndrome (PRRS) virus and anti–PRRS antibody", J. Vet. Diagn. Invest., 1993, pp. 163–165, vol. 5, American Assoc. of Vet. Lab. Diagnosticians, Columbia, MO.

Benfield et al., "Characterization of swine infertility and respiratory syndrome (SIRS) virus (isolate ATCC VR–2332)", J. Vet. Diagn. Invest., 1992, pp. 127–133, vol. 4, American Assoc. of Vet. Lab. Diagnosticians, Columbia, MO.

Blaha, "PRRS in Europe", Proc Am Assoc Swine Practitioners, 1993, pp. 313–315, American Assoc. of Swine Veterinarians, Perry, IA.

Burgess et al., "Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue", J. Cell. Biol., 1990, pp. 2129–2138, vol. 111, The Rockefeller University Press, USA.

Cafruny et al., "Antibody response of mice to lactate dehydrogenase–elevating virus during infection and immunization with inactivated virus", Virus Research, 1986, pp. 357–375, vol. 5, Elsevier Science Publishers B.V., The Netherlands.

Chen et al., "Sequences of 3' end of genome and of 5' end of open reading frame 1a of lactate dehydrogenase–elevating virus and common junction motifs between 5' leader and bodies of seven subgenomic mRNAs", J. Gen. Virology, 1993, pp. 643–660, vol. 74, Society of General Microbiology, Great Britain.

Christianson et al., "Porcine reproductive and respiratory syndrome: A review", Swine Health & Production, 1994, pp. 10–28, vol. 1, No. 2, American Assoc. of Swine Veterinarians, Perry, Iowa.

Christianson et al., "Experimental reproduction of swine infertility and respiratory syndrome in pregnant sows", Am. J. Vet. Res., 1992, pp. 485–488, vol. 53, American Veterinary Medical Assoc., Chicago, IL.

Collins et al., "Isolation of swine infertility and respiratory syndrome virus (isolate ATCC VR–2332) in North America and experimental reproduction of the disease in gnotobiotic pigs", J. Vet. Diagn. Invest., 1992, pp. 117–126, vol. 4, American Assoc. of Vet. Lab. Diagnosticians, Columbia, MO.

Collins et al., Pathenogenisis of PRRS, Proc. Allen D. Leman Swine Conf., 1993, pp. 47–48.

Collins, "Newly Recognized Respiratory Syndromes in North American Swine Herds", Amer. Assoc. of Swine Practitioners Newsletter, Sep./Oct. 1991, pp. 7, 10–11, American Assoc. of Swine Veterinarians, Perry, IA.
Collins et al., "Sow Culling and Mortality", Proceedings, Minnesota Swine Conference for Veterinarians, 1991, pp. 201–205, vol. 1.
Conzelmann et al., "Molecular Characterization of Porcine Reproductive and Respiratory Syndrome Virus, a Member of the Arterivirus Group", Virology, 1993, pp. 329–339, vol. 193, Academic Press, Inc., USA.
Dalziel et al., "Site–Specific Alteration of Murine Hepatitis Virus Type 4 Peplomer Glycoprotein E2 Results in Reduced Neurovirulence", J. Virol., 1986, pp. 463–471, vol. 59, ASM Press, Washington, DC.
De Vries et al., "Structural Proteins of Equine Arteritis Virus", J. Virol., 1992, pp. 6294–6303, vol. 66, ASM Press, Washington, DC.
De Vries et al., "All subgenomic mRNAs of equine arteritis virus contain a common leader sequence", Nucleic Acids Res., 1990, pp. 3241–3247, vol. 18, Oxford University Press, United Kingdom.
Dea et al., "Antigenic Variant of Swine Influenza Virus Causing Proliferative and Necrotizing Pneumonia in Pigs", J. Vet. Diagn. Invest., 1992, pp. 380–392, vol. 4, American Assoc. of Vet. Lab. Diagnosticians, Columbia, MO.
den Boon et al., "Equine Arteritis Virus is Not a Togavirus but Belongs to the Coronaviruslike Superfamily", J. Virol., 1990, pp. 2910–2920, vol. 65, No. 6, ASM Press, Washington, DC.
Domingo et al., "New observations on antigenic diversification of RNA viruses. Antigenic variation is not dependent on immune selection", J. Gen. Virology, 1993, pp. 2039–2045, vol. 74, Society of General Microbiology, Great Britain.
Ellis, Ronald W., "New Technologies for Making Vaccines", Vaccines, Plotkin et al. (Eds.), 1988, Chapter pp. 568–575, vol. 29, W.B. Saunders Company (Phil.).
Faaberg et al., "Disulfide Bonds Between Two Envelope Proteins of Lactate Dehydrogenase–Elevating Virus Are Essential for Viral Infectivity", J. Virol., 1995, pp. 613–617, vol. 69, ASM Press, Washington, DC.
Fiscus et al., "Antigenic Comparison of Feline Coronavirus Isolates: Evidence for Markedly Different Peplomer Glycoproteins", J. Virol., 1987, pp. 2607–2613, vol. 61, No. 8, ASM Press, Washington, DC.
Fleming et al., "Pathogenicity of Antigenic Variants of Murine Coronavirus JHM Selected with Monoclonal Antibodies", J. Virol., 1986, pp. 869–875, vol. 58, No. 3, ASM Press, Washington, DC.
Girard et al., "Experimentally Induced Porcine Proliferative and Necrotising Pneumonia With an Influenza A Virus", The Veterinary Record, 1992, pp. 206–207, vol. 130, British Veterinary Assoc., London, UK.
Godeny et al., Complete Genomic Sequence and Phylogenetic Analysis of the Lactate Dehydrogenase–Elevating Virus (LDV), Virology, 1993, pp. 585–596, vol. 194, Academic Press, Inc., USA.
Godney et al.,"Map Location of Lactate Dehydrogenase–Elevating Virus (LDV) Capsid Protein (Vp1) Gene", Virology, 1990, pp. 768–771, vol. 177, Academic Press, USA.
Goyal, "Porcine reproductive and respiratory syndrome", J. Vet. Diagn. Invest., 1993, pp. 656–664, vol. 5, American Assoc. of Vet. Lab. Diagnosticians, Columbia, MO.
Hahn et al., "Western equine encephalitis virus is a recombinant virus", Proc. Natl. Acad. Sci. USA, 1988, pp. 5997–6001, vol. 85, The National Academy of Sciences (publ.), USA.
Halbur et al., "Viral Contributors to the Porcine Respiratory Disease Complex", Proc. Am Assoc. Swine Pract., 1993, pp. 343–350, American Assoc. of Swine Veterinarians, Perry, IA.
Halbur et al., 1993 Central Veterinary Conf. Proc., Kansas City, Missouri, Aug. 14–17, 1993, pp. 750–759, Veterinary Medicine Publishing Co., USA.
Hill et al., Am. Assoc. Swine Practitioner Newsletter, vol. 4, No. 4, p. 47 (1992), American Assoc. of Swine Veterinarians, Perry, IA.
Hill et al., "Overview and History of Mystery Swine Disease (Swine Infertility/Respiratory Syndrome)", Proc. Mystery Swine Disease Comm. Mtg., Denver, Colorado, 1990, pp. 29–31.
Hooper et al., "Mice and rats (laboratory and feral) are not a reservoir for PRRS virus", J. Vet. Diagn. Invest., 1994, pp. 13–15, vol. 6, American Assoc. of Vet. Lab. Diagnosticians, Columbia, MO.
Joo, "PRRS: Diagnosis", Allen D. Leman Swine Conf., 1993, pp. 53–55, vol. 20.
Kapur et al., "Genetic Variation in Porcine Reproductive and Respiratory Syndrome Virus Isolates in the Midwestern United States", J. Gen. Virol., 1996, pp. 1271–1276, vol. 77, Society of General Microbiology, Great Britain.
Keffaber, "Reproductive Failure of Unknown Etiology", Am. Assoc. Swine Pract. Newsletter, 1989, pp. 1–9, vol. 1, No. 2, American Assoc. of Swine Veterinarians, Perry, IA.
Kim et al., "Enhanced replication of porcine reproductive and respiratory syndrome (PRRS) virus in a homogeneous subpopulation of MA–104 cell line", Arch. Virol., 1993, pp. 477–483, vol. 133, Springer–Verlag, Austria.
Kohler et al., "Continuous cultures of fused cells secreting antibody of predefined specificity", Nature, 1975, pp. 495–497, vol. 256, Nature Publishing Group, USA.
Koonin et al., "Evolution and Taxonomy of Positive–Strand RNA Viruses: Implications of Comparative Analysis of Amino Acid Sequences", Crtitical Rev. Biochem. Mol. Biol., 1993, pp. 375–430, vol. 28, No. 5, CRC Press, Inc..
Kuchler, Biochemical Methods in Cell Culture and Virology, Dowden, 1977, pp. 4–10, Hutchinson & Ross, Inc. (Stroudsburg, PA).
Kuo et al., "A Nested Set of Eight RNAs Is Formed in Macrophages Infected with Lactate Dehydrogenase–Elevating Virus", J. Virol., 1991, pp. 5118–5123, vol. 65, ASM Press, Washington, DC.
Kuo et al., "Lactate dehydrogenase–elevating virus (LDV): subgenomic mRNAs, mRNA leader and comparison of 3'–terminal sequences of two LDV isolates", Virus Res., 1992, pp. 55–72, vol. 23, Elsevier Science Publishers B.V., The Netherlands.
Lai, "RNA Recombination in Animal and Plant Viruses", Microbiol. Rev., 1992, pp. 61–79, vol. 56, No. 1, ASM Press, Washington, DC.
Lai, "Coronavirus: Organization, Replication and Expression of Genome", Annu. Rev. Microbiol., 1990, pp. 303–333, vol. 44, Annual Reviews Inc..
Lanza et al., "Pathogenicity of Concurrent Infection of Pigs with Porcine Respiratory Coronavirus and Swine Influenza", Res. Vet. Sci., 1992, pp. 309–314, vol. 53.

Laude et al., "Porcine respiratory coronavirus: molecular features and virus–host interactions", Vet. Res., 1993, pp. 125–150, vol. 24, EDP Sciences, France.

Lazar et al., "Transforming Growth Factor α: Mutation of Aspartic Acid 47 and Leucine 48 Results in Different Biological Activities", Mol. Cell. Biol., 1988, pp. 1247–1252, vol. 8, ASM Press, Washington, DC.

Loula, "Mystery Pig Disease", Agri Practice, Jan./Feb. 1991, pp. 23–24, vol. 12, No. 1, Veterinary Practice Publishing Co., Santa Barbara, CA.

Magar et al., "Immunohistochemical Detection of Porcine Reproductive and Respiratory Syndrome Virus Using Colloidal Gold," Can. J. Vet. Res., 1993, pp. 300–304, vol. 57, Canadian Veterinary Medical Assoc., Ottawa, Canada.

Mardassi et al., "Nucleotide sequence analysis of the 3'–terminal genomic region of the Quebec reference strain IAF–exp91 of PRRSV", Abstract. Conf. Res. Workers in Animal Dis., Chicago, IL, 1993, p. 43.

Mardassi et al., "Identification of major difference in the nucleocapsid protein genes of a Québec strain and European strains of porcine reproductive and respiratory syndrome virus", J. Gen. Virology, 1994, pp. 681–685, vol. 75, Society of General Microbiology, Great Britain.

Meng et al., "Molecular Cloning and Nucleotide Sequencing of the 3'–Terminal Genomic RNA of the Porcine Reproductive and Respiratory Syndrome Virus," Journal of General Virology, 1994, pp. 1795–1801, vol. 75, Society of General Microbiology, Great Britain.

Meng et al., "Development of a radiolabeled nucleic acid probe for the detection of encephalomyocarditis virus of swine", J. Vet. Diagn. Invest., 1993, pp. 254–258, vol. 5, American Assoc. of Vet. Lab. Diagnosticians, Columbia, MO.

Meulenberg et al., "Subgenomic RNAs of Lelystad virus contain a conserved leader–body junction sequence", J. Gen. Virology, 1993, pp. 1697–1701, vol. 74, Society of General Microbiology, Great Britain.

Meulenberg et al., "Lelystad Virus, the Causative Agent of Porcine Epidemic Abortion & Respiratory Syndrome (PEARS), is Related to LDV and EAV", Virology, 1993, vol. 192, No. 1, pp. 62–72, Academic Press, Inc., USA.

Meulenberg et al., "Characterization of Proteins Encoded by ORFs 2 to 7 of Lelystad Virus", Virology, 1995, pp. 155–163, vol. 206, Academic Press, Inc., Academic Press, USA.

Molitor, "Immune Responses to PRRS Virus", The Allen D. Leman Swine Conf., 1993, pp. 49–50.

Morin et al., "Severe Proliferative and Necrotizing Pneumonia in Pigs: a Newly Recognized Disease," Can. Vet. J., 1990, pp. 837–839, vol. 31, Canadian Veterinary Medical Assoc., Ontario, Canada.

Morozov et al., "Sequence Analysis of Open Reading Frames (ORFs) 2 to 4 of a U.S. Isolate of Porcine Reproductive and Respiratory Syndrome Virus", Arch. Virology, 1995, pp. 1313–1319, vol. 140, Springer–Verlag, Austria.

Morrison et al., "Serologic Evidence Incriminating a Recently Isolated Virus (ATCC VR–2332) as the Cause of Swine Infertility and Respiratory Syndrome (SIRS)," J. Vet. Diagn. Invest., 1992, pp. 186–188, vol. 4, American Assoc. of Vet. Lab. Diagnosticians, Columbia, MO.

Mounir et al., "Expression and Characterization of PRRSV Envelope and ns4 Proteins," American Society for Virology, Annual Meeting, Jul. 9–12, 1994, Madison, WI.

Murtaugh, "Porcine Respiratory and Reproductive Syndrome", Proc. Allen D. Leman Swine Conf., 1993, pp. 43–45.

Nelson et al., "Differentiation of U.S. and European Isolates of Porcine Reproductive and Respiratory Syndrome Virus by Monoclonal Antibodies", J. Clin. Microbiol., 1993, pp. 3184–3189, vol. 31, ASM Press, Washington, DC.

Parker et al., "Sequence Analysis Reveals Extensive Polymorphism and Evidence of Deletions within the E2 Glycoprotein Gene of Several Strains of Murine Hepatitis Virus", Virology, 1989, pp. 664–673, vol. 173, Academic Press, Inc., USA.

Paton et al., 'Blue ear' disease in pigs, The Veterinary Record, Jun. 29, 1991, p. 617, vol. 128, British Veterinary Assoc., London, UK.

Paton et al., "Isolation of a Lelystad Virus–like Agent from British Pigs and Scanning Electron Microscopy of Infected Macrophages," Vet. Microbiol., 1992, pp. 195–201, vol. 33, Elsevier Science Publishers B.V., Amsterdam.

Plagemann et al., "Lactate Dehydrogenase–Elevating Virus, Equine Arteritis Virus, and Simian Hemorrhagic Fever Virus: A New Group of Positive–Strand RNA Viruses", Advances in Virus Research, 1992, pp. 99–192, vol. 41, Academic Press, Inc., USA.

Plagemann, "LDV, EAV and SHFV: A New Group of Positive–Stranded RNA Viruses", Proc Am Assoc Swine Practitioners, 1992, pp. 8–15, vol. 4, American Assoc. of Swine Veterinarians, Perry, IA.

Plana et al., "Porcine Epidemic Abortion and Respiratory Syndrome (Mystery Swine Disease), Isolation in Spain of the Causative Agent and Experimental Reproduction of the Disease", Vet. Microbiol., 1992, pp. 203–211, vol. 33, Elsevier Science Publishers B.V., The Netherlands.

Plotkin et al., "New Technologies for Making Vaccines", Vaccines, 1988, published by W.B. Saunders Co. (Phil.), see p. 571.

Pol et al., "Pathological, ultrastructural, and immunohistochemical changes caused by Lelystad virus in experimentally induced infections of mystery swine disease (synonym: porcine epidemic abortion and respiratory syndrome (PEARS))", Veterinary Quarterly, 1991, pp. 137–143, vol. 13, Nijhoff (Publ.), The Hague.

Rasschaert et al., "Porcine respiratory coronavirus differs from transmissable gastroenteritis by a few genomic deletions", J. Gen. Virology, 1990, pp. 2599–2607, vol. 71, Society of General Microbiology, Great Britain.

Sirinarumitr et al., A pneumo–virulent United States isolate of porcine reproductive and respiratory syndrome virus induces apoptosis in bystander cells both in vitro and in vivo, Journal of General Virology, 1998, pp. 2989–2995, vol. 79, Society of General Microbiology, Great Britain.

Snijder et al., "The carboxyl–terminal part of the putative Berne virus polymerase is expressed by ribosomal frameshifting and contains sequence motifs which indicate that toro–and coronaviruses are evolutionarily related", Nucleic Acid Res., 1990, pp. 4535–4542, vol. 18, No. 15, Oxford University Press, Great Britain.

Spaan et al., "Coronaviruses: Structure and Genome Expression", J. Gen Virol., 1988, pp. 2939–2952, vol. 69, Society of General Microbiology, Great Britain.

Stevenson et al., "Endemic porcine reproductive and respiratory syndrome virus infection of nursery pigs in two swine herds without current reproductive failure", J. Vet. Diagn. Invest., 1993, pp. 432–434, vol. 5, American Assoc. of Vet. Lab. Diagnosticians, Columbia, MO.
Swenson et al., "Excretion of porcine reproductive and respiratory syndrome virus in semen after experimentally induced infection in boars", J. Am. Vet. Med. Assoc., 1994, pp. 1943–1948, vol. 204, American Veterinary Medical Assoc., Shaumburg, IL.
Swenson et al., "Porcine Reproductive and Respiratory Syndrome Virus in Experimentally Infected Boars: Isolation from Semen", Proc Am Assoc Swine Pract, 1993, pp. 719–720, American Assoc. of Swine Veterinarians, Perry, IA.
Swenson et al., "Porcine Reproductive and Respiratory Syndrome Virus in Experimentally Infectd Boars: Isolation from Semen", Proc Ann Meeting Livestock Conservation Institute, 1993, pp. 115–116.
Tizard, An Introduction to Vet Immunology, published in 1982 by W.B. Saunders Co. (Phil), see pages 41–43.
Van Alstine et al., "Diagnosis of porcine reproductive and respiratory syndrome", Swine Health & Production, 1993, pp. 24–28, vol. 1, No. 4, American Assoc. of Swine Veterinarians, Perry, Iowa.
Vaughn et al., "Three New Isolates of Porcine Respiratory Coronavirus with Various Pathogenicities and Spike (S) Gene Deletions," Journal of Clinical Microbiology, Jul. 1994, pp. 1809–1812, vol. 32, No. 7, ASM Press, Washington, DC.
The Veterinary Record, Jun. 8, 1991, p. 536, British Veterinary Assoc., London, UK.
The Veterinary Record, Jun. 22, 1991, p. 578, British Veterinary Assoc., London, UK.
The Veterinary Record, Jun. 1, 1991, p. 511, British Veterinary Assoc., London, UK.
The Veterinary Record, Mar. 2, 1991, p. 213, British Veterinary Assoc., London, UK.
The Veterinary Record, Oct. 19, 1991, pp. 367–368, British Veterinary Assoc., London, UK.
The Veterinary Record, Oct. 26, 1991, p. 370, British Veterinary Assoc., London, UK.
The Veterinary Record, Nov. 30, 1991, pp. 495–496, British Veterinary Assoc., London, UK.
The Veterinary Record, Porcine reproductive and respiratory syndrome (PRRS or blue–eared pig disease), Feb. 1, 1992, pp. 87–89, British Veterinary Assoc., London, UK.
The Veterinary Record, Aug. 3, 1991, pp. 102–103, British Veterinary Assoc., London, UK.
The Veterinary Record, Jun. 15, 1991, p. 574, British Veterinary Assoc., London, UK.
Weiland et al., "Monoclonal antibodies to the $GP_5$ of porcine reproductive and respiratory syndrome virus are more effective in virus neutralization than monoclonal antibodies to the $GP_4$", Veterinary Microbiology, 1999, pp. 171–186, vol. 66, Elsevier Science B.V., The Netherlands.
Wensvoort et al., "Mystery swine disease in the Netherlands: the isolation of Lelystad virus", Vet. Quarterly, 1991, pp. 121–130, vol. 13, Nijhoff (Publ.), The Hague.
Wensvoort et al., "Lelystad virus and the porcine epidemic abortion and respiratory syndrome", Vet. Res., 1993, pp. 117–124, vol. 24., EDP Sciences, France.
Wensvoort et al., Antigenic comparison of Lelystad virus and swine infertility and respirtory syndrome (SIRS) virus, J. Vet. Diagn. Invest., 1992, pp. 134–138, vol. 4, American Assoc. of Vet. Lab. Diagnosticians, Columbia, MO.
Woollen et al., "Chlamydial infection and perinatal mortality in a swine herd", J. Am. Vet. Med. Assoc., 1990, pp. 600–601, vol. 197, No. 5, American Veterinary Medical Assoc., Schaumburg, IL.
Zimmerman et al., "Susceptibility of Four Avian Species to PRRS Virus", Proc Ann Meeting Livestock Conservation Institute, 1993, pp. 107–108.
Zimmerman et al., "Transmission of PRRS Virus", The Allen D. Leman Swine Conf., 1993, pp. 51–52.
Zimmerman, "Mystery Swine Disease," USDA Abstracts, Dialog Computer Database, Jul. 1, 1990, pp. 501–504.

* cited by examiner

```
                                            +1>ORF2
VR2385    CCTGTCATTGAACCAACTTTAGGCCTGAATTGAGATGAAATGGGGTCTATGCAAAGCCTT    60
ISU3927   ...A................G..T..AG.C...A...C.........C............    60
ISU55     ...A.............................A..........................    60
ISU22     .................................A...........G.C............    60
VR2332    .................................A.............C............    60
ISU1894   ..C..............................A.............CG...........    60
ISU79     .................................A.............C............    60

VR2385    TTTGACAAAATTGGCCAACTTTTTGTGGATGCTTTCACGGAGTTCTTGGTGTCCATTGTT   120
ISU3927   ........G..C..T.............................................   120
ISU55     .......................C....................................   120
ISU22     ............................................................   120
VR2332    ............................................................   120
ISU1894   ............................................................   120
ISU79     ............................................................   120

VR2385    GATATCATTATATTTTTGGCCATTTTGTTTGGCTTCACCATCGCAGGTTGGCTGGTGGTC   180
ISU2927   ........C................................T..C..C............   180
ISU55     ............................................C...............   180
ISU22     ............................................C...............   180
VR2332    ............................................C...............   180
ISU1894   ........C...................................C...............   180
ISU79     ..............C.............................C...............   180

VR2385    TTTTGCATCAGATTGGTTTGCTCCGCGATACTCCGTGCGCGCCCTGCCATTCACTCTGAG   240
ISU3297   ......................................................C.....   240
ISU55     ...........................C................................   240
ISU22     ............................................................   240
VR2332    ....................................A.......................   240
ISU1894   ....................................A.......................   240
ISU79     ....................................A.......................   240

VR2385    CAATTACAGAAGATCCTATGAGGCCTTTCTCTCTCAGTGCCAGGTGGACATTCCCACCTG   300
ISU3297   ..............................T........................G....   300
ISU55     ..............................T.............................   300
ISU22     ...............T..............T..C........A.................   300
VR2332    ...............T..............T..C........A.................   300
ISU1894   ...............T............T.A..C........A.................   300
ISU79     ...............T..............T..C........A.................   300

VR2385    GGGAACTAAACATCCTTTGGGGATGCTTTGGCACCATAAGGTGTCAACCCTGATTGATGA   360
ISU3927   ......A.G.........A.................C.......................   360
ISU55     .....T...................T..................................   360
ISU22     .........................T.G................................   360
VR2332    ............................................................   360
ISU1894   .........................T..................................   360
ISU79     .........................T..................................   360
```

FIG. 1A

```
VR2385   AATGGTGTCGCGTCGAATGTACCGCATCATGGAAAAAGCAGGACAGGCTGCCTGGAAACA  420
ISU3927  ............................................................  420
ISU55    ............................................................  420
ISU22    ..........................................G.................  420
VR2332   ..........................................G.................  420
ISU1894  ...............C..........................G.................  420
ISU79    G...........................................................  420

VR2385   GGTAGTGAGCGAGGCTACGCTGTCTCGCATTAGTAGTTTGGATGTGGTGGCTCATTTTCA  480
ISU3927  ...G.....T........................G................C........  480
ISU55    ...G..................................................C.....  480
ISU22    ...G........................................................  480
VR2332   ...G........................................................  480
ISU1894  ...G....................C...................................  480
ISU79    ...G........................................................  480

VR2385   GCATCTTGCCGCCATTGAAGCCGAGACCTGTAAATATCTGGCCTCTCGGCTGCCCATGCT  540
ISU3927  ...C.......................T.........T...........T..........  540
ISU55    .....................................T......................  540
ISU22    .........T...........................T.......C..............  540
VR2332   ......A..............................T.......C..............  540
ISU1894  ...........................T.........T.......C..............  540
ISU79    ...............C.....................T.......C..............  540
                                      -89(mRNA3)
VR2385   ACACCACCTGCGCATGACAGGGTCAAATGTAACCATAGTGTATAATAGTACTTTGAATCA  600
ISU3927  ....A.......T..T........................C...................  600
ISU55    ....A.......................................................  600
ISU22    ....A.......................................................  600
VR2332   ....A...........................................C...........  600
ISU1894  ...TA..........A.....................................C.G.G..  600
ISU79    ....A......................................................G  600
                                                                  +1>
VR2385   GGTGTTTGCTGTTTTCCCAACCCCTGGTTCCCGGCCAAAGCTTCATGATTTCCAGCAATG  660
ISU3927  ..........A.............C.....T...........C........T........  660
ISU55    ....C.....A........................................T........  660
ISU22    ..........A........................................T........  660
VR2332   ..........A....T...................................T........  660
ISU1894  ..........A........................................T........  660
ISU79    ..........A.....................................C..T........  660
         ORF3
VR2385   GCTAATAGCTGTACATTCCTCTATATTTTCCTCTGTTGCAGCTTCTTGTACTCTTTTTGT  720
ISU3927  .....................C....CC................................  720
ISU55    ............................................................  720
ISU22    .T...................C.......................C..............  720
VR2332   .T...................C......................................  720
ISU1894  .T...................C......................................  720
ISU79    ............G........C................................C.....  720
```

FIG. 1B

```
VR2385    TGTGCTGTGGTTGCGGGTTCCAATGCTACGTACTGTTTTTGGTTTCCGCTGGTTAGGGGC   780
ISU3927   ....T.......A...A.G............T............................   780
ISU55     ................................T..C........................   780
VR2385    ............................................................   780
ISU22     ........................A......T............................   780
VR2332    ........................A...................................   780
ISU1894   ..........C................................................G   780
ISU79     ........................A...................................   780
                                **<ORF2
VR2385    AATTTTTCTTTCGAACTCACGGTGAATTACACGGTGTGCCCGCCTTGCCTCACCCGGCAA   840
ISU3927   ........C.....G....T.....................A.................G   840
ISU55     ....................A.....C...........T..A..................   840
VR2385    ............................................................   840
ISU22     ..............G.......................T..A..................   840
VR2332    ....................A.................T..A..................   840
ISU1894   ........C..........T..................T..A..................   840
ISU79     ...................TA....................A..................   840
                             ***
VR2385    GCAGCCGCAGAGGCCTACGAACCCGGCAGGTCCCTTTGGTGCAGGATAGGGCATGATCGA   900
ISU3927   .........C..AT..........AA......T..............C...A........   900
ISU55     ......A................T........T..................T.......C   900
ISU22     ............AT............T.....T..................T....C...   900
VR2332    ......A.....AT............T.....T..................T....C...   900
ISU1894   .............T............T.....T..................T....C...   900
ISU79     ..........................T.....T..................T.C......   900

VR2385    TGTGGGGAGGACGATCATGATGAACTAGGGTTTGTGGTGCCGTCTGGCCTCTCCAGCGAA   960
ISU3927   .....T...........C..C........A...ACA..A...C............AA...   960
ISU55     ....................C.......................................   960
ISU22     ....................C..G.........A....A..AC.....T...........   960
VR2332    ....................C..G.........A..A.A...C.................   960
ISU1894   ....................C..G.........A..A.A...C.................   960
ISU79     .....A........C.....C..G.........A..A.A.....................   960
                -236(mRNA3-1)
VR2385    GGCCACTTGACCAGTGCTTACGCCTGGTTGGCGTCCCTGTCCTTCAGCTATACGGCCCAG  1020
ISU3927   .T...T..........T.................TT...........T..C.........  1020
ISU55     ................T.................T......T.....T..C..A......  1020
ISU22     ...........T....T.................TTT.............C.........  1020
VR2332    ...........TG...T.................T.T.............C.........  1020
ISU1894   ...........T....T.................TTT.............C.........  1020
ISU79     ................T.................T.T.............C.........  1020
                                                     +1>ORF4-1
VR2385    TTCCATCCCGAGATATTCGGGATAGGGAATGTGAGTCGAGTCTATGTTGACATCAAGCAC  1080
ISU3927   ..T.......................A.........AAG.................T..T  1080
ISU55     ........T............................A...T.............G...T  1080
ISU22     .............................C...........T..............A..T  1080
VR2332    .........................................T..............A..T  1080
ISU1894   .........................................T..............A..T  1080
ISU79     .....C...................................T..............A..T  1080
```

FIG. 1C

```
VR2385    CAATTCATTTGCGCTGTTCATGATGGGCAGAACACCACCTTGCCCCACCATGACAACATT 1140
ISU3927   ...C.......T...........C....................T.G............. 1140
ISU55     ..............C.....C..C.........G....T.....T.G.........T... 1140
ISU22     ...C....C.....C.AA.....C.....A..............T.GT............ 1140
VR2332    ...C....C.....C.AA.....C....................T.GT............ 1140
ISU1894   ...C..........C.AA.....C..A......G..........T.GT........T... 1140
ISU79     ...C....C.....C.AA.....C....................T.GT............ 1140
                                                           -10(mRNA4)
VR2385    TCAGCCGTGCTTCAGACCTATTACCAGCATCAGGTCGACGGGGGCAATTGGTTTCACCTA 1200
ISU3927   ..T......T................A..C..A.....T..T.....C............ 1200
ISU55     .........T.C.....T........A.....A........C.................. 1200
ISU22     .........T................A.....A........T.................. 1200
VR2332    .........T................A.....A........C.................. 1200
ISU1894   .........T................A.....A.....T..C.................. 1200
ISU79     ..G......T................A.....A........C.................. 1200
            +1>ORF4                                                **
VR2385    GAATGGGTGCGTCCCTTCTTTTCCTCTTGGTTGGTTTTAAATGTCTCTTGGTTTCTCAGG 1260
ISU3927   ......C...............................G........C............ 1260
ISU55     ......C..................................................... 1260
ISU22     ......C.T.................A................................. 1260
VR2332    ......C.T.................G................................. 1260
ISU1894   ......C.T.................A.........................A....... 1260
ISU79     ......C...................A................................. 1260
          *<ORF3-1
VR2385    CGTTCGCCTGCAAGCCATGTTTCAGTTCGAGTCTTTCAGACATCAAGACCAACACCACCG 1320
ISU3927   ............................................................ 1320
ISU55     ...................................G.......T................ 1320
ISU22     .............A.....................G....T..T................ 1320
VR2332    .............A.....................G....T..T................ 1320
ISU1894   .............A.....C...............G....T..T...........T.... 1320
ISU79     .............A.....................G.......T................ 1320

VR2385    CAGCGGCAGGCTTTGCTGTCCTCCAAGACATCAGTTGCCTTAGGCATCGCAACTCGGCCT 1380
ISU3927   .G..A...AAT..C...........G......G.C............G........A..A 1380
ISU55     ............................................T............... 1380
ISU22     ........A.......................G.................G......... 1380
VR2332    ........A.........................................G......... 1380
ISU1894   ........A................................................... 1380
ISU79     ........A................................................... 1380
                                                 ***<ORF3
VR2385    CTGAGGCGATTCGCAAAGTCCCTCAGTGCCGCACGGCGATAGGGACACCCGTGTATATCA 1440
ISU3927   ........T........A.......................................... 1440
ISU55     ........T........A..........T..T..................A.......T. 1440
ISU22     .................A.............T..........................T. 1440
VR2332    .................A.............T........................G.T. 1440
ISU1894   .................A.............T..........................T. 1440
ISU79     .................A.............T.................TA.......T. 1440
```

FIG. 1D

```
VR2385   CTGTCACAGCCAATGTTACCGATGAGAATTATTTGCATTCCTCTGATCTTCTCATGCTTT  1500
ISU3927  ..A.............A..A........C...........T...................  1500
ISU55    ..G.............A.............................C.............  1500
ISU22    .CA.............G..A..............A.....T........C..........  1500
VR2332   .CA.............G..A..............A.....T........C..........  1500
ISU1894  .CA.............G..A..............A.....T........C..........  1500
ISU79    .CA.............G..A.....A........A.....T........C........C.  1500

VR2385   CTTCTTGCCTTTTCTATGCTTCTGAGATGAGTGAAAAGGGATTTAAGGTGGTATTTGGCA  1560
ISU3927  .C..............C.......................G...........G.......  1560
ISU55    ................C.............................A.............  1560
ISU22    ........................................G...................  1560
VR2332   ............................................................  1560
ISU1894  ................C....................A.....C................  1560
ISU79    ............................................G.......T.......  1560

VR2385   ATGTGTCAGGCATCGTGGCAGTGTGCGTCAACTTCACCAGTTACGTCCAACATGTCAAGG  1620
ISU3927  ............C......T......A....T..T.....C..T........C.......  1620
ISU55    ...................T..............T.....C...................  1620
ISU22    ...................T.....T.....T..T.....C..T.............G..  1620
VR2332   ...................T.....T.....T..T.....C...................  1620
ISU1894  ...................T.....T.....T..T.....C................G..  1620
ISU79    ...................T.....T.....T..T.....C.....T..........G..  1620

VR2385   AATTTACCCAACGTTCCTTGGTAGTTGACCATGTGCGGCTGCTCCATTTCATGACGCCCG  1680
ISU3927  .G...........C.....A..G..C.............................A..T.  1680
ISU55    .............C...........C.............................A..T.  1680
ISU22    .G...........C........G..C............T................A..T.  1680
VR2332   .G...........C...C....G..C............T................A..T.  1680
ISU1894  .G...........C...C....G..C............T................A..T.  1680
ISU79    .G...........C......A.G..C.............................A..T.  1680
                                                        ***<ORF4
VR2385   AGACCATGAGGTGGGCAACTGTTTTAGCCTGTCTTTTTACCATTCTGTTGGCAATTTGAA  1740
ISU3927  .A..T................................CG.....................  1740
ISU55    ......................................G.............C.......  1740
ISU22    ......................................G.....................  1740
VR2332   ......................................G.....................  1740
ISU1894  .A....................................G........C............  1740
ISU79    ...................C..................G.T...................  1740
               +1>ORF5
VR2385   TGTTTAAGTATGTTGGGGAAATGCTTGACCGCGGGCTGTTGCTCGCAATTGCTTTTTTTA  1800
ISU3927  ..............................................G..C.........G  1800
ISU55    .....................................A.......TC............G  1800
ISU22    ........C.....................................G........C...G  1800
VR2332   ................A.............................G........C...G  1800
ISU1894  ..............................................G........C...G  1800
ISU79    ...............................T..............G........C...G  1800
```

FIG. 1E

```
VR2385   TGGTGTATCGTGCCGTCTTGTTTTGTTGCGCTCGTCAGCGCCAACGGGAACAGCGGCTCA  1860
ISU3927  ................TC...C...C...................AAC.G...---...C  1860
ISU55    ....................G..............C.........A.C.G..A.A....T  1860
ISU22    ....T...........TC.......C..T.....C........G.AAC.G....A....C  1860
VR2332   ................TC.......C..T.....C..A.....G.AACG.....A....C  1860
ISU1894  ................TC.......C..T.....C..A.....G.CC.......A....C  1860
ISU79    ................TC......AC..T.....C.GA....C..A.C......A....T  1860

VR2385   AATTTACAGCTGATTTACAACTTGACGCTATGTGAGCTGAATGGCACAGATTGGCTAGCT  1920
ISU3927  C........T.......T...C............................C.....G...  1917
ISU55    C........T.......T....................................T.....  1920
ISU22    C..C........................................................  1920
VR2332   C..C........................................................  1920
ISU1894  C..C........................................................  1920
ISU79    C..C.G..AT..................................................  1920

VR2385   AATAAATTTGACTGGGCAGTGGAGTGTTTTGTCATTTTTCCTGTGTTGACTCACATTGTC  1980
ISU3927  ...........T.......A...............C.....C.................T  1977
ISU55    GG.G........................................................  1980
ISU22    ...........T.......A...............C.....C..T...............  1980
VR2332   ..C........T.......A...............C.....C..T...............  1980
ISU1894  G..........T.......A...............C.....C..T...............  1980
ISU79    G...G......T.......A.C.............C........T...............  1980

VR2385   TCTTATGGTGCCCTCACTACTAGCCATTTCCTTGACACAGTCGGTCTGGTCACTGTGTCT  2040
ISU3927  ..C........A.....C..C.............................T.........  2037
ISU55    ..C..............C..C.......................................  2040
ISU22    ..C.................C......................C.T.A............  2040
VR2332   ..C.................C......................C.T.A............  2040
ISU1894  ..C........................C...............CCT.A............  2040
ISU79    ..C.....C........C..C..................A.T.C.T.A............  2040

VR2385   ACCGCTGGGTTTGTTCACGGGCGGTATGTTCTGAGTAGCATGTACGCGGTCTGTGCCCTG  2100
ISU3927  .....C......CA...........................C..................  2097
ISU55    .....C..C...TCC..........................C..................  2100
ISU22    .....C.......................C...........C..................  2100
VR2332   .....C.......................C..A........C..................  2100
ISU1894  .....C.......................C..A........C..................  2100
ISU79    .....C.......................C..A........C..................  2100

VR2385   GCTGCGTTGATTTGCTTCGTCATTAGGCTTGCGAAGAATTGCATGTCCTGGCGCTACTCA  2160
ISU3927  ........T..................T..........C....................T  2157
ISU55    ...........................T..A.............................  2160
ISU22    ..........C.......A....C...T....A..........................G  2160
VR2332   ..........C................T....A........................G.G  2160
ISU1894  ........AGC................T....A.......................T..G  2160
ISU79    ..........C................T...T............................  2160
```

FIG.1F

```
VR2385   TGTACCAGATATACCAACTTTCTTCTGGACACTAAGGGCAGACTCTATCGTTGGCGGTCG  2220
ISU3927  ....................C......................................A  2217
ISU55    ............................................................  2220
ISU22    .......................C....................................  2220
VR2332   ............................................................  2220
ISU1894  .......................................................AT...  2220
ISU79    .....T.......................T..............................  2220

VR2385   CCTGTCATCATAGAGAAAAGGGGCAAAGTTGAGGTCGAAGGTCACCTGATCGACCTCAAA  2280
ISU3927  ..................G....T..G.................T...........A...  2277
ISU55    .......................T....................T..............G  2280
ISU22    ............................................T...............  2280
VR2332   ............................................T...............  2280
ISU1894  ............................................T...............  2280
ISU79    .................G..........................T.........T.....  2280

VR2385   AGAGTTGTGCTTGATGGTTCCGCGGCTACCCCTGTAACCAGAGTTTCAGCGGAACAATGG  2340
ISU3927  .A........................A......T..........................  2337
ISU55    ..........................A......A......A............G......  2340
VR2385   ............................................................  2340
ISU22    ......................T...A......A..........................  2340
VR2332   ......................T...A......A..........................  2340
ISU1894  ..............C.......T...A......A..........................  2340
ISU79    ......................T...A......A..........................  2340
                  ***<ORF5
VR2385   AGTCGTCCTTAG  2352
ISU3927  G.......C...  2349
ISU55    G...........  2352
VR2385   ............  2352
ISU22    G...........  2352
VR2332   G...........  2352
ISU1894  G...........  2352
ISU79    G...........  2352
```

FIG. 1G

```
A
VR2385   MKWGLC--K----AFLTKLAN-FLWMLSRSSWCPLLISLYFWPFCLASPSQVGWWSFASDWFAPRYSVRALPFTLSNYRRSYEAFLSQCQ   83
ISU22    ....P.--.----.....................................P.......................................   83
ISU79    ....P.--.----..........................S..........P.......................................   83
ISU55    ......--.----..........S..........................P.......................................   83
ISU1894  ....P.--.----.........................S...........P.......................................   83
ISU3927  .Q..P.--.----....RSV..................S..........LPA......................................   83
VR2332   ....P.--.----.....................................P.......................................   83
LV       .Q..H.GV.SASCSWTPS.SSLLV.LI-------.PF..---.Y..G....D.Y...F.E.....F.........P.......GL.PN.R   80

VR2385   VDIPTWGTKHPLGMLWHHKVSTLIDEMVSRRMYRIMEKAGQAAWKQVVSEATLSRISSLDVVAHFQHLAAIEAETCKYLASRLPMLHMLR  173
ISU22    .......................................................................................N..  173
ISU79    ..............F........................................................................N..  173
ISU55    .......I......F........................................................................N..  173
ISU1894  ..............F........................................................................N..  173
ISU3927  ....A...R................................................G.............................N..  173
VR2332   .......................................................................................N..  173
LV       P.V.QFAV......F..MR..H.........I.QT..HS.........G....TKL.G..I.T.......V..DS.RF.S...V..KN.A  170

VR2385   MTGSNVTIVYNSTLNQVFAVFPTPGSRPKLHDFQQWLIAVHSSIFSSVAASCTLFVVLWLRVPMLRTVFGFRWLGAIFLSNSR  256
ISU22    ...................I...........................................I..S.............S..  256
ISU79    ...............R...I...........................................I..................-  255
ISU55    .................L.I..............................................IA..............Q  256
ISU1894  I............SE....I.......................................................G..P...W  256
ISU3927  I........H.........I........................S................M....S...........P.S.W  256
VR2332   ...................I...........................................I..................Q  256
LV       V--G..SLQ..T..DR.ELI.....T....T..R....S..A.......S.V...I.....I.A..Y....H.PT.THH.S--  249
```

FIG.2A

Figure 2B:
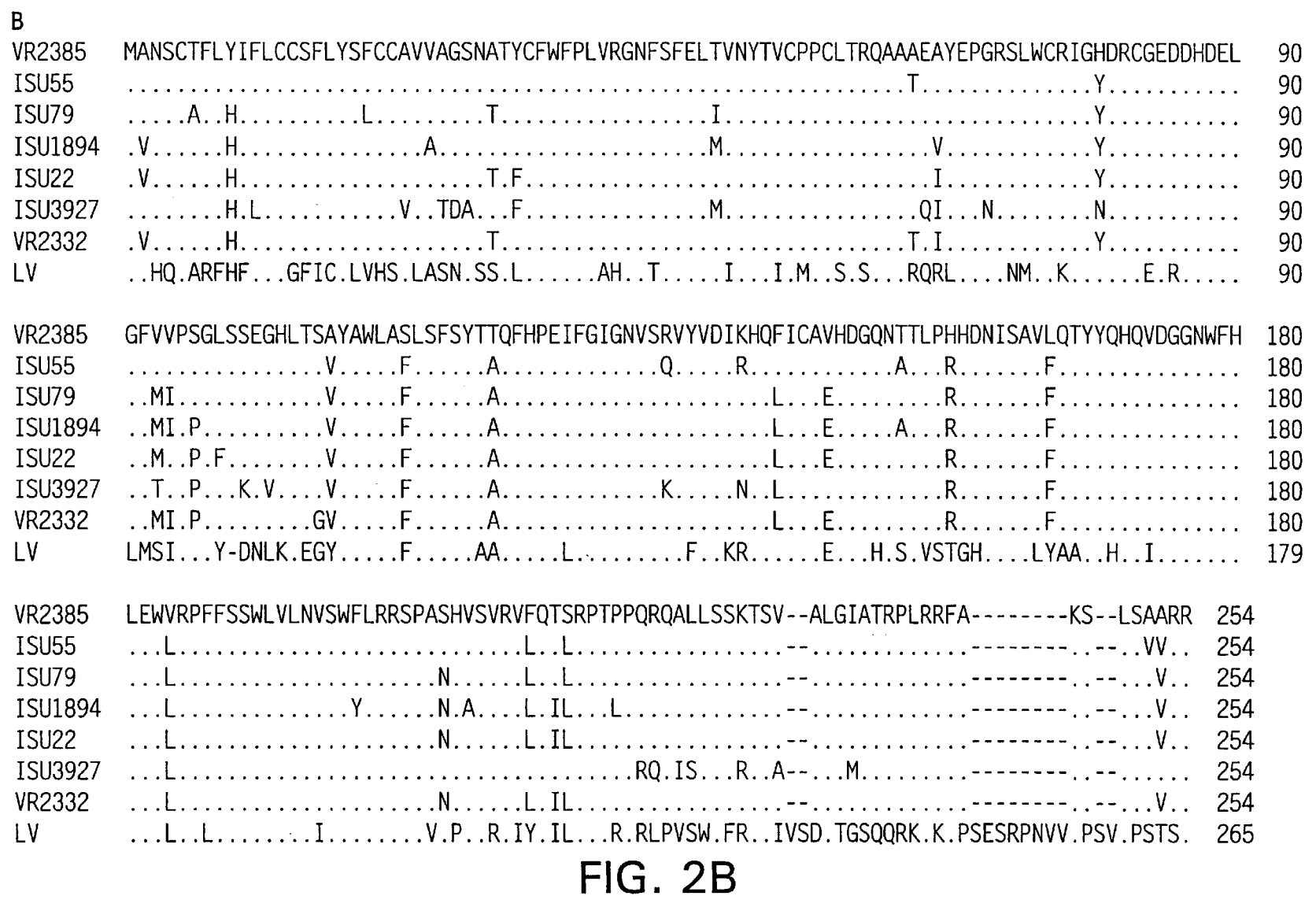

```
B
VR2385   MANSCTFLYIFLCCSFLYSFCCAVVAGSNATYCFWFPLVRGNFSFELTVNYTVCPPCLTRQAAAEAYEPGRSLWCRIGHDRCGEDDHDEL   90
ISU55    ...............................................................T..............Y...........   90
ISU79    .....A..H..........L.........T.................I..............................Y...........   90
ISU1894  .V......H...............A......................M.................V............Y...........   90
ISU22    .V......H....................T.F.................................I............Y...........   90
ISU3927  ........H.L...........V..TDA...F...............M................QI...N........N...........   90
VR2332   .V......H....................T.................................T.I............Y...........   90
LV       ..HQ.ARFHF...GFIC.LVHS.LASN.SS.L......AH..T.....I...I.M..S.S...RQRL....NM..K......E.R.....   90

VR2385   GFVVPSGLSSEGHLTSAYAWLASLSFSYTTQFHPEIFGIGNVSRVYVDIKHQFICAVHDGQNTTLPHHDNISAVLQTYYQHQVDGGNWFH  180
ISU55    ................V.....F......A.............Q.....R............A...R.......F...............  180
ISU79    ..MI............V.....F......A......................L...E.........R.......F...............  180
ISU1894  ..MI.P..........V.....F......A......................L...E.....A...R.......F...............  180
ISU22    ..M..P.F........V.....F......A......................L...E.........R.......F...............  180
ISU3927  ..T..P...K.V....V.....F......A.............K.....N..L.............R.......F...............  180
VR2332   ..MI.P.........GV.....F......A......................L...E.........R.......F...............  180
LV       LMSI...Y-DNLK.EGY.....F.....AA....L..........F..KR......E...H.S.VSTGH....LYAA..H..I.......  179

VR2385   LEWVRPFFSSWLVLNVSWFLRRSPASHVSVRVFQTSRPTPPQRQALLSSKTSV--ALGIATRPLRRFA--------KS--LSAARR  254
ISU55    ...L............................L..L.................--.............--------..--..VV..  254
ISU79    ...L.....................N......L..L.................--.............--------..--...V..  254
ISU1894  ...L..............Y......N.A....L.IL...L.............--.............--------..--...V..  254
ISU22    ...L.....................N......L.IL.................--.............--------..--...V..  254
ISU3927  ...L.....................................RQ.IS...R..A--...M.........--------..--......  254
VR2332   ...L.....................N......L.IL.................--.............--------..--...V..  254
LV       ...L..L........I........V.P..R.IY.IL...R.RLPVSW.FR..IVSD.TGSQQRK.K.PSESRPNVV.PSV.PSTS.  265
```

```
VR2385   MGASLLFLLVGFKCLLVSQAFACKPCFSSSLSDIKTNTTAAAGFAVLQDISCLRHRN-SASE---AIRKVPQCRTAIGTPVYITVTANVT   86
VR2332   .AS.....V......................A..........S.............D-....---....I............V.I.....   86
ISU55    .A.............................A......................Y..-....---.F..I...........M........   86
ISU1894  .AS.....M......................A..........S..............-....---....I..............I.....   86
ISU22    .AS.....M......................A..........S.......G.....D-....---....I..............I.....   86
ISU79    .A......M......................A..........S..............-....---....I...........M..I.....   86
ISU3927  .A..........E.............................N.......G....G.-.TT.---.F..I..............I.....   86
LV       .A.AT..F.A.AQHIM..E.........TH....E.........M.....N.F.PHGV..AQEKISFG.SS...E.V...Q...I.....   90

VR2385   DENYLHSSDLLMLSSCLFYASEMSEKGFKVVFGNVSGIVAVCVNFTSYVQHVKEFTQRSLVVDH-VRLLHFMTPETMRWATVLACLFTIL   175
VR2332   ................................................................-......................A..   175
ISU55    ................................................................-......................A..   175
ISU1894  ....................................................R...........-......................A..   175
ISU22    ....................................................R...........-......................A..   175
ISU79    ............................E.......................R.......M...-......................A..   175
ISU3927  .....................................T....I.....................-......................A..   175
LV       ..S..YNA......A...............I......V.SA.....D..A..TQH..QHHL.IDHI.....L..SA.....TI....A..   180

VR2385   LAI  178
VR2332   ...  178
ISU55    ...  178
ISU1894  ...  178
ISU22    ...  178
ISU79    ...  178
ISU3927  ...  178
LV       ...  183
```

FIG. 2C

```
D                                  *******
VR2385   MLGKCLTAGCCSQLLFLWCIVPSCFVA--LVSANGNSGSNLQLIYNLTLCELNGTDWLANKFDWAVECFVIFPVLTHIVSYGALTTSHFL   88
VR2332   ..E.........R..S......F..AV--.AN.SND.S.H...........................S......................   88
ISU55    .........Y..S..........W...--.A...SSNS.H...................GE.............................   88
ISU1894  ............R..S......F..AV--.AN.SA..S.H...................D.......S...................L..   88
ISU79    ............R..S...F..F..AV--.A..SNS.S.H...........................S......................   88
ISU22    .......V....R..S......F..TV--.AD.HS..S.H...................DR......S......................   88
ISU3927  ............RS........F.LA.--.....-..S.H...........................S......................   87
LV       .RCSHKLGRFLTPHSCF.WLFLL.TGLSWSF.D..GDS.TY.Y.....I.........SSH.G....T..LY..A...L.L.F......F   90

VR2385   DTVGLVTVSTAGFVHGRYVLSSMYAVCALAALICFVIRLAKNCMSWRYSCTRYTNFLLDTKGRLYRWRSPVIIEKRGKVEVEGHLIDLKR  178
VR2332   ...A..................I.........T.....F.........A.........................................  178
ISU55    .............S........I...............FT..................................................  178
ISU1894  ...A..................I.........A.....F............................H......................  178
ISU79    ..IA..................I.........T.....FV..................................................  178
ISU22    ...A..................I.........T..I..F...................................................  178
ISU3927  .............H........I........F......F....................................G.............K  177
LV       .AL..GA.......G.....C.V.GA..F..FV.....A.....AC..AR..F...IV.DR..VH..K..IVV..L..A..D.N.VTI.H  180

VR2385   VVLDGSAATPVTRVSAEQWSRP  200
VR2332   ......V...I........G..  200
ISU55    ..........I.K......G..  200
ISU1894  ......V...I........G..  200
ISU79    ......V...I........G..  200
ISU22    ......V...I........G..  200
ISU3927  ..........L........G..  199
LV       ...E.VK.Q.L..T.....EA-  201
```

| | -89 | +1>ORF3 |
|---|---|---|
| ISU-1894-mRNA3 | GUAACC . . . AUG | |
| ISU-79-mRNA3 | GUAACC . . . AUG | |
| | -236 | +1>ORF4 |
| ISU-1894 | UUGACu . . . AUG | |
| ISU-79-mRNA | UUGACC . . . AUG | |
| | -10 | +1>ORF4 |
| ISU-1894-mRNA4 | UUCACC . . . AUG | |
| ISU-79-mRNA4 | UUCACC . . . AUG | |

```
                                    -26 (mRNA2)                +1>ORF2
ISU79   GTTTTATTTCCCTCCGGGCCCTGTCATTGAACCAACTTTAGGCCTGAATTGAAATGAAAT  60
ISU1894 .....................C......................................

ISU79   GGGGTCCATGCAAAGCCTTTTTGACAAAATTGGCCAACTTTTTGTGGATGCTTTCACGGA 120
ISU1894 .......G.................................................... 120

ISU79   GTTCTTGGTGTCCATTGTTGATATCATTATATTCTTGGCCATTTTGTTTGGCTTCACCAT 180
ISU1894 ....C......................C.....T.......................... 180

ISU79   CGCCGGTTGGCTGGTGGTCTTTTGCATCAGATTGGTTTGCTCCGCGATACTCCGTACGCG 240
ISU1894 ............................................................ 240

ISU79   CCCTGCCATTCACTCTGAGCAATTACAGAAGATCTTATGAGGCCTTTCTTTCCCAGTGCC 300
ISU1894 ...............................................T.A.......... 300

ISU79   AAGTGGACATTCCCACCTGGGGAACTAAACATCCTTTGGGGATGTTTTGGCACCATAAGG 360
ISU1894 ............................................................ 360

ISU79   TGTCAACCCTGATTGATGAGATGGTGTCGCGTCGAATGTACCGCATCATGGAAAAAGCAG 420
ISU1894 ...................A..............C......................... 420

ISU79   GACAGGCTGCCTGGAAACAGGTGGTGAGCGAGGCTACGCTGTCTCGCATTAGTAGTTTGG 480
ISU1894 .G.........................................C................ 480

ISU79   ATGTGGTGGCTCATTTTCAGCATCTTGCCGCCATCGAAGCCGAGACCTGTAAATATTTGG 540
ISU1894 ..................................T...........T............. 540
                                                       -89(mRNA3)
ISU79   CCTCCCGGCTGCCCATGCTACACAACCTGCGCATGACAGGGTCAAATGTAACCATAGTGT 600
ISU1894 ......................T...........A......................... 600

ISU79   ATAATAGTACTTTGAATCGGGTGTTTGCTATTTTCCCAACCCCTGGTTCCCGGCCAAAGC 660
ISU1894 ............C.G.G.A......................................... 660
                       +1>ORF3
ISU79   TTCATGACTTTCAGCAATGGCTAATAGCTGTGCATTCCTCCATATTTTCCTCTGTTGCAG 720
ISU1894 .......T............T..........A............................ 720

ISU79   CTTCTTGTACTCTCTTTGTTGTGCTGTGGTTGCGGGTTCCAATACTACGTACTGTTTTTG 780
ISU1894 .............T...............C.............G................ 780
                                               ***<ORF2(ISU79)
ISU79   GTTTCCGCTGGTTAGGGGCAATTTTTCTTTCGAACTCATAGTGAATTACACGGTGTGCCC 840
ISU1894 ..................G........C...........G.................T.. 840
                                                   ***<ORF2(ISU1894)
```

FIG. 9A

```
ISU79    ACCTTGCCTCACCCGGCAAGCAGCCGCAGAGGCCTACGAACCCGGTAGGTCTCTTTGGTG 900
ISU1894  ................................T........................... 900

ISU79    CAGGATAGGGTACGATCGATGTGGAGAGGACGACCATGACGAGCTAGGGTTTATGATACC 960
IAU1894  ............T..C........G........T.......................... 960
                                     -236(ISU79 mRNA3-1)
ISU79    GTCTGGCCTCTCCAGCGAAGGCCACTTGACCAGTGTTTACGCCTGGTTGGCGTTCTTGTC1020
ISU1894  .C............................T.......................T.....1020

ISU79    CTTCAGCTACACGGCCCAGTTCCACCCCGAGATATTCGGGATAGGGAATGTGAGTCGAGT1080
ISU1894  ........................T...................................1080
          +1>ORF3-1
ISU79    TTATGTTGACATCAAACATCAACTCATCTGCGCCGAACATGACGGGCAGAACACCACCTT1140
ISU1894  ...........................T.................A......G.......1140

ISU79    GCCTCGTCATGACAACATTTCGGCCGTGTTTCAGACCTATTACCAACATCAAGTCGACGG1200
ISU1894  ...............T.....A...................................T..1200
                     -10(mRNA4)+1>ORF4
ISU79    CGGCAATTGGTTTCACCTAGAATGGCTGCGTCCCTTCTTTTCCTCATGGTTGGTTTTAAA1260
ISU1894  ...........................T................................1260
                        ***<ORF3-1
ISU79    TGTCTCTTGGTTTCTCAGGCGTTCGCCTGCAAACCATGTTTCAGTTCGAGTCTTGCAGAC1320
ISU1894  ...........A..........................C....................T1320

ISU79    ATTAAGACCAACACCACCGCAGCGGCAAGCTTTGCTGTCCTCCAAGACATCAGTTGCCTT1380
ISU1894  ..............T.............................................1380
                                                                   **
ISU79    AGGCATCGCAACTCGGCCTCTGAGGCGATTCGCAAAATCCCTCAGTGCCGTACGGCGATA1440
ISU1894  ............................................................1440
         *<ORF3
ISU79    GGGACACCTATGTATATTACCATCACAGCCAATGTGACAGATGAAAATTATTTACATTCT1500
ISU1894  ........CG..................................G...............1500

ISU79    TCTGATCTCCTCATGCTCTCTTCTTGCCTTTTCTATGCTTCTGAGATGAGTGAAAAGGGA1560
ISU1894  .................T.................C....................A...1560

ISU79    TTTGAGGTGGTTTTTGGCAATGTGTCAGGCATCGTGGCTGTGTGTGTCAATTTTACCAGC1620
ISU1894  ..CA.......A................................................1620
                                                    -105
ISU79    TACGTTCAACATGTCAGGGAGTTTACCCAACGCTCCTTGATGGTCGACCATGTGCGGCTG1680
ISU1894  .....C..............................C..G.................T..1680
                            -70            -55(ISU79 mRNA5)
ISU79    CTCCATTTCATGACACCTGAGACCATGAGGTGGGCAACCGTTTTAGCCTGTCTTTTTGCT1740
ISU1894  ....................A.................T....................C1740
                            -70(ISU1894 mRNA5)
```

FIG. 9B

```
                       ***<ORF4     +1>ORF5
ISU79   ATTCTGTTGGCAATTTGAATGTTTAAGTATGTTGGGGAAATGCTTGACCGTGGGCTGTTG1800
ISU1894 ......C...........................................C.........1800

ISU79   CTCGCGATTGCTTTCTTTGTGGTGTATCGTGCCGTTCTGTTTTACTGTGCTCGCCGACGC1860
ISU1894 ...........................................G...........A....1860

ISU79   CCACAGCAACAGCAGCTCTCATCTGCAATTGATTTACAACTTGACGCTATGTGAGCTGAA1920
ISU1894 .AG.GC............C.....A..GC...............................1920

ISU79   TGGCACAGATTGGCTAGCTGATAGATTTGATTGGGCAGTGGAGAGCTTTGTCATCTTTCC1980
ISU1894 .......................A.....................T..............1980

ISU79   TGTTTTGACTCACATTGTCTCCTATGGCGCCCTCACCACCAGCCATTTCCTTGACACAAT2040
ISU1894 C..........................T........T..T......C...........G.2040

ISU79   TGCTTTAGTCACTGTGTCTACCGCCGGGTTTGTTCACGGGCGGTATGTCCTAAGTAGCAT2100
ISU1894 C..C........................................................2100

ISU79   CTACGCGGTCTGTGCCCTGGCTGCGTTGACTTGCTTCGTCATTAGGTTTGTGAAGAATTG2160
ISU1894 ...........................AG...................CA..........2160

ISU79   CATGTCCTGGCGCTACTCATGTACTAGATATACCAACTTTCTTCTGGATACTAAGGGCAG2220
ISU1894 ...............T..G.....C.......................C...........2220

ISU79   ACTCTATCGTTGGCGGTCGCCTGTCATCATAGAGAAGAGGGGCAAAGTTGAGGTCGAAGG2280
ISU1894 ..............AT....................A.......................2280
                                                   -32      -23(mRNA6)
ISU79   TCATCTGATCGATCTCAAAAGAGTTGTGCTTGATGGTTCCGTGGCAACCCCTATAACCAG2340
ISU1894 ............C....................C..........................2340
                      +1>ORF6     ***<ORF5
ISU79   AGTTTCAGCGGAACAATGGGGTCGTCCTTAGATGACTTCTGTTATGATAGTACGGCTCCA2400
ISU1894 .........................................CC.................2400

ISU79   CAAAAGGTGCTTTTGGCATTTTCTATTACCTACACGCCAGTAATGATATATGCCCTAAAG2460
ISU1894 .................G.......................G..................2460

ISU79   GTGAGTCGCGGCCGACTGCTAGGGCTTCTGCACCTTTTGATTTTCCTGAACTGTGCTTTC2520
ISU1894 .........................................C........T.........2520

ISU79   ACCTTCGGGTACATGACATTCATGCACTTTCAGAGTACAAATAAGGTCGCGCTCACTATG2580
ISU1894 .....................G......................................2580
```

FIG. 9C

```
ISU79    GGAGCAGTAGTTGCACTCCTTTGGGGGGTGTACTCAGCCATAGAAACCTGGAAATTCATC2640
ISU1894  ............................................................2640

ISU79    ACCTCCAGATGCCGTTTGTGCTTGCTAGGCCGCAAGTACATTCTGGCCCCTGCCCACCAC2700
ISU1894  ............................................................2700
                                                 -129
ISU79    GTTGAAAGTGCCGCAGGCTTTCATCCGATTGCGGCAAATGATAACCACGCATTTGTCGTC2760
ISU1894  ............................................................2760

ISU79    CGGCGTCCCGGCTCCACTACGGTCAACGGCACATTGGTGCCCGGGTTGAAAAGCCTCGTG2820
ISU1894  ............................................................2820
                                    -15 (mRNA7)     +1>ORF7***<ORF6
ISU79    TTGGGTGGCAGAAAAGCTGTTAAACAGGGAGTGGTAAACCTTGTCAAATATGCCAAATAA2880
ISU1894  ............................................................2880

ISU79    CAACGGCAAGCAGCAGAAGAGAAAGAAGGGGGATGGCCAGCCAGTCAATCAGCTGTGCCA2940
ISU1894  ............................................................2940

ISU79    GATGCTGGGTAAGATCATCGCCCAGCAAAACCAGTCTAGAGGCAAGGGACCGGGAAAGAA3000
ISU1894  .....................T..............C.......................3000

ISU79    AAATAAGAAGAAAAACCCGGAGAAGCCCCATTTTCCTCTAGCGACTGAAGATGATGTCAG3060
ISU1894  ...C........................................................3060

ISU79    ACATCACTTTACCCCTAGTGAGCGGCAATTGTGTCTGTCGTCAATCCAAACTGCCTTTAA3120
ISU1894  .........C......................................G..C........3120

ISU79    TCAAGGCGCTGGGACTTGCACCCTGTCAGATTCAGGGAGGATAAGTTACACTGTGGAGTT3180
ISU1894  ............................................................3180
                                                                  **
ISU79    TAGTTTGCCTACGCATCATACTGTGCGCTTGATCCGCGTCACAGCATCACCCTCAGCATG3240
ISU1894  .........A..................................................3240
         *<ORF7
ISU79    ATGGGCTGGCATTCTTGAGGCATCCCAGTGTTTGAATTGGAAGAATGCGTGGT 3293
ISU1894  ..................................................... 3293
```

FIG. 9D

REACTIVITY[a] OF THE MAbs WITH PRRSV FIELD ISOLATES DETECTED WITH FIXED-CELL ELISA

| VIRUS ISOLATE | | MAbs TO GP4 PROTEIN | | | | MAbs TO GP5 PROTEIN | | | | | | MAb TO N |
|---|---|---|---|---|---|---|---|---|---|---|---|---|
| NAME | SOURCE | PP4bB3 | PP4bC5 | PP4cB11 | PP4dG6 | PP5eA12 | PP5eD3 | PP5dB4 | PP5cH5 | PP5cG12 | PP5bH4 | PP7eF11 |
| VR2385 | IOWA | 512 | 64 | 512 | 32 | >256 | >256 | >256 | 512 | 256 | 64 | >1600 |
| ISU28 | IOWA | 1024 | 64 | 128 | <32 | 256 | 256 | 128 | 128 | 64 | 32 | >3200 |
| RP20 | VIRGINIA | 512 | 256 | 1024 | 32 | 64 | 128 | 64 | 512 | 256 | <32 | >1600 |
| RP45 | MINNESOTA | 128 | 32 | 256 | 128 | 128 | >256 | >256 | 256 | 64 | 32 | >1600 |
| RP10 | IOWA | 128 | 32 | 16 | 128 | >256 | >256 | 128 | 64 | 64 | 32 | >3200 |
| RP11 | IOWA | 1024 | 8 | 32 | >256 | >256 | >256 | 128 | 128 | 32 | <32 | >1600 |
| ISU22 | IOWA | 512 | 64 | 32 | 32 | 128 | 128 | 64 | 128 | 32 | 32 | >3200 |
| ISU7229 | IOWA | 512 | 64 | 32 | <32 | 64 | 64 | 64 | 128 | 32 | 32 | >3200 |
| ISU-55 | IOWA | 512 | 16 | 16 | <32 | 128 | 128 | 64 | 128 | 64 | 32 | >3200 |
| RP29 | IOWA | 1024 | 512 | 64 | 32 | 128 | 128 | 32 | 128 | 64 | <32 | >3200 |
| RP12 | IOWA | 1024 | 64 | 1024 | 64 | <32 | 128 | <32 | 256 | 64 | <32 | >1600 |
| RP15 | MINNESOTA | 512 | 512 | 512 | <32 | <32 | <32 | <32 | 128 | 128 | <32 | >1600 |
| ISU4 | IOWA | 1024 | 128 | 32 | <32 | 32 | <32 | <32 | 128 | 64 | <32 | >3200 |
| RP18 | VIRGINIA | 1024 | 16 | 64 | <32 | <32 | <32 | 32 | 64 | 64 | 32 | >1600 |
| RP24 | IOWA | 1024 | 128 | 32 | <32 | <32 | 32 | 32 | 128 | 64 | 32 | >3200 |
| RP46 | MINNESOTA | 256 | 64 | 32 | 32 | 32 | 128 | 32 | 128 | 64 | 32 | >3200 |
| RP22 | IOWA | 512 | 32 | 32 | <32 | 64 | 64 | 32 | 128 | 64 | <32 | >3200 |
| RP40 | MISSOURI | 128 | 32 | 32 | 64 | 64 | 128 | 64 | 128 | 32 | 32 | >3200 |
| ISU33 | IOWA | 128 | 32 | 32 | <32 | 64 | 128 | 64 | 128 | 16 | <32 | >3200 |
| RP17 | VIRGINIA | 64 | 32 | 16 | 64 | 128 | 128 | 32 | 64 | 32 | <32 | >3200 |
| ISU51 | IOWA | <8 | <8 | <8 | 32 | 256 | 256 | 64 | <8 | 8 | <32 | 800 |
| RP36 | IOWA | 32 | <32 | <32 | 32 | <32 | 64 | 32 | 32 | 32 | 32 | >3200 |
| RP31 | IOWA | 32 | <32 | <32 | 32 | 32 | 32 | 64 | 128 | 64 | 32 | >3200 |

A. REACTIVITY WAS EXPRESSED AS TITERS OF THE REACTION OF MAbs WITH PRRSV ISOLATES. END-POINT TITERS WERE EXPRESSED AS THE RECIPROCAL OF THE HIGHEST DILUTION OF THE MAbs SHOWING ABSORBANCE $A_{405}$ LARGER THAN THE SUM OF AVERAGE NEGATIVE CONTROL'S $A_{405}$ PLUS 3 STANDARD DEVIATIONS.

FIG. 13

PRIMERS-USED TO AMPLIFY PRRSV ORFs 2 THROUGH 7 GENES WITH PCR

| ORF | FORWARD PRIMER | REVERSE PRIMER |
|---|---|---|
| 2 | 5'GCACGGATCCGAATTAACATG AAATGGGGT 3' | 5'CCACCTGCAGATTCACCGTGA GTTCGAAAG 3' |
| 3 | 5'CGTCGGATCCTCCTACAATGG CTAATAGCT 3' | 5'CGCGCTGCAGTGTCCCTATCG ACGTGCGGC3' |
| 4 | 5'GTATGGATCCGCAATTGGTTT CACCTATAA 3' | 5'ATAGGAATTCAACAAGACGGC ACGATACAC 3' |
| 5 | 5'TGCCAGGATCCGTGTTTAAAT ATGTTGGGG 3' | 5'CGTGGAATTCATAGAAAACGC CAAGAGCAC 3' |
| 6 | 5'GGGGATCCAGAGTTTCAGCGG 3' | 5'GGGAATTCTGGCACAGCTGAT TGAC 3' |
| 7 | 5'GGGGATCCTTGTTAAATATGC C 3' | 5'GGGAATTCACCACGCATTC 3' |

FIG. 21

RECOMBINANT PROTEINS OF PRRSV ORFs 2 TO 5 EXPRESSED IN INSECT CELLS

| ORF | PREDICTED $M_t$ OF PRODUCT (kDa)[a] | N-LINKED GLYCOSYLATION SITES[a] | EXPRESSED PRODUCTS IN INSECT CELLS (kDa)[b] | BANDS AFTER TUNICAMYCIN TREATMENT (kDa)[c] | POSSIBLE CORE PROTEIN (kDa)[d] |
|---|---|---|---|---|---|
| 2 | 29.5 | 2 | 27, 29 | 25, 27 | 25 |
| 3 | 28.7 | 7 | 22-43 | 22-27 | 27 |
| 4 | 19.5 | 4 | 15-30 | 15, 18 | 15 |
| 5 | 22.2 | 2 | 16-26 | 16, 18 | 16 |

A. PREDICTED $M_t$ OF PRODUCTS OF PRRSV ORFS 2 TO 5 AND N-GLYCOSYLATION SITES ARE BASED ON NUCLEOTIDE SEQUENCE STUDIES (MENG ET AL, 1994 & MOROZOV ET AL., 1995).

B. EXPRESSED PRODUCTS IN INSECT CELLS (DETAILS SEE RESULT SECTION AND FIG. 5).

C. BANDS AFTER TUNICAMYCIN TREATMENT WERE DETERMINED BY IMMUNOBLOTTING ANALYSIS (DETAILS SEE RESULT SECTION AND FIG. 6).

D. LEADER-FREE CORE PROTEINS ARE DETERMINED ON THE BASIS OF TUNICAMYCIN TREATMENT ANALYSIS. THE PRESENCE OF THE OTHER BANDS IN THE RECOMBINANT PRODUCTS AFTER TUNICAMYCIN TREATMENT WAS POSSIBLY DUE TO O-LINKED GLYCOSYLATION, PHOSPHORYLATION OR OTHER POST-TRANSLATIONAL MODIFICATIONS.

FIG. 22

ORF1A 5' END ALIGNMENT (55% homology)

| | | | | | | | |
|---|---|---|---|---|---|---|---|
| la VR2385 (1-1998) | ..........  | T.C.TGAT.  | ......C...T  | ....CAA..  | ...A...G.  | | 50 |
| la LV (1-1938) | ..........  | C.T.CTCC.  | ......T...C  | ......GGC.  | ...C....A.  | | 50 |
| CONSENSUS | ATGTCTGGGA | YGYTYKMYCG | GTGCAYGTGY | ACCCCSRMTG | CCMGGGTRTT | | 50 |

| | | | | | | | |
|---|---|---|---|---|---|---|---|
| la VR2385 (1-1998) | .AT.GCG.AA | ..........  | ..AC.......  | ..A..C....  | .....A.....  | | 100 |
| la LV (1-1938) | .TG.AAC.CC | ..........  | ..TT.......  | ..G..T.....  | ...G.......  | | 100 |
| CONSENSUS | TWKGRMSGMM | GGCCAAGTCT | MYTGCACACG | RTGYCTCAGT | GRCGGTCTC | | 100 |

| | | | | | | | |
|---|---|---|---|---|---|---|---|
| la VR2385 (1-1998) | .C..TC.C.T | GA.T..C..A | .CTT....G..T | .G.TGC.A...C.A..C | | | 150 |
| la LV (1-1938) | .T..CT.T.C | AG.G..T..G | .ACA....C..C..T.CAG | T...T.G..T | | | 150 |
| CONSENSUS | TYCTYYCYCY | RRAKCTYCAR | GMYWCTGASC | TYGGKGYRST | WGGCYTRTTY | | 150 |

| | | | | | | | |
|---|---|---|---|---|---|---|---|
| la VR2385 (1-1938) | ...G..CG | AA..GCCA. | .C.GG...C..T.G.C.CGT | ....T..C.. | | | 199 |
| la LV (1-1938) | ...A..TA | GG.CAAG. | .T.AC...A..CC.T.TCG | ....C..T.. | | | 200 |
| CONSENSUS | TACARGCCYR | RRGASMMRCT | YCRSTGGAAM | GTYSCYAYSK | GCATYCCYCA | | 200 |

| | | | | | | | |
|---|---|---|---|---|---|---|---|
| la VR2385 (1-1998) | .T..T..G. | .CT.C..CG. | ...AGC..C. | .....T..T. | .AA.C..T..A | | 249 |
| la LV (1-1938) | -G..G..A. | .TA.T..AT. | ...GTG...T | ....C..A. | .TG.T..C..T | | 249 |
| CONSENSUS | CKGTKGARTG | YWCYCYCOMKCC | GGRKSCTGYT | GGCTYTCWGC | WRTYTTYCCW | | 250 |

| | | | | | | | |
|---|---|---|---|---|---|---|---|
| la VR2385 (1-1998) | A.T..A..G | .....AGT. | .A.C.TG.. | ....AA..A | ..A.G.ACG | | 299 |
| la LV (1-1938) | T.G..G..T | .....TCC. | .C..T.AC.. | ....TC...C | ..C.T.GAA | | 299 |
| CONSENSUS | WTKGGRCGKA | TGACCWSYGG | MAAYCWSAAC | TTCCWMCAAM | GAMTKGTRMR | | 300 |

| | | | | | | | |
|---|---|---|---|---|---|---|---|
| la VR2385 (1-1998) | ...C.A.C. | .AG.TA..A | .A.C.....CCA | G.--...C | .TG..GT..T | | 347 |
| la LV (1-1938) | ...T.T.A. | .TT.GT..C | .T.A...TTG | C........T | .GA..CC..C | | 349 |
| CONSENSUS | GGTYGCWGMT | GWKTTKWACM | GWGMCGGYYR | STTGGCACCY | CKRCASYTTY | | 350 |

| | | | | | | | |
|---|---|---|---|---|---|---|---|
| la VR2385 (1-1998) | .AAG....  | .......... | ...T..A.G..T..CG | ........G.TGTT | | | 397 |
| la LV (11938) | .TGA...-- | .......... | ...C..G.C.C..AA | ........G.CACG | | | 397 |
| CONSENSUS | GWRRACTCTA | CAAGTTTAYG | ARCGSGGYTG | CMRCTGGTAC | CCSATYRYKG | | 400 |

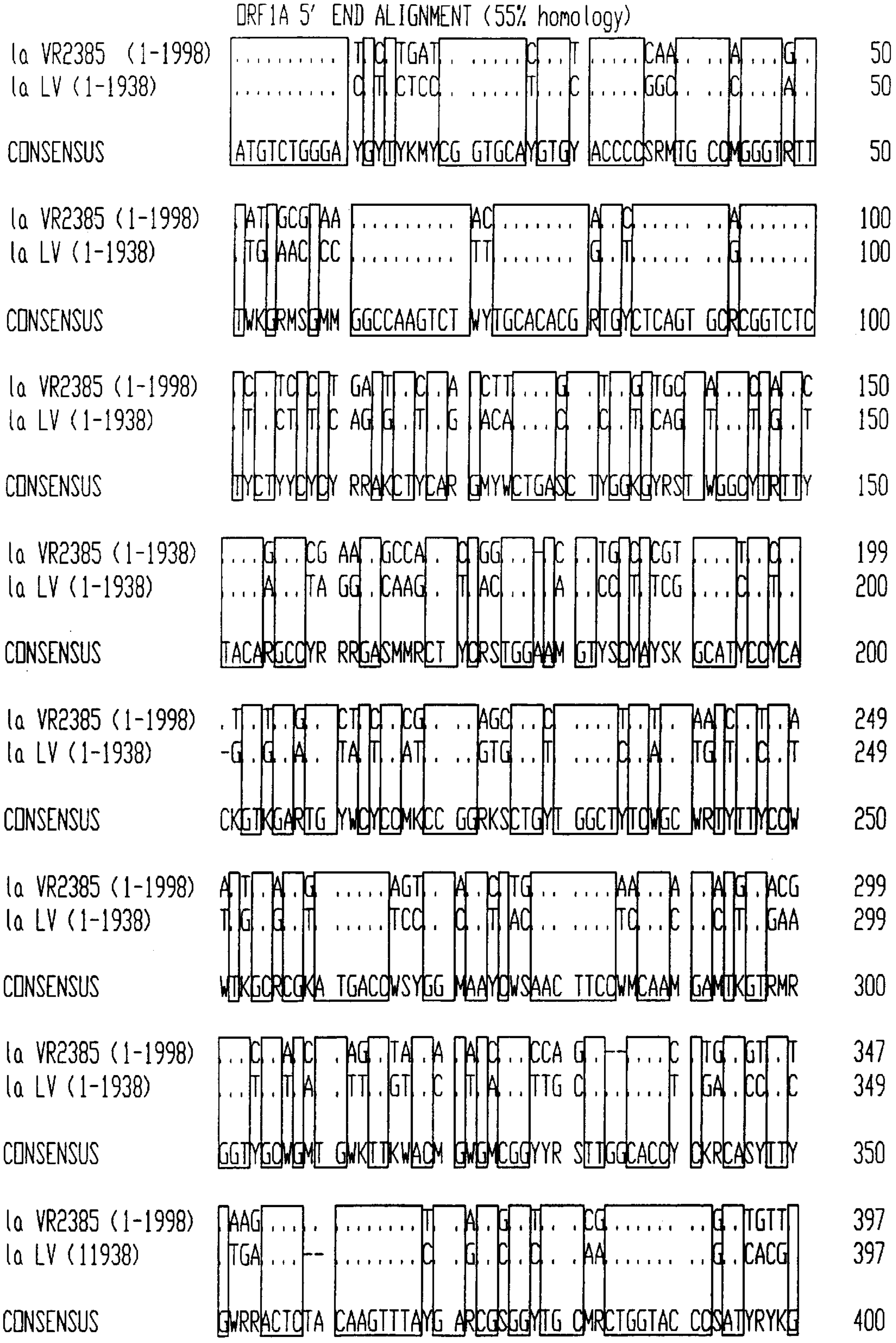

FIG.25A-1

ORF1A 5' END ALIGNMENT (55% homology)

```
la VR2385 (1-1998)   A  T  C   T AG   CC G T C   C      C A   T  GAGT T  447
la LV    (1-1938)       G  C   G  C  GA  GT T G T G        A G    C  ATCC C  447

CONSENSUS   GRCCYGTSCC YGGRRTGGSY KTKTTYGCSA ACTCCMTRCA YGTRWSYGAY  450

la VR2385 (1-1998)  A A  T        G  A  A    T  C    A   C    CT    GC C  G    497
la LV    (1-1938)   C G  G        T  T  C    C  T    G       TC     TT G  T    497

CONSENSUS   MARCCKTTCC CKGGWGCMAC YCAYGTGYTR ACYAACYYGC CKYTSCCKCA  500

la VR2385 (1-1998)    G CC AA  C T  A    T C  C       TGT   ATGG   CT  546
la LV    (1-1938)    -C GG TT  T G  C    C T  A       GAG   CATT   GC  546

CONSENSUS   GASASSCWWG YCKGMAGMCG TTYTGYCCMT TTGAGKRKGC TMWKKCTASY  550

la LV2385 (1-1998)    C T-AC ATTG TC  -- AC CCG   T T  --TG GG CG GG    591
la LV    (1-1938)     G C  GT GGAA AA    TG TTT   C G    CC CC TC AC    596

CONSENSUS   GTSTAYAGRY RKWRGWMATT TGWSGYYKTC AYGKACTYST SSCYSARSGG  600

la VR2385 (1-1998)  AAAG    CT GG CCCCTCG T G    AT GA         T   A   T  641
la LV    (1-1938)   TCGA    GC AT ATGTGGA C C    TC CG  --      C-- G C  C  641

CONSENSUS   WMRRTCTCSY RKGMYSYKSR YGSCGGAAWY SRAGTGAAAT TYGAARCYGY  650

la VR2385 (1-1998)   CC    -- -- T   AA T TT  -G AC  -G C    G   CCT  682
la LV    (1-1938)    TG         C    GT A AC   A GT   A A    T   TTC  691

CONSENSUS   CCYSGAGGTA CTACGGCYTG ARWTMGAWYG TCRGRYCGAR MTCCKCAYYY  700

la VR2385 (1-1998)  CC --- C  GC C  T GTA G   A   TA T C  CCT    -  728
la LV    (1-1938)   GG    T  TG T  C CCT C   C   G CG C G AGC       741

CONSENSUS   SSAGTTTYCC KSCYCAYCAY SYWGTSGACM TGKCYRASTK SGMSYTCACT  750

la VR2385 (1-1998)  -- G T    G CGT  G    TA --G GG  TGA CG  C  CA   C  774
la LV    (1-1938)     T C    A AAC   T    CT  A AC  CTC TT  T --TG   T  789

CONSENSUS   GAGKCYCCTG RGMRYGGTKT TTCYWTCARC RSGTYKMAYK DYAAYRCGGY  800
```

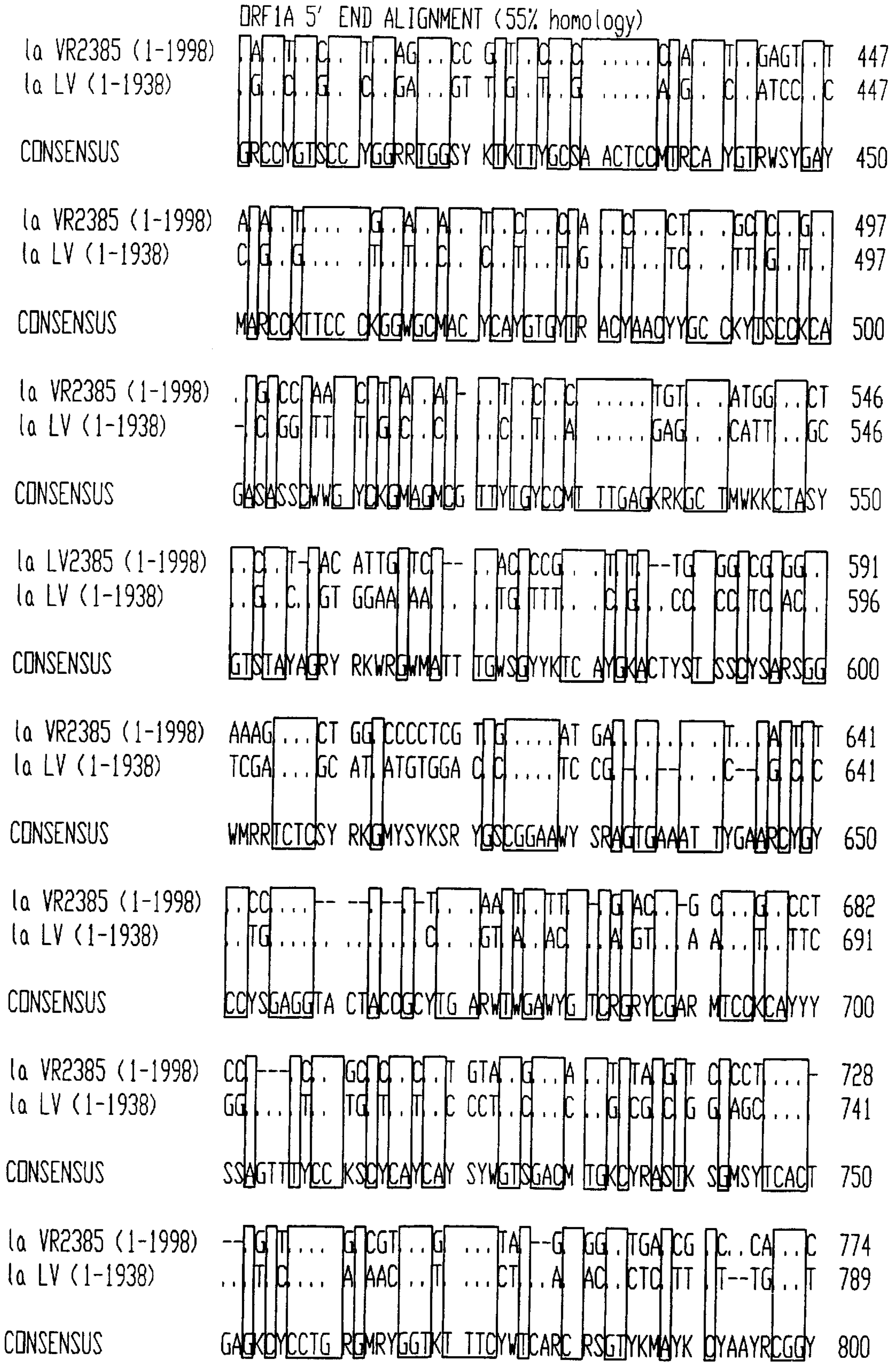

FIG.25A-2

ORF1A 5' END ALIGNMENT (55% homology)

```
Ia VR2385 (1-1998)  TG..C-C..CTGAA-- T.CCC..A .....C......T.GAGT.   821
Ia LV (1-1938)      CA..T.T..GAACC.. C.GTT..T .....G......C-TCTC.   838

CONSENSUS           YRCCTYGYCC ASWRMCMCGA YGTSYYTGAW GGCAASTGCT GGYGKMKCYT   850

Ia VR2385 (1-1998)  .T.AACTT.T-CCACG .....CAGA AAA.AAT CGCAT..   870
Ia LV (1-1938)      .C.TTTGG.C.GTGGC .....GGCT GCT.GGA AATTA..   888

CONSENSUS           GYTTWWYKKG CYASYCRSTS GAAGTSCRSW RCMAWGARRW MCRYCWWGCT   900

Ia VR2385 (1-1998)  A.CAA.T.C....G.....CAT.T ..TTC..C........A.   920
Ia LV (1-1938)      G.GCC.C.T....A.....TGG.C ..GCA..T........C.   938

CONSENSUS           RACSMMTTYG GYTACCARAC CAAGYRKGGY GTKYMTGGYA AGTACCTMCA   950

Ia VR2385 (1-1998)  ...G.....G......AAT.TCC.A.A...ACT..C ..AA...A   970
Ia LV (1-1938)      ...C.....T......CGC.CAT.T.T...GTC..T ..TG...T   988

CONSENSUS           GCGSAGGCTK CAAGTTMRYG GYMTYCGWGC WGTARYYGAY CCWRATGGWC   1000

Ia VR2385 (1-1998)  .T.CGT.- AC.TA.T CTCCTT.AG G.AG......C.C..T   1019
Ia LV (1-1938)      .C.TCA.. GA.CG.G TCTTCC-CC C.TC......A.G..C   1037

CONSENSUS           CYATYSWCGT TRMAGYRCTK YYYYGYYAMS SAGWSTTGGA TCMGSCACYT   1050

Ia VR2385 (1-1998)  ..AA...CG.GA.ACC..........G.TAGGA..CCTCAGAA   1069
Ia LV (1-1938)      ..CT...AT.AT.TGT..----..A.A.CTTCG..GACATCCC   1084

CONSENSUS           GAMWCTGGMK GRWGAWSYCA GCTACCCWGG RTTYGWKSRC CTSMYMWSMM   1100

Ia VR2385 (1-1998)  .AAGG..A...C.T..G TC..ATTGG ..A.AA.. ........T   1119
Ia LV (1-1938)      .TCCA..T...G.C..A GA..TACCA ..-T.CC.- --------C   1125

CONSENSUS           TWMGSRTTGW GCCSAAYACR KMGCCWWYSR CTGWCMMGGA TGAAAAAATY   1150

Ia VR2385 (1-1998)  ..C........T-.C........C.......G A.....GA   1168
Ia LV (1-1938)      ..T........-.C.T........T.......----C C-....-AC   1168

CONSENSUS           TTYCGGTTTG GCAGYGCAYA AGTGGTAYGG CGCTGGAAAS MGAGCAAGRM   1200
```

FIG. 25A-3

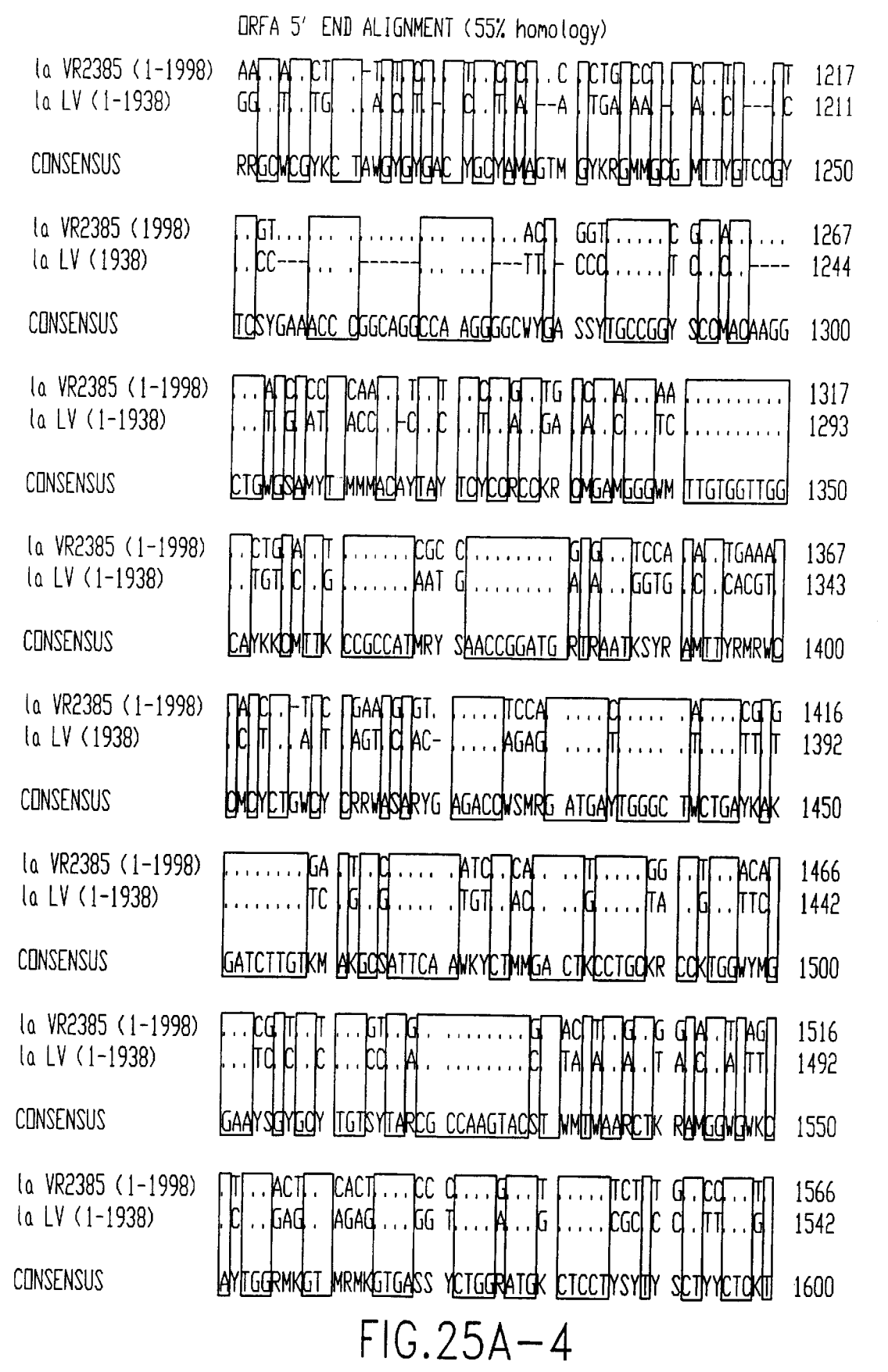

ORFA 5' END ALIGNMENT (55% homology)

la VR2385 (1-1998) AA.A.CT .-T.T.C. .T.C.C. .C .CTG.CC. .C.T...T 1217
la LV (1-1938) GG.T.TG .A.C.T.- C.T.A --A .TGA.AA- .A.C---C 1211

CONSENSUS RRGCWCGYKC TAWGYGYGAC YGCYAMAGTM GYKRGMMGCG MTTYGTCCGY 1250 la VR2385 (1998) ..GT...... .. ......... ...AC. GGT.....C G.A.... 1267
la LV (1938) ..CC---... .. -----.... ... ---TT- CCC.....T C.C.---- 1244

CONSENSUS TCSYGAAACC CGGCAGGCCA AGGGGCVYGA SSYTGCCGGY SCCMACAAGG 1300 la VR2385 (1-1998) ..A.C.CC.CAA..T.T .C.G.TG .C.A..AA .......... 1317
la LV (1-1938) ..T.G.AT.ACC.-C.C .T.A.GA .A.C..TC .......... 1293

CONSENSUS CTGWGSAMYT MMMACAYTAY TCYCCRCCKR CMGAMGGGWM TTGTGGTTGG 1350 la VR2385 (1-1998) .CTG.A.T ......CGC C........G.G..TCCA .A.TGAAA 1367
la LV (1-1938) .TGT.C.G ......AAT G........A.A..GGTG .C.CACGT 1343

CONSENSUS CAYKKCMTTK CCGCCATMRY SAACCGGATG RTRAATKSYR AMTTYRMRWC 1400 la VR2385 (1-1998) A.C.-T.C .GAA.G.GT. ....TCCA ....C..... .A...CG.G 1416
la LV (1938) C.T..A.T .AGT.C.AC- ....AGAG ....T..... .T...TT.T 1392

CONSENSUS CMCYCTGWCY CRRWASARYG AGACCWSMRG ATGAYTGGGC TWCTGAYKAK 1450 la VR2385 (1-1998) ........GA .T.C.... .ATC.CA. ..T....GG .T..ACA 1466
la LV (1-1938) ........TC .G.G.... .TGT.AC. ..G....TA .G..TTC 1442

CONSENSUS GATCTTGTKM AKGCSATTCA AWKYCTMMGA CTKCCTGCKR CCKTGGWYMG 1500 la VR2385 (1-1998) ...CG.T.T ...GT.G. .........G AC.T.G.G G.A.T.AG 1516
la LV (1-1938) ...TC.C.C ...CC.A. .........C TA.A.A.T A.C.A.TT 1492

CONSENSUS GAAYSCYGCY TGTSYTARCG CCAAGTACST WMTWAARCTK RAMGCWGWKC 1550 la VR2385 (1-1998) .T..ACT. CACT...CC C...G..T ....TCT.T G.CC..T 1566
la LV (1-1938) .C..GAG. AGAG...GG T...A..G ....CGC.C C.TT..G 1542

CONSENSUS AYTGGRMKGT MRMKGTGASS YCTGGRATGK CTCCTYSYTY SCTYYCTGKT 1600

FIG.25A-4

ORF1A 5' END ALIGNMENT (55% homology)

```
la VR2385 (1-1998)   ........-- .CA.-.GC. .T.G..GCA. AAG.GT.--- -.T..----   1605
la LV (1-1938)       .......... .TG...TT. .C.C..AGG. TGT.TC.... ..C......   1592

CONSENSUS            GAATGTGTGG TYRGCGKYTG YTSTGARSRC WRKGKYGCAC CGYCTTATCC  1650

la VR2385 (1-1998)   --------.. T.C..C.G.- -....G.... ..T...C.GA .T..ACC-.T  1644
la LV (1-1938)       .......... C.A..T.A.. .....C.... ..C...G.CG .C..CTT..A  1642

CONSENSUS            AGCAGACGGG YTMCCYARAC GTGCASTCGA GGYCTTSGSR TYTGMYYACW  1700

la VR2385 (1-1998)   .C.G..T.- -..CC.-.C. G...GA...G A.......C. .AG..G..T  1691
la LV (1-1938)       .A.A..C.. ...TT...T. A...CT...A T..---..A. .TT.-T..C  1688

CONSENSUS            GMCTRCCYTC CGAYYGTGYT RGCTSWGGTR WTGCACCTGM CTWKCAKTGY  1750

la VR2385 (1-1998)   ..TC......  .C......C. A.....C..  CGAT..--.G .TCGT.C.G.  1739
la LV (1-1938)       ..AT...-.. -T....--.A. G...-..T.. ACCC.....A .AATG.T.A.  1733

CONSENSUS            TAWYCCAGCC GYCCTGGCMG RAATGTCYGG MSMYTCGACR AWMKKTYGRC  1800

la VR2385 (1-1998)   T.........  .........T .T...A.T.. ...........T.-.CCC....C  1788
la LV (1-1938)       C.....-.... .....--A.C ...T.C---- ..--...C...TTT..-.T  1773

CONSENSUS            YTCCCCGGTC ACCACCGWGY GGWCYGTTTC GCAGTTCTYT AGYYYGTCAY  1850

la VR2385 (1-1998)   .........  ..C..CC.G. .C...C.C.C .TA.GG.... .TATCA...  1838
la LV (1-1938)       .--------  ..T..TA.T. -G...T-T.T .CC.CA.... .GCGGT...-  1812

CONSENSUS            AACGGAGGGA ATYACYMTKA CSAGGYGYGY TYMGSRAAAA TKMKSWGCCT  1900

la VR2385 (1-1998)   TT.TC...T. A...GG.CT GC........ .C...AC.AA ACC....G  1888
la LV (1-1938)       AC.GA...G. C..--TC.TC TA.......- -G...GG.TG TTG.--..A  1856

CONSENSUS            WYGKMAGGKG MTTGAKSAYY KMTGCTGTTC CSAGARSAWR WYSAACCGGR  1950

la VR2385 (1-1998)   .CAC..... ....G..... .....G.T. A.C..TA...C..........  1938
la LV (1-1938)       .TGT..---- -...C.---- -....C.-G. C.A..GC...T.-..-.....  1893

CONSENSUS            TYRYCCCGGA GGAGSTCGCA GCAAASATKG MCMTGKMCCT YCGTGGTGCA  2000
```

FIG.25A-5

ORF1A 5' END ALIGNMENT (55% homology)

```
Ia VR2385 (1-1998)   ...|.|.G.|...|...|.----|..|.....Q.T. G.G.AAG.G. .G.C.|-|-.|.1985|   |   |   |
Ia LV (1-1938)       .-|.|...A.|...|-----|..|.. --|-..T.C| C.A.GGG.C.|.T.T.|.....1932|   |   |

CONSENSUS            A|CAAAT|C|TR AAGA|ATGCTT|GG|C|CAGK|C|YT|SAR|ARR|S|CSC |G|YCY|G|TGT|CC 2050
```

```
                                                                         1998
Ia VR2385 (1-1998)   AC.C|G|T.... ...                                         1938
Ia LV (1-1938)       CT.GA|C|---- ---
                                                                              2063
CONSENSUS            MY|G|SRYAATG GAC
```

```
                        ORF1A middle DNA ALIGNMENT (52% homology)
Ia VR2385 (2817-3471)   A.....G. .CAG..-. . .TGA.--A C A G .G. . .CC--A.   2861
Ia LV (2773-3432)       G.....C. .ACT... . .CCG. ..C T C C .A. . .TT. .T.   2822

CONSENSUS               RAATTTGSCG AMMKCAAGCG CYSRCGTTTM YCMGSACRAG CCYYAATWGA   50

Ia VR2385 (2817-3471)   TT-TTTTC ATC.CAA .---. .- -.T.G G CTTTTCC CC   2903
Ia LV (2773-3432)       CC. AGGT CCA.TGC ..... .. . .A.A A AACCGGG AT   2872

CONSENSUS               YYGWGKCKGY MYMCTYRCMG ATGTCCATGC AAAWATRARG MWYYKSSTMY   100

Ia VR2385 (2817-3471)   .GCC.C. . .--AG.CA G GT TT. . . . .--. .G . .GGG.AGA   2948
Ia LV (2773-3432)       .TGA.G. . . .CC.GC T TG GC. . . . . . . .C . .CCC.GCC   2922

CONSENSUS               AKSAMCASTG CCTMSAASMT KGKKAKYCCG GTAGTCGTGS AASSSCARSM   150

Ia VR2385 (2817-3471)   .GTA GAA .T CT. TG G. .C C. . . .TAC. . .T . CATC.T.   2998
Ia LV (2773-3432)       .CAG AGT .G TC.-CA A. .G G. . . .GGG. . .C - TGAA.C.   2970

CONSENSUS               ASCWGRGRRW GKCYYGAGYR RAATSTSGGA TAKRSTGGAY GAYRWMAAYT   200

Ia VR2385 (2817-3471)   CT. . . . .T .T. . . . .G. . . .CT T C. . . .A. GA.ACA.C   3048
Ia LV (2773-3432)       TG. .-. .C .C -.-. .A. . . .AA C T--- .C. AT.TTG.T   3013

CONSENSUS               YKGCGCCTGY AYCATCAAGC RGTTCCMWGY YAAGCGTMGC RWTCWYRCGY   250

Ia VR2385 (2817-3471)   .AAT GG G . GAGAG. . .C T CCATT G T. . T. . .A T. .A.   3098
Ia LV (2773-3432)       .CTC AA T .-CTCCC. . .A G TTCAA A A.-C. . .T C--T-   3058

CONSENSUS               CCMWYARRTK CGSWSMSTGA CMTKAYYMWW GRCWCAGYCG CCWCYGAWGA   300

Ia VR2385 (2817-3471)   .T. .CC .TCCT.G A AA . .AG ......TGA .T . . . .C   3148
Ia LV (2773-3432)       .-C. .GA .GAAC.A C TG -.CA ......CCT .A-. . . .T   3104

CONSENSUS               TAYTYCCASGM AKMMYCGRGM WARTAGAMRA TGCCGGYSWG AWGTCCAACY   350

Ia VR2385 (2817-3471)   .. . .... ....TTC CC .GGAA. .C C GTA . . . .AA.TA.   3198
Ia LV (2773-3432)       -- . ---- ....CAG GG .TAGG. .T T AGT - . . .CC.CC.   3146

CONSENSUS               AGGGACCCTT GGCAYWSTSS GAKRRRAAAY YGRKWGATGA CCMMCCYMCC   400
```

FIG.25B-1

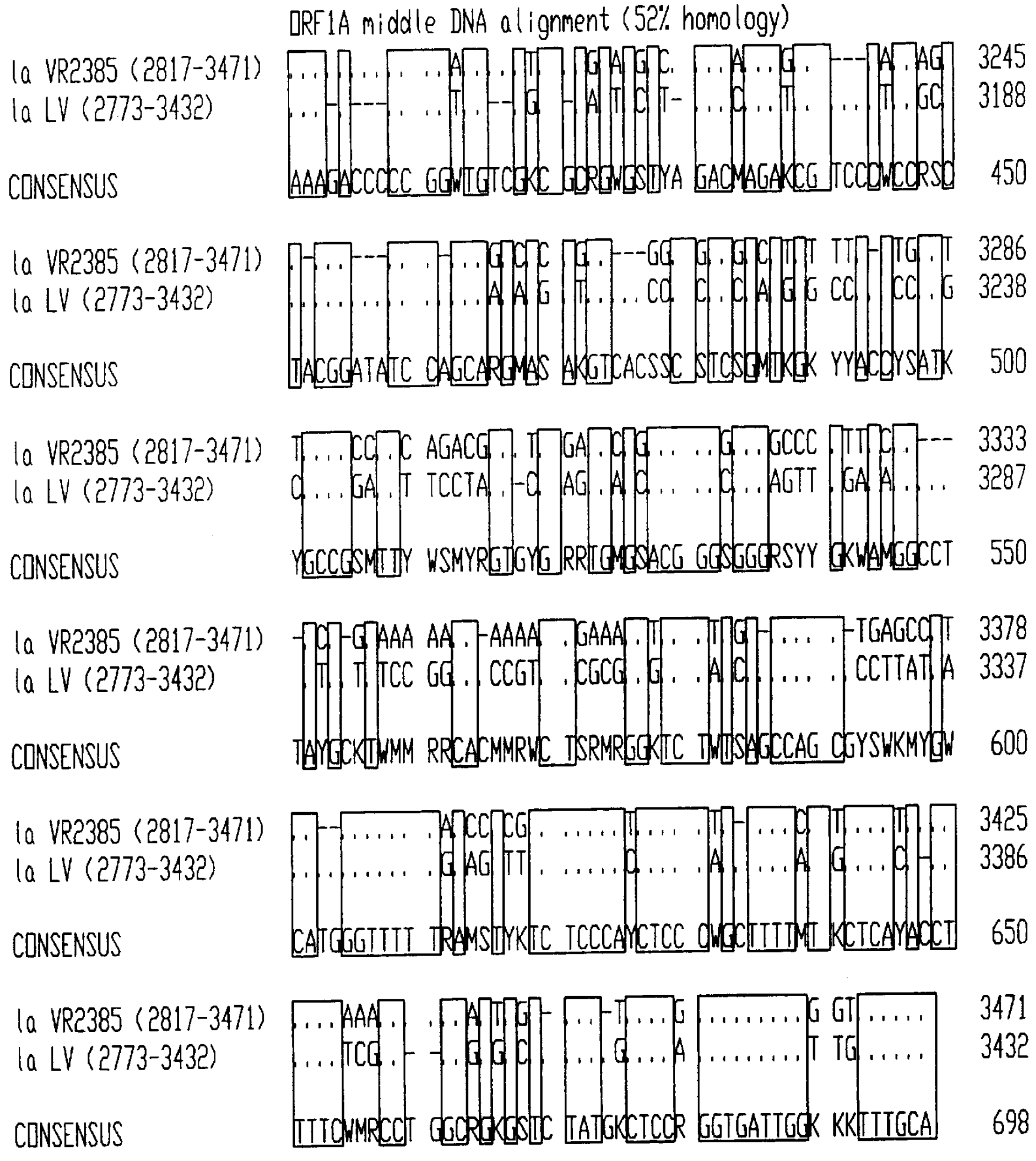

FIG.25B-2

ORF1A middle DNA alignment (52% homology)

```
la VR2385 (2817-3471)   ...  . .  . .A .  .T.  .GAG.C.  . .A. . .G.  ---  .A. .AG  3245
la LV (2773-3432)       ...  ---  . .T. .  -G.  .AT.C.T-  . .C. .T.  . .  .T. .GC  3188

CONSENSUS  AAAGACCCCC GGWTGTCGKC GCRGWGSTYA GACMAGAKCG TCCDWCCRSC  450

la VR2385 (2817-3471)   .-.  ---  . . .GC.C  .G. .---GG  .G. .G.C. .TT  TT -TG. .T  3286
la LV (2773-3432)       . .  ---  . . .AAG  .T. . .CC  .C. .C.AGG CC  . . .CC. .G  3238

CONSENSUS  TACGGATATC CAGCARGMAS AKGTCACSSC STCSDMTKGK YYACDYSATK  500

la VR2385 (2817-3471)   T. ..CC. .C AGACG. .T. GA. .C.G. .  . . .G. . .GCCC .TT .C. .---  3333
la LV (2773-3432)       C. ...GA. .T TCCTA. .-C .AG. .A.C. .  . . .C. . .AGTT .GA .A. ....  3287

CONSENSUS  YGCCGSMTTY WSMYRGTGYG RRTGMGSACG GGSGGGRSYY GKWAMGGCCT  550

la VR2385 (2817-3471)   -C. -G. AAA AA. -AAAA. .GAAA. .T. . .TG. . .  . . . -TGAGCC. T  3378
la LV (2773-3432)       .T. T. TCC GG. . CCGT. .CGCG. .G. . .AC. . .  . . . .CCTTAT. A  3337

CONSENSUS  TAYGCKTWMM RRCACMMRWC TSRMRGGKTC TWDSAGCCAG CGYSWKMYGW  600

la VR2385 (2817-3471)   .-.-. . . .ATCC .CG. . . . .T. . .  .T. . . . .C. .T. . . .T. . .  3425
la LV (2773-3432)       . . . . . . .G.AG .TT. . . . .C. . .  .A. . . . .A. .G. . .C. .-. .  3386

CONSENSUS  CATGGGTTTT TRAMSDYKTC TCCCAMCTCC CWGCTTTTMT KCTCAYACCT  650

la VR2385 (2817-3471)   ....AAA. .  . . .A.TG -  . . .T. . . .G  . . . . . . .G  GT. . . . .  3471
la LV (2773-3432)       ....TCG. -  -.GGC. .  . . G. . .A  . . . . . . .T  TG. . . . .  3432

CONSENSUS  TTTCWMRCCT GGCRKGSTC TATGKCTCCR GGTGATTGGK KKTTTGCA  698
```

ORF 1A middle DNA alignment (63% homology)

```
Ia VR2385 (3100-4198)  ..AA....C. ....TC T... ......A..T .....A AT.....C.   3917
Ia LV (3052-4159)      ..CC....T. ....AA G... ......G..A .....G CG.....G.   3878

CONSENSUS              TGTMAMAAGT GYTGGGGAWM KTGTATAAGR ACWGCTCCTR MKGAGGTSGC   850

Ia VR2385 (3100-4198)  .T....C..G .........A .A..T..G.. .A........ A.....TGA.   3966
Ia LV (3052-4159)      .C....T..A .........T .G..C..C.. .C........ T.....ATC.   3927

CONSENSUS              TYTTAAYGTR TTTCCTTTCW CRCGYGCSAC CMGTGTCGTC WCTTGTWKMC   900

Ia VR2385 (3100-4198)  C......... .G..TTGCG. .........C A.G..C..CA .TTTTC.C..   4016
Ia LV (3052-4159)      T......... .A..CCAAA. .........G G.T..T..TG .GCACT.G..   3977

CONSENSUS              YTGTGTGATC GRTTYYRMRC GCCAAAAGGS RTKGAYCCYR TKYWYYTSGC   950

Ia VR2385 (3100-4198)  C..T..G... .......... ..GCC..CCG A........T G.G.....CT   4066
Ia LV (3052-4159)      A..G..T... .......... ..CGT..TGA G........C C.T.....AC   4027

CONSENSUS              MACKGGKTGG CGCGGGTGCT GGSSYGGYSR RAGCCCCATY SAKCAACCMY   1000

Ia VR2385 (3100-4198)  CTG....A.. T..C..G.T. ...C.G.... .......... ...TA.G..T   4116
Ia LV (3052-4159)      ACC....G.. C..A..T.A. ...A.T.... .......... ...GT.T..C   4077

CONSENSUS              MYSAAAARCC YATMGCKTWT GCCMAKTTGG ATGAAAAGAA AATKWCKGCY   1050

Ia VR2385 (3100-4198)  AGG..T.... .C..CCAG.. T..T..C... .AC..A..CG .A..G...T.   4166
Ia LV (3052-4159)      CAA..G.... .T..TGTC.. A..C..T... .GT..G..TA .C..A...C.   4127

CONSENSUS              MRRACKGTGG TYGCYSWSCC WTAYGAYCCC ARYCARGCYR TMAARTGCYT   1100

Ia VR2385 (3100-4198)  .CGG..AT.. ........T. ...TG..G.. ..                      4198
Ia LV (3052-4159)      .AAA..TC.. ........A. ...CC..C.. ..                      4159

CONSENSUS              GMRRGTWYTG CAGGCGGGWG GGGYSATSGT GG                      1132
```

FIG.25B-5

ORF1A 3' END DNA ALIGNMENT (60% HOMOLOGY)

```
la VR2385 (4000-7197)  ..C..CA.TT TTC.C..C. .T.G...... ......G CC..CCGA..  4049
la LV    (3961-7188)   ..T..TG.GC ACT.C..A. .G.T...... ......C GT..TGAG..  4010

CONSENSUS              GAYCCYRDKY WYYTSGCMAC KGGKTGGCGC GGGTGCTGGS SYGGYSRRAG   50

la VR2385 (4000-7197)  ......TG.G .....CTCTG ...A..T.. C.G.T..... C.G......  4099
la LV    (3961-7188)   ......CC.T .....ACACC ...G..C.. A..T.A.... A.T......  4060

CONSENSUS              CCCCATYSAK CAACCMYMYS AAAARCCYAT MGGKTWTGCC MAKTTGGATG  100

la VR2385 (4000-7197)  .......... TA.G.TAGG ..T....C. .CCAG.T.. T..C.. ..AC  4149
la LV    (3961-7188)   .......... GT.T.CCAA ..G....T. .TGTC.A.. C.T.. ..GT  4110

CONSENSUS              AAAAGAAAAT KWCKGCYMRR ACKGTGGTYG CYSWSCCWTA YGAYCCCARY  150

la VR2385 (4000-7197)  ..A.CG.A. .G..T..CG G.AT...... .....T... TG..G...C  4199
la LV    (3961-7188)   ..G.TA.C. .A..C..AA A.TC...... .....A... CC..C...A  4160

CONSENSUS              CARGCCYRTMA ARTGCYTGMR RGTWYTGCAG GCGGGWGGGG YSATSGTGGM  200

la VR2385 (4000-7197)  TG..GGGTC ..AA.A.G. .CAAG.T.. ...CTG.T.A ...CG....  4249
la LV    (3961-7188)   CC..CTACA ..TG.G.C. .TCGT.G.. ...AGA.C.C ...TC....  4210

CONSENSUS              YSAGSCKRYM CCWRARGTSG TYMRKGTKTC CGMKRTYCCM TTCYSAGCCC  250

la VR2385 (4000-7197)  C....T. .T...G...G AA..TG... .T..A..T. ...C....T  4299
la LV    (3961-7188)   A....C. .A.---A...T CC...CA... .A..T.C.. ...T....A  4257

CONSENSUS              CMTTTTTYCC WACCGRAGTK MMAGTYRACC CWGAWTGYAG GGTYGTGGTW  300

la VR2385 (4000-7197)  ..CC.T... ....CACT. .A..TC.C..G .CT.C... .C..CA.A.  4349
la LV    (3961-7188)   ..TT.G... ....TGTG. .T..GG.T..C .GC.T... .G..AG.C.  4307

CONSENSUS              GAYYCKGACA CTTTYRYKGC MGCKSTYCGS TSYGGYTACT CSACMRCAMA  350

la VR2385 (4000-7197)  C.T.C.T .TGTA.GG .......C. .C.G...-G .TT.AAAAT  4398
la LV    (3961-7188)   A.G.T.G .CCGG.CA .......A. .T.A...A. .CC-CCCCC  4356

CONSENSUS              MCTKGTYCTK GGYSKRGGSR ACTTTGCCMA GYTRAATCRG AYYAMMMMYC  400
```

FIG.25C-1

ORF1A 3' END DNA ALIGNMENT (60% HOMOLOGY)

```
la VR2385 (4000-7197)  ...C---A .T---.... GCTTA.A .AGCAC TCTAG.     4442
la LV (3961-7188)      ...A...T .C....... AAGAT.T .GCTTT CACCT.     4406

CONSENSUS              AGGMACTCWA TYTCCACCAA RMCKWCWGGW GGRCSCYCWY AYMYCMCKGC  450

la VR2385 (4000-7197)  .CCCTG.T ..C...- .C.T...T ..GA.-G T.G.G.AT   4490
la LV (3961-7188)      .TGGCT.A .-.T.... .G.C--C ..TT..T A.C.C.TC   4453

CONSENSUS              TGYSSYKCAW GTTGYCTGCG TSGAYGGTYT TGKWCATTKC WTSCTSGGWY  500

la VR2385 (4000-7197)  .AT.G. TG GGTGGGT TCT.C..A CC.C..AA C.T.G..   4539
la LV (3961-7188)      .TG.C. AT ACCTCAA GTG.T..C GA.A..GC T.C.A..   4503

CONSENSUS              TTWKGTTSAC WKCRSYKSRW KYKTGYGGCM SMGGMACCRM YGAYCCRTGG  550

la VR2385 (4000-7197)  .CGT.C .G..GGCGT C..GG..C .A.TCCT CCCC..A   4589
la LV (3961-7188)      .TTA.T .T..TCATA T..AC..T .C.CGAG TTGG..T   4553

CONSENSUS              TGYKCWAAYC CKTTTKSMKW YCCTRSCTAY GGMCCYGSMK YYSTSTGCWC  600

la VR2385 (4000-7197)  G.CA.TG .CAT.CC AGCTCCC T.......C ...ACAG.C   4639
la LV (3961-7188)      C.TC.CT .TGG.TG CCGCGGG C.......A ...TTCT.G   4603

CONSENSUS              STCYMGAYTK TGYRTKTCYS MSSAYGSSST YACCCTGCCM TTGWYMKCAS  650

la VR2385 (4000-7197)  TT....GGG.T.GGTATC CA..AAT CCTAGCG ....ATTT   4689
la LV (3961-7188)      CC....ACA.C.TCCGGT AG..GGG GGATTTA ....GGCC   4653

CONSENSUS              YYGTGGCRSR AYTCKSYRKY MRAGARRTKG SSWTWKTYRT TTTGRTKYTY  700

la VR2385 (4000-7197)  .T..ACG GAGCA... T.TAGT. AGTG..A .T.T..C   4739
la LV (3961-7188)      .C..TGA CTCTT... C.CCCA. GCCT..G .A.C..T   4703

CONSENSUS              GTYTCCWTSR SWGSYWTGGC YCAYMGSWTG RSTYKTAARG CWGAYATGYT  750

la VR2385 (4000-7197)  -...AT.GCTT.AA.GCCAGCAT TT..GTACC TCTTA....   4788
la LV (3961-7188)      ....-GC.TTCG.TT.TGTGCTTC CC..CCCAT GAGCT....   4752

CONSENSUS              AGTGTRTYTT KYYKGCWWTT KSYRSYWAYG YYTGGSYMMY KMKYWCCTGG  800
```

FIG.25C-2

ORF1A 3' END DNA ALIGNMENT (60% HOMOLOGY)

```
la VR2385 (4000-7197)  .....G.T ....C.C. G.....G...A. ....C.A..                5232
la LV (3961-7188)      .....T.C ....T.T. C...--.C...C. ....T.C..                5196

CONSENSUS              GGGGTKTTYA CCATYGAYGG SAGAAGTCAA STGTCGTMAC TGCYGCMCAT   1250

la VR2385 (4000-7197)  ..CCTTCG .TA.T.......G.TT...GTGG.T..TAA.                   5282
la LV (3961-7188)      ..GTGAC .CG.A.......A.CA...CATC.A..CGC.                    5246

CONSENSUS              GTSYTKAMSG GYRACWCAGC TAGRGTYWCC GGSGWCKSCT WCAAYCRMAT   1300

la VR2385 (4000-7197)  ..TT.....GCC-TA.G..G...TC...ACGA T..C.--                   5329
la LV (3961-7188)      ..AC-.....CA CC.T..T...AT..-GTCC A.-T...                   5293

CONSENSUS              GCWYGACTTT SAMGAYMAAK GGKGATTWYG CCATRGYCSM WTGCCYGATG   1350

la VR2385 (4000-7197)  .T....A.GC.....C AAT CC..T TC....GA TGTG..T              5379
la LV (3961-7188)      .C....G.CT.....T GT-GT..G GT....AG GTCC--C               5340

CONSENSUS              AYTGGCARGG SGYTGCCCCY RWGASYCAAK KYTGCGARGR KGKAYSGACY   1400

la VR2385 (4000-7197)  ..C...... .T...T.. ...CT...C .......... .CG......        5429
la LV (3961-7188)      ..T...... .C...A.. ...AA...T .......... .TA......        5390

CONSENSUS              GGYCGTGCCT AYTGGCWAAC ATCMWCTGGY GTCGAACCCG GYRTCATTGG   1450

la VR2385 (4000-7197)  AA...A.. ........C. .C.CGCG. .........C .....C..A        5479
la LV (3961-7188)      GG...G.. ........T. .T.TAAC. .........G .....A..C        5440

CONSENSUS              RRAAGGRTTC GCCTTCTGMT TYACYRMSTG CGGCGATTCS GGGTCMCCMG   1500

la VR2385 (4000-7197)  .G..AC. GGC....G...GC.CG.T....G. A....T..                 5529
la LV (3961-7188)      .C..TA. ATT....T...AT.AA.C....C. T....C..                 5490

CONSENSUS              TSATCWCMGA RKCYGGTGAK CTTRTYGGMR TYCACACSGG WTCAAAYAAA   1550

la VR2385 (4000-7197)  .AA.GGGA .CAC.C. GCG..CTC ..CC.TTT .T ATG GGC            5579
la LV (3961-7188)      .TT.TTCT .TCT.G. AAC..TGA ..GG.ACC .C CCA CAA            5540

CONSENSUS              CWWGGKKSWG GYMTYGTSAC RMSCCCYKMA GGSSAGWYYT GYAMYRTSRM   1600
```

FIG.25C-4

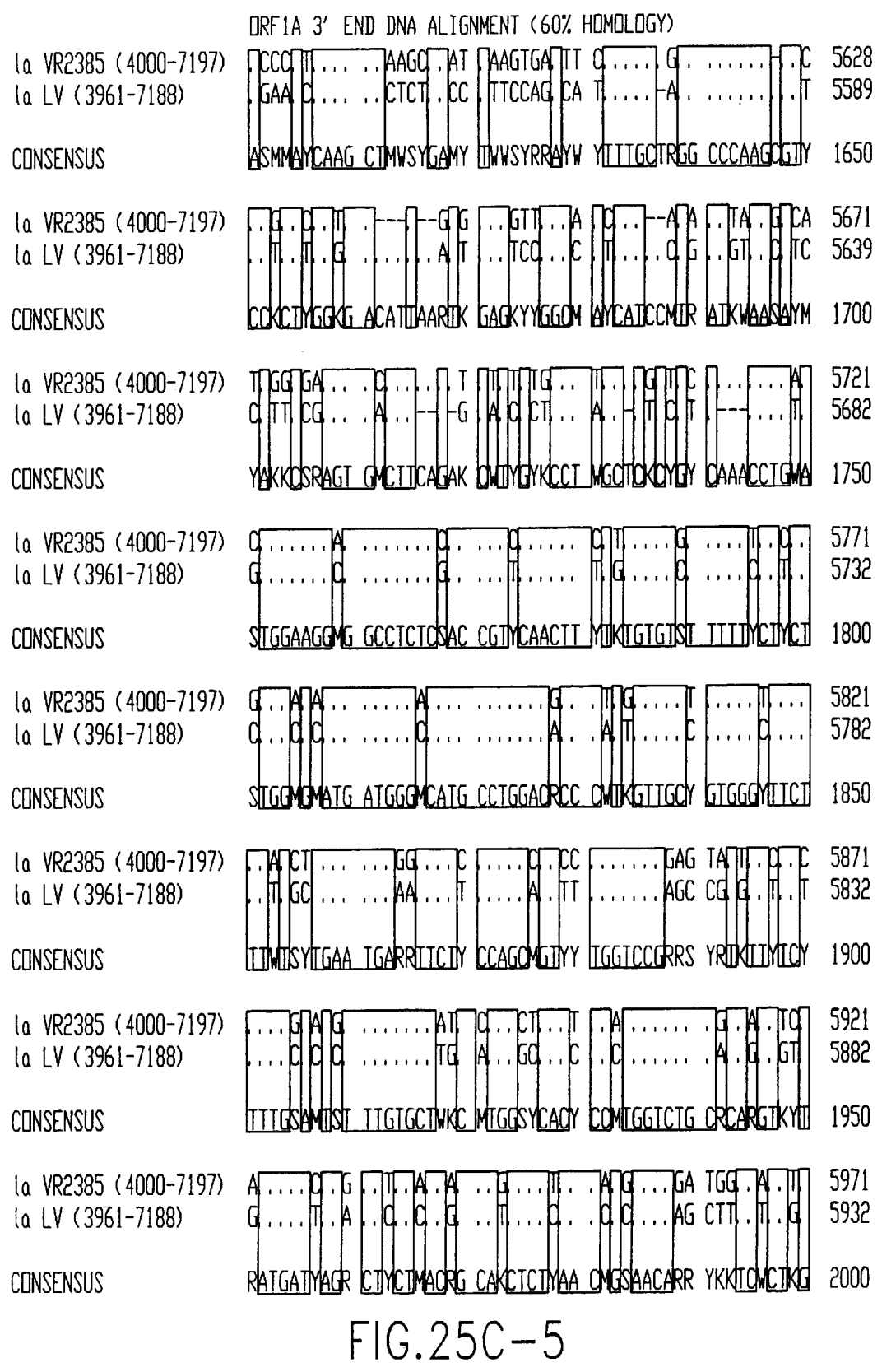

ORF1A 3' END DNA ALIGNMENT (60% HOMOLOGY)

```
la VR2385 (4000-7197)   .CCC.T.... ..AAGC..AT .AAGTGA.TT C.....G... .......-.C   5628
la LV (3961-7188)       .GAA.C.... ..CTCT..CC .TTCCAG.CA T.....-A.. ........T   5589

CONSENSUS               ASMMAYCAAG CTMWSYGAMY TWWSYRRAYW YTTTGCTRGG CCCAAGCGTY   1650

la VR2385 (4000-7197)   ..G..C..T. .---.--G.G ..GTT...A. C...--A.A. .TA..G.CA   5671
la LV (3961-7188)       ..T..T..G. .......A.T ..TCC...C. T.....C.G. .GT..C.TC   5639

CONSENSUS               CCKCTYGGKG ACATTAARTK GAGKYYGGCM AYCATCCMTR ATKWAASAYM   1700

la VR2385 (4000-7197)   T.GG.GA... C....T..T. T.TG..T..G .T.C.....A   5721
la LV (3961-7188)       C.TT.CG... A..--.-G.A .C.CT..A.- T.C.T.---..T   5682

CONSENSUS               YAKKCSRAGT GMCTTCAGAK CWTYGYKCCT MGCTCKCYGY CAAACCTGWA   1750

la VR2385 (4000-7197)   C.......A. ........C. ...C...... C.T....G.. ...T.C.   5771
la LV (3961-7188)       G.......C. ........G. ...T...... T.G....C.. ...C.T.   5732

CONSENSUS               STGGAAGGMG GCCTCTCSAC CGTYCAACTT YTKTGTGTST TTTTYCTYCT   1800

la VR2385 (4000-7197)   G...A.A... ......A... ........G. ..T.G.....T .....T...   5821
la LV (3961-7188)       C...C.C... ......C... ........A. ..A.T.....C .....C...   5782

CONSENSUS               STGGMGMATG ATGGGMCATG CCTGGACRCC CWTKGTTGCY GTGGGYTTCT   1850

la VR2385 (4000-7197)   ..A.CT.... ...GG...C. ....C..CC. ......GAG TA.T..C..C   5871
la LV (3961-7188)       ..T.GC.... ...AA...T. ....A..TT. ......AGC CG.G..T..T   5832

CONSENSUS               TTWTSYTGAA TGARRTTCTY CCAGCMGTYY TGGTCCGRRS YRTKTTYTCY   1900

la VR2385 (4000-7197)   ....G.A.G. ........AT .C..CT...T ..A....... .G.A..TC.   5921
la LV (3961-7188)       ....C.C.C. ........TG .A..GC...C ..C....... .A.G..GT.   5882

CONSENSUS               TTTGSAMTST TTGTGCTWKC MTGGSYCACY CCMTGGTCTG CRCARGTKYT   1950

la VR2385 (4000-7197)   A.....C..G ..T..A..A. ..G....T.. ..A.G...GA TGG..A..T.   5971
la LV (3961-7188)       G.....T..A ..C..C..G. ..T....C.. ..C.C...AG CTT..T..G.   5932

CONSENSUS               RATGATYAGR CTYCTMACRG CAKCTCTYAA CMGSAACARR YKKTCWCTKG   2000
```

FIG.25C-5

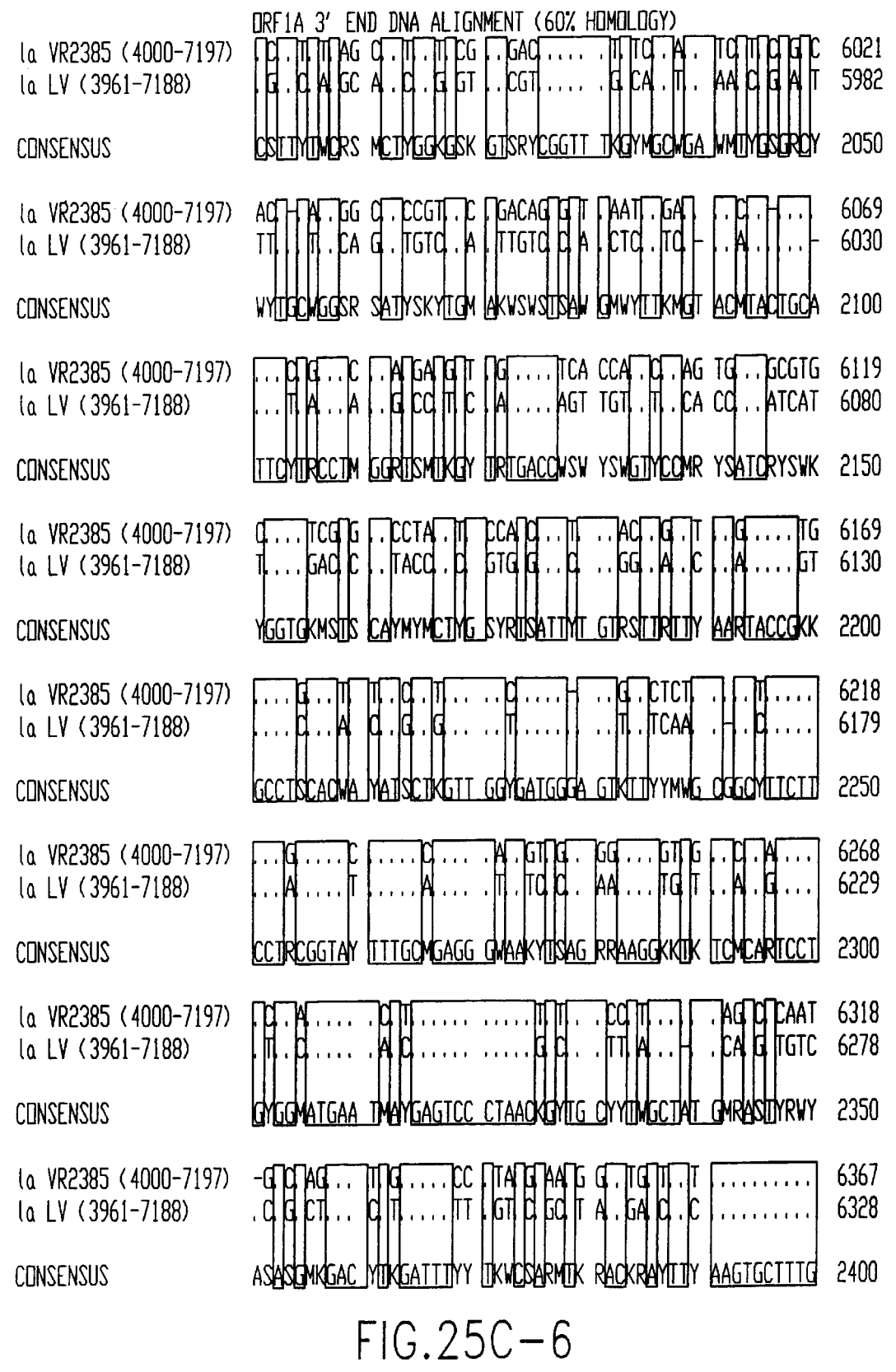

ORF1A 3' END DNA ALIGNMENT (60% HOMOLOGY)

```
la VR2385 (4000-7197)   .C.T.T.TAG C.T.T CG ..GAC.... .T TC.A. TC T C G C   6021
la LV (3961-7188)       .G.C.A GC A.C.G GT ..CGT.... .G CA.T. AA C G A T   5982

CONSENSUS               CSTTYTWCRS MCTYGGKGSK GTSRYCGGTT TKGYMGCWGA WMTYGSGRCY   2050

la VR2385 (4000-7197)   AC-A.GG C.CCGT.C .GACAG G T .AAT.GA. ..C.-...   6069
la LV (3961-7188)       TT..T.CA G.TGTC.A .TTGTC C A .CTC.TC- ..A....-   6030

CONSENSUS               WYTGCWGGSR SATYSKYTGM AKWSWSTSAW GMWYTTKMGT ACMTACTGCA   2100

la VR2385 (4000-7197)   ...C G..C .A GA G T .G....TCA CCA.C.AG TG..GCGTG   6119
la LV (3961-7188)       ...T A..A .G CC T C .A....AGT TGT.T.CA CC..ATCAT   6080

CONSENSUS               TTCYTRCCTM GGRTSMTKGY TRTGACCWSW YSWGTYCCMR YSATCRYSWK   2150

la VR2385 (4000-7197)   C....TCG G ..CCTA.T CCA C..T ..AC.G.T ..G....TG   6169
la LV (3961-7188)       T....GAC C ..TACC.C GTG G..C ..GG.A.C ..A....GT   6130

CONSENSUS               YGGTGKMSTS CAYMYMCTMG SYRTSATTMT GTRSTTRTTY AARTACCGKK   2200

la VR2385 (4000-7197)   ....G..T T.C.T....C....-....G.CTCT ....T....   6218
la LV (3961-7188)       ....C..A C.G.G....T....-....T.TCAA ..-.C....   6179

CONSENSUS               GCCTSCACWA YATSCTKGTT GGYGATGGGA GTKTTYYMWG CGGCYTTCTT   2250

la VR2385 (4000-7197)   ...G....C ....C.... .A.GT G. GG...GT G ..C.A...   6268
la LV (3961-7188)       ...A....T ....A.... .T.TC C. AA...TG T ..A.G...   6229

CONSENSUS               CCTRCGGTAY TTTGCMGAGG GWAAKYTSAG RRAAGGKKTK TCMCARTCCT   2300

la VR2385 (4000-7197)   .C.A.... .C T..... .....T T. .CC T.. ..AG C CAAT   6318
la LV (3961-7188)       .T.C.... .A C..... .....G C. .TT A..-..CA G TGTC   6278

CONSENSUS               GYGGMATGAA TMAYGAGTCC CTAACKGYTG CYYTMGCTAT GMRASTYRWY   2350

la VR2385 (4000-7197)   -G C AG..T G....CC .TA G AA G G.TG T.T .........   6367
la LV (3961-7188)       .C G CT..C T....TT .GT C GC T A.GA C.C .........   6328

CONSENSUS               ASASGMKGAC YTKGATTTYY TKWCSARMTK RACKRAYTTY AAGTGCTTTG   2400
```

FIG.25C-6

ORF1A 3' END DNA ALIGNMENT (60% HOMOLOGY)

```
la VR2385 (4000-7197)  ..G..CG- ..G.--TA ..A.A.G CC GGA.- A G.....   6802
la LV (3961-7188)      ..A..GA. ..A..CG ..G.T.A -AA CAC.  T T.....   6766

CONSENSUS              GARGACSRTC TTRAAGTYRA GARGAWGARG CMMASRMTGT GWAKCCCTCG   2850

la VR2385 (4000-7197)  ..A.T.TGT T..GGG..G ...AAG..C AG..T... .......AA   6852
la LV (3961-7188)      ..T.C.CAA C..CAA..C ...GTT..T GC..A... .......TC   6816

CONSENSUS              GCWTCYAYRW YATSRRTGGS AAARWKTACY RSAAAWTTTG GGACAAGWMT   2900

la VR2385 (4000-7197)  T.......TG TG....T-- -.G.---- -..---..T..A CA   6890
la LV (3961-7188)      A.......CA CC....C.. ..T.... ........A..C TG   6866

CONSENSUS              WCCGGTGAYR YSTTTTAYAC GGAKGATTCC CGGTACACCC AWGACMAYRC   2950

la VR2385 (4000-7197)  AGAG.--T G.--.-T.T.-....T .G.C..CC .CC ACT.--   6932
la LV (3961-7188)      TTTC...C A....C.A......A .A.G..TA .AG GTG..   6916

CONSENSUS              WKWTSAGGAY RGGTCAGCYG WCTACAGAGW CRGSGACYMT GMSCRYKTGC   3000

la VR2385 (4000-7197)  ---TG-... TG GA....----CT.-- T.G.G-- -A..CAC   6969
la LV (3961-7188)      ...CC.... CC AC........TC.. A.C.A.....C..TGG   6966

CONSENSUS              AAAYSACCCC YSARMAGGGA TTTGAYYCAA WGTSTGRAAC CCMTGTYRSC   3050

la VR2385 (4000-7197)  .T.AA AT -A..-T.C C T.-T..CC-C.C ..--T....   7013
la LV (3961-7188)      .C.TT TG .C...G.T T C...A..GG.T.G ....A....   7016

CONSENSUS              AYTGWWGWKA TMGGCGKTAY YAYGTATWAC ASSTAYCTSA TCAAWGGTAA   3100

la VR2385 (4000-7197)  .A.T.CT. ........ ..C.A.G.TG...... ....G...   7063
la LV (3961-7188)      .G.G.TC. .....---.. .G.T.C.CT------ .--T...   7054

CONSENSUS              GRAGKTYYTG GTCCCCGTCA ASCCWGASAA YKGAAGAGTC CAGTGKGAAG   3150

la VR2385 (4000-7197)  .......... T..G.G.. ..GC C .T GCAT...AA .GTCGACG T   7113
la LV (3961-7188)      .......... G..C.T.. ..AG T .C CTGG...GG .CAAACTT C   7104

CONSENSUS              CTGCCAAGCT KTCCSTKGAG CARSCYCTYG SYRKGATGRR CSWMRMYKGY   3200
```

FIG.25C-8

ORF1A 3' END DNA ALIGNMENT (60% HOMOLOGY)

```
la VR2385 (4000-7197)   ..A..G..T...CAAA..AC....G..A..G..AA.A..A....GA.A...    7163
la LV (3961-7188)       ..C..T..A...TGCC..GG....A..G..A..GC.C..C....AG.C...    7154

CONSENSUS               GAMCTKACWG CYRMMGARST GGARAARCTR AARMGMATMA TTRRTMAACT    3250

la VR2385 (4000-7197)   ...G..CC...TT.AG..G...TG..........C                           7197
la LV (3961-7188)       ...A..TT...C.CT..A...GC..........T                           7188

CONSENSUS               CCARGGYYTG ACYAMKGARC AGKSTTTAAA CTGY                      3284
```

ISU55 low passage / ISU55 high passage DNA alignment

```
ISU55s Lp (545-3240)  .....................................C.....................................  619
ISU55  Hp             .....................................T.....................................  75

CONSENSUS             TGTATAATAGTACTTTGAATCAGGTGCTTGCTATTTTYCCAACCCCTGGTTCCCGGCCAAAGCTTCATGATTTTC  75

ISU55s Lp (545-3240)  ...........................................................................  694
ISU55  Hp             ...........................................................................  150

CONSENSUS             AGCAATGGCTAATAGCTGTACATTCCTCCATATTTTCCTCTGTTGCAGCTTCTTGTACTCTTTTTGTTGTGCTGT  150

ISU55s Lp (545-3240)  ............................................................T..............  769
ISU55  Hp             ............................................................C..............  225

CONSENSUS             GGTTGCGGGTTCCAATGCTACGTATTGCTTTTGGTTTCCGCTGGTTAGGGGCAATTTTTCYTTCGAACTCACAGT  225

ISU55s Lp (545-3240)  ............................................C..............................  844
ISU55  Hp             ............................................T..............................  300

CONSENSUS             GAACTACACGGTGTGTCCACCTTGCCTCACCCGGCAAGCAGCCAYAGAGGCCTACGAACCTGGCAGGTCTCTTTG  300

ISU55s Lp (545-3240)  ...........................................................................  919
ISU55  Hp             ...........................................................................  375

CONSENSUS             GTGCAGGATAGGGTATGATCGCTGTGGGGAGGACGATCATGACGAACTAGGGTTTGTGGTGCCGTCTGGCCTCTC  375
```

FIG.27A

```
                      ISU55 low passage / isu55 high passage DNA alignment
ISU55s Lp (545-3240)  ...........................................................................  994
ISU55  Hp             ...........................................................................  450

CONSENSUS             CAGCGAAGGCCACTTGACCAGTGTTTACGCCTGGTTGGCGTTCCTGTCTTTCAGTTACACAGCCCAGTTCCATCC  450

ISU55s Lp (545-3240)  ........................................................T.................. 1069
ISU55  Hp             ........................................................C..................  525

CONSENSUS             TGAGATATTCGGGATAGGGAATGTGAGTCAAGTTTATGTTGACATCAGGCATCAATYCATTTGCGCCGTTCACGA  525

ISU55s Lp (545-3240)  ........................................................................... 1144
ISU55  Hp             ...........................................................................  600

CONSENSUS             CGGGCAGAACGCCACTTTGCCTCGCCATGACAATATTTCAGCCGTGTTCCAGACTTATTACCAACATCAAGTCGA  600

ISU55s Lp (545-3240)  ........................................................................... 1219
ISU55  Hp             ...........................................................................  675

CONSENSUS             CGGCGGCAATTGGTTTCACCTAGAATGGCTGCGTCCCTTCTTTTCCTCTTGGTTGGTTTTAAATGTCTCTTGGTT  675

ISU55s Lp (545-3240)  ..............C............................................................ 1294
ISU55  Hp             ..............T............................................................  750

CONSENSUS             TCTCAGGCGTTCGCYTGCAAGCCATGTTTCAGTTCGAGTCTTGCAGACATTAAGACCAACACCACCGCAGCGGCA  750
```

FIG.27B

ISU55 low passage / ISU high passage DNA alignment

```
ISU55s Lp (545-3240)   ...........................................................................  1369
ISU55  Hp              ...........................................................................  825

CONSENSUS              GGCTTTGCTGTCCTCCAAGACATCAGTTGCCTTAGGTATCGCAACTCGGCCTCTGAGGCGTTTCGCAAAATCCCT  825

ISU55s Lp (545-3240)   ...........................................................................  1444
ISU55  Hp              ...........................................................................  900

CONSENSUS              CAGTGTCGTACGGCGATAGGGACACCCATGTATATTACTGTCACAGCCAATGTAACCGATGAGAATTATTTGCAT  900

ISU55s Lp (545-3240)   ...........................................................................  1519
ISU55  Hp              ...........................................................................  975

CONSENSUS              TCCTCTGACCTTCTCATGCTTTCTTCTTGCCTTTTCTACGCTTCTGAGATGAGTGAAAAGGGATTTAAAGTGGTA  975

ISU55s Lp (545-3240)   ...........................................................................  1594
ISU55  Hp              ...........................................................................  1050

CONSENSUS              TTTGGCAATGTGTCAGGCATCGTGGCTGTGTGCGTCAACTTTACCAGCTACGTCCAACATGTCAAGGAATTTACC  1050

ISU55s Lp (545-3240)   ...........................................................................  1669
ISU55  Hp              ...........................................................................  1125

CONSENSUS              CAACGCTCCTTGGTAGTCGACCATGTGCGGCTGCTCCATTTCATGACACCTGAGACCATGAGGTGGGCAACTGTT  1125
```

FIG.27C

ISU55 low passage / ISU55 high passage DNA alignment

```
ISU55s Lp (545-3240)  ..................................G.......A................................ 1744
ISU55  Hp             ..................................A.......G................................ 1200

CONSENSUS             TTAGCCTGTCTTTTTGCCATTCTGTTGGCCATTTRAATGTTTRAGTATGTTGGGGAAATGCTTGACCGCGGGCTA 1200

ISU55s Lp (545-3240)  .......................................................................G... 1819
ISU55  Hp             .......................................................................T... 1275

CONSENSUS             TTGCTCGTCATTGCTTTTTTTGTGGTGTATCGTGCCGTCTTGGTTTGTTGCGCTCGCCAGCGCCAACAGCAKCAA 1275

ISU55s Lp (545-3240)  ....T...................................................................... 1894
ISU55  Hp             ....C...................................................................... 1350

CONSENSUS             CAGCYCTCATTTACAGTTGATTTATAACTTGACGCTATGTGAGCTGAATGGCACAGATTGGTTAGCTGGTGAATT 1350

ISU55s Lp (545-3240)  ........................................................................... 1969
ISU55  Hp             ........................................................................... 1425

CONSENSUS             TGACTGGGCAGTGGAGTGTTTTGTCATTTTTCCTGTGTTGACTCACATTGTCTCCTATGGTGCCCTCACCACCAG 1425

ISU55s Lp (545-3240)  ........................................................................... 2044
ISU55  Hp             ........................................................................... 1500

CONSENSUS             CCATTTCCTTGACACAGTCGGTCTGGTCACTGTGTCTACCGCCGGCTTTTCCCACGGGCGGTATGTTCTGAGTAG 1500
```

FIG.27D

ISU55 low passage / ISU55 high passage DNA alignment

```
ISU55s Lp (545-3240)  ...........................................................................  2119
ISU55  Hp             ...........................................................................  1575

CONSENSUS             CATCTACGCGGTCTGTGCCCTGGCTGCGTTGATTTGCTTCGTCATTAGGTTTACGAAGAATTGCATGTCCTGGCG  1575

ISU55s Lp (545-3240)  ...........................................................................  2194
ISU55  Hp             ...........................................................................  1650

CONSENSUS             CTACTCATGTACCAGATATACCAACTTTCTTCTGGACACTAAGGGCAGACTCTATCGTTGGCGGTCGCCTGTCAT  1650

ISU55s Lp (545-3240)  ...........................................................................  2269
ISU55  Hp             ...........................................................................  1725

CONSENSUS             CATAGAGAAAAGGGGTAAAGTTGAGGTCGAAGGTCATCTGATCGACCTCAAGAGAGTTGTGCTTGATGGTTCCGC  1725

ISU55s Lp (545-3240)  ..................G........................................................  2344
ISU55  Hp             ..................A........................................................  1800

CONSENSUS             GGCAACCCCTATAACCAAARTTTCAGCGGAGCAATGGGGTCGTCCTTAGATGACTTCTGCCATGATAGCACGGCT  1800

ISU55s Lp (545-3240)  ....A......................................................................  2419
ISU55  Hp             ....T......................................................................  1875

CONSENSUS             CCACWAAAGGTGCTTTTGGCGTTCTCTATTACCTACACGCCAGTGATGATATATGCCCTAAAAGTAAGTCGCGGC  1875
```

FIG.27E

ISU55 low passage / ISU55 high passage DNA alignment

```
ISU55s Lp (545-3240)  ......C....................................................................  2494
ISU55  Hp             ......T....................................................................  1950

CONSENSUS             CGACTGYTAGGGCTTCTGCACCTTTTGATCTTCCTAAATTGTGCTTTCACCTTCGGGTACATGACATTCGTGCAC  1950

ISU55s Lp (545-3240)  ...........................................................................  2569
ISU55  Hp             ...........................................................................  2025

CONSENSUS             TTTCAGAGCACAAACAAGGTCGCGCTCACTATGGGAGCAGTAGTTGCACTCCTTTGGGGGGTGTACTCAGCCATA  2025

ISU55s Lp (545-3240)  ...........................................................................  2644
ISU55  Hp             ...........................................................................  2100

CONSENSUS             GAAACCTGGAAATTCATCACCTCCAGATGCCGTTTGTGCTTGCTAGGCCGCAAGTACATTTTGGCCCCTGCCCAC  2100

ISU55s Lp (545-3240)  ...........................................................................  2719
ISU55  Hp             ...........................................................................  2175

CONSENSUS             CACGTTGAAAGTGCCGCAGGCTTTCATCCGATAGCGGCAAATGATAACCACGCATTTGTCGTCCGGCGTCCCGGC  2175

ISU55s Lp (545-3240)  ...........................................................................  2794
ISU55  Hp             ...........................................................................  2250

CONSENSUS             TCCACTACGGTTAACGGCACATTGGTGCCCGGGTTGAAAAGCCTCGTGTTGGGTGGCAGAAAAGCTGTCAAACAG  2250
```

FIG. 27F

ISU55 low passage / ISU55 high passage DNA alignment

```
ISU55s Lp (545-3240)  ...........................................................................  2869
ISU55  Hp             ...........................................................................  2325

CONSENSUS             GGAGTGGTAAACCTTGTTAAATATGCCAAATAACAACGGCAAGCAGCAGAAGAAAAAGAAGGGGGATGGCCAGCC  2325

ISU55s Lp (545-3240)  ...........................................................................  2944
ISU55  Hp             ...........................................................................  2400

CONSENSUS             AGTCAATCAGCTGTGCCAGATGCTGGGTAAGATCATCGCTCAGCAAAACCAGTCCAGAGGCAAGGGACCGGGAAA  2400

ISU55s Lp (545-3240)  ...........................................................................  3019
ISU55  Hp             ...........................................................................  2475

CONSENSUS             GAAAAACAAGAAGAAAAACCCGGAGAAGCCCCATTTTCCTCTAGCGACTGAAGATGATGTCAGACATCACTTCAC  2475

ISU55s Lp (545-3240)  ..............A...............................................C............  3094
ISU55  Hp             ..............T...............................................T............  2550

CONSENSUS             CTCTGGTGAGCGGCWATTGTGTCTGTCGTCAATCCAGACAGCCTTTAATCAAGGCGCTGGAAYTTGTACCCTGTC  2550

ISU55s Lp (545-3240)  ...........................................................................  3169
ISU55  Hp             ...........................................................................  2625

CONSENSUS             AGATTCAGGGAGGATAAGTTACACTGTGGAGTTTAGTTTGCCGACGCATCATACTGTGCGCCTGATCCGCGTCAC  2625
```

FIG.27G

ISU55 low passage / ISU55 high passage DNA alignment

```
ISU55s Lp (545-3240)  .................................................................C.....   3240
ISU55  Hp             .................................................................T.....   2696

CONSENSUS             AGCGTCACCCTCAGCATGATGAGCTGGCATTCTTGAGGCATCCCAGTGTTTGAATTGGAAGAATGYGTGGT   2696
```

FIG.27H

ORFs map of ISU55 Hp sequenced fragment of cDNA

START/STOP METHOD : AA span>=100
GENETIC CODE: universal

| | | | | |
|---|---|---|---|---|
| ORF3 | 80 | TO | 841 | LENGTH=762 |
| ORF4 | 625 | TO | 1158 | LENGTH=534 |
| ORF5 | 1172 | TO | 1771 | LENGTH=600 |
| ORF6 | 1759 | TO | 2280 | LENGTH=522 |
| ORF7 | 2273 | TO | 2641 | LENGTH=369 |

START/STOP METHOD : AA span>=100
GENETIC CODE: universal

| | | | | |
|---|---|---|---|---|
| ORF2 | 1 | TO | 768 | LENGTH=768 |
| ORF3 | 624 | TO | 1385 | LENGTH=762 |
| ORF4 | 1169 | TO | 1702 | LENGTH=534 |
| ORF5 | 1716 | TO | 2315 | LENGTH=600 |
| ORF6 | 2303 | TO | 2824 | LENGTH=522 |
| ORF7 | 2817 | TO | 3185 | LENGTH=369 |

ISU55 Hp ORFs 3-7
Sunday, October 4, 1998 7:29 PM
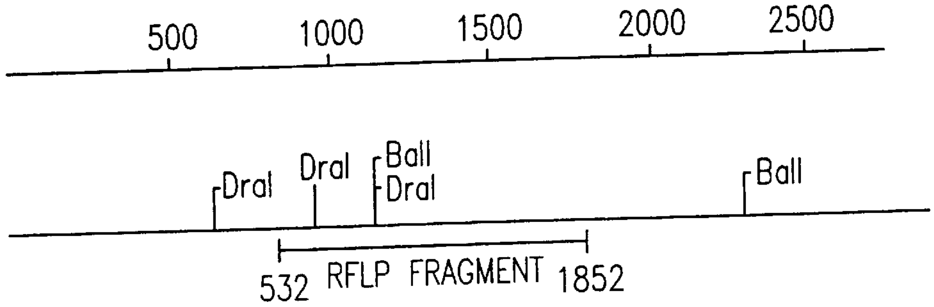
| ENZYME | #CUTS | POSITIONS | | |
|---|---|---|---|---|
| BalI | 2 | 1153 | 2319 | |
| DraI | 3 | 660 | 966 | 1159 |
55s 2-7 1p CUT SITE MAP
SUNDAY, OCTOBER 4, 1998 7:25 PM
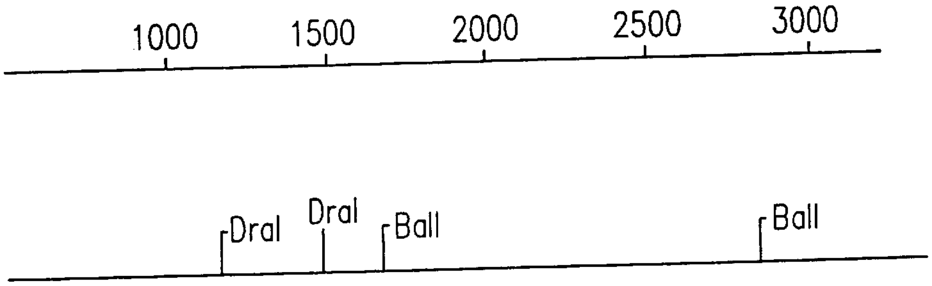
| ENZYME | #CUTS | POSITIONS | |
|---|---|---|---|
| BalI | 2 | 1697 | 2863 |
| DraI | 2 | 1204 | 1510 |
FIG.29

START/STOP METHOD : AA span>=110
GENETIC CODE: universal

ISU55hp ORFs LIST

| | | | | | |
|---|---|---|---|---|---|
| ORF1a | 191 | TO | 7699 | LENGTH=7509 | (2503 aa) |
| ORF1b | 7687 | TO | 12069 | LENGTH=4383 | (1461 aa) |
| ORF2 | 12074 | TO | 12841 | LENGTH= 768 | ( 256 aa) |
| ORF3 | 12697 | TO | 13458 | LENGTH= 762 | ( 254 aa) |
| ORF4 | 13242 | TO | 13775 | LENGTH= 534 | ( 178 aa) |
| ORF5 | 13789 | TO | 14388 | LENGTH= 600 | ( 200 aa, E PROTEIN) |
| ORF6 | 14376 | TO | 14897 | LENGTH= 522 | ( 174 aa, M PROTEIN) |
| ORF7 | 14890 | TO | 15258 | LENGTH= 369 | ( 123 aa, N PROTEIN) |

ISU55seq, 15,412 nt

```
NNGACGTATA GGTGTTGGCT CTATGCCTTG ACATTCGTAT TGTCAGGAGC   50
TGTGACCATT GGTACAGCCC AAAACTTGCT GCACAGAAAA CGCCCTTCTG  100
TGACAGCCTC CTTCAGGGAG CTTGGGGGTC TGTCCCTAGC ACCTTGCTTC  150
CGGAGTTGCA CTGCTTTACG GTCTCTCCAC CCTTTTAACC ATGTCTGGGA  200
TACTTGATCG GTGTACGTGC ACCCCCAATG CCAGGGTGTT TATGGCGGAG  250
GGCCAGGTCT ACTGCACACG ATGTCTCAGT GCACGGTCTC TCCTTCCTCT  300
GAATCTCCAG ACTCCCGAGC TTGGGGTGTT GGGTCTATTC TACAGGCCCG  350
AAGAACCACT CCGGTGGACG TTGCCACGTG CATTCCCCAC TGTTGAGTGT  400
TCCCCCGCTG GGGCCTGCTG GCTTTCTGCA ATCTTTCCAA TTGCGCGAAT  450
GACCAGTGGA AACCTGAACT TCCAACAAAG AATGGTACGG GTCGCAGCTG  500
AGCTTTACAG AGCCGGCCAG CTCACCCCTG TCGTCTTGAA GACTCTGCAA  550
GTTTACGAAC GGGGTTGCCG CTGGTACCCC ATTGTTGGAC CTGTCCCTGG  600
AGTGGCCGTT TTCGCCAACT CCCTACATGT GAGTGATAAA CCTTTCCCAG  650
GGGCAACTCA CGTGTTAACC AACCTGCCGC TCCCGCAGAG ACCCAAGCCC  700
GAAGACTTCT GCCCCTTTGA ATGCGCCATG GCCACCGTCT ATGACATTGG  750
TCATGACGCT GTCATGTACA TGGCCGGAGG GAAAGTCTCC TGGGCCCCTC  800
GTGGCGGGGA TGGAGTGAAA TTTGAAACTG TCCCCAAGGG GTTGGAGTTA  850
ACTGCGGACC GACTCCGCTC CTCCTTCCCG CCCCACCACG TAGTGGACAT  900
GTCCAGGTTT GCTTTCACAA CCCCTGAGTG TGGTGCCTCT ATGCGGGTCG  950
GACGCCAACG TGGCTGCCTC CCCGCTGGTA CTGTCCCTGA AGGCAACTGT 1000
TGGTGGAGCT TGTTTGGCTC GCTCCCACTG GAAGTTCTGA ACAAAGAAAT 1050
TCGCTATGCC AACCGATTTG GCTACCAAAC TAAGCATGGT GTCTCTGGCA 1100
AGTACCTACA GCGGAGGCTG CAAGTTAATG GTCTCCGGGC AGTAACTGAC 1150
ACACATGGAC CTATCGTCAT ACAATACTTC TCCGTTAAGG AGAGTTGGAT 1200
CCGCCACTTG AGACTGGCGG AAGAACCCAG CCTCCCTGGG TTTGAGGATC 1250
TCCTCAGAAT AAGGGTTGAG CCCAACACAT CGCCATTGCT TGGCAAGGGT 1300
GAAAAAATCT TCCGTTTTGG CAATCACAAA TGGTACGGCG CTGGAAAGAG 1350
AGCAAGGAAA GCACGCTCTA GTGCGACTGC TACGGTCGCT GACCGCGCTT 1400
TGTCCGCTCG TGAAACCCGG CTGGCCAAGG AGCACGAGGT TGCCGGCGCC 1450
AATAAGGCTG AGCACCTCAA GCACTACTCC CCGCCTGCCG AAGGGAATTG 1500
TGGTTGGCAC TGTATTTCCG CCATCGTCAA CCGGATGGTG AACTCCAAAT 1550
TTGAAACCAC CCTCCCCGAG AGAGTGAGAC CTCCAGATGA CTGGGCTACT 1600
GACGAGGATC TTGCGAACAC CATCCAAATC CTCAGGCTTC CTGCGGCCTT 1650
GGACAGGGGC GGTGCTTGTG TTAGCGCCAA GTATGTACTT AAGCTGGAAG 1700
GTGAACATTG GACTGTCTCT GTGACCCCTG GGATGTCTCC CTCTTTGCTC 1750
CCCCTTGAAT GCGTCCAGGG CTGTTGTGAT CATAAGAGCG GTCTTGGTTC 1800
CCCAGATACG GTCGAAGTTT CCGGATTTGA CCCTGCCTGC CTTGACCGGC 1850
TGGCTGAGGT GATGCACCTG CCTAGCAGTG CCATCCCAGC CGCTCTGGCC 1900
GAAATGTCCG GCGATTCCGA TCGTCCGGCT TCCCCGGTCA CCACTGTGTG 1950
GACGGTTTCG CAGTTCTTTG CCCGCCACAC AGGAGGGAAT CACCCTGACC 2000
AGGTGTGCTT AGGAAAAATC ATTAGCCTTT GTCAAGTGCT TGAGAGTTGC 2050
TGCTGTTTCC AGAACAAAAC CAACCGGGCC ACCCCGGAAG AGGTCGCGGC 2100
AAAAATTGAC CTGTACCTCC GCGGAGCAAC AGGTCTTGAA GAATGCTTGG 2150
CCAGGCTTGA GAGGGCTCGC CCACCGAGTG TAATGGACAC CTCCTTTGAT 2200
TGGAATGTTG TGCTTCCTGG GTTTGAGGCG GCAACTCAGA CAACCAAACC 2250
GCCCCAGGTC AACCAGTGTC GCGCTCTGGT CCCTGTTGTG ACTCAAGAGT 2300
CTTTGGACAA TGGCTCGGTT CCTCTGACCG CCTTCTCGCT GTCCAATTAC 2350
TACTACCGCG CGCAAGGAGA CGAGGTTCGT CACCGTGATA GGTTAAACGC 2400
CGTACTCTCC AAGTTGGAGG GTGCTGTTCG AGAAGAATAC GGGCTCATGC 2450
```

FIG.32A

CAACTGGACC TGGCCCGCGA CCCGCACTGC CGAGTGGGCT TGACGAGCTT 2500
AAAGACCAGA TGGAGGAGGA TCTGCTGAAA CTAGCCAATG CCCAGACAAC 2550
TTCAGAAATG ATGGCCTGGG CAGCCGAGCA GGTTGATCTA AAAGCTTGGG 2600
TTAAAAACTA CCCACGGTGG ACACCACCGC CCCCTCCACC AAGAGTCCAG 2650
CCTCGAAAAA CAAAGCCTGT CAAGAGTTTG CCAGAGAGCA AGCCTGTCCC 2700
CGCCCCGCGC AGGAAGGTTA GGTCCGATTG TGGCAGCCCG ATTTTATTGG 2750
GCGACAATGT TCCTAACAGT TGGGAAGATT TGACTGTTGG TGGCCCCCTT 2800
GATCTCTCGA CCTCACCCGA GCCGGTGACA CCTCCGAGTG AGCTTGCGCT 2850
CATGTCCGCA CCGCAACACA CTTTTAGGTC GGTGATACCC TTGGGTGAAC 2900
CGGCCCCAGT TCCCGCATTG CGCAAAACTG TGCCCCGACC GGTAACACCC 2950
TTGAGCGAGC CGATCCCTGT GTCCGCACCG CAATGCAAGT TTCAGCAGGT 3000
GGAAAAAGCG GATCTGGCGG CAGCAGCGCT GGCGTACCAG GACGAGCCCC 3050
TAGATTTGTC TGCATCCTCA CAAACTGAAT ATGAGGCTTC TCCCCTAGAA 3100
CCACTGCAGA GCATGGGCGT TCTAAAGGTG GAAGGACAAG AAGCTGAGGA 3150
AGTCCTGAGT GGAATCTCGG ACATACTGGA TGACATCAAC CCGGTGCCTG 3200
TATCATCAAA CGGCTCCCTG TCAAGCGTGA GGATCACACG CCCAAAATAC 3250
TCAGCTCAAG CCATCATCGA CTCGGGCGGG CCCTGCAGTG GGCACCTCCA 3300
AGGGATAAAG GAAACATGCC TCAGTATCAT GCGTGAGGCA TGTGATGCGA 3350
CTAAGCTTGA TGACCCTACT ACGCAGGAAT GGCTTTCTCG CATGTGGGAT 3400
AGGGTGGACA TGCTGACTTG GCGCAACACG TCTGCTTACC AGGCGCTTCG 3450
CACCTTAGAT AGCAGGTTTG AGTTTCTCCC AAAAATGATA CTCGAGACAC 3500
CGCCGCCCTA TCCGTGTGAG TTTGTGATGA TGCCTCACAC GCCTGCACCT 3550
TCTGTAAGTG CGGAGAGTGA TCTTACCATT GGCTCAGTCG CCACTGAAGA 3600
TGTTCCACGC ATCCTCGGGA AAATAGAAGA TGTCGGCGAG ATGACCAACC 3650
AGGGACCCTT GGCATTCTCC GAGGAAGAAC CGGTGGATCA CCAACCTGCC 3700
AAGGGCTCCC GGTCATTGTC GCGGAGGCCT GACGAGAGTA CACCAACTCT 3750
GTCCGCAAGC GCAGGTGGCA CCGACTTACC CACCGATTTG CCGCTTTCAG 3800
ACGGTGTGGA TGCGGACGGG GGGGGGCCGT TACGGACGGT AAAAAACAAA 3850
ACTGAAAGGC TCTTTGACCA ACTGAGCCGT CAGGTTTTTA ACCTCGTCTC 3900
CCATCTCCCT GTTTTCTTCT CACGCCTTCT CCTACCTGGC GGTGGTTATT 3950
CTCCGGGTGA TTGGGGCTTT GCAGCTTTTA CTCTATTGTG CCTCTTTTTG 4000
TGTTATAGCT ACCCAGCCTT TGGTATTGCT CCCCTTTTGG GTGTATTTTC 4050
TGGGTCTTCT CGGCGCGTTC GAATGGGGGT TTTTGGCTGC TGGTTGGCTT 4100
TTGCTGTTGG CCTGTTCAAG CCTGTGTCCG ACCCAGTCGG CACTGCTTGT 4150
GAGTTTGACT CGCCAGAGTG TAGAAACATC CTTCTTTCTT TTGAGCTTCT 4200
CAAACCTTGG GACCCTGTTC GCAGCCTTGT TGTGGGCCCC GTCGGTCTCG 4250
GTCTTGCCAT TCTTGGCAGG TTACTGGGCG GGGCACGCTG TATCTGGCAC 4300
TTTTTGCTTA GGCTTGGCAT TGTTACAGAT TGTATCCTGG CTGGAGCTTA 4350
TGTGCTTTCT CAAGGTAGGT GTAAAAAGTG CTGGGGATCT TGTATAAGAA 4400
CTGCTCCTAG TGAGGTCGCC TTTAACGTGT TTCCTTTTAC ACGTGCGACC 4450
AGGTCGTCAC TTACCAACTT GTGCGATCGG TTTTGTGCGC CAAAAGGCAT 4500
GGACCCCATT TTCCTCGCCA CTGGGTGGCG CGGGTGCTGG ACCGGCCGAA 4550
GCCCCATTGA GCAACCCTCT GAAAAACCCA TCGCGTTTGC CCAGTTGGAT 4600
GAAAAGAAGA TTACGGCTAA GACTGTGGTC GCCCAGCCTT ATGACCCCAA 4650
CCAAGCCGTA AAGTGTTTGC GGGTGTTACA GGCGGGCGGG GTGATGGTGG 4700
CTGAGGCAGT TCCAAAAGTG GTCAAGGTTT CCGCTGTCCC ATTCCGAGCC 4750
CCCTTCTTTC CCACTGGGGT GAAAGTTGAT CCTGGGTGCA GGATCGTGGT 4800
TGACCCCGAC ACCTTCACTG CAGCTCTCCG GTCTGGTTAC TCCACCACAA 4850
ACCTCGTCCT TGGTGTAGGG GACTTTGCCC AGCTGAATGG ATTAAAAATT 4900

FIG.32B

```
AGGCAAATTT CCAAGCCTTC TGGAGGAGGC CCACACCTCA TGGCTGCCCT 4950
GCATGTTGCT TGCTCGATGA CCTTGCACAT GCTTGCTGGG ATTTACGTGA 5000
CTGCGGTGGG TTCTTGCGGC ACCGGCACCA ACGATCCGTG GTGCGCTAAC 5050
CCGTTTGCCG TCCCTGGCTA TGGACCTGGA TCTCTCTGCA CGTCCAAATT 5100
GTGCATCTCC CAACATGGCC TCACCCTGCC CTTAACAGCA CTTGTTGCGG 5150
GATTCGGTAT TCAGGAAATT GCCTTGGTCG TTTTGATTTT TGTTTCCATC 5200
GGGGGCATGG CTCATAGGTT GAGTTGTAAG GCTGATATGC TGTGTGTTTT 5250
GCTTGCAATC GCCAGCTATG TTTGGGTACC TCTAACCTGG TTGCTTTGTG 5300
TGTTTCCCTG CTGGTTGCGC TGTTTTTCTT TGCACCCACT CACCATCCTA 5350
TGGTTGGTGT TTTTCTTGAT TTCTGTAAAT ATGCCTTCAG GAATCTTGGC 5400
CATGGTGTTG TTGGTTTCTC TTTGGCTTCT TGGACGTTAT ACTAATGTCG 5450
CTGGTCTTGT CACCCCTTAT GATATTCACC ATTACACCAG TGGCCCCCGC 5500
GGTGTTGCCG CCTTGGCTAC AGCACCAGAT GGGACCTACT TGGCCGCTGT 5550
CCGCCGCGCT GCGTTGACTG GCCGCACCAT GCTGTTTACC CCGTCTCAGC 5600
TTGGGTCCCT TCTTGAGGGC GCTTTTAGAA CTCAAAAGCC CTCGTTGAAC 5650
ACCGTCAATG TGGTCGGGTC CTCCATGGGC TCTGGCGGGG TGTTCACCAT 5700
CGACGGGAAA ATCAAGTGCG TAACTGCCGC ACATGTCCTT ACGGGCAATT 5750
CAGCTAGGGT TTCCGGGGTC GGTTTCAACC AAATGCTTGA CTTTGATGTA 5800
AAAGGAGACT TCGCCATGGC CGATTGCCCG GATTGGCAAG GGGCTGCTCC 5850
CAAGACCCAA TTCTGCAAGG ATGGATGGAC TGGCCGTGCC TACTGGCTAA 5900
CATCCTCTGG CGTCGAACCC GGTGTCATTG GAAAAGGATT CGCCTTCTGC 5950
TTCACCGCGT GCGGCGATTC CGGGTCCCCA GTGATCACCG AGGCCGGTGA 6000
GCTTGTCGGT GTCCACACGG GATCAAATAA ACAAGGAGGA GGCATCGTCA 6050
CGCGCCCCTC AGGCCAGTTT TGTAATGTGT CACCCGTCAA GCTAAGCGAA 6100
TTAAGTGAAT TCTTTGCTGG GCCTAAGGTC CCGCTCGGTG ATGTGAAGGT 6150
TGGCAGCCAT ATAATCAAAG ATATAGGCGA GGTACCTTCA GATCTTTGCG 6200
CCTTGCTTGC TGCCAAACCT GAACTGGAAG GAGGCCTCTC CACCGTCCAA 6250
CTTCTGTGTG TGTTTTTTCT CCTGTGGAGG ATGATGGGAC ATGCCTGGAC 6300
GCCCTTGGTT GCTGTGGGGT TCTTTATCTT GAATGAGGTT CTTCCAGCTG 6350
TCCTGGTCCG GAGTGTCTTC TCCTTTGGAA TGTTTGTGCT ATCCTGGCTC 6400
ACACCATGGT CTGCGCAAGT TCTGATGATC AGGCTTCTAA CAGCAGCTCT 6450
TAACAGGAAC AGAGGTTCAC TTGCCTTTTA CACCCTCGGT GCAATAACCG 6500
GCTTTGTCGC AGATCTTGCG GTTACTCAGG GACATCCGTT GCAGGCAGTG 6550
ATGAATTTGA GCACCTATGC ATTCCTGCCT CGGATGATGG TTGTGACCTC 6600
ACCAGTCCCA GTGATCGCGT GTGGTGTTGC GCACCTGCTT GCCATCATTT 6650
TGTACTTGTT TAAGTACCGC GGCCTGCACA AGATCCTTGT TGGCGATGGA 6700
GCGTTCTCTG CGGCTTTCTT CCTGCGATAC TTTGCCGAGG GAAAGTTGAG 6750
GGAAGGGGTG TCGCAATCCT GCGGAATGAA TCATGAGTCA CTGACTGGTG 6800
CCCTCGCCAT GAAACTCAAT GACGAGGACT TGGATTTCCT TACGAAATGG 6850
ACTGATTTTA AGTGCTTTGT TTCTGCATCC AACATGAGGA ATGCAGCGGG 6900
CCAATTTATC GAGGCTGCCT ATGCTAAAGC ACTTAGAGTA GAACTTGCCC 6950
AGTTGGTACA GGTTGATAAG GTTCGAGGCA CTATGGCCAA ACTAGAAGCT 7000
TTTGCTGACA CCGTGGCACC CCAACTCTCG CCCGGTGACA TTGTTGTCGC 7050
TCTTGGCCAT ACGCCTGTTG GCAGTATCTT CGACCTAAAG GTTGGTAGCA 7100
CTAAGCACAC CCTCCAAGCC ATTGAGACCA GATTTCTTGC TGGGTCCAAA 7150
```

FIG. 32C

```
ATGACCGTGG CGCGTGTCGT CGACCCGACC CCCACGCCCC CACCCGCACC 7200
CGTGCCCATC CCCCTCCCAC CGAAAGTTCT GGAGAATGGT CCCAACGCTT 7250
GGGGGGATGA GGATCGTTTG AATAAAAAAA AAAGGCGCAG GATGGAAGCC 7300
CTCGGCATCT ATGTTATGGG TGGGAAAAAG TACCAGAAAT TTTGGGATAA 7350
GAACTCCGGT GATGTGTTTT ATGAGGAGGT CCATAATAAC ACAGATGAGT 7400
GGGAGTGCCT CAGAGTTGGC GACCCTGCCG ACTTTGACCC TGAGAAGGGA 7450
ACTCTGTGTG GGCACGTCAC CATTGAGGAT AAGGCTTATC ATGTTTACGC 7500
CTCCCCATCC GGTAAGAAGT TCCTGGTCCC CGTCAACCCA GAAAACGGAA 7550
GAGTCCAATG GGAAGCTGCA AAGCTTTCCG TGGAGCAGGC CCTTGGTATG 7600
ATGAACGTCG ACGGCGAACT GACTGCCAAA GAACTGGAGA AACTGAAAAG 7650
AATAATTGAT AAACTCCAGT GCCTGACTAA GGAGCAGTGT TTAAACTGCT 7700
AGCCGCCAGC GGCTTGACCC GCTGTGGTCG CGGCGGCTTG GTTGTCACTG 7750
AGACAGCGGT AAAAATAGTC AAATTTCACA ACCGGACCTT CACCCTGGGA 7800
CCTGTGAATT TAAAAGTGGC CAGTGAGGTT GAGTTAAAAG ACGCGGTCGA 7850
GCACAACCAA CACCCGGTTG CAAGACCGGT TGATGGTGGT GTTGTGCTCC 7900
TGCGTTCTGC AGTTCCTTCA CTTATAGACG TCCTGATCTC CGGTGCCGAC 7950
GCATCTCCTA AGTTGCTCGC CCATCACGGG CCGGGGAACA CTGGGATCGA 8000
TGGCACGCTT TGGGATTTCG AGTCTGAGGC CACTAAAGAG GAAGTCGCAC 8050
TTAGTGCGCA AATAATACAG GCTTGTGACA TCAGGCGCGG GGACGCACCC 8100
AAAATTGATC TCCCCTACAA GCTGTACCCT GTTAGGGGCA ACCCTGAGCG 8150
GGTGAAAGGA GTTCTGAGGA ATACAAGGTT TGGAGACATA CCTTACAAGA 8200
CCCCCAGTGA CACTGGGAGC CCGGTGCACG CGGCCGCCTG CCTTACGCCT 8250
AACGCCACTC CGGTGACTGA CGGGCGCTCC ATCTTGGCCA CGACCATGCC 8300
CTCTGGGTTT GAGTTGTATG TACCGACCAT TCCAGCGTCT GTCCTTGATT 8350
ACCTTGATTC TAGGCCTGAC TGCCCTAAAC AGTTGACAGA GCACGGCTGT 8400
GAAGATGCCG CACTGAGAGA CCTCTCCAAA TATGACTTGT CCACCCAAGG 8450
CTTTGTTTTA CCTGGAGTTC TTCGCCTCGT GCGGAAATAC CTGTTTGCCC 8500
ATGTAGGTAA GTGCCCACCT GTTCACCGGC CTTCTACTTA TCCTGCTAAG 8550
AATTCTATGG CTGGACTAAA TGGGAACAGG TTCCCGACCA AGGATATTCA 8600
GAGCGTCCCT GAAATCGACG TTCTGTGCGC GCAGGCTGTG CGGGAAAACT 8650
GGCAGACTGT TACCCCTTGT ACCCTTAAGA AGCAGTATTG CGGGAAGAAG 8700
AAAACTAGGA CAATACTCGG CACCAATAAC TTCATCGCGC TGGCTCATCG 8750
GGCAGCGTTG AGTGGTGTCA CCCAGGGCTT CATGAAAAAG GCATTTAACT 8800
CGCCCATCGC CCTCGGAAAA AACAAATTTA AGGAGCTACA AACTCCGGTC 8850
CTAGGCAGAT GCCTTGAAGC TGATCTTGCA TCCTGCGACC GATCCACACC 8900
TGCAATTGTC CGTTGGTTTG CCGCCAATCT TCTTTATGAA CTTGCCTGTG 8950
CTGAAGATCA CCTGCCATCT TATGTGCTGA ACTGTTGCCA CGACTTATTG 9000
GTCACGCAGT CTGGCGCAGT GACTAAGAGA GGTGGCCTGT CATCTGGCGA 9050
CCCGATCACC TCTGTGTCTA ACACCATTTA CAGCTTGGTG ATCTATGCAC 9100
AGCACATGGT GCTCAGTTAC TTCAAAAGTG GTCACCCCCA CGGCCTTCTG 9150
TTCTTACAAG ACCAGCTAAA GTTTGAGGAC ATGCTCAAGG TTCAACCCCT 9200
GATCGTCTAT TCGGACGACC TCGTGCTGTA TGCCGAGTCT CCCACCATGC 9250
CAAACTACCA CTGGTGGGTT GAACATCTGA ATTTAATGCT GGGGTTTCAG 9300
ACGGACCCAA AGAAGACAGC TATAACAGAC TCGCCATCAT TTCTAGGCTG 9350
CAGGATAATA AATGGACGCC AGCTAGTCCC TAACCGTGAC AGGATTCTCG 9400
CGGCCCTCGC CTACCATATG AAGGCGAGTA ATGTTTCTCA ATACTACGCT 9450
TCGGCGGCTG CAATACTCAT GGACAGCTGT GCTTGTTTAG AGTATGATCC 9500
TGAATGGTTT GAAGAACTTA TAGTTGGAAT ATCGCAGTGC GCCCGCAAGG 9550
ACGGCTATAG CTTTCCCGGT CCGCCGTTCT TCTTGTCTAT GTGGGAAAAA 9600
CTCAGGTCTA ATTATGAGGG GAAGAAGTCG AGAGTGTGCG GGTACTGCGG 9650
```

FIG.32D

GGCCCCGGCC CCGTACGCTA CTGCCTGTGG CCTCGATGTC TGCATTTACC 9700
ACACCCACTT CCACCAGCAT TGTCCGGTTA TAATTTGGTG TGGCCACCCA 9750
GCGGGTTCTG GTTCTTGTAG TGAGTGCAAA TCCCCCGTGG GGAAAGGCAC 9800
AAGCCCTCTG GACGAGGTGT TAAAACAAGT CCCGTATAAA CCCCCACGGA 9850
CCATAATCAT GCATGTGGAA CAGGGTCTTA CCCCCCTTGA CCCAGGCAGA 9900
TACCAGACTC GCCGCGGATT GGTCTCCGTT AGGCGCGGAA TCAGGGGGAA 9950
TGAAGTTGAA CTACCAGACG GTGATTACGC TAGTACCGCC TTGCTCCCCA 10000
CCTGTAAAGA GATCAACATG GTCGCTGTCG CTTCTAATGT GTTGCGCAGC 10050
AGGTTCATCA TCGGTCCGCC CGGTGCTGGG AAGACATACT GGCTTCTACA 10100
ACAGGTCCAG GATGGTGATG TCATTTACAC ACCAACTCAC CAGACCATGC 10150
TTGACATGAT TAGAGCTTTG GGGACGTGCC GGTTCAACGT CCCAGCAGGC 10200
ACAACGCTGC AATTCCCTGT CCCCTCCCGT ACCGGTCCGT GGGTTCGCAT 10250
CCTAGCCGGC GGTTGGTGTC CTGGCAAGAA TTCCTTCCTG GATGAAGCAG 10300
CGTATTGCAA TCACCTTGAT GTCTTGAGGC TTCTTAGCAA AACTACCCTC 10350
ACCTGTCTGG GAGATTTCAA ACAACTCCAC CCAGTGGGTT TTGATTCTCA 10400
TTGCTATGTT TTTGACACTA TGCCTCAGAC TCAACTGAAG ACCATCTGGA 10450
GATTCGGACA GAATATTTGT GATGCCATCC AACCAGATTA CAGAGACAAA 10500
CTCATGTCCA TGGTCAACAC AACCCGTGTA ACCTACGTGG AGAGACCTGT 10550
CAGGCATGGG CAAGTCCTCA CCCCCTACCA CAGGGACCGA GAGGACGACG 10600
CCATCACCAT TGACTCCAGC CAAGGCGCCA CATTTGATGT GGTTACATTG 10650
CATTTGCCCA CTAAAGATTC ACTCAACAGG CAAAGAGCCC TTGTTGCTAT 10700
CACCAGGGCA AGACATGCTA TCTTTGTGTA TGACCCACAC AGGCAACTGC 10750
AGAGCCTATT TGATCTTCCT GCGAAAAGCA CCCCTGTCAA CCTCGCAGTG 10800
CACCGCGACG GGCAGCTGAT CGTGCTAGAT AGAAATAACA AAGAATGCAC 10850
GGTTGCTCAG GCTCTTGGCA ACGGAGATAA ATTTAGGGCC ACAGACAAGC 10900
GCGTTGTAGA CTCTCTCCGC GCCATTTGTG CTGATCTAGA AGGGTCTAGC 10950
TCTCCGCTCC CCAAGGTCGC CCACAACTTG GGATTTCATT TCTCACCTGA 11000
TTTGACACAG TTTGCCAAAC TCCCAGTAGA ACTTGCACCT CACTGGCCCG 11050
TGGTGACAAC CCAGAACAAT GAAAAGTGGC CAGATCGGCT GGTTGCTAGC 11100
CTTCGCCCTA TTCATAAATA TAGCCGCGCG TGCATTGGTG CCGGCTATAT 11150
GGTGGGCCCC TCGGTGTTTC TAGGCACCCC TGGGGTCGTG TCATACTACC 11200
TCACAAAATT TATTAAGGGC GAGGCTCAAG TGCTTCCGGA GACGGTCTTC 11250
AGCACCGGTC GAATTGAGGT AGATTGCCGG GAATACCTTG ATGATCGGGA 11300
GCGAGAAGTT GCTGCGTCCC TCCCACATGC CTTCATTGGC GACGTCAAAG 11350
GCACTACCGT TGGGGGATGT CACCATGTCA CTTCCAAATA CCTTCCGCGA 11400
TTCCTTCCTA AGGAATCAGT TGCGGTAGTC GGGGTTTCGA GCCCCGGAAA 11450
AGCCGCGAAA GCAGTGTGCA CACTGACAGA TGTGTACCTC CCAGACCTTG 11500
AAGCCTACCT CCACCCGGAA ACCCAGTCCA AGTGCTGGAA ATTGATGTTG 11550
GACTTCAAGG AAGTCCGACT GATGGTCTGG AAAGACAAGA CGGCCTATTT 11600
CCAACTTGAA GGCCGCTATT TCACCTGGTA TCAGCTTGCT AGCTACGCCT 11650
CGTACATCCG TGTTCCTGTC AACTCTGCGG TGTACTTAGA CCCCTGCATG 11700
GGCCCTGCCC TTTGCAACAG GAGAGTTATC GGGTCCACTC ATTGGGGAGC 11750
TGACCTCGCA GTCACCCCTT ATGATTACGG TGCCAAAATT ATTTTGTCTA 11800
GTGCGTACCA TGGTGAAATG CCTCCCGGGT ACAAGATTCT GGCGTGCGCA 11850
GAGTTCTCGC TTGACGACCC AGTCAAGTAC AAGCACACCT GGGGGTTTGA 11900
ATCGGATACA GCGTATCTGT ATGAGTTCAC CGGAAACGGT GAGGACTGGG 11950
AGGATTACAA TGATGCGTTT CGTGCGCGCC AGGAGGGGAA AGTCTATAAG 12000
GCCACTGCCA CCAGCATGAA GTTTTATTTT CCCCCGGGCC CTATCATTGA 12050
ACCAACTTTA GGCCTGAATT GAAATGAAAT GGGGTCTATG CAAAGCCTTT 12100
TTGACAAAAT TGGCCAACTT TTCGTGGATG CTTTCACGGA GTTCTTGGTG 12150
TCCATTGTTG ATATCATTAT ATTTTTGGCC ATTTTGTTTG GCTTCACCAT 12200

FIG.32E

CGCCGGTTGG CTGGTGGTCT TTTGCATCAG ATTGGTTTGC TCCGCGCTAC 12250
TCCGTGCGCG CCCTGCCATT CACTCTGAGC AATTACAGAA GATCCTATGA 12300
GGCCTTTCTT TCTCAGTGCC AGGTGGACAT TCCCACCTGG GGATTTAAAC 12350
ATCCTTTGGG GATGTTTTGG CACCATAAGG TGTCAACCCT GATTGATGAA 12400
ATGGTGTCGC GTCGAATGTA CCGCATCATG GATAAAGCAG GACAGGCTGC 12450
CTGGAAACAG GTGGTGAGCG AGGCTACGCT GTCTCGCATT AGTAGTTTGG 12500
ATGTGGTGGC TCACTTTCAG CATCTTGCCG CCATTGAAGC CGAGACCTGT 12550
AAATATTTGG CCTCTCGGCT GCCCATGCTA CACAACCTGC GCATGACAGG 12600
GTCAAATGTA ACCATAGTGT ATAATAGTAC TTTGAATCAG GTGCTTGCTA 12650
TTTTTCCAAC CCCTGGTTCC CGGCCAAAGC TTCATGATTT TCAGCAATGG 12700
CTAATAGCTG TACATTCCTC TATATTTTCC TCTGTTGCAG CTTCTTGTAC 12750
TCTTTTTGTT GTGCTGTGGT TGCGGGTTCC AATGCTACGT ATTGCTTTTG 12800
GTTTCCGCTG GTTAGGGGCA ATTTTTCCTT CGAACTCACA GTGAACTACA 12850
CGGTGTGTCC ACCTTGCCTC ACCCGGCAAG CAGCCATAGA GGCCTACGAA 12900
CCTGGCAGGT CTCTTTGGTG CAGGATAGGG TATGATCGCT GTGGGGAGGA 12950
CGATCATGAC GAACTAGGGT TTGTGGTGCC GTCTGGCCTC TCCAGCGAAG 13000
GCCACTTGAC CAGTGTTTAC GCCTGGTTGG CGTTCCTGTC TTTCAGTTAC 13050
ACAGCCCAGT TCCATCCTGA GATATTCGGG ATAGGGAATG TGAGTCAAGT 13100
TTATGTTGAC ATCAGGCATC AATCCATTTG CGCCGTTCAC GACGGGCAGA 13150
ACGCCACTTT GCCTCGCCAT GACAATATTT CAGCCGTGTT CCAGACTTAT 13200
TACCAACATC AAGTCGACGG CGGCAATTGG TTTCACCTAG AATGGCTGCG 13250
TCCCTTCTTT TCCTCTTGGT TGGTTTTAAA TGTCTCTTGG TTTCTCAGGC 13300
GTTCGCTTGC AAGCCATGTT TCAGTTCGAG TCTTGCAGAC ATTAAGACCA 13350
ACACCACCGC AGCGGCAGGC TTTGCTGTCC TCCAAGACAT CAGTTGCCTT 13400
AGGTATCGCA ACTCGGCCTC TGAGGCGTTT CGCAAAATCC CTCAGTGTCG 13450
TACGGCGATA GGGACACCCA TGTATATTAC TGTCACAGCC AATGTAACCG 13500
ATGAGAATTA TTTGCATTCC TCTGACCTTC TCATGCTTTC TTCTTGCCTT 13550
TTCTACGCTT CTGAGATGAG TGAAAAGGGA TTTAAAGTGG TATTTGGCAA 13600
TGTGTCAGGC ATCGTGGCTG TGTGCGTCAA CTTTACCAGC TACGTCCAAC 13650
ATGTCAAGGA ATTTACCCAA CGCTCCTTGG TAGTCGACCA TGTGCGGCTG 13700
CTCCATTTCA TGACACCTGA GACCATGAGG TGGGCAACTG TTTTAGCCTG 13750
TCTTTTTGCC ATTCTGTTGG CCATTTAAAT GTTTGAGTAT GTTGGGGAAA 13800
TGCTTGACCG CGGGCTATTG CTCGTCATTG CTTTTTTTGT GGTGTATCGT 13850
GCCGTCTTGG TTTGTTGCGC TCGCCAGCGC CAACAGCATC AACAGCCCTC 13900
ATTTACAGTT GATTTATAAC TTGACGCTAT GTGAGCTGAA TGGCACAGAT 13950
TGGTTAGCTG GTGAATTTGA CTGGGCAGTG GAGTGTTTTG TCATTTTTCC 14000
TGTGTTGACT CACATTGTCT CCTATGGTGC CCTCACCACC AGCCATTTCC 14050
TTGACACAGT CGGTCTGGTC ACTGTGTCTA CCGCCGGCTT TTCCCACGGG 14100
CGGTATGTTC TGAGTAGCAT CTACGCGGTC TGTGCCCTGG CTGCGTTGAT 14150
TTGCTTCGTC ATTAGGTTTA CGAAGAATTG CATGTCCTGG CGCTACTCAT 14200
GTACCAGATA TACCAACTTT CTTCTGGACA CTAAGGGCAG ACTCTATCGT 14250
TGGCGGTCGC CTGTCATCAT AGAGAAAAGG GGTAAAGTTG AGGTCGAAGG 14300
TCATCTGATC GACCTCAAGA GAGTTGTGCT TGATGGTTCC GCGGCAACCC 14350
CTATAACCAA AATTTCAGCG GAGCAATGGG GTCGTCCTTA GATGACTTCT 14400
GCCATGATAG CACGGCTCCA CTAAAGGTGC TTTTGGCGTT CTCTATTACC 14450
TACACGCCAG TGATGATATA TGCCCTAAAA GTAAGTCGCG GCCGACTGTT 14500
AGGGCTTCTG CACCTTTTGA TCTTCCTAAA TTGTGCTTTC ACCTTCGGGT 14550
ACATGACATT CGTGCACTTT CAGAGCACAA ACAAGGTCGC GCTCACTATG 14600
GGAGCAGTAG TTGCACTCCT TTGGGGGGTG TACTCAGCCA TAGAAACCTG 14650
GAAATTCATC ACCTCCAGAT GCCGTTTGTG CTTGCTAGGC CGCAAGTACA 14700
TTTTGGCCCC TGCCCACCAC GTTGAAAGTG CCGCAGGCTT TCATCCGATA 14750

FIG.32F

GCGGCAAATG ATAACCACGC ATTTGTCGTC CGGCGTCCCG GCTCCACTAC 14800
GGTTAACGGC ACATTGGTGC CCGGGTTGAA AAGCCTCGTG TTGGGTGGCA 14850
GAAAAGCTGT CAAACAGGGA GTGGTAAACC TTGTTAAATA TGCCAAATAA 14900
CAACGGCAAG CAGCAGAAGA AAAAGAAGGG GGATGGCCAG CCAGTCAATC 14950
AGCTGTGCCA GATGCTGGGT AAGATCATCG CTCAGCAAAA CCAGTCCAGA 15000
GGCAAGGGAC CGGGAAAGAA AAACAAGAAG AAAAACCCGG AGAAGCCCCA 15050
TTTTCCTCTA GCGACTGAAG ATGATGTCAG ACATCACTTC ACCTCTGGTG 15100
AGCGGCTATT GTGTCTGTCG TCAATCCAGA CAGCCTTTAA TCAAGGCGCT 15150
GGAATTTGTA CCCTGTCAGA TTCAGGGAGG ATAAGTTACA CTGTGGAGTT 15200
TAGTTTGCCG ACGCATCATA CTGTGCGCCT GATCCGCGTC ACAGCGTCAC 15250
CCTCAGCATG ATGAGCTGGC ATTCTTGAGG CATCCCAGTG TTTGAATTGG 15300
AAGAATGTGT GGTGAATGGC ACTGATTGAC ATTGTGCTTC TAAGTCACCT 15350
ATTCAATTAG GGCGACCGTG TGGGGGCAAA ATTTAATTGG CGTGAACCAC 15400
GCGGCCGAAA TTAAAAAAAA AAAA 15424

FIG.32G

```
NNGACGTATA GGTGTTGGCT CTATGCCTTG ACATTTGTAT TGTCAGGAGC    50
TGTGGCCATT GGCACAGCCC AAAAACTTGC TGCACGGAAA CACCCTTCTG   100
TGACAGCCTC CTTCAGGGGA GCTTGGGGTC TGTCCCTAGC ACCTTGCTTC   150
CGGAGTTGCA CTGCTTTACG GTCTCTCCAC CCCTTTAACC ATGTCTGGGA   200
TGCTTGATCG GTGCACGTGT ACCCCCAATG CCAGGGTGTT TATGGCGGAA   250
GGCCAAGTCT ACTGCACACG ATGCCTCAGT GCACGGTCTC TCCTTCCCCT   300
GAATCTCCAA GCTTCTGAGC TTGGGGTGCT AGGCCTATTC TACAGGCCCG   350
AAGAGCCACT CCGGTGGACG TTGCCACGTG CATTCCCCAC TGTTGAGTGC   400
TCCCCCGCCG GAGCCTGCTG GCTTTCTGCA ATCTTTCCAA TTGCACGGAT   450
GACCAGTGGA AACCTGAACT TCCAACAAAG AATGGTACGG GTCGCAGCTG   500
AGTTTAACAG AGCCGGCCAG TTCACCCCTG CAGTTTTGAA GACTCTACAA   550
GTTTATGAAC GGGGTTGCCG CTGGTACCCC ATTGTTGGAC CTGTCCCTGG   600
AGTGGCCGTT TTCGCCAACT CCCTACATGT GAGTGATAAA CCTTTCCCGG   650
GAGCAACTCA CGTGCTAACC AACCTGCCGC TCCCGCAGAG ACCCAAGCCT   700
GAAGACTTTT GCCCCTTTGA GTGTGCTATG GCTACTGTCT ATGACATTGG   750
TCATGACGCC GTCATGTATG TGGCCGAGGG GAAAGTCTCC TGGGCCCCTC   800
GTGGCGGAAA TGAAGTGAAA TTTGAAACTG TCCCCGAGGA GTTGAAATTG   850
ATTGCGGACC GGCTCCGCAC CTCCATCCCG CCCCACCATG TAGTGGACAT   900
GTCTAAGTTC GCCTTCACGG CTCCTGGGCG TGGTGTTTCT ATGCGGGTTG   950
AACGCCAACA CGGCTGCCTC CCCACTGACA CTGTCCCTGA AGGCAACTGC  1000
TGGTGGAGCT TGTTTAACTT GCTCCCACTG GAAGTCCAGA ACAAAGAAAT  1050
CCGCCATGCT AACCAATTTG GCTACCAGAC CAAGCATGGT GTTTCTGGCA  1100
AGTACCTACA GCGGAGGCTG CAAGTTAATG GTCTCCGAGC AGTAACTGAC  1150
CCAAATGGAC CTATCGTCGT ACAGTACTTC TCCGTTAAGG AGAGTTGGAT  1200
CCGCCACTTG AAACTGGCGG GAGAACCCAG CTACCCTGGG TTTGAGGACC  1250
TCCTCAGAAT AAGGGTTGAG CCCAATACGT CGCCATTGGC TGACAAGGAT  1300
GAAAAAATTT TCCGGTTTGG CAGTCACAAG TGGTACGGCG CTGGAAAGAG  1350
AGCAAGGAAA GCACGCTCTT GTGCGACTGC CACAGTCGCT GGCCGCGCTT  1400
TGTCCGTTCG TGAAACCCGG CAGGCCAAGG GGCACGAGGT TGCCGGCGCC  1450
AACAAGGCTG AGCACCTCAA ACATTATTCC CCGCCTGCCG AAGGGAATTG  1500
TGGTTGGCAC TGCATTTCCG CCATCGCCAA CCGGATGGTG AATTCCAAAT  1550
TTGAAACCAC CCTTCCCGAA AGAGTGAGAC CTCCAGATGA CTGGGCTACT  1600
GACGAGGATC TTGTGAATGC CATTCAAATC CTCAGACTTC CTGCGGCCTT  1650
GGACAGGAAC GGTGCTTGTG TTAGCGCCAA GTACGTACTT AAGCTGGAAG  1700
GTGAGCATTG GACTGTCACT GTGACCCCTG GGATGTCTCC TTCTTTGCTC  1750
CCTCTTGAAT GTGTTCAGGG CTGTTGTGAG CACAAGGGTG GTCTTGGTTC  1800
CCCAGATGCA GTCGAGGTCT TCGGATTTGA CCCTGCCTGC CTTGACCGGC  1850
TGGCTGAGGT GATGCACCTG CCTAGCAGTG TTATCCCAGC CGCCCTGGCC  1900
GAAATGTCCG GCGATTCCGA TCGTTCGGCT TCCCCGGTCA CCACCGTGTG  1950
GACTGTTTCG CAGTTCTTTG CCCGTCACAA CGGAGGGAAT CACCCTGACC  2000
AGGCGCGCTT AGGGAAAATT ATCAGCCTTT GTCAGGTGAT TGAGGACTGC  2050
TGCTGTTCCC AGAACAAAAC CAACCGGGTC ACCCCGGAGG AGGTCGCAGC  2100
AAAGATTGAC CTGTACCTCC GTGGTGCAAC AAATCTTGAA GAATGCTTGG  2150
CCAGGCTTGA GAAAGCGCGC CCGCCACGCG TAATGGACAC CTCCTTTGAT  2200
TGGGATGTTG TGCTCCCTGG GGTTGAGGCG GCAACTCAGA CGACCGAACT  2250
GCCCCGGGTC AACCAGTGTC GCGCTCTGGT CCCTGTTGTG ACTCAAAAGT  2300
CTCTGGACAA TAACTCGGTT CCTCTGACCG CCTTCTCGCT GTCCAATTAC  2350
TACTACCGTG CACAAGGTGA CGAGATTCGT CACCGTGACA GGCTAAACGC  2400
CGTACTCTCT AAGTTGGAGG GGGCTGTTCG AGAAGAATAT GGGCTCATGC  2450
```

FIG.33A

```
CGACTGGACC TGGCCCGCGA CCCGCACTGT CGAGCGGGCT CGATGGGCTT 2500
AAAGACAGAT GGAGAGATCT GCTGAAACTA GCCAACGCCC AGACAACCTC 2550
AGAAATGATG GCCTGGGCAG CCGAGCAGGT TGATCTAGAA GCTTGGGTCA 2600
AAAGCTACCC ACGGTGGACA CCACCACCCC CTCCGCCAAG AGTTCAGCCT 2650
CGAAAAGCGA AGCCTGTCAG GAGCTTGCCA GAGAGCAAGC CTGTCCCTGC 2700
CCCGCGCAGG AAGGTTAGAT CCGATCGTGG CAGCCCGGTT TTGTTGGGCG 2750
ACAATGTTCC TAACAGTTGG GAAGACTTGA CTGTCGGTGG CCCCCTTGAT 2800
CTCCTGACCC CACCCGAGTC AGTGACACCT CCGAGTGAGC TTGCGCTTAC 2850
GTCCGCGCCG CAACACACTT TTAGGCCGGT GACACCTTTG GGTGAACCGG 2900
CCCCAGTTCC CGCACCGCGC AGAACTGTGT CCCGACCGGT GACATCCTTG 2950
AATGGGCCGA TCCTTATGTC CGCACCGCGG CACAAGTTTC AGCAGGTGGA 3000
AAAAGCAAAT TTGGCGACAG CAACGCTGAC GTACCAGGAC GAGCCCCTAG 3050
ATTTGTCTGC ATCCTCACAG ACTGAATATG AGGCTTTTCC TCCAGCACCA 3100
CTGCAGAACA TGGGTATTCC GGAGGTGGAA GGGCAAGAAG CTGAGGAAGT 3150
CCTGAGTGGA ATCTCGGATA TACTGGATGA CATCAATTCT GCGCCTGTAT 3200
CATCAAGCGG TTCCCTGTCA AGCGTAGCGA TCACACGCCC AATAGGTGCG 3250
GAGAGTGACC TTACCATTGG CTCAGTCGCC ACTGAAGATA TTCCACGCAT 3300
CCTCGGGAAA ATAGAAGATG CCGGTGAGAT GTCCAACCAG GGACCCTTGG 3350
CATTCTCCGA GGAAAAACCG GTAGATGACC AACCTACCAA AGACCCCCGG 3400
ATGTCGTCGC GGAGGTCAGA CAAGAGCGCA CCAGCTCGGT CCGCAGGCAC 3450
AGGTGGCGTC GGCTTGTTTA CTGATTTGCC GCCTTCAGAC GGTGTGGATG 3500
CGGACGGGGG GGGCCCGTTA CGGACGGTAA AAACAAAAAC TGAAAGGTTC 3550
TTTGACCAGC TGAGCCGTCA GGTTTTTAAC CTCGTCTCCC ATCTCCCTGT 3600
TTTCTTCTCA TACCTTTTCA AACCTGGCAG TGGTTATTCT CCGGGTGATT 3650
GGGGTTTTGC AGCTTTTACT CTATTGTGCC TCTTTTTATG TTACAGTTAT 3700
CCAGCCTTTG GTATTGCTCC CCTCTTGGGT GTATTTTCTG GGTCTTCTCG 3750
GCGCGTCCGA ATGGGGGTTT TTGGTTGCTG GTTGGCTTTT GCTGTTGGTC 3800
TGTTCAAATC TGTGCCCGAC CCAGTCGGCA CTGCTTGTGA ATTTGACTCG 3850
CCAGAGTGCA GAAACATCCT TCATTCTTTT GAGCTTCTCA AACCTTGGGA 3900
CCCTGTTCGC AGCCTTGTTG TGGGCCCCGT CGGTCTCGGC CTTGCCATTC 3950
TTGGCAGGTT ACTGGGCGGG GCACGCTACA TCTGGCACTT TTTGCTTAGG 4000
CTTGGCATTG TTGCAGATTG TATCTTGGCT GGAGCTTATG TGCTTTCTCA 4050
AGGTAGGTGT AAAAAGTGCT GGGGATCTTG TATAAGAACT GCTCCTAATG 4100
AGGTCGCTTT TAACGTGTTT CCTTTCACAC GTGCGACCAG GTCGTCACTT 4150
GTTGACCTGT GTGATCGGTT TTGCGCGCCA AAAGGCATGG ACCCCATTTT 4200
TCTCGCCACT GGGTGGCGCG GGTGCTGGGC CGGCCGAAGC CCCATTGAGC 4250
AACCCTCTGA AAAACCTATC GCGTTTGCCC AGTTGGATGA AAAGAAAATT 4300
ACGGCTAGGA CTGTGGTCGC CCAGCCTTAT GACCCCAACC AAGCCGTAAA 4350
GTGCTTGCGG GTATTGCAGG CGGGTGGGGT GATGGTGGCT GAGGCGGTCC 4400
CAAAAGTGGT CAAGGTTTCC GCTGTTCCAT TCCGAGCCCC CTTTTTTCCT 4450
ACCGGAGTGA AAGTTGACCC TGAATGTAGG GTCGTGGTTG ACCCTGACAC 4500
TTTCACTGCA GCTCTCCGGT CTGGCTACTC CACCACAAAC CTTGTCCTTG 4550
GTGTAGGGGA CTTTGCCCAG CTGAATGGAT TAAAAATCAG GCAAATTTCC 4600
AAGCCTTCAG GAGGAGGCCC ACATCTCATG GCTGCCCTGC ATGTTGCCTG 4650
CTCGATGGTT TTGGACATGC TTGCTGGGAT TTATGTGACT GCGGTGGGTT 4700
CTTGCGGCAC CGGCACCAAC GATCCGTGGT GCGCTAACCC GTTTGGCGTC 4750
CCTGGCTACG GACCTGCCTC CCTCTGCACG TCCAGATTGT GCATTTCCCA 4800
GCATGCCCTT ACCCTGCCCT TGACAGCACT TGTGGCGGGA TTCGGTATCC 4850
AAGAAATTGC CTTAGTCGTT TTGATTTTTG TTTCCATCGG AGGCATGGCT 4900
CATAGGTTGA GTTGTAAAGC TGATATGCTG TGTATTTTGC TTGCAATTGC 4950
```

FIG.33B

CAGCAATGTT TGGGTACCTC TTACCTGGTT GCTTTGTGTG TTTCCTTGCT 5000
GGTTGCGCTG TTTTTCTTTG CACCCCCTTA CCATCCTATG GTTGGTGTTT 5050
TTCTTGATTT CTGTGAATAT GCCTTCAGGA ATCTTGGCCA TGGTGTTGTT 5100
GGTTTCTCTT TGGCTTCTTG GTCGTAATAC TAATGTTGCT GGTCTTGTCA 5150
CCCCCTACGA CATTCATCAT TACACCAGTG GCCCCCGCGG TGTTGCCGCC 5200
TTGGCTACCG CACCAGATGG GACTTACTTA GCCGCTGTCC GCCGTGCTGC 5250
GTTGACTGGC CGCACCATGC TGTTCACCCC GTCCCAGCTT GGGTCTCTTC 5300
TTGAGGGTGC TTTCAGAACT CGAAAGCCCT CACTGAACAC CGTCAATGTG 5350
GTCGGGTCCT CCATGGGCTC TGGCGGGGTG TTTACCATCG ACGGGAAAGT 5400
CAAGTGCGTA ACTGCCGCAC ATGTCCTTAC GGGTAACTCA GCTAGGGTTT 5450
CCGGGGTCGG CTTCAATCAA ATGCTTGACT TTGACGTAAA GGGGGATTTC 5500
GCCATAGCCG ATTGCCCGAA TTGGCAAGGG GCTGCCCCCA AGACCCAATT 5550
CTGCGAGGAT GGATGGACTG GCCGTGCCTA TTGGCTAACA TCCTCTGGCG 5600
TCGAACCCGG CGTCATTGGA AAAGGATTCG CCTTCTGCTT CACCGCGTGC 5650
GGCGATTCCG GGTCCCCAGT GATCACCGAG GCCGGTGAGC TTGTCGGCGT 5700
TCACACGGGA TCAAATAAAC AAGGGGGAGG CATCGTCACG CGCCCCTCAG 5750
GCCAGTTTTG TAATGTGGCA CCCATCAAGC TAAGCGAATT AAGTGAATTC 5800
TTTGCTGGGC CCAAGGTCCC GCTCGGTGAT GTGGAGGTTG GCAACCATAT 5850
AATTAAAGAC ATAGGCGAAG TGCCTTCAGA TCTTTGTGCC TTGCTCGCTG 5900
CCAAACCTGA ACTGGAAGGA GGCCTCTCCA CCGTCCAACT TCTTTGTGTG 5950
TTTTTTCTCC TGTGGAGAAT GATGGGACAT GCCTGGACGC CCTTGGTTGC 6000
TGTGGGTTTC TTTATCTTGA ATGAGGTTCT CCCAGCCGTC CTGGTCCGGA 6050
GTATTTTCTC CTTTGGAATG TTTGTGCTAT CCTGGCTCAC TCCATGGTCT 6100
GCGCAAGTTC TAATGATCAG GCTTCTAACA GCAGCTCTTA ACAGGAACAG 6150
ATGGTCACTT GCCTTTTTCA GCCTTGGTGC GGTGACCGGT TTTGTCGCAG 6200
ATCTTGCGGC CACTCAGGGG CATCCGTTGC AGACAGTGAT GAATTTGAGT 6250
ACCTATGCAT TCCTGCCTCG GATGATGGTT GTGACCTCAC CAGTCCCAGT 6300
GATCGCGTGC GGTGTCGTGC ACCTACTTGC CATCATTTTG TACTTGTTTA 6350
AGTACCGTGG CCTGCACTAT ATCCTTGTTG GCGATGGAGT GTTCTCTGCG 6400
GCTTTCTTCC TGCGGTACTT TGCCGAGGGA AAGTTGAGGG AAGGGTTGTC 6450
CCAATCCTGC GGAATGAATC ATGAGTCCCT AACTGTTGCC CTTGCTATGA 6500
GACTCAATGA CGAGGACTTG GATTTCCTTA CGAAATGGAC TGATTTTAAG 6550
TGCTTTGTTT CTGCGTCCAA CATGAGGAAT GCAGCGGGTC AATTTATCGA 6600
GGCTGCCTAT GCTAAAGCAC TTAGAGTAGA ACTTGCCCAG TTGGTGCAGG 6650
TTGATAAAGT TCGAGGTACT TTGGCCAAAC TTGAAGCTTT TGCTGATACC 6700
GTGGCACCCC AACTCTCGCC CGGTGACATT GTTGTCGCTC TCGGCCATAC 6750
GCCTGTTGGC AGTATCTTCG ACCTAAAGGT TGGTAGCACC AAGCATACCC 6800
TCCAAGCCAT TGAAACCAGA GTCCTTGCAG GGTCCAAAAT GACCGTGGCG 6850
CGCGTCGTCG ACCCGACCCC TACGCCCCCA CCCGCACCCG TGTCCATCCC 6900
CCTCCCACCG AAAGTCCTGG AGAATGCCCC CAACGCTTGG GGGGATGAGG 6950
ACCGTTTGAA TAAGAAGAAG AGGCCCAGGA TGGAAGCCCT CGGCATCTAT 7000
GTTATGGGTG GGAAAAAGTA CCAGAAATTT TGGGACAAGA ATTCCGGTGA 7050
TGTGTTTTAT GAGGAGGTCC ATGACAACAC AGATGAGTGG GAGTGTCTCA 7100
GAGTCGGCGA CCCTGCCGAC TTTGACCCTG AGAAGGGAAC TCTGTGTGGA 7150
CATGTCACCA TTGAAGATAA GGCTTACCAT GTTTACACCT CCTCATCTGG 7200
TAAGAAGTTC TTGGTCCCCG TCAACCCAGA GAATGGAAGA GTCCAGTGGG 7250
AAGCTGCCAA GCTTTCCGTG GAGCAGCCCC TTGGCATGAT GAACGTCGAC 7300
GGTGAACTGA CTGCCAAAGA ACTGGAGAAA CTGAAAAGAA TAATTGATAA 7350
ACTCCAGGGC CTGACTAAGG AGCAGTGTTT AAACTGCTAG CCGCCAGCGG 7400
CTTGACCCGC TGTGGTCGCG GCGGCTTAGT TGTTACTGAG ACAGCGGTGA 7450

FIG.33C

| | | | | | |
|---|---|---|---|---|---|
| AGATCGTCAA | ATTTCACAAC | CGGACCTTCA | CCTTGGGACC | TGTGAATTTA | 7500 |
| AAAGTGGCCA | GTGAGGTTGA | GCTGAAAGAC | GCGGTTGAGC | ACAACCAGCA | 7550 |
| CCCGGTTGCA | AGACCGGTTG | ATGGTGGTGT | TGTGCTCCTG | CGTTCTGCAG | 7600 |
| TTCCTTCGCT | TGTCGACGTC | TTAATCTCCG | GTGCTGATGC | ATCTCCCAAG | 7650 |
| TTACTTGCCC | ATCACGGGCC | GGGAAACACT | GGGATCGATG | GCACGCTCTG | 7700 |
| GGATTTTGAG | TCCGAAGCCA | TTAAAGAGGA | AGTCGCACTT | AGTGCGCAAA | 7750 |
| TAATACAGGC | TTGTGACATT | AGGCGCGGTG | ACGCACCTGA | AATTGGTCTC | 7800 |
| CCTTACAAAC | TATACCCTGT | TAGGGGCAAC | CCTGAGCGGG | TAAAAGGAGT | 7850 |
| TTTGCAGAAT | ACAAGGTTTG | GAGACATACC | TTACAAAACC | CCCAGTGACA | 7900 |
| CCGGAAGCCC | AGTGCACGCG | GCTGCCTGCC | TTACGCCCAA | CGCCACCCCG | 7950 |
| GTGACTGATG | GGCGCTCTGT | CTTGGCCACG | ACCATGCCCT | CCGGGTTCGA | 8000 |
| GTTGTATGTA | CCCACCATTC | CGGCGTCTGT | TCTTGATTAT | CTTGATTCTA | 8050 |
| GGCCTGACTG | CCCTAAACAG | TTGACAGAGC | ACGGCTGTGA | AGATGCCGCA | 8100 |
| TTGAGAGATC | TCTCCAAGTA | TGACTTGTCC | ACCCAAGGCT | TTGTTTTGCC | 8150 |
| TGGAGTTCTT | CGCCTTGTGC | GGAAGTACCT | GTTTGCCCAC | GTGGGTAAGT | 8200 |
| GCCCGTCCGT | TCATCGGCCT | TCCACTTACC | CCGCCAAAAA | TTCTATGGCT | 8250 |
| GGAATAAATG | GGAACAGGTT | TCCAACCAAG | GACATTCAGA | GCGTCCCTGA | 8300 |
| AATCGACGTT | CTGTGCGCAC | AGGCTGTGCG | AGAAAACTGG | CAAACTGTTA | 8350 |
| CCCCTTGTAC | CCTTAAGAAA | CAGTACTGCG | GGAAGAAGAA | GACTAGGACC | 8400 |
| ATACTCGGCA | CCAACAACTT | CATTGCGCTG | GCCCACCGGG | CAGCGTTGAG | 8450 |
| TGGTGTCACC | CAAGGCTTCA | TGAAAAAAGC | ATTTAACTCG | CCCATCGCCC | 8500 |
| TCGGGAAAAA | CAAATTTAAA | GAGCTACAGA | CTCCGGTCCT | GGGCAGGTGC | 8550 |
| CTTGAAGCTG | ATCTTGCATC | CTGCGATCGA | TCCACACCTG | CAATTGTCCG | 8600 |
| CTGGTTTGCC | GCCAATCTTC | TTTATGAACT | TTCCTGTGCT | GAAGAGCATC | 8650 |
| TACCGTCGTA | CGTGCTGAAC | TGCTGCCACG | ACCTACTGGT | CACGCAGTCC | 8700 |
| GGCGCAGTGA | CTAAGAGAGG | TGGCCTGTCG | TCTGGTGACC | CGATCACCTC | 8750 |
| TGTGTCCAAC | ACCATTTACA | GCTTGGTGAT | CTATGCACAG | CACATGGTGC | 8800 |
| TTAGTTACTT | CAAAAGTGGT | CATCCCCATG | GCCTTCTGTT | TTTACAAGAC | 8850 |
| CAGCTAAAGT | TTGAGGACAT | GCTCAAGGTC | CAACCCCTGA | TCGTCTATTC | 8900 |
| GGACGACCTT | GTGCTGTATG | CCGAGTCTCC | CACCATGCCA | AACTACCATT | 8950 |
| GGTGGGTTGA | ACATCTGAAT | CTGATGTTGG | GGTTTCAGAC | GGACCCAAAG | 9000 |
| AAGACAACCA | TAACAGACTC | ACCATCATTT | CTAGGCTGTA | GAATAGTAAA | 9050 |
| TGGACGCCAG | CTAGTCCCCA | ACCGTGACAG | GATTCTCGCG | GCCCTCGCCT | 9100 |
| ACCACATGAA | GGCGAGTAAT | GTTTCTGAAT | ACTACGCCTC | AGCGGCTGCA | 9150 |
| ATACTCATGG | ACAGCTGTGC | TTGTTTAGAG | TATGATCCTG | AATGGTTTGA | 9200 |
| AGAACTTGTA | GTTGGAATAG | CGCAGTGCGC | CCGCAAGGAC | GGCTACAGCT | 9250 |
| TTCCCGGCAC | GCCGTTCTTC | ATGTCCATGT | GGGAAAAACT | CAGGTCAAAT | 9300 |
| TATGAGGGGA | AAAAGTCGAG | AGTGTGCGGG | TACTGCGGGG | CCCCGGCCCC | 9350 |
| GTACGCTACT | GCCTGCGGCC | TTGACGTCTG | CATTTACCAC | ACCCACTTCC | 9400 |
| ACCAGCATTG | TCCAGTCACA | ATCTGGTGCG | GCCATCCAGC | GGGTTCTGGT | 9450 |
| TCTTGTAATG | AGTGCAAGTC | CCCCATAGGG | AAAGGCACAA | GCCCCCTAGA | 9500 |
| CGAGGTGCTA | GAACAAGTCC | CGTATAAGCC | CCCACGGACC | GTAATTATGC | 9550 |
| ATGTGGAGCA | GGGTCTTACC | CCCCTTGACC | CAGGTAGGTA | CCAGACTCGC | 9600 |
| CGCGGATTAG | TCTCCGTCAG | GCGTGGAATC | AAGGGAAATG | AAGTTGAACT | 9650 |
| ACCAGACGGT | GATTATGCTA | GTACCGCCTT | GCTCCCCACC | TGTAAAGAGA | 9700 |
| TCAACATGGT | CGCTGTCGCT | TCTAATGTGT | TGCGCAGCAG | GTTCATCATC | 9750 |
| GGTCCACCCG | GTGCTGGGAA | AACATACTGG | CTCCTTCAAC | AAGTCCAGGA | 9800 |
| TGGTGATGTT | ATTTACACAC | CAACTCACCA | GACCATGCTT | GACATGATCA | 9850 |
| GAGCTTTGGG | GACGTGCCGA | TTCAATGTCC | CTACAGGCAC | AACACTGCAG | 9900 |
| TTCCCTGTCC | CCTCCCGTAC | CGGTCCGTGG | GTTCGCATCC | TAGCCGGTGG | 9950 |

FIG.33D

```
TTGGTGTCCT GGCAAGAATT CCTTCCTGGA TGAAGCAGCG TATTACAATC 10000
ACCTTGATGT CTTGAGGCTT CTTAGTAAAA CTACCCTCAC CTGTCTGGGA 10050
GACTTTAAAC TACTCCACCC AGTGGGTTTT GATTCCCATT GCTATGTTTT 10100
TGACATCATG CCTCAGACTC AATTAAAGAC CATCTGGAGA TTTGGACAGA 10150
ATATCTGTGA TGCCATTCAA CCAGATTACA GGGACAAACT CATGTCCATG 10200
GTCAACACAA CCCGTGTAAC TTACGTGGAA AAACCCGTCA GGTATGGGCA 10250
AGTCCTTACC CCCTACCATA AGGACCGAGA GGACGGCGCC ATCACCATTG 10300
ACTCCAGTCA AGGTGCCACG TTTGATGTGG TTACATTGCA TTTGCCCACT 10350
AAAGATTCAC TCAACAGGCA AAGAGCCCTT GTTGCTATCA CTAGGGCAAG 10400
ACATGCAATT TTTGTGTATG ACCCACACAA GCAACTGCAG AGCCTGTTTG 10450
ATCTCCCTGC AAAAGGCACA CCCGTCAACC TCGCTGTGCA CCGCGACGGG 10500
CAGCTTATTG TGCTGGATAG AAATAACAAG GAATGCACGG TTGCTCAGGC 10550
TCTAGGCAAT GGAGATAAAT TTAGGGCCAC AGACAAACGC GTTGTGGATT 10600
CTCTCCGCGC CATTTGTGCT GATCTAGAAG GGTCGAGCTC TCCGCTCCCC 10650
AAGGTCGCAC ACAACTTGGG ATTTTATTTC TCACCTGATT TAACGCAGTT 10700
TGCTAAACTC CCAGTAGAAC TTGCACCCCA CTGGCCCGTG GTGACAACTC 10750
AGAACAATGA AAAGTGGCCA GATCGGCTGG TTACCAGCCT TCGCCCTATC 10800
CATAAATATA GCCGCGCGTG CATTGGTGCC GGCTATATGG TGGGTCCCTC 10850
GGTGTTCCTG GGCACTCCTG GGGTCGTGTC ATACTACCTC ACAAAATTTG 10900
TTAAGGGCGA GGCTCAAGTG CTTCCGGAGA CGATCTTCAG CACCGGCCGA 10950
ATTGAGGTAG ATTGCCGGGA ATATCTTGAT GATCGGGAGC GAGAAGTTGC 11000
TGCGTCCCTC CCACATGCCT TCATTGGTGA CGTCAAAGGC ACTACCGTTG 11050
GGGGATGTCA CCATGTCACC TCCAAATACC TTCCGCGCTT CCTTCCCAAG 11100
GAAACAGTTG CGGTAGTCGG GGTTTCAAGC CCCGGAAAAG CCGCGAAAGC 11150
AGTGTGCACA CTGACAGATG TGTACCTCCC AGACCTTGAA GCCTATCTCC 11200
ACCCGGAGAC TCAGTCCAAG TGCTGGAAAT TGATGTTGGA CTTCAAGGAA 11250
GTTCGACTGA TGGTCTGGAA AGACAAAACA GCCTATTTCC AACTTGAAGG 11300
TCGCTACTTC ACCTGGTATC AGCTTGCTAG CTATGCCTCG TACATCCGTG 11350
TTCCTGTCAA CTCTACGGTG TACTTGGACC CCTGCATGGG CCCCGCCCTT 11400
TGCAACAGGA GAGTCGTCGG GTCCACCCAC TGGGGGGCTG ACCTCGCAGT 11450
CACCCCTTAT GATTACGGCG CTAAAATCAT CCTGTCTAGC GCGTACCATG 11500
GTGAAATGCC CCCCGGATAC AAAATTCTGG CGTGCGCGGA ATTCTCGTTG 11550
GATGACCCAG TCAGGTATAA ACATACCTGG GGGTTTGAAT CGGATACAGC 11600
GTATCTATAT GAGTTCACCG GAAACGGTGA GGACTGGGAG GATTACAATG 11650
ATGCGTTCCG TGCGCGCCAG AAAGGGAAAA TTTACAAGGC CACTGCCACC 11700
AGCATGAAGT TTTATTTCCC TCCGGGCCCT GTCATTGAAC CAACTTTAGG 11750
CCTGAATTGA GATGAAATGG GGTCTATGCA AAGCCTTTTT GACAAAATTG 11800
GCCAACTTTT TGTGGATGCT TTCACGGAGT TCTTGGTGTC CATTGTTGAT 11850
ATCATTATAT TTTTGGCCAT TTTGTTTGGC TTCACCATCG CAGGTTGGCT 11900
GGTGGTCTTT TGCATCAGAT TGGTTTGCTC CGCGATACTC CGTGCGCGCC 11950
CTGCCATTCA CTCTGAGCAA TTACAGAAGA TCCTATGAGG CCTTTCTCTC 12000
TCAGTGCCAG GTGGACATTC CCACCTGGGG AACTAAACAT CCTTTGGGGA 12050
TGCTTTGGCA CCATAAGGTG TCAACCCTGA TTGATGAAAT GGTGTCGCGT 12100
CGAATGTACC GCATCATGGA AAAAGCAGGA CAGGCTGCCT GGAAACAGGT 12150
AGTGAGCGAG GCTACGCTGT CTCGCATTAG TAGTTTGGAT GTGGTGGCTC 12200
ATTTTCAGCA TCTTGCCGCC ATTGAAGCCG AGACCTGTAA ATATCTGGCC 12250
TCTCGGCTGC CCATGCTACA CCACCTGCGC ATGACAGGGT CAAATGTAAC 12300
CATAGTGTAT AATAGTACTT TGAATCAGGT GTTTGCTGTT TTCCCAACCC 12350
CTGGTTCCCG GCCAAAGCTT CATGATTTCC AGCAATGGCT AATAGCTGTA 12400
CATTCCTCTA TATTTTCCTC TGTTGCAGCT TCTTGTACTC TTTTTGTTGT 12450
```

FIG.33E

```
GCTGTGGTTG CGGGTTCCAA TGCTACGTAC TGTTTTTGGT TTCCGCTGGT 12500
TAGGGGCAAT TTTTCTTTCG AACTCACGGT GAATTACACG GTGTGCCCGC 12550
CTTGCCTCAC CCGGCAAGCA GCCGCAGAGG CCTACGAACC CGGCAGGTCC 12600
CTTTGGTGCA GGATAGGGCA TGATCGATGT GGGGAGGACG ATCATGATGA 12650
ACTAGGGTTT GTGGTGCCGT CTGGCCTCTC CAGCGAAGGC CACTTGACCA 12700
GTGCTTACGC CTGGTTGGCG TTCCTGTCCT TCAGCTATAC GGCCCAGTTC 12750
CATCCCGAGA TATTCGGGAT AGGGAATGTG AGTCGAGTCT ATGTTGACAT 12800
CAAGCACCAA TTCATTTGCG CTGTTCATGA TGGGCAGAAC ACCACCTTGC 12850
CCCACCATGA CAACATTTCA GCCGTGTTTC AGACCTATTA CCAGCATCAG 12900
GTCGACGGGG GCAATTGGTT TCACCTAGAA TGGCTGCGTC CCTTCTTTTC 12950
CTCTTGGTTG GTTTTAAATG TCTCTTGGTT TCTCAGGCGT TCGCCTGCAA 13000
GCCATGTTTC AGTTCGAGTC TTTCAGACAT CAAGACCAAC ACCACCGCAG 13050
CGGCAGGCTT TGCTGTCCTC CAAGACATCA GTTGCCTTAG GCATCGCAAC 13100
TCGGCCTCTG AGGCGATTCG CAAAGTCCCT CAGTGCCGCA CGGCGATAGG 13150
GACACCCGTG TATATCACTG TCACAGCCAA TGTTACCGAT GAGAATTATT 13200
TGCATTCCTC TGATCTTCTC ATGCTTTCTT CTTGCCTTTT CTATGCTTCT 13250
GAGATGAGTG AAAAGGGATT TAAGGTGGTA TTTGGCAATG TGTCAGGCAT 13300
CGTGGCAGTG TGCGTCAACT TCACCAGTTA CGTCCAACAT GTCAAGGAAT 13350
TTACCCAACG TTCCTTGGTA GTTGACCATG TGCGGCTGCT CCATTTCATG 13400
ACGCCCGAGA CCATGAGGTG GGCAACTGTT TTAGCCTGTC TTTTTACCAT 13450
TCTGTTGGCA ATTTGAATGT TTAAGTATGT TGGGGAAATG CTTGACCGCG 13500
GGCTGTTGCT CGCAATTGCT TTTTTTATGG TGTATCGTGC CGTCTTGTTT 13550
TGTTGCGCTC GTCAGCGCCA ACGGGAACAG CGGCTCAAAT TTACAGCTGA 13600
TTTACAACTT GACGCTATGT GAGCTGAATG GCACAGATTG GCTAGCTAAT 13650
AAATTTGACT GGGCAGTGGA GTGTTTTGTC ATTTTTCCTG TGTTGACTCA 13700
CATTGTCTCT TATGGTGCCC TCACTACTAG CCATTTCCTT GACACAGTCG 13750
GTCTGGTCAC TGTGTCTACC GCTGGGTTTG TTCACGGGCG GTATGTTCTG 13800
AGTAGCATGT ACGCGGTCTG TGCCCTGGCT GCGTTGATTT GCTTCGTCAT 13850
TAGGCTTGCG AAGAATTGCA TGTCCTGGCG CTACTCATGT ACCAGATATA 13900
CCAACTTTCT TCTGGACACT AAGGGCAGAC TCTATCGTTG GCGGTCGCCT 13950
GTCATCATAG AGAAAAGGGG CAAAGTTGAG GTCGAAGGTC ACCTGATCGA 14000
CCTCAAAAGA GTTGTGCTTG ATGGTTCCGC GGCTACCCCT GTAACCAGAG 14050
TTTCAGCGGA ACAATGGAGT CGTCCTTAGA TGACTTCTGT CATGATAGCA 14100
CGGCTCCACA AAAGGTGCTC TTGGCGTTTT CTATTACCTA CACGCCAGTG 14150
ATGATATATG CCCTAAAGGT GAGTCGCGGC CGACTGCTAG GGCTTCTGCA 14200
CCTTTTGGTC TTCCTGAATT GTGCTTTCAC CTTCGGGTAC ATGACATTCG 14250
TGCACTTTCA GAGTACAAAT AAGGTCGCGC TCACTATGGG AGCAGTAGTT 14300
GCACTCCTTT GGGGGGTGTA CTCAGCCATA GAAACCTGGA AATTCATCAC 14350
CTCCAGATGC CGTTTGTGCT TGCTAGGCCG CAAGTACATT CTGGCCCCTG 14400
CCCACCACGT TGAAAGTGCC GCAGGCTTTC ATCCGATTGC GGCAAATGAT 14450
AACCACGCAT TTGTCGTCCG GCGTCCCGGC TCCACTACGG TCAACGGCAC 14500
ATTGGTGCCC GGGTTAAAAA GCCTCGTGTT GGGTGGCAGA AAAGCTGTTA 14550
AACAGGGAGT GGTAAACCTT GTTAAATATG CCAAATAACA CCGGCAAGCA 14600
GCAGAAGAGA AAGAAGGGGG ATGGCCAGCC AGTCAATCAG CTGTGCCAGA 14650
TGCTGGGTAA GATCATCGCT CACCAAAACC AGTCCAGAGG CAAGGGACCG 14700
GGAAAGAAAA ATAAGAAGAA AAACCCGGAG AAGCCCCATT TCCCTCTAGC 14750
GACTGAAGAT GATGTCAGAC ATCACTTTAC CCCTAGTGAG CGTCAATTGT 14800
GTCTGTCGTC AATCCAGACC GCCTTTAATC AAGGCGCTGG GACTTGCACC 14850
CTGTCAGATT CAGGGAGGAT AAGTTACACT GTGGAGTTTA GTTTGCCTAC 14900
GCATCATACT GTGCGCCTGA TCCGCGTCAC AGCATCACCC TCAGCATGAT 14950
```

FIG.33F

```
GGGCTGGCAT TCTTGAGGCA TCCCAGTGTT TGAATTGGAA GAATGCGTGG 15000
TGAATGGCAC TGATTGACAT TGTGCCTCTA AGTCACCTAT TCAATTAGGG 15050
CGACCGTGTG GGGGTAAGAT TTAATTGGCG AGAACCACAC GGCCGAAATT 15100
AAAAAAAAAA AAA                                        15113
```

FIG.33G

```
ISU55    .......... .......... .......... .....C.... .......... ....A.....   60
VR2385   .......... .......... .......... .....T.... .......... ....G.....   60
CONSEN.  NNGACGTATA GGTGTTGGCT CTATGCCTTG ACATTYGTAT TGTCAGGAGC TGTGRCCATT   60

ISU55    ..T....... ....-..... .......A.. ..G....... .......... ......-...  118
VR2385   ..C....... .......... .....-.G.. ..A....... .......... ..........  119
CONSEN.  GGYACAGCCC AAAAACTTGC TGCACAGRAA ACRCCCTTCT GTGACAGCCT CCTTCAGGGG  120

ISU55    .......... .......... .......... .......... .......... ..........  178
VR2385   .....-.... .......... .......... .......... .......... ..........  178
CONSEN.  AGCTTGGGGG TCTGTCCCTA GCACCTTGCT TCCGGAGTTG CACTGCTTTA CGGTCTCTCC  180

ISU55    ....T..... .......... ...A...... .....T.... .C........ ..........  238
VR2385   ....C..... .......... ...G...... .....C.... .T........ ..........  238
CONSEN.  ACCCYTTTAA CCATGTCTGG GATRCTTGAT CGGTGYACGT GYACCCCCAA TGCCAGGGTG  240

ISU55    .......... .G.....G.. .......... .....T.... .......... .........T  298
VR2385   .......... .A.....A.. .......... .....C.... .......... .........C  298
CONSEN.  TTTATGGCGG ARGGCCARGT CTACTGCACA CGATGYCTCA GTGCACGGTC TCTCCTTCCY  300

ISU55    .......... .GA..C.C.. .......... T.G..T.... .......... ......A...  358
VR2385   .......... .AG..T.T.. .......... C.A..C.... .......... ......G...  358
CONSEN.  CTGAATCTCC ARRCTYCYGA GCTTGGGGTG YTRGGYCTAT TCTACAGGCC CGAAGARCCA  360

ISU55    .......... .......... .......... .......... .T........ T..G......  418
VR2385   .......... .......... .......... .......... .C........ C..A......  418
CONSEN.  CTCCGGTGGA CGTTGCCACG TGCATTCCCC ACTGTTGAGT GYTCCCCCGC YGGRGCCTGC  420

ISU55    .......... .......... ......G..A .......... .......... ..........  478
VR2385   .......... .......... ......A..G .......... .......... ..........  478
CONSEN.  TGGCTTTCTG CAATCTTTCC AATTGCRCGR ATGACCAGTG GAAACCTGAA CTTCCAACAA  480

ISU55    .......... .......... ....C..T.. .......... ..C....... ..TC..C...  538
VR2385   .......... .......... ....T..A.. .......... ..T....... ..CA..T...  538
CONSEN.  AGAATGGTAC GGGTCGCAGC TGAGYTTWAC AGAGCCGGCC AGYTCACCCC TGYMGTYTTG  540

ISU55    ........G. .......C.. .......... .......... .......... ..........  598
VR2385   ........A. .......T.. .......... .......... .......... ..........  598
CONSEN.  AAGACTCTRC AAGTTTAYGA ACGGGGTTGC CGCTGGTACC CCATTGTTGG ACCTGTCCCT  600
```

FIG.34A

```
ISU55    .......... .......... .......... .......... .......... A..G......  658
VR2385   .......... .......... .......... .......... .......... G..A......  658
CONSEN.  GGAGTGGCCG TTTTCGCCAA CTCCCTACAT GTGAGTGATA AACCTTTCCC RGGRGCAACT  660

ISU55    ......T... .......... .......... .......... .C........ C.........  718
VR2385   ......C... .......... .......... .......... .T........ T.........  718
CONSEN.  CACGTGYTAA CCAACCTGCC GCTCCCGCAG AGACCCAAGC CYGAAGACTT YTGCCCCTTT  720

ISU55    ..A..C..C. ....C..C.. .......... .......... .T........ CA......GA  778
VR2385   ..G..T..T. ....T..T.. .......... .......... .C........ TG......AG  778
CONSEN.  GARTGYGCYA TGGCYACYGT CTATGACATT GGTCATGACG CYGTCATGTA YRTGGCCGRR  780

ISU55    .......... .......... .........G G..G...... .......... .......A..  838
VR2385   .......... .......... .........A A..A...... .......... .......G..  838
CONSEN.  GGGAAAGTCT CCTGGGCCCC TCGTGGCGGR RATGRAGTGA AATTTGAAAC TGTCCCCRAG  840

ISU55    .G....G.G. .A.C...... ...A...... T.....T... .......... C.........  898
VR2385   .A....A.A. .G.T...... ...G...... A.....A... .......... T.........  898
CONSEN.  GRGTTGRART TRAYTGCGGA CCGRCTCCGC WCCTCCWTCC CGCCCCACCA YGTAGTGGAC  900

ISU55    .....C.G.. .T..T..... AA.C....A. T......CC. .......... C.G.......  958
VR2385   .....T.A.. .C..C..... GG.T....G. C......TT. .......... T.A.......  958
CONSEN.  ATGTCYARGT TYGCYTTCAC RRCYCCTGRG YGTGGTGYYT CTATGCGGGT YGRACGCCAA  960

ISU55    .GT....... ......G...G T......... .......... .T........ ........GG. 1018
VR2385   .AC....... ......A...A C......... .......... .C........ ........AA. 1018
CONSEN.  CRYGGCTGCC TCCCCRCTGR YACTGTCCCT GAAGGCAACT GYTGGTGGAG CTTGTTTRRC 1020

ISU55    .C........ ........T.T .......... ..T...T... .C....G... .........A 1078
VR2385   .T........ ........C.A .......... ..C...C... .T....A... .........G 1078
CONSEN.  TYGCTCCCAC TGGAAGTYCW GAACAAAGAA ATYCGCYATG CYAACCRATT TGGCTACCAR 1080

ISU55    ..T....... ....C..... .......... .......... .......... .........G 1138
VR2385   ..C....... ....T..... .......... .......... .......... .........A 1138
CONSEN.  ACYAAGCATG GTGTYTCTGG CAAGTACCTA CAGCGGAGGC TGCAAGTTAA TGGTCTCCGR 1140

ISU55    .......... ..A..C.... .......... A....A.... .......... .......... 1198
VR2385   .......... ..C..A.... .......... G....G.... .......... .......... 1198
CONSEN.  GCAGTAACTG ACMCAMATGG ACCTATCGTC RTACARTACT TCTCCGTTAA GGAGAGTTGG 1200
```

FIG.34B

```
ISU55     .......... ...G...... ..A....... ...CT..... .......... T......... 1258
VR2385    .......... ...A...... ..G....... ...TA..... .......... C......... 1258
CONSEN.   ATCCGCCACT TGARACTGGC GGRAGAACCC AGCYWCCCTG GGTTTGAGGA YCTCCTCAGA 1260

ISU55     .......... .......C.. A......... CT..G..... G......... C.....T... 1318
VR2385    .......... .......T.. G......... GC..A..... A......... T.....G... 1318
CONSEN.   ATAAGGGTTG AGCCCAAYAC RTCGCCATTG SYTGRCAAGG RTGAAAAAAT YTTCCGKTTT 1320

ISU55     ....A..... .A........ .......... .......... .......... .A........ 1378
VR2385    ....G..... .G........ .......... .......... .......... .T........ 1378
CONSEN.   GGCARTCACA ARTGGTACGG CGCTGGAAAG AGAGCAAGGA AAGCACGCTC TWGTGCGACT 1380

ISU55     ..T..G.... ...A...... ........C. .......... ...T...... ..A....... 1438
VR2385    ..C..A.... ...G...... ........T. .......... ...A...... ..G....... 1438
CONSEN.   GCYACRGTCG CTGRCCGCGC TTTGTCCGYT CGTGAAACCC GGCWGGCCAA GGRGCACGAG 1440

ISU55     .......... ....T..... .......... ..G..C..C. .......... .......... 1498
VR2385    .......... ....C..... .......... ..A..T..T. .......... .......... 1498
CONSEN.   GTTGCCGGCG CCAAYAAGGC TGAGCACCTC AARCAYTAYT CCCCGCCTGC CGAAGGGAAT 1500

ISU55     .......... ....T..... ........T. .......... ....C..... .......... 1558
VR2385    .......... ....C..... ........C. .......... ....T..... .......... 1558
CONSEN.   TGTGGTTGGC ACTGYATTTC CGCCATCGYC AACCGGATGG TGAAYTCCAA ATTTGAAACC 1560

ISU55     .....C.... .G........ .......... .......... .......... .....C...C 1618
VR2385    .....T.... .A........ .......... .......... .......... .....T...T 1618
CONSEN.   ACCCTYCCCG ARAGAGTGAG ACCTCCAGAT GACTGGGCTA CTGACGAGGA TCTTGYGAAY 1620

ISU55     A....C.... .......G.. .......... .........G G......... .......... 1678
VR2385    G....T.... .......A.. .......... .........A A......... .......... 1678
CONSEN.   RCCATYCAAA TCCTCAGRCT TCCTGCGGCC TTGGACAGGR RCGGTGCTTG TGTTAGCGCC 1680

ISU55     .....T.... .......... ......A... .........T .......... .......... 1738
VR2385    .....C.... .......... ......G... .........A .......... .......... 1738
CONSEN.   AAGTAYGTAC TTAAGCTGGA AGGTGARCAT TGGACTGTCW CTGTGACCCC TGGGATGTCT 1740

ISU55     ..C....... ....C..... ...C..C... .......... .T..T...A. C......... 1798
VR2385    ..T....... ....T..... ...T..T... .......... .G..C...G. T......... 1798
CONSEN.   CCYTCTTTGC TCCCYCTTGA ATGYGTYCAG GGCTGTTGTG AKCAYAAGRG YGGTCTTGGT 1800
```

FIG.34C

```
 ISU55    .........A .G.....A.. T.C....... .......... .......... ..........  1858
VR2385    .........G .A.....G.. C.T....... .......... .......... ..........  1858
CONSEN.   TCCCCAGATR CRGTCGARGT YTYCGGATTT GACCCTGCCT GCCTTGACCG GCTGGCTGAG  1860

 ISU55    .......... .......... ..CC...... .....T.... .......... ..........  1918
VR2385    .......... .......... ..TT...... .....C.... .......... ..........  1918
CONSEN.   GTGATGCACC TGCCTAGCAG TGYYATCCCA GCCGCYCTGG CCGAAATGTC CGGCGATTCC  1920

 ISU55    ......C... .......... ......T... .....G.... .......... ......C...  1978
VR2385    ......T... .......... ......C... .....T.... .......... ......T...  1978
CONSEN.   GATCGTYCGG CTTCCCCGGT CACCACYGTG TGGACKGTTT CGCAGTTCTT TGCCCGYCAC  1980

 ISU55    .CA....... .......... .....T.T.. .....A.... .C..T..... ......A...  2038
VR2385    .AC....... .......... .....C.C.. .....G.... .T..C..... ......G...  2038
CONSEN.   AMMGGAGGGA ATCACCCTGA CCAGGYGYGC TTAGGRAAAA TYATYAGCCT TTGTCARGTG  2040

 ISU55    C.....AGT. .........T .......... .......... C......... A........G  2098
VR2385    A.....GAC. .........C .......... .......... T......... G........A  2098
CONSEN.   MTTGAGRRYT GCTGCTGTTY CCAGAACAAA ACCAACCGGG YCACCCCGGA RGAGGTCGCR  2100

 ISU55    .....A.... .......... ...C..A... ...GG..... .......... ..........  2158
VR2385    .....G.... .......... ...T..T... ...AA..... .......... ..........  2158
CONSEN.   GCAAARATTG ACCTGTACCT CCGYGGWGCA ACARRTCTTG AAGAATGCTT GGCCAGGCTT  2160

 ISU55    ....GG..T. ....A..GA. T......... .......... .....A.... ......T...  2218
VR2385    ....AA..G. ....G..AC. C......... .......... .....G.... ......C...  2218
CONSEN.   GAGARRGCKC GCCCRCCRMG YGTAATGGAC ACCTCCTTTG ATTGGRATGT TGTGCTYCCT  2220

 ISU55    ...T...... .......... ...A...A.. .C.....A.. .......... ..........  2278
VR2385    ...G...... .......... ...G...G.. .T.....G.. .......... ..........  2278
CONSEN.   GGGKTTGAGG CGGCAACTCA GACRACCRAA CYGCCCCRGG TCAACCAGTG TCGCGCTCTG  2280

 ISU55    .......... ........G. ....T..... ...GG..... .......... ..........  2338
VR2385    .......... ........A. ....C..... ...AA..... .......... ..........  2338
CONSEN.   GTCCCTGTTG TGACTCAARA GTCTYTGGAC AATRRCTCGG TTCCTCTGAC CGCCTTCTCG  2340

 ISU55    .......... .......... C..G.....A ......G... .......... T...T.....  2398
VR2385    .......... .......... T..A.....T ......A... .......... C...C.....  2398
CONSEN.   CTGTCCAATT ACTACTACCG YGCRCAAGGW GACGAGRTTC GTCACCGTGA YAGGYTAAAC  2400
```

FIG.34D

```
ISU55   .......... .C........ ...T...... .......... .C........ ...A......  2458
VR2385  .......... .T........ ...G...... .......... .T........ ...G......  2458
CONSEN. GCCGTACTCT CYAAGTTGGA GGGKGCTGTT CGAGAAGAAT AYGGGCTCAT GCCRACTGGA  2460

ISU55   .......... .......... .C....T... ..T..C.A.. .......... ..........  2518
VR2385  .......... .......... .T....C... ..C..T.G.. .......-.. .......-.-  2515
CONSEN. CCTGGCCCGC GACCCGCACT GYCGAGYGGG CTYGAYGRGC TTAAAGACCA GATGGAGGAG  2520

ISU55   .......... .......... T......... ..T....... .......... ..........  2578
VR2385  .......... .......... C......... ..C....... .......... ..........  2575
CONSEN. GATCTGCTGA AACTAGCCAA YGCCCAGACA ACYTCAGAAA TGATGGCCTG GGCAGCCGAG  2580

ISU55   .......... ..A....... ...T....A. .......... .......... G........A  2638
VR2385  .......... ..G....... ...C....G. .......... .......... A........G  2635
CONSEN. CAGGTTGATC TARAAGCTTG GGTYAAAARC TACCCACGGT GGACACCACC RCCCCCTCCR  2640

ISU55   ........C. .......... .A.A...... ....A...T. .......... ..........  2698
VR2385  ........T. .......... .G.G...... ....G...C. .......... ..........  2695
CONSEN. CCAAGAGTYC AGCCTCGAAA ARCRAAGCCT GTCARGAGYT TGCCAGAGAG CAAGCCTGTC  2700

ISU55   ..C....... .......... ...G...... T......... ..A....A.. ..........  2758
VR2385  ..T....... .......... ...A...... C......... ..G....G.. ..........  2755
CONSEN. CCYGCCCCGC GCAGGAAGGT TAGRTCCGAT YGTGGCAGCC CGRTTTTRTT GGGCGACAAT  2760

ISU55   .......... .......... T........T .......... ........TC ....T.....  2818
VR2385  .......... .......... C........C .......... ........CT ....C.....  2815
CONSEN. GTTCCTAACA GTTGGGAAGA YTTGACTGTY GGTGGCCCCC TTGATCTCYY GACCYCACCC  2820

ISU55   ...C.G.... .......... .......... ..C.T..... .A........ ..........  2878
VR2385  ...T.A.... .......... .......... ..T.C..... .G........ ..........  2875
CONSEN. GAGYCRGTGA CACCTCCGAG TGAGCTTGCG CTYAYGTCCG CRCCGCAACA CACTTTTAGG  2880

ISU55   T......T.. .C........ .......... .........T T.....A... ....C.....  2938
VR2385  C......C.. .T........ .......... .........C C.....G... ....T.....  2935
CONSEN. YCGGTGAYAC CYTTGGGTGA ACCGGCCCCA GTTCCCGCAY YGCGCARAAC TGTGYCCCGA  2940

ISU55   .....A...C ......GC.A ........C. G......... ...AATG... ..........  2998
VR2385  .....G...T ......AT.G ........T. A......... ...GGCA... ..........  2995
CONSEN. CCGGTRACAY CCTTGARYGR GCCGATCCYT RTGTCCGCAC CGCRRYRCAA GTTTCAGCAG  3000
```

FIG.34E

```
ISU55   .......... .GG..C.... .G.....G.. ...G...... .......... ..........  3058
VR2385  .......... .AA..T.... .A.....A.. ...A...... .......... ..........  3055
CONSEN. GTGGAAAAAG CRRATYTGGC GRCAGCARCG CTGRCGTACC AGGACGAGCC CCTAGATTTG  3060

ISU55   .......... ....A..... .......... .C...C.T.. A......... ..G......C  3118
VR2385  .......... ....G..... .......... .T...T.C.. C......... ..A......T  3115
CONSEN. TCTGCATCCT CACARACTGA ATATGAGGCT TYTCCYCYAG MACCACTGCA GARCATGGGY  3120

ISU55   G...TAA... .......A.. .......... .......... .......... ...C......  3178
VR2385  A...CGG... .......G.. .......... .......... .......... ...T......  3175
CONSEN. RTTCYRRAGG TGGAAGGRCA AGAAGCTGAG GAAGTCCTGA GTGGAATCTC GGAYATACTG  3180

ISU55   .......... .CC.G.T... .......... .A...C.... .......... GAG.......  3238
VR2385  .......... .TT.T.C... .......... .G...T.... .......... AGC.......  3235
CONSEN. GATGACATCA AYYCKGYGCC TGTATCATCA ARCGGYTCCC TGTCAAGCGT RRSGATCACA  3240

ISU55   .......... .......... .......... .......... .......... ..........  3298
VR2385  .......--- ---------- ---------- ---------- ---------- ----------  3242
CONSEN. CGCCCAAAAT ACTCAGCTCA AGCCATCATC GACTCGGGCG GGCCCTGCAG TGGGCACCTC  3300

ISU55   .......... .......... .......... .......... .......... ..........  3358
VR2385  ---------- ---------- ---------- ---------- ---------- ----------  3242
CONSEN. CAAGGGATAA AGGAAACATG CCTCAGTATC ATGCGTGAGG CATGTGATGC GACTAAGCTT  3360

ISU55   .......... .......... .......... .......... .......... ..........  3418
VR2385  ---------- ---------- ---------- ---------- ---------- ----------  3242
CONSEN. GATGACCCTA CTACGCAGGA ATGGCTTTCT CGCATGTGGG ATAGGGTGGA CATGCTGACT  3420

ISU55   .......... .......... .......... .......... .......... ..........  3478
VR2385  ---------- ---------- ---------- ---------- ---------- ----------  3242
CONSEN. TGGCGCAACA CGTCTGCTTA CCAGGCGCTT CGCACCTTAG ATAGCAGGTT TGAGTTTCTC  3480

ISU55   .......... .......... .......... .......... .......... ..........  3538
VR2385  ---------- ---------- ---------- ---------- ---------- ----------  3242
CONSEN. CCAAAAATGA TACTCGAGAC ACCGCCGCCC TATCCGTGTG AGTTTGTGAT GATGCCTCAC  3540

ISU55   .......... ........A. .......... ..T....... .......... ..........  3598
VR2385  ---------- ------..G. .......... ..C....... .......... ..........  3286
CONSEN. ACGCCTGCAC CTTCTGTARG TGCGGAGAGT GAYCTTACCA TTGGCTCAGT CGCCACTGAA  3600
```

FIG.34F

```
ISU55   ...G...... .......... .......... ....T...C. .....A.... ..........  3658
VR2385  ...A...... .......... .......... ....C...T. .....T.... ..........  3346
CONSEN. GATRTTCCAC GCATCCTCGG GAAAATAGAA GATGYCGGYG AGATGWCCAA CCAGGGACCC  3660

ISU55   .......... ........G. ......G... C........G ....G.G.T. ....TCA.T.  3718
VR2385  .......... ........A. ......A... G........A ....A.A.C. ....ATG.C.  3406
CONSEN. TTGGCATTCT CCGAGGAARA ACCGGTRGAT SACCAACCTR CCAARGRCYC CCGGWYRTYG  3720

ISU55   .........C .T...G.... TA.....A.. .T.......A ..G....... .AC..A...A  3778
VR2385  .........T .A...A.... CG.....G.. .G.......G ..A....... .GT..G...G  3466
CONSEN. TCGCGGAGGY CWGACRAGAG YRCACCARCT CKGTCCGCAR GCRCAGGTGG CRYCGRCTTR  3780

ISU55   CCC..C.... ......T... .......... .......... .......G.. ..........  3838
VR2385  TTT..T.... ......C... .......... .......... .......C.. ..........  3526
CONSEN. YYYACYGATT TGCCGCYTTC AGACGGTGTG GATGCGGACG GGGGGGGSCC GTTACGGACG  3840

ISU55   .......AC. .......... .C........ ..A....... .......... ..........  3898
VR2385  .......CA. .......... .T........ ..G....... .......... ..........  3586
CONSEN. GTAAAAAMMA AAACTGAAAG GYTCTTTGAC CARCTGAGCC GTCAGGTTTT TAACCTCGTC  3900

ISU55   .......... .......... ....CG.... C..CT..... ..G....... ..........  3958
VR2385  .......... .......... ....TA.... T..AA..... ..A....... ..........  3646
CONSEN. TCCCATCTCC CTGTTTTCTT CTCAYRCCTT YTCMWACCTG GCRGTGGTTA TTCTCCGGGT  3960

ISU55   ........C. .......... .......... .......... .G.....T.. C..C......  4018
VR2385  ........T. .......... .......... .......... .A.....C.. T..T......  3706
CONSEN. GATTGGGGYT TTGCAGCTTT TACTCTATTG TGCCTCTTTT TRTGTTAYAG YTAYCCAGCC  4020

ISU55   .......... .......T.. .......... .......... .......... T.........  4078
VR2385  .......... .......C.. .......... .......... .......... C.........  3766
CONSEN. TTTGGTATTG CTCCCCTYTT GGGTGTATTT TCTGGGTCTT CTCGGCGCGT YCGAATGGGG  4080

ISU55   ........C. .......... .......... ..C....... .GC.....T. ..........  4138
VR2385  ........T. .......... .......... ..T....... .AT.....C. ..........  3826
CONSEN. GTTTTTGGYT GCTGGTTGGC TTTTGCTGTT GGYCTGTTCA ARYCTGTGYC CGACCCAGTC  4140

ISU55   .......... ....G..... .......... ..T....... ......T... ..........  4198
VR2385  .......... ....A..... .......... ..C....... ......A... ..........  3886
CONSEN. GGCACTGCTT GTGARTTTGA CTCGCCAGAG TGYAGAAACA TCCTTCWTTC TTTTGAGCTT  4200
```

FIG.34G

```
ISU55   .......... .......... .......... .......... .......... ...T......  4258
VR2385  .......... .......... .......... .......... .......... ...C......  3946
CONSEN. CTCAAACCTT GGGACCCTGT TCGCAGCCTT GTTGTGGGCC CCGTCGGTCT CGGYCTTGCC  4260

ISU55   .......... .......... .......... .GT....... .......... ..........  4318
VR2385  .......... .......... .......... .AC....... .......... ..........  4006
CONSEN. ATTCTTGGCA GGTTACTGGG CGGGGCACGC TRYATCTGGC ACTTTTTGCT TAGGCTTGGC  4320

ISU55   ......A... .........C .......... .......... .......... ..........  4378
VR2385  ......G... .........T .......... .......... .......... ..........  4066
CONSEN. ATTGTTRCAG ATTGTATCYT GGCTGGAGCT TATGTGCTTT CTCAAGGTAG GTGTAAAAAG  4380

ISU55   .......... .......... .......... .G........ .C........ .........T  4438
VR2385  .......... .......... .......... .A........ .T........ .........C  4126
CONSEN. TGCTGGGGAT CTTGTATAAG AACTGCTCCT ARTGAGGTCG CYTTTAACGT GTTTCCTTTY  4440

ISU55   .......... .......... ....ACCA.. T....C.... .......T.. ..........  4498
VR2385  .......... .......... ....GTTG.. C....T.... .......C.. ..........  4186
CONSEN. ACACGTGCGA CCAGGTCGTC ACTTRYYRAC YTGTGYGATC GGTTTTGYGC GCCAAAAGGC  4500

ISU55   .......... ....C..... .......... .......... ..A....... ..........  4558
VR2385  .......... ....T..... .......... .......... ..G....... ..........  4246
CONSEN. ATGGACCCCA TTTTYCTCGC CACTGGGTGG CGCGGGTGCT GGRCCGGCCG AAGCCCCATT  4560

ISU55   .......... .......... C......... .......... .......... G.........  4618
VR2385  .......... .......... T......... .......... .......... A.........  4306
CONSEN. GAGCAACCCT CTGAAAAACC YATCGCGTTT GCCCAGTTGG ATGAAAAGAA RATTACGGCT  4620

ISU55   .A........ .......... .......... .......... .......T.. ......G..A  4678
VR2385  .G........ .......... .......... .......... .......C.. ......A..G  4366
CONSEN. ARGACTGTGG TCGCCCAGCC TTATGACCCC AACCAAGCCG TAAAGTGYTT GCGGGTRTTR  4680

ISU55   ........C. .......... .........A ..T....... .......... .........C  4738
VR2385  ........T. .......... .........G ..C....... .......... .........T  4426
CONSEN. CAGGCGGGYG GGGTGATGGT GGCTGAGGCR GTYCCAAAAG TGGTCAAGGT TTCCGCTGTY  4740

ISU55   .......... .......C.. ...C..T..G .......... .T....GG.. C...A.....  4798
VR2385  .......... .......T.. ...T..C..A .......... .C....AA.. T...G.....  4486
CONSEN. CCATTCCGAG CCCCCTTYTT TCCYACYGGR GTGAAAGTTG AYCCTGRRTG YAGGRTCGTG  4800
```

FIG.34H

```
ISU55    ........C. ....C.... .......... ........T. .......... ......C...  4858
VR2385   ........T. ....T.... .......... ........C. .......... ......T...  4546
CONSEN.  GTTGACCCYG ACACYTTCAC TGCAGCTCTC CGGTCTGGYT ACTCCACCAC AAACCTYGTC  4860

ISU55    .......... .......... .......... .......... .T........ ..........  4918
VR2385   .......... .......... .......... .......... .C........ ..........  4606
CONSEN.  CTTGGTGTAG GGGACTTTGC CCAGCTGAAT GGATTAAAAA TYAGGCAAAT TTCCAAGCCT  4920

ISU55    ..T....... .......C.. .......... .......... .T........ .ACC...C..  4978
VR2385   ..A....... .......T.. .......... .......... .C........ .GTT...G..  4666
CONSEN.  TCWGGAGGAG GCCCACAYCT CATGGCTGCC CTGCATGTTG CYTGCTCGAT GRYYTTGSAC  4980

ISU55    .......... .......C.. .......... .......... .......... ..........  5038
VR2385   .......... .......T.. .......... .......... .......... ..........  4726
CONSEN.  ATGCTTGCTG GGATTTAYGT GACTGCGGTG GGTTCTTGCG GCACCGGCAC CAACGATCCG  5040

ISU55    .......... .........C .......... ..T....... GA..T..... .........A  5098
VR2385   .......... .........G .......... ..C....... CC..C..... .........G  4786
CONSEN.  TGGTGCGCTA ACCCGTTTGS CGTCCCTGGC TAYGGACCTG SMTCYCTCTG CACGTCCARA  5100

ISU55    ........C. ....A...G. ..C....... .....A.... ........T. ..........  5158
VR2385   ........T. ....G...C. ..T....... .....G.... ........G. ..........  4846
CONSEN.  TTGTGCATYT CCCARCATGS CCTYACCCTG CCCTTRACAG CACTTGTKGC GGGATTCGGT  5160

ISU55    ..T..G.... .......G.. .......... .......... ....G..... ..........  5218
VR2385   ..C..A.... .......A.. .......... .......... ....A..... ..........  4906
CONSEN.  ATYCARGAAA TTGCCTTRGT CGTTTTGATT TTTGTTTCCA TCGGRGGCAT GGCTCATAGG  5220

ISU55    .......... .G........ .......G.. .......... .C......T. ..........  5278
VR2385   .......... .A........ .......A.. .......... .T......A. ..........  4966
CONSEN.  TTGAGTTGTA ARGCTGATAT GCTGTGTRTT TTGCTTGCAA TYGCCAGCVA TGTTTGGGTA  5280

ISU55    .....A.... .......... .........C .......... .......... .........A  5338
VR2385   .....T.... .......... .........T .......... .......... .........C  5026
CONSEN.  CCTCTWACCT GGTTGCTTTG TGTGTTTCCY TGCTGGTTGC GCTGTTTTTC TTTGCACCCM  5340

ISU55    ..C....... .......... .......... ........A. .......... ..........  5398
VR2385   ..T....... .......... .......... ........G. .......... ..........  5086
CONSEN.  CTYACCATCC TATGGTTGGT GTTTTTCTTG ATTTCTGTRA ATATGCCTTC AGGAATCTTG  5400
```

FIG.34I

```
ISU55    .......... .......... .......... .....A...T .......... C.........  5458
VR2385   .......... .......... .......... .....T...A .......... T.........  5146
CONSEN.  GCCATGGTGT TGTTGGTTTC TCTTTGGCTT CTTGGWCGTW ATACTAATGT YGCTGGTCTT  5460

ISU55    ........T. .T..T..... C......... .......... .......... ..........  5518
VR2385   ........C. .C..C..... T......... .......... .......... ..........  5206
CONSEN.  GTCACCCCYT AYGAYATTCA YCATTACACC AGTGGCCCCC GCGGTGTTGC CGCCTTGGCT  5520

ISU55    ..A....... .......C.. ...G...... ........C. .......... ..........  5578
VR2385   ..C....... .......T.. ...A...... ........T. .......... ..........  5266
CONSEN.  ACMGCACCAG ATGGGACYTA CTTRGCCGCT GTCCGCCGYG CTGCGTTGAC TGGCCGCACC  5580

ISU55    ........T. .......T.. .........C .......... .C.....T.. .....A....  5638
VR2385   ........C. .......C.. .........T .......... .T.....C.. .....G....  5326
CONSEN.  ATGCTGTTYA CCCCGTCYCA GCTTGGGTCY CTTCTTGAGG GYGCTTTYAG AACTCRAAAG  5640

ISU55    .....GT... .......... .......... .......... .......... ......C...  5698
VR2385   .....AC... .......... .......... .......... .......... ......T...  5386
CONSEN.  CCCTCRYTGA ACACCGTCAA TGTGGTCGGG TCCTCCATGG GCTCTGGCGG GGTGTTYACC  5700

ISU55    .......... ..A....... .......... .......... .......C.. T.........  5758
VR2385   .......... ..G....... .......... .......... .......T.. C.........  5446
CONSEN.  ATCGACGGGA AARTCAAGTG CGTAACTGCC GCACATGTCC TTACGGGYAA YTCAGCTAGG  5760

ISU55    .......... ....T..... C......... ........T. ....A..A.. C........G  5818
VR2385   .......... ....C..... T......... ........C. ....G..G.. T........A  5506
CONSEN.  GTTTCCGGGG TCGGYTTCAA YCAAATGCTT GACTTTGAYG TAAARGGRGA YTTCGCCATR  5820

ISU55    .......... ..G....... .........T .......... ........A. ..........  5878
VR2385   .......... ..A....... .........C .......... ........G. ..........  5566
CONSEN.  GCCGATTGCC CGRATTGGCA AGGGGCTGCY CCCAAGACCC AATTCTGCRA GGATGGATGG  5880

ISU55    .......... ....C..... .......... .......... ....T..... ..........  5938
VR2385   .......... ....T..... .......... .......... ....C..... ..........  5626
CONSEN.  ACTGGCCGTG CCTAYTGGCT AACATCCTCT GGCGTCGAAC CCGGYGTCAT TGGAAAAGGA  5940

ISU55    .......... .......... .......... .......... .......... ..........  5998
VR2385   .......... .......... .......... .......... .......... ..........  5686
CONSEN.  TTCGCCTTCT GCTTCACCGC GTGCGGCGAT TCCGGGTCCC CAGTGATCAC CGAGGCCGGT  6000
```

FIG.34J

```
ISU55   .......... .T..C..... .......... ........A. .......... ..........  6058
VR2385  .......... .C..T..... .......... ........G. .......... ..........  5746
CONSEN. GAGCTTGTCG GYGTYCACAC GGGATCAAAT AAACAAGGRG GAGGCATCGT CACGCGCCCC  6060

ISU55   .......... .......... .T.....G.. .......... .......... ..........  6118
VR2385  .......... .......... .G.....A.. .......... .......... ..........  5806
CONSEN. TCAGGCCAGT TTTGTAATGT GKCACCCRTC AAGCTAAGCG AATTAAGTGA ATTCTTTGCT  6120

ISU55   .....T.... .......... ........A.. ........G.. ........C.. ...T......  6178
VR2385  .....C.... .......... ........G.. ........A.. ........T.. ...C......  5866
CONSEN. GGGCCYAAGG TCCCGCTCGG TGATGTGRAG GTTGGCARCC ATATAATYAA AGAYATAGGC  6180

ISU55   ..G..A.... .......... C........T .......... .......... ..........  6238
VR2385  ..A..G.... .......... T........C .......... .......... ..........  5926
CONSEN. GARGTRCCTT CAGATCTTTG YGCCTTGCTY GCTGCCAAAC CTGAACTGGA AGGAGGCCTC  6240

ISU55   .......... .......G.. .......... .......... .G........ ..........  6298
VR2385  .......... .......T.. .......... .......... .A........ ..........  5986
CONSEN. TCCACCGTCC AACTTCTKTG TGTGTTTTTT CTCCTGTGGA GRATGATGGG ACATGCCTGG  6300

ISU55   .......... .......... G......... .......... ....T..... T.........  6358
VR2385  .......... .......... T......... .......... ....C..... C.........  6046
CONSEN. ACGCCCTTGG TTGCTGTGGG KTTCTTTATC TTGAATGAGG TTCTYCCAGC YGTCCTGGTC  6360

ISU55   ......G.C. .......... .......... .......... .....A.... ..........  6418
VR2385  ......A.T. .......... .......... .......... .....T.... ..........  6106
CONSEN. CGGAGTRTYT TCTCCTTTGG AATGTTTGTG CTATCCTGGC TCACWCCATG GTCTGCGCAA  6420

ISSUE   .....G.... .......... .......... .......... ......G.T.. ..........  6478
VR2385  .....A.... .......... .......... .......... ......T.G.. ..........  6166
CONSEN. GTTCTRATGA TCAGGCTTCT AACAGCAGCT CTTAACAGGA ACAGAKGKTC ACTTGCCTTT  6480

ISU55   .A..C...C. ....AA.A.. ...C...... .......... ...TT..... ...A......  6538
VR2385  .T..G...T. ....GG.G.. ...T...... .......... ...CC..... ...G......  6226
CONSEN. TWCASCCTYG GTGCRRTRAC CGGYTTTGTC GCAGATCTTG CGGYYACTCA GGGRCATCCG  6540

ISU55   ......G... .......... ...C...... .......... .......... ..........  6598
VR2385  ......A... .......... ...T...... .......... .......... ..........  6286
CONSEN. TTGCAGRCAG TGATGAATTT GAGYACCTAT GCATTCCTGC CTCGGATGAT GGTTGTGACC  6600
```

FIG.34K

```
ISU55    .......... .......... ...T.....T .C......G. .......... ..........  6658
VR2385   .......... .......... ...C.....C .T......A. .......... ..........  6346
CONSEN.  TCACCAGTCC CAGTGATCGC GTGYGGTGTY GYGCACCTRC TTGCCATCAT TTTGTACTTG  6660

ISU55    .......... .C........ .A.G...... .......... ...C...... ..........  6718
VR2385   .......... .T........ .T.T...... .......... ...T...... ..........  6406
CONSEN.  TTTAAGTACC GYGGCCTGCA CWAKATCCTT GTTGGCGATG GAGYGTTCTC TGCGGCTTTC  6720

ISU55    ........A. .......... .......... .........G ....G..... ..........  6778
VR2385   ........G. .......... .......... .........T ....C..... ..........  6466
CONSEN.  TTCCTGCGRT ACTTTGCCGA GGGAAAGTTG AGGGAAGGGK TGTCSCAATC CTGCGGAATG  6780

ISU55    .......... .A..G....G ......C..C ....A..... .......... ..........  6838
VR2385   .......... .C..A....T ......T..T ....G..... .......... ..........  6526
CONSEN.  AATCATGAGT CMCTRACTGK TGCCCTYGCY ATGARACTCA ATGACGAGGA CTTGGATTTC  6840

ISU55    .......... .......... .......... ........A. .......... ..........  6898
VR2385   .......... .......... .......... ........G. .......... ..........  6586
CONSEN.  CTTACGAAAT GGACTGATTT TAAGTGCTTT GTTTCTGCRT CCAACATGAG GAATGCAGCG  6900

ISU55    ..C....... .......... .......... .......... .......... .........A  6958
VR2385   ..T....... .......... .......... .......... .......... .........G  6646
CONSEN.  GGYCAATTTA TCGAGGCTGC CTATGCTAAA GCACTTAGAG TAGAACTTGC CCAGTTGGTR  6960

ISU55    .......... .G........ C...A..... .....A.... .......... C.........  7018
VR2385   .......... .A........ T...T..... .....T.... .......... T.........  6706
CONSEN.  CAGGTTGATA ARGTTCGAGG YACTWTGGCC AAACTWGAAG CTTTTGCTGA YACCGTGGCA  7020

ISU55    .......... .......... .......... .....T.... .......... ..........  7078
VR2385   .......... .......... .......... .....C.... .......... ..........  6766
CONSEN.  CCCCAACTCT CGCCCGGTGA CATTGTTGTC GCTCTYGGCC ATACGCCTGT TGGCAGTATC  7080

ISU55    .......... .......... ...T.....C .......... .......G.. ....T.T...  7138
VR2385   .......... .......... ...C.....T .......... .......A.. ....G.C...  6826
CONSEN.  TTCGACCTAA AGGTTGGTAG CACYAAGCAY ACCCTCCAAG CCATTGARAC CAGAKTYCTT  7140

ISU55    ..T....... .......... ......T... .......... ....C..... ..........  7198
VR2385   ..A....... .......... ......C... .......... ....T..... ..........  6886
CONSEN.  GCWGGGTCCA AAATGACCGT GGCGCGYGTC GTCGACCCGA CCCCYACGCC CCCACCCGCA  7200
```

FIG.34L

```
ISU55    ......C... .......... .........T .......... GT........ ..........  7258
VR2385   ......T... .......... .........C .......... CC........ ..........  6946
CONSEN.  CCCGTGYCCA TCCCCCTCCC ACCGAAAGTY CTGGAGAATG SYCCCAACGC TTGGGGGGAT  7260

ISU55    .....T.... .......A.. A..A....G. .......... .......... ..........  7318
VR2385   .....C.... .......G.. G..G....C. .......... .......... ..........  7006
CONSEN.  GAGGAYCGTT TGAATAARAA RAARAGGCSC AGGATGGAAG CCCTCGGCAT CTATGTTATG  7320

ISU55    .......... .......... .........T .....C.... .......... ..........  7378
VR2385   .......... .......... .........C .....T.... .......... ..........  7066
CONSEN.  GGTGGGAAAA AGTACCAGAA ATTTTGGGAY AAGAAYTCCG GTGATGTGTT TTATGAGGAG  7380

ISU55    ......A.T. .......... .........C ........T. .......... ..........  7438
VR2385   ......G.C. .......... .........T ........C. .......... ..........  7126
CONSEN.  GTCCATRAYA ACACAGATGA GTGGGAGTGY CTCAGAGTYG GCGACCCTGC CGACTTTGAC  7440

ISU55    .......... .......... ...G..C... ........G. .......... T.........  7498
VR2385   .......... .......... ...A..T... ........A. .......... C.........  7186
CONSEN.  CCTGAGAAGG GAACTCTGTG TGGRCAYGTC ACCATTGARG ATAAGGCTTA YCATGTTTAC  7500

ISU55    G.....C... .C........ ....C..... .......... ....A..C.. .........A  7558
VR2385   A.....T... .T........ ....T..... .......... ....G..T.. .........G  7246
CONSEN.  RCCTCCYCAT CYGGTAAGAA GTTCYTGGTC CCCGTCAACC CAGARAAYGG AAGAGTCCAR  7560

ISU55    .......... .A........ .......... G.......T. .......... ......C...  7618
VR2385   .......... .C........ .......... C.......C. .......... ......T...  7306
CONSEN.  TGGGAAGCTG CMAAGCTTTC CGTGGAGCAG SCCCTTGGYA TGATGAACGT CGACGGYGAA  7620

ISU55    .......... .......... .......... .......... .......... .T........  7678
VR2385   .......... .......... .......... .......... .......... .G........  7366
CONSEN.  CTGACTGCCA AAGAACTGGA GAAACTGAAA AGAATAATTG ATAAACTCCA GKGCCTGACT  7680

ISU55    .......... .......... .......... .......... .......... ..........  7738
VR2385   .......... .......... .......... .......... .......... ..........  7426
CONSEN.  AAGGAGCAGT GTTTAAACTG CTAGCCGCCA GCGGCTTGAC CCGCTGTGGT CGCGGCGGCT  7740

ISU55    .G.....C.. .......... ..A..A..A. .......... .......... ......C...  7798
VR2385   .A.....T.. .......... ..G..G..C. .......... .......... ......T...  7486
CONSEN.  TRGTTGTYAC TGAGACAGCG GTRAARATMG TCAAATTTCA CAACCGGACC TTCACCYTGG  7800
```

FIG.34M

```
ISU55    .......... .......... .......... .....T.A.. .........C ..........  7858
VR2385   .......... .......... .......... .....C.G.. .........T ..........  7546
CONSEN.  GACCTGTGAA TTTAAAAGTG GCCAGTGAGG TTGAGYTRAA AGACGCGGTY GAGCACAACC  7860

ISU55    .A........ .......... .......... .......... .......... ..........  7918
VR2385   .G........ .......... .......... .......... .......... ..........  7606
CONSEN.  ARCACCCGGT TGCAAGACCG GTTGATGGTG GTGTTGTGCT CCTGCGTTCT GCAGTTCCTT  7920

ISU55    .A...A.A.. ....C.G... ........C. .C........ T.....G..C ..........  7978
VR2385   .G...G.C.. ....T.A... ........T. .T........ C.....A..T ..........  7666
CONSEN.  CRCTTRTMGA CGTCYTRATC TCCGGTGCYG AYGCATCTCC YAAGTTRCTY GCCCATCACG  7980

ISU55    .......G.. .......... .......... .T........ C.....T..G ....C.....  8038
VR2385   .......A.. .......... .......... .C........ T.....C..A ....T.....  7726
CONSEN.  GGCCGGGRAA CACTGGGATC GATGGCACGC TYTGGGATTT YGAGTCYGAR GCCAYTAAAG  8040

ISU55    .......... .......... .......... .......... ...C...... ..G.......  8098
VR2385   .......... .......... .......... .......... ...T...... ..T.......  7786
CONSEN.  AGGAAGTCGC ACTTAGTGCG CAAATAATAC AGGCTTGTGA CATYAGGCGC GGKGACGCAC  8100

ISU55    .CA......A ......C... ..G..G.... .......... .......... .....G....  8158
VR2385   .TG......G ......T... ..A..A.... .......... .......... .....A....  7846
CONSEN.  CYRAAATTGR TCTCCCYTAC AARCTRTACC CTGTTAGGGG CAACCCTGAG CGGGTRAAAG  8160

ISU55    .....C..AG .......... .......... .......... G......... .....T..G.  8218
VR2385   .....T..CA .......... .......... .......... A......... .....C..A.  7906
CONSEN.  GAGTTYTGMR GAATACAAGG TTTGGAGACA TACCTTACAA RACCCCCAGT GACACYGGRA  8220

ISU55    ....G..... ......C... .......... .T........ T......... ..C.......  8278
VR2385   ....A..... ......T... .......... .C........ C......... ..T.......  7966
CONSEN.  GCCCRGTGCA CGCGGCYGCC TGCCTTACGC CYAACGCCAC YCCGGTGACT GAYGGGCGCT  8280

ISU55    .CA....... .......... .....T.... .T........ ......G... .....A....  8338
VR2385   .TG....... .......... .....C.... .C........ ......C... .....G....  8026
CONSEN.  CYRTCTTGGC CACGACCATG CCCTCYGGGT TYGAGTTGTA TGTACCSACC ATTCCRGCGT  8340

ISU55    ....C..... ...C...... .......... .......... .......... ..........  8398
VR2385   ....T..... ...T...... .......... .......... .......... ..........  8086
CONSEN.  CTGTYCTTGA TTAYCTTGAT TCTAGGCCTG ACTGCCCTAA ACAGTTGACA GAGCACGGCT  8400
```

FIG.34N

```
ISU55    .......... ....C..... ..C....... .A........ .......... ..........  8458
VR2385   .......... ....T..... ..T....... .G........ .......... ..........  8146
CONSEN.  GTGAAGATGC CGCAYTGAGA GAYCTCTCCA ARTATGACTT GTCCACCCAA GGCTTTGTTT  8460

ISU55    .A........ .........C ........A. .......... ...T..A... ........AC  8518
VR2385   .G........ .........T ........G. .......... ...C..G... ........GT  8206
CONSEN.  TRCCTGGAGT TCTTCGCCTY GTGCGGAART ACCTGTTTGC CCAYGTRGGT AAGTGCCCRY  8520

ISU55    .T.....C.. ......T... ..T..T..T. .G........ .......C.. ..........  8578
VR2385   .C.....T.. ......C... ..C..C..C. .A........ .......A.. ..........  8266
CONSEN.  CYGTTCAYCG GCCTTCYACT TAYCCYGCYA ARAATTCTAT GGCTGGAMTA AATGGGAACA  8580

ISU55    ....C..G.. ......T... .......... .......... .......... ..G.......  8638
VR2385   ....T..A.. ......C... .......... .......... .......... ..A.......  8326
CONSEN.  GGTTYCCRAC CAAGGAYATT CAGAGCGTCC CTGAAATCGA CGTTCTGTGC GCRCAGGCTG  8640

ISU55    ....G..... ......G... .......... .......... ...G.....T ..........  8698
VR2385   ....A..... ......A... .......... .......... ...A.....C ..........  8386
CONSEN.  TGCGRGAAAA CTGGCARACT GTTACCCCTT GTACCCTTAA GAARCAGTAY TGCGGGAAGA  8700

ISU55    ....A..... ...A...... ........T. .......C.. ......T..T ..........  8758
VR2385   ....G..... ...C...... ........C. .......T.. ......C..C ..........  8446
CONSEN.  AGAARACTAG GACMATACTC GGCACCAAYA ACTTCATYGC GCTGGCYCAY CGGGCAGCGT  8760

ISU55    .......... ......G... .......... .G........ .......... ........A.  8818
VR2385   .......... ......A... .......... .A........ .......... ........G.  8506
CONSEN.  TGAGTGGTGT CACCCARGGC TTCATGAAAA ARGCATTTAA CTCGCCCATC GCCCTCGGRA  8820

ISU55    .......... ...G...... ..A....... ....A..... A......... ..........  8878
VR2385   .......... ...A...... ..G....... ....G..... G......... ..........  8566
CONSEN.  AAAACAAATT TAARGAGCTA CARACTCCGG TCCTRGGCAG RTGCCTTGAA GCTGATCTTG  8880

ISU55    .......... C......... .......... ....T..... .......... ..........  8938
VR2385   .......... T......... .......... ....C..... .......... ..........  8626
CONSEN.  CATCCTGCGA YCGATCCACA CCTGCAATTG TCCGYTGGTT TGCCGCCAAT CTTCTTTATG  8940

ISU55    .....G.... .........T ..C..G..A. .T..T..... ......T... ......T..T  8998
VR2385   .....T.... .........G ..T..A..G. .G..C..... ......C... ......C..C  8686
CONSEN.  AACTTKCCTG TGCTGAAGAK CAYCTRCCRT CKTAYGTGCT GAACTGYTGC CACGACYTAY  9000
```

FIG.340

```
ISU55    .......... ...T...... .......... .......... ...A.....C ..........  9058
VR2385   .......... ...C...... .......... .......... ...G.....T ..........  8746
CONSEN.  TGGTCACGCA GTCYGGCGCA GTGACTAAGA GAGGTGGCCT GTCRTCTGGY GACCCGATCA  9060

ISU55    .......... T......... .......... .......... .......... .....C....  9118
VR2385   .......... C......... .......... .......... .......... .....T....  8806
CONSEN.  CCTCTGTGTC YAACACCATT TACAGCTTGG TGATCTATGC ACAGCACATG GTGCTYAGTT  9120

ISU55    .......... ......C... ..C....... ....C..... .......... ..........  9178
VR2385   .......... ......T... ..T....... ....T..... .......... ..........  8866
CONSEN.  ACTTCAAAAG TGGTCAYCCC CAYGGCCTTC TGTTYTTACA AGACCAGCTA AAGTTTGAGG  9180

ISU55    .......... ...T...... .......... .......... ...C...... ..........  9238
VR2385   .......... ...C...... .......... .......... ...T...... ..........  8926
CONSEN.  ACATGCTCAA GGTYCAACCC CTGATCGTCT ATTCGGACGA CCTYGTGCTG TATGCCGAGT  9240

ISU55    .......... .......... ..C....... .......... ....T.A... C.........  9298
VR2385   .......... .......... ..T....... .......... ....C.G... T.........  8986
CONSEN.  CTCCCACCAT GCCAAACTAC CAYTGGTGGG TTGAACATCT GAATYTRATG YTGGGGTTTC  9300

ISU55    .......... .......... G.T....... ....G..... .......... ..C..G...A  9358
VR2385   .......... .......... A.C....... ....A..... .......... ..T..A...G  9046
CONSEN.  AGACGGACCC AAAGAAGACA RCYATAACAG ACTCRCCATC ATTTCTAGGC TGYAGRATAR  9360

ISU55    .......... .......... ..T....... .......... .......... ........T.  9418
VR2385   .......... .......... ..C....... .......... .......... ........C.  9106
CONSEN.  TAAATGGACG CCAGCTAGTC CCYAACCGTG ACAGGATTCT CGCGGCCCTC GCCTACCAYA  9420

ISU55    .......... .......... C......... .T..G..... .......... ..........  9478
VR2385   .......... .......... G......... .C..A..... .......... ..........  9166
CONSEN.  TGAAGGCGAG TAATGTTTCT SAATACTACG CYTCRGCGGC TGCAATACTC ATGGACAGCT  9480

ISU55    .......... .......... .......... .......... .A........ ...T......  9538
VR2385   .......... .......... .......... .......... .G........ ...G......  9226
CONSEN.  GTGCTTGTTT AGAGTATGAT CCTGAATGGT TTGAAGAACT TRTAGTTGGA ATAKCGCAGT  9540

ISU55    .......... .........T .......... .TC....... ....T....T ..........  9598
VR2385   .......... .........C .......... .CA....... ....A....C ..........  9286
CONSEN.  GCGCCCGCAA GGACGGCTAY AGCTTTCCCG GYMCGCCGTT CTTCVTGTCY ATGTGGGAAA  9600
```

FIG.34P

```
ISU55    .......... T......... .....G.... .......... .......... ..........  9658
VR2385   .......... A......... .....A.... .......... .......... ..........  9346
CONSEN.  AACTCAGGTC WAATTATGAG GGGAARAAGT CGAGAGTGTG CGGGTACTGC GGGGCCCCGG  9660

ISU55    .......... .........T .....C..T. .......... .......... ..........  9718
VR2385   .......... .........C .....T..C. .......... .......... ..........  9406
CONSEN.  CCCCGTACGC TACTGCCTGY GGCCTYGAYG TCTGCATTTA CCACACCCAC TTCCACCAGC  9720

ISU55    .......G.. T.T...T... ..T.....C. .......... .......... .G........  9778
VR2385   .......A.. C.C...C... ..C.....T. .......... .......... .A........  9466
CONSEN.  ATTGTCCRGT YAYAATYTGG TGYGGCCAYC CAGCGGGTTC TGGTTCTTGT ARTGAGTGCA  9780

ISU55    .A.......G G......... ........T. .G........ .T..A..... ..........  9838
VR2385   .G.......A A......... ........C. .A........ .C..G..... ..........  9526
CONSEN.  ARTCCCCCRT RGGGAAAGGC ACAAGCCCYC TRGACGAGGT GYTARAACAA GTCCCGTATA  9840

ISU55    .A........ ....A....C .......... .A........ .......... ........C.  9898
VR2385   .G........ ....G....T .......... .G........ .......... ........T.  9586
CONSEN.  ARCCCCCACG GACCRTAATY ATGCATGTGG ARCAGGGTCT TACCCCCCTT GACCCAGGYA  9900

ISU55    .A........ .......... ..G....... .T.....C.. .....G...G ..........  9958
VR2385   .G........ .......... ..A....... .C.....T.. .....A...A ..........  9646
CONSEN.  GRTACCAGAC TCGCCGCGGA TTRGTCTCCG TYAGGCGYGG AATCARGGGR AATGAAGTTG  9960

ISU55    .......... .........C .......... .......... .......... ..........  10018
VR2385   .......... .........T .......... .......... .......... ..........  9706
CONSEN.  AACTACCAGA CGGTGATTAY GCTAGTACCG CCTTGCTCCC CACCTGTAAA GAGATCAACA  10020

ISU55    .......... .......... .......... .......... .........G ..........  10078
VR2385   .......... .......... .......... .......... .........A ..........  9766
CONSEN.  TGGTCGCTGT CGCTTCTAAT GTGTTGCGCA GCAGGTTCAT CATCGGTCCR CCCGGTGCTG  10080

ISU55    ....G..... ......T..A .....G.... .......... ...C...... ..........  10138
VR2385   ....A..... ......C..T .....A.... .......... ...T...... ..........  9826
CONSEN.  GGAARACATA CTGGCTYCTW CAACARGTCC AGGATGGTGA TGTYATTTAC ACACCAACTC  10140

ISU55    .......... .......... ..T....... .......... ...G.....C .....AG...  10198
VR2385   .......... .......... ..C....... .......... ...A.....T .....TA...  9886
CONSEN.  ACCAGACCAT GCTTGACATG ATYAGAGCTT TGGGGACGTG CCGRTTCAAY GTCCCWRCAG  10200
```

FIG.34Q

```
ISU55    .......G.. ...A...... .......... .......... .......... ..........  10258
VR2385   .......A.. ...G...... .......... .......... .......... ..........  9946
CONSEN.  GCACAACRCT GCARTTCCCT GTCCCCTCCC GTACCGGTCC GTGGGTTCGC ATCCTAGCCG  10260

ISU55    .C........ .......... .......... .......... ........G. ..........  10318
VR2385   .T........ .......... .......... .......... ........A. ..........  10006
CONSEN.  GYGGTTGGTG TCCTGGCAAG AATTCCTTCC TGGATGAAGC AGCGTATTRC AATCACCTTG  10320

ISU55    .......... .........C .......... .......... ......T..C ....A.....  10378
VR2385   .......... .........T .......... .......... ......C..T ....T.....  10066
CONSEN.  ATGTCTTGAG GCTTCTTAGY AAAACTACCC TCACCTGTCT GGGAGAYTTY AAACVACTCC  10380

ISU55    .......... .........T .......... .........C T......... ......C.G.  10438
VR2385   .......... .........C .......... .........T C......... ......T.A.  10126
CONSEN.  ACCCAGTGGG TTTTGATTCY CATTGCTATG TTTTTGACAY YATGCCTCAG ACTCAAYTRA  10440

ISU55    .......... ......C... ........T. .......... C......... .....A....  10498
VR2385   .......... ......T... ........C. .......... T......... .....G....  10186
CONSEN.  AGACCATCTG GAGATTYGGA CAGAATATYT GTGATGCCAT YCAACCAGAT TACAGRGACA  10500

ISU55    .......... .......... .......... ....C..... ...G.G...T ......C...  10558
VR2385   .......... .......... .......... ....T..... ...A.A...C ......T...  10246
CONSEN.  AACTCATGTC CATGGTCAAC ACAACCCGTG TAACYTACGT GGARARACCY GTCAGGYATG  10560

ISU55    .......... C......... ..C.G..... .........A .......... ..........  10618
VR2385   .......... T......... ..T.A..... .........G .......... ..........  10306
CONSEN.  GGCAAGTCCT YACCCCCTAC CAYARGGACC GAGAGGACGR CGCCATCACC ATTGACTCCA  10620

ISU55    .C.....C.. ...A...... .......... .......... .......... ..........  10678
VR2385   .T.....T.. ...G...... .......... .......... .......... ..........  10366
CONSEN.  GYCAAGGYGC CACRTTTGAT GTGGTTACAT TGCATTTGCC CACTAAAGAT TCACTCAACA  10680

ISU55    .......... .......... .....C.... .......... T..C...... ..........  10738
VR2385   .......... .......... .....T.... .......... A..T...... ..........  10426
CONSEN.  GGCAAAGAGC CCTTGTTGCT ATCACYAGGG CAAGACATGC WATYTTTGTG TATGACCCAC  10740

ISU55    ...G...... .........A ........T. ....G...A. ...C..T... ........A.  10798
VR2385   ...A...... .........G ........C. ....A...G. ...A..C... ........T.  10486
CONSEN.  ACARGCAACT GCAGAGCCTR TTTGATCTYC CTGCRAAARG CACMCCYGTC AACCTCGCWG  10800
```

FIG.34R

```
ISU55   .......... .........G ..C.....A. .......... ...A...... ..........  10858
VR2385  .......... .........T ..T.....G. .......... ...G...... ..........  10546
CONSEN. TGCACCGCGA CGGGCAGCTK ATYGTGCTRG ATAGAAATAA CAARGAATGC ACGGTTGCTC  10860

ISU55   .......T.. ...C...... .......... .......... G........A ..C.......  10918
VR2385  .......A.. ...T...... .......... .......... A........G ..T.......  10606
CONSEN. AGGCTCTWGG CAAYGGAGAT AAATTTAGGG CCACAGACAA RCGCGTTGTR GAYTCTCTCC  10920

ISU55   .......... .......... ........T. .......... .......... ..C.......  10978
VR2385  .......... .......... ........G. .......... .......... ..A.......  10666
CONSEN. GCGCCATTTG TGCTGATCTA GAAGGGTCKA GCTCTCCGCT CCCCAAGGTC GCMCACAACT  10980

ISU55   ........C. .......... .....G..A. .......C.. .......... ..........  11038
VR2385  ........T. .......... .....A..G. .......T.. .......... ..........  10726
CONSEN. TGGGATTTYA TTTCTCACCT GATTTRACRC AGTTTGCYAA ACTCCCAGTA GAACTTGCAC  11040

ISU55   .T........ .......... ..C....... .......... .......... ......G.T.  11098
VR2385  .C........ .......... ..T....... .......... .......... ......A.C.  10786
CONSEN. CYCACTGGCC CGTGGTGACA ACYCAGAACA ATGAAAAGTG GCCAGATCGG CTGGTTRCYA  11100

ISU55   .......... ...T...... .......... .......... .......... ........C.  11158
VR2385  .......... ...C...... .......... .......... .......... ........T.  10846
CONSEN. GCCTTCGCCC TATYCATAAA TATAGCCGCG CGTGCATTGG TGCCGGCTAT ATGGTGGGYC  11160

ISU55   .......... T..A.....C .......... .......... .......... ...A......  11218
VR2385  .......... C..G.....T .......... .......... .......... ...G......  10906
CONSEN. CCTCGGTGTT YCTRGGCACY CCTGGGGTCG TGTCATACTA CCTCACAAAA TTTRTTAAGG  11220

ISU55   .......... .......... ......G... .......... T......... ..........  11278
VR2385  .......... .......... ......A... .......... C......... ..........  10966
CONSEN. GCGAGGCTCA AGTGCTTCCG GAGACGRTCT TCAGCACCGG YCGAATTGAG GTAGATTGCC  11280

ISU55   .......C.. .......... .......... .......... .......... ..........  11338
VR2385  .......T.. .......... .......... .......... .......... ..........  11026
CONSEN. GGGAATAYCT TGATGATCGG GAGCGAGAAG TTGCTGCGTC CCTCCCACAT GCCTTCATTG  11340

ISU55   .C........ .......... .......... .......... ...T...... ..........  11398
VR2385  .T........ .......... .......... .......... ...C...... ..........  11086
CONSEN. GYGACGTCAA AGGCACTACC GTTGGGGGAT GTCACCATGT CACYTCCAAA TACCTTCCGC  11400
```

FIG.34S

```
ISU55   .......... T......T.. .......... .......... G......... ..........  11458
VR2385  .......... C......A.. .......... .......... A......... ..........  11146
CONSEN. GCTTCCTTCC YAAGGAAWCA GTTGCGGTAG TCGGGGTTTC RAGCCCCGGA AAAGCCGCGA  11460

ISU55   .......... .......... .......... .......... .........C ..........  11518
VR2385  .......... .......... .......... .......... .........T ..........  11206
CONSEN. AAGCAGTGTG CACACTGACA GATGTGTACC TCCCAGACCT TGAAGCCTAY CTCCACCCGG  11520

ISU55   .A..C..... .......... .......... .......... ......C... ..........  11578
VR2385  .G..T..... .......... .......... .......... ......T... ..........  11266
CONSEN. ARACYCAGTC CAAGTGCTGG AAATTGATGT TGGACTTCAA GGAAGTYCGA CTGATGGTCT  11580

ISU55   .......... G..G...... .......... ....C..... T......... ..........  11638
VR2385  .......... A..A...... .......... ....T..... C......... ..........  11326
CONSEN. GGAAAGACAA RACRGCCTAT TTCCAACTTG AAGGYCGCTA YTTCACCTGG TATCAGCTTG  11640

ISU55   .......C.. .......... .......... ........G. .........A ..........  11698
VR2385  .......T.. .......... .......... ........A. .........G ..........  11386
CONSEN. CTAGCTAYGC CTCGTACATC CGTGTTCCTG TCAACTCTRC GGTGTACTTR GACCCCTGCA  11700

ISU55   .......T.. .......... ........TA .......... T..T.....A ..........  11758
VR2385  .......C.. .......... ........CG .......... C..C.....G ..........  11446
CONSEN. TGGGCCCYGC CCTTTGCAAC AGGAGAGTYR TCGGGTCCAC YCAYTGGGGR GCTGACCTCG  11760

ISU55   .......... .......... ..T..C.... .T..TT.... ...T...... ..........  11818
VR2385  .......... .......... ..C..T.... .C..CC.... ...C...... ..........  11506
CONSEN. CAGTCACCCC TTATGATTAC GGYGCYAAAA TYATYYTGTC TAGYGCGTAC CATGGTGAAA  11820

ISU55   ....T..... G....G.... .......... .A..G..... .C.T..C... .......A..  11878
VR2385  ....C..... A....A.... .......... .G..A..... .T.G..T... .......G..  11566
CONSEN. TGCCYCCCGG RTACAARATT CTGGCGTGCG CRGARTTCTC GYTKGAYGAC CCAGTCARGT  11880

ISU55   .C..G..C.. .......... .......... .......... G......... ..........  11938
VR2385  .T..A..T.. .......... .......... .......... A......... ..........  11626
CONSEN. AYAARCAYAC CTGGGGGTTT GAATCGGATA CAGCGTATCT RTATGAGTTC ACCGGAAACG  11940

ISU55   .......... .......... .......... .T........ ....G.G... ...G.C..T.  11998
VR2385  .......... .......... .......... .C........ ....A.A... ...A.T..C.  11686
CONSEN. GTGAGGACTG GGAGGATTAC AATGATGCGT TYCGTGCGCG CCAGRARGGG AAARTYTAYA  12000
```

FIG.34T

```
ISU55   .......... .......... .......... .T..C..... ....A..... .......... 12058
VR2385  .......... .......... .......... .C..T..... ....G..... .......... 11746
CONSEN. AGGCCACTGC CACCAGCATG AAGTTTTATT TYCCYCCGGG CCCTRTCATT GAACCAACTT 12060

ISU55   .......... ....A..... .......... .......... .......... .......... 12118
VR2385  .......... ....G..... .......... .......... .......... .......... 11806
CONSEN. TAGGCCTGAA TTGARATGAA ATGGGGTCTA TGCAAAGCCT TTTTGACAAA ATTGGCCAAC 12120

ISU55   ....C..... .......... .......... .......... .......... .......... 12178
VR2385  ....T..... .......... .......... .......... .......... .......... 11866
CONSEN. TTTTYGTGGA TGCTTTCACG GAGTTCTTGG TGTCCATTGT TGATATCATT ATATTTTTGG 12180

ISU55   .......... .......... .....C.... .......... .......... .......... 12238
VR2385  .......... .......... .....A.... .......... .......... .......... 11926
CONSEN. CCATTTTGTT TGGCTTCACC ATCGCMGGTT GGCTGGTGGT CTTTTGCATC AGATTGGTTT 12240

ISU55   ........C. .......... .......... .......... .......... .......... 12298
VR2385  ........A. .......... .......... .......... .......... .......... 11986
CONSEN. GCTCCGCGMT ACTCCGTGCG CGCCCTGCCA TTCACTCTGA GCAATTACAG AAGATCCTAT 12300

ISU55   .......... .T........ .......... .......... .....TT... .......... 12358
VR2385  .......... .C........ .......... .......... .....AC... .......... 12046
CONSEN. GAGGCCTTTC TYTCTCAGTG CCAGGTGGAC ATTCCCACCT GGGGAWYTAA ACATCCTTTG 12360

ISU55   ......T... .......... .......... .......... .......... .......... 12418
VR2385  ......C... .......... .......... .......... .......... .......... 12106
CONSEN. GGGATGYTTT GGCACCATAA GGTGTCAACC CTGATTGATG AAATGGTGTC GCGTCGAATG 12420

ISU55   .......... ....T..... .......... .......... ....G..... .......... 12478
VR2385  .......... ....A..... .......... .......... ....A..... .......... 12166
CONSEN. TACCGCATCA TGGAWAAAGC AGGACAGGCT GCCTGGAAAC AGGTRGTGAG CGAGGCTACG 12480

ISU55   .......... .......... .......... .....C.... .......... .......... 12538
VR2385  .......... .......... .......... .....T.... .......... .......... 12226
CONSEN. CTGTCTCGCA TTAGTAGTTT GGATGTGGTG GCTCAYTTTC AGCATCTTGC CGCCATTGAA 12540

ISU55   .......... ........T. .......... .......... .....A.... .......... 12598
VR2385  .......... ........C. .......... .......... .....C.... .......... 12286
CONSEN. GCCGAGACCT GTAAATATYT GGCCTCTCGG CTGCCCATGC TACACMACCT GCGCATGACA 12600
```

FIG.34U

```
ISU55    .......... .......... .......... .......... .....C.... .A....T...  12658
VR2385   .......... .......... .......... .......... .....T.... .G....C...  12346
CONSEN.  GGGTCAAATG TAACCATAGT GTATAATAGT ACTTTGAATC AGGTGYTTGC TRTTTTYCCA  12660

ISU55    .......... .......... .......... ..T....... .......... ..........  12718
VR2385   .......... .......... .......... ..C....... .......... ..........  12406
CONSEN.  ACCCCTGGTT CCCGGCCAAA GCTTCATGAT TTYCAGCAAT GGCTAATAGC TGTACATTCC  12720

ISU55    .......... .......... .......... .......... .......... ..........  12778
VR2385   .......... .......... .......... .......... .......... ..........  12466
CONSEN.  TCTATATTTT CCTCTGTTGC AGCTTCTTGT ACTCTTTTTG TTGTGCTGTG GTTGCGGGTT  12780

ISU55    .......... ...T..C... .......... .......... .........C ..........  12838
VR2385   .......... ...C..T... .......... .......... .........T ..........  12526
CONSEN.  CCAATGCTAC GTAYTGYTTT TGGTTTCCGC TGGTTAGGGG CAATTTTTCY TTCGAACTCA  12840

ISU55    .A.....C.. .........T ..A....... .......... .......AT. ..........  12898
VR2385   .G.....T.. .........C ..G....... .......... .......GC. ..........  12586
CONSEN.  CRGTGAAYTA CACGGTGTGY CCRCCTTGCC TCACCCGGCA AGCAGCCRYA GAGGCCTACG  12900

ISU55    ....T..... ...T...... .......... ..T....... C......... ..........  12958
VR2385   ....C..... ...C...... .......... ..C....... A......... ..........  12646
CONSEN.  AACCYGGCAG GTCYCTTTGG TGCAGGATAG GGYATGATCG MTGTGGGGAG GACGATCATG  12960

ISU55    .C........ .......... .......... .......... .......... .......T..  13018
VR2385   .T........ .......... .......... .......... .......... .......C..  12706
CONSEN.  AYGAACTAGG GTTTGTGGTG CCGTCTGGCC TCTCCAGCGA AGGCCACTTG ACCAGTGYTT  13020

ISU55    .......... .......... ..T.....T. .C..A..... .........T ..........  13078
VR2385   .......... .......... ..C.....C. .T..G..... .........C ..........  12766
CONSEN.  ACGCCTGGTT GGCGTTCCTG TCYTTCAGYT AYACRGCCCA GTTCCATCCY GAGATATTCG  13080

ISU55    .......... ........A. ..T....... ......G... T....C.... .....C....  13138
VR2385   .......... ........G. ..C....... ......A... C....T.... .....T....  12826
CONSEN.  GGATAGGGAA TGTGAGTCRA GTYTATGTTG ACATCARGCA YCAATYCATT TGCGCYGTTC  13140

ISU55    .C..C..... ....G....T .....T.G.. .......T.. .......... ..C.....T.  13198
VR2385   .T..T..... ....A....C .....C.A.. .......C.. .......... ..T.....C.  12886
CONSEN.  AYGAYGGGCA GAACRCCACY TTGCCYCRCC ATGACAAYAT TTCAGCCGTG TTYCAGACYT  13200
```

FIG.34V

```
ISU55    .......A.. ...A...... ..C....... .......... .......... ..........  13258
VR2385   .......G.. ...G...... ..G....... .......... .......... ..........  12946
CONSEN.  ATTACCARCA TCARGTCGAC GGSGGCAATT GGTTTCACCT AGAATGGCTG CGTCCCTTCT  13260

ISU55    .......... .......... .......... .......... ........T. ..........  13318
VR2385   .......... .......... .......... .......... ........C. ..........  13006
CONSEN.  TTTCCTCTTG GTTGGTTTTA AATGTCTCTT GGTTTCTCAG GCGTTCGCYT GCAAGCCATG  13320

ISU55    .......... ......G... ....T..... .......... .......... ..........  13378
VR2385   .......... ......T... ....C..... .......... .......... ..........  13066
CONSEN.  TTTCAGTTCG AGTCTTKCAG ACATYAAGAC CAACACCACC GCAGCGGCAG GCTTTGCTGT  13380

ISU55    .......... .......... .....T.... .......... .........T .........A  13438
VR2385   .......... .......... .....C.... .......... .........A .........G  13126
CONSEN.  CCTCCAAGAC ATCAGTTGCC TTAGGYATCG CAACTCGGCC TCTGAGGCGW TTCGCAAART  13440

ISU55    .........T ..T....... .......... .A.......T .......... .......A..  13498
VR2385   .........C ..C....... .......... .G.......C .......... .......T..  13186
CONSEN.  CCCTCAGTGY CGYACGGCGA TAGGGACACC CRTGTATATY ACTGTCACAG CCAATGTWAC  13500

ISU55    .......... .......... .......C.. .......... .......... .......C..  13558
VR2385   .......... .......... .......T.. .......... .......... .......T..  13246
CONSEN.  CGATGAGAAT TATTTGCATT CCTCTGAYCT TCTCATGCTT TCTTCTTGCC TTTTCTAYGC  13560

ISU55    .......... .......... .......A.. .......... .......... ..........  13618
VR2385   .......... .......... .......G.. .......... .......... ..........  13306
CONSEN.  TTCTGAGATG AGTGAAAAGG GATTTAARGT GGTATTTGGC AATGTGTCAG GCATCGTGGC  13620

ISU55    T......... .....T.... .C........ .......... .......... ....C.....  13678
VR2385   A......... .....C.... .T........ .......... .......... ....T.....  13366
CONSEN.  WGTGTGCGTC AACTTYACCA GYTACGTCCA ACATGTCAAG GAATTTACCC AACGYTCCTT  13680

ISU55    ......C... .......... .......... ......A..T .......... ..........  13738
VR2385   ......T... .......... .......... ......G..C .......... ..........  13426
CONSEN.  GGTAGTYGAC CATGTGCGGC TGCTCCATTT CATGACRCCY GAGACCATGA GGTGGGCAAC  13740

ISU55    .......... .........G .......... ...C....A. ......G... ..........  13798
VR2385   .......... .........A .......... ...A....G. ......A... ..........  13486
CONSEN.  TGTTTTAGCC TGTCTTTTTR CCATTCTGTT GGCMATTTRA ATGTTTRAGT ATGTTGGGGA  13800
```

FIG.34W

ISU55 .......... ........A. ......TC.. .......... G......... .......... 13858
VR2385 .......... ........G. ......CA.. .......... A......... .......... 13546
CONSEN. AATGCTTGAC CGCGGGCTRT TGCTCGYMAT TGCTTTTTTT RTGGTGTATC GTGCCGTCTT 13860

ISU55 .G........ .....C.... ......A.C. T..A.A..C. TC........ T.......T. 13918
VR2385 .T........ .....T.... ......G.G. A..G.G..T. AA........ C.......C. 13606
CONSEN. GKTTTGTTGC GCTCGYCAGC GCCAACRGSA WCARCRGCYC WMATTTACAG YTGATTTAYA 13920

ISU55 .......... .......... .......... .....T.... .GG.G..... .......... 13978
VR2385 .......... .......... .......... .....C.... .AA.A..... .......... 13666
CONSEN. ACTTGACGCT ATGTGAGCTG AATGGCACAG ATTGGYTAGC TRRTRAATTT GACTGGGCAG 13980

ISU55 .......... .......... .......... .......... ...C...... ........C. 14038
VR2385 .......... .......... .......... .......... ...T...... ........T. 13726
CONSEN. TGGAGTGTTT TGTCATTTTT CCTGTGTTGA CTCACATTGT CTCYTATGGT GCCCTCACYA 14040

ISU55 .C........ .......... .......... .......... ......C..C ...TCC.... 14098
VR2385 .T........ .......... .......... .......... ......T..G ...GTT.... 13786
CONSEN. CYAGCCATTT CCTTGACACA GTCGGTCTGG TCACTGTGTC TACCGCYGGS TTTKYYCACG 14100

ISU55 .......... .......... ..C....... .......... .......... .......... 14158
VR2385 .......... .......... ..G....... .......... .......... .......... 13846
CONSEN. GGCGGTATGT TCTGAGTAGC ATSTACGCGG TCTGTGCCCT GGCTGCGTTG ATTTGCTTCG 14160

ISU55 ........T. .A........ .......... .......... .......... .......... 14218
VR2385 ........C. .G........ .......... .......... .......... .......... 13906
CONSEN. TCATTAGGYT TRCGAAGAAT TGCATGTCCT GGCGCTACTC ATGTACCAGA TATACCAACT 14220

ISU55 .......... .......... .......... .......... .......... .......... 14278
VR2385 .......... .......... .......... .......... .......... .......... 13966
CONSEN. TTCTTCTGGA CACTAAGGGC AGACTCTATC GTTGGCGGTC GCCTGTCATC ATAGAGAAAA 14280

ISU55 ....T..... .......... .....T.... .......... G......... .......... 14338
VR2385 ....C..... .......... .....C.... .......... A......... .......... 14026
CONSEN. GGGGYAAAGT TGAGGTCGAA GGTCAYCTGA TCGACCTCAA RAGAGTTGTG CTTGATGGTT 14340

ISU55 .......A.. ....A..... .A.A...... ....G..... .G........ .......... 14398
VR2385 .......T.. ....G..... .G.G...... ....A..... .A........ .......... 14086
CONSEN. CCGCGGCWAC CCCTRTAACC ARARTTTCAG CGGARCAATG GRGTCGTCCT TAGATGACTT 14400

FIG.34X

```
ISU55   ...C...... .......... ...T...... ...T...... ..C....... ..........  14458
VR2385  ...T...... .......... ...A...... ...C...... ..T....... ..........  14146
CONSEN. CTGYCATGAT AGCACGGCTC CACWAAAGGT GCTYTTGGCG TTYTCTATTA CCTACACGCC  14460

ISU55   .......... .......... .A..A..... .......... T......... ..........  14518
VR2385  .......... .......... .G..G..... .......... C......... ..........  14206
CONSEN. AGTGATGATA TATGCCCTAA ARGTRAGTCG CGGCCGACTG YTAGGGCTTC TGCACCTTTT  14520

ISU55   .A.......A .......... .......... .......... .......... .......C..  14578
VR2385  .G.......G .......... .......... .......... .......... .......T..  14266
CONSEN. GRTCTTCCTR AATTGTGCTT TCACCTTCGG GTACATGACA TTCGTGCACT TTCAGAGYAC  14580

ISU55   ...C...... .......... .......... .......... .......... ..........  14638
VR2385  ...T...... .......... .......... .......... .......... ..........  14326
CONSEN. AAAYAAGGTC GCGCTCACTA TGGGAGCAGT AGTTGCACTC CTTTGGGGGG TGTACTCAGC  14640

ISU55   .......... .......... .......... .......... .......... ..........  14698
VR2385  .......... .......... .......... .......... .......... ..........  14386
CONSEN. CATAGAAACC TGGAAATTCA TCACCTCCAG ATGCCGTTTG TGCTTGCTAG GCCGCAAGTA  14700

ISU55   ....T..... .......... .......... .......... .......... .A........  14758
VR2385  ....C..... .......... .......... .......... .......... .T........  14446
CONSEN. CATTYTGGCC CCTGCCCACC ACGTTGAAAG TGCCGCAGGC TTTCATCCGA TWGCGGCAAA  14760

ISU55   .......... .......... .......... .......... .....T.... ..........  14818
VR2385  .......... .......... .......... .......... .....C.... ..........  14506
CONSEN. TGATAACCAC GCATTTGTCG TCCGGCGTCC CGGCTCCACT ACGGTYAACG GCACATTGGT  14820

ISU55   .........G .......... .......... .......... ..C....... ..........  14878
VR2385  .........A .......... .......... .......... ..T....... ..........  14566
CONSEN. GCCCGGGTTR AAAAGCCTCG TGTTGGGTGG CAGAAAAGCT GTYAAACAGG GAGTGGTAAA  14880

ISU55   .......... .......... ....A..... .......... ..A....... ..........  14938
VR2385  .......... .......... ....C..... .......... ..G....... ..........  14626
CONSEN. CCTTGTTAAA TATGCCAAAT AACAMCGGCA AGCAGCAGAA GARAAAGAAG GGGGATGGCC  14940

ISU55   .......... .......... .......... .......... ......G... ..........  14998
VR2385  .......... .......... .......... .......... ......C... ..........  14686
CONSEN. AGCCAGTCAA TCAGCTGTGC CAGATGCTGG GTAAGATCAT CGCTCASCAA AACCAGTCCA  15000
```

FIG.34Y

```
ISU55     .......... .......... .....C.... .......... .......... .....T....  15058
VR2385    .......... .......... .....T.... .......... .......... .....C....  14746
CONSEN.   GAGGCAAGGG ACCGGGAAAG AAAAAYAAGA AGAAAAACCC GGAGAAGCCC CATTTYCCTC  15060

ISU55     .......... .......... .......... .C...T..G. ......G.T. ..........  15118
VR2385    .......... .......... .......... .T...C..G. ......T.A. ..........  14806
CONSEN.   TAGCGACTGA AGATGATGTC AGACATCACT TYACCYCTRG TGAGCGKCWA TTGTGTCTGT  15120

ISU55     .......... ...A...... .......... ....A.T... T......... ..........  15178
VR2385    .......... ...C...... .......... ....G.C... C......... ..........  14866
CONSEN.   CGTCAATCCA GACMGCCTTT AATCAAGGCG CTGGRAYTTG YACCCTGTCA GATTCAGGGA  15180

ISU55     .......... .......... .......... .G........ .......... ..........  15238
VR2385    .......... .......... .......... .T........ .......... ..........  14926
CONSEN.   GGATAAGTTA CACTGTGGAG TTTAGTTTGC CKACGCATCA TACTGTGCGC CTGATCCGCG  15240

ISU55     .......G.. .......... .....A.... .......... .......... ..........  15298
VR2385    .......A.. .......... .....G.... .......... .......... ..........  14986
CONSEN.   TCACAGCRTC ACCCTCAGCA TGATGRGCTG GCATTCTTGA GGCATCCCAG TGTTTGAATT  15300

ISU55     .........T .......... .......... .........T .......... ..........  15358
VR2385    .........C .......... .......... .........C .......... ..........  15046
CONSEN.   GGAAGAATGY GTGGTGAATG GCACTGATTG ACATTGTGCY TCTAAGTCAC CTATTCAATT  15360

ISU55     .......... ........C. .A........ ....T..... ..G....... ..........  15418
VR2385    .......... ........T. .G........ ....A..... ..A....... ..........  15106
CONSEN.   AGGGCGACCG TGTGGGGGYA ARATTTAATT GGCGWGAACC ACRCGGCCGA AATTAAAAAA  15420

ISU55     ......-  15424
VR2385    .......  15113
CONSEN.   AAAAAAA  15427
```

FIG.34Z

PROTEINS ENCODED BY POLYNUCLEIC ACIDS OF PORCINE REPRODUCTIVE AND RESPIRATORY SYNDROME VIRUS (PRRSV)

This application is a U.S. national stage application of PCT/US99/02630, filed Feb. 8, 1999, which is a continuation-in-part of U.S. application Ser. No. 09/019,793, filed Feb. 6, 1998, now U.S. Pat. No. 6,380,376, which is a continuation-in-part of application Ser. No. 08/478,316, filed Jun. 7, 1995, now U.S. Pat. No. 6,251,397, which is a continuation-in-part of application Ser. No. 08/301,435, filed on Sep. 1, 1994, now U.S. Pat. No. 6,592,873, which is a continuation-in-part of application Ser. No. 08/131,625, filed on Oct. 5, 1993, now U.S. Pat. No. 5,695,766, which is a continuation-in-part of application Ser. No. 07/969,071, filed on Oct. 30, 1992, now abandoned. The entire contents of the foregoing applications are incorporated herein by reference in their entireties.

BACKGROUND OF THE INVENTION

1. Field of the Invention

The present invention concerns polynucleic acids isolated from a porcine reproductive and respiratory syndrome virus (PRRSV), a protein and/or a polypeptide encoded by the polynucleic acids, a vaccine which protects pigs from a PRRSV based on the protein or polynucleic acids, methods of making the proteins, polypeptides and polynucleic acids, a method of protecting a pig from PRRS using the vaccine, a method of producing the vaccine, a method of treating a pig infected by or exposed to a PRRSV, and a method of detecting a PRRSV.

2. Discussion of the Background

Porcine reproductive and respiratory syndrome (PRRS), a new and severe disease in swine, was first reported in the U.S.A. in 1987, and was rapidly recognized in many western European countries (reviewed by Goyal, J. Vet. Diagn. Invest., 1993, 5:656–664; and in U.S. application Ser. No. 08/131,625, now U.S. Pat. No. 5,695,766, and Ser. No. 08/301,435). The disease is characterized by reproductive failure in sows and gilts, pneumonia in young growing pigs, and an increase in preweaning mortality (Wensvoort et al., Vet. Q., 13:121–130, 1991; Christianson et al., 1992, Am. J. Vet. Res. 53:485–488; U.S. application Ser. No. 08/131,625, now U.S. Pat. No. 5,695,766, and Ser. No. 08/301,435).

The causative agent of PRRS, porcine reproductive and respiratory syndrome virus (PRRSV), was identified first in Europe and then in the U.S.A. (Collins et al., 1992, J. Vet. Diagn. Invest., 4:117–126). The European strain of PRRSV, designated as Lelystad virus (LV), has been cloned and sequenced (Meulenberg et al., 1993, Virology, 192:62–72 and J. Gen. Virol., 74:1697–1701; Conzelmann et al., 1993, Virology, 193:329–339).

PRRSV was provisionally classified in the proposed new virus family of Arteriviridae, which includes equine arteritis virus (EAV), lactate dehydrogenase-elevating virus (LDV) and simian hemorrhagic fever virus (SHFV) (Plagemann and Moennig, 1992, Adv. Virus. Res., 41:99–192; Godeny et al., 1993, Virology, 194:585–596; U.S. application Ser. No. 08/131,625, now U.S. Pat. No. 5,695,766, and Ser. No. 08/301,435). This group of single plus-strand RNA viruses shares many characteristics such as genome organization, replication strategy, morphology and macrophage tropism (Meulenberg et al., 1993; U.S. application Ser. No. 08/131,625, now U.S. Pat. No. 5,695,766, and Ser. No. 08/301,435). Subclinical infections and persistent viremia with concurrent antibody production are also characteristic histopathologic properties of the arteriviruses.

Antigenic, genetic and pathogenic variations have been reported among PRRSV isolates (Wensvoort et al., 1992, J. Vet. Diagn. Invest., 4:134–138; Mardassi et al., 1994, J. Gen. Virol., 75:681–685; U.S. application Ser. No. 08/131,625, now U.S. Pat. No. 5,695,766, and Ser. No. 08/301,435). Furthermore, U.S. and European PRRSV represent two distinct genotypes (U.S. application Ser. No. 08/131,625, now U.S. Pat. No. 5,695,766, and Ser. No. 08/301,435). Antigenic variability also exists among different North American isolates as well (Wensvoort et al., 1992). Marked differences in pathogenicity have been demonstrated not only between U.S. and European isolates, but also among different U.S. isolates (U.S. application Ser. No. 08/131,625, now U.S. Pat. No. 5,695,766, and Ser. No. 08/301,435).

The genomic organization of arteriviruses resembles coronaviruses and toroviruses in that their replication involves the formation of a 3'-coterminal nested set of subgenomic mRNAs (sg mRNAs) (Chen et al., 1993, J. Gen. Virol. 74:643–660; Den Boon et al., 1990, J. Virol., 65:2910–2920; De Vries et al., 1990, Nucleic Acids Res., 18:3241–3247; Kuo et al., 1991, J. Virol., 65:5118–5123; Kuo et al., 1992; U.S. application Ser. No. 08/131,625, now U.S. Pat. No. 5,695,766, and Ser. No. 08/301,435). Partial sequences of several North American isolates have also been determined (U.S. application Ser. No. 08/131,625, now U.S. Pat. No. 5,695,766, and Ser. No. 08/301,435; Mardassi et al., 1994, J. Gen. Virol., 75:681–685).

The genome of PRRSV is polyadenylated, about 15 kb in length and contains eight open reading frames (ORFs; Meulenberg et al., 1993; U.S. application Ser. No. 08/131,625, now U.S. Pat. No. 5,695,766, and Ser. No. 08/301,435). ORFs 1a and 1b probably encode viral RNA polymerase (Meulenberg et al., 1993). ORFs 5, 6 and 7 were found to encode a glycosylated membrane protein (E), an unglycosylated membrane protein (M) and a nucleocapsid protein (N), respectively (Meulenberg et al., 1995). ORFs 2 to 4 appear to have the characteristics of membrane-associated proteins (Meulenberg et al., 1993; U.S. application Ser. No. 08/301,435). However, the translation products of ORFs 2 to 4 were not detected in virus-infected cell lysates or virions (Meulenberg et al., 1995).

The major envelope glycoprotein of EAV encoded by ORF 5 may be the virus attachment protein, and neutralizing monoclonal antibodies (MAbs) are directed to this protein (de Vries, *J. Virol.* 1992; 66:6294–6303; Faaberg, *J. Virol.* 1995; 69:613–617). The primary envelope glycoprotein of LDV, a closely related member of PRRSV, is also encoded by ORF 5, and several different neutralizing MAbs were found to specifically immunoprecipitate the ORF 5 protein (Cafruny et al., *Vir. Res.,* 1986; 5:357–375). Therefore, it is likely that the major envelope protein of PRRSV encoded by ORF 5 may induce neutralizing antibodies against PRRSV.

Several hypervariable regions within the ORF5 were identified and were predicted to be antigenic (U.S. application Ser. Nos. 08/131,625 and 08/301,435). It has been proposed that antigenic variation of viruses is the result of direct selection of variants by the host immune responses (reviewed by Domingo et al., *J. Gen. Virol.* 1993, 74:2039–2045). Thus, these hypervariable regions are likely due to the host immune selection pressure and may explain the observed antigenic diversity among PRRSV isolates.

The M and N proteins of U.S. PRRSV isolates, including ISU 3927, are highly conserved (U.S. application Ser. No. 08/301,435). The M and N proteins are integral to preserving the structure of PRRSV virions, and the N protein may be under strict functional constraints. Therefore, it is unlikely either that (a) the M and N proteins are subjected to major antibody selection pressure or that (b) ORFs 6 and 7, which are likely to encode the M and N proteins, are responsible for or correlated to viral virulence. Interestingly, however, higher sequence variation of the LDV M protein was observed between LDV isolates with differing neurovirulence (Kuo et al., 1992, *Vir. Res.* 23:55–72).

ORFs 1a and 1b are predicted to translate into a single protein (viral polymerase) by frameshifting. ORFs 2 to 6 may encode the viral membrane associated proteins.

In addition to the genomic RNA, many animal viruses produce one or more sg mRNA species to allow expression of viral genes in a regulated fashion. In cells infected with PRRSV, seven species of virus-specific mRNAs representing a 3'-coterminal nested set are synthesized (mRNAs 1 to 7, in decreasing order of size). mRNA 1 represents the genomic mRNA. Each of the sg mRNAs contains a leader sequence derived from the 5'-end of the viral genome.

The numbers of the sg mRNAs differ among arteriviruses and even among different isolates of the same virus. A nested set of 6 sg mRNAs was detected in EAV-infected cells and European PRRSV-infected cells. However, a nested set of six (LDV-C) or seven (LDV-P) sg mRNAs, in addition to the genomic RNA, is present in LDV-infected cells. The additional sg mRNA 1-1 of LDV-P contains the 3'-end of ORF 1b and can potentially be translated to a protein which represents the C-terminal end of the viral polymerase. Sequence analysis of the sg mRNAs of LDV and EAV indicates that the leader-mRNA junction motif is conserved. Recently, the leader-mRNA junction sequences of the European LV were also shown to contain a common motif, UCAACC, or a highly similar sequence.

The sg mRNAs have been shown to be packaged into the virions in some coronaviruses, such as bovine coronavirus (BCV) and transmissible gastroenteritis virus (TGEV). However, only trace amounts of the sg mRNAs were detected in purified virions of mouse hepatitis virus (MHV), another coronavirus. The sg mRNAs of LDV, a closely related member of PRRSV, are also not packaged in the virions, and only the genomic RNA was detected in purified LDV virions.

The sg mRNAs of LDV and EAV have been characterized in detail. However, information regarding the sg mRNAs of PRRSV strains, especially the U.S. PRRSV, is very limited. Thus, a need is felt for a more thorough molecular characterization of the sg mRNAs of U.S. PRRSV.

The packaging signal of MHV is located in the 3'-end of ORF 1b, thus only the genomic RNA of MHV is packaged. The sg mRNAs of BCV and TGEV, however, are found in purified virions. The packaging signal of BCV and TGEV has not been determined. The Aura alphavirus sg mRNA is efficiently packaged into the virions, presumably because the packaging signal is present in the sg mRNA. The sindbis virus 26S sg mRNA is not packaged into virions because the packaging signal is located in the genome segment (not present in sg mRNA).

Several mechanisms are involved in the generation of the sg mRNAs. It has been proposed that coronaviruses utilize a unique leader RNA-primed transcription mechanism in which a leader RNA is transcribed from the 3' end of the genome-sized negative-stranded template RNA, dissociates from the template, and then rejoins the template RNA at downstream intergenic regions to prime the transcription of sg mRNAs. The model predicts that the 5'-leader contains a specific sequence at its 3'-end which is repeated further downstream in the genome, preceding each of the ORFs 2 to 7. The leader joins to the body of each of the sg mRNAs via the leader-mRNA junction segment.

The various strains of PRRSV continue to be characterized (Halbur et al., J. Vet. Diagn. Invest. 8:11–20 (1996); Meng et al., J. Vet. Diagn. Invest. 8:374–381 (1996); Meng et al., J. Gen. Virol. 77:1265–1270 (1996); Meng et al., J. Gen. Virol. 76:3181–3188 (1995); Meng et al., Arch. Virol. 140:745–755 (1995); Halbur et al., Vet. Pathol. 32:200–204 (1995); Morozov et al., Arch. Virol. 140:1313–1319 (1995); Meng et al., J. Gen Virol. 75:1795–1801 (1994); Halbur et al., J. Vet. Diagn. Invest. 6:254–257 (1994), all of which are incorporated herein by reference in their entireties.)

> "PRRSV is an important cause of pneumonia in nursery and weaned pigs. PRRSV causes significant economic losses from pneumonia in nursery pigs (the exact extent of which are not fully known). Reproductive disease was the predominant clinical outcome of PRRSV infections during the past few years, due to the early prevalence of relatively low virulence strains of PRRSV. Respiratory disease has now become the main problem associated with PRRSV, due to the increasing prevalence of relatively high virulence strains of PRRSV. A need is felt for a vaccine to protect against disease caused by the various strains of PRRSV.

Surprisingly, the market for animal vaccines in the U.S. and worldwide is larger than the market for human vaccines. Thus, there exists an economic incentive to develop new veterinary vaccines, in addition to the substantial public health benefit which is derived from protecting farm animals from disease.

SUMMARY OF THE INVENTION

Accordingly, it is an object of the present invention to provide a DNA sequence encoding a porcine reproductive and respiratory syndrome virus (PRRSV) which contains SEQ ID NO:55 (ISU-12) or SEQ ID NO:54 (ISU-55).

It is another object of the invention to provide a DNA sequence encoding an open reading frame of ISU-12 including nucleotides 191–7387 of SEQ ID NO:68 (ORF1a), nucleotides 7375–11757 of SEQ ID NO:69 (ORF 1b), nucleotides 11762–12529 of SEQ ID NO:70 (ORF 2), nucleotides 12385–13116 of SEQ ID NO:71 (ORF 3), nucleotides 12930–13463 of SEQ ID NO:72 (ORF 4), nucleotides 13477–14076 of SEQ ID NO:73 (ORF 5), nucleotides 14064–14585 of SEQ ID NO:74 (ORF 6) and nucleotides 14578–14946 of SEQ ID NO:75 (ORF 7);

or of ISU-55 of ISU-12 including nucleotides 191–7699 of SEQ ID NO:76 (ORF1a), nucleotides 7657–12009 of SEQ ID NO:77 (ORF 1b), nucleotides 12074–12841 of SEQ ID NO:78 (ORF 2), nucleotides 12697–13458 of SEQ ID NO:79 (ORF 3), nucleotides 13242–13775 of SEQ ID NO:80 (ORF 4), nucleotides 13789–14388 of SEQ ID NO:81 (ORF 5), nucleotides 14376–14897 of SEQ ID NO:82 (ORF 6) and nucleotides 14890–15258 of SEQ ID NO:83 (ORF 7).

It is also an object of the invention to provide a polypeptide encoded by the DNA sequence encoding ISU-12 or ISU-55, or one or more ORFs thereof.

Yet another object of the invention is to provide a composition for inducing antibodies against PRRSV comprising one or more polypeptides encoded by the DNA sequences of one or more ORF of ISU-12 or ISU-55.

Another object of the invention is to provide a method of protecting a pig from a porcine reproductive and respiratory disease, by administering an effective amount of the polypeptides encoded by the DNA sequences of one or more ORFs of ISU-12 or ISU-55 to a pig in need of protection against said disease.

It is yet another object of the invention to provide a method of distinguishing PRRSV strain ISU-55 from other strains of PRRSV by:

(a) amplifying a DNA sequence of the PRRSV using the following two primers.

55F 5'-CGTACGGCGATAGGGACACC-3' (SEQ ID NO:84)

and

3RFLP 5'-GGCATATATCATCACTGGCG-3' (SEQ ID NO:85);

(b) digesting the amplified sequence of step (a) with DraI; and (c) correlating the presence of three restriction fragments of 626 bp, 187 bp and 135 bp with a PRRSV ISU-55 strain.

These and other objects, which will become apparent during the following description of the preferred embodiments, have been provided by a purified and/or isolated polypeptide selected from the group consisting of proteins encoded by one or more open reading frames (ORF's) of an Iowa strain of porcine reproductive and respiratory syndrome virus (PRRSV), proteins at least 94% but less than 100% homologous with a protein encoded by an ORF 2 of an Iowa strain of PRRSV, proteins at least 88% but less than 100% homologous with a protein encoded by ORF 3 of an Iowa strain of PRRSV, proteins at least 93% homologous with an ORF 4 of an Iowa strain of PRRSV, proteins at least 90% homologous with an ORF 5 of an Iowa strain of PRRSV, proteins at least 97% but less than 100% homologous with proteins encoded by one or both of ORF 6 and ORF 7 of an Iowa strain of PRRSV, antigenic regions of such proteins which are at least 5 amino acids in length and which effectively stimulate protection in a porcine host against a subsequent challenge with a PRRSV isolate, and combinations thereof; an isolated polynucleic acid which encodes such a polypeptide or polypeptides; a vaccine comprising an effective amount of such a polynucleotide or polypeptide(s); antibodies which specifically bind to such a polynucleotide or polypeptide; methods of producing the same; and methods of (i) effectively protecting a pig against PRRS, (ii) treating a pig exposed to a PRRSV or suffering from PRRS, and (iii) detecting a PRRSV using the same.

BRIEF DESCRIPTION OF THE FIGURES

FIGS. 1A, 1B, IC, ID, 1E, IF and 1G shows a nucleotide sequence comparison of ORFs 2 to 5 of U.S. isolates ISU 79 (SEQ ID NO:7), ISU 1894 (SEQ ID NO:6), ISU 3927 (SEQ ID NO:2), ISU 22 (SEQ ID NO:4), and ISU 55 (SEQ ID NO:3) with other known PRRSV isolates (SEQ ID NOS:1 and 5);

FIGS. 2A, 2B, 2C and 2D respectively show the alignment of the deduced amino acid sequences of ORF 2, ORF 3, ORF 4 and ORF 5 of U.S. isolates ISU 79 (SEQ ID NOS:10, 18, 24, 36), ISU 1894 (SEQ ID NOS:12, 14, 27, 35), ISU 22 (SEQ ID NOS:9, 20, 28, 37), ISU 55 (SEQ ID NOS:11, 17, 26, 34), and ISU 3927 (SEQ ID NOS:13, 21, 30, 38) with other known PRRSV isolates (SEQ ID NOS:8, 14, 15, 16, 22, 23, 24, 25, 31, 32, 33, 39);

FIGS. 9A, 9B, 9C and 9D shows the sequence alignment of ORFs 2 to 7 of ISU 1894 (SEQ ID NO:40) and ISU 79 (SEQ ID NO:41), where the start codon of each ORF is indicated by +>, the termination codon of each ORF is indicated by asterisks (*), the determined or predicted leader-mRNA junction sequences are underlined and the locations of the leader-mRNA junction sequences relative to the start codon of each ORF are indicated by minus (−) numbers of nucleotides upstream of each ORF.

FIG. 13. Titers of monoclonal antibodies.

FIG. 21. Primers (SEQ ID NOS:42–53) used to amplify PRRSV ORFs 2 through 7 genes with PCR. The underlined sequence within each primer indicates the unique restriction enzyme site that was introduced to facilitate subsequent cloning steps.

FIG. 22. Recombinant proteins of PRRSV ORFs 2 to 5 expressed in insect cells. a=predicted $M_r$ of products of PRRSV ORFs 2 to 5 and N-glycosylation sites are based on nucleotide sequence studies (Meng et al, 1994 & Morozov et al, 1995). b=expressed products in inset cells. c=bands after tunicamycin treatment were determined by immunoblotting analysis. d=leader-free core proteins are determined on the basis of tunicamycin treatment analysis. the presence of the other bands in the recombinant products after tunicamycin treatment was possibly due to O-linked glycosylation, phosphorylation or other post-translational modifications.

FIG. 25 shows alignments of ORF1a of VR 2385 and LV.

FIG. 26 shows the results of nested RT PCR with leader and ORF specific primers to amplify PCR products corresponding to mRNAs 4a, 5a and 7a.

FIG. 27 shows the DNA sequence alignment of low passage (SEQ ID NO:64) and high passage (SEQ ID NO:65) ISU55.

FIG. 29 is a restriction map showing the addition DraI site in the sequence of the high passage ISU-55 strain.

FIG. 32 shows the nucleotide sequence of ISU-55 (SEQ ID NO:54).

FIG. 33 shows the nucleotide sequence of ISU-12 (VR2385) (SEQ ID NO:55).

FIG. 34 shows the alignment of the nucleotide sequence of ISU-55 (SEQ ID NO:54) and ISU-12 (VR2385) (SEQ ID NO:55).

DETAILED DESCRIPTION OF THE PREFERRED EMBODIMENTS

Figure 3:
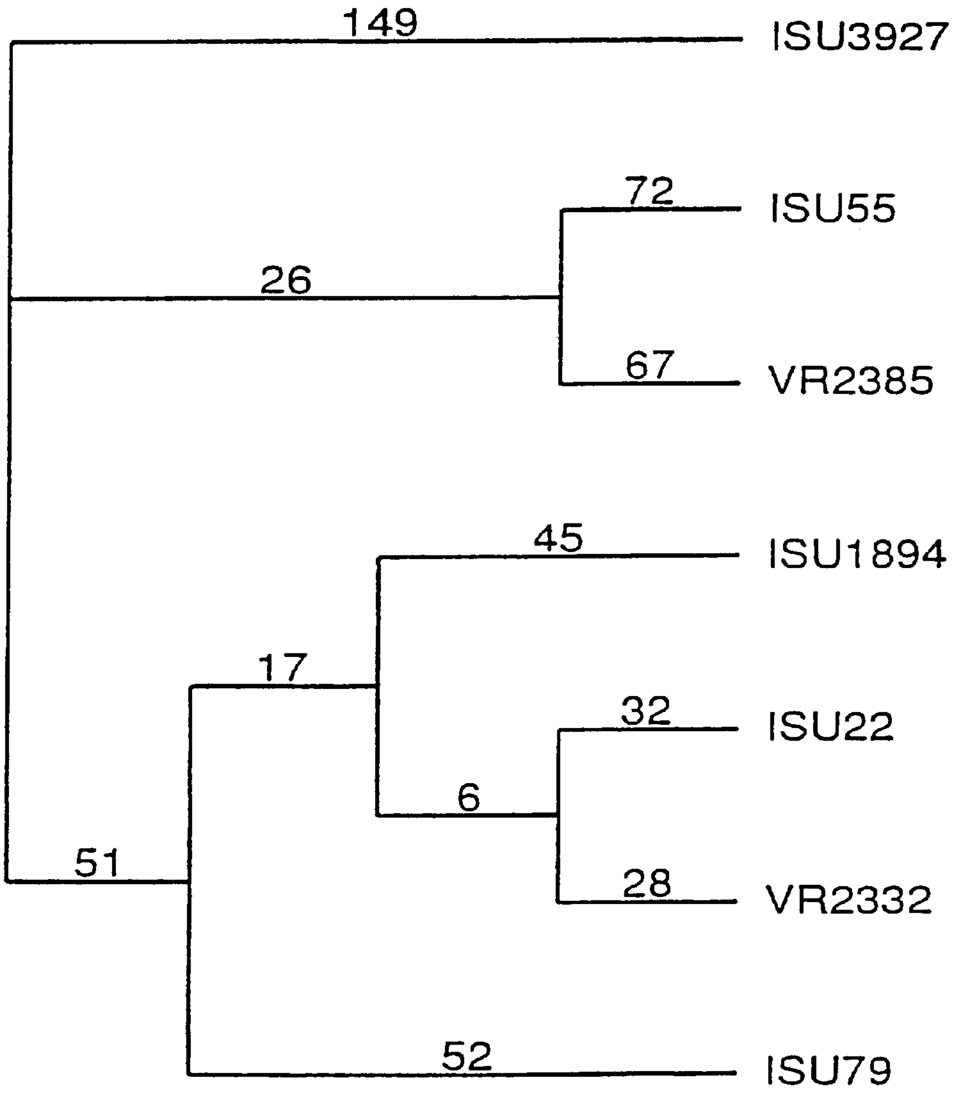
FIG. 3 shows a phylogenetic tree based on the nucleotide sequences of ORFs 2 to 7 of seven U.S. PRRSV isolates with differing virulence.

In the present application, the nucleotide sequences of the ORFs 2 to 5 of a low virulence isolate and four other Iowa strain PRRSV isolates with "moderate" and high virulence have been determined. Based on comparisons of ORFs 2 to 7 of various PRRSV isolates, the least virulent U.S. isolate known (ISU 3927) has relatively high sequence variations in ORFs 2 to 4, as compared to the variations in other U.S. isolates. Furthermore, based on analysis of the sequences of the ORFs, at least three minor genotypes exist within the major genotype of U.S. PRRSV.

Sequence analysis of the ORF 5 protein of different PRRSV isolates reveal three hypervariable regions which contained non-conserved amino acid substitutions. These regions are hydrophilic and also antigenic as predicted by computer analysis.

In the present invention, a "porcine reproductive and respiratory syndrome virus" or "PRRSV" refers to a virus which causes the diseases PRRS, PEARS, SIRS, MSD and/or PIP (the term "PIP" now appears to be disfavored), including the Iowa strain of PRRSV, other strains of PRRSV found in the United States (e.g., VR 2332), strains of PRRSV found in Canada (e.g., IAF-exp91), strains of PRRSV found in Europe (e.g., Lelystad virus, PRRSV-10), and closely-related variants of these viruses which may have appeared and which will appear in the future.

The "Iowa strain" of PRRSV includes (a) PRRSV isolates deposited in the American Type Culture Collection 10801 University Boulevard, Manassas, Va. 20110-2205 by the present inventors and/or described in this application and/or in either of prior U.S. application Ser. No. 08/131,625, now U.S. Pat. No. 5,695,766, and Ser. No. 08/301,435, (b) PRRS viruses which produce more than six sg mRNAs when cultured or passaged in CRL 11171 cells, (c) PRRSVs which produce at least 40% gross lung lesions or lung consolidation in 5-week-old caesarean-derived, colostrum-deprived piglets 10 days post-infection, (d) a PRRSV isolate having a genome which encodes a protein having the minimum homology to a PRRSV ORF described in Table 2 below, and/or (d) any PRRSV isolate having the identifying characteristics of such a virus.

The present vaccine is effective if it protects a pig against infection by a porcine reproductive and respiratory syndrome virus (PRRSV). A vaccine protects a pig against infection by a PRRSV if, after administration of the vaccine to one or more unaffected pigs, a subsequent challenge with a biologically pure virus isolate (e.g., VR 2385, VR 2386, or other virus isolate described below) results in a lessened severity of any gross or histopathological changes (e.g., lesions in the lung) and/or of symptoms of the disease, as compared to those changes or symptoms typically caused by the isolate in similar pigs which are unprotected (i.e., relative to an appropriate control). More particularly, the present vaccine may be shown to be effective by administering the vaccine to one or more suitable pigs in need thereof, then after an appropriate length of time (e.g., 14 weeks), challenging with a large sample ($10^{3-7}$ $TCID_{50}$) of a biologically pure PRRSV isolate. A blood sample is then drawn from the challenged pig after about one week, and an attempt to isolate the virus from the blood sample is then performed (e.g., see the virus isolation procedure exemplified in Experiment VIII below). Isolation of the virus is an indication that the vaccine may not be effective, and failure to isolate the virus is an indication that the vaccine may be effective.

Thus, the effectiveness of the present vaccine may be evaluated quantitatively (i.e., a decrease in the percentage of consolidated lung tissue as compared to an appropriate control group) or qualitatively (e.g., isolation of PRRSV from blood, detection of PRRSV antigen in a lung, tonsil or lymph node tissue sample by an immunoperoxidase assay method [described below], etc.). The symptoms of the porcine reproductive and respiratory disease may be evaluated quantitatively (e.g., temperature/ fever), semi-quantitatively (e.g., severity of respiratory distress [explained in detail below], or qualitatively (e.g., the presence or absence of one or more symptoms or a reduction in severity of one or more symptoms, such as cyanosis, pneumonia, heart and/or brain lesions, etc.).

An unaffected pig is a pig which has either not been exposed to a porcine reproductive and respiratory disease infectious agent, or which has been exposed to a porcine reproductive and respiratory disease infectious agent but is not showing symptoms of the disease. An affected pig is one which shows symptoms of PRRS or from which PRRSV can be isolated.

The clinical signs or symptoms of PRRS may include lethargy, respiratory distress, "thumping" (forced expiration), fevers, roughened haircoats, sneezing, coughing, eye edema and occasionally conjunctivitis. Lesions may include gross and/or microscopic lung lesions, myocarditis, lymphadenitis, encephalitis and rhinitis. In addition, less virulent and non-virulent forms of PRRSV and of the Iowa strain have been found, which may cause either a subset of the above symptoms or no symptoms at all. Less virulent and non-virulent forms of PRRSV can be used according to the present invention to provide protection against porcine reproductive and respiratory diseases nonetheless.

The phrase "polynucleic acid" refers to RNA or DNA, as well as mRNA and cDNA corresponding to or complementary to the RNA or DNA isolated from the virus or infectious agent. An "ORF" refers to an open reading frame, or polypeptide-encoding segment, isolated from a viral genome, including a PRRSV genome. In the present polynucleic acid, an ORF can be included in part (as a fragment) or in whole, and can overlap with the 5'- or 3'-sequence of an adjacent ORF (see for example, FIG. 1 and Experiment 1 below). A "polynucleotide" is equivalent to a polynucleic acid, but may define a distinct molecule or group of molecules (e.g., as a subset of a group of polynucleic acids).

In the Experiments described hereinbelow, the isolation, cloning and sequencing of ORFs 2 to 5 of (a) a low virulence U.S. PRRSV isolate and (b) two other U.S. PRRSV isolates of varying virulence were determined. The nucleotide and deduced amino acid sequences of these three U.S. isolates were compared with the corresponding sequences of other known PRRSV isolates (see, for example, U.S. application Ser. No. 08/301,435). The results indicate that considerable genetic variations exist not only between U.S. PRRSV and European PRRSV, but also among the U.S. isolates as well.

The amino acid sequence identity between the seven U.S. PRRSV isolates studied was 91–99% in ORF 2, 86–98% in ORF 3, 92–99% in ORF 4 and 88–97% in ORF 5. The least virulent U.S. isolate known (ISU 3927) has higher sequence variations in ORFs 2 to 4 than in ORFs 5 to 7, as compared to other U.S. isolates. Three hypervariable regions with antigenic potential have been identified in the major envelope glycoprotein encoded by ORF 5.

Pairwise comparison of the sequences of ORFs 2 to 7 and phylogenetic tree analysis implied the existence of at least three groups of PRRSV variants (or minor genotypes) within the major genotype of U.S. PRRSV. The least virulent U.S. isolate known forms a distinct branch from other U.S. isolates with differing virulence. The results of this study have implications for the taxonomy of PRRSV and vaccine development.

In a further experiment, the sg mRNAs in PRRSV-infected cells were characterized. The data showed that a 3'-coterminal nested set of six or seven sg mRNAs is formed in cells infected with different isolates of PRRSV. However, unlike some of the coronaviruses and alphavirus, the sg mRNAs of PRRSV are not packaged into the virion, and only was the genomic RNA of PRRSV detected in purified virions. Variations in the numbers of the sg mRNAs among different PRRSV isolates with differing virulence were also observed. Further sequence analysis of ORFs 2 to 7 of two U.S. isolates and their comparison with the European LV reveal the heterogeneic nature of the leader-mRNA junction sequences of PRRSV.

As demonstrated in Experiment 2 below, a 3'-coterminal nested set of six or more sg mRNAs is formed in cells infected with different isolates of PRRSV. The presence of a nested set of sg mRNAs further indicates that U.S. PRRSV, like the European isolate Lelystad virus (LV), belongs to the newly proposed Arteriviridae family including LDV, EAV and SHFV. Northern blot analysis with ORF-specific probes indicates that the structure of the PRRSV sg mRNAs is polycistronic, and each of the sg mRNAs except for sg mRNA 7 contains multiple ORFs. Therefore, the sequence of each sg mRNA is contained within the 3'-portion of the next larger sg mRNA, and not all 5'-ends of the sg mRNAs overlap with the sequences of the smaller sg mRNAs.

There is no apparent correlation, however, between the numbers of sg mRNAs and viral pneumovirulence. An additional species, sg mRNA 3-1, was found to contain a small ORF (ORF 3-1) with a coding capacity of 45 amino acids at its 5'-end.

In Experiment 2 below, the sg mRNAs of PRRSV are shown not to be packaged into the virions. Whether sg mRNAs are packaged into virions may depend an whether the sg mRNAs contain a packaging signal. Since the sg mRNAs of PRRSV are not packaged into virions, the encapsidation signal of PRRSV is likely localized in the ORF 1 region which is unique to the viral genome, but which is not present in the sg mRNAs.

In Experiment 2 below, the junction segments (the leader-mRNA junction sequences) of sg mRNAs 3 and 4 of two U.S. isolates of PRRSV, ISU 79 and ISU 1894, are determined. The knowledge of the leader-mRNA junction sequence identities provides means for effectively producing (a) chimeric viruses to be used as an infectious clone and/or as a vaccine, and (b) vectors for inserting or "shuttling" one or more genes into a suitable, infectable host. Methods for designing and producing such chimeric viruses, infectious clones and vectors are known (see, for example, Sambrook et al, "Molecular Cloning: A Laboratory Manual", 2nd ed., Cold Spring Harbor Laboratory, Cold Spring Harbor, N.Y.).

The leader-mRNA junction sequence of sg mRNAs 3 and 4 of the two isolates are different (TTGACC for mRNA 3-1 of ISU 79, GTAACC for mRNA 3, and TTCACC for mRNA 4). Most of the nucleotide differences in the junctions are present in the first 3 nucleotides. The last 3 nucleotides are invariable, suggesting that the joining of the leader sequence to the bodies of sg mRNAs occurs within the 5'-end of the leader-mRNA junction sequence. Similar observations have been reported for LV, EAV and LDV.

The acquisition of the additional sg mRNA 3-1 in isolate ISU 79 is due to a single nucleotide substitution which generates a new leader mRNA junction sequence. This substitution occurs in the last nucleotide of the junction segment, suggesting that the last nucleotide of the leader-mRNA junction motif is critical for the binding of the leader and for the initiation of transcription.

Although the sequence homology between the leader and the intergenic regions of coronaviruses led to the hypothesis that basepairing might be essential in the leader-primed transcription, no experimental evidence has documented for the requirement of base-pairing in transcription of the sg mRNAs. For example, the sequence at the 3'-end of the leader of both coronaviruses and arteriviruses that is involved in the fusion process remains unknown.

Several lines of evidence support the leader-primed transcription mechanism for coronaviruses, but the presence of negative-stranded sg mRNAs and sg replicative intermediates (sg RI) in coronavirus-infected cells suggests that the mechanism involved in sg mRNA synthesis is more complex than mere base-pairing of the leader sequence with a junction sequence. However, negative-stranded sg mRNAs have not been detected in arteriviruses except for LDV, and sg RIs have been detected only in EAV-infected cells. Therefore, sg mRNA synthesis in arteriviruses, and particularly in PRRSV, may be less complicated than in coronaviruses.

Sequence analysis of the ORFs 2 to 7 of two U.S. PRRSV isolates and comparison of the sequences with LV reveals the heterogeneity of the leader-mRNA junction sequences. The presence of the leader-mRNA junction motifs at positions which do not correspond to a sg mRNA raises a question as to whether the short stretch of only six nucleotides which are conserved in the leader and junction sequences in the genomes of PRRSV and other arteriviruses is sufficient for efficient binding of the leader to these specific junction sites upstream of the ORFs. This apparent discrepancy, however, may be explained by the following two possibilities.

First, additional structural elements, such as secondary structures or the sequences surrounding the leader-mRNA junction segment, are expected to be involved in the fusion (binding) of the leader to the specific sites. It has been shown that, in MHV, the sequence flanking the consensus sequence (leader-mRNA junction sequence) of UCUAAAC affects the efficiency of sg DI RNA transcription, and that the consensus sequence was necessary but not sufficient in and of itself for the synthesis of the DI mRNA.

Second, the distance between two leader-mRNA junction regions may affect the transcription of sg mRNAs. It has been demonstrated that the downstream leader-mRNA junction region was suppressing sg DI RNA synthesis of MHV from the upstream leader-mRNA junction region. The suppression was significant when the two leader-mRNA junction sequence separation was less than 35 nucleotides. However, significant inhibition of larger sg DI RNA synthesis (from the upstream leader-mRNA junction sequence) was not observed when the two leader-mRNA junction regions were separated by more than 100 nucleotides.

The previously reported experimental results are consistent with the observations reported in Experiment 2 below, where an additional species of sg mRNA 3-1, in addition to the sg mRNA 4, is observed in some of the PRRSV isolates. The leader-mRNA junction sequences of sg mRNAs 4 and 3-1 in the Iowa strain of PRRSV are separated by about 226 nucleotides. Therefore, the synthesis of the larger sg mRNA 3-1 from the upstream leader-mRNA junction sequence is not suppressed by the presence of the downstream leader-mRNA 4 junction sequence.

In contrast, multiple potential leader-mRNA junction sequences were found at different positions upstream of ORFs 3, 5, 6 and 7, but there were no sg mRNAs corresponding to these leader-mRNA junction motifs in the Northern blot analysis. Most of these leader-mRNA junction sequences are separated by less than 50 nucleotides from the downstream leader-mRNA junction region, except for ORF 7 (in which the two potential leader-mRNA junction sequences are separated by 114 nucleotides). However, sg mRNA 7 in Northern blot analysis showed a widely-diffused band. Therefore, transcription of the larger sg mRNA 7 from the upstream leader-mRNA junction sequence may not be significantly suppressed by the downstream junction sequence, but it is not easily distinguishable from the abundant sg mRNA 7 by Northern blot analysis.

The Present Polynucleotides and Polypeptides

ORF's 2–7 of plaque-purified PRRSV isolate ISU-12 (SEQ ID NOS:70–75) (deposited on Oct. 30, 1992, in the American Type Culture Collection, 12301 Parklawn Drive, Rockville, Md. 20852, U.S.A., under the accession numbers VR 2385 [3×plaque-purified] and 20 VR 2386 [non-plaque-purified]) and ORF's 6–7 of PRRSV isolates ISU-22 (SEQ ID NOS:74 and 75), ISU-55 (SEQ ID NOS:82 and 83), ISU3927 (deposited on Sep. 29, 1993, in the American Type Culture Collection under the accession numbers VR 2429, VR 2430 and VR 2431, respectively), ISU-79 and ISU-1894 (deposited on Aug. 31, 1994, in the American Type Culture Collection under the accession numbers VR 2474 and VR 2475, respectively) are described in detail in U.S. application Ser. No. 08/301,435. However, the techniques used to isolate, clone and sequence these genes can be also applied to the isolation, cloning and sequencing of the genomic polynucleic acids of any PRRSV. Thus, the present invention is not limited to the specific sequences disclosed in the Experiments below.

For example, primers for making relatively large amounts of DNA by the polymerase chain reaction (and if desired, for making RNA by transcription and/or protein by translation in accordance with known in vivo or in vitro methods) can be designed on the basis of sequence information where more than one sequence obtained from a PRRSV genome has been determined (e.g., ORF's 2–7 of VR 2385, VR 2429, VR 2430, VR 2431, VR 2474, ISU-1894, VR 2332 and Lelystad virus). A region from about 15 to 50 nucleotides in length having at least 80% and preferably at least 90% identity is selected from the determined sequences. A region where a deletion occurs in one of the sequences (e.g., of at least 5 nucleotides) can be used as the basis for preparing a selective primer for selective amplification of the polynucleic acid of one strain or type of PRRSV over another (e.g., for the differential diagnosis of North American and European PRRSV strains).

Once the genomic polynucleic acid is amplified and cloned into a suitable host by known methods, the clones can be screened with a probe designed on the basis of the sequence information disclosed herein. For example, a region of from about 50 to about 500 nucleotides in length is selected on the basis of either a high degree of identity (e.g., at least 90%) among two or more sequences (e.g., in ORF's 6–7 of the Iowa strains of PRRSV disclosed in Experiment III below), and a polynucleotide of suitable length and sequence identity can be prepared by known methods (such as automated synthesis, or restriction of a suitable fragment from a polynucleic acid containing the selected region, PCR amplification using primers which hybridize specifically to the polynucleotide, and isolation by electrophoresis). The polynucleotide may be labeled with, for example, $^{32}P$ (for radiometric identification) or biotin (for detection by fluorometry). The probe is then hybridized with the polynucleic acids of the clones and detected according to known methods.

The present Inventors have discovered that one or more of ORFs 2–4 may be related to the virulence of PRRSV. For example, at least one isolate of PRRSV which shows relatively low virulence also appears to have a deletion in ORF 4 (see, for example, Experiments VIII–XI in U.S. application Ser. No. 08/301,435). Furthermore, the least virulent known isolate (VR 2431) shows a relatively high degree of variance in both nucleotide and amino acid sequence information in ORFs 2–4, as compared to other U.S. PRRSV isolates. Thus, in one embodiment, the present invention concerns polynucleotides and polypeptides related to ORFs 2–4 of VR 2431.

In a further embodiment, the present invention is concerned with a polynucleic acid obtained from a PRRSV isolate which confers immunogenic protection directly or indirectly against a subsequent challenge with a PRRSV, but in which the polynucleic acid is deleted or mutated to an extent which would render a PRRSV containing the polynucleic acid either low-virulent (i.e., a "low virulence" (lv) phenotype; see the corresponding explanation in U.S. application Ser. No. 08/301,435) or non-virulent (a so-called "deletion mutant"). Preferably, one or more of ORFs 2–4 is/are deleted or mutated to an extent which would render a PRRS virus non-virulent. However, it may be desirable to retain regions of one or more of ORFs 2–4 in the present polynucleic acid which (i) encode an antigenic and/or immunoprotective peptide fragment and which (ii) do not confer virulence to a PRRS virus containing the polynucleic acid.

The present invention also encompasses a PRRSV per se in which one or more of ORFs 2–4 is deleted or mutated to an extent which renders it either low-virulent or non-virulent (e.g., VR 2431). Such a virus is useful as a vaccine or as a vector for transforming a suitable host (e.g., MA-104, PSP 36, CRL 11171, MARC-145 or porcine alveolar macrophage cells) with a heterologous gene. Preferred heterologous genes which may be expressed using the present deletion mutant may include those encoding a protein or an antigen other than a porcine reproductive and respiratory syndrome virus antigen (e.g., pseudorabies and/or swine influenza virus proteins and/or polypeptide-containing antigens, a porcine growth hormone, etc.) or a polypeptide-based adjuvant (such as those discussed in U.S. application Ser. No. 08/301,435 for a vaccine composition).

It may also be desirable in certain embodiments of the present polynucleic acid which contain, for example, the 3'-terminal region of a PRRSV ORF (e.g., from 200 to 700 nucleotides in length), at least part of which may overlap with the 5'-region of the ORF immediately downstream. Similarly, where the 3'-terminal region of an ORF may overlap with the 5'-terminal region of the immediate downstream ORF, it may be desirable to retain the 5'-region of the ORF which overlaps with the ORF immediately downstream.

The present inventors have also discovered that ORF 5 in the PRRSV genome appears to be related to replication of the virus in mammalian host cells capable of sustaining a culture while infected with PRRSV. Accordingly, the present invention is also concerned with polynucleic acids obtained from a PRRSV genome in which ORF 5 may be present in multiple copies (a so-called "overproduction mutant"). For example, the present polynucleic acid may contain at least two, and more preferably, from 2 to 10 copies of ORF 5 from a high-replication (hr) phenotype PRRSV isolate.

Interestingly, the PRRSV isolate ISU-12 has a surprisingly large number of potential start codons (ATG/AUG sequences) near the 5'-terminus of ORF 5, possibly indicating alternate start sites of this gene. Thus, alternate forms of the protein encoded by ORF 5 of a PRRSV isolate may exist, particularly where alternate ORF's encode a protein having a molecular weight similar to that determined experimentally (e.g., from about 150 to about 250 amino acids in length). The most likely coding region for ORF 5 of ISU-12 is indicated in FIG. 1.

One can prepare deletion and overproduction mutants in accordance with known methods. For example, one can prepare a mutant polynucleic acid which contains a "silent" or degenerate change in the sequence of a region encoding a polypeptide. By selecting and making an appropriate degenerate mutation, one can substitute a polynucleic acid sequence recognized by a known restriction enzyme (see, for example, Experiment 2 below). Thus, if a silent, degenerate mutation is made at one or two of the 3'-end of an ORF and the 5'-end of a downstream ORF, one can insert a synthetic polynucleic acid (a so-called "cassette") which may contain a polynucleic acid encoding one or multiple copies of an hr ORF 5 protein product, of a PRRSV or other viral envelope protein and/or an antigenic fragment of a PRRSV protein.

The "cassette" may be preceded by a suitable initiation codon (ATG), and may be suitably terminated with a termination codon at the 3'-end (TAA, TAG or TGA). Of course, an oligonucleotide sequence which does not encode a polypeptide may be inserted, or alternatively, no cassette may be inserted. By doing so, one may provide a so-called deletion mutant.

The present invention also concerns regions and positions of the polypeptides encoded by ORFs of VR 2431 which may be responsible for the low virulence of this isolate. Accordingly, the present isolated and/or purified polypeptide may be one or more encoded by a "low-virulence mutation" of one or more of ORFs 2, 3 and 4 of a PRRSV (or a low-virulence fragment thereof at least 5 amino acids in length) in which one or more of positions 12–14 of the polypeptide encoded by ORF 2 are RGV (in which "R", "G" and "V" are the one-letter abbreviations for the corresponding amino acids), positions 4446 are LPA, position 88 is A, position 92 is R, position 141 is G, position 183 is H, position 218 is S, position 240 is S and positions 252–256 are PSSSW, or any combination thereof. Other amino acid residue identities which can be further combined with one or more of the above amino acid position identities include those at position 174 (I) and position 235 (M).

The present isolated and/or purified polypeptide may also be one encoded by an ORF 3 of a PRRSV in which one or more of the specified amino acid identities may be selected from those at positions 11 (L), 23 (V), 26–28 (TDA), 65–66 (QI), 70 (N), 79 (N), 93 (T), 100–102 (KEV), 134 (K), 140 (N), 223–227 (RQRIS), 234 (A) and 235 (M), or any combination thereof, which may be further combined with one or more of positions 32 (F), 38 (M), 96 (P), 143 (L), 213–217 (FQTS), 231 (R), and 252 (A).

The present isolated and/or purified polypeptide may also be one encoded by an ORF 4 of a PRRSV in which one or more of the specified amino acid identities may be selected from those at positions 13 (E), 43 (N), 56 (G), 58–59 (TT), 134 (T), 139 (I) and any combination thereof, which may be further combined with one or more of positions 2–3 (AA), 51 (G) and 63 (P).

The present invention also concerns polynucleotide sequences encoding polypeptide sequences of 5 or more amino acids, preferably 10 or more amino acids, and up to the full length of the polypeptide, encoded by any one of ORFs 2–4 of VR 2431, in which the polynucleotides at the codon(s) corresponding to the amino acid positions detailed in the preceding three paragraphs are replaced with polynucleotides encoding the corresponding amino acids of the proteins encoded by the corresponding ORF of VR 2431.

In a further embodiment of the present invention, the polynucleic acid encodes one or more proteins, or antigenic regions thereof, of a PRRSV. Preferably, the present nucleic acid encodes at least one antigenic region of a PRRSV membrane (envelope) protein. More preferably, the present polynucleic acid encodes a hypervariable region from a ORF 5 PRRSV protein product (see the discussion below) or (b) contains at least one copy of the ORF-5 gene from a high virulence (hv) phenotype isolate of PRRSV (see the description of "hv phenotype" in U.S. application Ser. No. 08/301,435) and a sufficiently long fragment, region or sequence of at least one of ORF-2, ORF-3, ORF4, ORF-5 and/or ORF-6 from the genome of a PRRSV isolate to encode an antigenic region of the corresponding protein(s) and effectively stimulate protection against a subsequent challenge with, for example, a hv phenotype PRRSV isolate.

Even more preferably, at least one entire envelope protein encoded by ORF-2, ORF-3, ORF-5 and/or ORF-6 of a PRRSV is contained in the present polynucleic acid, and the present polynucleic acid excludes or modifies a sufficiently long portion of one of ORFs 2–4 from a PRRSV to render a PRRSV containing the same either low-virulent or non-virulent. Most preferably, the polynucleic acid is isolated from the genome of an isolate of the Iowa strain of PRRSV (for example, VR 2385 (3×plaque-purified ISU-12), VR 2386 (non-plaque-purified ISU-12), VR 2428 (ISU-51), VR 2429 (ISU-22), VR 2430 (ISU-55), VR 2431 (ISU-3927), VR 2474 (ISU-79) and/or ISU-1894).

A further preferred embodiment of the present invention includes a polynucleotide encoding an amino acid sequence from a hypervariable region of ORF 5 of a PRRSV, preferably of an Iowa strain of PRRSV. Thus, such polynucleotides encode one (or more) of the following amino acid sequences:

TABLE 1

| Hypervariable Region 1 (Positions 32–38) | Hypervariable Region 2 (Positions 57–66) | Hypervariable Region 3 (Positions 120–128) |
|---|---|---|
| NGNSGSN (SEQ ID NO:86) | | |
| SNDSSSH (SEQ ID NO:87) | ANKFDWAVET (SEQ ID NO:94) | LICFVIRLA (SEQ ID NO:100) |
| SSSNSSH (SEQ ID NO:88) | ANKFDWAVEP (SEQ ID NO:95) | LTCFVIRFA (SEQ ID NO:101) |
| SANSSSH (SEQ ID NO:89) | AGEFDWAVET (SEQ ID NO:96) | LICFVIRFT (SEQ ID NO:102) |
| HSNSSSH (SEQ ID NO:90) | ADKFDWAVEP (SEQ ID NO:97) | LACFVIRFA (SEQ ID NO:103) |
| SNSSSSH (SEQ ID NO:91) | ADRFDWAVEP (SEQ ID NO:98) | LTCFVIRFV (SEQ ID NO:104) |
| NNSSSSH (SEQ ID NO:92) | SSHFGWAVET (SEQ ID NO:99) | LTCFIIRFA (SEQ ID NO:105) |
| NGGDSST(Y) (SEQ ID NO:93) | | FICFVIRFA (SEQ ID NO:106) |
| | | FVCFVIRAA (SEQ ID NO:107) |

In this embodiment, the polynucleotide may encode further amino acid sequences of a PRRSV ORF 5 (as disclosed in FIG. 3 or in U.S. application Ser. No. 08/131,625, now U.S. Pat. No. 5,695,766, or Ser. No. 08/301,435), as long as one or more of the hypervariable regions at positions 32–38, 57–66 and/or 120–128 are included. (The present invention specifically excludes the proteins and polynucleotides of ORF 5 of LV and VR 2332.)

A further preferred embodiment of the present invention concerns a purified preparation which may comprise, consist essentially of or consist of a polynucleic acid having a sequence of the formula (I) or (II):

$$5'\text{-}\alpha\text{-}\beta\text{-}3' \qquad (I)$$

$$5'\text{-}\alpha\text{-}\beta\text{-}\gamma\text{-}3' \qquad (II)$$

wherein α encodes at least one polypeptide, or antigenic or low-virulence fragment thereof encoded by a polynucleotide selected from the group consisting of ORFs 2, 3 and 4 of an Iowa strain of PRRSV and regions thereof encoding such antigenic and/or low-virulence fragments; and $\beta$ is at least one copy of an ORF 5 from an Iowa strain of PRRSV or an antigenic fragment thereof (e.g. one or more hypervariable regions), preferably a full-length copy from a high replication (hr) phenotype; and $\gamma$ encodes at least one polypeptide or antigenic fragment thereof encoded by a polynucleotide selected from the group consisting of ORF 6 and ORF 7 of an Iowa strain of PRRSV and regions thereof encoding the antigenic fragments.

Alternatively, the present invention may concern a purified preparation which may comprise, consist essentially of or consist of a polynucleic acid having a sequence of the formula (III):

$$5{=}\text{-}\beta\text{-}\delta\text{-}\gamma\text{-}3' \qquad \text{(III)}$$

where $\beta$ and $\gamma$ are as defined above; and $\delta$ is either a covalent bond or a linking polynucleic acid which does not materially affect transcription and/or translation of the polynucleic acid. Preferably, $\beta$ is a polynucleotide encoding at least one hypervariable region of a protein encoded by an ORF 5 of an Iowa strain of PRRSV, and more preferably, encodes a full-length protein encoded by an ORF 5 of an Iowa strain of PRRSV.

The present invention may also concern a purified preparation which may comprise, consist essentially of or consist of a polynucleic acid having a sequence of the formula (IV):

$$5'\text{-}\alpha\text{-}\beta\text{-}\delta\text{-}\gamma\text{-}3' \qquad \text{(IV)}$$

where $\alpha$, $\beta$, $\gamma$ and $\delta$ are as defined in formulas (I)–(III) above.

The present invention may also concern a purified preparation which may comprise, consist essentially of or consist of a polynucleic acid, an expression vector or a plasmid having a sequence of the formula (V):

$$5'\text{-}\epsilon\text{-}\zeta\text{-}\iota\text{-}\kappa\text{-}\xi\text{-}3' \qquad \text{(V)}$$

where $\epsilon$, which is optionally present, is a 5'-terminal polynucleotide sequence which provides a means for operationally expressing the polynucleotides $\alpha$, $\beta$, $\gamma$ and $\delta$; $\zeta$ is a polynucleotide of the formula KTVACC, where K is T, G or U, and V is A, G or C; $\iota$ is a polynucleotide of at most about 130 (preferably at most 100) nucleotides in length; $\kappa$ is a polynucleotide comprising one or more genes selected from the group consisting of a conventional marker or reporter gene, $\alpha$, $\beta$, $\gamma$, and operationally linked combinations thereof, where $\alpha$, $\beta$, and $\gamma$ are as defined in formulas (I)–(IV) above; and $\xi$, which is optionally present, is a 3'-terminal polynucleotide sequence which does not suppress the operational expression of the polynucleotides $\alpha$, $\beta$, $\gamma$ and $\delta$, and which may be operationally linked to $\epsilon$ (for example, in a plasmid).

Suitable marker or reporter genes include, e.g., those providing resistance to an antibiotic such as neomycin, erythromycin or chloramphenicol; those encoding a known, detectable enzyme such as $\beta$-lactamase, DHFR, horseradish peroxidase, glucose-6-phosphate dehydrogenase, alkaline phosphatase, and enzymes disclosed in U.S. Pat. No. 4,190,496, col. 32, line 33 through col. 38, line 44 (incorporated herein by reference), etc.; and those encoding a known antibody (e.g., mouse IgG, rabbit IgG, rat IgG, etc.) or known antigenic protein such as Protein A, Protein G, bovine serum albumin (BSA), keyhole limpet hemocyanin (KLH), bovine gamma globulin (BGG), lactalbumin, polylysine, polyglutamate, lectin, etc.

The polynucleotide $\iota$ is preferably a polynucleotide sequence at least 80% homologous to a polynucleotide sequence from a PRRSV genome located between a leader-mRNA junction sequence and the start codon of the ORF immediately downstream. "About 130" nucleotides in length refers to a length of the polynucleotide $\iota$ which does not adversely affect the operational expression of $\kappa$. For example, in ISU 79, a leader-mRNA junction sequence which does not suppress expression of ORF 7 can be found 129 bases upstream from the start codon of ORF 7 (see Experiment 2 below). Suitable exemplary sequences for the polynucleotide $\iota$ can be deduced from the sequences shown in FIGS. 1 and 9.

The present polynucleic acid may also comprise, consist essentially of or consist of combinations of the above sequences, either as a mixture of polynucleotides or covalently linked in either a head-to-tail (sense-antisense) or head-to-head fashion. Polynucleic acids complementary to the above sequences and combinations thereof (antisense polynucleic acid) are also encompassed by the present invention. Thus, in addition to possessing multiple or variant copies of ORF 5, the present polynucleic acid may also contain multiple or variant copies of one or more of ORF's 1–7, including antigenic or hypervariable regions of ORF 5, of Iowa strain PRRSV's.

Similar to the methods described above and in the Experiments described below and in U.S. application Ser. No. 08/131,625, now U.S. Pat. No. 5,695,766, and Ser. No. 08/301,435, one can prepare a library of recombinant clones (e.g., using *E. coli* as a host) containing suitably prepared restriction fragments of a PRRSV genome (e.g., inserted into an appropriate plasmid expressible in the host). The clones are then screened with a suitable probe (e.g, based on a conserved sequence of ORF's 2–3; see, for example, FIG. 22 of U.S. application Ser. No. 08/301,435). Positive clones can then be selected and grown to an appropriate level. The polynucleic acids can then be isolated from the positive clones in accordance with known methods. A suitable primer for PCR can then be designed and prepared as described above to amplify the desired region of the polynucleic acid. The amplified polynucleic acid can then be isolated and sequenced by known methods.

The present purified preparation may also contain a polynucleic acid selected from the group consisting of sequences having at least 97% sequence identity (or homology) with at least one of ORFs 5–7 of VR 2385, VR 2430 and/or VR 2431; and sequences encoding a polypeptide having at least the minimum sequence identity (or homology) with at least one of ORF's 2–5 of VR 2385, VR 2428, VR 2429, VR 2430, VR 2431, VR 2474 and ISU-1894, as follows:

TABLE 2

| | Minimum % Homology with ORF: | | | |
|---|---|---|---|---|
| Relative to Isolate: | 2 | 3 | 4 | 5 |
| VR 2385 | 99 | 92 | 95 | 90 |
| VR 2429 | 100 | 99 | 99 | 98 |
| VR 2430 | 98 | 95 | 96 | 90 |
| VR 2431 | 94 | 88 | 93 | 92 |
| VR 2474 | 99 | 97 | 97 | 95 |
| ISU 1894 | 97 | 97 | 99 | 97 |

Preferably, the polynucleic acid excludes or modifies a sufficiently long region or portion of one or more of ORFs 2–4 of the hv PRRSV isolates VR 2385, VR 2429, ISU-28, ISU-79 and/or ISU-984 to render the isolate low-virulent or non-virulent.

In the context of the present application, "homology" refers to the percentage of identical nucleotide or amino acid residues in the sequences of two or more viruses, aligned in accordance with a conventional method for determining homology (e.g., the MACVECTOR or GENEWORKS computer programs, aligned in accordance with the procedure described in Experiment III in U.S. application Ser. No. 08/301,435).

Preferably, the present isolated polynucleic acid encodes a protein, polypeptide, or antigenic fragment thereof which is at least 10 amino acids in length and in which non-homologous amino acids which are non-essential for antigenicity may be conservatively substituted. An amino acid residue in a protein, polypeptide, or antigenic fragment thereof is conservatively substituted if it is replaced with a member of its polarity group as defined below:

Basic amino acids:
- lysine (Lys), arginine (Arg), histidine (His)

Acidic amino acids:
- aspartic acid (Asp), glutamic acid (Glu), asparagine (Asn), glutamine (Gln)

Hydrophilic, nonionic amino acids:
- serine (Ser), threonine (Thr), cysteine (Cys), asparagine (Asn), glutamine (Gln)

Sulfur-containing amino acids:
- cysteine (Cys), methionine (Met)

Hydrophobic, aromatic amino acids:
- phenylalanine (Phe), tyrosine (Tyr), tryptophan (Trp)

Hydrophobic, nonaromatic amino acids:
- glycine (Gly), alanine (Ala), valine (Val), leucine (Leu), isoleucine (Ile), proline (Pro)

More particularly, the present polynucleic acid encodes one or more of the protein(s) encoded by the second, third, fourth, fifth, sixth and/or seventh open reading frames (ORF's 2–7) of the PRRSV isolates VR 2385, VR 2386, VR 2428, VR 2429, VR 2430, VR 2431, VR 2474 and/or ISU-1894 (e.g., one or more of the sequences shown in FIG. 3 and/or SEQ ID NOS:15, 17, 19, 43, 45, 47, 49, 51, 53, 55, 57, 59, 61, 63 and 65 of U.S. application Ser. No. 08/301, 435).

ORF's 6 and 7 are not likely candidates for controlling virulence and replication phenotypes of PRRSV, as the nucleotide sequences of these genes are highly conserved among high virulence (hv) and low virulence (lv) isolates (see Experiment III of U.S. application Ser. No. 08/301, 435). However, ORF 5 in PRRSV isolates appears to be less conserved among high replication (hr) and low replication (lr) isolates. Therefore, it is believed that the presence of an ORF 5 from an hr PRRSV isolate in the present polynucleic acid will enhance the production and expression of a recombinant vaccine produced from the polynucleic acid.

Furthermore, ORF 5 of PRRSV contains three hydrophilic, hypervariable regions typically associated with antigenicity in a polypeptide. Thus, the present invention also encompasses polynucleotides encoding a polypeptide comprising one or more hypervariable regions of a PRRSV ORF 5, preferably a polypeptide of the formula a-b-c-d-e-f-g, where:

a is an amino group, a poly(amino acid) corresponding to positions 1–31 of a protein encoded by a PRSSV ORF 5, or a fragment of such a poly(amino acid) which does not adversely affect the antigenicity of the polypeptide;

b is an amino acid sequence selected from the group consisting of those sequences listed under Hypervariable Region No. 1 in Table 1 above, c is an amino acid sequence corresponding to positions 39–56 of a protein encoded by a PRSSV ORF 5 (preferably a sequence of the formula LQLIYNLTLCELNGTDWL (SEQ ID NO:108), in which one or more [preferably 1–10] amino acids may be conservatively substituted), d is an amino acid sequence selected from the group consisting of those sequences listed under Hypervariable Region No. 2 in Table 1 above, e is an amino acid sequence corresponding to positions 67–119 of a protein encoded by a PRRSV ORF 5, in which one or more (preferably 1–20, and more preferably 1–10) amino acid residues may be conservatively substituted and which does not adversely affect the antigenicity of the polypeptide, f is an amino acid sequence selected from the group consisting of those sequences listed under Hypervariable Region No. 3 in the Table above, and g is a carboxy group (a group of the formula —COOH), an amino acid sequence corresponding to positions 129–200 of a protein encoded by a PRSSV ORF 5 or a fragment thereof which does not adversely affect the antigenicity of the polypeptide.

Accordingly, it is preferred that the present polynucleic acid, when used for immunoprotective purposes (e.g., in the preparation of a vaccine), contain at least one copy of ORF 5 from a high-replication isolate (i.e., an isolate which grows to a titer of $10^6$–$10^7$ $TCID_{50}$ in, for example, CRL 11171 cells; also see the discussions in Experiments VIII–XI U.S. application Ser. No. 08/301,435).

On the other hand, the lv isolate VR 2431 appears to be a deletion mutant, relative to hv isolates (see Experiments III and VIII–XI U.S. application Ser. No. 08/301,435). The deletion appears to be in ORF 4, based on Northern blot analysis. Accordingly, when used for immunoprotective purposes, the present polynucleic acid preferably does not contain a region of ORF 4 from an hv isolate responsible for high virulence, and more preferably, excludes the region of ORF 4 which does not overlap with the adjacent ORF's 3 and 5.

It is also known (at least for PRRSV) that neither the nucleocapsid protein nor antibodies thereto confer immunological protection against PRRSV to pigs. Accordingly, the present polynucleic acid, when used for immunoprotective purposes, contains one or more copies of one or more regions from ORF's 2, 3, 4, 5 and 6 of a PRRSV isolate encoding an antigenic region of the viral envelope protein, but which does not result in the symptoms or histopathological changes associated with PRRS when administered to a pig. Preferably, this region is immunologically cross-reactive with antibodies to envelope proteins of other PRRSV isolates.

Similarly, the protein encoded by the present polynucleic acid confers protection against PRRS to a pig administered a composition comprising the protein, and antibodies to this protein are immunologically cross-reactive with the envelope proteins of other PRRSV isolates. More preferably, the present polynucleic acid encodes the entire envelope protein of a PRRSV isolate or a protein at least 80% homologous thereto and in which non-homologous residues are conservatively substituted, or alternatively a protein at least 98% homologous thereto. Most preferably, the present polynucleotide is one of the sequences shown in FIG. 1, encompassing at least one of the open reading frames recited therein.

Relatively short segments of polynucleic acid (about 20 bp or longer) in the genome of a virus can be used to screen or identify tissue and/or biological fluid samples from infected animals, and/or to identify related viruses, by methods described herein and known to those of ordinary skill in the fields of veterinary and viral diagnostics and veterinary medicine. Accordingly, a further aspect of the present invention encompasses an isolated (and if desired, purified) polynucleic acid consisting essentially of a fragment of from 15 to 2000 bp, preferably from 18 to 1000 bp, and more preferably from 21 to 100 bp in length, derived from ORF's 2–7 of a PRRSV genome (preferably the Iowa strain of PRRSV). Particularly preferably, the present isolated polynucleic acid fragments are obtained from a terminus of one or more of ORF's 2–7 of the genome of the Iowa strain of PRRSV, and most preferably, are selected from the group consisting of the primers described in Experiments 1 and 2 below and SEQ ID NOS:1–12, 22 and 28–34 of U.S. application Ser. No. 08/301,435.

The present invention also concerns a diagnostic kit for assaying a porcine reproductive and respiratory syndrome virus, comprising (a) a first primer comprising a polynucleotide having a sequence of from 10 to 50 nucleotides in length which hybridizes to a genomic polynucleic acid from an Iowa strain of porcine reproductive and respiratory syndrome virus at a temperature of from 25 to 75° C., (b) a second primer comprising a polynucleotide having a sequence of from 10 to 50 nucleotides in length, said sequence of said second primer being found in said genomic polynucleic acid from said Iowa strain of porcine reproductive and respiratory syndrome virus and being downstream from the sequence to which the first primer hybridizes, and (c) a reagent which enables detection of an amplified polynucleic acid. Preferably, the reagent is an intercalating dye, the fluorescent properties of which change upon intercalation into double-stranded DNA.

The present isolated polynucleic acid fragments can be obtained by: (i) digestion of the cDNA corresponding to (complementary to) the viral polynucleic acids with one or more appropriate restriction enzymes, (ii) amplification by PCR (using appropriate primers complimentary to the 5' and 3'-terminal regions of the desired ORF(s) or to regions upstream of the 5'-terminus or downstream from the 3'-terminus) and cloning, or (iii) synthesis using a commercially available automated polynucleotide synthesizer.

Another embodiment of the present invention concerns one or more proteins or antigenic fragments thereof from a PRRS virus, preferably from the Iowa strain of PRRSV. As described above, an antigenic fragment of a protein from a PRRS virus (preferably from the Iowa strain of PRRSV) is at least 5 amino acids in length, particularly preferably at least 10 amino acids in length, and provides or stimulates an immunologically protective response in a pig administered a composition containing the antigenic fragment.

Methods of determining the antigenic portion of a protein are known to those of ordinary skill in the art (see the description above). In addition, one may also determine an essential antigenic fragment of a protein by first showing that the full-length protein is antigenic in a host animal (e.g., a pig). If the protein is still antigenic in the presence of an antibody which specifically binds to a particular region or sequence of the protein, then that region or sequence may be non-essential for immunoprotection. On the other hand, if the protein is no longer antigenic in the presence of an antibody which specifically binds to a particular region or sequence of the protein, then that region or sequence is considered to be essential for antigenicity.

Three hypervariable regions in ORF 5 of PRRSV have been identified by comparing the amino acid sequences of the ORF 5 product of all available PRRSV isolates (see, for example, FIG. 2D). Amino acid variations in these three regions are significant, and are not structurally conserved (FIG. 2D). All three hypervariable regions are hydrophilic and antigenic. Thus, these regions are likely to be exposed to the viral membrane and thus be under host immune selection pressure.

The present invention also concerns a protein or antigenic fragment thereof encoded by one or more of the polynucleic acids defined above, and preferably by one or more of the ORF's of a PRRSV, more preferably of the Iowa strain of PRRSV. The present proteins and antigenic fragments are useful in immunizing pigs against PRRSV, in serological tests for screening pigs for exposure to or infection by PRRSV (particularly the Iowa strain of PRRSV), etc.

For example, the present protein may be selected from the group consisting of the proteins encoded by ORF's 2–7 of VR 2385, ISU-22 (VR 2429), ISU-55 (VR 2430), ISU-1894, ISU-79 (VR 2474) and ISU-3927 (VR 2431) (e.g., one or more of the sequences shown in FIG. 2 and/or SEQ ID NOS:15, 17, 19, 43, 45, 47, 49, 51, 53, 55, 57, 59, 61, 67, 69 and 71 of U.S. application Ser. No. 08/301,435); antigenic regions of at least one of these proteins having a length of from 5 amino acids to less than the full length of the protein; polypeptides having the minimum homology with the protein encoded by the PRSSV ORF indicated in Table 2 above; and polypeptides at least 97% homologous with a protein encoded by one of the ORF's 6–7 of VR 2385, VR 2429, VR 2430, ISU-1894, ISU-79 and VR 2431 (e.g., SEQ ID NOS:17, 19, 43, 45, 47, 49, 51, 53, 55, 57, 59 and 61 of U.S. application Ser. No. 08/301,435). Preferably, the present protein has a sequence encoded by an ORF selected from the group consisting of ORFs 2–5 of VR 2385, VR 2428, VR 2429, VR 2430, VR 2431, VR 2474 and ISU-1894 (see, for example, FIGS. 2A–D); variants thereof which provide effective immunological protection to a pig administered the same and in which from 1 to 100 (preferably from 1 to 50 and more preferably from 1 to 25) deletions or conservative substitutions in the amino acid sequence exist; and antigenic fragments thereof at least 5 and preferably at least 10 amino acids in length which provide effective immunological protection to a pig administered the same.

More preferably, the present protein variant or protein fragment has a binding affinity (or association constant) of at least 1% and preferably at least 10% of the binding affinity of the corresponding full-length, naturally-occurring protein to a monoclonal antibody which specifically binds to the full-length, naturally-occurring protein (i.e., the protein encoded by a PRRSV ORF).

The present invention also concerns a method of producing a polypeptide, comprising expressing the present polynucleic acid in an operational expression system, and purifying the expressed polypeptide from the expression system. Suitable expression systems include those conventionally used for either in vitro or in vivo expression of proteins and polypeptides, such as a rabbit reticulocyte system for in vitro expression, and for in vivo expression, a modified or chimeric PRRSV (used to infect an injectable host cell line, such as MA-104, CRL 11171, PSP-36, PSP-36-SAH, MARC-145 and porcine alveolar macrophages), or a conventional expression vector containing the present polynucleic acid, under the operational control of a known promoter (e.g., a thymidine kinase promoter, SV40, etc.) for use in conventional expression systems (e.g., bacterial plasmids and corresponding host bacteria, yeast expression systems and corresponding host yeasts, etc.). The expressed polypeptide or protein is then purified or isolated from the expression system by conventional purification and/or isolation methods.

Other features of the invention will become apparent in the course of the following descriptions of exemplary embodiments, which are given for illustration of the invention, and are not intended to be limiting thereof.

EXAMPLE 1

Summary

The sequences of ORFs 2 to 5 of one low virulence, one "moderate" virulence and one high virulence U.S. PRRSV isolate have been determined and analyzed. Comparisons with known sequences of other PRRSV isolates show that considerable sequence variations at both nucleotide and amino acid levels exist in ORFs 2 to 5 of seven U.S. isolates with differing virulence. However, ORFs 6 and 7 of these seven U.S. isolates are highly conserved (U.S. application Ser. No. 08/301,435). Extensive sequence variations were also found in ORFs 2 to 7 between the European LV and the U.S. isolates. The least virulent U.S. PRRSV isolate known (ISU-3927) displayed the most sequence variation, in comparison with other U.S. isolates.

The phylogenetic relationship of the U.S. isolates was also analyzed. Phylogenetic analysis of the ORFs 2 to 7 of the U.S. isolates indicated that there are at least three groups of PRRSV variants (or minor genotypes) within the major U.S. PRRSV genotype. Consequently, it is highly likely that a number of additional major or minor genotypes will be identified as more virus isolates from different geographic regions are examined.

Interestingly, the least virulent U.S. isolate known (ISU 3927) forms a branch distinct from other U.S. isolates. Analysis of the nucleotide and amino acid sequences also showed that the isolate ISU 3927 exhibits the most variations in ORFs 2 to 4, relative to other U.S. isolates. Many of these variations in isolate ISU 3927 result in non-conserved amino acid substitutions. However, these non-conserved changes in isolate ISU 3927, as compared to other U.S. isolates, do not appear to be limited to a particular region; they are present throughout ORFs 2 to 4. Therefore, a specific correlation between sequence variations and viral virulence is not yet fully elucidated (although certain positions in ORF 3 appear to be possibly related to virulence; see FIG. 2B, positions 30, 48, 54–56, 134, 140, 143, 147, 153, 206, and 215; amino acids at one or more of these positions may serve as a basis for mutating other known proteins encoded by a PRRSV ORF 3).

Results

The amino acid sequence identity between seven U.S. PRRSV isolates was 91–99% in ORF 2, 86–98% in ORF 3, 92–99% in ORF 4 and 88–97% in ORF 5. The least virulent U.S. isolate known has higher sequence variations in the ORFs 2 to 4 than in ORFs 5 to 7, as compared to other U.S. isolates. Three hypervariable regions with antigenic potential were identified in the major envelope glycoprotein encoded by ORF 5.

Pairwise comparison of the sequences of ORFs 2 to 7 and phylogenetic tree analysis implied the existence of at least three groups of PRRSV variants (or minor genotypes) within the major genotype of U.S. PRRSV. The least virulent U.S. isolate known forms a distinct branch from other U.S. isolates with differing virulence. The results of this study have implications for the taxonomy of PRRSV and vaccine development.

FIG. 1 shows a nucleotide sequence comparison of ORFs 2 to 5 of U.S. isolates ISU 3927 (SEQ ID NO:2), ISU 22 (SEQ ID NO:4) and ISU 55 (SEQ ID NO:3) with other known PRRSV isolates. The nucleotide sequence of VR 2385 (SEQ ID NO:1) is shown on top, and only differences are indicated. The start codon of each ORF is indicated by +>, and the termination codon of each ORF is indicated by asterisks (*). The leader-mRNA junction sequences for subgenomic mRNAs 3, 4 and 3-1 are 5 underlined, and the locations of the junction sequences relative to the start codon of each ORF are indicated by minus (−) numbers of nucleotides upstream of each ORF. The sequences of VR 2385 (U.S. application Ser. No. 08/131,625, now U.S. Pat. No. 5,695,766, and Ser. No. 08/301,435), VR 2332, ISU 79 and ISU 1894 (U.S. application Ser. No. 08/301,435) used in this alignment were previously reported.

Materials and Methods

Cells and viruses:

The ATCC CRL 11171 cell line was used to propagate the PRRSV. The cells were grown in Dulbecco's minimal essential medium (DMEM) supplemented with 10% fetal bovine serum (FBS) and 1×antibiotics (penicillin G 10,000 unit/ml, streptomycin 10,000 mg/ml and amphotericin B 25 mg/ml).

Three U.S. isolates of PRRSV used in this study, designated as ISU 22, ISU 55 and ISU 3927, were isolated from pig lungs obtained from different farms in Iowa during PRRS outbreaks. All three isolates were plaque-purified three times on CRL 11171 cells before further experimentation. Comparative pathogenicity studies showed that isolate ISU 3927 is the least virulent isolate among 10 different U.S. PRRSV isolates. Isolate ISU 22 is a high virulence isolate and isolate ISU 55 is "moderately" pathogenic. All of the three virus isolates used in this experiment were at seventh passage.

Isolation of PRRSV intracellular RNAs:

Confluent monolayers of CRL 11171 cells were infected with the three U.S. isolates of PRRSV, ISU 22, ISU 55 and ISU 3927, respectively, at a multiplicity of infection (m.o.i.) of 0.1. At 24 hrs. postinfection, the infected cells were washed three times with cold PBS buffer. The total intracellular RNAs were then isolated by guanidinium isothiocyanate and phenol-chloroform extraction (Stratagene). The presence of virus-specific RNA species in the RNA preparation was confirmed by Northern blot hybridization (data not shown). The total intracellular RNAs were quantified spectrophotometrically.

Reverse transcription and polymerase chain reaction (RT-PCR):

First strand complementary (c) DNA was synthesized from the total intracellular RNAs by reverse transcription using random primers as described previously (Meng et al., 1993, J. Vet. Diagn. Invest., 5:254–258). For amplification of the entire protein coding regions of the ORFs 2 to 5 of the three isolates of PRRSV, two sets of primers were designed on the basis of the sequences of VR 2385 and LV. Primers JM259 (5'-GGGGATCCTTTTGTGGAGCCGT-3') (SEQ ID NO:109) and JM260 (5'-GGGGAATTCGGGATAGGGAATGTG-3') (SEQ ID NO:110) amplified the sequence of ORFs 4 and 5, and primers XM992 (5'-GGGGGATCCTGTTGGTAATAG(A)GTCTG-3) (SEQ ID NO:111) and XM993 (5'-GGTGAATTCGTTTTATTTCCCTCCGGGC-3') (SEQ ID NO:112) amplified the sequence of ORFs 2 and 3. Unique restriction sites (EcoRI or BamHI) at the 5' end of these primers were introduced to facilitate cloning. A degenerate base, G (A), was synthesized in primer XM 992 based on the sequences of VR 2385 and LV (Meulenberg et al., 1993; U.S. application Ser. No. 08/301,435). PCR was performed as described previously (Meng et al., 1993, J. Vet. Diagn. Invest., 5:254–258).

Cloning and nucleotide sequencing:

The RT-PCR products were analyzed by a 0.8% agarose gel electrophoresis. The two PCR fragments representing ORFs 2 and 3 as well as ORFs 4 and 5, respectively, were purified by the glassmilk procedure (GENECLEAN kit, BIO 101, Inc.). The purified fragments were each digested with BamHI and EcoRI, and cloned into the vector pSK+ as described previously (Meng et al., 1993). The *E. Coli* DH 5α cells were used for transformation of recombinant plasmids. White colonies were selected and grown in LB broth containing 100 mg/ml ampicillin. The *E. Coli* cells containing recombinant plasmid were lysed with lysozyme, and the plasmids were then isolated by using the Qiagen column (QIAGEN Inc.).

Plasmids containing viral inserts were sequenced with an automated DNA Sequence (Applied Biosystem, Inc.). Three or more independent CDNA clones representing the entire sequence of ORFs 2 to 5 from each of the three PRRSV isolates were sequenced with universal and reverse primers. Several virus-specific primers, XM969 (5'-GATAGAGTCTGCCCTTAG-3') (SEQ ID NO:113), XM970 (5'-GGTTTCACCTAGAATGGC-3') (SEQ ID NO:114), XM1006 (5'-GCTTCTGAGATGAGTGA-3') (SEQ ID NO:115), XM077 (5'-CAACCAGGCGTAAACACT-3') (SEQ ID NO:116) and XM078 (5'-CTGAGCAATTACAGAAG-3') (SEQ ID NO:117), were also used to determine the sequence of ORFs 2 to 5.

Sequence analyses:

Sequence data were combined and analyzed by using MacVector (International Biotechnologies, Inc.) and GeneWorks (IntelliGenetics, Inc.) computer software programs. Phylogenetic analyses were performed using the PAUP software package version 3.1.1 (David L. Swofford, Illinois Natural History Survey, Champaign, Ill.). PAUP employs the maximum parsimony algorithm to construct phylogenetic trees.

Results

Nucleotide sequence analyses of ORFs 2 to 5:

The sequences of ORFs 2 to 5 of five PRRSV isolates, ISU 79 (SEQ ID NO:7), ISU 1894 (SEQ ID NO:6), ISU 22 (SEQ ID NO:4), ISU 55 (SEQ ID NO:3) and ISU 3927 (SEQ ID NO:2), were determined and compared with other known PRRSV isolates including VR 2385 (SEQ ID NO:1), VR 2332 (SEQ ID NO:5) and LV (Meulenberg et al., 1993). The sequences of ORFs 6 and 7 of isolates VR 2385, ISU 22, ISU 55, ISU 79, ISU 1894 and ISU 3927 were reported previously (U.S. application Ser. No. 08/301,435). The isolates used in this experiment have been shown to differ in pneumovirulence in experimentally-infected pigs (U.S. application Ser. No. 08/131,625, now U.S. Pat. No. 5,695,766, and Ser. No. 08/301,435). ISU 3927 is the least virulent isolate among ten different U.S. PRRSV isolates (U.S. application Ser. No. 08/131,625, now U.S. Pat. No. 5,695,766, and U.S. application Ser. No. 08/301,435).

Like other U.S. PRRSV isolates, ORFs 2 to 4 of these isolates overlapped each other (FIG. 1). However, unlike LV, ORFs 4 and 5 of the U.S. isolates are separated by 10 nucleotides (FIG. 1). ORFs 4 and 5 of LV overlapped by one nucleotide. The single nucleotide substitution from A of the start codon of ORF 5 in LV to T in the U.S. isolates places the start codon of ORF 5 of the U.S. isolates 10 nucleotides downstream of the ORF 4 stop codon. Therefore, a 10-nucleotide noncoding sequence appears between ORFs 4 and 5 of the known U.S. isolates (FIG. 1).

ORF 2 of ISU 79 (SEQ ID NO:7) is 3 nucleotides shorter than other U.S. isolates. The single nucleotide substitution from TGG to TAG just before the stop codon of ORF 2 creates a new stop codon in ISU 79 (FIG. 1). A 3-nucleotide deletion was also found in ORF 5 of ISU 3927 (SEQ ID NO:2), compared to other U.S. isolates (FIG. 1). The size of ORFs 2 to 5 of all the U.S. isolates are identical, except for the ORF 2 of ISU 79 and ORF 5 of ISU 3927, both of which are 3 nucleotides shorter than the other ORFs (FIG. 1).

Sequence comparisons of ORFs 2 to 5 of the seven U.S. PRRSV isolates shown in FIG. 1 indicate that there are considerable nucleotide sequence variations in ORFs 2 to 5 of the U.S. isolates (FIG. 1). The nucleotide sequence identity was 96–98% in ORF 2, 92–98% in ORF 3, 92–99% in ORF 4, and 90–98% in ORF 5 between VR 2385, VR 2332, ISU 22, ISU 55, ISU 79, and ISU 1894 (Table 3).

The least virulent isolate ISU 3927 has the most variations among the seven U.S. isolates (FIG. 1 and Table 3). The nucleotide sequence identity between ISU 3927 and other U.S. isolates was 93–94% in ORF 2, 89–90% in ORF 3, and 91–93% in ORF 4 (Table 3). Like ORFs 6 and 7 (U.S. application Ser. No. 08/301,435), ORF 5 of ISU 3927 has no significant changes except for a 3-nucleotide deletion (FIG. 1). ORF 5 of ISU 3927 shares 91–93% nucleotide sequence identity with the ORF 5 of other U.S. isolates (Table 3).

However, extensive sequence variation was found in ORFs 2 to 5 between LV and the U.S. isolates (FIG. 1 and Table 3). The nucleotide sequence identity between LV and the U.S. isolates was 65–67% in ORF 2, 61–64% in ORF 3, 63–66% in ORF 4, and 61–63% in ORF 5 (Table 3). Extensive genetic variations in ORFs 6 and 7 between LV and U.S. PRRSV also exists (U.S. application Ser. No. 08/131,625, now U.S. Pat. No. 5,695,766, and Ser. No. 08/301,435). These results indicate that the least virulent isolate ISU 3927 is also the most distantly related of the U.S. isolates, with genetic variations occurring mostly in ORFs 2 to 4.

The single nucleotide substitution from TGG to TAG before the stop codon in ORF 2 observed in ISU 79 was also present in isolates ISU 55 and ISU 3927, both of which produce seven sg mRNAs, but not in isolates ISU 22, ISU 1894 or VR 2385, which each synthesize only six sg mRNAs (U.S. application Ser. No. 08/131,625, now U.S. Pat. No. 5,695,766, and Ser. No. 08/301,435). The results indicate that the leader-mRNA 4-1 junction sequence of ISU 55 and ISU 3927 is very likely to be the same as ISU 79 (FIG. 1).

The leader-mRNA junction sequences for sg mRNAs 3 and 4 of ISU 79 and ISU 1894 were determined to be GUAACC at 89 nucleotides upstream of ORF 3 for sg mRNA 3, and UUCACC at 10 nucleotides upstream of ORF 4 for sg mRNA 4 (U.S. application Ser. No. 08/301,435; see also Experiment 2 below). A sequence comparison of isolates ISU 22, ISU 55 and ISU 3927 with isolates VR 2385, ISU 79 and ISU 1894 indicates that the leader-mRNA junction sequences for sg mRNAs 3 and 4 are conserved among the U.S. isolates (FIG. 1).

Analysis of the Deduced Amino Acid Sequences Encoded by ORFs 2 to 5

FIG. 2 shows the alignment of the deduced amino acid sequences of ORF 2 (A), ORF 3 (B), ORF 4 (C) and ORF 5 (D) of U.S. isolates ISU 22, ISU 55 and ISU 3927 with other known PRRSV isolates. The sequence of VR 2385 is shown on top, and only differences are indicated. Deletions are indicated by (–). The proposed signal peptide sequence in the ORF 5 of LV (D) is underlined (Meulenberg et al., 1995). Three hypervariable regions with antigenic potentials in ORF 5 (D) were indicated by asterisks (*). The published sequences used in this alignment were LV (Meulenberg et al., 1993), VR 2385 (U.S. application Ser. No. 08/131,625, now U.S. Pat. No. 5,695,766, and Ser. No. 08/301,435), VR 2332, ISU 79 and ISU 1894 (U.S. application Ser. No. 08/301,435).

On the basis of its high content of basic amino acids and its hydrophilic nature, the translation product of ORF 7 is predicted to be the nucleocapsid protein (U.S. application Ser. No. 08/131,625, now U.S. Pat. No. 5,695,766, and Ser. No. 08/301,435; Meulenberg et al., 1993; Conzelmann et al., 1993; Mardassi et al., 1994). The ORF 6 product lacks a potential amino-terminal signal sequence and contains several hydrophobic regions which may represent the potential transmembrane fragments. Therefore, the ORF 6 product was predicted to be the M protein (U.S. application Ser. No. 08/131,625, now U.S. Pat. No. 5,695,766, and Ser. No. 08/301,435; Meulenberg et al., 30 1993; Conzelmann et al., 1993).

Computer analysis shows that the products encoded by ORFs 2 to 5 of the U.S. isolates all have hydropathy characteristics reminiscent of membrane-associated proteins. The translation products of ORFs 2 to 5 each contain a hydrophobic amino terminus. The N-terminal hydrophobic sequences may function as a signal sequence for each of these ORFs, and they may be involved in the transportation of ORFs 2 to 5 to the endoplasmic reticulum of infected cells. At least one additional hydrophobic domain in each of ORFs 2 to 5 was found at the carboxy termini. These additional hydrophobic domains may function as membrane anchors.

The deduced amino acid sequences of ORFs 2 to 5 of the seven U.S. isolates examined also varied considerably (FIG. 2), indicating that most of the nucleotide differences observed in FIG. 1 are not silent mutations. The amino acid sequence identity between VR 2385, VR 2332, ISU 22, ISU 55, ISU 79, and ISU 1894 was 95–99% in ORF 2, 90–98% in ORF 3, 94–98% in ORF 4, and 88–97% in ORF 5 (Table 3).

Again, the least virulent isolate ISU 3927 displayed more variations with other U.S. isolates in ORFs 2 to 4 (FIG. 2 and Table 3) than in ORFs 5 to 7 (U.S. application Ser. No. 08/301,435 and Table 3). ORFs 2 to 5 of LV share only 57–61%, 55–56%, 65–67%, and 51–55% amino acid sequence identity with those ORFs of the U.S. isolates, respectively (Table 3). Deletions or insertions were found throughout ORFs 2 to 5 in comparing European LV and U.S. isolates (FIG. 2).

Sequence comparison of the ORF 5 product showed that the N-terminal region of ORF 5 is extremely variable, both (a) between U.S. isolates and LV and also (b) among the various U.S. isolates (FIG. 2D). In LV, the first 32–33 amino acid residues of ORF 5 may represent the signal sequence (Meulenberg et al., 1995; FIG. 2D). Therefore, the potential signal sequence of ORF 5 in all the PRRSV isolates is very heterogeneous. This heterogeneity is not due to any host immune selection pressure, because the signal peptide will be cleaved out and not be present in mature virions.

Three additional hypervariable regions were also identified by comparing the amino acid sequences of ORF 5 of all the PRRSV isolates available (FIG. 2D). Amino acid variations in these three regions are significant, and are not structurally conserved (FIG. 2D). Computer analysis indicates that all three hypervariable regions are hydrophilic and antigenic. Thus, it is likely that these regions are exposed to the viral membrane and are under host immune selection pressure. However, further experiments may be necessary to confirm the specific functions of these hypervariable regions as antigenic determinants in the ORF 5 envelope protein.

The Phylogenetic Relationships Among U.S. Isolates of PRRSV

It has been shown previously that U.S. PRRSV and European PRRSV represent two distinct genotypes, based on analysis of the M and N genes (U.S. application Ser. No. 08/301,435). To determine the phylogenetic relationships of U.S. PRRSV isolates, ORFs 2 to 7 of the seven U.S. PRRSV isolates shown in FIGS. 1 and 2 were first aligned with the GeneWorks program (intelligenetics, Inc.). The PAUP program (David L. Swofford, Illinois Natural History Survey, Champaign, Ill.) was then used to construct phylogenetic tree illustrating relationship among U.S. isolates of PRRSV.

The phylogenetic tree of FIG. 3 was constructed by maximum parsimony methods with the aid of the PAUP software package version 3.1.1. The branch with the shortest length (most parsimonious) was found by implementing the exhaustive search option. The branch lengths (numbers of amino acid substitutions) are given above each branch. The sequences used in the analysis are LV, VR 2385, VR 2332, ISU 79 and ISU 1894.

The phylogenetic tree indicates that at least three groups of variants (or minor genotypes) exist within the major U.S. PRRSV genotype. The least virulent U.S. PRRSV isolate ISU 3927 forms a branch distinct from other U.S. isolates (FIG. 3). Isolates ISU 22, ISU 79, ISU 1894, and VR 2332 form another branch, representing a second minor genotype. The third minor genotype is represented by isolates ISU 79 and VR 2385 (FIG. 3). A very similar tree was also obtained by analyzing the last 60 nucleotides of ORF 1b of the seven U.S. isolates presented in FIG. 1 (data not shown). Identical tree topology was also produced by the unweighted pair-group method with arithmetic mean (UPGMA) using the GeneWorks program (data not shown).

In summary, the different genotypes of PRRSV have been confirmed and further elucidated. At least three minor genotypes within the major genotype of U.S. PRRSV have been identified, based on an analysis of the sequence of ORFs 2 to 7. Genetic variations not only between the European PRRSV and the U.S. PRRSV but among the U.S. PRRSV isolates have also been further confirmed as well, indicating the heterogeneous nature of PRRSV. The least virulent U.S. PRRSV isolate ISU 3927 has unexpectedly high sequence variations in ORFs 2 to 4, as compared to other U.S. isolates.

TABLE 3

Nucleotide and deduced amino acid sequence identities (%) of ORFs 2 to 5 of PRRSV

| | VR2385 | ISU22 | ISU55 | ISU79 | ISU1894 | ISU3927 | VR2332 | LV |
|---|---|---|---|---|---|---|---|---|
| ORF 2 | | | | | | | | |
| VR2385 | ** | 97 | 96 | 96 | 95 | 91 | 98 | 58 |
| ISU22 | 97 | ** | 96 | 98 | 96 | 93 | 99 | 59 |
| ISU55 | 98 | 97 | ** | 96 | 95 | 91 | 97 | 61 |
| ISU79 | 96 | 97 | 97 | ** | 96 | 91 | 98 | 60 |

TABLE 3-continued

Nucleotide and deduced amino acid sequence identities (%) of ORFs 2 to 5 of PRRSV

| | VR2385 | ISU22 | ISU55 | ISU79 | ISU1894 | ISU3927 | VR2332 | LV |
|---|---|---|---|---|---|---|---|---|
| ISU1894 | 96 | 97 | 96 | 96 | ** | 93 | 96 | 57 |
| ISU3927 | 94 | 94 | 94 | 93 | 93 | ** | 93 | 58 |
| VR2332 | 97 | 98 | 97 | 98 | 97 | 94 | ** | 59 |
| LV | 65 | 66 | 66 | 67 | 66 | 65 | 66 | ** |
| ORF 3 | | | | | | | | |
| VR2385 | ** | 91 | 94 | 92 | 90 | 87 | 91 | 55 |
| ISU22 | 92 | ** | 93 | 96 | 96 | 88 | 98 | 56 |
| ISU55 | 94 | 93 | ** | 94 | 93 | 87 | 94 | 56 |
| ISU79 | 94 | 96 | 94 | ** | 95 | 87 | 96 | 56 |
| ISU1894 | 92 | 97 | 93 | 96 | ** | 86 | 96 | 55 |
| ISU3927 | 90 | 90 | 89 | 90 | 90 | ** | 87 | 55 |
| VR2332 | 93 | 98 | 94 | 97 | 97 | 90 | ** | 56 |
| LV | 64 | 63 | 62 | 63 | 63 | 61 | 63 | ** |
| ORF 4 | | | | | | | | |
| VR2385 | ** | 94 | 96 | 94 | 95 | 83 | 94 | 66 |
| ISU22 | 93 | ** | 94 | 97 | 99 | 93 | 98 | 66 |
| ISU55 | 96 | 94 | ** | 96 | 96 | 93 | 95 | 67 |
| ISU79 | 93 | 97 | 94 | ** | 98 | 92 | 96 | 66 |
| ISU1894 | 92 | 98 | 94 | 96 | ** | 93 | 98 | 66 |
| ISU3927 | 91 | 93 | 92 | 91 | 91 | ** | 92 | 67 |
| VR2332 | 94 | 99 | 95 | 97 | 98 | 92 | ** | 65 |
| LV | 66 | 66 | 63 | 65 | 66 | 65 | 65 | ** |
| ORF 5 | | | | | | | | |
| VR2385 | ** | 90 | 91 | 88 | 89 | 91 | 89 | 54 |
| ISU22 | 93 | ** | 90 | 94 | 96 | 92 | 97 | 52 |
| ISU55 | 94 | 92 | ** | 89 | 89 | 90 | 89 | 51 |
| ISU79 | 91 | 95 | 91 | ** | 95 | 89 | 94 | 53 |
| ISU1894 | 92 | 97 | 90 | 94 | ** | 91 | 96 | 53 |
| ISU3927 | 91 | 93 | 91 | 91 | 91 | ** | 91 | 55 |
| VR2332 | 93 | 98 | 91 | 95 | 97 | 92 | ** | 53 |
| LV | 63 | 63 | 63 | 61 | 62 | 63 | 63 | ** |

Note: The amino acid sequence comparisons are presented in the upper right half, and the nucleotide sequence comparisons are presented in the lower left half.

EXAMPLE 2

During the replication of PRRSV, six subgenomic mRNAs (sg mRNAs), in addition to the genomic RNA, are synthesized. These sg mRNAs were characterized in this experiment.

The sg mRNAs of PRRSV form a 3'-coterminal nested set in PRRSV-infected cells. Each of these sg mRNAs is polycistronic and contains multiple open reading frames, except for sg mRNA 7 (as shown by Northern blot analysis using ORF-specific probes). The sg mRNAs were not packaged into virions, and only the genomic RNA was detected in purified virions, suggesting that the encapsidation signal of PRRSV is likely localized in the ORF 1 region.

The numbers of sg mRNAs in PRRSV-infected cells varies among PRRSV isolates with differing virulence. An additional species of sg mRNA in some PRRSV isolates was shown in Experiment 1 above to be derived from the sequence upstream of ORF 4, and has been designated as sg mRNA 3-1.

The leader-mRNA junction sequences of sg mRNAs 3 and 4 of isolates ISU 79 and ISU 1894, as well as sg mRNA 3-1 of the isolate ISU 79, contain a common six nucleotide sequence motif, T(G)TA(G/C)ACC. Sequence analysis of the genomic RNA of these two U.S. isolates and comparison with Lelystad virus (LV) revealed heterogeneity of the leader-mRNA junction sequences among PRRSV isolates. The numbers, locations and the sequences of the leader-mRNA junction regions varied between U.S. isolates and LV, as well as among U.S. isolates. The last three nucleotides, ACC, of the leader-mRNA junction sequences are invariable. Variations were found in the first three nucleotides.

By comparing the 5'-terminal sequence of sg mRNA 3-1 with the genomic sequence of ISU 79 and ISU 1894, it was found that a single nucleotide substitution, from T in ISU 1894 to C in ISU 79, led to a new leader-mRNA junction sequence in ISU 79, and therefore, an additional species of sg mRNA (sg mRNA 3–1). A small ORF, designated as ORF 3-1, with a coding capacity of 45 amino acids was identified at the 5'-end of sg mRNA 3-1.

Materials and Methods

Viruses and cells

The PRRSV isolates used (ISU 22, ISU 55, ISU 79, ISU 1894 and ISU 3927) were isolated from pig lungs obtained from different farms in Iowa. A continuous cell line, ATCC CRL 11171, was used for isolation and growth (culturing) of viruses. These PRRSV isolates were biologically cloned by three rounds of plaque purification and grown on the CRL 11171 cells. All of the virus isolates used in this study were at the seventh passage.

ISU 22 and ISU 79 are highly pathogenic and produce from 50 to 80% consolidation of the lung tissues in experimentally-infected five-week-old caesarean-derived colostrum-deprived pigs necropsied at 10 days post-inoculation. By contrast, ISU 55, ISU 1894 and ISU 3927 are of low pathogenicity and produce only 10 to 25% consolidation of lung tissues in the same experiment (U.S. application Ser. No. 08/131,625, now U.S. Pat. No. 5,695,766, and Ser. No. 08/301,435).

Preparation of Virus-specific Total Intracellular RNAs, Poly (A)+ RNA and Virion RNA Confluent monolayers of CRL 11171 cells were infected with different isolates of PRRSV at the seventh passage at a multiplicity of infection (m.o.i.) of 0.1. PRRSV-specific total intracellular RNAs were isolated from PRRSV-infected cells by a conventional guanidinium isothiocyanate method (Stratagene). The poly (A)+ RNA was enriched from the total intracellular RNAs by oligo (dT)-cellulose column chromatography (Invitrogen).

For isolation of PRRSV virion RNA, confluent CRL 11171 cells were infected with isolate ISU 3927 of PRRSV at a m.o.i. of 0.1. When more than 70% of the infected cells showed a cytopathic effect, the cultures were frozen and thawed three times, and the culture medium was clarified at 1200×g for 20 min. at 4° C. The virus was then precipitated with polyethylene glycol and subsequently purified by cesium chloride gradient centrifugation as described in U.S. application Ser. No. 08/131,625, now U.S. Pat. No. 5,695,766. The purified virus was treated with RNase A at a final concentration of 20 μg/ml for 90 min. at 37° C. The virus was then pelleted, and the virion RNA was isolated using a conventional guanidinium isothiocyanate method.

cDNA Synthesis and Polymerase Chain Reaction cDNA was synthesized from total intracellular RNAs by reverse transcription using random primers and amplified by the polymerase chain reaction (RT-PCR) as described previously (Meng et al., 1993, J. Vet. Diagn. Invest., 5:254–258).

Northern Blot Analyses

Ten μg of total intracellular RNAs from virus infected cells and mock-infected cells were used per lane in a formaldehyde-agarose gel. For separation of poly (A)+ RNA and virion RNA, fifteen ng of virion RNA and 0.2 μg of poly (A)+ RNA were loaded per lane. The RNA was denatured with formaldehyde according to a conventional method (Sambrook et al, "Molecular Cloning: A Laboratory Manual", 2nd ed., Cold Spring Harbor Laboratory, Cold Spring Harbor, N.Y.). Electrophoretic separation of RNA, RNA blotting, and hybridization were performed as described in U.S. application Ser. No. 08/131,625, now U.S. Pat. No. 5,695,766. In some experiments, glyoxal-DMSO agarose gels were also performed as described in U.S. application Ser. No. 08/131,625, now U.S. Pat. No. 5,695,766.

For preparation of probes, a specific cDNA fragment from each of the ORFs 1b to 7 was generated by RT-PCR with ORF-specific primers. The primers were designed in such a way that each primer pair amplifies only a specific fragment of a given ORF, and the overlapping, neighboring ORFs are not included in any given cDNA probe. The primer pairs for generating cDNA probes representing ORFs 1b through 7 are IM729/IM782 for ORF 1b, IM312/IM313 for ORF 2, XM1022/IM258 for ORF 3, XM1024/XMI 023 for ORF 4, PP287/PP286 for ORF 5, PP289/XM780 for ORF 6, and PP285/PP284 for ORF 7 (Table 4).

Cloning, Sequencing and Nucleotide Sequence Analyses

Primers for RT-PCR were designed on the basis of PRRSV isolate VR 2385 sequences, which amplified the entire protein coding regions of ORFs 2 to 5 of PRRSV isolates ISU 79 and ISU 1894. Primers JM259 and JM260 were used for amplification of ORFs 4 and 5, and XM992 and XM993 for amplification of ORFs 2 and 3 (Table 4). Unique restriction sites (EcoRI and BamHI) at the termini of the PCR products were introduced, thus enabling a cassette approach to replacement of these ORFs.

The PCR products of ORFs 2–3 and ORFs 4–5 of ISU 79 and ISU 1984 were each digested with EcoRI and BamHI, then purified and cloned into vector pSK+ as described previously (Meng et al., 1993, J. Vet. Diagn. Invest., 5:254–258). Plasmids containing viral inserts were sequenced with a conventional automated DNA sequencer (Applied Biosystem, Inc.). At least three cDNA clones representing the entire sequence of ORFs 2 to 5 from each virus isolate were sequenced with universal and reverse primers, as well as other virus-specific sequencing primers (XM969, XM970, XM1006, XM078 and XM077; see Table 4).

To determine the leader-mRNA junction sequences of sg mRNAs 3, 4 and 3-1, primer pair IM755 and DP586 (Table 4) was used for RT-PCR to amplify the corresponding 5'-terminal sequences. The resulting PCR products were purified and sequenced by direct PCR sequencing using virus specific primers XMD77 and XM141 (Table 4). The sequences were combined and analyzed by MacVector (International Biotechnologies, Inc.) and GeneWorks (IntelliGenetics, Inc) computer software programs.

Oligonucleotides

The synthetic oligonucleotides used in this study were summarized in Table 4. These oligonucleotides were synthesized as single stranded DNA using an automated DNA synthesizer (Applied Biosystem) and purified by high pressure liquid chromatography (HPLC).

Results

Sg mRNAs Are Not Packaged Into PRRSV Virions

To determine whether the sg mRNAs of PRRSV are packaged, virions of PRRSV isolate ISU 3927 were purified by CsCl gradient. The purified virions were treated with RNase A before pelleting the virion and extracting RNA, to remove any RNA species which may have adhered to the virion surface. RNAs from RNase A-treated virions along with the total intracellular RNAs from isolate ISU 3927 of PRRSV-infected cells were separated in a formaldehyde gel and hybridized with a probe generated from the 3'-terminal sequence of the viral genome by PCR with primers PP284 and PP285 (U.S. application Ser. No. 08/131,625, now U.S. Pat. No. 5,695,766; Table 4).

Figure 4:
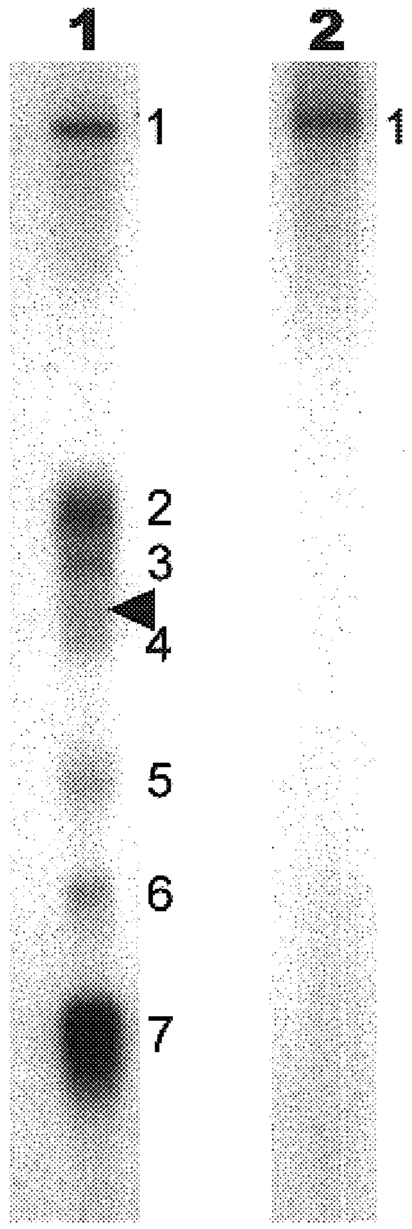
FIG. 4 shows a Northern blot analysis of RNAs isolated from ISU 3927-infected CRL 11171 cells (lane 1) and from purified virions of ISU 3927 (lane 2)

Only the genomic RNA was detected in the purified virions of PRRSV isolate ISU 3927 (FIG. 4), and no detectable amounts of sg mRNAs were observed in the purified virions even after 3 weeks exposure. In contrast, seven species of sg mRNAs, in addition to the genomic RNA, were detected in ISU 3927-infected cells (FIG. 4). Similar results were observed with two other U.S. isolates, ISU 55 and ISU 79.

Variation in the Numbers of the sg mRNAs Among U.S. PRRSV Isolates with Differing Virulence All arteriviruses known prior to the present invention, including U.S. PRRSV and European PRRSV, have been shown to produce six sg mRNAs, except for three LDV variants (LDV-P, LDV-a and LDV-v), which synthesize seven sg mRNAs. However, a nested set of six sg mRNAs is produced in the LDV-C strain.

To compare if there are any variations in the sg mRNAs among U.S. PRRSV isolates, confluent monolayers of CRL 11171 cells were infected with five different isolates of U.S. PRRSV with differing virulence at a m.o.i. of 0.1. Total intracellular RNAs were isolated from virus-infected cells at 24 h post-infection. A cDNA fragment was generated from the extreme 3'-end of the viral genome by PCR with primers PP284 and PP285 (Table 4). The cDNA fragment was labeled with $^{32}P$-dCTP by the random primer extension method, and hybridized with the total intracellular RNAs (separated on a formaldehyde gel).

Figure 5:
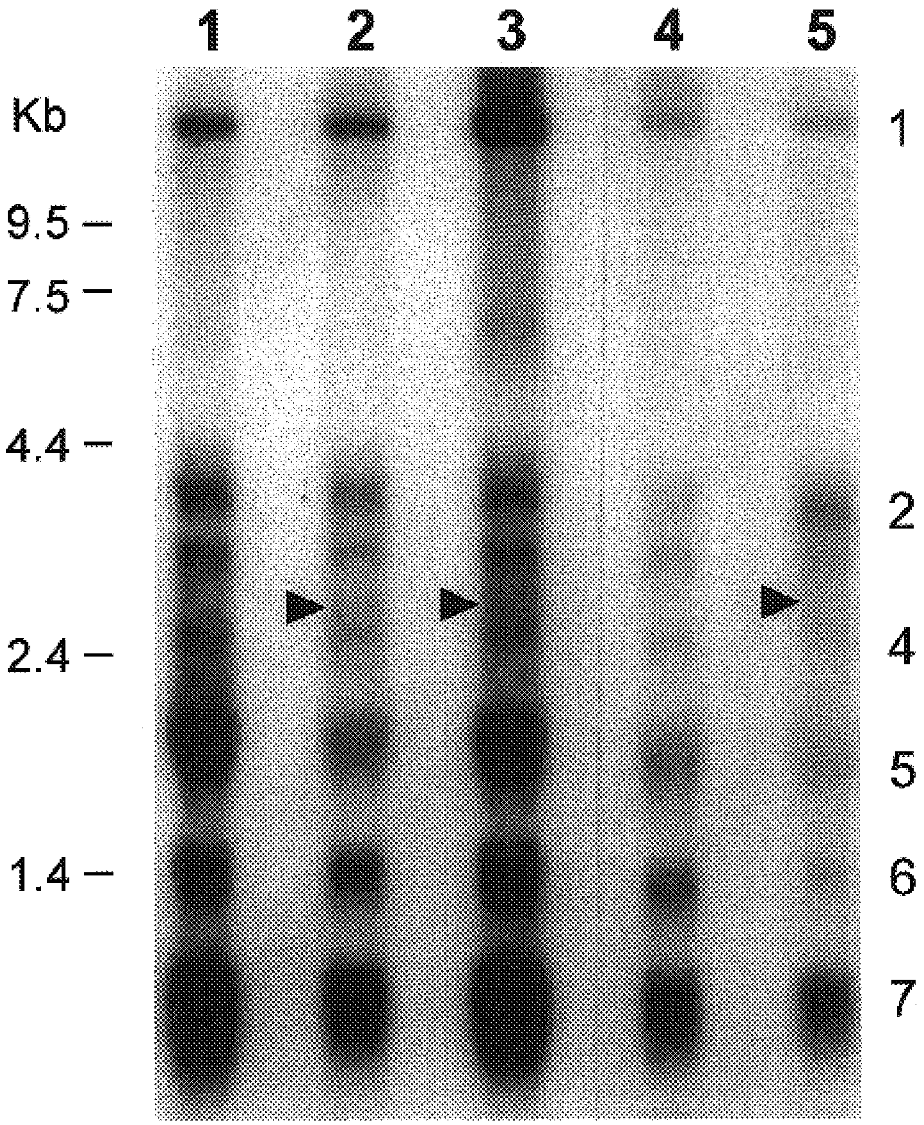
FIG. 5 shows a Northern blot analysis of total intracellular RNAs isolated from CRL 11171 cells infected with ISU22 (lane 1), ISU 55 (lane 2), ISU 79 (lane 3), ISU 1894 (lane 4) and ISU 3927 (lane 5), respectively.

Analyses of the RNAs showed that a nested set of six or more sg mRNAs, in addition to the genomic RNA, was present in cells infected with one of the five isolates of U.S. PRRSV with differing virulence (FIG. 5). Similar results were obtained when the total intracellular RNAs were separated on a glyoxal-DMSO agarose gel. PRRSV isolates ISU 55, ISU 79 and ISU 3927 produced seven easily distinguishable sg mRNAs, whereas isolates ISU 22 and ISU 1894 produced six sg mRNAs (FIG. 5). The U.S. PRRSV isolate VR 2385 also produces six sg mRNAs (U.S. application Ser. No. 08/131,625, now U.S. Pat. No. 5,695,766). An additional species of sg mRNA was located between sg mRNAs 3 and 4, and was designated as sg mRNA 4–1. The sg mRNAs differed little, if any, in size among the five isolates of PRRSV (FIG. 5). There appears to be no correlation, however, between the pneumovirulence and the numbers of the sg mRNAs observed in these five isolates.

Sg mRNA 3-1 Is Not a Defective-interfering RNA and Is Not a Result of Nonspecific Binding of the Probes to Ribosomal RNAs It has been shown that, in coronaviruses, a variety of defective interfering RNA (DI RNA) of different sizes were generated when MHV was serially passaged in tissue culture at a high m.o.i. DI RNAs were also observed in cells infected with torovirus during undiluted passage. Therefore, the possibility of sg mRNA 3-1 of PRRSV being a DI RNA was investigated.

To exclude this possibility, the original virus stock of PRRSV isolate ISU 79, which produces the additional species of sg mRNA 3-1, was passaged four times in CRL 11171 cells at different m.o.i. of 0.1, 0.01 and 0.001, respectively. In a control experiment, four undiluted passages of the original virus stock of ISU 79 were performed. After four passages, total intracellular RNAs were isolated from virus-infected cells and Northern blot analysis was repeated with the same probe generated from the extreme 3'-end of the viral genome.

Figure 6A:
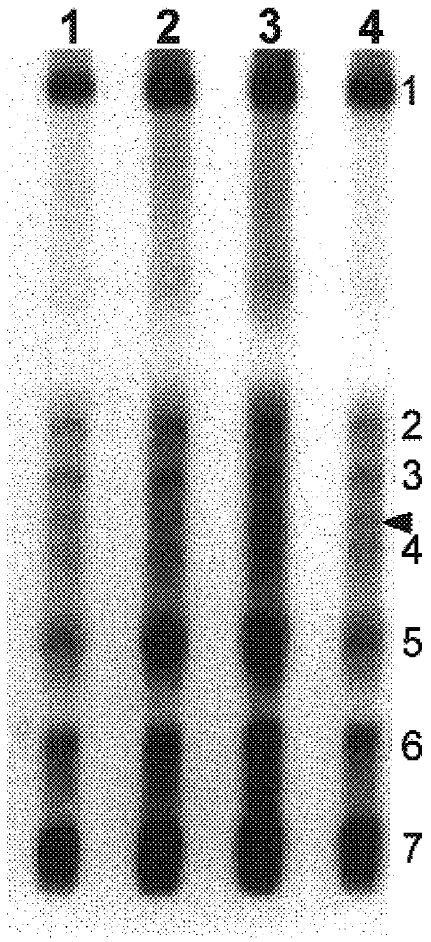
FIGS. 6A and 6B show a Northern hybridization of total RNAs isolated from CRL 11171 cells infected with ISU 79 at different multiplicities of infection (m.o.i.) (A), and polyadenylated RNA from cells infected with PRRSV isolates ISU 55 and ISU 79 (B)

Analyses of the sg mRNAs showed that the additional species of sg mRNA 3-1 was still present in all RNA preparations with different m.o.i., as well as in RNA preparations from undiluted passages (FIG. 6A). Moreover, there was no interference or reduction in the synthesis of other sg mRNAs in the presence of sg mRNA 3-1, as is usually the case with DI RNA.

It has been demonstrated that the DI RNAs of MHV disappeared after two high-dilution passages. Therefore, if the original virus stock of ISU 79 contained DI RNA, then the DI RNA should disappear after four high-dilution passages. The experimental data above suggests that, unlike DI RNA, the replication of sg mRNA 3-1 is independent of the amount of standard virus. Thus, sg mRNA 3-1 is not a DI RNA.

In Northern blot analysis of total intracellular RNAS, the probes may nonspecifically bind to the 18S and 28S ribosomal RNAs, which are abundant in total cytoplasmic RNA preparations. Alternatively, the abundant ribosomal RNAs may cause retardation of virus-specific sg mRNAs which may co-migrate corrugate with the ribosomal RNAs in the gel.

Two additional bands due to the nonspecific binding of probes to the ribosomal RNAs have been observed in LV-infected cells and LDV-infected cells. Therefore, it is possible that sg mRNA 3-1 of PRRSV is due to the nonspecific binding of probes to the ribosomal RNAs.

Figure 6B:
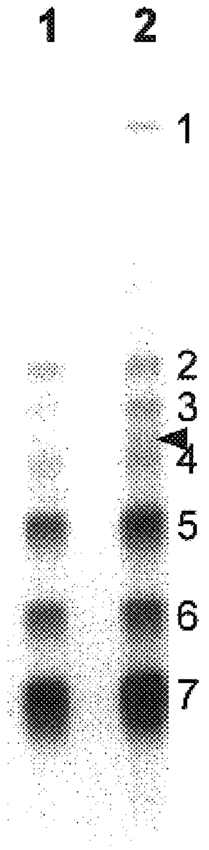

To rule out this possibility, polyadenylated RNA was isolated from total intracellular RNAs of CRL 11171 cells infected with either of two PRRSV isolates, ISU 55 and ISU 79. Both ISU 55 and ISU 79 produce the additional species of sg mRNA 3-1 (FIG. 5). Northern blot analysis of the polyadenylated RNA showed that the additional species of sg mRNA 3-1 in cells infected with either of these two isolates was still present (FIG. 6B), indicating that sg mRNA 3-1 is not due to the nonspecific binding of a probe to the ribosomal RNAS.

The sg mRNAs Represent a 3'-coterminal Nested Set and the sg mRNA 4-1 Is Derived from the Sequence Upstream of ORF 4

Six sg mRNAs, in addition to the genomic RNA, are detected in cells infected with VR 2385 using a cDNA probe from the extreme 3'-end of the viral genome (U.S. application Ser. No. 08/131,625, now U.S. Pat. No. 5,695,766). Thus, like Berne virus (BEV), LDV, EAV, coronaviruses and LV, the replication of U.S. PRRSV also requires the synthesis of a 3'-coterminal nested set of sg mRNAs (U.S. application Ser. No. 08/131,625, now U.S. Pat. No. 5,695,766, and Ser. No. 08/301,435).

To analyze these sg mRNAs in more detail, seven cDNA fragments specific for each of ORFs 1b through 7 were amplified by PCR. The design of primers for PCR was based on the sequence of VR 2385. The sequences and locations of the primers, IM729 and IM782 for ORF 1b, IM312 and IM313 for ORF 2, XM1022 and IM258 for ORF 3, XM1024 and XM1023 for ORF 4, PP286 and PP287 for ORF 5, PP289 and XM780 for ORF 6, and PP284 and PP285 for ORF 7 and the 3' noncoding region (NCR), are shown in Table 4. The primers were designed in such a way that each set of primers will only amplify a fragment from a particular ORF, and the overlapping sequences between neighboring ORFs are not included in any given fragment. Therefore, each of these seven DNA fragments represents only one particular ORF except for fragment 7, which represents both ORF 7 and the 3'-NCR.

These seven DNA fragments were labeled with $^{32}$P-dCTP and hybridized to Northern blots of total intracellular RNAs extracted from cells infected with either of two U.S. isolates of PRRSV, ISU 1894 and ISU 79. Total intracellular RNAs isolated from mock-infected CRL 11171 cells were included as a control.

Figure 7A:
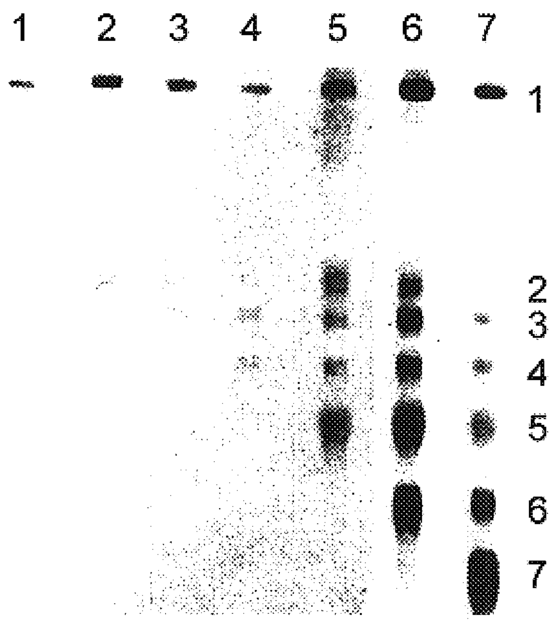
FIGS. 7A and 7B show a Northern blot analysis of total intracellular mRNAs isolated from CRL 11171 cells infected with ISU 1894 (A) and ISU 79 (B)
Figures 6, 25A:
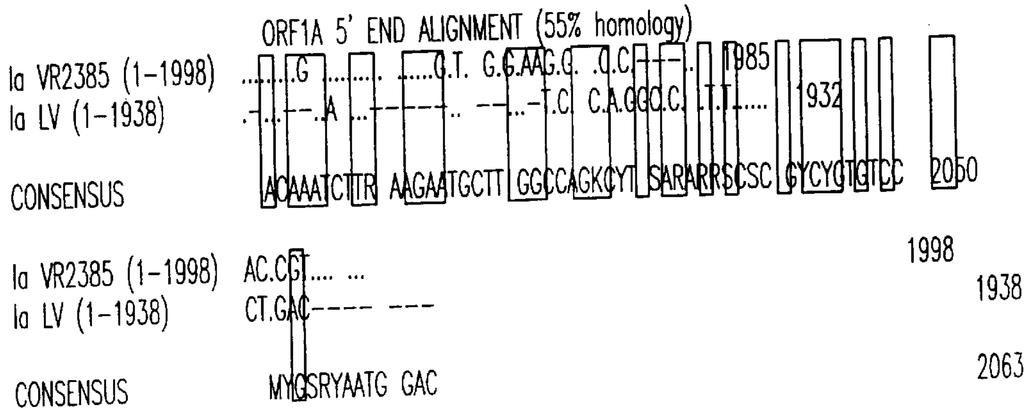
FIG. 25A shows the 5' end alignment (SEQ ID NOS:58 and 59).
Figures 3, 25B:
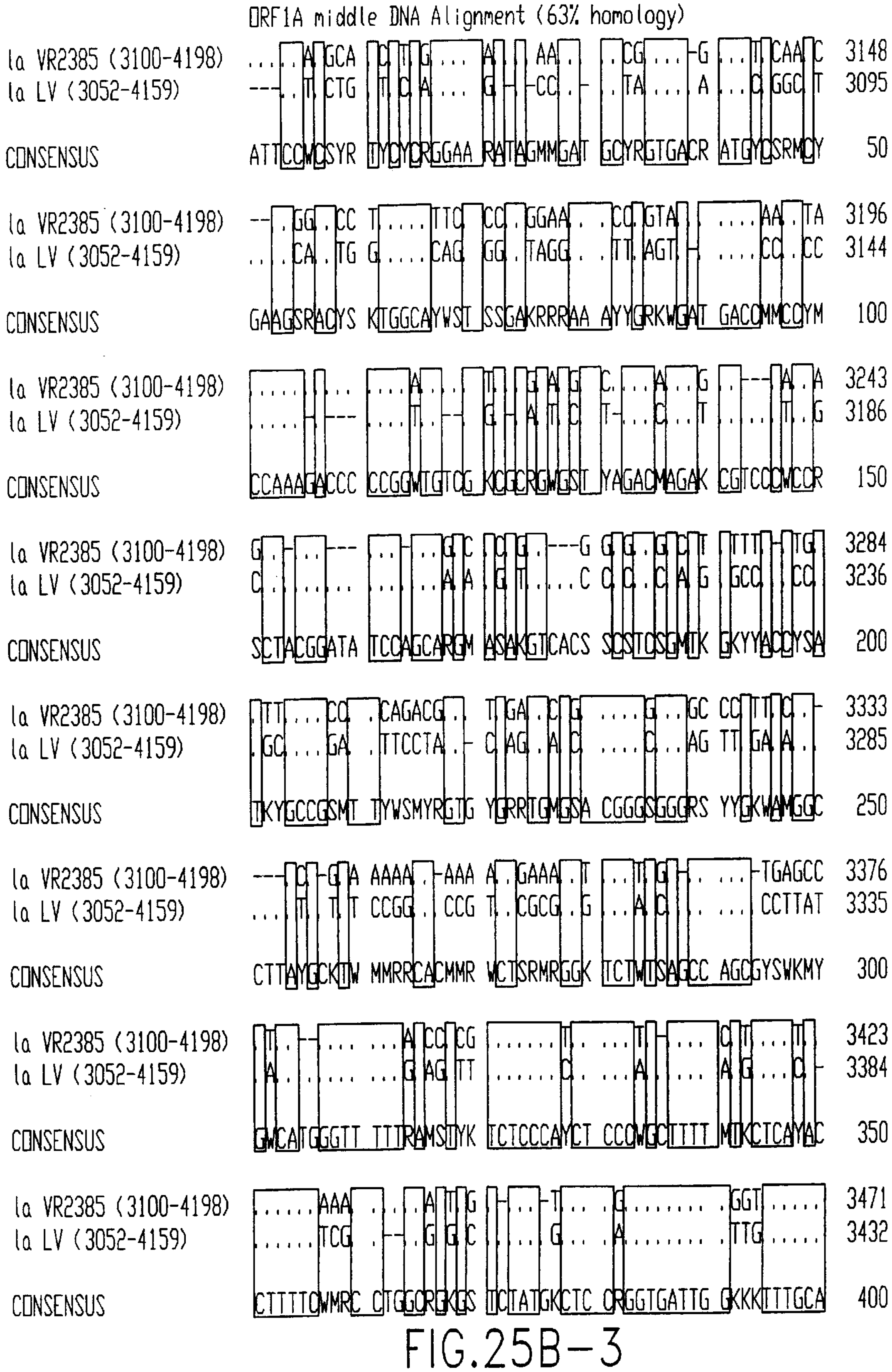
FIG. 25B shows the middle DNA alignment (SEQ ID NOS:60, 61, 66, 67).
Figures 4, 25B:
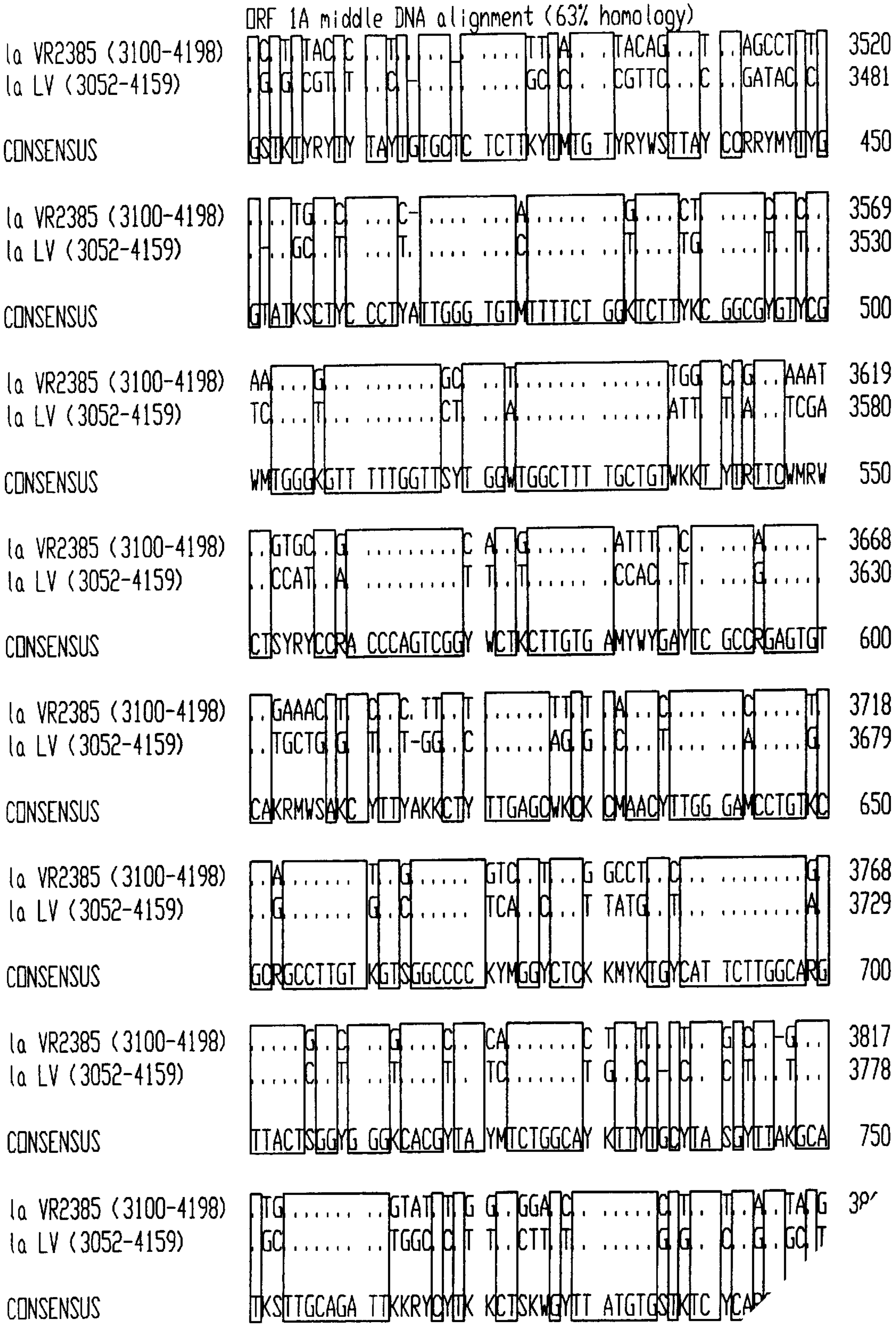
Figures 3, 25C:
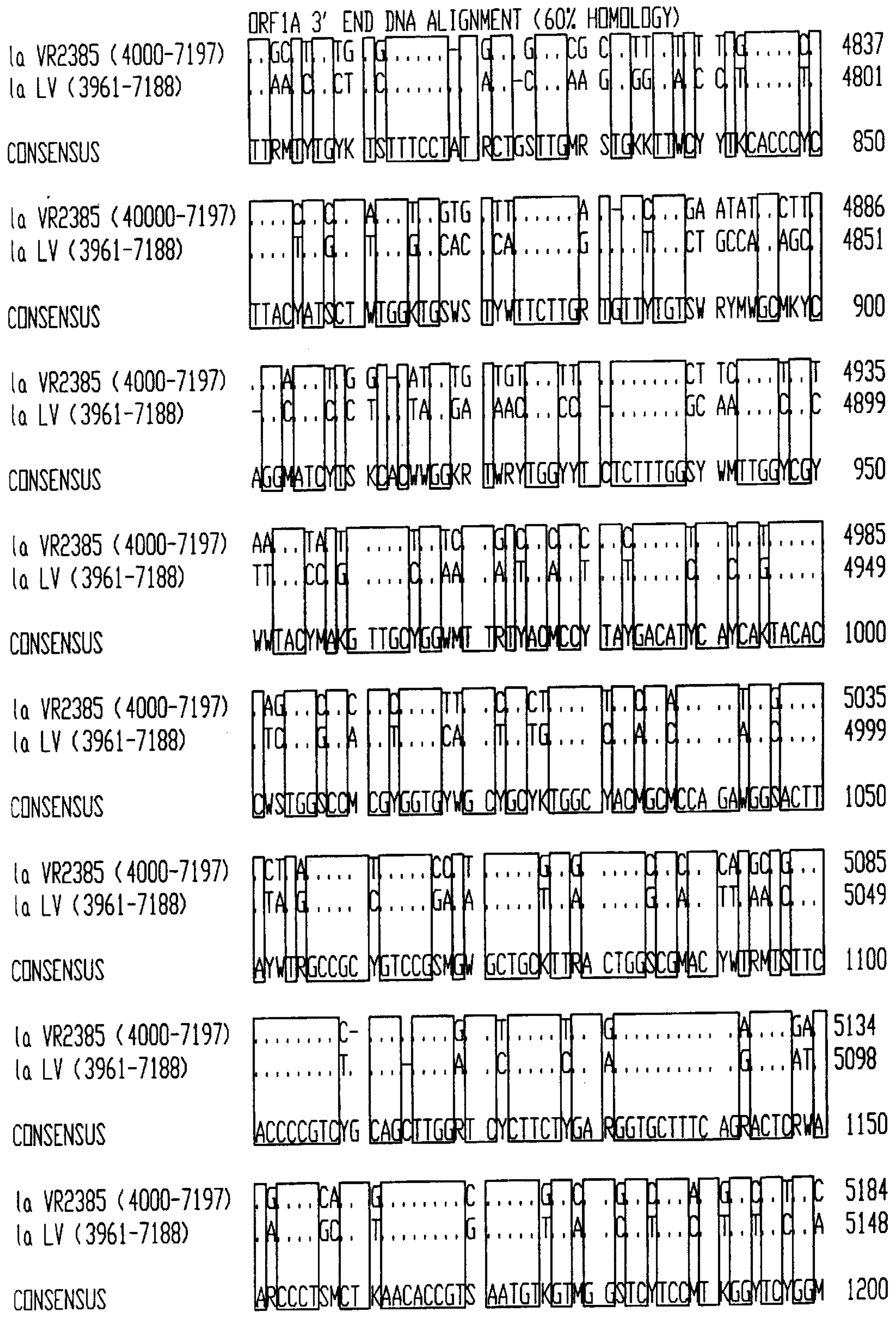
FIG. 25C shows the 3' end alignment (SEQ ID NOS:62 and 63).
Figures 7, 25C:
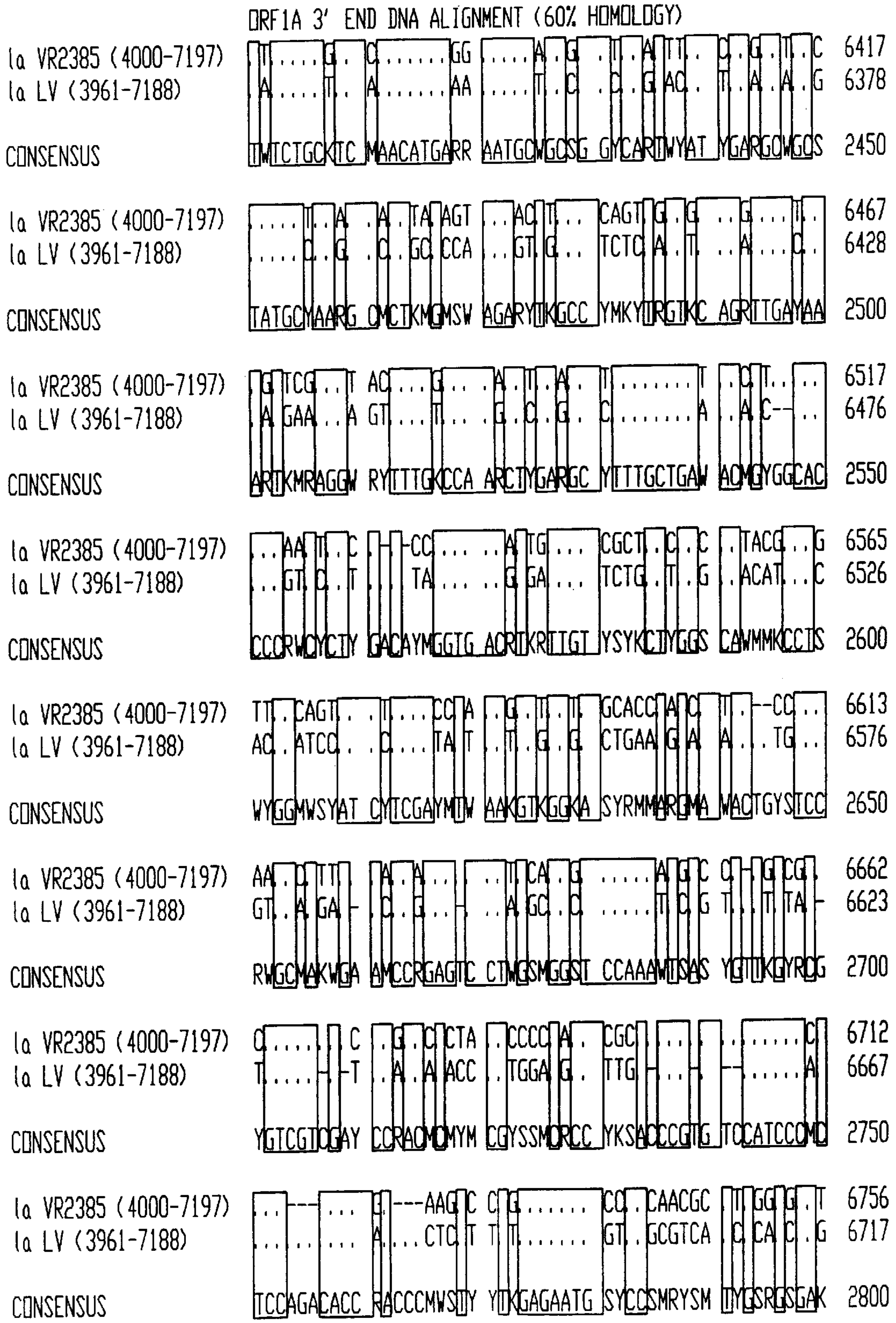

Northern blot analyses showed that Probe 1, generated from ORF 1b, hybridized only with the genomic RNA. Probes 2 through 7 each hybridized with one more additional RNA species besides the genomic RNA (FIG. 7). The results indicate that a 3'-coterminal nested set of six (ISU 1894) or more (ISU 79) sg mRNAs is formed in PRRSV-infected cells (FIGS. 7A and 7B), with the smallest 3'-terminal RNA (sg mRNA 7) encoding ORF 7. The sg mRNAs of U.S. PRRSV all contain the 3'-end of the genomic RNA, but extend for various distances towards the 5'-end of the genome, depending on the size of the given sg mRNA.

The sg mRNA 3-1 of PRRSV isolate ISU 79 hybridized with probes 4 through 7, but not with probes 1, 2 and 3 (FIG. 7B), suggesting that sg mRNA 3-1 contains ORFs 4 through 7 as well as the 3'-NCR. Therefore, sg mRNA 3-1 is generated from the sequence upstream of ORF 4.

A Single Nucleotide Substitution Leads to the Acquisition of the Additional Species of sg mRNA 3-1

Figure 7B:
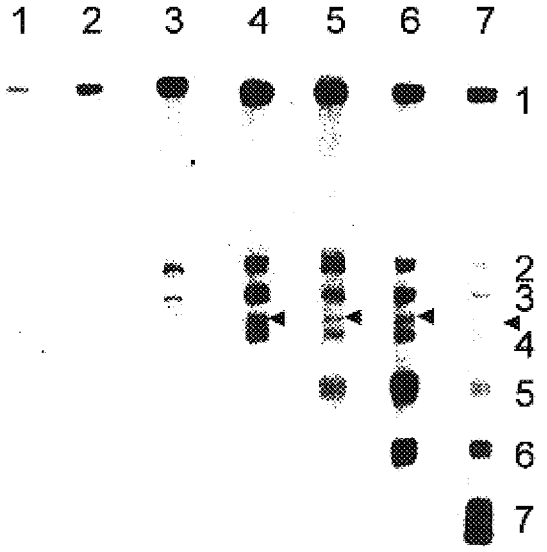

Northern blot hybridization data showed that sg mRNA 3-1 is derived from the sequence upstream of ORF 4 (FIG. 7B). To determine the exact location and the leader-mRNA junction sequence of sg mRNA 3-1, a set of primers, IM755 and DP586, was designed (Table 4). The forward primer IM755 was based on the 3'-end of the leader sequence of VR 2385, and the reverse primer DP586 is located in ORF 4 (Table 4).

RT-PCR with primers IM755 and DP586 was performed using total intracellular RNAs isolated from cells infected with either of ISU 1894 or ISU 79. ISU 79 produces sg mRNA 3-1, but ISU 1894 does not (FIG. 5). A 30-second PCR extension time was applied to preferentially amplify the short fragments representing the 5'-terminal sequences of sg mRNAs 3, 4 and 3-1.

Figures 8A, 8B:
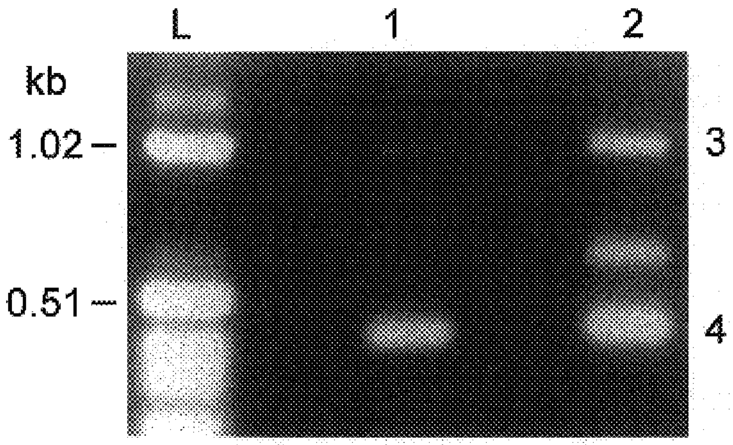
FIGS. 8A and 8B show RT-PCR amplification of the 5'-terminal sequences of the sg mRNAs 3 and 4 of ISU 1894 (lane 1) and sg mRNAs 3, 4 and 4-1 of ISU 79 (lane 2) (A) where lane L is a 1-kb marker; and the leader-mRNA junction sequences of sg mRNAs 3 and 4 of ISU 79 and ISU 1894 and of sg mRNA 4-1 of ISU 79 (B), where the locations of the leader-mRNA junction sequences in the genomes relative to the start codon of each ORF were indicated by minus (−) numbers of nucleotides upstream of the ORFs.
Figure 10A:
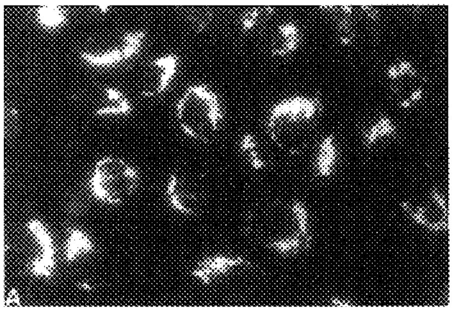
FIG. 10. Immunofluorescence assay of the MAbs with PRRSV-infected cells. Hybridoma supernatant was tested with IFA on infected ATCC CRL 11171 cells. Typical immunofluorescence from reaction with protein-specific MAbs is shown here. A. GP4-specific MAb, PP4bB3; B. E-specific MAb, PP5dB4; C. N-specific MAb, PPeFl1; and D. Negative control, PPAc8.
Figure 10B:
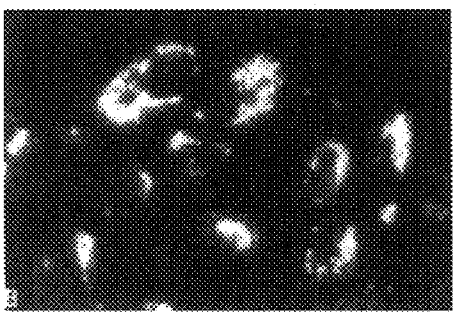
Figure 10C:
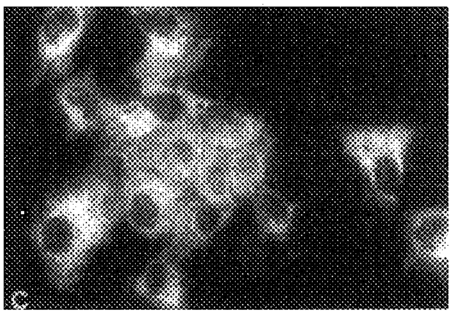
Figure 10D:
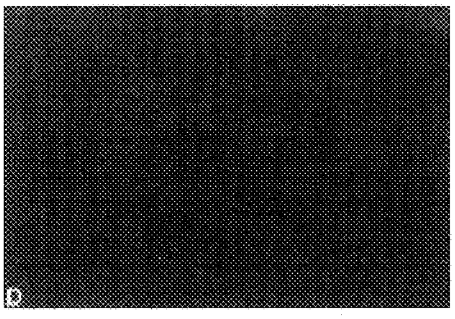

Analysis of the RT-PCR products showed that two fragments with sizes of about 1.1 kb and 0.45 kb were amplified from the total RNAs of ISU 1894 virus-infected cells (FIG. 8A). These two fragments represent 5'-portions of sg mRNAs 3 and 4, respectively. In addition to the two fragments observed in the isolate of ISU 1894, a third fragment of about 0.6 kb representing the 5'-portion of sg mRNA 3-1 was also amplified from total RNAs of cells infected with ISU 79 (FIG. 8A).

Figures 9, 25C:
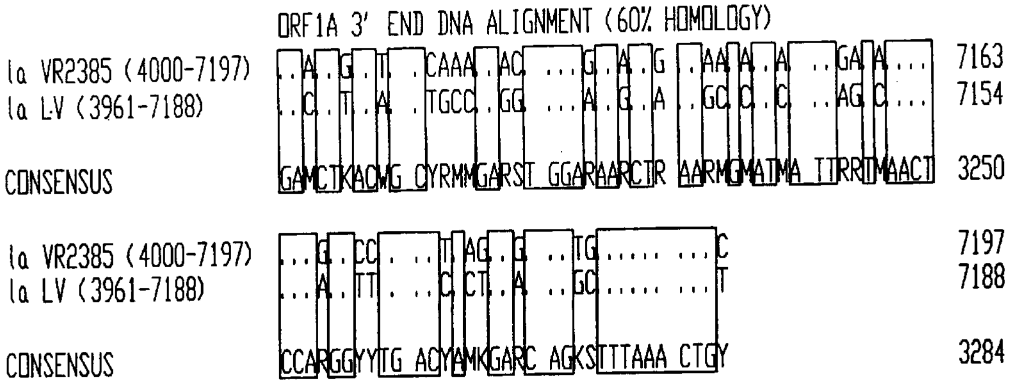

To determine the leader-mRNA junction sequences of sg mRNAs 3, 4 and 3-1 the RT-PCR products of ISU 79 and ISU 1894 were purified from an agarose gel using a GENECLEAN kit (Bio 101, Inc.), and sequenced directly with an automated DNA Sequencer (Applied Biosystems). The primers used for sequencing the 5'-end of the RT-PCR products (XM141 and XM077, Table 4) were designed on the basis of the genomic sequences of ISU 79 and ISU 1894 (FIG. 9). The leader-mRNA junction sequences (in which the leader joins the mRNA body during the synthesis of sg mRNAs) of sg mRNAs 3, 4, and 3-1 of the two U.S. PRRSV isolates were determined by comparing the sequences of the 5'-end of the sg mRNAs and the genomic RNA of the two isolates (FIG. 8B).

The leader-mRNA junction sequences of sg mRNAs 3 and 4 of ISU 1894 and ISU 79 were identical. For sg mRNA 3, the leader-junction sequence (GU<u>AACC</u>) is located 89 nucleotides upstream of ORF 3. For sg mRNA 4, UU<u>CACC</u> is located 10 nucleotides upstream of ORF 4 (FIG. 8B and FIG. 9). The leader-mRNA junction sequence of sg mRNA 3-1 of ISU 79 is UU<u>GACC</u>, located 236 nucleotides upstream of ORF 4 (FIGS. 8B and 9).

Sequence alignment of the genomic sequences of ISU 79 and ISU 1894 shows that a single nucleotide substitution, from T in ISU 1894 to C in ISU 79, leads to the acquisition of an additional leader-mRNA junction sequence, UU <u>GACC</u>, in ISU 79 (FIGS. 8B and 9). Therefore, an additional species of sg mRNA (3-1) is formed (FIG. 5). In addition to ORFs 4 to 7 contained within sg mRNA 4, sg mRNA 3-1 contains at the 5'-end an additional small ORF (ORF 3-1) with a coding capacity of 45 amino acids (FIG. 9). This small ORF stops just one nucleotide before the start codon of ORF 4.

Sequence Analyses of ORFs 2 to 7 of Two U.S. Isolates Reveal Heterogeneity of the Leader mRNA Junction Sequences ORFs 2 to 5 of ISU 79 and ISU 1894 were cloned and sequenced (see Experiment 1 above). ISU 79 produces seven easily distinguishable sg mRNAs, whereas ISU 1894 produces six distinguishable sg mRNAs (FIGS. 5 and 7). At least three cDNA clones at any given region of ORFs 2 to 5 were sequenced for each virus isolate, using universal and reverse primers as well as virus-specific primers XM969, XM970, XM1006, XM078, and XM077 (Table 4). The sequences of ORFs 6 and 7 of ISU 1894 and ISU 79 are disclosed in U.S. application Ser. No. 08/301,435.

Sequence analysis showed that the ORFs 2 to 7 of ISU 79 (SEQ ID NO:40) and ISU 1894 (SEQ ID NO:41) overlap each other except for a 10-nucleotide noncoding region between ORF 4 and ORF 5. The same observation was previously made for VR 2385 (U.S. application Ser. No. 08/301,435). This is very unusual, since all members of the proposed Arteriviridae family, including LV, contain overlapping ORFs. However, the ORFs of coronaviruses are separated by intergenic noncoding sequences. Therefore, U.S. PRRSV appears to be somewhat similar to the coronaviruses in terms of the genomic organization in junction regions of ORFs 4 and 5.

ORF 2 of ISU 1894 was one amino acid longer than that of ISU 79 (FIG. 9). The stop codon of ORF 2, TAG, was changed to TGG in ISU 1894 immediately followed by a new stop codon (TGA) in ISU 1894 (FIG. 9). The sizes of other ORFs of ISU 79 and ISU 1894 were identical (FIG. 9). There were no deletions or insertions in ORFs 2 to 7 of these isolates. However, numerous substitutions are present throughout the entire sequence of ORFs 2 to 7 between ISU 79 and ISU 1894 (FIG. 9).

The numbers and locations of the determined or predicted leader-mRNA junction sequences varied between ISU 1894 and ISU 79 (FIG. 9). In addition to the regular leader-mRNA 4 junction sequence, TT<u>CACC</u>, 10 nucleotides upstream of ORF 4, there was an additional leader-mkNA 3-1 junction sequence (TT<u>GACC</u>) located 236 nucleotides upstream of ORF 4 in ISU 79 (FIG. 9). The leader-mRNA junction sequences of sg mRNAs 4 and 3-1 were separated by 226 nucleotides, which correlated with the estimated sizes of sg mRNAs 4 and 3-1 observed in Northern blot analysis (FIG. 5) and RT-PCR amplification (FIG. 8A).

The leader-mRNA 3 junction sequence is identical between ISU 1894 and ISU 79, GT<u>AACC</u>, located 89 nucleotides upstream of ORF 3. The predicted leader-mRNA junction sequences of sg mRNAs 2 and 6 of ISU 1894 and ISU 79 were also the same (FIG. 9).

However, the predicted leader-mRNA 5 junction sequences of ISU 1894 and ISU 79 are different (FIG. 9). There are 3 potential leader-mRNA 5 junction sequences for ISU 79 (GC<u>AACC</u>, GA<u>GAAC</u> and TC<u>GACC</u>, located 55, 70 and 105 nucleotides upstream of ORF 5, respectively). Two potential leader-mRNA 5 junction sequences were also found in ISU 1894 (GA<u>AACC</u> and TC<u>GACC</u>, located 70 and 105 nucleotides upstream of ORF 5, respectively) (FIG. 9). The differences were due to the two-nucleotide substitutions in the predicted leader-mRNA 5 junction sequences of these isolates (FIG. 9).

In addition to the leader-mRNA 7 junction sequence 15 nucleotides upstream of ORF 7, an additional leader-mRNA 7 junction sequence was found (AT<u>AACC</u>), located 129 nucleotides upstream of ORF 7 in each of these two isolates (FIG. 9). However, the sg mRNA corresponding to this additional leader-mRNA 7 junction sequence was not clearly distinguishable from the abundant sg mRNA 7 which produced a widely-diffused band-in the Northern blot (FIGS. 5, 6 and 7).

Variations in the numbers and locations of the leader-mRNA junction sequences between LV and the two U.S. isolates analyzed in this experiment were also found by comparing the leader-mRNA junction sequences of LV with those of the two U.S. isolates ISU 1894 and ISU 79. Taken together, these data indicate that the sg mRNAs of PRRSV are polymorphic, and the numbers and the exact sizes of the sg mRNAs depend on the particular PRRSV isolate analyzed. However, a nested set of six sg mRNAs most likely reflects the standard arterivirus genome organization and transcription.

| Oligo Name | Sequence | Location (nucleotides) | Polarity |
|---|---|---|---|
| IM729 | 5'-GACTGATGGTCTGGAAAG-3' (SEQ ID NO:118) | ORF1b, -507 to -490 upstream of ORF2 | + |
| IM782 | 5'-CTGTATCCGATTCAAACC-3' (SEQ ID NO:119) | ORF1b, -180 to -163 upstream of ORF2 | - |
| IM312 | 5'-AGGTTGGCTGGTGGTCTT-3' (SEQ ID NO:120) | ORF2, 131 to 148 downstream of ORF2 | - |
| IM313 | 5'-TCGCTCACTACCTGTTTC-3' (SEQ ID NO:121) | ORF2, 381 to 398 downstream of ORF2 | - |
| XM1022 | 5'-TGTGCCCGCCTTGCCTCA-3' (SEQ ID NO:122) | ORF3, 168 to 175 downstream of ORF3 | - |
| IM268 | 5'-AAACCAATTGCCCCCGTC-3' (SEQ ID NO:123) | ORF3, 520 to 537 downstream of ORF3 | - |
| XM1024 | 5'-TATATCACTGTCACAGCC-3' (SEQ ID NO:124) | ORF4, 232 to 249 downstream of ORF4 | + |
| XM1023 | 5'CAAATTGCCAACAGAATG-3' (SEQ ID NO:125) | ORF4, 519 to 536 downstream of ORF4 | - |
| PP287 | 5'-CAACTTGACGCTATGTGAGC-3' (SEQ ID NO:126) | ORF5, 129 to 148 downstream of ORF5 | + |
| PP286 | 5'-GCCGCGGAACCATCAAGCAC-3' (SEQ ID NO:127) | ORF5, 538 to 667 downstream of ORF5 | - |
| PP289 | 5'-GACTGCTAGGGCTTCTGCAC-3' (SEQ ID NO:128) | ORF6. 119 to 138 downstream of ORF6 | + |
| XM780 | 5'-CGTTGACCGTAGTGGAGC-3' (SEQ ID NO:129) | ORF6, 416 to 433 downstream of ORF6 | - |
| PP285 | 5'-CCCCATTTCCCTCTAGCGACTG-3' (SEQ ID NO:130) | ORF7, 157 to 178 downstream of ORF7 | + |
| PP284 | 5'-CGGCCGTGTGGTTCTCGCCAAT-3' (SEQ ID NO:131) | 3'NCR, -27 to -6 upstream of poly (A) | - |
| JM260 | 5'-GGGGAATTCGGGATAGGGAATGTG-3' (SEQ ID NO:132) | ORF3, 338 to 356 downstream of ORF3 | + |
| JM259 | 5'-GGGGATCCTTTTGTGGAGCCGT-3' (SEQ ID NO:133) | ORF6, 34 to 52 downstream of ORF6 | - |
| XM993 | 5'-GGTGAATTCGTTTTATTTCCCTCCGGGC-3' (SEQ ID NO:134) | ORF1b, -53 to -35 upstream of ORF2 | + |
| XM992 | 5'-GGGGGATCCTGTTGGTAATAG/AGTCTG-3' (SEQ ID NO:135) | ORF3, -50 to -34 upstream of ORF4 | - |
| XM970 | 5'-GGTTTCACCTAGAATGGC-3' (SEQ ID NO:136) | ORF2, 522 to 550 downstream of ORF2 | + |
| XM969 | 5'-GATAGAGTCTGCCCTTAG-3' (SEQ ID NO:137) | ORF5, 443 to 460 downstream of ORF6 | - |
| XM1006 | 5'-GCTTCTGAGATGAGTGA-3' (SEQ ID NO:138) | ORF4, 316 to 332 downstream of ORF4 | + |
| XM078 | 5'-CTGAGCAATTACAGAAG-3' (SEQ ID NO:139) | ORF2, 202 to 218 downstream of ORF2 | + |
| XM077 | 5'-CAACCAGGCGTAAACACT-3' (SEQ ID NO:140) | ORF3, 316 to 333 downstream of ORF3 | - |
| IM755 | 5'-GACTGCTTTACGGTCTCTC-3' (SEQ ID NO:141) | Leader, 3' end of the leader sequence | + |
| DP586 | 5'-GATGCCTGACACATTGCC-3' (SEQ ID NO:142) | ORF4, 355 to 372 downstream of ORF4 | - |
| XM141 | 5'-CTGCAAGACTCGAACTGAA-3' (SEQ ID NO:143) | ORF4, 78 to 97 downstream of ORF4 | - |

The oligonucleotides were designed on the basis of sequence data presented in this application and U.S. application Ser. No. 08/131,625, now U.S. Pat. No. 5,695,766, and Ser. No. 08/301,435.

EXAMPLE 3

Cell line ATCC CRL 11171 was used for the propagation of PRRSV isolates. The maintenance of the cell line and isolation of virus were the same as previously described (Meng et al., *J. Gen. Virol.* 75:1795–1801 (1994); Meng et al., *J. of Veterinary Diagnostic Investigation* 8:374–381 (1996). Plasmacytoma cell line SP2/O was used for cell fusion in MAb preparation. PRRSV ATCC VR 2385 was used as antigen for screening of hybridomas secreting PRRSV specific monoclonal antibodies.

Indirect Immunofluorescence Assay (IFA)

Monolayers of ATCC CRL 11171 cells were inoculated with PRRSV VR 2385 at 0.1 multiplicities of infection, incubated for 48 hrs and fixed with methanol. Hybridoma supernatant was incubated on the fixed-cell monolayer at 37° C. for 30 min. Fluorescein-labeled goat anti-mouse IgG (H+L) conjugate was used to detect the specific reaction. One PRRSV N (ORF 7 products) specific monoclonal antibody, PP7eF11 was used as a positive control and cell culture supernatant from a non-PRRSV specific MAb, PPAc8 was used as a negative control.

MAb Preparation

The whole cell lysates from insect cells infected with recombinant baculoviruses of PRRSV ORFs 4 and 5 were used as immunogen to immunize mice. Construction of the recombinant baculoviruses containing the PRRSV ORFs 4 and 5 was done with the strategies as previously described (Bream et al. *J. Virol.* 67:2665–2663 (1993)). Briefly, PRRSV ORFs 4 and 5 genes were PCR amplified separately from the template of pPSP.PRRSV2-7 plasmid (Morozov et al., *Archives of Virology* 140:1313–1319 (1995)) with primers containing restriction sites of BamHI and EcoRI. The amplified fragments were cut with the restriction enzymes indicated above and ligated into the vector PVL1393 (Invitrogen). The inserted genes were under control of the polyhedrin gene promoter (O'Reilly et al., *Baculovirus Expression Vectors: A Laboratory Manual,* pages 107–234, 2nd Edition, New York: W. H. Freeman and Company (1992)) and verified with restriction enzyme digestion and PCR amplification. Then the recombinant vector DNA and linearized *Autographa California* inultinuclear polyhedrosis virus DNA (Invitrogen) were co-transfected into Sf9 cells as described in the instruction manual. The inserted genes in the recombinant baculoviruses were verified with hybridization and PCR amplification (O'Reilly et al., 1992). The recombinant viruses were used to inoculate insect cells and the cell lysate was used for immunization of mice. The immunization was carried out with 3 to 5 times of intraperitoneal injections at two weeks interval. Spleenocytes were hybridized with SP2/O myeloma cells as previously described (Brown & Ling, "Murine Moncolonal Antibodies," In *Antibodies: a practical approach,* pp. 81–104, Edited by Catty D. Zoxford, Washing, D.C. IRL Press (1988)). Hybridomas were screened for secreting PRRSV specific antibodies with IFA to detect reaction with PRRSV ATCC VR 2385. Positive hybridomas were selected and cloned three times. Four MAbs were developed to the GP4 and six Mabs to the protein. Mabs were isotyped with MonoAb ID kits (Zymed Laboratories Inc).

Enzyme-linked Immunosorbent Assay (ELISA)

ELISA has been well described (Harlow & Lane, *Antibodies: A laboratory manual,* pp. 471–612, Cold Spring Harbor Laboratory New York (1988); Ausubel et al., *Short protocols in molecular biology,* pp. 11.5–11.7, 2nd Edition, New York, Greene Publishing Associates and John Wiley & Sons (1992)). Coating antigens were extracted with 1% Triton X-100 from PRRSV VR 2385-infected cells. MAbs were tested for binding activity in ELISA with the antigens binding to plates. Extract from normal cells and cell culture medium from the non-PRRSV specific MAb, PPAc8 were included as a negative antigen and a negative antibody controls respectively. The PRRSV N-specific MAb, PP7eF11 was used as a positive control. Specific reactions were detected with goat anti-mouse IgG (H+L) peroxidase conjugate and revealed with substrate 2,2'-azino-bis (3-ethylbenzthiazoline-6-sulfonic acid)(ABTS). Then the optical density was measured at 405 nm ($A_{405}$).

Fixed-cell ELISA was conducted as previously reported (van Nieuwstadt et al., *J. Virol.* 70:4767–4772 (1991)) to test the reactivity of MAbs with PRRSV field isolates. Briefly, monolayers of ATCC CRL 11171 cells were inoculated with PRRSV field isolates at 0.001 multiplicities of infection, incubated for 48 hrs and fixed with methanol. Then the cells were blocked with 1% BSA for 1 hour at room temperature. Cell culture supernatant of MAbs were diluted in two-fold series and added to the fixed-cell plates. The PP7eF11 and PPAc8 were used as positive and negative controls respectively. Specific reactions were detected as described above.

Immunoblotting

Western immunoblot analyses were carried out as described previously (Harlow & Lane, *Antibodies:A laboratory manual,* pp. 471–612, Cold Spring Harbor Laboratory, New York (1988)). Protein samples were treated under different conditions before separated in gel. For denaturing conditions samples were treated at 100° C. for 3 minutes in Laemmli sample buffer containing 2% SDS and 5% 2-mercaptoethanol and run in SDS-PAGE. Under nondenaturing conditions, samples were treated at 40° C. for 20 min in sample buffer containing 1% triton X-100 and run in PAGE. Then separated proteins were transferred to nitrocellulose membrane by electrophoresis. The nitrocellulose membrane was blocked with 3% BSA. MAbs were screened for the reactivity with the antigens on the membrane with multi-screening apparatus. Pig anti-PRRSV serum was used as a positive control and cell culture supernatant from PPAc8 as a negative control. Bound antibodies were detected by incubation with goat anti-mouse IgG+IgA+IgM peroxidase conjugate or goat anti-pig IgG peroxidase conjugate followed by color development in 4-chloro-1-naphthol substrate.

Virus Neutralization (VN) Test

Virus neutralizing activity of MAbs was tested as described previously (Mecham et al., *Viral Immunol.* 3:161–170 (1990) & White et al., *J. Gen. Virol.* 71:4767–4772 (1990)) with some modifications. Hybridoma supernatant was mixed with the same volume of PRRSV dilution containing 30–70 plaque forming units, which was diluted with DMEM containing 10% guinea pig complement. The virus-antibody mixture was incubated at 37° C. for 1 hr, and then transferred to the monolayer of ATCC CRL 11171 cells in six-well plate for 1 more hr incubation at 37° C. Then an agarose-medium mixture overlaid the monolayer. After 3-day incubation at 37° C., the monolayer was stained with 0.05% neutral red in agarose. Pig anti-PRRSV serum was used as a positive control and hybridoma cell culture medium from a non-PRRSV specific MAb was included as a negative control.

PRRSV Specific Mabs Identified with IFA

Hybridomas were screened with IFA on PRRSV VR 2385-infected ATCC CRL 11171 cells. IFA positive hybridomas were selected, amplified and cloned. Six MAbs were developed against PRRSV E protein and four to the GP4. All of them showed strong perinuclear fluorescence with a little difference in intensity, which was different from the cytoplasmic staining of PRRSV N protein specific MAb (FIG. 10). This result indicated that the GP4 and E glycoproteins were synthesized and accumulated in subcellular compartments in PRRSV-infected cells as transferring of oligosaccharides to a glycoprotein is generally processed in a particular compartment such as the endoplasmic reticulum and the Golgi complex (Pfeffer et al., *Ann. Rev. Biochem.* 56:829–852 (1987)). GP4 and E were predicted as membrane-associated glycoproteins (Meng et al., 1994 & Morozov et al., *Archives of Virology* 140:1313–1319 (1995)). In contrast, the PRRSV N protein is highly basic and hydrophilic, and is synthesized in the cytoplasm of PRRSV-infected cells, which was shown by the observation of cytosol distribution of fluorescence in IFA with N-specific MAb staining. All the MAbs were identified as subtype IgM.

Reactivity with PRRSV Antigen in ELISA

Figure 11:
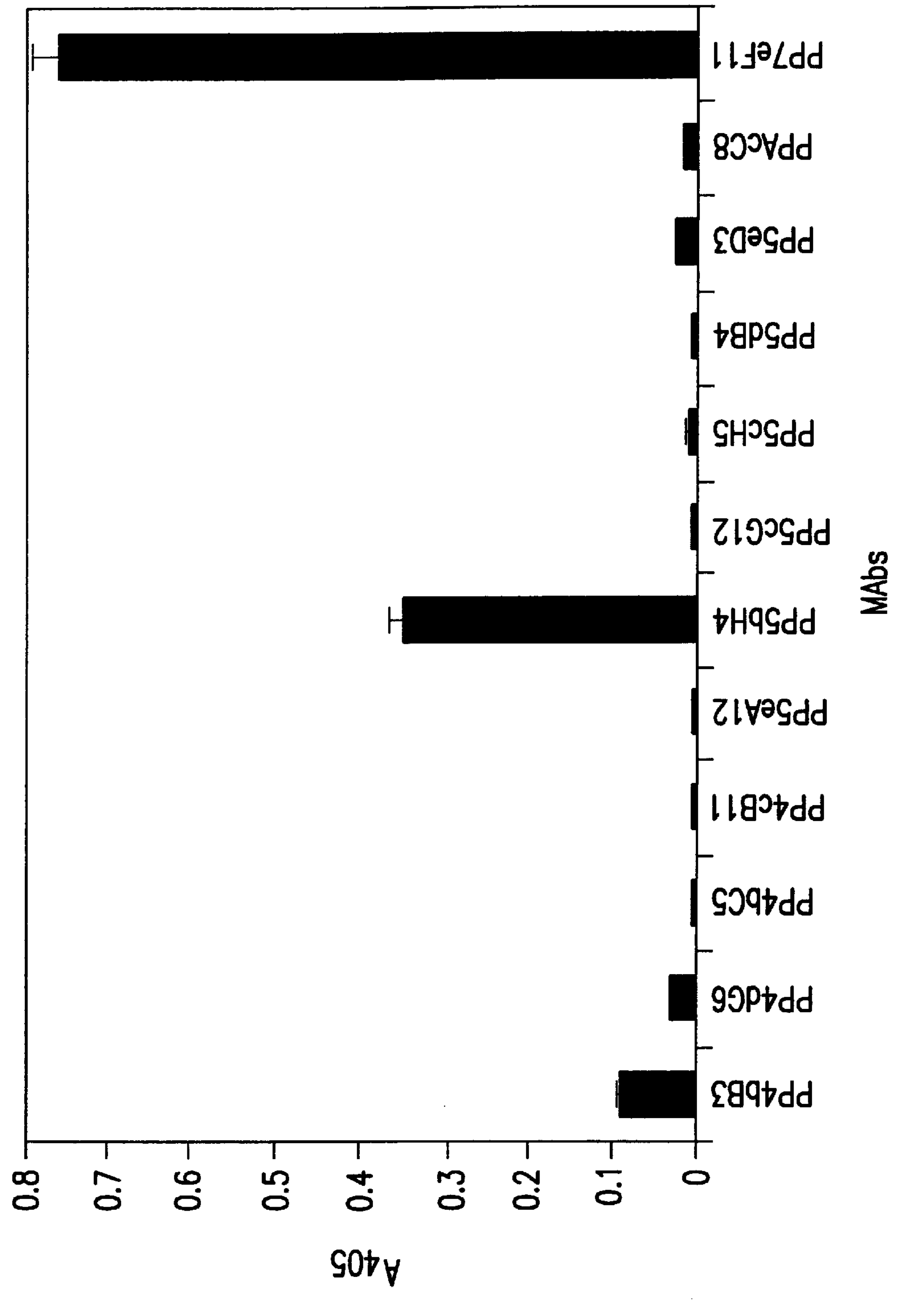
FIG. 11. Reactivity of the MAbs and detergent extracted PRRSV antigen in ELISA. Plates were coated with antigen extracted from PRRSV-infected cells with detergent 1% Triton X-100 and blocked with 1% BSA. Hybridoma supernatant was tested along with positive and negative controls, PPeF11 and PPAc8 respectively. Specific reactions were detected with anti-mouse IgG peroxidase conjugate. ABTS substrate was incubated in the plates for 20 min before A405 was measured. The first four MAbs starting from PP4bB3 are GP4-specific antibodies, and the next six MAbs starting from PP5bH4 are E-specific antibodies.

In order to determine the sensitivity of the epitopes to detergent treatment, ELISAs were run to test the reactivity of the MAbs with 1% Triton X-100 extracted PRRSV antigen. Among the MAbs to the E protein, only PP5bH4 showed strong reactivity to the PRRSV antigen (FIG. 11). No clear reaction was detected between the rest of the E-specific MAbs and the PRRSV antigen. Among the MAbs to the GP4, only PP4bB3 showed a mild reactivity with the PRRSV antigen. The other three of the MAbs to GP4 failed to show any reactivity. The negative controls did not show reaction in ELISA.

Out of the 10 MAbs, only PP5bH4 and PP4bB3 showed reactivity in the ELISA with detergent extracted PRRSV antigen. This result indicated that the epitope recognized by PP5bH4 was resistant to Triton X-100 treatment and the epitope of PP4bB3 was partially resistant to the detergent. The epitopes recognized by the other 8 MAbs were sensitive to the treatment, and may be conformationally dependent. Triton X-100 is generally selected to disrupt cell membranes for its nondenaturing property (Deutscher, "Guide to protein purification," *Methods in Enzymology,* Vol. 182, San diego, Calif., Academic Press, Inc. (1990)), but in this test the epitopes in the PRRSV proteins were somehow altered during the extraction process as monitored by the MAb binding.

Immunoblotting Assay

Figure 12:
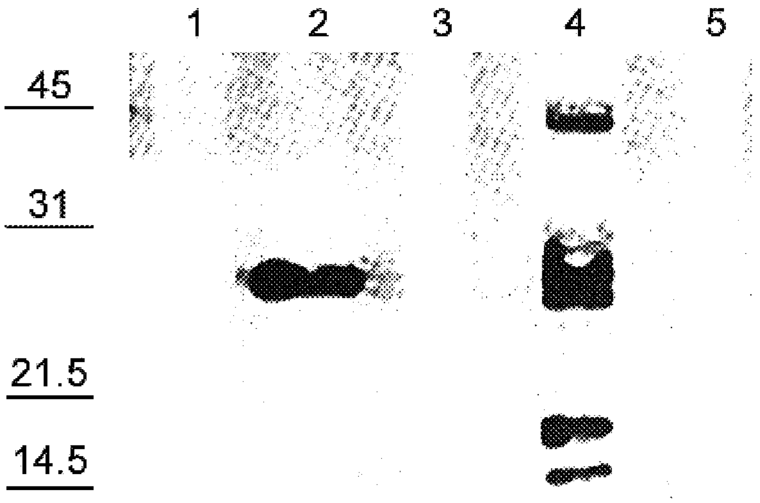
FIG. 12. Reactivity of the E specific MAbs and extract of PRRSV virions in Immunoblotting. MW standards (in kDa) are indicated on the left side of the figure. Lanes: 1, PP5dB4; 2, PP5bH4; 3, Negative control: PPAc8; 4, Positive control: pig anti-PRRSV serum; 5, Negative control: normal pig serum.
Figure 14:
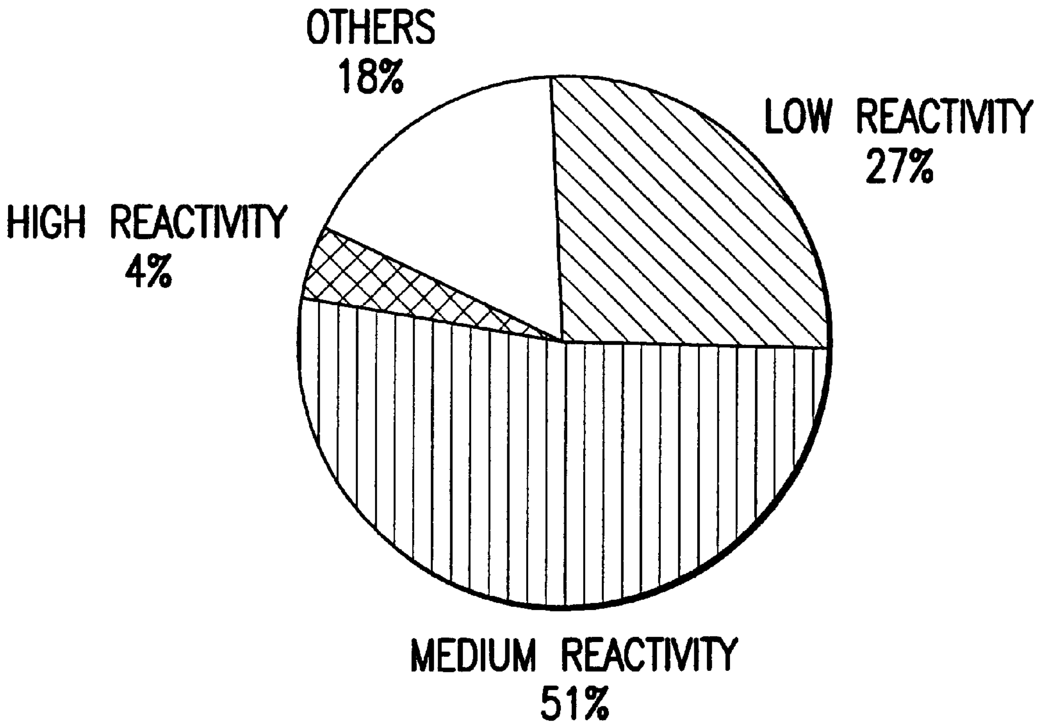
FIG. 14. Reactivity pattern of PRRSSV isolates with the MAbs to PRRSV. Titers of the MAbs were shown in FIG. 13. The reactivity pattern was determined according to the titers of at least 6 MAbs with any one isolate: <=32—low reactivity; 64 to 128—medium reactivity; >=256—high reactivity. Those isolates not belonging to the groups above were grouped as other. Total isolates tested were 23.
Figure 15A:
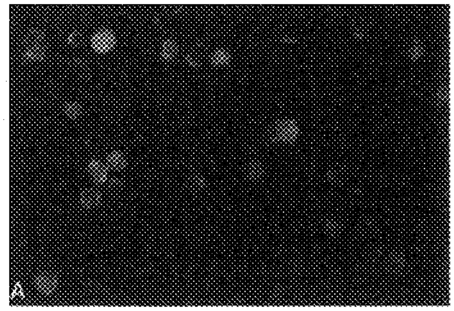
FIG. 15. Immunofluorescence detection of recombinant protein expression in insect cells. The High Five™ cells were infected with vAc-P2 (A), vAc-P3 (B), vAc-P4 (C) and wt AcMNPV (D), fixed with methanol and reacted with pig anti-PRRSV serum. Specific reactions were detected by fluorescein-labeled goat anti-pig IgG conjugate and observed under fluorescence microscope.
Figure 15C:
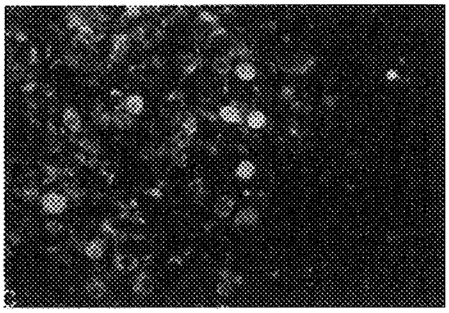
Figure 15B:
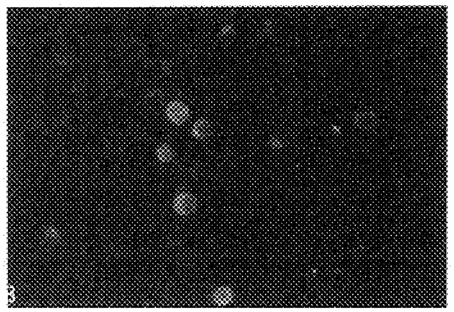
Figure 15D:
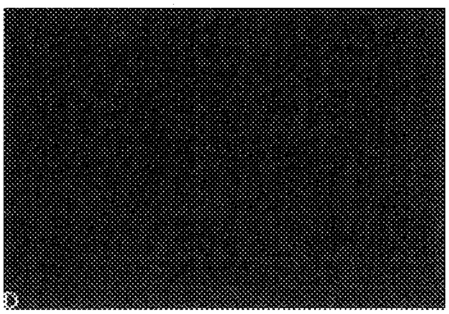
Figure 16A:
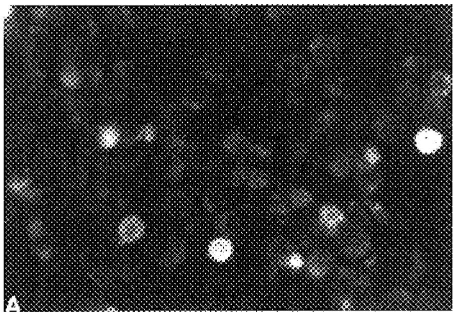
FIG. 16. Cell surface expression of recombinant proteins in High Five™ cells. The insect cells were inoculated with vAc-P5 (A), vAc-M (B), vAc-N (C) and wt AcMNPV (D), incubated for 72 hrs, and stained at 4° C. without fixation and permeabilization. Pig anti-PRRSV serum was used to react with cell surface recombinant proteins and fluorescein-labeled goat anti-pig IgG conjugate was utilized to detect any specific reactions, which was observed under fluorescence microscope.
Figure 16C:
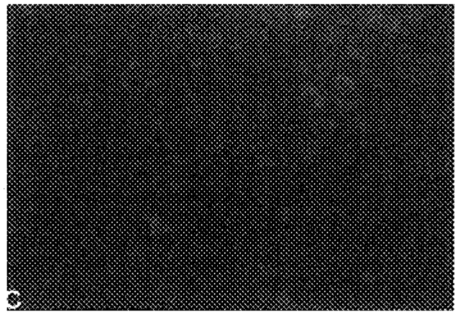
Figure 16B:
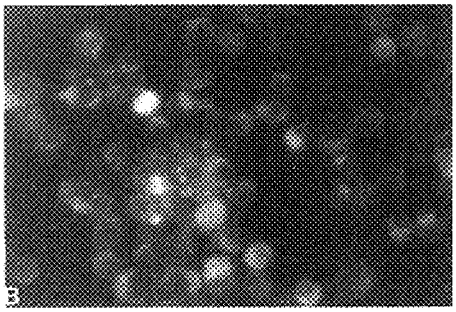
Figure 16D:
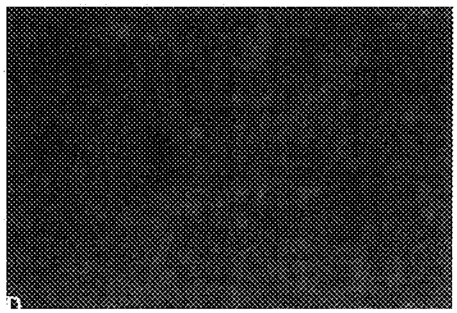
Figure 17A:
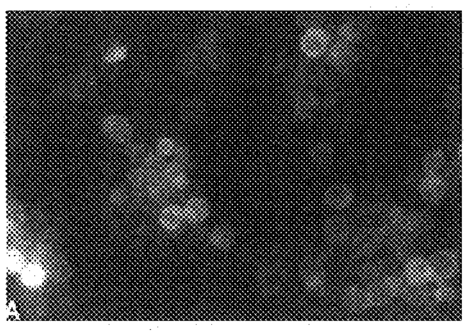
FIG. 17. Immunofluorescence detection of recombinant GP2, GP3 and GP4 proteins expressed in insect cells. The High Five™ cells were infected with recombinant baculovirus vAc-P2 containing ORF 2 (A), vAc-P3 containing ORF 3 (B), vAc-P4 containing ORF 4 (C) or wt AcMNPV (D), fixed with methanol and reacted with pig anti-PRRSV serum. Specific reactions were detected by fluorescein-labeled goat anti-pig IgG conjugate and observed under fluorescence microscope.
Figure 17C:
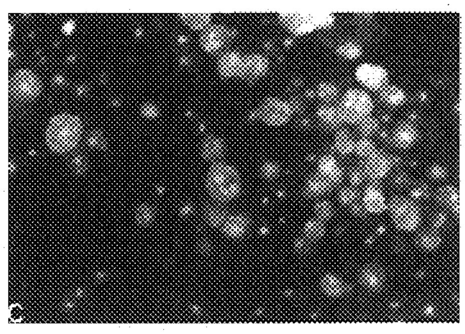
Figure 17B:
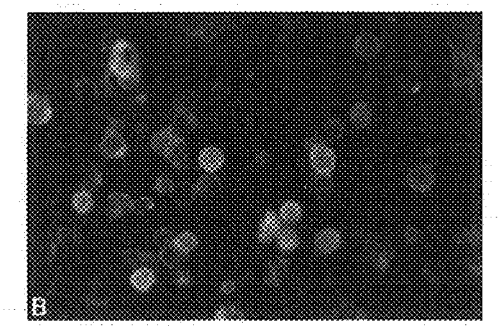
Figure 17D:
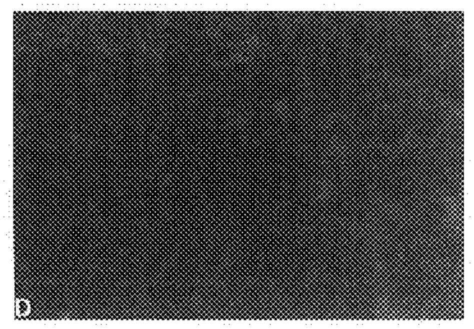
Figure 18A:
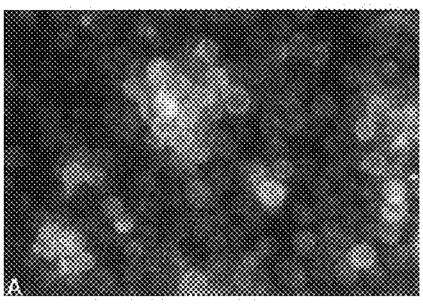
FIG. 18. Immunofluorescence detection of recombinant protein GP5, M and N expression in insect cells. The High Five™ cells were infected with recombinant baculovirus vAc-P5 containing ORF 5 (A), vAc-M containing the M gene (B), vAc-N containing the N gene (C) or wt AcMNPV (D), fixed with methanol and reacted with pig anti-PRRSV serum. Immunofluorescence is present in the cytoplasm in cells expressing E, M and N proteins.
Figure 18C:
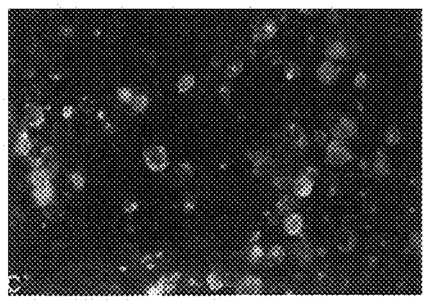
Figure 18B:
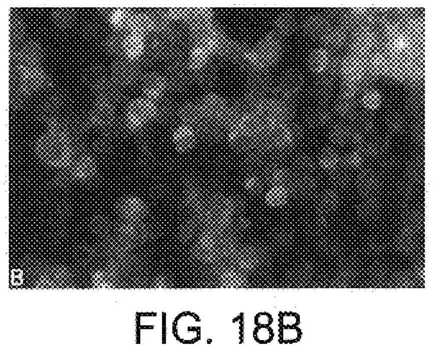
Figure 18D:
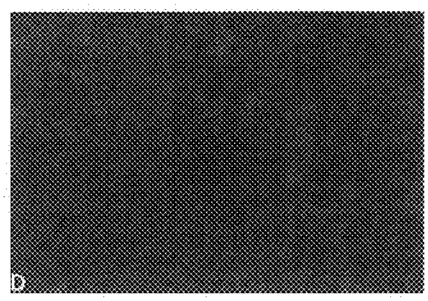

Western-blotting was carried out to determine the reactivity of the MAbs with PRRSV antigen to confirm the speculation that the MAbs were against conformationally dependent epitopes. Under denatured conditions in SDS-PAGE, only the PP5bH4 recognized a band of purified PRRSV virions in the position of 26 kDa which corresponded with the putative E detected with pig anti-PRRSV serum (FIG. 12). Then immunoblotting was carried out with non-denatured PAGE to test if the epitopes were preserved under nondenaturing conditions. Among the six MAbs to E, only PP5bH4 showed reaction with the PRRSV antigen. Of the MAbs to GP4, none recognized the PRRSV antigen in purified virions or in infected cells under either conditions in this test (result not shown).

The MAbs except PP5bH4 failed to recognize the PRRSV antigen in immunoblot, which indicated that the epitopes recognized by these MAbs were not derived from continuous structure. MAb PP5bH4 reacted with PRRSV in the position of 26 kDa, which confirmed the report about the molecular mass of E (Meulenberg et al., *Virology* 192:62–72 (1995)). This result showed that the epitopes recognized by the other 9 MAbs were sensitive to detergent treatment and corresponded to that of ELISA. Again the result indicated that the epitopes were conformationally dependent. PP4bB3 failed to show any reaction with PRRSV antigen in Western-blot, which could be due to the epitope loss or alternation during PAGE and transfer.

Virus Neutralizing Activity

Plaque-reduction assay was run to test whether there was any virus neutralizing activity among the MAbs to the E and GP4 proteins. Only one E-specific MAb, PP5dB4 showed the ability of homologous neutralization to the VR 2385 isolate. All the other MAbs failed to show any neutralizing activity to this isolate. The positive control, pig anti-PRRSV serum also showed virus neutralizing activity.

Among the ten MAbs to GP4 and E, at least PP5dB4 showed homologous virus neutralizing activity against PRRSV VR 2385. The neutralizing epitope was conformationally dependent as PP5dB4 failed to recognize PRRSV antigen in ELISA and in Western-blot. Also the neutralizing activity of PP5dB4 indicates that at least part of the epitope is located on the virion surface and accessible by the MAb. The mechanism of neutralizing activity of PP5dB4 is not clear. It could be due to blocking of the virus binding or entry into the cells.

Reactivity with Other PRRSV Isolates

PRRSV field isolates were propagated to test the cross-reactivity of the MAbs in fixed-cell ELISA and to determine the epitope presence in other PRRSV isolates (Table 5). Fixed-cell ELISA was used because most of these MAbs recognized conformationally dependent epitopes and these epitopes could be preserved in fixed cells. All the MAbs react with all the isolates but with different titers. The result indicates that the epitopes recognized by the MAbs were conserved among the isolates tested. However, there were antigenic differences among the isolates tested. Reactivity intensity was arbitrarily defined as high if titers were greater than or equal to 256, as medium if titers were 64 to 128, and as low if titers were smaller than or equal to 32. Out of the 23 isolates tested, only PRRSV VR 2385 had high reactivity with 7 of the 10 MAbs. Five isolates had low reactivity with at least 6 of the 10 MAbs, 12 isolates had medium reactivity with at least 6 of the 10 MAbs and the other 5 isolates had low reactivity with half of the MAbs. The MAb PP4dG6 and PP5bH4 showed lower reactivity with most of the isolates than other MAbs. The PP4bB3 showed the strongest reactivity among all the MAbs against GP4 and E proteins. The titer difference was as high as 64-fold for the reaction of one MAb with the different isolates, such as the titers of MAb PP4cBl 1 reacting with PRRSV RP 10 and RP 12, 16 and 1024 respectively. On the other hand, the titer difference of MAbs with one isolate was as high as 128-fold, such as the titers of MAbs PP4bB3 and PP4bC5 reacting with PRRSV RP11, 1024 and 8 respectively. This result indicated that the epitopes recognized by the different MAbs were different. The positive MAb control show strong reactivity with all the isolates except the ISU-51. The reactivity difference of MAbs with PRRSV isolates was consistent with the report that the amino acid sequence identity of VR 2385, ISU22, ISU55 and RP45 was 94–98% in ORF 4 and 88–97% in ORF 5 (Meng et al., *J. Gen. Virol.* 140:745–755 (1995)).

In summary, six MAbs were developed to the PRRSV E protein and four to the GP4. All of them except PP5bH4 were against conformationally dependent epitopes as determined by ELISA and immunoblotting. MAb PP5dB4 showed virus neutralizing activity against VR 2385. Reactivity pattern of the MAbs with PRRSV field isolates indicated that there are antigenic difference in PRRSV GP4 and E, which confirmed previous reports on MAbs against PRRSV N and ORF 3 product (Nelson et al., *J. Clinical Microbiology* 31:3184–3189 (1993); Drew et al., *J. General Virol.* 76:1361–1369 (1995); Wieczorek-Krohmer et al., *Veterinary Microbiology* 51:257–266 (1996)).

EXAMPLE 4

Cells and Viruses

ATCC CRL11171 cells were used to propagate PRRSV and PRRSV purification was done as previously described (Meng et al., *J. Gen. Virol.,* 75:1795–1801(1994); Meng et al., *J. Vet. Diag. Invest.* 8:374–381(1996); Halbur et al. *Vet. Pathol.* 32:648–660, (1995). PRRSV isolate ATCC VR 2385 (Meng et al., 1994 & Morozov et al., 1995) was used for PCR amplification of ORFs 2 to 4 genes.

*Spodoptera frugiperda* clone 9 (Sf9) and High Five™ (Invitrogen) insect cells were cultured for propagation of baculovirus. The baculovirus strain *Autographa California* multinuclear polyhedrosis virus (AcMNPV) was used as parent virus for recombinant baculovirus construction.

Construction of AcMNPV Recombinant Transfer Vector

Construction of the baculovirus transfer vectors containing the PRRSV ORFs 2, 3 and 4 separately was done with the strategies as previously described (Bream et al., *J. Virol.* 67:2655–2663(1993). Briefly, PRRSV ORFs 2 to 4 genes were PCR amplified separately from the template of pPSP. PRRSV2–7 plasmid with primers containing restriction sites of BamHI and Pst I for genes of ORFs 2 and 3, BamHI and EcoRI for ORF 4.

The forward primer for ORF2 was 5'GCA CGG ATCCGAATTAACATGAAATGGGGT3' (SEQ ID NO:42) and the reverse primer was 5'CCAC CT GCAGATTCACCGTGAGTTCGAAAG3' (SEQ ID NO:48). The forward primer for ORF3 was 5'CGTC GGATCCTCCTACAATGGCTAATAGCT3' (SEQ ID NO:43) and the reverse primer was 5'CGCG CTGCAGTGTCCCTATCGACGTGCGGC3' (SEQ ID NO:49). The forward primer for ORF4 was 5'GTAT GGATCCGCAATTGGTTTCACCTATAA3' (SEQ ID NO:44) and the reverse primer was 5'ATAG GAATTCAACAAGACGGCACGATACAC3' (SEQ ID NO:50). The amplified fragments were cut with restriction enzymes as indicated above and ligated into the vector pFastBAC1 (GIBCO BRL) for ORFs 2 and 3 fragments, and the vector PVL1393 (Invitrogen) for ORF 4 fragment. The inserted genes were under control of the polyhedrin gene promotor (O'Reilly et al., Baculovirus Expression Vectors: A Laboratory Manual, W. H. Freeman & Co., NY (1992) and verified with restriction enzyme digestion and PCR amplification. Then the recombinant vectors containing the ORFs 2 to 4 genes separately were isolated and designated as pPSP.Ac-p2 for ORF 2 transfer vector, pPSP.Ac-p3 for ORF 3 transfer vector and pPSP.Ac-p4 for ORF 4 transfer vector. For pPSP.Ac-p2 and pPSP.Ac-p3, their DNA were isolated and transfected into competent DH10BAC *E. Coli* cells (GIBCO BRL) containing the whole genome of baculovirus called Bacmid.

Transfection and Selection of Recombinant Viruses

For ORFs 2 and 3, recombinant viruses were generated with the BAC-TO-BAC™ expression system (GIBCO BRL). The isolated recombinant Bacmid DNA were transfected into Sf9 insect cells and then the cell culture medium was collected as virus stock. For ORF 4 recombinant virus construction, pPSP.Ac-p4 DNA and linearized AcMNPV DNA (Invitrogen) were co-transfected into Sf9 cells as described in the instruction manual. Putative recombinant baculoviruses were selected following three rounds of occlusion body-negative plaque purification. The inserted genes in the recombinant viruses were verified with hybridization and PCR amplification (O'Reilly et al., 1992). Four recombinants were selected for each of the 3 strains of recombinant baculoviruses. Indirect immunofluorescence assays with pig anti-PRRSV serum showed that the four recombinants for each strain had similar level of protein expression. One was chosen from each strain for further study and designated as vAc-P2 for recombinant virus of ORF 2, vAc-P3 for that of ORF 3, and vAc-P4 for that of ORF4.

Indirect Immunofluorescence Assay (IFA)

IFA was well described elsewhere (O'Reilly et al., 1992). Briefly, Monolayer of High Five™ cells were infected with wild type (wt) AcMNPV or recombinant viruses of vAc-P2, vAc-P3 and vAc-P4 respectively at a multiplicity of infection of 0.1 and incubated for 72 hrs. Pig anti-PRRSV serum was used to detect specific proteins expressed in insect calls. Total protein expression was detected in the infected cells fixed, stained and observed under fluorescence microscope. Cell surface expression was detected on unfixed and unpermeabilized cells incubated with pig anti-PRRSV serum for 1 hr at 4° C., stained with fluorescein-labeled goat anti-pig IgG conjugate for 1 hr at 4° C., and then observed under fluorescence microscope.

Immunoblotting

Western immunoblotting was conducted as previously described (Harlow & Lane, Antibodies: A Laboratory Manual, Cold Spring Harbor Laboratory (1988)). Cell extract from insect cells infected with recombinant viruses or wt AcMNPV were used for this analysis. The proteins were separated with SDS-PAGE and transferred to nitrocellulose membrane by electrophoresis. The membrane was incubated with pig anti-PRRSV serum for 1 hour at room temperature. Specific reactions were detected with goat anti-pig IgG peroxidase conjugate, followed by color development in 4-chloro-1-naphthol substrate.

Tunicamycin Treatment

High Five ™ cells were infected with vAc-P2, vAc-P3, vAc-P4 or wt AcMNPV and incubated with 5 μg/ml tunicamycin in cell-culture medium from 0 to 72 hrs post infection. Non-treated insect cells were infected at the same time as controls. Cell lysate was harvested for SDS-PAGE and immunoblotting (O'Reilly et al., 1992).

Immunogenicity of the Recombinant Proteins

Cell lysates of insect cells infected with vAc-P2, vAc-P3 and vAc-P4 were used to test the recombinant protein's immunogenicity in rabbits. Two twelve-week old rabbits were injected intramuscularly and subcutaneously for each of these recombinant proteins. Blood was collected 10 days after two booster injections. Antibodies were tested with indirect ELISA (Ausubel et al., Short Protocols in Molecular Biology, pp. 11.5–11.7, 2$^{nd}$ Edition, N.Y. Green Publishing Associates and John Wiley and Sons (1992)). Purified PRRSV virions were sonicated and used to coat 96-well plates and goat anti-rabbit IgG peroxidase conjugate was used to detect anti-PRRSV antibodies in rabbit serum samples. Pre-immune rabbit serum was used as negative control. Substrate 2,2'-azino-bis(3-ethylbenzthiazoline-6-sulfonic acid) (ABTS) was used to reveal specific reactions.

Results

Construction and Verification of Recombinant Viruses

Details of construction strategy are mentioned under Methods. For ORFs 2 and 3, the recombinant baculoviruses were selected from *E. coli* containing the recombinant Bacmid and then collected from transfection of Sf9 insect cells. The recombinant viruses were further confirmed by DNA hybridization and PCR amplification. Both hybridization of DNA from infected cells with specific probes from the PRRSV genes of ORFs 2 to 4 and PCR amplification showed that the recombinant baculoviruses had the right genes cloned (data not shown).

Surface Immunofluorescence of Recombinant Viruses vAc-P2, vAc-P3 and vAc-P4

High Five™ cells were infected with vAc-P2, vAc-P3, vAc-P4, or wt AcMNPV, incubated for 72 hrs, and fixed with methanol for examination of total protein expression by IFA with pig anti-PRRSV serum. Unfixed and unpermeabilized insect cells were stained at 4° C. to detect cell surface immunofluorescence by IFA. There was weak cytoplasmic fluorescence in vAc-P2 infected cells, intense cytoplasmic fluorescence in vAc-P3 or vAc-P4 infected insect cells and no specific fluorescence in wt AcMNPV infected cells (FIG. 17). There was clear cell surface immunofluorescence in vAc-P2, vAc-P3 and vAc-P4 infected insect cells stained at 4° C. without fixation and permeabilization (FIG. 15). No cell surface staining was detected in wt AcMNPV infected insect cells. Also, recombinant virus infected insect cells in the absence of antibody did not show any fluorescence (data not shown).

Analysis of Expressed Recombinant Proteins

Figure 19A:
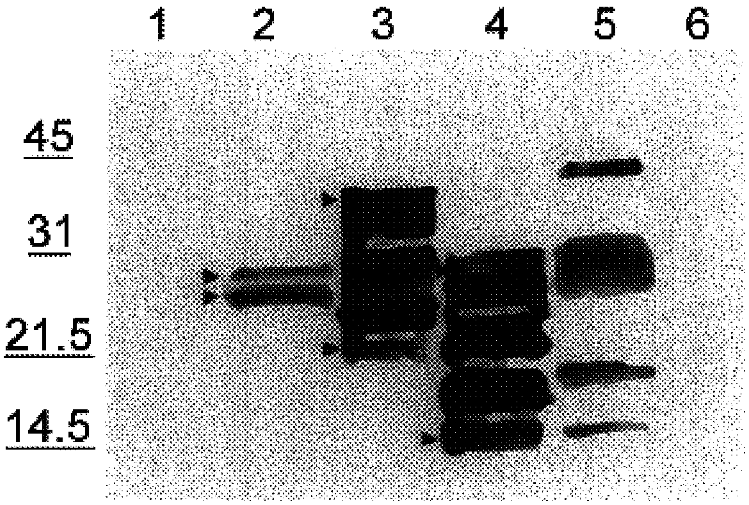
FIG. 19. Immunoblotting detection of recombinant protein expression in insect cells. Whole protein was separated in 15% gel in SDS-PAGE and transferred to nitrocellulose membrane. Pig anti-PRRSV serum was used to incubate the membrane and specific reactions were detected by goat anti-pig IgG peroxidase conjugate. MW standards (in kDa) are indicated on the left side of the figure. Lanes: 1. wt AcMNPV infected High Five™ cells; 2, vAc-P2 infected High Five™ cells; 3. vAc-P3 infected High Five™ cells; 4, vAc-P4 infected High Five™ cells; 5, purified PRRSV virions; 6, normal ATCC CRL 11171 cells. (B). Lanes: 1, vAc-P5 infected High Five™ cells; 2, wt AcMNPV infected High Five™ cells; 3, vAc-M infected High Five™ cells; 4, vAc-N infected High Five™ cells; 5, purified PRRSV virus; 6, normal ATCC CRL 11171 cells. The arrows indicate the positions or ranges in M, of recombinant proteins. The images were scanned with Hewlett Packard ScanJet 3c/T scanner and program of Adobe Photoshop 3.0 (Adobe System Inc.).

Monolayer of High Five™ cells was infected at a multiplicity of infection of 0.1 with vAc-P2, vAc-P3, vAc-P4, or wt AcMNPV and incubated for 72 hrs. Expression of the recombinant proteins in insect cells was analyzed with whole cell extracts. Total protein samples were run on SDS-PAGE, transferred to nitrocellulose membrane by western-blotting and detected with pig anti-PRRSV serum (FIG. 19A). Purified PRRS virions were added and analyzed in the same gel. The ORF 2 product expressed in insect cells was detected as 27 and 29 kDa bands in $M_r$. The ORF 3 product was detected as 22, 25, 27–31 and 35–43 kDa multi-band species. The signals in $M_r$ of 27–31 and 3543 kDa were hard to differentiate into single bands and may be due to differential glycosylation or partial proteolysis. The ORF 4 product was found as 15, 18, 22, 24, 28 and 30 kDa multi-band species. These specific bands were not detected in wt AcMNPV infected insect cells. There were at least four bands in purified PRRSV sample: 15, 19, 27–31 and 45 kDa in $M_r$. The specific bands detected in purified PRRS virions were not observed in normal cell control (FIG. 19A).

The Recombinant Proteins were Glycosylated

Figure 20A:
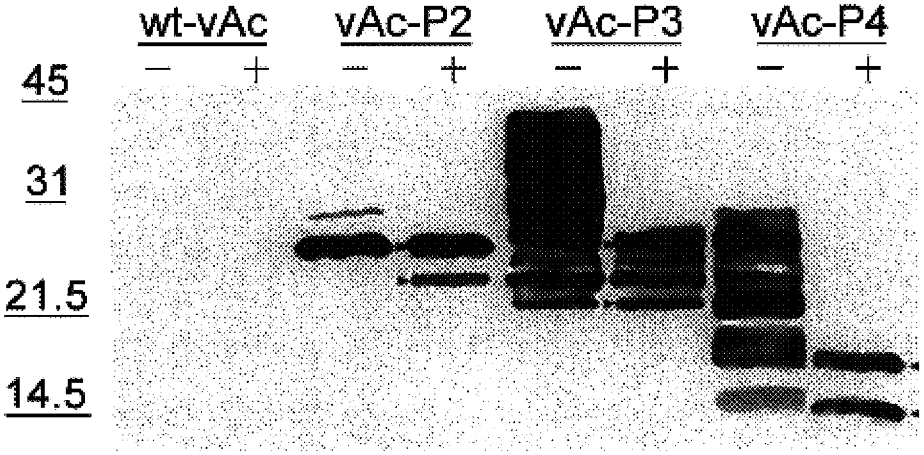
FIG. 20. Glycosylation analysis of the recombinant proteins E, M and N expressed in insect cells. (A). Tunicamycin treatment of insect cells infected with vAc-P2, vAc-P3, vAc-P4 or wt AcMNPV. (B). Tunicamycin treatment of insect cells infected with vAc-P5, vAc-M, vAc-N or wt AcMNPV.

Tunicamycin treatment of insect cells infected with recombinant baculoviruses or wt AcMNPV was conducted to test if the recombinant proteins were N-glycosylated as tunicamycin inhibit N-linked glycosylation. After the treatment, the 29 kDa band of the ORF 2 recombinant protein was disappeared, a kDa appeared and the 27 kDa species remained unchanged (FIG. 20A). For the ORF 3 recombinant protein, the species of 27–31 and 35–43 kDa were disappeared and the 22–27 kDa bands remained unchanged. The 27 kDa species of ORF 3 recombinant protein became more abundant after tunicamycin treatment. After the N-glycosylation inhibition, the ORF 4 recombinant protein was shown as 15 and 18 kDa species only and the bands of 22–30 kDa were disappeared. The 15 and 18 kDa bands became sharper and darker after the tunicamycin treatment. No signal was detected in extracts from wt AcMNPV infected insect cells.

Immunogenicity of the Recombinant Proteins

The recombinant proteins of ORFs 2 to 4 products were tested for immunogenicity by immunization of rabbits with lysates of insect cells infected with vAc-P2, vAc-P3 and vAc-P4. The presence of anti-PRRSV antibodies in the rabbit serum samples was detected by ELISA. The average titers of immunized rabbits were 192, 128 and 382 for the groups of vAc-P2, vAc-P3 and vAc-P4 cell lysate respectively (Table 6).

Discussion

The genes of ORFs 2 to 4 of PRRSV were cloned into BEVS and the recombinant proteins were expressed in insect cells. The cloning strategy for ORFs 2 and 3 was much faster than that for ORF 4 as the selection process of recombinant baculovirus was done in *E. Coli* instead of choosing occlusion body-negative plaques on Sf9 cells. Sf9 cells were used for the propagation of baculovirus, and High Five™ cells were used for protein expression as protein yield in High Five™ cells was believed to be higher than that in Sf9 cells (Wickham et al. Biotechnology Progress 8:391–396 (1992) & Davis et al., In Vitro Cell and Developmental Biology 29A: 388–390 (1993)). The High Five™ cells were adapted to serum free medium, which benefits for future protein purification, and can be adapted to suspension culture, which is suitable for large scale industrial production.

The recombinant proteins were shown by IFA to express in insect cells infected with vAc-P2, vAc-P3 and vAc-P4 recombinant viruses. There was weak cytoplasmic fluorescence in vAc-P2 infected cells, strong cytoplasmic fluorescence in vAc-P3 and vAc-P4 infected cells. The reason for the weak fluorescence of vAc-P2 infected cells is not known and could be due to epitope alternation after fixation with methanol. The unfixed and unpermeabilized insect cells were stained at 4° C. to make sure that the pig anti-PRRSV antibody reacted with cell surface proteins only and did not enter into cytoplasm. There was clear cell surface immunofluorescence on the insect cells infected with vAc-P2, vAc-P3 or vAc-P4, which indicates that the recombinant proteins were efficiently processed and transported to cell surface. This result indicates that ORFs 2 to 4 products are membrane-associated proteins, which is consistent with the predictions from sequence studies (Morozov et al., Archives of Virology 140:1313–1319 (1995)). However, it is not clear if these products are also transported to cell surface of PRRSV infected mammalian cells or assembled into virions as surface proteins. Recent report showed that the ORFs 3 and 4 products are viral structural proteins (VAN Nieuwstadt et al, J. Virol. 70:4767–4772 (1996)). Further experiment is needed to investigate the destiny of these proteins.

Immunoblotting results showed that the recombinant proteins were efficiently expressed in insect cells. The ORF 2 product was detected as 27 and 29 kDa species in $M_r$. Tunicamycin treatment eliminated the 29 kDa band and introduced the 25 kDa species with the 27 kDa unchanged, which indicated that the 29 kDa was N-glycosylated. The predicted $M_r$ of PRRSV VR 2385 ORF 2 is 29.5 kDa with two potential glycosylation sites (Morozov et al., 1995). The 25 kDa species may be the core protein of ORF 2 if the 37–38 signal sequence (Meulenberg et al., Virology 192:62–72 (1995)) are removed in the mature protein. The 4 kDa difference between the 29 and 25 kDa bands may be due to carbohydrate structures as one glycosyl moiety has a $M_r$ of about 2–3 kDa (Trimble et al., J. Biol. Chem. 250:2562–2567 (1983)). The 27 kDa species was not sensitive to the tunicamycin treatment and may be modified by O-linked glycosylation or other post-translational modifications.

The ORF 3 product in insect cells was shown as 22–43 kDa multi-band species detected by immunoblotting. The 28–43 kDa species were eliminated by tunicamycin treatment of vAc-P3 infected insect cells, which indicated that they were N-linked glycoproteins and the multi-bands were due to differential glycosylation. The predicted Mr of PRRSV VR 2385 ORF 3 product is 28.7 kDa (about 2 kDa less than the counterpart of LV) with 7 potential N-linked glycosylation sites (Morozov et al., 1995). The 27 kDa species of ORF 3 recombinant protein may be the core protein because it became more abundant after tunicamycin treatment (FIG. 20A) and because a 27 kDa band appeared and a 45 kDa band disappeared after endoglycosidase F treatment of purified PR RSV virion (data not shown). The species smaller than 27 kDa may be truncated proteins or products of proteolysis. The 27–43 kDa bands in nontreated sample are hard to differentiate into individual bands, which may be due to overloading or partial proteolysis. The 43 kDa species may be the fully glycosylated product as there are 7 N-linked glycosylation sites and about 2–3 kDa are counted for each glycosyl moiety (Trimble et al., 1983). The recent report showed that ORF 3 of LV encode a 45–50 kDa structural protein and that recombinant proteins of ORF 3 in insect cells were detected as 28–44 kDa in $M_r$ by radioimmunoprecipitation (VAN Nieuwstadt et al., 1996). The 28 kDa species was found as the core protein of LV ORF 3 product. It seems there is difference in Mr of recombinant proteins from ORF 3 of US PRRSV and LV, which may be due to the different expression system used or the difference in this gene between the two isolates. Another report showed that the recombinant fusion protein of carboxyterminal 199 amino acids of LV ORF 3 expressed in baculovirus was not N-glycosylated (Katz et al., Vet. Microbiol. 44:65–76 (1995)), which demonstrates the diversity of expressed products from the same gene.

The ORF 4 product in insect cells was detected as 15–30 kDa multi-band species. After tunicamycin treatment the 22–30 kDa bands were eliminated and the 15, 18 kDa bands remained unchanged, which indicated that the 22–30 kDa species were N glycosylated to various degrees. The ORF 4 of PRRSV VR 2385 was predicted to encode a 19.5 kDa protein with 4 potential N glycosylation sites (Morozov et al., 1995). The 15 kDa species of ORF 4 product may be the core protein and the 18 kDa band may be the core protein plus O-linked glycosyl moiety or other modifications. It was reported that LV ORF 4 encoded a 31–35 kDa structural protein and that the recombinant protein of ORF 4 expressed in insect cells was detected as 20–29 kDa species with a 17 kDa core protein (VAN Nieuwstadt et al., 1996). Again, the reason for the difference in Mr may be due to the cloned gene's difference and the different expression systems. Another report demonstrated the difference by showing that ORF 4 is not a well conserved region (Kwang et al., J. Vet. Diag. Invest. 6:293–296 (1994)).

The immunization of rabbits with the recombinant proteins showed that they had induced anti-PRRSV antibodies. This result indicates that these recombinant proteins may have the similar immunogenicity as their native counterparts in PRRSV infected mammalian cells.

This study showed that the ORFs 2 to 4 of PRRSV VR 2385 were expressed in BEVS and detected both in cytoplasm and on cell surface of insect cells. The recombinant proteins of ORFs 2 to 4 were N-linked glycoproteins with differential glycosylation. The purified PRRSV virions were analyzed as the same time and showed 4 bands in immunoblotting. But due to lack of oligoclonal or monoclonal antibodies it is hard to tell if any of ORFs 2 to 4 products was detected in the purified virions. The reaction of pig anti-PRRSV serum with the recombinant proteins indicated that the native counterpart of these proteins induced immune response in natural host. The induction of anti-PRRSV antibodies in rabbits indicated that these recombinant proteins had similar immunogenicity as the native ORFs 2 to 4 products in PRRSV infected natural host.

TABLE 6

Rabbit antiserum titers tested with ELISA

| Groups of insect cells infected with | Number of rabbits | Means of titers* |
|---|---|---|
| vAc-P2 | 2 | 192 |
| vAc-P3 | 2 | 128 |
| vAc-P4 | 2 | 384 |

*Titers were expressed as the reciprocals of the highest dilutions shown positive in ELISA.

EXAMPLE 5

Cells and Viruses

ATCC CRL11171 cells were used to propagate PRRSV (Meng et al., 1994 and 1996; Halbur et al., 1995). *Spodoptera frugiperda* clone 9 (Sf9) and High Five™ (Invitrogen) insect cells were used for propagation of baculovirus. PRRSV isolate VR 2385 (Meng et al., 1994 and 1996) was used for gene amplification and cloning into BEVS. PRRSV virions were purified as previously described (Meng et al., 1994). The baculovirus strain *Autographa california* multinuclear polyhedrosis virus (ACMNPV) was used as parent virus for recombinant virus construction.

Construction of ACMNPV Recombinant Transfer Vector

The nucleic acid sequence of the ORFs 5–7 of PRRSV VR2385 was previously described (Meng et al. 1994). Construction of the baculovirus transfer vectors containing the PRRSV ORFs 5 to 7 separately was done with the strategies as described previously (Bream et al. 1993). Briefly, PRRSV ORFs 5 to 7 genes were PCR amplified separately from the template pPSP.PRRSV2–7 plasmid with primers containing restriction sites of BamHI and EcoRI.

The forward primer for ORF5 was 5'TGCCA GGATCCGTGTTTAAATATGTTGGGG3' (SEQ ID NO:45) and the reverse primer was 5'CGTG GAATTCATAGAAAACGCCAAGAGCAC3' (SEQ ID NO:51). The forward primer for ORF6 was 5'GG GGATCCAGAGTTTCAGCGG3' (SEQ ID NO:46) and the reverse primer was 5'GG GAATTCTGGCACAGCTGATTGAC3' (SEQ ID NO:52). The forward primer for ORF7 was 5'GG GGATCCTTGTTAAATATGCC3' (SEQ ID NO:47) and the reverse primer was 5'GGGAATTCACCACGCATTC3' (SEQ ID NO:53). The fragments amplified were cut with BamHI and EcoRI isolated and figated into vector PVL1393 (Invitrogen) which was also cut with BamHI and EcoRI to insure correct orientations. The inserted genes were under control of the polyhedrin gene promotor (O'Reilly et al., 1992) and verified with restriction enzyme digestion and PCR amplification. The recombinant vectors containing the ORFs 5 to 7 genes separately were isolated, pPSP.Ac-E for ORF5, pPSP.Ac-M for ORF6 and pPSP.Ac-N for ORF7 transfer vectors.

Transfection and Selection of Recombinant Viruses

Sf9 insect cells were cotransfected with linearized AcMNPV DNA (Invitrogen) and recombinant plasmid DNA of pPSP.Ac-E, pPSP.Ac-M, and pPSP.Ac-N respectively as per manufacturer's instructions. Putative recombinant viruses were selected following three-round of purification of occlusion-negative plaques. The inserted genes in the recombinant viruses were verified with hybridization and PCR amplification (O'Reilly et al., 1992). Four recombinants were selected for each of the 3 strains of recombinant viruses and were found to be similar in immunofluorescence assays using pig anti-PRRSV serum. One recombinant virus was chosen arbitrarily from each strain and designated as vAc-E1 for recombinant virus containing ORF5, vAc-M1 for that with ORF6, and vAc-N1 for that with ORF7.

Immunoblotting

Western immunoblot analyses were carried out as described previously (Harlow and Lane, 1988). Whole proteins from infected insect cells, purified PRRSV or normal cells were used as samples. Proteins were separated with SDS-PAGE and transferred to nitrocellulose membrane by electrophoresis. The nitrocellulose membrane was blocked with 3% BSA and reacted with pig anti-PRRSV serum for 1 hour at room temperature. Bound antibodies were detected by incubation with goat anti-pig IgG peroxidase conjugate, followed by color development with 4-chloro-1-naphthol substrate.

Tunicamycin Treatment

Infected High Five™ cells were incubated with 5 $\mu$g/ml tunicamycin in cell-culture medium from 0 to 72 hr post infection and harvested for SDS-PAGE (O'Reilly et al., 1992).

Cleavage with Glycosidases

Endoglycosidase F/N-glycosidase F mixture (PNGase F) and endoglycosidase H (Boehringer-Mannheim Biochemicals) were used to treat lysates from infected High Five™ cells (0.1 PFU/cell; 72 hr post infection) in the case of recombinant proteins or purified PRRSV as per manufacturer's instructions. Briefly, $10^5$ cells were lysed with 30 $\mu$g lysis buffer. Then 10 $\mu$g of cell lysates was digested with PNGase F, endoglycosidase H or kept untreated and used as non-treated control. The samples were incubated at 37° C. for 24 hrs before analysis on SDS-PAGE.

Radioimmunoprecipitation (RIP)

High Five™ cells infected with recombinant baculovirus or wild type (wt) AcMNPV and uninfected High Five™ cells were washed once with methionine-free medium and starved for one hour at 48 hr post-infection. Then 50 ci/ml Tran$^{35}$S-label (methionine and cystine) (Amersham Life Science Inc.) in methionine-free medium was added to the infected cells. Three hours later the cells were rinsed with PBS and laced in RIPA lysis buffer (10 mM Tris-HCI, pH8.0; 1 mM EDTA; 150 mM NaCl; 1% NP40; 1% sodium deoxycholate; 0.1% SDS). Immunoprecipitation and gel electrophoresis were performed as described previously (Hutchinson et al., J. Virol. 66:2240–2250 (1992).

Indirect Immunofluorescence Assay (IFA)

IFA was conducted as previously described (O'Reilly et al., 1992). Monolayer of High Five™ cells were inoculated with wt AcMNPV or recombinant baculoviruses, incubated for 72 hrs and fixed to detect all recombinant protein expression with pig anti-PRRSV serum. The inoculated insect cells were also examined for the presence of cell surface proteins. Unfixed and unpermeabilized cells were reacted with the pig antiserum at 4° C. for 1 hr, incubated with fluorescein-labeled goat anti-pig IgG conjugate for 1 more hr at 4° C. and then observed under fluorescent microscope.

Immunogenicity of the Recombinant Proteins

Twelve-week old rabbits were injected intramuscularly and subcutaneouslly with lysates of insect cells infected with vAc-E1, vAc-M1 and vAc-N1. Two rabbits were immunized for each of E, M, and N recombinant proteins. Two booster injections were given in an interval of three weeks. The injection dose was cell lysates from 2x$10^6$ insect cells. Blood was collected 10 days after the second booster injection. Antibodies were tested with indirect ELISA. Purified PRRSV virions were sonicated and used to coat 96-well plates and goat anti-rabbit IgG peroxidase conjugate was used to detect anti-PRRSV antibodies in rabbit serum samples. Pre-immune rabbit serum was used as negative control. Substrate 2,2'-azino-bis(3-ethylbenzthiazoline-6-sulfonic acid) (ABTS) was used to reveal specific reactions.

Results

Confirmation for the presence of PRRSV Gene in Recombinant Baculovirus

Hybridization and PCR amplification were performed to verify the presence the cloned genes in recombinant baculovirus. Hybridization of probes from the PRRSV genes with recombinant baculovirus showed that the PRRSV genes were present in the recombinant baculovirus. PCR amplification with specific primers from PRRSV genes showed single band from the recombinant virus and absent from the wt AcMNPV (results not shown). These tests confirmed that the recombinant baculoviruses contain the PRRSV genes ORFs 5 to 7. Surface immunofluorescence of recombinant viruses vAc-E1 and vAc-M1, but not vAc-N1. High Five™ cells infected with vAc-E1, vAc-M1, vAc-N1, and wt AcMNPV were examined for the presence of total expressed protein and cell surface expression. There was weak cytoplasmic fluorescence in vAc-E1 and vAc-M1-infected cells. In contrast, there was intense cytoplasmic fluorescence in vAc-N1-infected insect cells and no fluorescence in wt AcMNPV infected cells (FIG. 18). Clear cell surface immunofluorescence was detected in vAc-E1 and vAc-M1 infected insect cells (FIG. 16). However, there was no surface immunofluorescence in insect cells infected with vAc-N1 or wt AcMNPV. Also, in the absence of antibody insect cells infected with the recombinant viruses did not show any fluorescence (data not shown).

Analysis of ORFs 5–7 Products Expressed in Insect Cells

To analyze the expression of the expected proteins in insect cells, confluent monolayers of High Five™ cells were infected at a multiplicity of infection of 0.1 PFU/cell with vAc-E1, vAc-M1 and vAc-N1 respectively and incubated for 72 hr. Total protein samples were run on SDS-PAGE and analyzed by western-blotting using pig anti-PRRSV serum (FIG. 19A). The recombinant protein E expressed in insect cells was detected as multi-band species of 16,18, 20, 24, and 26 kDa. The E expressed in insect cells showed more diversity and lower $M_r$ compared with the native E, 26 kDa species, in the purified PRRSV (FIG. 19A). The M expressed in insect cells was detected as a 19 kDa band, which corresponded to the native M in purified PRRSV. The N expressed in insect cells was detected as a 15 kDa band, which also corresponded to the native N in the purified PRRSV. These specific bands were not detected in normal insect cells (results not shown) and those infected with wt AcMNPV. Purified PRRS virions were analyzed in the same gel. There were at least five bands: 15, 19, 24, 26–30 and 45 kDa. The specific bands detected in purified PRRS virions were not observed in normal mammalian cell controls.

Glycosylation Analysis of Baculovirus Expressed E, M, and N

Figure 20B:
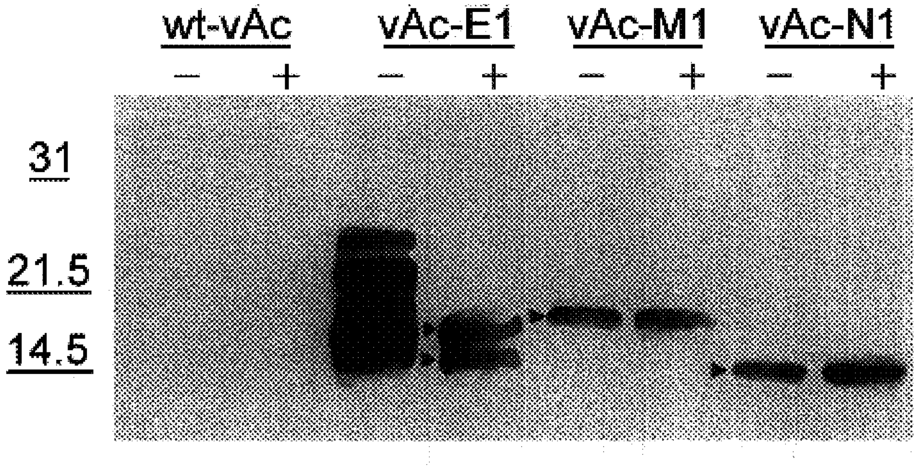

To determine if the E, M, and N expressed in insect cells underwent N-glycosylation, the insect cells infected with the recombinant baculoviruses were treated with tunicamycin to inhibit N-linked glycosylation. After tunicamycin treatment, the 20–26 kDa species were not detected in insect cells infected with the vAc-E1 (FIG. 20B), while the 16 and 18 kDa bands became more abundant. In the cells infected with vAc-M1 and vAc-N1, no changes in $M_r$ of M and N proteins were detected after the tunicamycin treatment (FIG. 20B).

Immunogenicity of the Recombinant Proteins

The recombinant proteins E, M, and N were tested for immunogenicity by immunization of rabbits with lysates of insect cells infected with vAc-E1, vAc-M1 and vAc-N1. Then ELISA was carried out to test for the presence of anti-PRRSV antibodies in the rabbit serum samples. The average titers of E, M and N immunized rabbits were 384, 320 and 2,056 respectively (Table 7).

Discussion

Recombinant baculoviruses containing the genes E, M, and N of PRRSV were constructed to express E, M, and N in insect cells. Sf9 cells were used for the propagation of baculovirus, and High Five™ cells were used for protein expression as protein yield in High Five TM cells was believed to be higher than that in Sf9 cells (Wickham et al., 1992 and Davis et al., 1993).

Immunofluorescence analysis showed that E, M and N were expressed in insect cells infected with recombinant viruses containing those genes and showed that E and M were transported to the cell surface in insect cells. This result indicates that E and M expressed in insect cells are membrane-associated proteins and efficiently processed in post-translational modification. The reason for low intensity of cytoplasmic immunofluorescence of E and M in insect cells is unclear. It may be due to the epitope loss or modification after fixation of the infected insect cells. In insect cells infected with vAc-N1, only intense cytoplasmic immunofluorescence was observed and no surface fluorescence was detected. This result indicated that baculovirus expressed N was not transported to cell surface but located in the cytosol. This characteristic is consistent with its nature as a very hydrophilic nucleocapsid protein as predicated from sequence studies (Meng et al., 1994).

Figure 19B:
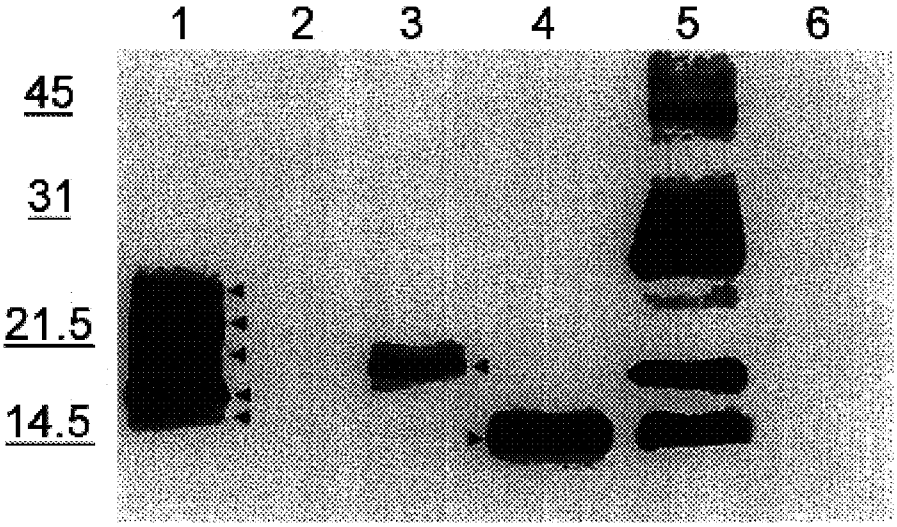

The recombinant E protein showed multi-bands in immunoblotting, the bands with $M_r$ smaller than 26 kDa were not found in the purified PRRSV. The E expressed in insect cells showed more diversity and lower $M_r$ compared with the native E, 26 kDa species, in the purified PRRSV (FIG. 19). The multi-bands may be due to differential glycosylation in insect cells during post-translational modification. Tunicamycin treatment eliminated the 20–26 kDa bands and increased the intensity of the 16 kDa band. The presence of the 18 kDa band after treatment could be due to O-linked glycosylation, phosphorylation or other post-translational modifications. The 20–26 bands represent those of differential N-glycosylated species of E in insect cells. The 16 kDa band may be the non-glycosylated leader-free core protein. Preliminary studies of PNGase F and endoglycosidase H treatment of recombinant protein E showed that it underwent complex glycosylation. The recombinant M and N did not undergo N-linked glycosylation as both the tunicamycin and PNGase F and endoglycosidase H treatments did not alter the mobilities of the 19 and 15 kDa bands. These results indicate that the recombinant protein E of 20–26 kDa is N-glycosylated, and that the recombinant M and N proteins expressed in insect cells are not N-glycosylated. The changes in mobility after tunicamycin treatment were consistent with the presence of two N-linked glycosylation sites in the E polypeptide as determined from sequence studies (Meng et al., 1994). However, sequence studies indicated that there are 2 and 1 potential N-linked glycosylation sites in the M and N polypeptides respectively. In the baculovirus expressed M and N, there was no N-linked glycosylation detected. Compared with the native counterparts, the recombinant proteins in insect cells were much more abundant as seen from the immunoblot (the loading amount of the recombinant proteins was about one percent of the PRRSV lane in FIG. 19). However, it is difficult to measure the difference without oligoclonal or monoclonal antibodies.

For the purified PRRSV, there are at least five bands: 15, 19, 24, 26–30 and 45 kDa. This result is consistent with the previous reports that there are at least three structural proteins in the PRRSV virion (Conzelmann et al., Virology 193:329–339 (1993); Nelson et al., J. Clin. Microbiol. 31:3184–3189 (1994) and Mardassi et al., Arch. Virol. 140:1405–1418 (1994)). The 45 kDa band in the purified PRRSV may be the ORF3 product as reported (Kapur et al., J. Gen. Virol. 77:1271–1276 (1996)). The nature of the 24, 27–30 kDa species can not be figured out. After treatment with PNGase F and endoglycosidase H, the band pattern changed for the PRRSV sample. In the PNGase F treated PRRSV, the 16-kDa band may represent the non-glycosylated leader-removed core protein of E, the 27-kDa band may indicate another structural protein of PRRSV besides E, M and N. However, the nature of these bands needs to be determined by oligoclonal or monoclonal antibodies.

The results from rabbit immunization test indicated that the antibodies generated from the immunization of rabbits with the recombinant proteins could recognize the native PRRSV viral antigens. The recombinant proteins showed the same antigenicity as their native counterparts in PRRSV infected mammalian cells, especially the recombinant N which induced higher antibody titers in rabbits than did E and M.

TABLE 7

Rabbit antiserum titers tested with ELISA

| Groups of insect cells infected with | Number of rabbits | Means of titers* |
|---|---|---|
| vAc-E1 | 2 | 384 |
| vAc-M1 | 2 | 320 |
| vAc-N1 | 2 | 2056 |

*Titers were expressed as the reciprocals of the highest dilutions of serum that showed positive reading.

EXAMPLE 6

Porcine Reproductive and Respiratory Syndrome Virus (PRRSV), Modified Live Virus vaccine was prepared as a lyophilized viral cake and reconstituted with sterile water and administered by either the subcutaneous (SC) or intramuscular (IM) route. The objective of this study was to confirm the immunogenicity of a PRRSV vaccine in three week-old swine by vaccinating either IM or SC with one 2 mL dose. Also to be determined was whether the PRRSV vaccine was safe and efficacious in three week-old pigs vaccinated with a single 2 mL dose, given with IM or SC, in protecting pigs against challenge with virulent PRRSV strain ISU-12.

Animal Selection

Seventy crossbred PRRSV seronegative pigs (IDEXX ELISA sample to positive ratio of <0.4) were purchased from Evergreen Partners, Morris, Minn. and utilized in this study. All pigs were three weeks old at the time of vaccination.

Composition of the Vaccine

The PRRSV vaccine comprising virus strain ISU-55 was produced at virus passage level X+5. The vaccine was stored between 2°–7° C. prior to use. The vaccine was titrated in five replicates.

Vaccination Schedule—Efficacy Testing

The stock vaccine was prepared by reconstituting the lyophilized virus portion with sterile water. The stock vaccine was diluted to the minimum protective dose level (approximately $10^6$ $TCID_{50}$ per dose) in culture medium. A representative aliquot of the prepared vaccine was retained at −70° C. for quantitation of viral antigen. The 70 PRRSV seronegative susceptible pigs used in this study were randomly distributed into four treatment groups and vaccinated as follows:

| Group | Vaccine | Route | Dose | Number | Vaccination |
|---|---|---|---|---|---|
| Group A | PRRSV vaccine | IM | 2 mL | 20 pigs | Vaccination at 3 weeks of age. |
| Group B | PRRSV vaccine | SC | 2 mL | 20 pigs | Vaccination at 3 weeks of age. |
| Group C (Controls) | N/A* | N/A | N/A | 20 pigs | N/A |
| Group D (Controls) | N/A | N/A | N/A | 10 pigs | N/A |

*N/A—Not applicable

Injection sites were in the right neck (IM) or in the right flank fold (SC). The control pigs (Groups C and D) were not vaccinated with any vaccine or placebo vaccine.

Prior to vaccination, all pigs were bled for a prevaccination serology. Control animals were bled prior to challenge to ensure that they remained seronegative to PRRSV (IDEXX ELISA S/P ratio <0.4).

Challenge and Observation Procedure

Thirty-six (36) days after the vaccination, each of the 20 pigs in Groups A, B and C were commingled in a common isolation room and challenged with virulent PRRSV. Group D animals were left as nonchallenged controls. The virulent ISU-12 PRRSV challenge virus was obtained from Iowa State University, Ames, Iowa. The virulent ISU-12 PRSV challenge virus was maintained as a frozen (−70° C.) stock after expansion in PSP36 cells. Individual pigs were challenged intranasally with 2 mL of the challenge virus. The PRRSV challenge stock was thawed and diluted to $10^4$ $TCID_{50}$ per 2 mL just before challenge. The challenge virus was held on ice during challenge. An aliquot of the challenge virus preparation was retained and held at −70° C. for subsequent titration on PSP36 cells. The animals were observed on −1, and 0 days post challenge (DPC) to establish a baseline and 1 to 10 DPC for various clinical signs.

Clinical Observation

The pigs were evaluated each day for post challenge clinical signs such as inappetence, lethargy, depression, diarrhea, neurological symptoms, dyspnea, cyanosis and death.

Lung Lesion Scoring

The lungs of each individual pig were examined for gross lesions at necropsy 10 days post challenge. The scorer of gross lung lesions was blinded to the identity of the treatment group to which each pig belonged. Briefly, the score for lung lesions in each lobe were recorded by estimating the percent of the lobe exhibiting PRRSV-like lesions (based on color and texture) and multiplied by the number of points possible for that lobe. Maximum score for each lobe was determined by the relative percentage of the total lung volume occupied by the lobe. Then the scores from the dorsal and ventral aspects of all lobes were added to obtain the total score for each pig. The maximum total score possible for each animal was 100.

Statistical Analysis

The clinical sign and gross lung lesion scores for the vaccinates and the controls were compared using analysis of variance (General Linear Model). The use of analysis of variance models using nonranked gross lung lesion scores was justified by the fit of the scores within a normal probability distribution. A comparison of the residuals of the parametric analysis indicated they were distributed normally, substantiating the major assumptions for analysis of variance. Therefore, data analysis using ranked gross lung lesion scores was not necessary. All statistical analyses were performed on an IBM computer using SAS software.

Results and Discussions

PRRSV Antigen Titers in the VS Code Vaccine

The PRRSV vaccine antigen titration results are shown in Table 8. The average PRRSV titer per dose of vaccine from five replicate titrations was $10^{3.92}$ $TCID_{50}$.

Clinical Observations

Following vaccination, there were no clinical signs observed in any of the vaccinated pigs. Following challenge with virulent PRRSV ISU-12 p6, the vaccinates and control pigs did not show significant clinical signs of respiratory or neurologic disease during the 10 day post challenge observation period.

Gross Lung Lesion Pathology

The results of gross lung lesion scoring are given in Table 9. Following PRRSV challenge, the gross lung lesion scores ranged from 0–29 with a mean score of 14.15 in the IM vaccinated pigs (Group A), from 1–27 with a mean score of 11.20 in the SC vaccinated pigs (Group B), from 7–57 with a mean score of 25–80 in the nonvaccinated challenge control pigs (Group C), and 1–28 with a mean score of 10.90 in the non-vaccinated nonchallenged control pigs (Group D). Both IM and SC vaccinated pigs had significantly less lung lesions than the nonvaccinated challenged control pigs ($p<0.05$). The vaccinated pigs did not have significantly different gross lung lesion scores than the gross lung lesion scores from nonvaccinated nonchallenged pigs ($P>0.05$). The nonvaccinated challenged control pigs had significantly higher gross lung lesions than the nonvaccinated nonchallenged control pigs ($P<0.05$).

Conclusion

The results of the study demonstrate that Porcine Reproductive and Respiratory Syndrome Virus, Modified Live Virus Vaccine is efficacious for use in healthy pigs three weeks of age or older as an aid in the prevention of respiratory disease caused by virulent PRRSV challenge. One hundred percent of the three week-old pigs vaccinated with the modified live vaccine did not show any adverse local or systemic clinical effects following vaccination. These pigs remained healthy and active for the entire 36 day post vaccination observation period. Pigs vaccinated with a dose of $10^{3.92}$ $TCID_{50}$ vaccine either intramuscularly or subcutaneously showed significant reduction ($p<0.05$) in gross lung lesion development over nonvaccinated challenged control pigs following challenge with a heterologous irulent PRRSV challenge strain, ISU-12. The post challenge gross lung lesion scores of avaccinated pigs were statistically indistinguishable from the nonvaccinated nonchallenged controls ($p>0.05$). Analysis of the residuals of the parametric analysis of variance indicated that they were distributed normally, substantiating the major assumptions for analysis of variance. One hundred percent of the vaccinated pigs remained free of clinical signs during the post challenge period.

TABLE 8

PRRSV Immunogenicity Study: PRRSV Antigen Level of Vaccine*

| Replicate Titration Number | Viral Titer per 2 mL dose |
|---|---|
| 1 | $10^{3.80}$ |
| 2 | $10^{3.93}$ |
| 3 | $10^{4.13}$ |
| 4 | $10^{3.93}$ |
| 5 | $10^{3.80}$ |
| Average | $10^{3.92}$ |

*in log $TCID_{50}$

TABLE 9

PRRSV Immunogenicity Study: PRRSV Gross Lung Lesion Scoring 10 DPC

| | Group | | | |
|---|---|---|---|---|
| Pig Number | A IM Vaccinates | B SC Vaccinates | C Non Vaccinated Challenged Controls | D Non Vaccinated Non Challenged Controls |
| 1 | 21 | 7 | 53 | 4 |
| 2 | 1 | 12 | 7 | 8 |
| 3 | 19 | 5 | 57 | 1 |
| 4 | 12 | 17 | 12 | 2 |
| 5 | 29 | 3 | 18 | 3 |
| 6 | 5 | 18 | 35 | 11 |
| 7 | 18 | 19 | 20 | 24 |
| 8 | 6 | 5 | 28 | 14 |
| 9 | 4 | 7 | 32 | 28 |
| 10 | 0 | 8 | 41 | 14 |
| 11 | 16 | 3 | 27 | |
| 12 | 12 | 27 | 19 | |
| 13 | 9 | 16 | 40 | |
| 14 | 29 | 19 | 10 | |
| 15 | 17 | 1 | 24 | |
| 16 | 20 | 13 | 15 | |
| 17 | 26 | 12 | 9 | |
| 18 | 21 | 14 | 9 | |
| 19 | 6 | 13 | 35 | |
| 20 | 12 | 5 | 25 | |

TABLE 9-continued

| PRRSV Immunogenicity Study: PRRSV Gross Lung Lesion Scoring 10 DPC | | | | |
|---|---|---|---|---|
| | Group | | | |
| Pig Number | A IM Vaccinates | B SC Vaccinates | C Non Vaccinated Challenged Controls | D Non Vaccinated Non Challenged Controls |
| Mean | 14.15 | 11.20 | 25.80 | 10.90 |
| StandardDeviation | 8.86 | 6.84 | 14.47 | 9.3 |

EXAMPLE 7

Complete Sequence of PRRSV Isolate VR 2385

Materials and Methods

Virus and Cells. The PRRSV isolate VR2355, passage 7 was used in this study. A continuous cell line, ATCC CRL 11171 was used for growth of the virus and isolation of viral RNA and total RNA from the virus-infected cell culture.

Cloning of cDNA and PCR amplification. For characterization of the ORF 1 region of genome of VR2385 a random cDNA λ library was constructed using the Uni-Zap cDNA cloning kit (Stratagene, La Jolla, Calif.). Briefly, the CRL11171 cells were infected with VR2385 virus at a M.O.I. of 0.1 and the total RNA from infected cells was isolated at 24 hrs post infection by using a guanidinium thiocyanate method. Initially, probe specific for 5' end of ORF2 was used to screen the random cDNA library. Plaques that hybridized with the probe were isolated and purified. The phagemids containing viral cDNA inserts were rescued by in vitro excision using ExAssist helper phage and *E. coli* SOLR cells (Stratagene, LaJolla, Calif.). After hybridizations with ORFI-specific overlapping fragments, several recombinant phagemids with virus specific cDNA inserts with sizes ranging from 2 to 6 kb were selected. The plasmids containing virus cDNA inserts were subsequently purified and sequenced by Sanger's dideoxynucleotide chain termination method with an automated DNA sequencer (Applied Biosystems, Foster City, Calif.). Universal, reverse and PRRSV-specific internal primers were used to determine the sequence. At least 2 independent cDNA clones representing sequence of ORFs 1a and 1b were sequenced. One region, not represented in the library (nt 1950–2050) was PCR amplified with primers IM687 (5'-CCCCATTGTTGGACCTGTCC-3') (SEQ ID NO:144) and IM2500 (5'-GTCACAACAGGGACCGAGC-3') (SEQ ID NO:145) using Tag DNA polymerase with addition of the proofreading Tag Extender (Stratagene). The sequencing data were assembled and analyzed using MacVector (International Biotechnologies, Inc., CT) and GeneWorks (IntelliGenetics, CA) computer programs.

Primer extension experiments and RNA sequencing. Primer extension experiments were performed using Sure-Script Preamplification System for First Strand cDNA Synthesis (Gibco BRL). $^{32}$P-labeled oligonucleotide RNS (5'-CCAAGCTCCCCTGAAGGAGGCTGTCAC-3') (SEQ ID NO:146) was mixed with 0.5 μg of viral RNA of VR2385 in total volume of 12 μl and RNA was denatured for 10 min at 90° C. The sample was adjusted to a total volume 19 μl with first strand cDNA buffer and incubated for 5 min at 42° C. for primer annealing. Super Script II reverse transcriptase was then added to the reaction and the reaction mixture was incubated at 42° C. or 50° C. for min. Samples were analyzed in 40% polyacrylamide gel. Primer extension products were run next to the sequencing reactions of pPR59 clone, containing partial sequence of the leader. Oligonucleotide RNS served as a primer for the sequencing reaction.

Direct sequencing of purified viral RNA was performed using RT RNA Sequencing Kit (USB, Cleveland, Ohio) with γ$^{32}$P-labeled oligonucleotide RNS (5'-CCAAGCTCCCCTGAAGGAGGCT GTCAC-3') (SEQ ID NO:147) and 151Ext (5'-AGCATCCCAGACATGGTTAAAGGGG-3') (SEQ ID NO:148). Sequencing was performed according to the manufacturer's instructions using 0.5 μg of purified viral RNA per sequencing reaction.

Results

Leader Sequence of PRRSV VR2385

Previously, oligo dT and random cDNA libraries of PRRSV VR2385 in λZap vector and here constructed the sequence for portion of ORF1b and complete ORFs-2–7 were determined. The partial leader sequence of VR2385 (SEQ ID NO:56), 161 nucleotides upstream of the ATG start codon of ORF1, was obtained from clone pPR59. It has been shown previously that the leader sequence of LDV is 156 nucleotides, and that the leader sequence of LV (SEQ ID NO:57) (a European isolate of PRRSV) was 221 nucleotides. In order to determine the complete leader sequence of U.S. PRRSV, primer extension experiments were performed. In one experiment cDNA was synthesized using SuperScript II reverse transcriptase at 42° C. and 50° C. In another experiment rTth DNA polymerase in the presence of Mn was used for cDNA synthesis at 60° C. to minimize potential of secondary structures in leader RNA during cDNA synthesis. In all experiments the length of generated cDNA fragments were the same, about 190 nucleotides. In order to detect the complete leader sequence of PRRSV VR2385, direct sequencing of viral RNA was performed. Virion RNA isolated from virus purified through sucrose gradient was used in a direct RNA sequencing reaction. Direct RNA sequencing was performed with a primer complementary to the leader sequence at positions between 10 and 67 nt upstream of the AUG start codon of ORF1a. In addition to the 161 nt leader sequence previously detected by screening of the cDNA library with leader specific probe, an additional 27 nucleotides of the leader sequence were identified. The two nucleotides at the extreme 5' end of the leader could not be identified due to the strong bands observed in all four lanes in the sequencing gel. The size of the leader determined by direct RNA sequencing correlated with results of the primer extension experiments. To further confirm the data obtained by direct RNA sequencing, RT-PCR was performed with a 16 b.p. primer, corresponding to the extreme 5' end of the leader, and an antisense primer located 10 nt upstream of the 3' end of the leader. An expected 180 b.p. PCR fragment was amplified which is in agreement with the results obtained by direct RNA sequencing. Therefore, the putative size of the leader of PRRSV VR2385 was 190 nt, which is smaller than those reported for LV (221 nt), EAV (212 nt) and SHFV (208 nt), but larger than the leader sequence reported for LDV (156 nt). The sequence of the junction region at the 3' end of the leader was TTTAACC. The ATG start codon of ORF1a is located immediately downstream of this sequence. Similar results were also reported for LV, LDV and SHFV, in which the start codon of ORF1a is also located after the junction sequence. However, the genome of EAV leader junction sequence was reported 13 nt upstream of the start codon of ORF1a. The percentage of nucleotide sequence identity between the leader sequence of VR2385 and those of LV, LDV and SHFV were 55%, 47% and 38%, respectively. Surprisingly, only the last 44 nucleotides at the 3' end of the leader of VR2385 possess significant homology with the leader sequence of LV (86% identity in this region). Relatively higher homology was also found in this 44 nt region between VR2385 and LDV (64%) and SHFV(63%). No significant homology was found between leader sequences of VR2385 and EAV.

Cloning and Sequencing of PRRSV Genome

Figure 23:
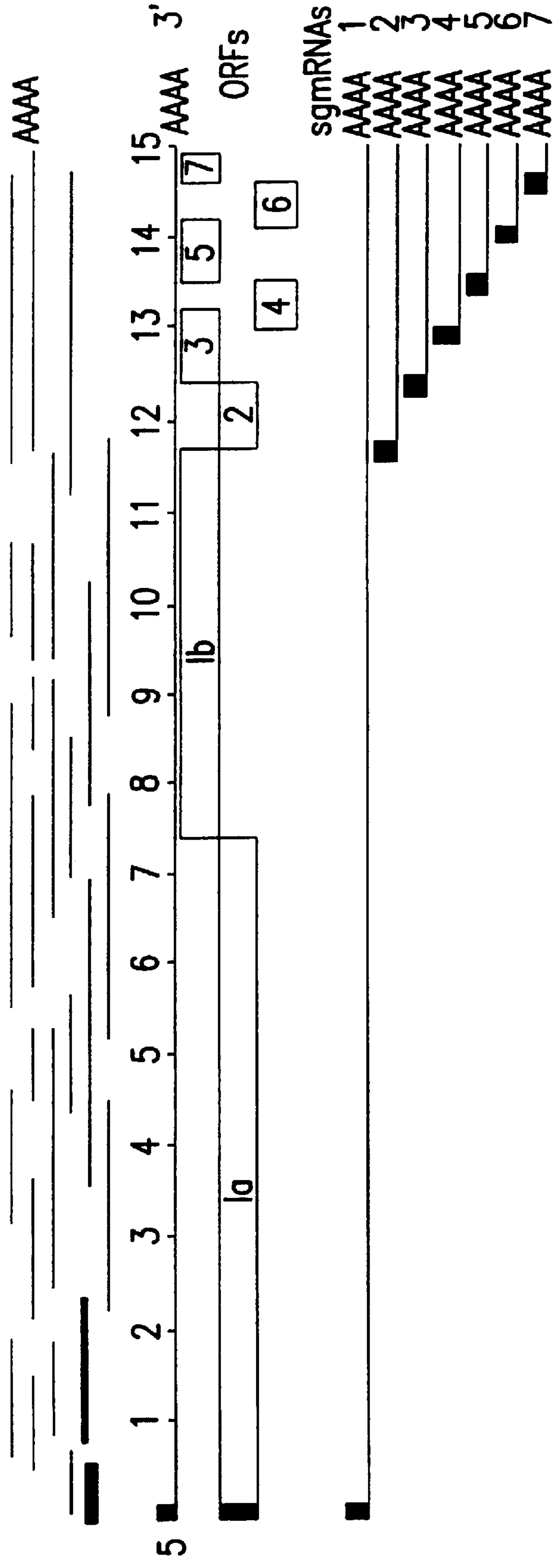
FIG. 23 shows 20 overlapping cDNA clones sequenced from the VR 2385 cDNA library.

To analyze ORF1 of PRRSV VR 2385, a random primed cDNA library in λZap vector was constructed from total RNA of virus-infected cells. More than twenty overlapping cDNA clones from cDNA library were selected and sequenced (FIG. 23). For most regions, the sequence was determined from at least two independent clones. The region corresponding to nucleotides 1900–2050 was not represented in the cDNA library, and this genomic region was PCR amplified and sequenced. Sequence analysis showed that the genomic RNA of PRRSV (U.S. isolate VR2385), excluding the polyA sequence, is 15100 nucleotides in length.

Functional Domains in ORFs 1a/1b and Homology with Related Viruses

The predicted size of ORF1a is 7197 nucleotides. It extends from nucleotides 191 to 7387 (excluding the stop codon TAG) and encodes a 2399 amino acid polyprotein. The leader-genome junction region is similar to that of LV, and the ATG start codon is located immediately after TTTAACC sequence of the leader. Differences were identified when compared the ORF1 sequences of LV and VR2385. ORF 1a in LV is 7188 nucleotides long and encodes 2396 amino acids, which is only 3 amino acids shorter than that of VR2385. Pairwise comparison of nucleotide sequences of VR2385 (SEQ ID NOS:58, 60, 62, 66) and LV (SEQ ID NOS:59, 61, 63, 67) indicated that the 5' end of ORF1a is more divergent than the 3' end. The nucleotide sequence 55% identities between VR2385 and LV is 61% in the 3' end of ORF 1a, (from nucleotides 3050 to 7387) in the first 1500 nucleotides of ORF 1a 55%, and 46% in a region between nucleotides 1500 to 2500. The most variable region within ORF1a was located between nucleotides 2500 and 3000, where there was no significant homology between VR2385 and LV. The amino acid identity was 49% for region from 1 to 530 aa, 55% for region from 1100 to 2399 amino acids, and no significant homology in the region extending from amino acids 530 to 1100. Comparison of the ORF1a sequences of VR2385 (SEQ ID NOS:58, 60, 62, 66) and LV (SEQ ID NOS:59, 61, 63, 67) revealed that there is a 52% homology in first 2000 nucleotides and 55% homology in the last 3800 nucleotides of ORF la (corresponding to 3400–7197 nt in VR2385 and 2850–6678 nt in LDV). The region between 2000 to 3400 nt of VR2385 and 2500 to 2850 nt of LDV is highly variable with more than 500 nt deletion in LDV genome. Comparison of the predicted amino acid sequences showed that there is a 36% of homology for the region extended from amino acids 1 to 500, and 39% for the region, that includes the last 1300 amino acids of predicted proteins (1120 to 2353 aa in VR2385 and 940 to 2226 aa in LDV).

Analysis of the predicted protein encoded by ORF1a of VR2385 revealed the presence of two papain-like cysteine protease domains (aa 63–165 and aa 261–347) and one 3C-like serine protease domain (aa 1542–1644), similar to those described for other arteriviruses and coronaviruses. The hydrophilic profiles of ORF1a proteins of VR2385 were similar to those of LV and LDV. The 5' half of the proteins (first 1100 aa in VR2385) were mostly hydrophilic, the extreme 3' end (aa 2230–2399 in VR2385) was hydrophilic and the 3' half of the protein contains 4 hydrophobic regions (129–1207 aa, 1240–1286 aa, 1478–1643 aa and 1846–2076 regions of VR2385).

The VR2385 ORF1b is 4389 nucleotides long and it extends from nucleotide 7369 to 11757 (excluding stop codon TGA), and encoded a 1463 aa protein. Comparison of the nucleotide and predicted amino acid sequences of VR2385 ORF1b with those of LV, LDV and EAV confirmed that ORF1b is more conserved than ORF1a. Nucleotide and amino acid homology between VR2385 and LV was 64 and 67% in ORF1b and 58 and 53% in ORF1a, respectively. Comparison of the predicted proteins of VR2385 and EAV showed a 36% homology. The predicted ORF1b protein of VR2385 contains a putative polymerase domain (amino acids 373–576), a putative zinc finger domain (amino acid 647–689), and an RNA helicase domain (amino acids 793–1015) similar to those described for LV, LDV, EAV and coronaviruses.

Molecular characterization of ORF1 regions of coronaviruses and arteriviruses showed that the ORF1 polyprotein is expressed through two overlapping ORFs, ORF1a and ORF1b. The expression of ORF1b, which overlaps with ORF1a in −1 frame, takes place through a so-called ribosomal frameshifting mechanism which allows the ribosome to bypass the ORF1a stop codon and translate ORF1b-encoded protein. The frameshift region consists of a "slippery sequence" followed by pseudoknot structure. Analysis of the ORF1a/ORF1b junction region of VR2385 indicated that the potential slippery sequence (5'-UUUAAAC-3') is located 3 nucleotides upstream of the stop codon of ORF1a and the proposed pseudoknot structure. This region is very conserved in corona- and arteriviruses and the nucleotide sequence homology in this region between VR2385 and LV was 86%.

Figure 24:
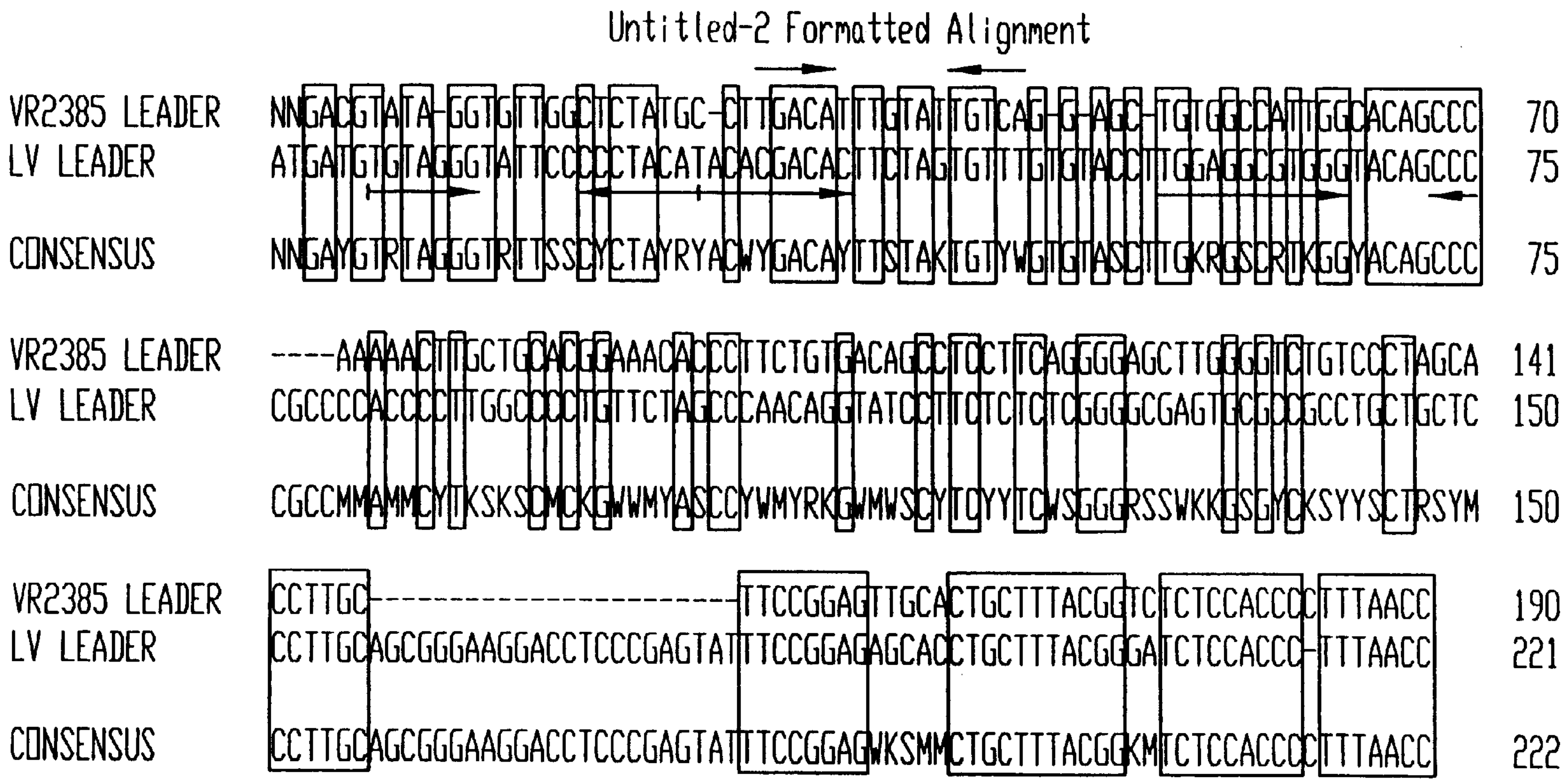
FIG. 24 shows the DNA alignment of the leader sequence of VR 2385 (SEQ ID NO:56) and LV (SEQ ID NO:57).

Comparison of the leader sequences of VR2385 and LV indicated that these two viruses diverged from each other by point mutations and possibly through recombination. The extensive sequence differences in the leader sequences of these two viruses indicated the leader that sequence in PRRSV is not conserved, and is subject to extensive mutational changes. The most conserved region in the leader was the last 44 nucleotides at the 3' end, where nucleotide sequence acid identity was 86% between VR2385 and LV, and 68% between VR2385 and LDV. The putative leader sequence of VR2385 was 190 nt, which is 31 nt shorter than that of LV, and 35 nt longer than that of LDV. As shown in FIG. 24, there is a 20 nt deletion in the VR2385 leader (located after nucleotide 145) compared to the leader sequence of the LV. Comparison of the leader sequences of VR2385 and LDV indicates that the highest homology score was obtained when a 20 nt gap was introduced into the corresponding region of the leader sequence of LDV (FIG. 24). Similarly, the highest homology score was obtained when a 50 nt gap was introduced into the LDV leader during alignment of the LV and LDV leader sequences. This result suggests that this region of the leader is not critical for virus replication, and deletions may occur in this region of the leader during virus evolution. This observation also could explain the observed differences in the length leader sequences among VR 2385, LV and LDV.

EXAMPLE 8

Characterization of the Leader Sequence and Leader-body Junction Sites in Subgenomic mRNAs of PRRSV VR 2385

In order to determine the complete leader sequence of PRRSV VR2385, several approaches were utilized including screening of oligo dT cDNA library with leader-specific $^{32}$P-labeled PCR probe, RNA ligation of the viral RNA (RNA circularization) with T4 RNA ligase followed by RT-PCR with ORF7 and leader specific primers, and direct sequencing of the 5' end of viral RNA (Example 7). First, a 100 b.p. fragment of leader sequence was used as a probe to detect cDNA clones containing the leader sequence from an oligo dT λ library. Eight cDNA clones were analyzed and sequenced, and these clones were found to represent leader sequences of mRNAs 7 (5 clones), 6 (2 clones) and 2 (1 clone). The size of leader sequence varied from 160 to 163 nucleotides in 6 of the 7 clones. In one of the clones which represents mRNA6, the leader specific sequence was 172 nucleotides. It is possible that strong secondary structure within the leader of the virus prevented complete cDNA synthesis of the leader RNA during the construction of the λ Zap library. In a second experiment, the 3' and 5' ends of viral RNA were ligated head to tail by using T4 RNA ligase. After phenol chloroform extraction and precipitation, the ligated RNA was subjected to an RT-PCR reaction with primers IM1003 (antisense oligonucleotide, complementary to the 3' end of the leader sequence) and IM1004 (oligonucleotide, corresponding to a segment of the 3' non-coding region of the genome, 100 nucleotides upstream of the poly(A) tail). A diffuse band of the PCR products with sizes ranging from 250 to 350 nucleotides was purified from agarose gel, and cloned into the pSK+ vector. Seven independent clones were sequenced. Sequence analysis indicated that the polyA sequence at the 3' end of the genome and the leader sequence at the 5' end of the genome were ligated together in all 7 clones, but only 95–96 nucleotides from the 3' end of the leader sequence were ligated with 3' end of the viral genome. The sizes of the polyA sequenced clones varied in each clone ranging from 9 to 42 nucleotides, indicating that sequenced clones were independent. The putative full-length leader sequence of VR2385 was determined by direct RNA sequencing of the 5'-end of virion RNA isolated from sucrose gradient purified virus (Example 7).

Leader mRNA Junction Sequences and Intergenic Regions within the Genome of VR2385

In order to characterize leader body junction regions of sg RNAs of the VR2385 strain, RT-PCR was performed with leader specific primer and primers, specific for each sg mRNA. Total RNAs isolated at 20 hours post infection (h.p.i.) were used for RT-PCR. The predominant bands were isolated from agarose gel, cloned and sequenced. Direct sequencing of the PCR products was also performed. In order to identify leader body junction region in the genome of the PRRSV, a leader specific $^{32}$P-labeled probe was used to screen a random cDNA library generated from viral RNA, and several clones containing leader-ORF1a junction regions were isolated and sequenced. The leader body junction regions of sg mRNAs 2 to 7 were characterized.

Table 10 summarizes the leader-body junction regions of all sg mRNAs and their corresponding regions in the virus genome. Only a single junction site was detected for sg mRNAs 2, 3, and 6, whereas two sites were detected for sg mRNAs 4, 5 and 7, designated as 4a, 4b, 5a, 5b and 7a, 7b. The leader genome junction region in VR2385 was represented by a sequence CCACCCCTTTAACC (SEQ ID NO:175).

TABLE 10

Sequence of the Leader-body Junction Regions of Subgenomic mRNAs of VR2385

| RNA | SEQUENCE | | N of clones |
|---|---|---|---|
| 5'-leader | CCACCCCTTTAACC | (SEQ ID NO:149) | 4 |
| mRNA2 | CCACCCCttgaacc | (SEQ ID NO:150) | 3 |
| genome | cctgtcattgaacc | (SEQ ID NO:151) | |
| mRNA3 | CCACCCCtgtaacc | (SEQ ID NO:152) | 2 |
| | CCACCCCTTtaacc | (SEQ ID NO:153) | 1 |
| genome | ggtcaaatgtaacc | (SEQ ID NO:154) | |
| mRNA4b | CCACCCCTttgacc | (SEQ ID NO:155) | 1 |
| genome | aaggccacttgacc | (SEQ ID NO:156) | |
| mRNA4b | CCACCCCtttcacc | (SEQ ID NO:157) | 2 |
| | CCACCCCgtttcacc | (SEQ ID NO:158) | 1 |
| genome | caattggtttcacc | (SEQ ID NO:159) | |
| mRNA5.a | CCACCCcgtcaact | (SEQ ID NO:160) | 1 |
| genome | agtgtgcgtcaact | (SEQ ID NO:161) | |
| mRNA5.b | CCACCCCtttagcc | (SEQ ID NO:162) | 2 |
| | CCACCCCttttagcc | (SEQ ID NO:163) | 1 |
| genome | caactgttttagcc | (SEQ ID NO:164) | |
| mRNA6 | CCACCCCTgtaacc | (SEQ ID NO:165) | 3 |
| | CCACCCCTTtaacc | (SEQ ID NO:166) | 1 |
| genome | ctacccctgtaacc | (SEQ ID NO:167) | |
| mRNA7.a | CCACCCCTTtaacc | (SEQ ID NO:168) | 5 |
| | CCACCCCTataacc | (SEQ ID NO:169) | 1 |
| genome | ggcaaatgataacc | (SEQ ID NO:170) | |
| mRNA7.b | CCACCCCCTtaaacc | (SEQ ID NO:171) | 1 |
| genome | agggagtggtaaacc | (SEQ ID NO:172) | |

The Leader Body mRNAs Junction Regions Varied in sg mRNAs 3, 4, 5b, 6 and 7a

Table 11 compares the intergenic regions in genomes of VR2385, LV, LDV and EAV. The intergenic regions of VR2385, LV and LDV are very similar. Most variations were found in the first three nucleotides of these regions, whereas the last four nucleotides are conserved and in most regions are represented by the sequence AACC. Variations were also found in the first two nucleotides of this junction sequence (GACC and CACC in the intergenic region of ORF4 of VR2385, AGCC in the intergenic region of ORF5b of VR2385, GACC in the intergenic region of ORF3 in LV, and ACC in the intergenic region of ORF2 of LDV). The intergenic region for sg mRNA5a of VR2385 is GUCAACU, which is similar to that of EAV.

TABLE 11

Sequence of the 3' end of the leader in the genome (RNA1) and junction sites of subgenomic mRNAs 2 to 7 of VR2385, LV, LDV and EAV.

| RNA | VR2385 | LV | LDV | EAV |
|---|---|---|---|---|
| 1 | UUUAACC | UUUAACC | UAUAACC | AUCAACU |
| 2 | UUGAACC | GUAAACC | UAU-ACC | UUCAACU |
| 3.1 | UGUAACC | GUUGACC | UGUAACC | GUCAA-U |
| 3.2 | | | | AUCAACU |
| 3.3 | | | | AU-AAUU |
| 4a | CUUGACC | | | |
| 4b | UUUCACC | UUCAACC | UGUAACC | GUCAACU |
| 5.a | GUCAACU | | | |
| 5.b | UUUAGCC | UACAACC | UAUAACC | GUCAACU |
| 6 | UAUAACC | CUCAACC | UAAAACC | GUCAACC |
| 7.a | GAUAACC | | | |
| 7.b | GUAAACC | GUUAACC | CCUAACC | CUCAACU |

Figure 26:
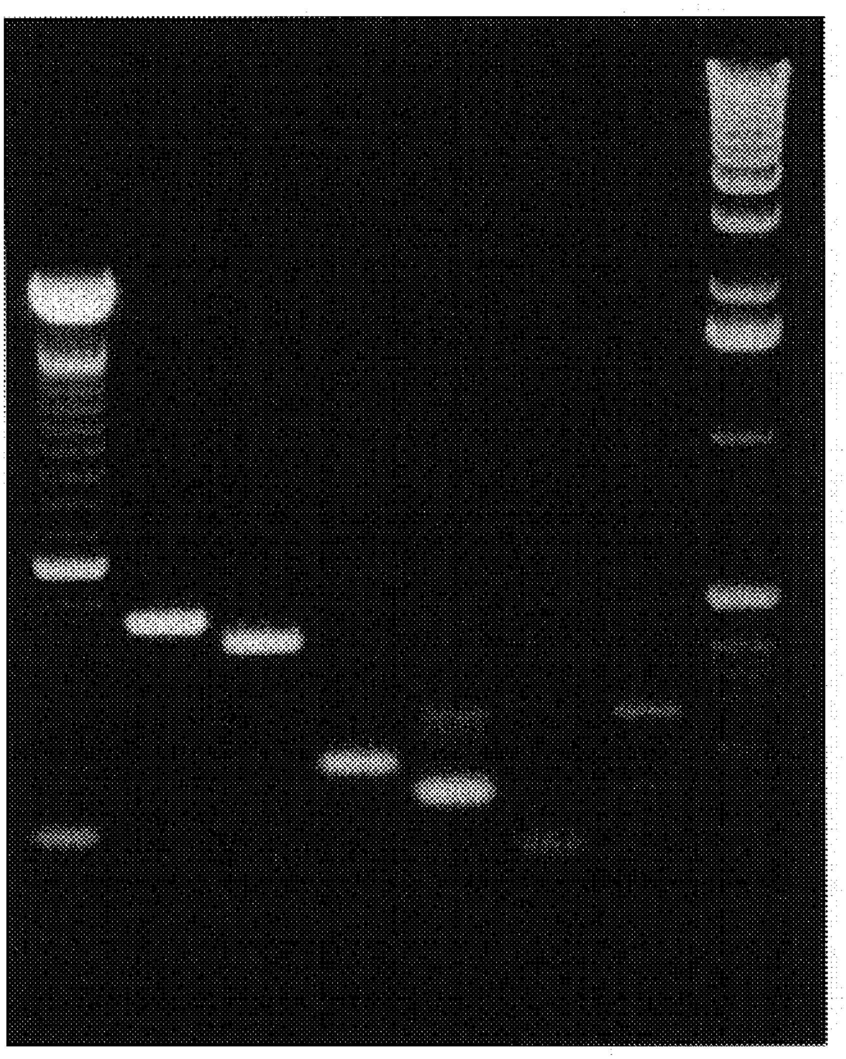

The positions of intergenic sites upstream of the start codon of the corresponding ORFs vary from 4 to 231 nucleotides. Table 12 compares the location of intergenic sites in the genomes of VR2385 and LV (numbers represents distance in nucleotides between the intergenic site and AUG start codon of the corresponding ORF.) The locations of these sites in the genome of VR2385 and LV differ in sg mRNAs 3, 4, 5 and 6. Three alternative intergenic sites for the synthesis of sg mRNAs 4,5 and 7 of VR2385 genome were also identified. Previously, that only six bands of sg mRNAs were detected in the cells infected with VR2385 by Northern blot hybridization analysis. To confirm that the additional sg mRNAs are actually synthesized during the replication of VR2385, a nested RT-PCR was performed by using leader and ORF specific primers. The amplified PCR products were similar in sizes corresponding to additional mRNAs 4a 5a and 7a (FIG. 26). The results indicated that the intergenic sites 4b and 5b of sg mRNAs 4 and 5 which is located closer to the start codon of the corresponding ORF were frequently used in sg mRNA synthesis. The sg mRNAs 4 and 5 were predominantly generated from intergenic sites 4b and 5b while only a minor population was generated by using alternative sites 4a and 5a. In the case of sg mRNA7 the integenic site 7a located 123 nt upstream of start codon of ORF7 was frequently used, whereas site 7b located 9 nt upstream of start codon of ORF7 was less involved in sg mRNA7 synthesis.

TABLE 12

Location of the intergenic sites inside of the genome of VR2385 and LV.

| RNA | Position of the junction site VR2385 | LV |
|---|---|---|
| RNA2 | 20 | 38 |
| RNA3 | 83 | 11 |
| RNA4 | 231 & 4 | 83 |
| RNA5 | 157 & 40 | 32 |
| RNA6 | 17 | 24 |
| RNA7 | 123 & 9 | 9 |

Comparison of the leader genome junction sequence with sequences of the intergenic regions and sequences of leader body junction regions in sg mRNAs indicated that only the last seven nucleotides of leader (TTTAACC) possess homology with the sequences of the intergenic regions in the genome of VR2385. The overall homology varies from 5 to 7 nt, and the only exception was sg mRNA6 where 11 out of 12 nt in the intergenic region are similar to the 3' end of the leader sequence. In the leader body junction regions of the sg mRNA, the CCACCCC sequence is conserved and generated from leader. The sequence following CCACCCC, however, varied for different sg mRNAs, but has a high level of homology with the TTTAACC sequence at the 3' end of the leader. The variations in the leader body junction sequences detected for different sg mRNAs indicates that leader body joining is imprecise. Nucleotide sequence comparisons between the 3' end of the leader, leader body junction regions of the sg mRNAs and intergenic regions within the genome of VR2385 allowed detection of regions of actual joining between leader and body of sg mRNA (Table II, underlined).

Conclusions

The mechanism of subgenomic mRNA synthesis of U.S. isolates of PRRSV is similar to that of LV, LDV and EAV. Intergenic regions detected in VR2385 were more variable and were located at different sites when compared to LV. Variations in leader body junction sequences indicate that leader body joining is imprecise. The locations of actual leader body joining sites in sg mRNAs suggest that mechanism(s) other than leader priming may be involved in the synthesis of sg mRNAs. Alternative leader-body junction sites in the genomes of U.S. isolates of PRRSV can result in the variation of the number of sg mRNA among different strains of PRRSV.

EXAMPLE 9

The following provides a reliable test for the identification and differentiation of high passage ISU55 strain of PRRSV from field isolates of PRRSV. In previous studies the sequence of the low passage ISU55 strain (passage 7) was determined and this sequence was used to develop an RFLP test for differentiation of ISU55 hp strain. As a first step, the sequence of ISU55 p-7 was analyzed to identify variable regions containing unique restriction sites. After computer sequence analysis and comparison with sequences of different PRRSV strains, a specific region containing two unique restriction sites was identified at the 3' end of ORF4. These two restriction sites were DraI (TTT/AAA) at position 1510 and BalI (MscI) (TGG/CCA) at position 1697 relative to the location upstream of the ATG start codon of ORF2 in ISU55 (p-7) sequence. These two restriction sites were present only in the corresponding region of ISU55 strain but not in the other PRRSV strains.

Figure 28A:
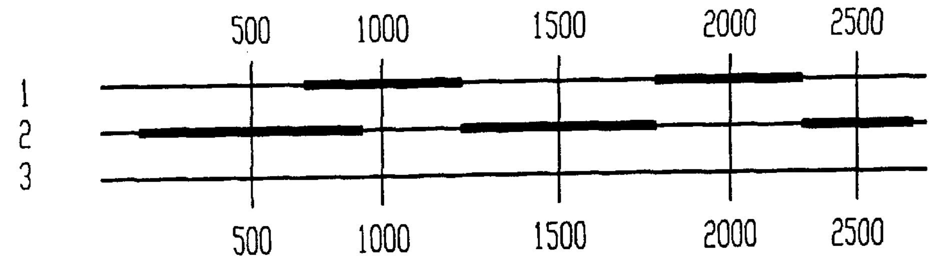
FIG. 28 shows the ORF maps of ISU-55 high passage and low passage strains.
Figure 28B:
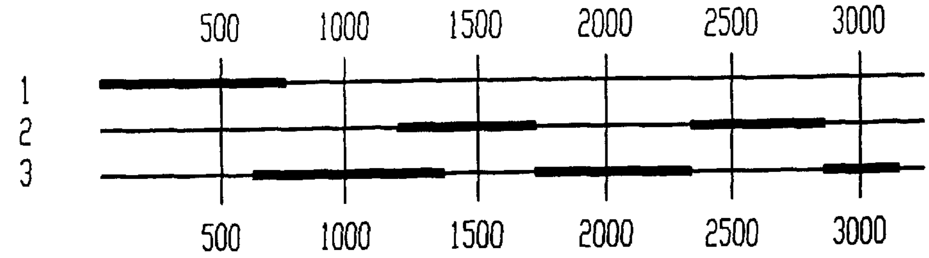

In order to confirm the results of the computer analysis, the sequence of high passage ISU55 strain was determined. The genomic region including ORFs 3 to 7 (2696 b.p.) was amplified by PCR and sequenced. The sequence of high passage ISU55 (SEQ ID NO:65) was compared with that of the ISU55 passage 7 (SEQ ID NO:64). The results of this comparison are shown in FIG. 27 (cDNA alignment), FIG. 28 (ORF maps) and FIG. 29 (restriction pattern with restriction enzymes DraI and BalI). The sequences of the low passage and high passage of PRRSV ISU55 were very conserved. There were only 15 nucleotide substitutions in high passage ISU55 strain. The sizes and relative positions of ORFs 3 to 7 remain the same. A single nucleotide change in the high passage virus created an additional DraI site in the sequence of the high passage virus compared to the low passage ISU55 (FIG. 29). This finding affords an opportunity to distinguish the high passage virus from the low passage ISU55 virus. A BLAST search was conducted to compare specific regions of ISU55 high passage strain with other PRRSV sequences available in the GenBank database. The 237 b.p. fragment including the unique restriction sites of ISU 55 high passage strain (two DraI sites at position 966 and 1159 and BalI site at position 1157, restriction map of ISU55 hp.) was used as the template for comparison. The results of the BLAST search indicated that these sites are unique for ISU55 high passage strain and are not present in 24 other PRRSV isolates available in the database.

The ORF5 (603 bp.) of ISU55 high passage strain was also compared with the ORF5 of other PRRSV strains. As expected, ISU55 passage 7 strain has the highest homology score and there are only 3 nucleotide substitutions. The strain with the second highest homology score was NADC8 which has 33 nucleotide substitutions in ORF5 compared to the ORF5 of ISU55 hp strain. The rest of PRRSV strains compared in the BLAST search displayed more variations (up to 63 nt changes) in the ORF5. These-data clearly indicate that ISU55 PRRSV strain is different from all other PRRSV strains characterized so far.

Figure 30:
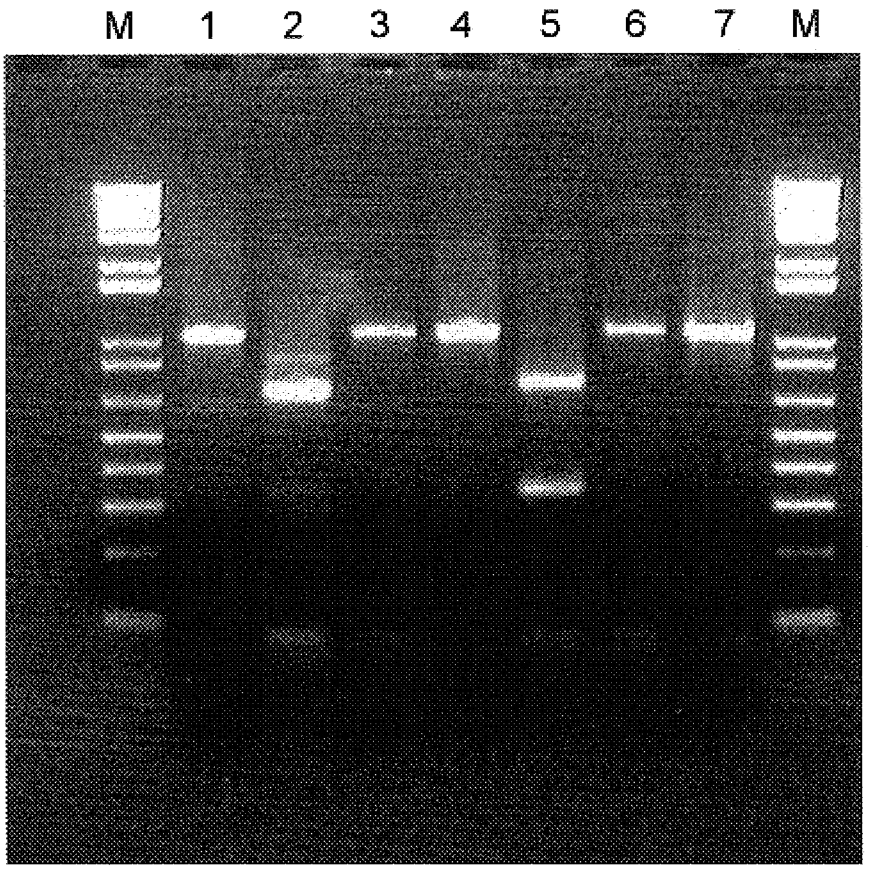
FIG. 30 shows the results of a RFLP test on total RNA isolated from ISU-55 hp, ISU-12 lp and ISU-12hp strains and used in RT PCR with primers 55F and 3RFLP.

A PCR-RFLP was developed to differentiate ISU55 high passage strain from ISU55 lp virus and other strains of PRRSV. For the RFLP test two primers were synthesized: forward primer 55F 5'-CGTACGGCGATAGGGACACC-3' (SEQ ID NO:173) (pos. 823) and reverse primer 3RFLP 5'-GGCATATATCATCACTGGCG-3' (SEQ ID NO:174) (pos. 1838) (positions from the 5' end of 2696 bp. sequenced fragment of ISU55 high passage strain). The reverse primer for the PCR-RFLP test was the same as the one used in a PCR-RFLP test to differentiate MLV ResPRRSV vaccine strain since this primer has been used in the PCR-RFLP with a large number of PRRSV isolates and shown to be specific (Wesley et al, J. Vet. Diagn. Invest., 10:140–144 (1998); Wesley et al, Amer. Assoc. Of Swine Practitioners, pp. 141–143 (1996); Andreyev et al, Arch. Virol., 142:993–1001 (1997); Mengeling et al, 1997, all of which are incorporated herein by reference in their entireties). These two primers amplify a 1026 bp cDNA fragment of PRRSV ISU55 high passage strain. After digestion with restriction enzyme with DraI three fragments (626 bp, 187 bp and 135 bp) will be generated. After digestion with BalI, two fragments with sizes 626 and 322 bp will be formed. After PCR and restriction enzyme digestions of other PRRSV strains, a 1026 bp fragment will be formed according to the analysis of computer data. To validate the PCR-RFLP test, total RNA was isolated from ISU55 hp, ISU12 lp, ISU12 hp strains and subjected to RT-PCR with primers 55F and 3RFLP. A 1026 bp fragment was amplified from all the isolates. These fragments were purified and digested with restriction enzymes DraI and BalI. The resulting products were analyzed in 1.5% agarose gel. FIG. 30 shows the results of the test. Line one shows an untreated 1026 bp PCR fragment of ISU5 hp strain. Line 2 and 5 shows PCR products of ISU55 hp digested with DraI (line 2) and BalI (line 5). The 626 bp, 187 bp and 135 bp fragments were formed after digestion with DraI, and 626 and 322 bp. fragments were formed after digestion with BalI. Lines 3, 4, 6, and 7 show results of DraI digestion (lines 3 and 4) and BalI digestion (lines 6 and 7) of PCR products of ISU12 lp (lines 3 and 6) and ISU12 hp (lines 4 and 7) strains. In all reactions with ISU12 lp and hp strains a PCR fragment of 1026 bp was detected. These data correlate with the predictions for the PCR-RFLP differentiation test for the ISU55 hp strain.

Obviously, numerous modifications and variations of the present invention are possible in light of the above teachings. It is therefore to be understood that within the scope of the appended claims, the invention may be practiced otherwise than as specifically described herein.

EXAMPLE 10

Sequencing of the Genome of the attenuated PRRSV Vaccine Strain (ISU55 p49)

Figure 31:
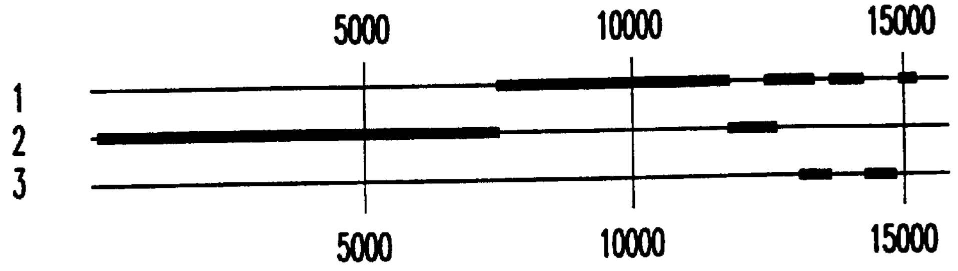

After the sequence of VR2385 strain was determined, generated sequencing information was used in order to determine sequence of the attenuated vaccine PRRSV strain (Vaccine Strain). The entire genome of Vaccine Strain was amplified in 21 overlapping fragments and sequenced. When sequencing data were combined, the entire size of the genome was 15,412 nucleotides, which is 309 nt longer compared to the length of the genome of VR2385 strain. The ORFs map and their locations are shown on FIG. 31. Genome comparison of Vaccine Strain and VR2385 strains showed the same sizes and relative locations of the ORFs 1b through ORF7. The ORF1a was the most variable and one 309 nucleotides deletion was found in the genome of VR2385 compared to the sequence of Vaccine Strain. This deletion was in frame and located in the region of ORF1a at position 3242 nucleotide from the 5' end of genome of VR2385 PRRSV. Another three nucleotides were deleted in the region 2504–2515 nt of the genome causing 1 aa deletion compare to the genome of Vaccine Strain. Results of genome comparison of different ORFs of Vaccine Strain and VR2385 strain are summarized in the Table 13. Overall DNA homology between these strains was about 91% with 14094 nucleotides identical in both strains. Not including 309 nt deletion DNA homology was 93%. Leader sequence was determined only for VR2385 strain by direct sequencing of the viral RNA and 17 bp primer 15 specific for 5' end of the leader of VR2385 was used to amplify 170 nt portion of the leader of Vaccine Strain. Comparison of these sequences showed overall homology of 94% with single nucleotides deletions in both strains: nucleotides A (pos. 75) and G (pos. 119) of VR2385 leader are missing in the leader of Vaccine Strain, and nucleotides A (pos. 87) and G (pos. 124) of Vaccine Strain leader are missing in the leader of VR385 strain.

The ORF1a in the Vaccine Strain extends from nts 191 to 7699 and encodes 2503 amino acid (aa) protein, which is 103 aa longer compare to the ORF 1a protein of VR2385 strain. Overall aa identity in between ORF1a predicted proteins of the Vaccine Strain and VR2385 was 88% (92% not including deletion in VR2385). Comparison with ORF1a protein of LV showed approximately 47% of aa identity overall, but several regions with different protein similarity can be identified. Relatively conservative 5' end (aa 1 to 529 in Vaccine Strain and aa 1 to 521 in LV, 50% aa identity), relatively conservative 3' end (aa 1232 to 2503 in Vaccine Strain and aa 1115 to 2396 in LV, 58% aa identity), and hypervariable region (HVR) in between (aa 530 to 1231 in Vaccine Strain and aa 522 to 1114 in LV, aa identity less than 40%). When we studied homology in HVR in more details, we were able to detect one short region (94 aa), where aa homology was 50% between Vaccine Strain and LV. This region extends from aa 1015 to 1108 in the Vaccine Strain and aa 929 to 1021 in LV. Interestingly, in exception of the first four aa (ITRK) this region was deleted in VR2385 strain. To summarize, homology in the ORF 1a predicted protein can be presented as follows: conservative region 1 (aa 1 to 529 in the vaccine Strain/VR2385 strain, aa 1 to 521 in LV, 90% a identity between Vaccine Strain and VR2385, 50% aa identity between Vaccine/VR2385 strains and LV), hypervariable region (HVR) (aa 530 to 1231 in the Vaccine Strain, aa 520 to 1127 in the VR2385 strain, aa 522 to 1232 in LV, 84% aa identity between Vaccine Strain and VR2385, 103 aa deletion in the ORF 1a protein of VR2385, less then 40% aa identity between Vaccine/VR2385 strains and LV), and conservative region 2 (aa 1232 to 2503 in the Vaccine Strain, aa 1128 to 2399 in the VR2385 strain, aa 1128 to 2396 in LV, 96% aa identity between Vaccine Strain and 57% aa identity between Vaccine/VR2385 strains and LV). The 94 amino acid fragment (aa 929 to 1021) in the HVR of the Vaccine Strain posses 50% aa homology with LV, and this region is deleted in VR2385 strain.

The ORF 1b in the Vaccine Strain extends from nts 7687 to 12069 and encodes 1461 aa protein, which is similar in size to that of VR2385. Nucleotide and amino acid comparison showed, that ORF1b is much more conservative compare to ORF1a. Nucleotide homology between Vaccine Strain and VR2388 was 93%, with 97% homology of their predicted proteins. Comparison with ORF1b of LV (1462 aa) showed 67% of aa identity. One variable region was detected at the 3' end of ORF1b (aa 1367–1461) compare to LV.

The ORF2 to ORF7 region of the vaccine strain showed similar genome organization to that of VR2385, with similar sizes and relative locations of the ORFs. Data of homology comparison between Vaccine Strain and VR2385 are presented in the Table 13, Nucleotide (amino acid) identity of Vaccine Strain with LV was 66% (61%) for ORF2, 61% (55%) for ORF3, 66% (67%) for ORF4, 63% (51%) for ORF5, 68% (79%) for ORF6, and 60% (58%) for ORF7.

TABLE 13

Comparison of the ORFs and DNA homology between VR2385 p8, ISU55 p49 (Vaccine Strain) and LV

| | Size of the ORF (nucleotides) | | | Homology with VR2385 mt (aa) | |
|---|---|---|---|---|---|
| ORF | VR2385 | ISU55 | LV | ISU55 | LV |
| 1a | 7197 | 7509 | 7188 | 89 (88) | |
| 1b | 4383 | 4383 | 4386 | 93 (97) | 64 (67) |
| 2 | 768 | 768 | 747 | 97 (95) | 65 (60) |
| 3 | 762 | 762 | 795 | 94 (95) | 64 (55) |
| 4 | 534 | 534 | 549 | 96 (97) | 66 (66) |
| 5 | 600 | 600 | 603 | 93 (90) | 63 (54) |
| 6 | 522 | 522 | 519 | 97 (98) | 68 (78) |
| 7 | 369 | 369 | 384 | 96 (94) | 60 (57) |

EXAMPLE 11

Analysis of Deletions in VR 2385 Isolates

A PCR product amplified from VR 2385 PRRSV showed the presence of a 445 bp deletion in the ORF1a. The 445 bp deletion, as well as the 309 bp deletion noted above, were in frame, overlapped and appeared to of independent origin. It was assumed that after plaque purification these deletion variants appeared in the population of VR2385 and the variant with the 445 nt deletion became predominant in the virus stock. This variant appears to be stable based on PCR studies of RNA isolated from low passage virus, high passage virus and from virus passed twice through pig. The 309 bp deletion variant appeared to be minor and could be amplified from some virus stocks with specific primers only by nested PCR.

EXAMPLE 12

Characterization of Serially Passaged PRRSV

To determine if attenuation occurs due to cell culture passage, VR 2385 passage 7 (p7) and VR 2385 passage 85 (p85) were used to infect 3 week-old pigs. At 10 days post-infection, estimated gross lung lesions and clinical respiratory scores were significantly higher in the pigs infected with the lower passage virus. The ORF 2–7 region of the genome was sequenced and compared. Genetic analysis of the two passages of VR 2385 shows that ORF 6 was the most conserved, with 100% homology at the amino acid level. The remaining ORFs showed amino acid homology of 95–98%, with ORF2 of VR 2385 p85 containing a premature stop codon resulting in a putative 10 amino acid truncation.

What is claimed is:

1. An isolated DNA sequence encoding a porcine reproductive and respiratory syndrome virus (PRRSV) consisting of SEQ ID NO:54 (ISU-55).

2. An isolated DNA sequence comprising nucleotides 191–7699 of SEQ ID NO:54 (ORF 1a), nucleotides 7687–12069 of SEQ ID NO:54 (ORF 1b), nucleotides 12074–12841 of SEQ ID NO:54 (ORF 2), nucleotides 12692–13458 of SEQ ID NO:54 (ORF 3), nucleotides 13212–13775 of SEQ ID NO:54 (ORF 4), nucleotides 13789–14388 of SEQ ID NO:54 (ORF 5), nucleotides 14376–14592 of SEQ ID NO:54 (ORF 6)) or nucleotides 14890–15258 of SEQ ID NO:54 (ORF 7).

3. A polypeptide encoded by the isolated DNA sequence of claim 2.

4. A composition for inducing antibodies against PRRSV comprising one or more polypeptides encoded by the isolated DNA sequences of claim 2.

5. The composition of claim 4 further comprising an adjuvant.

6. A composition for inducing antibodies against PRRSV comprising a PRRSV encoded by SEQ ID NO:54 (ISU-55), and a physiologically acceptable carrier.

7. The composition of claim 6, wherein said composition reduces lung lesions in five-week-old colostrum-deprived, caesarean-derived pigs by a statistically significant amount wherein said amount is significant a p value less than 0.01, relative to lung lesions in uninoculated five-week-old colostrum-deprived, caesarean-derived pigs.

8. The composition of claim 6 further comprising an adjuvant.

9. A method of protecting a pig from a porcine reproductive and respiratory disease, comprising administering an effective amount of the composition of claim 6 to a pig in need of protection against said disease.

10. The method of claim 9, wherein said effective amount is administered orally or parenterally.

11. The method of claim 9, wherein said effective amount is administered intramuscularly, intradermally, intravenously, intraperitoneally, subcutaneously or intranasally.

12. An isolated DNA sequence comprising nucleotides 12692–13458 of SEQ ID NO:54 (ORF 3), nucleotides 13212–13775 of SEQ ID NO:54 (ORF 4), or nucleotides 13789–14388 of SEQ ID NO:54 (ORF 5).

13. A polypeptide encoded by the isolated DNA sequence of claim 12.

14. A composition for inducing antibodies against PRRSV comprising one or more polypeptides encoded by the isolated DNA sequences of claim 12.

15. The composition of claim 14, wherein said composition reduces lung lesions in five-week-old colostrum-deprived, caesarean-derived pigs by a statistically significant amount wherein said amount is significant a p value less than 0.01, relative to lung lesions in uninoculated five-week-old colostrum-deprived, caesarean-derived pigs.

16. The composition of claim 14 further comprising an adjuvant.

17. A method of protecting a pig from a porcine reproductive and respiratory disease, comprising administering an effective amount of the composition of claim 14 to a pig in need of protection against said disease.

18. The method of claim 17, wherein said effective amount is administered orally or parenterally.

19. The method of claim 17, wherein said effective amount is administered intramuscularly, intradermally, intravenously, intraperitoneally, subcutaneously or intranasally.

20. An isolated DNA sequence comprising nucleotides 14376–14592 of SEQ ID NO:54 (ORF 6) or nucleotides 14890–15258 of SEQ ID NO:54 (ORF 7).

21. A polypeptide encoded by the isolated DNA sequence of claim 20.

22. A composition for inducing antibodies against PRRSV comprising one or more polypeptides encoded by the isolated DNA sequence of claim 20.

23. The composition of claim 22 further comprising an adjuvant.

24. An isolated DNA sequence comprising nucleotides 12074–12841 of SEQ ID NO:54 (ORF 2).

25. A polypeptide encoded by the isolated DNA sequence of claim 24.

26. A composition for inducing antibodies against PRRSV comprising one or more polypeptides encoded by the isolated DNA sequences of claim 24.

27. The composition of claim 26 further comprising an adjuvant.

* * * * *

SEQUENCE LISTING

```
<160> NUMBER OF SEQ ID NOS: 175

<210> SEQ ID NO 1
<211> LENGTH: 2352
<212> TYPE: DNA
<213> ORGANISM: Porcine reproductive and respiratory syndrome virus

<400> SEQUENCE: 1

cctgtcattg aaccaacttt aggcctgaat tgagatgaaa tggggtctat gcaaagcctt      60

tttgacaaaa ttggccaact ttttgtggat gctttcacgg agttcttggt gtccattgtt     120

gatatcatta tatttttggc cattttgttt ggcttcacca tcgcaggttg gctggtggtc     180

ttttgcatca gattggtttg ctccgcgata ctccgtgcgc gccctgccat tcactctgag     240

caattacaga agatcctatg aggcctttct ctctcagtgc caggtggaca ttcccacctg     300

gggaactaaa catcctttgg ggatgctttg gcaccataag gtgtcaaccc tgattgatga     360

aatggtgtcg cgtcgaatgt accgcatcat ggaaaaagca ggacaggctg cctggaaaca     420

ggtagtgagc gaggctacgc tgtctcgcat tagtagtttg gatgtggtgg ctcattttca     480

gcatcttgcc gccattgaag ccgagacctg taaatatctg gcctctcggc tgcccatgct     540

acaccacctg cgcatgacag ggtcaaatgt aaccatagtg tataatagta ctttgaatca     600

ggtgtttgct gttttcccaa cccctggttc ccggccaaag cttcatgatt tccagcaatg     660

gctaatagct gtacattcct ctatattttc ctctgttgca gcttcttgta ctcttttttgt    720

tgtgctgtgg ttgcgggttc caatgctacg tactgttttt ggtttccgct ggttaggggc     780

aatttttctt tcgaactcac ggtgaattac acggtgtgcc cgccttgcct cacccggcaa     840

gcagccgcag aggcctacga acccggcagg tcccttttggt gcaggatagg gcatgatcga    900

tgtggggagg acgatcatga tgaactaggg tttgtggtgc cgtctggcct ctccagcgaa     960
```

-continued ggccacttga ccagtgctta cgcctggttg gcgtccctgt ccttcagcta tacggcccag 1020
ttccatcccg agatattcgg gatagggaat gtgagtcgag tctatgttga catcaagcac 1080
caattcattt gcgctgttca tgatgggcag aacaccacct tgccccacca tgacaacatt 1140
tcagccgtgc ttcagaccta ttaccagcat caggtcgacg ggggcaattg gtttcaccta 1200
gaatgggtgc gtcccttctt ttcctcttgg ttggttttaa atgtctcttg gtttctcagg 1260
cgttcgcctg caagccatgt ttcagttcga gtctttcaga catcaagacc aacaccaccg 1320
cagcggcagg ctttgctgtc ctccaagaca tcagttgcct taggcatcgc aactcggcct 1380
ctgaggcgat tcgcaaagtc cctcagtgcc gcacggcgat agggacaccc gtgtatatca 1440
ctgtcacagc caatgttacc gatgagaatt atttgcattc ctctgatctt ctcatgcttt 1500
cttcttgcct tttctatgct tctgagatga gtgaaaaggg atttaaggtg gtatttggca 1560
atgtgtcagg catcgtggca gtgtgcgtca acttcaccag ttacgtccaa catgtcaagg 1620
aatttaccca acgttccttg gtagttgacc atgtgcggct gctccatttc atgacgcccg 1680
agaccatgag gtgggcaact gttttagcct gtctttttac cattctgttg gcaatttgaa 1740
tgtttaagta tgttggggaa atgcttgacc gcgggctgtt gctcgcaatt gcttttttta 1800
tggtgtatcg tgccgtcttg ttttgttgcg ctcgtcagcg ccaacgggaa cagcggctca 1860
aatttacagc tgatttacaa cttgacgcta tgtgagctga atggcacaga ttggctagct 1920
aataaatttg actgggcagt ggagtgtttt gtcatttttc ctgtgttgac tcacattgtc 1980
tcttatggtg ccctcactac tagccatttc cttgacacag tcggtctggt cactgtgtct 2040
accgctgggt ttgttcacgg gcggtatgtt ctgagtagca tgtacgcggt ctgtgccctg 2100
gctgcgttga tttgcttcgt cattaggctt gcgaagaatt gcatgtcctg gcgctactca 2160
tgtaccagat ataccaactt tcttctggac actaagggca gactctatcg ttggcggtcg 2220
cctgtcatca tagagaaaag gggcaaagtt gaggtcgaag gtcacctgat cgacctcaaa 2280
agagttgtgc ttgatggttc cgcggctacc cctgtaacca gagtttcagc ggaacaatgg 2340
agtcgtcctt ag 2352

<210> SEQ ID NO 2
<211> LENGTH: 2349
<212> TYPE: DNA
<213> ORGANISM: Porcine reproductive and respiratory syndrome virus

<400> SEQUENCE: 2
cctatcattg aaccaacttt gggtctagac tgaaatgcaa tggggtccat gcaaagcctt 60
tttgacaaga tcggtcaact ttttgtggat gctttcacgg agttcttggt gtccattgtt 120
gatatcatca tatttttggc cattttgttt ggcttcacca ttgccggctg gctggtggtc 180
ttttgcatca gattggtttg ctccgcgata ctccgtgcgc gccctgccat tcaccctgag 240
caattacaga agatcctatg aggcctttct ttctcagtgc caggtggaca ttcccgcctg 300
gggaacaaga catcctttag ggatgctttg gcaccacaag gtgtcaaccc tgattgatga 360
aatggtgtcg cgtcgaatgt accgcatcat ggaaaaagca ggacaggctg cctggaaaca 420
ggtggtgagt gaggctacgc tgtctcgcat tagtggtttg gatgtggtgg cccattttca 480
gcaccttgcc gccattgaag ccgagacttg taaatatttg gcctctcggt tgcccatgct 540
acacaacctg cgtattacag ggtcaaatgt aaccatagtg cataatagta ctttgaatca 600
ggtgtttgct attttcccaa cccccggttc tcggccaaag ctccatgatt ttcagcaatg 660

-continued

```
gctaatagct gtacattcct cgatatcctc ctctgttgca gcttcttgta ctctttttgt    720
tgtgttgtgg ttacggatgc caatgctacg ttctgttttt ggtttccgct ggttaggggc    780
aatttttcct tcgagctcat ggtgaattac acggtgtgcc caccttgcct cacccggcaa    840
gcagccgcac agatctacga acccaacagg tctctttggt gcaggatcgg gaatgatcga    900
tgtggtgagg acgatcacga cgaactagga tttacagtac cgcctggcct ctccaaagaa    960
gtccatttga ccagtgttta cgcctggttg gcgtttctgt ccttcagtaa cacggcccag   1020
tttcatcccg agatattcgg aatagggaat gtgagtaagg tctatgttga catcaatcat   1080
caactcattt gtgctgttca tgacgggcag aacaccacct tgcctcgcca tgacaacatt   1140
tctgccgtgt ttcagaccta ttaccaacac caagtcgatg gtggcaactg gtttcaccta   1200
gaatggctgc gtcccttctt ttcctcttgg ttggttttga atgtctcctg gtttctcagg   1260
cgttcgcctg caagccatgt ttcagttcga gtctttcaga catcaagacc aacaccaccg   1320
cggcagcaaa tttcgctgtc ctccaggaca tcggctgcct taggcatggc aactcgacca   1380
ctgaggcgtt tcgcaaaatc cctcagtgcc gcacggcgat agggacaccc gtgtatatca   1440
ctatcacagc caatgtaaca gatgagaact atttgcattc ttctgatctt ctcatgcttt   1500
cctcttgcct ttctacgct tctgagatga gtgaaaaggg gtttaaggtg gtgtttggca   1560
atgtgtcagg caccgtggct gtgtgcatca attttaccag ctatgtccaa cacgtcaagg   1620
agtttaccca acgctcctta gtggtcgacc atgtgcggct gctccatttc atgacacctg   1680
aaactatgag gtgggcaact gttttagcct gtcttttcgc cattctgttg gcaatttgaa   1740
tgtttaagta tgttggggaa atgcttgacc gcgggctgtt gctcgcgatc gctttttttg   1800
tggtgtatcg tgccgttctg tcttgctgcg ctcgtcagcg ccaacaacag cagctcccat   1860
ttacagttga tttataacct gacgctatgt gagctgaatg gcacagactg gctggctaat   1920
aaatttgatt gggcagtgga gagttttgtc atctttcccg tgttgactca cattgtttcc   1980
tatggtgcac tcaccaccag ccatttcctt gacacagtcg gtctggttac tgtgtctacc   2040
gccgggtttc atcacgggcg gtatgttctg agtagcatct acgcggtctg tgccctggct   2100
gcgtttattt gcttcgtcat taggtttgcg aagaactgca tgtcctggcg ctactcttgt   2160
accagatata ccaacttcct tctggacact aagggcagcc tctatcgttg gcggtcacct   2220
gtcatcatag agaaaggggg taaggttgag gtcgaaggtc atctgatcga cctaaaaaaa   2280
gttgtgcttg atggttccgc ggcaacccct ttaaccagag tttcagcgga acaatggggt   2340
cgtccctag                                                           2349
```

<210> SEQ ID NO 3
<211> LENGTH: 2352
<212> TYPE: DNA
<213> ORGANISM: Porcine reproductive and respiratory syndrome virus

<400> SEQUENCE: 3

```
cctatcattg aaccaacttt aggcctgaat tgaaatgaaa tggggtctat gcaaagcctt     60
tttgacaaaa ttggccaact tttcgtggat gctttcacgg agttcttggt gtccattgtt    120
gatatcatta tatttttggc cattttgttt ggcttcacca tcgccggttg gctggtggtc    180
ttttgcatca gattggtttg ctccgcgata ctccgtgcgc gccctgccat tcactctgag    240
caattacaga agatcctatg aggcctttct ttctcagtgc caggtggaca ttcccacctg    300
gggaattaaa catcctttgg ggatgctttg gcaccataag gtgtcaaccc tgattgatga    360
aatggtgtcg cgtcgaatgt accgcatcat ggaaaaagca ggacaggctg cctggaaaca    420
```

-continued

```
ggtggtgagc gaggctacgc tgtctcgcat tagtagtttg gatgtggtgg ctcactttca    480
gcatcttgcc gccattgaag ccgagacctg taaatatttg gcctctcggc tgcccatgct    540
acacaacctg cgcatgacag ggtcaaatgt aaccatagtg tataatagta ctttgaatca    600
ggtgcttgct attttcccaa cccctggttc ccggccaaag cttcatgatt ttcagcaatg    660
gctaatagct gtacattcct ctatattttc ctctgttgca gcttcttgta ctctttttgt    720
tgtgctgtgg ttgcgggttc caatgctacg tattgctttt ggtttccgct ggttaggggc    780
aatttttctt tcgaactcac agtgaactac acggtgtgtc caccttgcct cacccggcaa    840
gcagccacag aggcctacga acctggcagg tctctttggt gcaggatagg gtatgatcgc    900
tgtggggagg acgatcatga tgaactaggg tttgtggtgc cgtctggcct ctccagcgaa    960
ggccacttga ccagtgttta cgcctggttg gcgttcctgt ctttcagtta cacagcccag   1020
ttccatcctg agatattcgg gatagggaat gtgagtcaag tttatgttga catcaggcat   1080
caattcattt gcgccgttca cgacgggcag aacgccactt tgcctcgcca tgacaatatt   1140
tcagccgtgt tccagactta ttaccaacat caagtcgacg gcggcaattg gtttcaccta   1200
gaatggctgc gtcccttctt ttcctcttgg ttggttttaa atgtctcttg gtttctcagg   1260
cgttcgcctg caagccatgt ttcagttcga gtcttgcaga cattaagacc aacaccaccg   1320
cagcggcagg ctttgctgtc ctccaagaca tcagttgcct taggtatcgc aactcggcct   1380
ctgaggcgtt tcgcaaaatc cctcagtgtc gtacggcgat agggacaccc atgtatatta   1440
ctgtcacagc caatgtaacc gatgagaatt atttgcattc ctctgacctt ctcatgcttt   1500
cttcttgcct tttctacgct tctgagatga gtgaaaaggg atttaaagtg gtatttggca   1560
atgtgtcagg catcgtggct gtgtgcgtca actttaccag ctacgtccaa catgtcaagg   1620
aatttaccca acgctccttg gtagtcgacc atgtgcggct gctccatttc atgacacctg   1680
agaccatgag gtgggcaact gttttagcct gtctttttgc cattctgttg gccatttgaa   1740
tgtttaagta tgttggggaa atgcttgacc gcgggctatt gctcgtcatt gctttttttg   1800
tggtgtatcg tgccgtcttg gtttgttgcg ctcgccagcg ccaacagcag caacagctct   1860
catttacagt tgatttataa cttgacgcta tgtgagctga atggcacaga ttggttagct   1920
ggtgaatttg actgggcagt ggagtgtttt gtcatttttc ctgtgttgac tcacattgtc   1980
tcctatggtg ccctcaccac cagccatttc cttgacacag tcggtctggt cactgtgtct   2040
accgccggct tttcccacgg gcggtatgtt ctgagtagca tctacgcggt ctgtgccctg   2100
gctgcgttga tttgcttcgt cattaggttt acgaagaatt gcatgtcctg gcgctactca   2160
tgtaccagat ataccaactt tcttctggac actaagggca gactctatcg ttggcggtcg   2220
cctgtcatca tagagaaaag gggtaaagtt gaggtcgaag gtcatctgat cgacctcaag   2280
agagttgtgc ttgatggttc cgcggcaacc cctataacca aagtttcagc ggagcaatgg   2340
ggtcgtcctt ag                                                       2352
```

<210> SEQ ID NO 4
<211> LENGTH: 2351
<212> TYPE: DNA
<213> ORGANISM: Porcine reproductive and respiratory syndrome virus

<400> SEQUENCE: 4

```
cctgtcattg aaccaacttt aggcctgaat tgaaatgaaa tgggggccat gcaaagcctt     60
tttgacaaaa ttggccaact tttgtggat gctttcacgg agttcttggt gtccattgtt    120
```

-continued

```
gatatcatta tatttttggc cattttgttt ggcttcacca tcgccggttg gctggtggtc    180
ttttgcatca gattggtttg ctccgcgata ctccgtgcgc gccctgccat tcactctgag    240
caattacaga agatcttatg aggcctttct ttcccagtgc caagtggaca ttcccacctg    300
gggaactaaa catcctttgg ggatgttgtg gcaccataag gtgtcaaccc tgattgatga    360
aatggtgtcg cgtcgaatgt accgcatcat ggaaaaagca gggcaggctg cctggaaaca    420
ggtggtgagc gaggctacgc tgtctcgcat tagtagtttg gatgtggtgg ctcattttca    480
gcatcttgct gccattgaag ccgagacctg taaatatttg gcctcccggc tgcccatgct    540
acacaacctg cgcatgacag ggtcaaatgt aaccatagtg tataatagta ctttgaatca    600
ggtgtttgct attttcccaa cccctggttc ccggccaaag cttcatgatt ttcagcaatg    660
gttaatagct gtacattcct ccatattttc ctctgttgca gcttcctgta ctctttttgt    720
tgtgctgtgg ttgcgggttc caatactacg ttctgttttt ggtttccgct ggttaggggc    780
aatttttctt tcgagctcac ggtgaattac acggtgtgtc caccttgcct cacccggcaa    840
gcagccgcag agatctacga acccggtagg tctctttggt gcaggatagg gtatgaccga    900
tgtggggagg acgatcatga cgagctaggg tttatggtac cacctggctt ctccagcgaa    960
ggccacttga ctagtgttta cgcctggttg gcgtttttgt ccttcagcta cacggcccag   1020
ttccatcccg agatattcgg gatagggaac gtgagtcgag tttatgttga catcaaacat   1080
caactcatct gcgccgaaca tgacgggcaa aacaccacct tgcctcgtca tgacaacatt   1140
tcagccgtgt ttcagaccta ttaccaacat caagtcgacg gtggcaattg gtttcaccta   1200
gaatggcttc gtcccttctt ttcctcatgg ttggttttaa atgtctcttg gtttctcagg   1260
cgttcgcctg caaaccatgt ttcagttcga gtcttgcaga tattaagacc aacaccaccg   1320
cagcggcaag ctttgctgtc ctccaagaca tcggttgcct taggcatcgc gactcggcct   1380
ctgaggcgat tcgcaaaatc cctcagtgcc gtacggcgat agggacaccc gtgtatatta   1440
ccatcacagc caatgtgaac gatgagaatt atttacattc ttctgatctc ctcatgcttt   1500
cttcttgcct tttctatgct tctgagatga gtgaaaaggg gtttaaggtg gtatttggca   1560
atgtgtcagg catcgtggct gtgtgtgtca attttaccag ctatgtccaa catgtcaggg   1620
agtttaccca acgctccttg gtggtcgacc atgtgcggtt gctccatttc atgacacctg   1680
agaccatgag gtgggcaact gttttagcct gtctttttgc cattctgttg gcaatttgaa   1740
tgtttaagca tgttggggaa atgcttgacc gcgggctgtt gctcgcgatt gctttctttg   1800
tggtttatcg tgccgttctg ttttgctgtg ctcgccagcg ccagcaacag cagcagctcc   1860
catctacagt tgatttataa cttgacgcta tgtgagctga atggcacaga ttggttagct   1920
aataaatttg attgggcagt ggagagtttt gtcatctttc ccgttttgac tcacattgtc   1980
tcctatggtg ccctcactac cagccatttc cttgacacag tcgctttagt cactgtgtct   2040
accgccgggt ttgttcacgg gcggtatgtc ctgagtagca tctacgcggt ctgtgccctg   2100
gctgcgttga cttgcttcat catcaggttt gcaaagaatt gcatgtcctg gcgctactcg   2160
tgtaccagat ataccaactt tctcctggac actaagggca gactctatcg ttggcggtcg   2220
cctgtcatca tagagaaaag gggcaaagtt gaggtcgaag gtcactgatc gacctcaaaa   2280
gagttgtgct tgatggttcc gtggcaaccc ctataaccag agattcagcg gaacaatggg   2340
gtcgtcctta g                                                         2351
```

<210> SEQ ID NO 5
<211> LENGTH: 1947

-continued

<212> TYPE: DNA
<213> ORGANISM: Porcine reproductive and respiratory syndrome virus

<400> SEQUENCE: 5

```
cctgtcattg aaccaacttt aggcctgaat tgaaatgaaa tggggtccat gcaaagcctt     60
tttgacaaaa ttggccaact ttttgtggat gctttcacgg agttcttggt gtccattgtt    120
gatatcatta tattcttggc cattttgttt ggcttcacca tcgccggttg gctggtggtc    180
ttttgcatca gattggtttg ctccgcgata ctccgtacgc gccctgccat tcactctgag    240
caattacaga agatcttatg aggcctttct ttcccagtgc caagtggaca ttcccacctg    300
gggaactaaa catcctttgg ggatgttttg gcaccataag gtgtcaaccc tgattgatga    360
gatggtgtcg cgtcgaatgt accgcatcat ggaaaaagca ggacaggctg cctggaaaca    420
ggtggtgagc gaggctacgc tgtctcgcat tagtagtttg gatgtggtgg ctcattttca    480
gcatcttgcc gccatcgaag ccgagacctg taaatatttg gcctcccggc tgcccatgct    540
acacaacctg cgcatgacag ggtcaaatgt aaccatagtg tataatagta ctttgaatcg    600
ggtgtttgct attttcccaa cccctggttc ccggccaaag cttcatgact ttcagcaatg    660
gctaatagct gtgcattcct ccatattttc ctctgttgca gcttcttgta ctctctttgt    720
tgtgctgtgg ttgcgggttc caatactacg tactgttttt ggtttccgct ggttaggggc    780
aatttttctt tcgaactcat agtgaattac acggtgtgcc caccttgcct cacccggcaa    840
gcagccgcag aggcctacga acccggtagg tctctttggt gcaggatagg gtacgatcga    900
tgtggagagg acgaccatga cgagctaggg tttatgatac cgtctggcct ctccagcgaa    960
ggccacttga ccagtctgag gcgattcgca aaatccctca gtgccgtacg gcgataggga   1020
cacctatgta tattaccatc acagccaatg tgacagatga aaattattta cattcttctg   1080
atctcctcat gctctcttct tgccttttct atgcttctga gatgagtgaa aagggatttg   1140
aggtggtttt tggcaatgtg tcaggcatcg tggctgtgtg tgtcaatttt accagctacg   1200
ttcaacatgt cagggagttt acccaacgct ccttgatggt cgaccatgtg cggctgctcc   1260
atttcatgac acctgagacc atgaggtggg caaccgtttt agcctgtctt tttgctattc   1320
tgttggcaat ttgaatgttt aagtatgttg gggaaatgct tgaccgtggg ctgttgctcg   1380
cgattgcttt ctttgtggtg tatcgtgccg ttctgtttta ctgtgctcgc cgacgcccac   1440
agcaacagca gctctcatct gcaattgatt tacaacttga cgctatgtga gctgaatggc   1500
acagattggc tagctgatag atttgattgg gcagtggaga gctttgtcat ctttcctgtt   1560
ttgactcaca ttgtctccta tggcgccctc accaccagcc atttccttga cacaattgct   1620
ttagtcactg tgtctaccgc cgggtttgtt cacgggcggt atgtcctaag tagcatctac   1680
gcggtctgtg ccctggctgc gttgacttgc ttcgtcatta ggtttgtgaa gaattgcatg   1740
tcctggcgct actcatgtac tagatatacc aactttcttc tggatactaa gggcagactc   1800
tatcgttggc ggtcgcctgt catcatagag aagaggggca aagttgaggt cgaaggtcat   1860
ctgatcgatc tcaaaagagt tgtgcttgat ggttccgtgg caacccctat aaccagagtt   1920
tcagcggaac aatggggtcg tccttag                                       1947
```

<210> SEQ ID NO 6
<211> LENGTH: 2352
<212> TYPE: DNA
<213> ORGANISM: Porcine reproductive and respiratory syndrome virus

<400> SEQUENCE: 6

-continued

```
cctgtcattg aaccaacttt aggcctgaat tgagatgaaa tggggtctat gcaaagcctt      60
tttgacaaaa ttggccaact ttttgtggat gctttcacgg agttcttggt gtccattgtt     120
gatatcatta tatttttggc cattttgttt ggcttcacca tcgcaggttg gctggtggtc     180
ttttgcatca gattggtttg ctccgcgata ctccgtgcgc gccctgccat tcactctgag     240
caattacaga agatcctatg aggcctttct ctctcagtgc caggtggaca ttcccacctg     300
gggaactaaa catcctttgg ggatgctttg gcaccataag gtgtcaaccc tgattgatga     360
aatggtgtcg cgtcgaatgt accgcatcat ggaaaaagca ggacaggctg cctggaaaca     420
ggtagtgagc gaggctacgc tgtctcgcat tagtagtttg gatgtggtgg ctcattttca     480
gcatcttgcc gccattgaag ccgagacctg taaatatctg gcctctcggc tgcccatgct     540
acaccacctg cgcatgacag ggtcaaatgt aaccatagtg tataatagta ctttgaatca     600
ggtgtttgct gttttcccaa cccctggttc ccggccaaag cttcatgatt tccagcaatg     660
gctaatagct gtacattcct ctatattttc ctctgttgca gcttcttgta ctctttttgt     720
tgtgctgtgg ttgcgggttc caatgctacg tactgttttt ggtttccgct ggttaggggc     780
aatttttctt tcgaactcac ggtgaattac acggtgtgcc cgccttgcct cacccggcaa     840
gcagccgcag aggcctacga acccggcagg tccctttggt gcaggatagg gcatgatcga     900
tgtggggagg acgatcatga tgaactaggg tttgtggtgc cgtctggcct ctccagcgaa     960
ggccacttga ccagtgctta cgcctggttg gcgtccctgt ccttcagcta tacggcccag    1020
ttccatcccg agatattcgg gatagggaat gtgagtcgag tctatgttga catcaagcac    1080
caattcattt gcgctgttca tgatgggcag aacaccacct tgccccacca tgacaacatt    1140
tcagccgtgc ttcagaccta ttaccagcat caggtcgacg ggggcaattg gtttcaccta    1200
gaatgggtgc gtcccttctt ttcctcttgg ttggttttaa atgtctcttg gtttctcagg    1260
cgttcgcctg caagccatgt ttcagttcga gtctttcaga catcaagacc aacaccaccg    1320
cagcggcagg ctttgctgtc ctccaagaca tcagttgcct taggcatcgc aactcggcct    1380
ctgaggcgat tcgcaaagtc cctcagtgcc gcacggcgat agggacaccc gtgtatatca    1440
ctgtcacagc caatgttacc gatgagaatt atttgcattc ctctgatctt ctcatgcttt    1500
cttcttgcct tttctatgct tctgagatga gtgaaaaggg atttaaggtg gtatttggca    1560
atgtgtcagg catcgtggca gtgtgcgtca acttcaccag ttacgtccaa catgtcaagg    1620
aatttaccca acgttccttg gtagttgacc atgtgcggct gctccatttc atgacgcccg    1680
agaccatgag gtgggcaact gttttagcct gtctttttac cattctgttg gcaatttgaa    1740
tgtttaagta tgttggggaa atgcttgacc gcgggctgtt gctcgcaatt gcttttttta    1800
tggtgtatcg tgccgtcttg ttttgttgcg ctcgtcagcg ccaacgggaa cagcggctca    1860
aatttacagc tgatttacaa cttgacgcta tgtgagctga atggcacaga ttggctagct    1920
aataaatttg actgggcagt ggagtgtttt gtcatttttc ctgtgttgac tcacattgtc    1980
tcttatggtg ccctcactac tagccatttc cttgacacag tcggtctggt cactgtgtct    2040
accgctgggt ttgttcacgg gcggtatgtt ctgagtagca tgtacgcggt ctgtgccctg    2100
gctgcgttga tttgcttcgt cattaggctt gcgaagaatt gcatgtcctg gcgctactca    2160
tgtaccagat ataccaactt tcttctggac actaagggca gactctatcg ttggcggtcg    2220
cctgtcatca tagagaaaag gggcaaagtt gaggtcgaag gtcacctgat cgacctcaaa    2280
agagttgtgc ttgatggttc cgcggctacc cctgtaacca gagtttcagc ggaacaatgg    2340
agtcgtcctt ag                                                        2352
```

-continued

<210> SEQ ID NO 7
<211> LENGTH: 2352
<212> TYPE: DNA
<213> ORGANISM: Porcine reproductive and respiratory syndrome virus

<400> SEQUENCE: 7
cccgtcattg aaccaacttt aggcctgaat tgaaatgaaa tggggtccgt gcaaagcctt 60
tttgacaaaa ttggccaact ttttgtggat gctttcacgg agttcctggt gtccattgtt 120
gatatcatca tatttttggc cattttgttt ggcttcacca tcgccggttg gctggtggtc 180
ttttgcatca gattggtttg ctccgcgata ctccgtacgc gccctgccat tcactctgag 240
caattacaga agatcttatg aggccttttt atcccagtgc caagtggaca ttcccacctg 300
gggaactaaa catcctttgg ggatgttttg gcaccataag gtgtcaaccc tgattgatga 360
aatggtgtcg cgtcgcatgt accgcatcat ggaaaaagca gggcaggctg cctggaaaca 420
ggtggtgagc gaggctacgc tgtcccgcat tagtagtttg gatgtggtgg ctcattttca 480
gcatcttgcc gccattgaag ccgagacttg taaatatttg gcctcccggc tgcccatgct 540
acataacctg cgcataacag ggtcaaatgt aaccatagtg tataatagta cttcggagca 600
ggtgtttgct attttcccaa cccctggttc ccggccaaag cttcatgatt ttcagcaatg 660
gttaatagct gtacattcct ccatattttc ctctgttgca gcttcttgta ctctttttgt 720
tgtgctgtgg ctgcgggttc caatgctacg tactgttttt ggtttccgct ggttaggggg 780
aatttttcct tcgaactcat ggtgaattac acggtgtgtc caccttgcct cacccggcaa 840
gcagccgcag aggtctacga acccggtagg tctctttggt gcaggatagg gtatgaccga 900
tgtggggagg acgatcatga cgagctaggg tttatgatac cgcctggcct ctccagcgaa 960
ggccacttga ctagtgttta cgcctggttg gcgtttttgt ccttcagcta cacggcccag 1020
ttccatcccg agatattcgg gatagggaat gtgagtcgag tttatgttga catcaaacat 1080
caactcattt gcgccgaaca tgacggacag aacgccacct tgcctcgtca tgacaatatt 1140
tcagccgtgt ttcagaccta ttaccaacat caagtcgatg gcggcaattg gtttcaccta 1200
gaatggcttc gtcccttctt ttcctcatgg ttggttttaa atgtctcttg gtatctcagg 1260
cgttcgcctg caaaccatgc ttcagttcga gtcttgcaga tattaagacc aacactaccg 1320
cagcggcaag ctttgctgtc ctccaagaca tcagttgcct taggcatcgc aactcggcct 1380
ctgaggcgat tcgcaaaatc cctcagtgcc gtacggcgat agggacaccc gtgtatatta 1440
ccatcacagc caatgtgaca gatgagaatt atttacattc ttctgatctc ctcatgcttt 1500
cttcttgcct tttctacgct tctgagatga gtgaaaaagg attcaaggtg gtatttggca 1560
atgtgtcagg catcgtggct gtgtgtgtca attttaccag ctacgtccaa catgtcaggg 1620
agtttaccca acgctccctg gtggtcgacc atgtgcggtt gctccatttc atgacacctg 1680
aaaccatgag gtgggcaact gttttagcct gtctttttgc cattctgctg gcaatttgaa 1740
tgtttaagta tgttggggaa atgcttgacc gcgggctgtt gctcgcgatt gctttctttg 1800
tggtgtatcg tgccgttctg ttttgctgtg ctcgccaacg ccagcgccaa cagcagctcc 1860
catctacagc tgatttacaa cttgacgcta tgtgagctga atggcacaga ttggctagct 1920
gataaatttg attgggcagt ggagagtttt gtcatctttc ccgttttgac tcacattgtc 1980
tcctatggtg ccctcactac tagccatctc cttgacacag tcgccttagt cactgtgtct 2040
accgccgggt ttgttcacgg gcggtatgtc ctaagtagca tctacgcggt ctgtgccctg 2100

-continued

```
gctgcgttag cttgcttcgt cattaggttt gcaaagaatt gcatgtcctg gcgctattcg   2160

tgtaccagat ataccaactt tcttctggac actaagggca gactctatcg ttggcattcg   2220

cctgtcatca tagagaaaag gggcaaagtt gaggtcgaag gtcatctgat cgacctcaaa   2280

agagttgtgc ttgacggttc cgtggcaacc cctataacca gagtttcagc ggaacaatgg   2340

ggtcgtcctt ag                                                       2352
```

<210> SEQ ID NO 8
<211> LENGTH: 256
<212> TYPE: PRT
<213> ORGANISM: Porcine reproductive and respiratory syndrome virus

<400> SEQUENCE: 8

```
Met Lys Trp Gly Leu Cys Lys Ala Phe Leu Thr Lys Leu Ala Asn Phe
  1               5                  10                  15

Leu Trp Met Leu Ser Arg Ser Ser Trp Cys Pro Leu Leu Ile Ser Leu
             20                  25                  30

Tyr Phe Trp Pro Phe Cys Leu Ala Ser Pro Ser Gln Val Gly Trp Trp
         35                  40                  45

Ser Phe Ala Ser Asp Trp Phe Ala Pro Arg Tyr Ser Val Arg Ala Leu
     50                  55                  60

Pro Phe Thr Leu Ser Asn Tyr Arg Arg Ser Tyr Glu Ala Phe Leu Ser
 65                  70                  75                  80

Gln Cys Gln Val Asp Ile Pro Thr Trp Gly Thr Lys His Pro Leu Gly
                 85                  90                  95

Met Leu Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Met Leu Arg Met Thr Gly
                165                 170                 175

Ser Asn Val Thr Ile Val Tyr Asn Ser Thr Leu Asn Gln Val Phe Ala
            180                 185                 190

Val Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Met Leu Arg Thr
225                 230                 235                 240

Val Phe Gly Phe Arg Trp Leu Gly Ala Ile Phe Leu Ser Asn Ser Arg
                245                 250                 255
```

<210> SEQ ID NO 9
<211> LENGTH: 256
<212> TYPE: PRT
<213> ORGANISM: Porcine reproductive and respiratory syndrome virus

<400> SEQUENCE: 9

```
Met Lys Trp Gly Pro Cys Lys Ala Phe Leu Thr Lys Leu Ala Asn Phe
  1               5                  10                  15

Leu Trp Met Leu Ser Arg Ser Ser Trp Cys Pro Leu Leu Ile Ser Leu
             20                  25                  30
```

-continued

Tyr Phe Trp Pro Phe Cys Leu Ala Ser Pro Ser Pro Val Gly Trp Trp
35 40 45

Ser Phe Ala Ser Asp Trp Phe Ala Pro Arg Tyr Ser Val Arg Ala Leu
50 55 60

Pro Phe Thr Leu Ser Asn Tyr Arg Arg Ser Tyr Glu Ala Phe Leu Ser
65 70 75 80

Gln Cys Gln Val Asp Ile Pro Thr Trp Gly Thr Lys His Pro Leu Gly
85 90 95

Met Leu Trp His His Lys Val Ser Thr Leu Ile Asp Glu Met Val Ser
100 105 110

Arg Arg Met Tyr Arg Ile Met Glu Lys Ala Gly Gln Ala Ala Trp Lys
115 120 125

Gln Val Val Ser Glu Ala Thr Leu Ser Arg Ile Ser Ser Leu Asp Val
130 135 140

Val Ala His Phe Gln His Leu Ala Ala Ile Glu Ala Glu Thr Cys Lys
145 150 155 160

Tyr Leu Ala Ser Arg Leu Pro Met Leu His Asn Leu Arg Met Thr Gly
165 170 175

Ser Asn Val Thr Ile Val Tyr Asn Ser Thr Leu Asn Gln Val Phe Ala
180 185 190

Ile Phe Pro Thr Pro Gly Ser Arg Pro Lys Leu His Asp Phe Gln Gln
195 200 205

Trp Leu Ile Ala Val His Ser Ser Ile Phe Ser Ser Val Ala Ala Ser
210 215 220

Cys Thr Leu Phe Val Val Leu Trp Leu Arg Val Pro Ile Leu Arg Ser
225 230 235 240

Val Phe Gly Phe Arg Trp Leu Gly Ala Ile Phe Leu Ser Ser Ser Arg
245 250 255

<210> SEQ ID NO 10
<211> LENGTH: 255
<212> TYPE: PRT
<213> ORGANISM: Porcine reproductive and respiratory syndrome virus

<400> SEQUENCE: 10

Met Lys Trp Gly Pro Cys Lys Ala Phe Leu Thr Lys Leu Ala Asn Phe
1 5 10 15

Leu Trp Met Leu Ser Arg Ser Ser Trp Cys Pro Leu Leu Ile Ser Leu
20 25 30

Ser Phe Trp Pro Phe Cys Leu Ala Ser Pro Ser Pro Val Gly Trp Trp
35 40 45

Ser Phe Ala Ser Asp Trp Phe Ala Pro Arg Tyr Ser Val Arg Ala Leu
50 55 60

Pro Phe Thr Leu Ser Asn Tyr Arg Arg Ser Tyr Glu Ala Phe Leu Ser
65 70 75 80

Gln Cys Gln Val Asp Ile Pro Thr Trp Gly Thr Lys His Pro Leu Gly
85 90 95

Met Phe Trp His His Lys Val Ser Thr Leu Ile Asp Glu Met Val Ser
100 105 110

Arg Arg Met Tyr Arg Ile Met Glu Lys Ala Gly Gln Ala Ala Trp Lys
115 120 125

Gln Val Val Ser Glu Ala Thr Leu Ser Arg Ile Ser Ser Leu Asp Val
130 135 140

Val Ala His Phe Gln His Leu Ala Ala Ile Glu Ala Glu Thr Cys Lys

-continued

```
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu Asn Arg Val Phe Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Ile Leu Arg Thr
225                 230                 235                 240

Val Phe Gly Phe Arg Trp Leu Gly Ala Ile Phe Leu Ser Asn Ser
                245                 250                 255


<210> SEQ ID NO 11
<211> LENGTH: 256
<212> TYPE: PRT
<213> ORGANISM: Porcine reproductive and respiratory syndrome virus

<400> SEQUENCE: 11

Met Lys Trp Gly Leu Cys Lys Ala Phe Leu Thr Lys Leu Ala Asn Phe
  1               5                  10                  15

Ser Trp Met Leu Ser Arg Ser Ser Trp Cys Pro Leu Leu Ile Ser Leu
            20                  25                  30

Tyr Phe Trp Pro Phe Cys Leu Ala Ser Pro Ser Pro Val Gly Trp Trp
        35                  40                  45

Ser Phe Ala Ser Asp Trp Phe Ala Pro Arg Tyr Ser Val Arg Ala Leu
     50                  55                  60

Pro Phe Thr Leu Ser Asn Tyr Arg Arg Ser Tyr Glu Ala Phe Leu Ser
 65                  70                  75                  80

Gln Cys Gln Val Asp Ile Pro Thr Trp Gly Ile Lys His Pro Leu Gly
                 85                  90                  95

Met Phe Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu Asn Gln Val Leu Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Met Leu Arg Ile
225                 230                 235                 240

Ala Phe Gly Phe Arg Trp Leu Gly Ala Ile Phe Leu Ser Asn Ser Gln
                245                 250                 255


<210> SEQ ID NO 12
<211> LENGTH: 256
```

-continued

<212> TYPE: PRT
<213> ORGANISM: Porcine reproductive and respiratory syndrome virus

<400> SEQUENCE: 12

```
Met Lys Trp Gly Pro Cys Lys Ala Phe Leu Thr Lys Leu Ala Asn Phe
  1               5                  10                  15

Leu Trp Met Leu Ser Arg Ser Ser Trp Cys Pro Leu Leu Ile Ser Ser
             20                  25                  30

Tyr Phe Trp Pro Phe Cys Leu Ala Ser Pro Ser Pro Val Gly Trp Trp
         35                  40                  45

Ser Phe Ala Ser Asp Trp Phe Ala Pro Arg Tyr Ser Val Arg Ala Leu
     50                  55                  60

Pro Phe Thr Leu Ser Asn Tyr Arg Arg Ser Tyr Glu Ala Phe Leu Ser
 65                  70                  75                  80

Gln Cys Gln Val Asp Ile Pro Thr Trp Gly Thr Lys His Pro Leu Gly
                 85                  90                  95

Met Phe Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Ile Thr Gly
                165                 170                 175

Ser Asn Val Thr Ile Val Tyr Asn Ser Thr Ser Glu Gln Val Phe Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Met Leu Arg Thr
225                 230                 235                 240

Val Phe Gly Phe Arg Trp Leu Gly Gly Ile Phe Pro Ser Asn Ser Trp
                245                 250                 255
```

<210> SEQ ID NO 13
<211> LENGTH: 256
<212> TYPE: PRT
<213> ORGANISM: Porcine reproductive and respiratory syndrome virus

<400> SEQUENCE: 13

```
Met Gln Trp Gly Pro Cys Lys Ala Phe Leu Thr Arg Ser Val Asn Phe
  1               5                  10                  15

Leu Trp Met Leu Ser Arg Ser Ser Trp Cys Pro Leu Leu Ile Ser Ser
             20                  25                  30

Tyr Phe Trp Pro Phe Cys Leu Ala Ser Pro Leu Pro Ala Gly Trp Trp
         35                  40                  45

Ser Phe Ala Ser Asp Trp Phe Ala Pro Arg Tyr Ser Val Arg Ala Leu
     50                  55                  60

Pro Phe Thr Leu Ser Asn Tyr Arg Arg Ser Tyr Glu Ala Phe Leu Ser
 65                  70                  75                  80

Gln Cys Gln Val Asp Ile Pro Ala Trp Gly Thr Arg His Pro Leu Gly
                 85                  90                  95
```

-continued

```
Met Leu Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Gly Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Ile Thr Gly
                165                 170                 175

Ser Asn Val Thr Ile Val His Asn Ser Thr Leu Asn Gln Val Phe Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Ser Ser Ser Val Ala Ala Ser
    210                 215                 220

Cys Thr Leu Phe Val Val Leu Trp Leu Arg Met Pro Met Leu Arg Ser
225                 230                 235                 240

Val Phe Gly Phe Arg Trp Leu Gly Ala Ile Phe Pro Ser Ser Ser Trp
                245                 250                 255


<210> SEQ ID NO 14
<211> LENGTH: 256
<212> TYPE: PRT
<213> ORGANISM: Porcine reproductive and respiratory syndrome virus

<400> SEQUENCE: 14

Met Lys Trp Gly Pro Cys Lys Ala Phe Leu Thr Lys Leu Ala Asn Phe
  1               5                  10                  15

Leu Trp Met Leu Ser Arg Ser Ser Trp Cys Pro Leu Leu Ile Ser Leu
            20                  25                  30

Tyr Phe Trp Pro Phe Cys Leu Ala Ser Pro Ser Pro Val Gly Trp Trp
        35                  40                  45

Ser Phe Ala Ser Asp Trp Phe Ala Pro Arg Tyr Ser Val Arg Ala Leu
    50                  55                  60

Pro Phe Thr Leu Ser Asn Tyr Arg Arg Ser Tyr Glu Ala Phe Leu Ser
 65                  70                  75                  80

Gln Cys Gln Val Asp Ile Pro Thr Trp Gly Thr Lys His Pro Leu Gly
                85                  90                  95

Met Leu Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu Asn Gln Val Phe Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
    210                 215                 220
```

-continued

Cys Thr Leu Phe Val Val Leu Trp Leu Arg Val Pro Ile Leu Arg Thr
225 230 235 240

Val Phe Gly Phe Arg Trp Leu Gly Ala Ile Phe Leu Ser Asn Ser Gln
245 250 255

<210> SEQ ID NO 15
<211> LENGTH: 249
<212> TYPE: PRT
<213> ORGANISM: Porcine reproductive and respiratory syndrome virus

<400> SEQUENCE: 15

Met Gln Trp Gly His Cys Gly Val Lys Ser Ala Ser Cys Ser Trp Thr
1 5 10 15

Pro Ser Leu Ser Ser Leu Leu Val Trp Leu Ile Leu Pro Phe Ser Leu
20 25 30

Pro Tyr Cys Leu Gly Ser Pro Ser Gln Asp Gly Tyr Trp Ser Phe Phe
35 40 45

Ser Glu Trp Phe Ala Pro Arg Phe Ser Val Arg Ala Leu Pro Phe Thr
50 55 60

Leu Pro Asn Tyr Arg Arg Ser Tyr Glu Gly Leu Leu Pro Asn Cys Arg
65 70 75 80

Pro Asp Val Pro Gln Phe Ala Val Lys His Pro Leu Gly Met Phe Trp
85 90 95

His Met Arg Val Ser His Leu Ile Asp Glu Met Val Ser Arg Arg Ile
100 105 110

Tyr Gln Thr Met Glu His Ser Gly Gln Ala Ala Trp Lys Gln Val Val
115 120 125

Gly Glu Ala Thr Leu Thr Lys Leu Ser Gly Leu Asp Ile Val Thr His
130 135 140

Phe Gln His Leu Ala Ala Val Glu Ala Asp Ser Cys Arg Phe Leu Ser
145 150 155 160

Ser Arg Leu Val Met Leu Lys Asn Leu Ala Val Gly Asn Val Ser Leu
165 170 175

Gln Tyr Asn Thr Thr Leu Asp Arg Val Glu Leu Ile Phe Pro Thr Pro
180 185 190

Gly Thr Arg Pro Lys Leu Thr Asp Phe Arg Gln Trp Leu Ile Ser Val
195 200 205

His Ala Ser Ile Phe Ser Ser Val Ala Ser Ser Val Thr Leu Phe Ile
210 215 220

Val Leu Trp Leu Arg Ile Pro Ala Leu Arg Tyr Val Phe Gly Phe His
225 230 235 240

Trp Pro Thr Ala Thr His His Ser Ser
245

<210> SEQ ID NO 16
<211> LENGTH: 254
<212> TYPE: PRT
<213> ORGANISM: Porcine reproductive and respiratory syndrome virus

<400> SEQUENCE: 16

Met Ala Asn Ser Cys Thr Phe Leu Tyr Ile Phe Leu Cys Cys Ser Phe
1 5 10 15

Leu Tyr Ser Phe Cys Cys Ala Val Val Ala Gly Ser Asn Ala Thr Tyr
20 25 30

Cys Phe Trp Phe Pro Leu Val Arg Gly Asn Phe Ser Phe Glu Leu Thr
35 40 45

-continued

```
Val Asn Tyr Thr Val Cys Pro Pro Cys Leu Thr Arg Gln Ala Ala Ala
     50                  55                  60

Glu Ala Tyr Glu Pro Gly Arg Ser Leu Trp Cys Arg Ile Gly His Asp
 65                  70                  75                  80

Arg Cys Gly Glu Asp Asp His Asp Glu Leu Gly Phe Val Val Pro Ser
                 85                  90                  95

Gly Leu Ser Ser Glu Gly His Leu Thr Ser Ala Tyr Ala Trp Leu Ala
            100                 105                 110

Ser Leu Ser Phe Ser Tyr Thr Thr Gln Phe His Pro Glu Ile Phe Gly
        115                 120                 125

Ile Gly Asn Val Ser Arg Val Tyr Val Asp Ile Lys His Gln Phe Ile
    130                 135                 140

Cys Ala Val His Asp Gly Gln Asn Thr Thr Leu Pro His His Asp Asn
145                 150                 155                 160

Ile Ser Ala Val Leu Gln Thr Tyr Tyr Gln His Gln Val Asp Gly Gly
                165                 170                 175

Asn Trp Phe His Leu Glu Trp Val Arg Pro Phe Phe Ser Ser Trp Leu
            180                 185                 190

Val Leu Asn Val Ser Trp Phe Leu Arg Arg Ser Pro Ala Ser His Val
        195                 200                 205

Ser Val Arg Val Phe Gln Thr Ser Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Ala Arg Arg
                245                 250


<210> SEQ ID NO 17
<211> LENGTH: 254
<212> TYPE: PRT
<213> ORGANISM: Porcine reproductive and respiratory syndrome virus

<400> SEQUENCE: 17

Met Ala Asn Ser Cys Thr Phe Leu Tyr Ile Phe Leu Cys Cys Ser Phe
  1               5                  10                  15

Leu Tyr Ser Phe Cys Cys Ala Val Val Ala Gly Ser Asn Ala Thr Tyr
            20                  25                  30

Cys Phe Trp Phe Pro Leu Val Arg Gly Asn Phe Ser Phe Glu Leu Thr
        35                  40                  45

Val Asn Tyr Thr Val Cys Pro Pro Cys Leu Thr Arg Gln Ala Ala Thr
     50                  55                  60

Glu Ala Tyr Glu Pro Gly Arg Ser Leu Trp Cys Arg Ile Gly Tyr Asp
 65                  70                  75                  80

Arg Cys Gly Glu Asp Asp His Asp Glu Leu Gly Phe Val Val Pro Ser
                 85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Gln Val Tyr Val Asp Ile Arg His Gln Phe Ile
    130                 135                 140

Cys Ala Val His Asp Gly Gln Asn Ala Thr Leu Pro Arg His Asp Asn
145                 150                 155                 160

Ile Ser Ala Val Phe Gln Thr Tyr Tyr Gln His Gln Val Asp Gly Gly
```

-continued

```
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Ser His Val
        195                 200                 205

Ser Val Arg Val Leu Gln Thr Leu Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Val Val Arg Arg
                245                 250
```

<210> SEQ ID NO 18
<211> LENGTH: 254
<212> TYPE: PRT
<213> ORGANISM: Porcine reproductive and respiratory syndrome virus

<400> SEQUENCE: 18

```
Met Ala Asn Ser Cys Ala Phe Leu His Ile Phe Leu Cys Cys Ser Phe
  1               5                  10                  15

Leu Tyr Ser Leu Cys Cys Ala Val Val Ala Gly Ser Asn Thr Thr Tyr
             20                  25                  30

Cys Phe Trp Phe Pro Leu Val Arg Gly Asn Phe Ser Phe Glu Leu Ile
         35                  40                  45

Val Asn Tyr Thr Val Cys Pro Pro Cys Leu Thr Arg Gln Ala Ala Ala
     50                  55                  60

Glu Ala Tyr Glu Pro Gly Arg Ser Leu Trp Cys Arg Ile Gly Tyr Asp
 65                  70                  75                  80

Arg Cys Gly Glu Asp Asp His Asp Glu Leu Gly Phe Met Ile Pro Ser
                 85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Arg Val Tyr Val Asp Ile Lys His Gln Leu Ile
    130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Asn His Val
        195                 200                 205

Ser Val Arg Val Leu Gln Thr Leu Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250
```

<210> SEQ ID NO 19
<211> LENGTH: 254
<212> TYPE: PRT
<213> ORGANISM: Porcine reproductive and respiratory syndrome virus -continued

<400> SEQUENCE: 19

Met Val Asn Ser Cys Thr Phe Leu His Ile Phe Leu Cys Cys Ser Phe
1 5 10 15

Leu Tyr Ser Phe Cys Cys Ala Val Ala Ala Gly Ser Asn Ala Thr Tyr
20 25 30

Cys Phe Trp Phe Pro Leu Val Arg Gly Asn Phe Ser Phe Glu Leu Met
35 40 45

Val Asn Tyr Thr Val Cys Pro Pro Cys Leu Thr Arg Gln Ala Ala Ala
50 55 60

Glu Val Tyr Glu Pro Gly Arg Ser Leu Trp Cys Arg Ile Gly Tyr Asp
65 70 75 80

Arg Cys Gly Glu Asp Asp His Asp Glu Leu Gly Phe Met Ile Pro Pro
85 90 95

Gly Leu Ser Ser Glu Gly His Leu Thr Ser Val Tyr Ala Trp Leu Ala
100 105 110

Phe Leu Ser Phe Ser Tyr Thr Ala Gln Phe His Pro Glu Ile Phe Gly
115 120 125

Ile Gly Asn Val Ser Arg Val Tyr Val Asp Ile Lys His Gln Leu Ile
130 135 140

Cys Ala Glu His Asp Gly Gln Asn Ala Thr Leu Pro Arg His Asp Asn
145 150 155 160

Ile Ser Ala Val Phe Gln Thr Tyr Tyr Gln His Gln Val Asp Gly Gly
165 170 175

Asn Trp Phe His Leu Glu Trp Leu Arg Pro Phe Phe Ser Ser Trp Leu
180 185 190

Val Leu Asn Val Ser Trp Tyr Leu Arg Arg Ser Pro Ala Asn His Ala
195 200 205

Ser Val Arg Val Leu Gln Ile Leu Arg Pro Thr Leu Pro Gln Arg Gln
210 215 220

Ala Leu Leu Ser Ser Lys Thr Ser Val Ala Leu Gly Ile Ala Thr Arg
225 230 235 240

Pro Leu Arg Arg Phe Ala Lys Ser Leu Ser Ala Val Arg Arg
245 250

<210> SEQ ID NO 20
<211> LENGTH: 254
<212> TYPE: PRT
<213> ORGANISM: Porcine reproductive and respiratory syndrome virus

<400> SEQUENCE: 20

Met Val Asn Ser Cys Thr Phe Leu His Ile Phe Leu Cys Cys Ser Phe
1 5 10 15

Leu Tyr Ser Phe Cys Cys Ala Val Val Ala Gly Ser Asn Thr Thr Phe
20 25 30

Cys Phe Trp Phe Pro Leu Val Arg Gly Asn Phe Ser Phe Glu Leu Thr
35 40 45

Val Asn Tyr Thr Val Cys Pro Pro Cys Leu Thr Arg Gln Ala Ala Ala
50 55 60

Glu Ile Tyr Glu Pro Gly Arg Ser Leu Trp Cys Arg Ile Gly Tyr Asp
65 70 75 80

Arg Cys Gly Glu Asp Asp His Asp Glu Leu Gly Phe Met Val Pro Pro
85 90 95

Gly Phe Ser Ser Glu Gly His Leu Thr Ser Val Tyr Ala Trp Leu Ala
100 105 110

-continued

```
Phe Leu Ser Phe Ser Tyr Thr Ala Gln Phe His Pro Glu Ile Phe Gly
        115                 120                 125

Ile Gly Asn Val Ser Arg Val Tyr Val Asp Ile Lys His Gln Leu Ile
    130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Asn His Val
        195                 200                 205

Ser Val Arg Val Leu Gln Ile Leu Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250


<210> SEQ ID NO 21
<211> LENGTH: 254
<212> TYPE: PRT
<213> ORGANISM: Porcine reproductive and respiratory syndrome virus

<400> SEQUENCE: 21

Met Ala Asn Ser Cys Thr Phe Leu His Ile Leu Leu Cys Cys Ser Phe
  1               5                  10                  15

Leu Tyr Ser Phe Cys Cys Val Val Val Thr Asp Ala Asn Ala Thr Phe
            20                  25                  30

Cys Phe Trp Phe Pro Leu Val Arg Gly Asn Phe Ser Phe Glu Leu Met
        35                  40                  45

Val Asn Tyr Thr Val Cys Pro Pro Cys Leu Thr Arg Gln Ala Ala Ala
     50                  55                  60

Gln Ile Tyr Glu Pro Asn Arg Ser Leu Trp Cys Arg Ile Gly Asn Asp
 65                  70                  75                  80

Arg Cys Gly Glu Asp Asp His Asp Glu Leu Gly Phe Thr Val Pro Pro
                85                  90                  95

Gly Leu Ser Lys Glu Val His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Lys Val Tyr Val Asp Ile Asn His Gln Leu Ile
    130                 135                 140

Cys Ala Val His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Ser His Val
        195                 200                 205

Ser Val Arg Val Phe Gln Thr Ser Arg Pro Thr Pro Pro Arg Gln Gln
    210                 215                 220

Ile Ser Leu Ser Ser Arg Thr Ser Ala Ala Leu Gly Met Ala Thr Arg
225                 230                 235                 240
```

-continued

```
Pro Leu Arg Arg Phe Ala Lys Ser Leu Ser Ala Ala Arg Arg
                245                 250


<210> SEQ ID NO 22
<211> LENGTH: 254
<212> TYPE: PRT
<213> ORGANISM: Porcine reproductive and respiratory syndrome virus

<400> SEQUENCE: 22

Met Val Asn Ser Cys Thr Phe Leu His Ile Phe Leu Cys Cys Ser Phe
  1               5                  10                  15

Leu Tyr Ser Phe Cys Cys Ala Val Val Ala Gly Ser Asn Thr Thr Tyr
             20                  25                  30

Cys Phe Trp Phe Pro Leu Val Arg Gly Asn Phe Ser Phe Glu Leu Thr
         35                  40                  45

Val Asn Tyr Thr Val Cys Pro Pro Cys Leu Thr Arg Gln Ala Ala Thr
     50                  55                  60

Glu Ile Tyr Glu Pro Gly Arg Ser Leu Trp Cys Arg Ile Gly Tyr Asp
 65                  70                  75                  80

Arg Cys Gly Glu Asp Asp His Asp Glu Leu Gly Phe Met Ile Pro Pro
                 85                  90                  95

Gly Leu Ser Ser Glu Gly His Leu Thr Gly Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Arg Val Tyr Val Asp Ile Lys His Gln Leu Ile
    130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Asn His Val
        195                 200                 205

Ser Val Arg Val Leu Gln Ile Leu Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250


<210> SEQ ID NO 23
<211> LENGTH: 265
<212> TYPE: PRT
<213> ORGANISM: Porcine reproductive and respiratory syndrome virus

<400> SEQUENCE: 23

Met Ala His Gln Cys Ala Arg Phe His Phe Phe Leu Cys Gly Phe Ile
  1               5                  10                  15

Cys Tyr Leu Val His Ser Ala Leu Ala Ser Asn Ser Ser Ser Thr Leu
             20                  25                  30

Cys Phe Trp Phe Pro Leu Ala His Gly Asn Thr Ser Phe Glu Leu Thr
         35                  40                  45

Ile Asn Tyr Thr Ile Cys Met Pro Cys Ser Thr Ser Gln Ala Ala Arg
     50                  55                  60
```

-continued

```
Gln Arg Leu Glu Pro Gly Arg Asn Met Trp Cys Lys Ile Gly His Asp
 65                  70                  75                  80

Arg Cys Glu Glu Arg Asp His Asp Glu Leu Leu Met Ser Ile Pro Ser
                 85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Pro Glu Leu Phe Gly Ile
        115                 120                 125

Gly Asn Val Ser Arg Val Phe Val Asp Lys Arg His Gln Phe Ile Cys
    130                 135                 140

Ala Glu His Asp Gly His Asn Ser Thr Val Ser Thr Gly His Asn Ile
145                 150                 155                 160

Ser Ala Leu Tyr Ala Ala Tyr Tyr His His Gln Ile Asp Gly Gly Asn
                165                 170                 175

Trp Phe His Leu Glu Trp Leu Arg Pro Leu Phe Ser Ser Trp Leu Val
            180                 185                 190

Leu Asn Ile Ser Trp Phe Leu Arg Arg Ser Pro Val Ser Pro Val Ser
        195                 200                 205

Arg Arg Ile Tyr Gln Ile Leu Arg Pro Thr Arg Pro Arg Leu Pro Val
    210                 215                 220

Ser Trp Ser Phe Arg Thr Ser Ile Val Ser Asp Leu Thr Gly Ser Gln
225                 230                 235                 240

Gln Arg Lys Arg Lys Phe Pro Ser Glu Ser Arg Pro Asn Val Val Lys
                245                 250                 255

Pro Ser Val Leu Pro Ser Thr Ser Arg
            260                 265
```

<210> SEQ ID NO 24
<211> LENGTH: 178
<212> TYPE: PRT
<213> ORGANISM: Porcine reproductive and respiratory syndrome virus

<400> SEQUENCE: 24

```
Met Gly Ala Ser Leu Leu Phe Leu Leu Val Gly Phe Lys Cys Leu Leu
  1               5                  10                  15

Val Ser Gln Ala Phe Ala Cys Lys Pro Cys Phe Ser Ser Ser Leu Ser
            20                  25                  30

Asp Ile Lys Thr Asn Thr Thr Ala Ala Ala Gly Phe Ala Val Leu Gln
        35                  40                  45

Asp Ile Ser Cys Leu Arg His Arg Asn Ser Ala Ser Glu Ala Ile Arg
    50                  55                  60

Lys Val Pro Gln Cys Arg Thr Ala Ile Gly Thr Pro Val Tyr Ile Thr
 65                  70                  75                  80

Val Thr Ala Asn Val Thr Asp Glu Asn Tyr Leu His Ser Ser Asp Leu
                 85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125

Val Asn Phe Thr Ser Tyr Val Gln His Val Lys Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Thr Ile Leu Leu
```

-continued

```
                165                 170                 175

Ala Ile


<210> SEQ ID NO 25
<211> LENGTH: 178
<212> TYPE: PRT
<213> ORGANISM: Porcine reproductive and respiratory syndrome virus

<400> SEQUENCE: 25

Met Ala Ser Ser Leu Leu Phe Leu Val Val Gly Phe Lys Cys Leu Leu
  1               5                  10                  15

Val Ser Gln Ala Phe Ala Cys Lys Pro Cys Phe Ser Ser Ser Leu Ala
             20                  25                  30

Asp Ile Lys Thr Asn Thr Thr Ala Ala Ala Ser Phe Ala Val Leu Gln
         35                  40                  45

Asp Ile Ser Cys Leu Arg His Arg Asp Ser Ala Ser Glu Ala Ile Arg
     50                  55                  60

Lys Ile Pro Gln Cys Arg Thr Ala Ile Gly Thr Pro Val Tyr Val Thr
 65                  70                  75                  80

Ile Thr Ala Asn Val Thr Asp Glu Asn Tyr Leu His Ser Ser Asp Leu
                 85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125

Val Asn Phe Thr Ser Tyr Val Gln His Val Lys Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile


<210> SEQ ID NO 26
<211> LENGTH: 178
<212> TYPE: PRT
<213> ORGANISM: Porcine reproductive and respiratory syndrome virus

<400> SEQUENCE: 26

Met Ala Ala Ser Leu Leu Phe Leu Leu Val Gly Phe Lys Cys Leu Leu
  1               5                  10                  15

Val Ser Gln Ala Phe Ala Cys Lys Pro Cys Phe Ser Ser Ser Leu Ala
             20                  25                  30

Asp Ile Lys Thr Asn Thr Thr Ala Ala Ala Gly Phe Ala Val Leu Gln
         35                  40                  45

Asp Ile Ser Cys Leu Arg Tyr Arg Asn Ser Ala Ser Glu Ala Phe Arg
     50                  55                  60

Lys Ile Pro Gln Cys Arg Thr Ala Ile Gly Thr Pro Met Tyr Ile Thr
 65                  70                  75                  80

Val Thr Ala Asn Val Thr Asp Glu Asn Tyr Leu His Ser Ser Asp Leu
                 85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125
```

-continued

```
Val Asn Phe Thr Ser Tyr Val Gln His Val Lys Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile


<210> SEQ ID NO 27
<211> LENGTH: 178
<212> TYPE: PRT
<213> ORGANISM: Porcine reproductive and respiratory syndrome virus

<400> SEQUENCE: 27

Met Ala Ser Ser Leu Leu Phe Leu Met Val Gly Phe Lys Cys Leu Leu
  1               5                  10                  15

Val Ser Gln Ala Phe Ala Cys Lys Pro Cys Phe Ser Ser Ser Leu Ala
             20                  25                  30

Asp Ile Lys Thr Asn Thr Thr Ala Ala Ala Ser Phe Ala Val Leu Gln
         35                  40                  45

Asp Ile Ser Cys Leu Arg His Arg Asn Ser Ala Ser Glu Ala Ile Arg
     50                  55                  60

Lys Ile Pro Gln Cys Arg Thr Ala Ile Gly Thr Pro Val Tyr Ile Thr
 65                  70                  75                  80

Ile Thr Ala Asn Val Thr Asp Glu Asn Tyr Leu His Ser Ser Asp Leu
                 85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125

Val Asn Phe Thr Ser Tyr Val Gln His Val Arg Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile


<210> SEQ ID NO 28
<211> LENGTH: 178
<212> TYPE: PRT
<213> ORGANISM: Porcine reproductive and respiratory syndrome virus

<400> SEQUENCE: 28

Met Ala Ser Ser Leu Leu Phe Leu Met Val Gly Phe Lys Cys Leu Leu
  1               5                  10                  15

Val Ser Gln Ala Phe Ala Cys Lys Pro Cys Phe Ser Ser Ser Leu Ala
             20                  25                  30

Asp Ile Lys Thr Asn Thr Thr Ala Ala Ala Ser Phe Ala Val Leu Gln
         35                  40                  45

Asp Ile Gly Cys Leu Arg His Arg Asp Ser Ala Ser Glu Ala Ile Arg
     50                  55                  60

Lys Ile Pro Gln Cys Arg Thr Ala Ile Gly Thr Pro Val Tyr Ile Thr
 65                  70                  75                  80

Ile Thr Ala Asn Val Thr Asp Glu Asn Tyr Leu His Ser Ser Asp Leu
                 85                  90                  95
```

-continued

```
Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125

Val Asn Phe Thr Ser Tyr Val Gln His Val Arg Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile


<210> SEQ ID NO 29
<211> LENGTH: 178
<212> TYPE: PRT
<213> ORGANISM: Porcine reproductive and respiratory syndrome virus

<400> SEQUENCE: 29

Met Ala Ala Ser Leu Leu Phe Leu Met Val Gly Phe Lys Cys Leu Leu
  1               5                  10                  15

Val Ser Gln Ala Phe Ala Cys Lys Pro Cys Phe Ser Ser Ser Leu Ala
             20                  25                  30

Asp Ile Lys Thr Asn Thr Thr Ala Ala Ala Ser Phe Ala Val Leu Gln
         35                  40                  45

Asp Ile Ser Cys Leu Arg His Arg Asn Ser Ala Ser Glu Ala Ile Arg
     50                  55                  60

Lys Ile Pro Gln Cys Arg Thr Ala Ile Gly Thr Pro Met Tyr Ile Thr
 65                  70                  75                  80

Ile Thr Ala Asn Val Thr Asp Glu Asn Tyr Leu His Ser Ser Asp Leu
                 85                  90                  95

Leu Met Leu Ser Ser Cys Leu Phe Tyr Ala Ser Glu Met Ser Glu Lys
            100                 105                 110

Gly Phe Glu Val Val Phe Gly Asn Val Ser Gly Ile Val Ala Val Cys
        115                 120                 125

Val Asn Phe Thr Ser Tyr Val Gln His Val Arg Glu Phe Thr Gln Arg
    130                 135                 140

Ser Leu Met Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile


<210> SEQ ID NO 30
<211> LENGTH: 178
<212> TYPE: PRT
<213> ORGANISM: Porcine reproductive and respiratory syndrome virus

<400> SEQUENCE: 30

Met Ala Ala Ser Leu Leu Phe Leu Leu Val Gly Phe Glu Cys Leu Leu
  1               5                  10                  15

Val Ser Gln Ala Phe Ala Cys Lys Pro Cys Phe Ser Ser Ser Leu Ser
             20                  25                  30

Asp Ile Lys Thr Asn Thr Thr Ala Ala Ala Asn Phe Ala Val Leu Gln
         35                  40                  45

Asp Ile Gly Cys Leu Arg His Gly Asn Ser Thr Thr Glu Ala Phe Arg
```

-continued

```
     50                  55                  60

Lys Ile Pro Gln Cys Arg Thr Ala Ile Gly Thr Pro Val Tyr Ile Thr
 65                  70                  75                  80

Ile Thr Ala Asn Val Thr Asp Glu Asn Tyr Leu His Ser Ser Asp Leu
                 85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Thr Val Ala Val Cys
        115                 120                 125

Ile Asn Phe Thr Ser Tyr Val Gln His Val Lys Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile


<210> SEQ ID NO 31
<211> LENGTH: 183
<212> TYPE: PRT
<213> ORGANISM: Porcine reproductive and respiratory syndrome virus

<400> SEQUENCE: 31

Met Ala Ala Ala Thr Leu Phe Phe Leu Ala Gly Ala Gln His Ile Met
  1               5                  10                  15

Val Ser Glu Ala Phe Ala Cys Lys Pro Cys Phe Ser Thr His Leu Ser
            20                  25                  30

Asp Ile Glu Thr Asn Thr Thr Ala Ala Ala Gly Phe Met Val Leu Gln
        35                  40                  45

Asp Ile Asn Cys Phe Arg Pro His Gly Val Ser Ala Ala Gln Glu Lys
     50                  55                  60

Ile Ser Phe Gly Lys Ser Ser Gln Cys Arg Glu Ala Val Gly Thr Pro
 65                  70                  75                  80

Gln Tyr Ile Thr Ile Thr Ala Asn Val Thr Asp Glu Ser Tyr Leu Tyr
                 85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
        115                 120                 125

Val Ser Ala Cys Val Asn Phe Thr Asp Tyr Val Ala His Val Thr Gln
    130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
            180


<210> SEQ ID NO 32
<211> LENGTH: 200
<212> TYPE: PRT
<213> ORGANISM: Porcine reproductive and respiratory syndrome virus

<400> SEQUENCE: 32

Met Leu Gly Lys Cys Leu Thr Ala Gly Cys Cys Ser Gln Leu Leu Phe
  1               5                  10                  15
```

-continued

```
Leu Trp Cys Ile Val Pro Ser Cys Phe Val Ala Leu Val Ser Ala Asn
                20                  25                  30

Gly Asn Ser Gly Ser Asn Leu Gln Leu Ile Tyr Asn Leu Thr Leu Cys
            35                  40                  45

Glu Leu Asn Gly Thr Asp Trp Leu Ala Asn Lys Phe Asp Trp Ala Val
    50                  55                  60

Glu Cys Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Val His Gly Arg Tyr Val Leu Ser Ser Met Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Ala Ala Thr Pro Val Thr Arg Val
            180                 185                 190

Ser Ala Glu Gln Trp Arg Ser Pro
        195                 200


<210> SEQ ID NO 33
<211> LENGTH: 200
<212> TYPE: PRT
<213> ORGANISM: Porcine reproductive and respiratory syndrome virus

<400> SEQUENCE: 33

Met Leu Glu Lys Cys Leu Thr Ala Gly Cys Cys Ser Arg Leu Leu Ser
  1               5                  10                  15

Leu Trp Cys Ile Val Pro Phe Cys Phe Ala Val Leu Ala Asn Ala Ser
                20                  25                  30

Asn Asp Ser Ser Ser His Leu Gln Leu Ile Tyr Asn Leu Thr Leu Cys
            35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
```

-continued 180 185 190

Ser Ala Glu Gln Trp Gly Arg Pro
195 200

<210> SEQ ID NO 34
<211> LENGTH: 200
<212> TYPE: PRT
<213> ORGANISM: Porcine reproductive and respiratory syndrome virus

<400> SEQUENCE: 34

Met Leu Gly Lys Cys Leu Thr Ala Gly Tyr Cys Ser Ser Leu Leu Phe
1 5 10 15

Leu Trp Cys Ile Val Pro Ser Trp Phe Val Ala Leu Ala Ser Ala Asn
20 25 30

Ser Ser Asn Ser Ser His Leu Gln Leu Ile Tyr Asn Leu Thr Leu Cys
35 40 45

Glu Leu Asn Gly Thr Asp Trp Leu Ala Gly Glu Phe Asp Trp Ala Val
50 55 60

Glu Cys Phe Val Ile Phe Pro Val Leu Thr His Ile Val Ser Tyr Gly
65 70 75 80

Ala Leu Thr Thr Ser His Phe Leu Asp Thr Val Gly Leu Val Thr Val
85 90 95

Ser Thr Ala Gly Phe Ser His Gly Arg Tyr Val Leu Ser Ser Ile Tyr
100 105 110

Ala Val Cys Ala Leu Ala Ala Leu Ile Cys Phe Val Ile Arg Phe Thr
115 120 125

Lys Asn Cys Met Ser Trp Arg Tyr Ser Cys Thr Arg Tyr Thr Asn Phe
130 135 140

Leu Leu Asp Thr Lys Gly Arg Leu Tyr Arg Trp Arg Ser Pro Val Ile
145 150 155 160

Ile Glu Lys Arg Gly Lys Val Glu Val Glu Gly His Leu Ile Asp Leu
165 170 175

Lys Arg Val Val Leu Asp Gly Ser Ala Ala Thr Pro Ile Thr Lys Val
180 185 190

Ser Ala Glu Gln Trp Gly Arg Pro
195 200

<210> SEQ ID NO 35
<211> LENGTH: 200
<212> TYPE: PRT
<213> ORGANISM: Porcine reproductive and respiratory syndrome virus

<400> SEQUENCE: 35

Met Leu Gly Lys Cys Leu Thr Ala Gly Cys Cys Ser Arg Leu Leu Ser
1 5 10 15

Leu Trp Cys Ile Val Pro Phe Cys Phe Ala Val Leu Ala Asn Ala Ser
20 25 30

Ala Asn Ser Ser Ser His Leu Gln Leu Ile Tyr Asn Leu Thr Leu Cys
35 40 45

Glu Leu Asn Gly Thr Asp Trp Leu Ala Asp Lys Phe Asp Trp Ala Val
50 55 60

Glu Ser Phe Val Ile Phe Pro Val Leu Thr His Ile Val Ser Tyr Gly
65 70 75 80

Ala Leu Thr Thr Ser His Leu Leu Asp Thr Val Ala Leu Val Thr Val
85 90 95

Ser Thr Ala Gly Phe Val His Gly Arg Tyr Val Leu Ser Ser Ile Tyr

-continued

```
            100                 105                 110

Ala Val Cys Ala Leu Ala Ala Leu Ala Cys Phe Val Ile Arg Phe Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp His Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200


<210> SEQ ID NO 36
<211> LENGTH: 200
<212> TYPE: PRT
<213> ORGANISM: Porcine reproductive and respiratory syndrome virus

<400> SEQUENCE: 36

Met Leu Gly Lys Cys Leu Thr Val Gly Cys Cys Ser Arg Leu Leu Ser
  1               5                  10                  15

Leu Trp Cys Ile Val Pro Phe Cys Phe Thr Val Leu Ala Asp Ala His
            20                  25                  30

Ser Asn Ser Ser Ser His Leu Gln Leu Ile Tyr Asn Leu Thr Leu Cys
        35                  40                  45

Glu Leu Asn Gly Thr Asp Trp Leu Ala Asp Arg Phe Asp Trp Ala Val
     50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Ile Ala Leu Val Thr Val
                 85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Val
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200


<210> SEQ ID NO 37
<211> LENGTH: 199
<212> TYPE: PRT
<213> ORGANISM: Porcine reproductive and respiratory syndrome virus

<400> SEQUENCE: 37

Met Leu Gly Lys Cys Leu Thr Ala Gly Cys Cys Ser Arg Leu Leu Ser
  1               5                  10                  15

Leu Trp Phe Ile Val Pro Phe Cys Phe Ala Val Leu Ala Ser Ala Ser
```

-continued

```
                20                  25                  30

Asn Ser Ser Ser Ser His Leu Gln Leu Ile Tyr Asn Leu Thr Leu Cys
            35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Ile Ile Arg Phe Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Gly Arg Pro
        195


<210> SEQ ID NO 38
<211> LENGTH: 199
<212> TYPE: PRT
<213> ORGANISM: Porcine reproductive and respiratory syndrome virus

<400> SEQUENCE: 38

Met Leu Gly Lys Cys Leu Thr Ala Gly Cys Cys Ser Arg Ser Leu Phe
1               5                   10                  15

Leu Trp Cys Ile Val Pro Phe Cys Leu Ala Ala Leu Val Ser Ala Asn
            20                  25                  30

Asn Ser Ser Ser His Leu Gln Leu Ile Tyr Asn Leu Thr Leu Cys Glu
        35                  40                  45

Leu Asn Gly Thr Asp Trp Leu Ala Asn Lys Phe Asp Trp Ala Val Glu
    50                  55                  60

Ser Phe Val Ile Phe Pro Val Leu Thr His Ile Val Ser Tyr Gly Ala
65                  70                  75                  80

Leu Thr Thr Ser His Phe Leu Asp Thr Val Gly Leu Val Thr Val Ser
                85                  90                  95

Thr Ala Gly Phe His His Gly Arg Tyr Val Leu Ser Ser Ile Tyr Ala
            100                 105                 110

Val Cys Ala Leu Ala Ala Phe Ile Cys Phe Val Ile Arg Phe Ala Lys
        115                 120                 125

Asn Cys Met Ser Trp Arg Tyr Ser Cys Thr Arg Tyr Thr Asn Phe Leu
    130                 135                 140

Leu Asp Thr Lys Gly Arg Leu Tyr Arg Trp Arg Ser Pro Val Ile Ile
145                 150                 155                 160

Glu Lys Gly Gly Lys Val Glu Val Glu Gly His Leu Ile Asp Leu Lys
                165                 170                 175

Lys Val Val Leu Asp Gly Ser Ala Ala Thr Pro Leu Thr Arg Val Ser
            180                 185                 190
```

-continued

```
Ala Glu Gln Trp Gly Arg Pro
        195


<210> SEQ ID NO 39
<211> LENGTH: 201
<212> TYPE: PRT
<213> ORGANISM: Porcine reproductive and respiratory syndrome virus

<400> SEQUENCE: 39

Met Arg Cys Ser His Lys Leu Gly Arg Phe Leu Thr Pro His Ser Cys
  1               5                  10                  15

Phe Trp Trp Leu Phe Leu Leu Cys Thr Gly Leu Ser Trp Ser Phe Ser
             20                  25                  30

Asp Asn Gly Gly Asp Ser Ser Thr Tyr Gln Tyr Ile Tyr Asn Leu Thr
         35                  40                  45

Ile Cys Glu Leu Asn Gly Thr Asp Trp Leu Ser Ser His Phe Gly Trp
     50                  55                  60

Ala Val Glu Thr Phe Val Leu Tyr Pro Val Ala Thr His Ile Leu Ser
 65                  70                  75                  80

Leu Gly Phe Leu Thr Thr Ser His Phe Phe Asp Ala Leu Gly Leu Gly
                 85                  90                  95

Ala Val Ser Thr Ala Gly Phe Val Gly Gly Arg Tyr Val Leu Cys Ser
            100                 105                 110

Val Tyr Gly Ala Cys Ala Phe Ala Ala Phe Val Cys Phe Val Ile Arg
        115                 120                 125

Ala Ala Lys Asn Cys Met Ala Cys Arg Tyr Ala Arg Thr Arg Phe Thr
    130                 135                 140

Asn Phe Ile Val Asp Asp Arg Gly Arg Val His Arg Trp Lys Ser Pro
145                 150                 155                 160

Ile Val Val Glu Lys Leu Gly Lys Ala Glu Val Asp Gly Asn Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
        195                 200


<210> SEQ ID NO 40
<211> LENGTH: 3293
<212> TYPE: DNA
<213> ORGANISM: Porcine reproductive and respiratory syndrome virus

<400> SEQUENCE: 40

gttttatttc cctccgggcc ctgtcattga accaacttta ggcctgaatt gaaatgaaat     60

ggggtccatg caaagccttt ttgacaaaat tggccaactt tttgtggatg ctttcacgga    120

gttcttggtg tccattgttg atatcattat attcttggcc attttgtttg gcttcaccat    180

cgccggttgg ctggtggtct tttgcatcag attggtttgc tccgcgatac tccgtacgcg    240

ccctgccatt cactctgagc aattacagaa gatcttatga ggcctttctt tcccagtgcc    300

aagtggacat tcccacctgg ggaactaaac atcctttggg gatgttttgg caccataagg    360

tgtcaaccct gattgatgag atggtgtcgc gtcgaatgta ccgcatcatg gaaaaagcag    420

gacaggctgc ctggaaacag gtggtgagcg aggctacgct gtctcgcatt agtagtttgg    480

atgtggtggc tcattttcag catcttgccg ccatcgaagc cgagacctgt aaatatttgg    540

cctcccggct gcccatgcta cacaacctgc gcatgacagg gtcaaatgta accatagtgt    600

ataatagtac tttgaatcgg gtgtttgcta ttttcccaac ccctggttcc cggccaaagc    660
```

-continued

```
ttcatgactt tcagcaatgg ctaatagctg tgcattcctc catattttcc tctgttgcag    720
cttcttgtac tctctttgtt gtgctgtggt tgcgggttcc aatactacgt actgtttttg    780
gtttccgctg gttaggggca atttttcttt cgaactcata gtgaattaca cggtgtgccc    840
accttgcctc acccggcaag cagccgcaga ggcctacgaa cccggtaggt ctctttggtg    900
caggataggg tacgatcgat gtggagagga cgaccatgac gagctagggt ttatgatacc    960
gtctggcctc tccagcgaag gccacttgac cagtgtttac gcctggttgg cgttcttgtc   1020
cttcagctac acggcccagt tccaccccga gatattcggg atagggaatg tgagtcgagt   1080
ttatgttgac atcaaacatc aactcatctg cgccgaacat gacgggcaga acaccacctt   1140
gcctcgtcat gacaacattt cggccgtgtt tcagacctat taccaacatc aagtcgacgg   1200
cggcaattgg tttcacctag aatggctgcg tcccttcttt tcctcatggt tggttttaaa   1260
tgtctcttgg tttctcaggc gttcgcctgc aaaccatgtt tcagttcgag tcttgcagac   1320
attaagacca acaccaccgc agcggcaagc tttgctgtcc tccaagacat cagttgcctt   1380
aggcatcgca actcggcctc tgaggcgatt cgcaaaatcc ctcagtgccg tacggcgata   1440
gggacaccta tgtatattac catcacagcc aatgtgacag atgaaaatta tttacattct   1500
tctgatctcc tcatgctctc ttcttgcctt ttctatgctt ctgagatgag tgaaaaggga   1560
tttgaggtgg tttttggcaa tgtgtcaggc atcgtggctg tgtgtgtcaa ttttaccagc   1620
tacgttcaac atgtcaggga gtttacccaa cgctccttga tggtcgacca tgtgcggctg   1680
ctccatttca tgacacctga gaccatgagg tgggcaaccg ttttagcctg tctttttgct   1740
attctgttgg caatttgaat gtttaagtat gttggggaaa tgcttgaccg tgggctgttg   1800
ctcgcgattg ctttctttgt ggtgtatcgt gccgttctgt tttactgtgc tcgccgacgc   1860
ccacagcaac agcagctctc atctgcaatt gatttacaac ttgacgctat gtgagctgaa   1920
tggcacagat tggctagctg atagatttga ttgggcagtg gagagctttg tcatctttcc   1980
tgttttgact cacattgtct cctatggcgc cctcaccacc agccatttcc ttgacacaat   2040
tgctttagtc actgtgtcta ccgccgggtt tgttcacggg cggtatgtcc taagtagcat   2100
ctacgcggtc tgtgccctgg ctgcgttgac ttgcttcgtc attaggtttg tgaagaattg   2160
catgtcctgg cgctactcat gtactagata taccaacttt cttctggata ctaagggcag   2220
actctatcgt tggcggtcgc ctgtcatcat agagaagagg ggcaaagttg aggtcgaagg   2280
tcatctgatc gatctcaaaa gagttgtgct tgatggttcc gtggcaaccc ctataaccag   2340
agtttcagcg gaacaatggg gtcgtcctta gatgacttct gttatgatag tacggctcca   2400
caaaaggtgc ttttggcatt ttctattacc tacacgccag taatgatata tgccctaaag   2460
gtgagtcgcg gccgactgct agggcttctg caccttttga ttttcctgaa ctgtgctttc   2520
accttcgggt acatgacatt catgcacttt cagagtacaa ataaggtcgc gctcactatg   2580
ggagcagtag ttgcactcct ttggggggtg tactcagcca tagaaacctg gaaattcatc   2640
acctccagat gccgtttgtg cttgctaggc cgcaagtaca ttctggcccc tgcccaccac   2700
gttgaaagtg ccgcaggctt tcatccgatt gcggcaaatg ataaccacgc atttgtcgtc   2760
cggcgtcccg gctccactac ggtcaacggc acattggtgc ccgggttgaa aagcctcgtg   2820
ttgggtggca gaaaagctgt taaacaggga gtggtaaacc ttgtcaaata tgccaaataa   2880
caacggcaag cagcagaaga gaaagaaggg ggatggccag ccagtcaatc agctgtgcca   2940
gatgctgggt aagatcatcg cccagcaaaa ccagtctaga ggcaagggac cgggaaagaa   3000
```

-continued

```
aaataagaag aaaaacccgg agaagcccca ttttcctcta gcgactgaag atgatgtcag   3060

acatcacttt accccctagtg agcggcaatt gtgtctgtcg tcaatccaaa ctgcctttaa   3120

tcaaggcgct gggacttgca ccctgtcaga ttcagggagg ataagttaca ctgtggagtt   3180

tagtttgcct acgcatcata ctgtgcgctt gatccgcgtc acagcatcac cctcagcatg   3240

atgggctggc attcttgagg catcccagtg tttgaattgg aagaatgcgt ggt           3293
```

<210> SEQ ID NO 41
<211> LENGTH: 3293
<212> TYPE: DNA
<213> ORGANISM: Porcine reproductive and respiratory syndrome virus

<400> SEQUENCE: 41

```
gttttatttc cctccgggcc ccgtcattga accaacttta ggcctgaatt gaaatgaaat     60

ggggtccgtg caaagccttt ttgacaaaat tggccaactt tttgtggatg ctttcacgga    120

gttcctggtg tccattgttg atatcatcat atttttggcc attttgtttg gcttcaccat    180

cgccggttgg ctggtggtct tttgcatcag attggtttgc tccgcgatac tccgtacgcg    240

ccctgccatt cactctgagc aattacagaa gatcttatga ggccttttta tcccagtgcc    300

aagtggacat tcccacctgg ggaactaaac atcctttggg gatgttttgg caccataagg    360

tgtcaaccct gattgatgaa atggtgtcgc gtcgcatgta ccgcatcatg gaaaaagcag    420

ggcaggctgc ctggaaacag gtggtgagcg aggctacgct gtcccgcatt agtagtttgg    480

atgtggtggc tcattttcag catcttgccg ccattgaagc cgagacttgt aaatatttgg    540

cctcccggct gcccatgcta cataacctgc gcataacagg gtcaaatgta accatagtgt    600

ataatagtac ttcggagcag gtgtttgcta ttttcccaac ccctggttcc cggccaaagc    660

ttcatgattt tcagcaatgg ttaatagctg tacattcctc catattttcc tctgttgcag    720

cttcttgtac tctttttgtt gtgctgtggc tgcgggttcc aatgctacgt actgtttttg    780

gtttccgctg gttaggggga atttttcctt cgaactcatg gtgaattaca cggtgtgtcc    840

accttgcctc acccggcaag cagccgcaga ggtctacgaa cccggtaggt ctctttggtg    900

caggataggg tatgaccgat gtggggagga cgatcatgac gagctagggt ttatgatacc    960

gcctggcctc tccagcgaag gccacttgac tagtgtttac gcctggttgg cgtttttgtc   1020

cttcagctac acggcccagt tccatcccga gatattcggg atagggaatg tgagtcgagt   1080

ttatgttgac atcaaacatc aactcatttg cgccgaacat gacggacaga acgccacctt   1140

gcctcgtcat gacaatattt cagccgtgtt tcagacctat taccaacatc aagtcgatgg   1200

cggcaattgg tttcacctag aatggcttcg tcccttcttt tcctcatggt tggttttaaa   1260

tgtctcttgg tatctcaggc gttcgcctgc aaaccatgct tcagttcgag tcttgcagat   1320

attaagacca acactaccgc agcggcaagc tttgctgtcc tccaagacat cagttgcctt   1380

aggcatcgca actcggcctc tgaggcgatt cgcaaaatcc ctcagtgccg tacggcgata   1440

gggacacccg tgtatattac catcacagcc aatgtgacag atgagaatta tttacattct   1500

tctgatctcc tcatgctttc ttcttgcctt ttctacgctt ctgagatgag tgaaaaagga   1560

ttcaaggtgg tatttggcaa tgtgtcaggc atcgtggctg tgtgtgtcaa ttttaccagc   1620

tacgtccaac atgtcaggga gtttacccaa cgctccctgg tggtcgacca tgtgcggttg   1680

ctccatttca tgacacctga aaccatgagg tgggcaactg ttttagcctg tctttttgcc   1740

attctgctgg caatttgaat gtttaagtat gttggggaaa tgcttgaccg cgggctgttg   1800

ctcgcgattg ctttctttgt ggtgtatcgt gccgttctgt tttgctgtgc tcgccaacgc   1860
```

-continued

```
cagcgccaac agcagctccc atctacagct gatttacaac ttgacgctat gtgagctgaa   1920

tggcacagat tggctagctg ataaatttga ttgggcagtg gagagttttg tcatctttcc   1980

cgttttgact cacattgtct cctatggtgc cctcactact agccatctcc ttgacacagt   2040

cgccttagtc actgtgtcta ccgccgggtt tgttcacggg cggtatgtcc taagtagcat   2100

ctacgcggtc tgtgccctgg ctgcgttagc ttgcttcgtc attaggtttg caaagaattg   2160

catgtcctgg cgctattcgt gtaccagata taccaacttt cttctggaca ctaagggcag   2220

actctatcgt tggcattcgc ctgtcatcat agagaaaagg ggcaaagttg aggtcgaagg   2280

tcatctgatc gacctcaaaa gagttgtgct tgacggttcc gtggcaaccc ctataaccag   2340

agtttcagcg gaacaatggg gtcgtcctta gatgacttct gccatgatag tacggctcca   2400

caaaaggtgc ttttggcgtt ttctattacc tacacgccag tgatgatata tgccctaaag   2460

gtgagtcgcg gccgactgct agggcttctg cacctttga tcttcctgaa ttgtgctttc   2520

accttcgggt acatgacatt cgtgcacttt cagagtacaa ataaggtcgc gctcactatg   2580

ggagcagtag ttgcactcct ttgggggtg tactcagcca tagaaacctg gaaattcatc   2640

acctccagat gccgtttgtg cttgctaggc cgcaagtaca ttctggcccc tgcccaccac   2700

gttgaaagtg ccgcaggctt tcatccgatt gcggcaaatg ataaccacgc atttgtcgtc   2760

cggcgtcccg gctccactac ggtcaacggc acattggtgc ccgggttgaa aagcctcgtg   2820

ttgggtggca gaaaagctgt taaacaggga gtggtaaacc ttgtcaaata tgccaaataa   2880

caacggcaag cagcagaaga gaaagaaggg ggatggccag ccagtcaatc agctgtgcca   2940

gatgctgggt aagatcatcg ctcagcaaaa ccagtccaga ggcaagggac cgggaaagaa   3000

aaacaagaag aaaaacccgg agaagcccca ttttcctcta gcgactgaag atgatgtcag   3060

acatcacttc acccctagtg agcggcaatt gtgtctgtcg tcaatccaga ccgcctttaa   3120

tcaaggcgct gggacttgca ccctgtcaga ttcagggagg ataagttaca ctgtggagtt   3180

tagtttgcca acgcatcata ctgtgcgctt gatccgcgtc acagcatcac cctcagcatg   3240

atgggctggc attcttgagg catcccagtg tttgaattgg aagaatgcgt ggt          3293
```

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence:Synthetic DNA

<400> SEQUENCE: 42
gcacggatcc gaattaacat gaaatggggt 30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence:Synthetic DNA

<400> SEQUENCE: 43
cgtcggatcc tcctacaatg gctaatagct 30

<210> SEQ ID NO 44
<211> LENGTH: 30
<212> TYPE: DNA

-continued

```
<213> ORGANISM: Artificial Sequence
<220> FEATURE:
<223> OTHER INFORMATION: Description of Artificial Sequence:Synthetic
      DNA

<400> SEQUENCE: 44

gtatggatcc gcaattggtt tcacctataa                                    30


<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 45

tgccaggatc cgtgtttaaa tatgttgggg                                    30


<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 46

ggggatccag agtttcagcg g                                             21


<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 47

ggggatcctt gttaaatatg cc                                            22


<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 48

ccacctgcag attcaccgtg agttcgaaag                                    30


<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 49

cgcgctgcag tgtccctatc gacgtgcggc                                    30


<210> SEQ ID NO 50
<211> LENGTH: 30
<212> TYPE: DNA
<213> ORGANISM: Artificial Sequence
```

-continued

<220> FEATURE:
<223> OTHER INFORMATION: Description of Artificial Sequence:Synthetic DNA

<400> SEQUENCE: 50
ataggaattc aacaagacgg cacgatacac 30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence:Synthetic DNA

<400> SEQUENCE: 51
cgtggaattc atagaaaacg ccaagagcac 30

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence:Synthetic DNA

<400> SEQUENCE: 52
gggaattctg gcacagctga ttgac 25

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence:Synthetic DNA

<400> SEQUENCE: 53
gggaattcac cacgcattc 19

<210> SEQ ID NO 54
<211> LENGTH: 15420
<212> TYPE: DNA
<213> ORGANISM: Porcine reproductive and respiratory syndrome virus

<400> SEQUENCE: 54
nngacgtata ggtgttggct ctatgccttg acattcgtat tgtcaggagc tgtgaccatt 60
ggtacagccc aaaacttgct gcacagaaaa cgcccttctg tgacagcctc cttcagggag 120
cttgggggtc tgtccctagc accttgcttc cggagttgca ctgctttacg gtctctccac 180
ccttttaacc atgtctggga tacttgatcg gtgtacgtgc acccccaatg ccagggtgtt 240
tatggcggag ggccaggtct actgcacacg atgtctcagt gcacggtctc tccttcctct 300
gaatctccag actcccgagc ttggggtgtt gggtctattc tacaggcccg aagaaccact 360
ccggtggacg ttgccacgtg cattccccac tgttgagtgt tccccgctg gggcctgctg 420 gctttctgca atctttccaa ttgcgcgaat gaccagtgga aacctgaact tccaacaaag 480
aatggtacgg gtcgcagctg agctttacag agccggccag ctcacccctg tcgtcttgaa 540
gactctgcaa gtttacgaac ggggttgccg ctggtacccc attgttggac ctgtccctgg 600
agtggccgtt ttcgccaact ccctacatgt gagtgataaa cctttcccag gggcaactca 660
cgtgttaacc aacctgccgc tcccgcagag acccaagccc gaagacttct gcccctttga 720

-continued

```
atgcgccatg gccaccgtct atgacattgg tcatgacgct gtcatgtaca tggccggagg    780
gaaagtctcc tgggcccctc gtggcgggga tggagtgaaa tttgaaactg tccccaaggg    840
gttggagtta actgcggacc gactccgctc ctccttcccg ccccaccacg tagtggacat    900
gtccaggttt gctttcacaa cccctgagtg tggtgcctct atgcgggtcg gacgccaacg    960
tggctgcctc cccgctggta ctgtccctga aggcaactgt tggtggagct tgtttggctc   1020
gctcccactg gaagttctga acaaagaaat tcgctatgcc aaccgatttg gctaccaaac   1080
taagcatggt gtctctggca agtacctaca gcggaggctg caagttaatg gtctccgggc   1140
agtaactgac acacatggac ctatcgtcat acaatacttc tccgttaagg agagttggat   1200
ccgccacttg agactggcgg aagaacccag cctccctggg tttgaggatc tcctcagaat   1260
aagggttgag cccaacacat cgccattgct tggcaagggt gaaaaaatct tccgttttgg   1320
caatcacaaa tggtacggcg ctggaaagag agcaaggaaa gcacgctcta gtgcgactgc   1380
tacggtcgct gaccgcgctt tgtccgctcg tgaaacccgg ctggccaagg agcacgaggt   1440
tgccggcgcc aataaggctg agcacctcaa gcactactcc ccgcctgccg aagggaattg   1500
tggttggcac tgtatttccg ccatcgtcaa ccggatggtg aactccaaat ttgaaaccac   1560
cctccccgag agagtgagac ctccagatga ctgggctact gacgaggatc ttgcgaacac   1620
catccaaatc ctcaggcttc ctgcggcctt ggacaggggc ggtgcttgtg ttagcgccaa   1680
gtatgtactt aagctggaag gtgaacattg gactgtctct gtgacccctg ggatgtctcc   1740
ctctttgctc ccccttgaat gcgtccaggg ctgttgtgat cataagagcg gtcttggttc   1800
cccagatacg gtcgaagttt ccggatttga ccctgcctgc cttgaccggc tggctgaggt   1860
gatgcacctg cctagcagtg ccatcccagc cgctctggcc gaaatgtccg gcgattccga   1920
tcgtccggct tccccggtca ccactgtgtg gacggtttcg cagttctttg cccgccacac   1980
aggagggaat caccctgacc aggtgtgctt aggaaaaatc attagccttt gtcaagtgct   2040
tgagagttgc tgctgtttcc agaacaaaac caaccgggcc accccggaag aggtcgcggc   2100
aaaaattgac ctgtacctcc gcggagcaac aggtcttgaa gaatgcttgg ccaggcttga   2160
gagggctcgc ccaccgagtg taatggacac ctcctttgat tggaatgttg tgcttcctgg   2220
gtttgaggcg gcaactcaga caaccaaacc gccccaggtc aaccagtgtc gcgctctggt   2280
ccctgttgtg actcaagagt ctttggacaa tggctcggtt cctctgaccg ccttctcgct   2340
gtccaattac tactaccgcg cgcaaggaga cgaggttcgt caccgtgata ggttaaacgc   2400
cgtactctcc aagttggagg gtgctgttcg agaagaatac gggctcatgc caactggacc   2460
tggcccgcga cccgcactgc cgagtgggct tgacgagctt aaagaccaga tggaggagga   2520
tctgctgaaa ctagccaatg cccagacaac ttcagaaatg atggcctggg cagccgagca   2580
ggttgatcta aaagcttggg ttaaaaacta cccacggtgg acaccaccgc cccctccacc   2640
aagagtccag cctcgaaaaa caaagcctgt caagagtttg ccagagagca agcctgtccc   2700
cgccccgcgc aggaaggtta ggtccgattg tggcagcccg attttattgg gcgacaatgt   2760
tcctaacagt tgggaagatt tgactgttgg tggccccctt gatctctcga cctcacccga   2820
gccggtgaca cctccgagtg agcttgcgct catgtccgca ccgcaacaca cttttaggtc   2880
ggtgataccc ttgggtgaac cggccccagt tcccgcattg cgcaaaactg tgccccgacc   2940
ggtaacaccc ttgagcgagc cgatccctgt gtccgcaccg caatgcaagt ttcagcaggt   3000
ggaaaaagcg gatctggcgg cagcagcgct ggcgtaccag gacgagcccc tagatttgtc   3060
tgcatcctca caaactgaat atgaggcttc tcccctagaa ccactgcaga gcatgggcgt   3120
```

-continued

```
tctaaaggtg gaaggacaag aagctgagga agtcctgagt ggaatctcgg acatactgga   3180
tgacatcaac ccggtgcctg tatcatcaaa cggctccctg tcaagcgtga ggatcacacg   3240
cccaaaatac tcagctcaag ccatcatcga ctcgggcggg ccctgcagtg ggcacctcca   3300
agggataaag gaaacatgcc tcagtatcat gcgtgaggca tgtgatgcga ctaagcttga   3360
tgaccctact acgcaggaat ggctttctcg catgtgggat agggtggaca tgctgacttg   3420
gcgcaacacg tctgcttacc aggcgcttcg caccttagat agcaggtttg agtttctccc   3480
aaaaatgata ctcgagacac cgccgcccta tccgtgtgag tttgtgatga tgcctcacac   3540
gcctgcacct tctgtaagtg cggagagtga tcttaccatt ggctcagtcg ccactgaaga   3600
tgttccacgc atcctcggga aaatagaaga tgtcggcgag atgaccaacc agggaccctt   3660
ggcattctcc gaggaagaac cggtggatca ccaacctgcc aagggctccc ggtcattgtc   3720
gcggaggcct gacgagagta caccaactct gtccgcaagc gcaggtggca ccgacttacc   3780
caccgatttg ccgctttcag acggtgtgga tgcggacggg ggggggccgt tacggacggt   3840
aaaaaacaaa actcaaaggc tctttgacca actgagccgt caggttttta acctcgtctc   3900
ccatctccct gttttcttct cacgccttct cctacctggc ggtggttatt ctccgggtga   3960
ttggggcttt gcagctttta ctctattgtg cctctttttg tgttatagct acccagcctt   4020
tggtattgct cccctttttgg gtgtattttc tgggtcttct cggcgcgttc gaatgggggt   4080
ttttggctgc tggttggctt ttgctgttgg cctgttcaag cctgtgtccg acccagtcgg   4140
cactgcttgt gagtttgact cgccagagtg tagaaacatc cttctttctt ttgagcttct   4200
caaaccttgg gaccctgttc gcagccttgt tgtgggcccc gtcggtctcg gtcttgccat   4260
tcttggcagg ttactgggcg gggcacgctg tatctggcac tttttgctta ggcttggcat   4320
tgttacagat tgtatcctgg ctggagctta tgtgctttct caaggtaggt gtaaaaagtg   4380
ctggggatct tgtataagaa ctgctcctag tgaggtcgcc tttaacgtgt ttccttttac   4440
acgtgcgacc aggtcgtcac ttaccaactt gtgcgatcgg ttttgtgcgc caaaaggcat   4500
ggaccccatt ttcctcgcca ctgggtggcg cgggtgctgg accggccgaa gccccattga   4560
gcaaccctct gaaaaaccca tcgcgtttgc ccagttggat gaaaagaaga ttacggctaa   4620
gactgtggtc gcccagcctt atgaccccaa ccaagccgta aagtgtttgc gggtgttaca   4680
ggcgggcggg gtgatggtgg ctgaggcagt tccaaaagtg gtcaaggttt ccgctgtccc   4740
attccgagcc cccttctttc ccactggggt gaaagttgat cctgggtgca ggatcgtggt   4800
tgaccccgac accttcactg cagctctccg gtctggttac tccaccacaa acctcgtcct   4860
tggtgtaggg gactttgccc agctgaatgg attaaaaatt aggcaaattt ccaagccttc   4920
tggaggaggc ccacacctca tggctgccct gcatgttgct tgctcgatga ccttgcacat   4980
gcttgctggg atttacgtga ctgcggtggg ttcttgcggc accggcacca acgatccgtg   5040
gtgcgctaac ccgtttgccg tccctggcta tggacctgga tctctctgca cgtccaaatt   5100
gtgcatctcc caacatggcc tcaccctgcc cttaacagca cttgttgcgg gattcggtat   5160
tcaggaaatt gccttggtcg ttttgatttt tgtttccatc gggggcatgg ctcataggtt   5220
gagttgtaag gctgatatgc tgtgtgtttt gcttgcaatc gccagctatg tttgggtacc   5280
tctaacctgg ttgctttgtg tgtttccctg ctggttgcgc tgtttttctt tgcacccact   5340
caccatccta tggttggtgt ttttcttgat ttctgtaaat atgccttcag gaatcttggc   5400
catggtgttg ttggtttctc tttggcttct tggacgttat actaatgtcg ctggtcttgt   5460
```

-continued

```
caccccttat gatattcacc attacaccag tggcccccgc ggtgttgccg ccttggctac   5520
agcaccagat gggacctact tggccgctgt ccgccgcgct gcgttgactg gccgcaccat   5580
gctgtttacc ccgtctcagc ttgggtccct tcttgagggc gcttttagaa ctcaaaagcc   5640
ctcgttgaac accgtcaatg tggtcggtcc tccatgggct ctggcggggt gttcaccatc   5700
gacgggaaaa tcaagtgcgt aactgccgca catgtcctta cgggcaattc agctagggtt   5760
tccggggtcg gtttcaacca aatgcttgac tttgatgtaa aaggagactt cgccatggcc   5820
gattgcccgg attggcaagg ggctgctccc aagacccaat tctgcaagga tggatggact   5880
ggccgtgcct actggctaac atcctctggc gtcgaacccg gtgtcattgg aaaaggattc   5940
gccttctgct tcaccgcgtg cggcattccg ggtccccagt gatcaccgag gccggtgagc   6000
ttgtcggtgt ccacacggga tcaaataaac aaggaggagg catcgtcacg cgcccctcag   6060
gccagttttg taatgtgtca cccgtcaagc taagcgaatt aagtgaattc tttgctgggc   6120
ctaaggtccc gctcggtgat gtgaaggttg gcagccatat aatcaaagat ataggcgagg   6180
taccttcaga tctttgcgcc ttgcttgctg ccaaacctga actggaagga ggcctctcca   6240
ccgtccaact tctgtgtgtg ttttttctcc tgtggaggat gatgggacat gcctggacgc   6300
ccttggttgc tgtggggttc tttatcttga atgaggttct tccagctgtc ctggtccgga   6360
gtgtcttctc ctttggaatg tttgtgctat cctggctcac accatggtct gcgcaagttc   6420
tgatgatcag gcttctaaca gcagctctta acaggaacag aggttcactt gccttttaca   6480
ccctcggtgc aataaccggc tttgtccaga tcttgcggtt actcagggac atccgttgca   6540
ggcagtgatg aatttgagca cctatgcatt cctgcctcgg atgatggttg tgacctcacc   6600
agtcccagtg atcgcgtgtg gtgttgcgca cctgcttgcc atcattttgt acttgtttaa   6660
gtaccgcggc ctgcacaaga tccttgttgg cgatggagcg ttctctgcgg ctttcttcct   6720
gcgatacttt gccgagggaa agttgaggga aggggtgtcg caatcctgcg gaatgaatca   6780
tgagtcactg actggtgccc tcgccatgaa actcaatgac gaggacttgg atttccttac   6840
gaaatggact gattttaagt gctttgtttc tgcatccaac atgaggaatg cagcgggcca   6900
atttatcgag gctgcctatg ctaaagcact tagagtagaa cttgcccagt tggtacaggt   6960
tgataaggtt cgaggcacta tggccaaact agaagctttt gctgacaccg tggcacccca   7020
actctcgccc ggtgacattg ttgtcgctct tggccatacg cctgttggca gtatcttcga   7080
cctaaaggtt ggtagcacta agcacaccct ccaagccatt gagaccagat ttcttgctgg   7140
gtccaaaatg accgtggcgc gtgtcgtcga cccgaccccc acgcccccac ccgcacccgt   7200
gcccatcccc ctcccaccga aagttctgga gaatggtccc aacgcttggg gggatgagga   7260
tcgtttgaat aaaaaaaaaa ggcgcaggat ggaagccctc ggcatctatg ttatgggtgg   7320
gaaaaagtac cagaaatttt gggataagaa ctccggtgat gtgttttatg aggaggtcca   7380
taataacaca gatgagtggg agtgcctcag agttggcgac cctgccgact ttgaccctga   7440
gaagggaact ctgtgtgggc acgtcaccat tgaggataag gcttatcatg tttacgcctc   7500
cccatccggt aagaagttcc tggtccccgt caacccagaa aacggaagag tccaatggga   7560
agctgcaaag ctttccgtgg agcaggccct tggtatgatg aacgtcgacg gcgaactgac   7620
tgccaaagaa ctggagaaac tgaaaagaat aattgataaa ctccagtgcc tgactaagga   7680
gcagtgttta aactgctagc cgccagcggc ttgacccgct gtggtcgcgg cggcttggtt   7740
gtcactgaga cagcggtaaa aatagtcaaa tttcacaacc ggaccttcac cctgggacct   7800
gtgaatttaa aagtggccag tgaggttgag ttaaaagacg cggtcgagca caaccaacac   7860
```

-continued

```
ccggttgcaa gaccggttga tggtggtgtt gtgctcctgc gttctgcagt tccttcactt   7920
atagacgtcc tgatctccgg tgccgacgca tctcctaagt tgctcgccca tcacgggccg   7980
gggaacactg ggatcgatgg cacgctttgg gatttcgagt ctgaggccac taaagaggaa   8040
gtcgcactta gtgcgcaaat aatacaggct tgtgacatca ggcgcgggga cgcacccaaa   8100
attgatctcc cctacaagct gtaccctgtt aggggcaacc ctgagcgggt gaaaggagtt   8160
ctgaggaata caaggtttgg agacatacct tacaagaccc ccagtgacac tgggagcccg   8220
gtgcacgcgg ccgcctgcct tacgcctaac gccactccgg tgactgacgg gcgctccatc   8280
ttggccacga ccatgccctc tgggtttgag ttgtatgtac cgaccattcc agcgtctgtc   8340
cttgattacc ttgattctag gcctgactgc cctaaacagt tgacagagca cggctgtgaa   8400
gatgccgcac tgagagacct ctccaaatat gacttgtcca cccaaggctt tgttttacct   8460
ggagttcttc gcctcgtgcg gaaatacctg tttgcccatg taggtaagtg cccacctgtt   8520
caccggcctt ctacttatcc tgctaagaat tctatggctg gactaaatgg gaacaggttc   8580
ccgaccaagg atattcagag cgtccctgaa atcgacgttc tgtgcgcgca ggctgtgcgg   8640
aaaactggca gactgttacc ccttgtaccc ttaagaagca gtattgcggg aagaagaaaa   8700
ctaggacaat actcggcacc aataacttca tcgcgctggc tcatcgggca gcgttgagtg   8760
gtgtcaccca gggcttcatg aaaaaggcat ttaactcgcc catcgccctc ggaaaaaaca   8820
aatttaagga gctacaaact ccggtcctag gcagatgcct tgaagctgat cttgcatcct   8880
gcgaccgatc cacacctgca attgtccgtt ggtttgccgc caatcttctt tatgaacttg   8940
cctgtgctga agatcacctg ccatcttatg tgctgaactg ttgccacgac ttattggtca   9000
cgcagtctgg cgcagtgact aagagaggtg gcctgtcatc tggcgacccg atcacctctg   9060
tgtctaacac catttacagc ttggtgatct atgcacagca catggtgctc agttacttca   9120
aaagtggtca cccccacggc cttctgttct tacaagacca gctaaagttt gaggacatgc   9180
tcaaggttca accccctgatc gtctattcgg acgacctcgt gctgtatgcc gagtctccca   9240
ccatgccaaa ctaccactgg tgggttgaac atctgaattt aatgctgggg tttcagacgg   9300
acccaaagaa gacagctata acagactcgc catcatttct aggctgcagg ataataaatg   9360
gacgccagct agtccctaac cgtgacagga ttctcgcggc cctcgcctac catatgaagg   9420
cgagtaatgt ttctcaatac tacgcttcgg cggctgcaat actcatggac agctgtgctt   9480
gtttagagta tgatcctgaa tggtttgaag aacttatagt tggaatatcg cagtgcgccc   9540
gcaaggacgg ctatagcttt cccggtccgc cgttcttctt gtctatgtgg gaaaaactca   9600
ggtctaatta tgaggggaag aagtcgagag tgtgcgggta ctgcggggcc ccggccccgt   9660
acgctactgc ctgtggcctc gatgtctgca tttaccacac ccacttccac cagcattgtc   9720
cggttataat ttggtgtggc cacccagcgg gttctggttc ttgtagtgag tgcaaatccc   9780
ccgtggggaa aggcacaagc cctctggacg aggtgttaaa acaagtcccg tataaacccc   9840
cacggaccat aatcatgcat gtggaacagg gtcttacccc ccttgaccca ggcagatacc   9900
agactcgccg cggattggtc tccgttaggc gcggaatcag ggggaatgaa gttgaactac   9960
cagacggtga ttacgctagt accgccttgc tccccacctg taaagagatc aacatggtcg  10020
ctgtcgcttc taatgtgttg cgcagcaggt tcatcatcgg tccgcccggt gctgggaaga  10080
catactggct tctacaacag gtccaggatg gtgatgtcat ttacacacca actcaccaga  10140
ccatgcttga catgattaga gctttgggga cgtgccggtt caacgtccca gcaggcacaa  10200
```

-continued

```
cgctgcaatt ccctgtcccc tcccgtaccg gtccgtgggt tcgcatccta gccggcggtt  10260
ggtgtcctgg caagaattcc ttcctggatg aagcagcgta ttgcaatcac cttgatgtct  10320
tgaggcttct tagcaaaact accctcacct gtctgggaga tttcaaacaa ctccacccag  10380
tgggttttga ttctcattgc tatgtttttg acactatgcc tcagactcaa ctgaagacca  10440
tctggagatt cggacagaat atttgtgatg ccatccaacc agattacaga gacaaactca  10500
tgtccatggt caacacaacc cgtgtaacct acgtggagag acctgtcagg catgggcaag  10560
tcctcacccc ctaccacagg gaccgagagg acgacgccat caccattgac tccagccaag  10620
gcgccacatt tgatgtggtt acattgcatt tgcccactaa agattcactc aacaggcaaa  10680
gagcccttgt tgctatcacc agggcaagac atgctatctt tgtgtatgac ccacacaggc  10740
aactgcagag cctatttgat cttcctgcga aaagcacccc tgtcaacctc gcagtgcacc  10800
gcgacgggca gctgatcgtg ctagatagaa ataacaaaga atgcacggtt gctcaggctc  10860
ttggcaacgg agataaattt agggccacag acaagcgcgt tgtagactct ctccgcgcca  10920
tttgtgctga tctagaaggg tctagctctc cgctccccaa ggtcgcccac aacttgggat  10980
ttcatttctc acctgatttg acacagtttg ccaaactccc agtagaactt gcacctcact  11040
ggcccgtggt gacaacccag aacaatgaaa agtggccaga tcggctggtt gctagccttc  11100
gccctattca taaatatagc cgcgcgtgca ttggtgccgg ctatatggtg ggcccctcgg  11160
tgtttctagg cacccctggg gtcgtgtcat actacctcac aaaatttatt aagggcgagg  11220
ctcaagtgct tccggagacg gtcttcagca ccggtcgaat tgaggtagat tgccgggaat  11280
accttgatga tcgggagcca gaagttgctg cgtccctccc acatgccttc attggcgacg  11340
tcaaaggcac taccgttggg ggatgtcacc atgtcacttc caaatacctt ccgcgcttcc  11400
ttcctaagga atcagttgcg gtagtcgggg tttcgagccc cggaaaagcc gcgaaagcag  11460
tgtgcacact gacagatgtg tacctcccag accttgaagc ctacctccac ccggaaaccc  11520
agtccaagtg ctggaaattg atgttggact tcaaggaagt ccgactgatg gtctggaaag  11580
acaagacggc ctatttccaa cttgaaggcc gctatttcac ctggtatcag cttgctagct  11640
acgcctcgta catccgtgtt cctgtcaact ctgcggtgta cttagacccc tgcatgggcc  11700
ctgccctttg caacaggaga gttatcgggt ccactcattg gggagctgac ctcgcagtca  11760
ccccttatga ttacggtgcc aaaattattt tgtctagtgc gtaccatggt gaaatgcctc  11820
ccgggtacaa gattctggcg tgcgcagagt tctcgcttga cgacccagtc aagtacaagc  11880
acacctgggg gtttgaatcg gatacagcgt atctgtatga gttcaccgga aacggtgagg  11940
actgggagga ttacaatgat gcgtttcgtg cgcgccagga ggggaaagtc tataaggcca  12000
ctgccaccag catgaagttt tattttcccc cgggccctat cattgaacca actttaggcc  12060
tgaattgaaa tgaaatgggg tctatgcaaa gcctttttga caaaattggc caacttttcg  12120
tggatgcttt cacggagttc ttggtgtcca ttgttgatat cattatattt ttggccattt  12180
tgtttggctt caccatcgcc ggttggctgg tggtcttttg catcagattg gtttgctccg  12240
cgctactccg tgcgcgccct gccattcact ctgagcaatt acagaagatc ctatgaggcc  12300
tttctttctc agtgccaggt ggacattccc acctggggat ttaaacatcc tttggggatg  12360
ttttggcacc ataaggtgtc aaccctgatt gatgaaatgg tgtcgcgtcg aatgtaccgc  12420
atcatggata aagcaggaca ggctgcctgg aaacaggtgg tgagcgaggc tacgctgtct  12480
cgcattagta gtttggatgt ggtggctcac tttcagcatc ttgccgccat tgaagccgag  12540
acctgtaaat atttggcctc tcggctgccc atgctacaca acctgcgcat gacagggtca  12600
```

-continued

```
aatgtaacca tagtgtataa tagtactttg aatcaggtgc ttgctatttt tccaacccct  12660
ggttcccggc caaagcttca tgattttcag caatggctaa tagctgtaca ttcctctata  12720
ttttcctctg ttgcagcttc ttgtactctt tttgttgtgc tgtggttgcg ggttccaatg  12780
ctacgtattg cttttggttt ccgctggtta ggggcaattt ttccttcgaa ctcacagtga  12840
actacacggt gtgtccacct tgcctcaccc ggcaagcagc catagaggcc tacgaacctg  12900
gcaggtctct ttggtgcagg atagggtatg atcgctgtgg ggaggacgat catgacgaac  12960
tagggtttgt ggtgccgtct ggcctctcca gcgaaggcca cttgaccagt gtttacgcct  13020
ggttggcgtt cctgtctttc agttacacag cccagttcca tcctgagata ttcgggatag  13080
ggaatgtgag tcaagtttat gttgacatca ggcatcaatc catttgcgcc gttcacgacg  13140
ggcagaacgc cactttgcct cgccatgaca atatttcagc cgtgttccag acttattacc  13200
aacatcaagt cgacggcggc aattggtttc acctagaatg gctgcgtccc ttcttttcct  13260
cttggttggt tttaaatgtc tcttggtttc tcaggcgttc gcttgcaagc catgtttcag  13320
ttcgagtctt gcagacatta agaccaacac caccgcagcg gcaggctttg ctgtcctcca  13380
agacatcagt tgccttaggt atcgcaactc ggcctctgag gcgtttcgca aaatccctca  13440
gtgtcgtacg gcgataggga cacccatgta tattactgtc acagccaatg taaccgatga  13500
gaattatttg cattcctctg accttctcat gctttcttct tgccttttct acgcttctga  13560
gatgagtgaa aagggattta aagtggtatt tggcaatgtg tcaggcatcg tggctgtgtg  13620
cgtcaacttt accagctacg tccaacatgt caaggaattt acccaacgct ccttggtagt  13680
cgaccatgtg cggctgctcc atttcatgac acctgagacc atgaggtggg caactgtttt  13740
agcctgtctt tttgccattc tgttggccat ttaaatgttt gagtatgttg gggaaatgct  13800
tgaccgcggg ctattgctcg tcattgcttt ttttgtggtg tatcgtgccg tcttggtttg  13860
ttgcgctcgc cagcgccaac agcatcaaca gccctcattt acagttgatt tataacttga  13920
cgctatgtga gctgaatggc acagattggt tagctggtga atttgactgg gcagtggagt  13980
gttttgtcat tttcctgtg ttgactcaca ttgtctccta tggtgccctc accaccagcc  14040
atttccttga cacagtcggt ctggtcactg tgtctaccgc cggcttttcc cacgggcggt  14100
atgttctgag tagcatctac gcggtctgtg ccctggctgc gttgatttgc ttcgtcatta  14160
ggtttacgaa gaattgcatg tcctggcgct actcatgtac cagatatacc aactttcttc  14220
tggacactaa gggcagactc tatcgttggc ggtcgcctgt catcatagag aaaaggggta  14280
aagttgaggt cgaaggtcat ctgatcgacc tcaagagagt tgtgcttgat ggttccgcgg  14340
caacccctat aaccaaaatt tcagccgagc aatggggtcg tccttagatg acttctgcca  14400
tgatagcacg gctccactaa aggtgctttt ggcgttctct attacctaca cgccagtgat  14460
gatatatgcc ctaaaagtaa gtcgcggccg actgttaggg cttctgcacc ttttgatctt  14520
cctaaattgt gctttcacct tcgggtacat gacattcgtg cactttcaga gcacaaacaa  14580
ggtcgcgctc actatgggag cagtagttgc actcctttgg ggggtgtact cagccataga  14640
aacctggaaa ttcatcacct ccagatgccg tttgtgcttg ctaggccgca agtacatttt  14700
ggcccctgcc caccacgttg aaagtgccgc aggctttcat ccgatagcgg caaatgataa  14760
ccacgcattt gtcgtccggc gtcccggctc cactacggtt aacggcacat tggtgcccgg  14820
gttgaaaagc ctcgtgttgg gtggcagaaa agctgtcaaa cagggagtgg taaaccttgt  14880
taaatatgcc aaataacaac ggcaagcagc agaagaaaaa gaagggggat ggccagccag  14940
```

-continued

```
tcaatcagct gtgccagatg ctgggtaaga tcatcgctca gcaaaaccag tccagaggca  15000
agggaccggg aaagaaaaac aagaagaaaa acccggagaa gccccatttt cctctagcga  15060
ctgaagatga tgtcagacat cacttcacct ctggtgagcg gctattgtgt ctgtcgtcaa  15120
tccagacagc ctttaatcaa ggcgctggaa tttgtaccct gtcagattca gggaggataa  15180
gttacactgt ggagtttagt ttgccgacgc atcatactgt gcgcctgatc cgcgtcacag  15240
cgtcaccctc agcatgatga gctggcattc ttgaggcatc ccagtgtttg aattggaaga  15300
atgtgtggtg aatggcactg attgacattg tgcttctaag tcacctattc aattagggcg  15360
xaccgtgtggg ggcaaaattt aattggcgtg aaccacgcgg ccgaaattaa aaaaaaaaaa 15420
```

<210> SEQ ID NO 55
<211> LENGTH: 15103
<212> TYPE: DNA
<213> ORGANISM: Porcine reproductive and respiratory syndrome virus

<400> SEQUENCE: 55

```
nngacgtata ggtgttggct ctatgccttg acatttgtat tgtcaggagc tgtggccatt     60
ggcacagccc aaaaacttgc tcacggaaac acccttctct gacagcctcc ttcaggggag    120
cttggggtct gtccctagca ccttgcttcc ggagttgcac tgctttaccg tctctccacc    180
cctttaacca tgtctgggat gcttgatcgg tgcacgtgta cccccaatgc cagggtgttt    240
atggcggaag gccaagtcta ctgcacacga tgcctcagtg cacggtctct ccttcccctg    300
aatctccaag cttctgagct tggggtgcta ggcctattct acaggcccga agagccactc    360
cggtggacgt tgccacgtgc attccccact gttgagtgct cccccgccgg agcctgctgg    420
ctttctgcaa tctttccaat tgcacggatg accagtggaa acctgaactt ccaacaaaga    480
atggtacggg tcgcagctga gtttaacaga gccggccagt tcacccctgc agttttgaag    540
actctacaag tttatgaacg ggttgccgc tggtacccca ttgttggacc tgtccctgga    600
gtggccgttt tcgccaactc cctacatgtg agtgataaac ctttcccggg agcaactcac    660
gtgctaacca acctgccgct cccgcagaga cccaagcctg aagacttttg cccctttgag    720
tgtgctatgg ctactgtcta tgacattggt catgacgccg tcatgtatgt ggccgagggg    780
aaagtctcct gggcccctcg tggcggaaat gaagtgaaat ttgaaactgt ccccgaggag    840
ttgaaattga ttgcggaccg gctccgcacc tccatcccgc cccaccatgt agtggacatg    900
tctaagttcg ccttcacggc tcctgggcgt ggtgtttcta tgcgggttga acgccaacac    960
ggctgcctcc ccactgacac tgtccctgaa ggcaactgct ggtggagctt gtttaacttg   1020
ctcccactgg aagtccagaa caaagaaatc cgccatgcta accaatttgg ctaccagacc   1080
aagcatggtg tttctggcaa gtacctacag cggaggctgc aagttaatgg tctccgagca   1140
gtaactgacc caaatggacc tatcgtcgta cagtacttct ccgttaagga gagttggatc   1200
cgccacttga aactggcggg agaacccagc taccctgggt ttgaggacct cctcagaata   1260
agggttgagc ccaatacgtc gccattggct gacaaggatg aaaaaatttt ccggtttggc   1320
agtcacaagt ggtacggcgc tggaaagaga gcaaggaaag cacgctcttg tgcgactgcc   1380
acagtcgctg gccgcgcttt gtccgttcgt gaaacccggc aggccaaggg gcacgaggtt   1440
gccggcgcca acaaggctga gcacctcaaa cattattccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
attcaaatcc tcagacttcc tgcggccttg gacaggaacg gtgcttgtgt tagcgccaag   1680
```

-continued

```
tacgtactta agctggaagg tgagcattgg actgtcactg tgacccctgg gatgtctcct   1740
tctttgctcc ctcttgaatg tgttcagggc tgttgtgagc acaagggtgg tcttggttcc   1800
ccagatgcag tcgaggtctt cggatttgac cctgcctgcc ttgaccggct ggctgaggtg   1860
atgcacctgc ctagcagtgt tatcccagcc gccctggccg aaatgtccgg cgattccgat   1920
cgttcggctt ccccggtcac caccgtgtgg actgtttcgc agttctttgc ccgtcacaac   1980
ggagggaatc accctgacca ggcgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatggacacc tcctttgatt gggatgttgt gctccctggg   2220
gttgaggcgg caactcagac gaccgaactg ccccgggtca accagtgtcg cgctctggtc   2280
cctgttgtga ctcaaaagtc tctggacaat aactcggttc ctctgaccgc cttctcgctg   2340
tccaattact actaccgtgc acaaggtgac gagattcgtc accgtgacag gctaaacgcc   2400
gtactctcta agttggaggg ggctgttcga gaagaatatg ggctcatgcc gactggacct   2460
ggcccgcgac ccgcactgtc gagcgggctc gatgggctta aagacagatg gagagatctg   2520
ctgaaactag ccaacgccca gacaacctca gaaatgatgg cctgggcagc cgagcaggtt   2580
gatctagaag cttgggtcaa aagctaccca cggtggacac caccaccccc tccgccaaga   2640
gttcagcctc gaaaagcgaa gcctgtcagg agcttgccag agagcaagcc tgtccctgcc   2700
ccgcgcagga aggttagatc cgatcgtggc agcccggttt tgttgggcga caatgttcct   2760
aacagttggg aagacttgac tgtcggtggc cccccttgatc tcctgacccc acccgagtca   2820
gtgacacctc cagtgagctt gcgcttacgt ccgcgccgca acacactttt aggccggtga   2880
cacctttggg tgaaccggcc ccagttcccg caccgcgcag aactgtgtcc cgaccggtga   2940
catccttgaa tgggccgatc cttatgtccg caccgcggca caagtttcag caggtggaaa   3000
aagcaaattt ggcgacagca acgctgacgt accaggacga gcccctagat ttgtctgcat   3060
cctcacagac tgaatatgag gcttttcctc cagcaccact gcagaacatg ggtattccgg   3120
aggtggaagg gcaagaagct gaggaagtcc tgagtggaat ctcgatatac tggatgacat   3180
caattctgcc ctgtatcatc aagcggttcc ctgtcaagcg tagcgatcac acgcccaata   3240
ggtgcggaga gtgaccttac cattggctca gtcgccactg aagatattcc acgcatcctc   3300
gggaaaatag aagatgccgg tgagatgtcc aaccagggac ccttggcatt ctccgaggaa   3360
aaaccggtag atgaccaacc taccaaagac ccccggatgt cgtcgcggag gtcagacaag   3420
agcgcaccag ctcggtccgc aggcacaggt ggcgtcggct tgtttactga tttgcccctt   3480
cagacggtgt ggatgcggac ggggggggcc cgttacggac ggtaaaaaca aaaactgaaa   3540
ggttctttga ccagctgagc cgtcaggttt ttaacctcgt ctcccatctc cctgttttct   3600
tctcatacct tttcaaacct ggcagtggtt attctccggg tgattggggt tttgcagctt   3660
ttactctatt gtgcctcttt ttatgttaca gttatccagc ctttggtatt gctcccctct   3720
tgggtgtatt ttctgggtct tctcggcgcg tccgaatggg ggtttttggt tgctggttgg   3780
cttttgctgt tggtctgttc aaatctgtgc ccgacccagt cggcactgct tgtgaatttg   3840
actcgccaga gtgcagaaac atccttcatt cttttgagct tctcaaacct tgggaccctg   3900
ttcgcagcct tgttgtgggc cccgtcggtc tcggccttgc cattcttggc aggttactgg   3960
gcggggcacg ctacatctgg cactttttgc ttaggcttgg cattgttgca gattgtatct   4020
```

-continued

```
tggctggagc ttatgtgctt tctcaaggta ggtgtaaaaa gtgctgggga tcttgtataa   4080
gaactgctcc taatgaggtc gcttttaacg tgtttccttt cacacgtgcg accaggtcgt   4140
cacttgttga cctgtgtgat cggttttgcg cgccaaaagg catggacccc atttttctcg   4200
ccactgggtg gcgcgggtgc tgggccggcc gaagccccat tgagcaaccc tctgaaaaac   4260
ctatcgcgtt tgcccagttg gatgaaaaga aaattacggc taggactgtg gtcgcccagc   4320
cttatgaccc caaccaagcc gtaaagtgct tgcgggtatt gcaggcgggt ggggtgatgg   4380
tggctgaggc ggtcccaaaa gtggtcaagg tttccgctgt tccattccga gccccctttt   4440
ttcctaccgg agtgaaagtt gaccctgaat gtagggtcgt ggttgaccct gacactttca   4500
ctgcagctct ccggtctggc tactccacca caaaccttgt ccttggtgta ggggactttg   4560
cccagctgaa tggattaaaa atcaggcaaa tttccaagcc ttcaggagga ggcccacatc   4620
tcatggctgc cctgcatgtt gcctgctcga tggttttgga catgcttgct gggatttatg   4680
tgactgcggt gggttcttgc ggcaccggca ccaacgatcc gtggtgcgct aacccgtttg   4740
gcgtccctgg ctacggacct gcctccctct gcacgtccag attgtgcatt tcccagcatg   4800
cccttaccct gcccttgaca gcacttgtgg cgggattcgg tatccaagaa attgccttag   4860
tcgttttgat tttgtttcc atcggaggca tggctcatag gttgagttgt aaagctgata   4920
tgctgtgtat tttgcttgca attgccagca atgtttgggt acctcttacc tggttgcttt   4980
gtgtgtttcc ttgctggttg cgctgttttt ctttgcaccc ccttaccatc ctatggttgg   5040
tgtttttctt gatttctgtg aatatgcctt caggaatctt ggccatggtg ttgttggttt   5100
ctctttggct tcttggtcgt aatactaatg ttgctggtct tgtcaccccc tacgacattc   5160
atcattacac cagtggcccc cgcggtgttg ccgccttggc taccgcacca gatgggactt   5220
acttagccgc tgtccgccgt gctgcgttga ctggccgcac catgctgttc accccgtccc   5280
agcttgggtc tcttcttgag ggtgctttca gaactcgaaa gccctcactg aacaccgtca   5340
atgtggtcgg gtcctccatg ggctctggcg gggtgtttac catcgacggg aaagtcaagt   5400
gcgtaactgc cgcacatgtc cttacgggta actcagctag ggtttccggg gtcggcttca   5460
atcaaatgct tgactttgac gtaaaggggg atttcgccat agccgattgc ccgaattggc   5520
aaggggctgc ccccaagacc caattctgcg aggatggatg gactggccgt gcctattggc   5580
taacatcctc tggcgtcgaa cccggcgtca ttggaaaagg attcgccttc tgcttcaccg   5640
cgtgcggcga ttccgggtcc ccagtgatca ccgaggccgg tgagcttgtc ggcgttcaca   5700
cgggatcaaa taaacaaggg ggaggcatcg tcacgcgccc ctcaggccag ttttgtaatg   5760
tggcacccat caagctaagc gaattaagtg aattctttgc tgggcccaag gtcccgctcg   5820
gtgatgtgga ggttggcaac catataatta aagacatagg cgaagtgcct tcagatcttt   5880
gtgccttgct cgctgccaaa cctgaactgg aaggaggcct ctccaccgtc caacttcttt   5940
gtgtgttttt tctcctgtgg agaatgatgg gacatgcctg gacgcccttg gttgctgtgg   6000
gtttctttat cttgaatgag gttctcccag ccgtcctggt ccggagtatt ttctcctttg   6060
gaatgtttgt gctatcctgg ctcactccat ggtctgcgca agttctaatg atcaggcttc   6120
taacagcagc tcttaacagg aacagatggt cacttgcctt tttcagcctt ggtgcggtga   6180
ccggttttgt cgcagatctt gcggccactc aggggcatcc gttgcagaca gtgatgaatt   6240
tgagtaccta tgcattcctg cctcggatga tggttgtgac ctcaccagtc ccagtgatcg   6300
cgtgcggtgt cgtgcaccta cttgccatca ttttgtactt gtttaagtac cgtggcctgc   6360
actatatcct tgttggcgat ggagtgttct ctgcggcttt cttcctgcgg tactttgccg   6420
```

-continued

```
agggaaagtt gagggaaggg ttgtcccaat cctgcggaat gaatcatgag tccctaactg   6480
ttgcccttgc tatgagactc aatgacgagg acttggattt ccttacgaaa tggactgatt   6540
ttaagtgctt tgtttctgcg tccaacatga ggaatgcagc gggtcaattt atcgaggctg   6600
cctatgctaa agcacttaga gtagaacttg cccagttggt gcaggttgat aaagttcgag   6660
gtactttggc caaacttgaa gcttttgctg ataccgtggc accccaactc tcgcccggtg   6720
acattgttgt cgctctcggc catacgcctg ttggcagtat cttcgaccta aaggttggta   6780
gcaccaagca taccctccaa gccattgaaa ccagagtcct tgcagggtcc aaaatgaccg   6840
tggcgcgcgt cgtcgacccg acccctacgc ccccacccgc acccctgtcc atccccctcc   6900
caccgaaagt cctggagaat gcccccaacg cttgggggga tgaggaccgt ttgaataaga   6960
agaagaggcc caggatggaa gccctcggca tctatgttat gggtgggaaa aagtaccaga   7020
aattttggga caagaattcc ggtgatgtgt tttatgagga ggtccatgac aacacagatg   7080
agtgggagtg tctcagagtc ggcgaccctg ccgactttga ccctgagaag ggaactctgt   7140
gtggacatgt caccattgaa gataaggctt accatgttta cacctcctca tctggtaaga   7200
agttcttggt ccccgtcaac ccagagaatg gaagagtcca gtgggaagct gccaagcttt   7260
ccgtggagca gcccctaggc atgatgaacg tcgacggtga actgactgcc aaagaactgg   7320
agaaactgaa aagaataatt gataaactcc agggcctgac taaggagcag tgtttaaact   7380
gctagccgcc agcggcttga cccgctgtgg tcgcggcggc ttagttgtta ctgagacagc   7440
ggtgaagatc gtcaaatttc acaaccggac cttcaccttg ggacctgtga atttaaaagt   7500
ggccagtgag gttgagctga aagacgcggt tgagcacaac cagcacccgg ttgcaagacc   7560
ggttgatggt ggtgttgtgc tcctgcgttc tgcagttcct tcgcttgtcg acgtcttaat   7620
ctccggtgct gatgcatctc ccaagttact tgcccatcac gggccgggaa acactgggat   7680
cgatggcacg ctctgggatt ttgagtccga agccattaaa gaggaagtcg cacttagtgc   7740
gcaaataata caggcttgtg acattaggcg cggtgacgca cctgaaattg gtctccctta   7800
caaactatac cctgttaggg gcaaccctga gcgggtaaaa ggagttttgc agaatacaag   7860
gtttggagac ataccttaca aaacccccag tgacaccgga agcccagtgc acgcggctgc   7920
ctgccttacg cccaacgcca ccccggtgac tgatgggcgc tctgtcttgg ccacgaccat   7980
gccctccggg ttcgagttgt atgtacccac cattccggcg tctgttcttg attatcttga   8040
ttctaggcct gactgcccta aacagttgac agagcacggc tgtgaagatg ccgcattgag   8100
agatctctcc aagtatgact tgtccaccca aggctttgtt ttgcctggag ttcttcgcct   8160
tgtgcggaag tacctgtttg cccacgtggg taagtgcccg tccgttcatc ggccttccac   8220
ttaccccgcc aaaaattcta tggctggaat aaatgggaac aggtttccaa ccaaggacat   8280
tcagagcgtc cctgaaatcg acgttctgtg cgcacaggct gtgcgagaaa actggcaaac   8340
tgttacccct tgtaccctta agaaacagta ctgcgggaag aagaagacta ggaccatact   8400
cggcaccaac aacttcattg cgctggccca ccgggcagcg ttgagtggtg tcacccaagg   8460
cttcatgaaa aaagcattta actcgcccat cgccctcggg aaaaacaaat ttaaagagct   8520
acagactccg gtcctcggca ggtgccttga agctgatctt gcatcctgcg atcgatccac   8580
acctgcaatt gtccgctggt ttgccgccaa tcttctttat gaactttcct gtgctgaaga   8640
gcatctaccg tcgtacgtgc tgaactgctg ccacgaccta ctggtcacgc agtccggcgc   8700
agtgactaag agaggtggcc tgtcgtctgg tgacccgatc acctctgtgt ccaacaccat   8760
```

-continued

```
ttacagcttg gtgatctatg cacagcacat ggtgcttagt tacttcaaaa gtggtcatcc   8820
ccatggcctt ctgtttttac aagaccagct aaagtttgag gacatgctca aggtccaacc   8880
cctgatcgtc tattcggacg accttgtgct gtatgccgag tctcccacca tgccaaacta   8940
ccattggtgg gttgaacatc tgaatctgat gttggggttt cagacggacc caaagaagac   9000
aaccataaca gactcaccat catttctagg ctgtagaata gtaaatggac gccagctagt   9060
ccccaaccgt gacaggattc tcgcggccct cgcctaccac atgaaggcga gtaatgtttc   9120
tgaatactac gcctcagcgg ctgcaatact catggacagc tgtgcttgtt tagagtatga   9180
tcctgaatgg tttgaagaac ttgtagttgg aatagcgcag tgcgcccgca aggacggcta   9240
cagctttccc ggcacgccgt tcttcatgtc catgtgggaa aaactcaggt caaattatga   9300
ggggaaaaag tcgagagtgt gcgggtactg cggggccccg gccccgtacg ctactgcctg   9360
cggccttgac gtctgcattt accacaccca cttccaccag cattgtccag tcacaatctg   9420
gtgcggccat ccagcgggtt ctggttcttg taatgagtgc aagtccccca tagggaaagg   9480
cacaagcccc ctagacgagg tgctagaaca agtcccgtat aagcccccac ggaccgtaat   9540
tatgcatgtg gagcagggtc ttaccccccct tgacccaggt aggtaccaga ctcgccgcgg   9600
attagtctcc gtcaggcgtg gaatcaaggg aaatgaagtt gaactaccag acggtgatta   9660
tgctagtacc gccttgctcc ccacctgtaa agagatcaac atggtcgctg tcgcttctaa   9720
tgtgttgcgc agcaggttca tcatcggtcc acccggtgct gggaaaacat actggctcct   9780
tcaacaagtc caggatggtg atgttattta cacaccaact caccagacca tgcttgacat   9840
gatcagagct ttggggacgt gccgattcaa tgtccctaca ggcacaacac tgcagttccc   9900
tgtcccctcc cgtaccggtc cgtgggttcg catcctagcc ggtggttggt gtcctggcaa   9960
gaattccttc ctggatgaag cagcgtatta caatcacctt gatgtcttga ggcttcttag  10020
taaaactacc ctcacctgtc tgggagactt taaactactc cacccagtgg gttttgattc  10080
ccattgctat gtttttgaca tcatgcctca gactcaatta aagaccatct ggagatttgg  10140
acagaatatc tgtgatgcca ttcaaccaga ttacagggac aaactcatgt ccatggtcaa  10200
cacaacccgt gtaacttacg tggaaaaacc cgtcaggtat gggcaagtcc ttacccccta  10260
ccataaggac cgagaggacg gcgccatcac cattgactcc agtcaaggtg ccacgtttga  10320
tgtggttaca ttgcatttgc ccactaaaga ttcactcaac aggcaaagag cccttgttgc  10380
tatcactagg gcaagacatg caatttttgt gtatgaccca cacaagcaac tgcagagcct  10440
gtttgatctc cctgcaaaag gcacacccgt caacctcgct gtgcaccgcg acgggcagct  10500
tattgtgctg gatagaaata acaaggaatg cacggttgct caggctctag gcaatggaga  10560
taaatttagg gccacagaca aacgcgttgt ggattctctc cgcgccattt gtgctgatct  10620
agaagggtcg agctctccgc tccccaaggt cgcacacaac ttgggatttt atttctcacc  10680
tgatttaacg cagtttgcta aactcccagt agaacttgca ccccactggc ccgtggtgac  10740
aactcagaac aatgaaaagt ggccagatcg gctggttacc agccttcgcc ctatccataa  10800
atatagccgc gcgtgcattg gtgccggcta tatggtgggt ccctcggtgt tcctgggcac  10860
tcctggggtc gtgtcatact acctcacaaa atttgttaag ggcgaggctc aagtgcttcc  10920
ggagacgatc ttcagcaccg gccgaattga ggtagattgc cgggaatatc ttgatgatcg  10980
ggagcgagaa gttgctgcgt ccctcccaca tgccttcatt ggtgacgtca aaggcactac  11040
cgttgggggga tgtcaccatg tcacctccaa ataccttccg cgcttccttc ccaaggaaac  11100
agttgcggta gtcggggttt caagccccgg aaaagccgcg aaagcagtgt gcacactgac  11160
```

-continued

```
agatgtgtac ctcccagacc ttgaagccta tctccacccg gagactcagt ccaagtgctg  11220
gaaattgatg ttggacttca aggaagttca ctgatggtct ggaaagacaa aacagcctat  11280
ttccaacttg aaggtcgcta cttcacctgg tatcagcttg ctagctatgc ctcgtacatc  11340
cgtgttcctg tcaactctac ggtgtacttg gacccctgca tgggccccgc cctttgcaac  11400
aggagagtcg tcgggtccac ccactggggg gctgacctcg cagtcacccc ttatgattac  11460
ggcgctaaaa tcatcctgtc tagcgcgtac catggtgaaa tgccccccgg atacaaaatt  11520
ctggcgtgcg cggaattctc gttggatgac ccagtcaggt ataaacatac ctggggggttt  11580
gaatcggata cagcgtatct atatgagttc accggaaacg gtgaggactg ggaggattac  11640
aatgatgcgt tccgtgcgcg ccagaaaggg aaaatttaca aggccactgc caccagcatg  11700
aagttttatt tccctccggg ccctgtcatt gaaccaactt taggcctgaa ttgagatgaa  11760
atggggtcta tgcaaagcct ttttgacaaa attggccaac tttttgtgga tgctttcacg  11820
gagttcttgg tgtccattgt tgatatcatt atatttttgg ccattttgtt tggcttcacc  11880
atcgcaggtt ggctggtggt cttttgcatc agattggttt gctccgcgat actccgtgcg  11940
cgccctgcca ttcactctga gcaattacag aagatcctat gaggcctttc tctctcagtg  12000
ccaggtggac attcccacct ggggaactaa acatcctttg gggatgcttt ggcaccataa  12060
ggtgtcaacc ctgattgatg aaatggtgtc gcgtcgaatg taccgcatca tggaaaaagc  12120
aggacaggct gcctggaaac aggtagtgag cgaggctacg ctgtctcgca ttagtagttt  12180
ggatgtggtg gctcattttc agcatcttgc cgccattgaa gccgagacct gtaaatatct  12240
ggcctctcgg ctgcccatgc tacaccacct gcgcatgaca gggtcaaatg taaccatagt  12300
gtataatagt actttgaatc aggtgtttgc tgttttccca acccctggtt cccggccaaa  12360
gcttcatgat ttccagcaat ggctaatagc tgtacattcc tctatatttt cctctgttgc  12420
agcttcttgt actctttttg ttgtgctgtg gttgcgggtt ccaatgctac gtactgtttt  12480
tggtttccgc tggttagggg caatttttct ttcgaactca cggtgaatta cacggtgtgc  12540
ccgccttgcc tcacccggca agcagccgca gaggcctacg aacccggcag gtccctttgg  12600
tgcaggatag ggcatgatcg atgtggggag gacgatcatg atgaactagg gtttgtggtg  12660
ccgtctggcc tctccagcga aggccacttg accagtgctt acccctggtt ggcgttcctg  12720
tccttcagct atacggccca gttccatccc gagatattcg ggatagggaa tgtgagtcga  12780
gtctatgttg acatcaagca ccaattcatt tgcgctgttc atgatgggca gaacaccacc  12840
ttgccccacc atgacaacat ttcagccgtg tttcagacct attaccagca tcaggtcgac  12900
gggggcaatt ggtttcacct agaatggctg cgtcccttct tttcctcttg gttggtttta  12960
aatgtctctt ggtttctcag gcgttcgcct gcaagccatg tttcagttcg agtctttcag  13020
acatcaagac caacaccacc gcagcggcag gctttgctgt cctccaagac atcagttgcc  13080
ttaggcatcg caactcggcc tctgaggcga ttcgcaaagt ccctcagtgc cgcacggcga  13140
tagggacacc cgtgtatatc actgtcacag ccaatgttac cgatgagaat tatttgcatt  13200
cctctgatct tctcatgctt tcttcttgcc ttttctatgc ttctgagatg agtgaaaagg  13260
gatttaaggt ggtatttggc aatgtgtcag gcatcgtggc agtgtgcgtc aacttcacca  13320
gttacgtcca acatgtcaag gaatttaccc aacgttcctt ggtagttgac catgtgcggc  13380
tgctccattt catgacgccc gagaccatga ggtgggcaac tgttttagcc tgtcttttta  13440
ccattctgtt ggcaatttga atgtttaagt atgttgggga aatgcttgac cgcgggctgt  13500
```

-continued

```
tgctcgcaat tgcttttttt atggtgtatc gtgccgtctt gttttgttgc gctcgtcagc  13560
gccaacggga acagcggctc aaatttacag ctgatttaca acttgacgct atgtgagctg  13620
aatggcacag attggctagc taataaattt gactgggcag tggagtgttt tgtcattttt  13680
cctgtgttga ctcacattgt ctcttatggt gccctcacta ctagccattt ccttgacaca  13740
gtcggtctgg tcactgtgtc taccgctggg tttgttcacg ggcggtatgt tctgagtagc  13800
atgtacgcgg tctgtgccct ggctgcgttg atttgcttcg tcattaggct tgcgaagaat  13860
tgcatgtcct ggcgctactc atgtaccaga tataccaact ttcttctgga cactaagggc  13920
agactctatc gttggcggtc gcctgtcatc atagagaaaa ggggcaaagt tgaggtcgaa  13980
ggtcacctga tcgacctcaa aagagttgtg cttgatggtt ccgcggctac ccctgtaacc  14040
agagtttcag cggaacaatg gagtcgtcct tagatgactt ctgtcatgat agcacggctc  14100
cacaaaaggt gctcttggcg ttttctatta cctacacgcc agtgatgata tatgccctaa  14160
aggtgagtcg cggccactgc tagggcttct gcaccttttg gtcttcctga attgtgcttt  14220
caccttcggg tacatgacat tcgtgcactt tcagagtaca aataaggtcg cgctcactat  14280
gggagcagta gttgcactcc tttggggggt gtactcagcc atacaaacct ggaaattcat  14340
cacctccaga tgccgtttgt gctgctaggc cgcaagtaca ttctggcccc tgcccaccac  14400
gttgaaagtg ccgcaggctt tcatccgatt gcggcaaatg ataaccacgc atttgtcgtc  14460
cggcgtcccg gctccactac ggtcaacggc acattggtgc ccgggttaaa aagcctcgtg  14520
ttggtggcag aaaagctgtt aaacagggag tggtaaacct tgttaaatat gccaaataac  14580
accggcaagc agcagaagag aaagaagggg gatggccagc cagtcaatca gctgtgccag  14640
atgctgggta agatcatcgc tcaccaaaac cagtccagag gcaagggacc gggaaagaaa  14700
aataagaaga aaaacccgga gaagccccat ttccctctag cgactgaaga tgatgtcaga  14760
catcacttta cccctagtga gcgtcaattg tgtctgtcgt caatccagac cgcctttaat  14820
caaggcgctg ggacttgcac cctgtcagat tcagggagga taagttacac tgtggagttt  14880
agtttgccta cgcatcatac tgtgcgcctg atccgcgtca cagcatcacc ctcagcatga  14940
tgggctggca ttcttgaggc atcccagtgt ttgaattgaa gaatgcgtgg tgaatggcac  15000
tgattgacat tgtgcctcta agtcacctat tcaattaggg cgaccgtgtg gggtaagat   15060
ttaattggcg agaaccacac ggccgaaatt aaaaaaaaaa aaa                    15103
```

<210> SEQ ID NO 56
<211> LENGTH: 189
<212> TYPE: DNA
<213> ORGANISM: Porcine reproductive and respiratory syndrome virus

<400> SEQUENCE: 56

```
nngacgtata ggtgttggct ctatgccttg acatttgtat tgtcaggagc tgtggccatt     60
ggcacagccc aaaaacttgc tcacggaaac acccttctct gacagcctcc ttcaggggag    120
cttggggtct gtccctagca ccttgcttcc ggagttgcac tgctttaccg tctctccacc    180
cctttaacc                                                            189
```

<210> SEQ ID NO 57
<211> LENGTH: 221
<212> TYPE: DNA
<213> ORGANISM: Porcine reproductive and respiratory syndrome virus

<400> SEQUENCE: 57

```
atgatgtgta gggtattccc cctacataca cgacacttct agtgtttgtg taccttggag     60
```

-continued

```
gcgtgcgtac agccccgccc caccccttgg cccctgttct agcccaacag gtatccttct    120

ctctcggggc gagtgcgccg cctgctgctc ccttgcagcg ggaaggacct cccgagtatt    180

tccggagagc acctgcttta cgggatctcc accctttaac c                        221
```

<210> SEQ ID NO 58
<211> LENGTH: 1998
<212> TYPE: DNA
<213> ORGANISM: Porcine reproductive and respiratory syndrome virus

<400> SEQUENCE: 58

```
atgtctggga tgcttgatcg gtgcacgtgt acccccaatg ccagggtgtt tatggcggaa     60

ggccaagtct actgcacacg atgcctcagt gcacggtctc tccttcccct gaatctccaa    120

gcttctgagc ttggggtgct aggcctattc tacaggcccg aagagccact ccggtggacg    180

ttgccacgtg cattccccac tgttgagtgc tcccccgccg gagcctgctg gctttctgca    240

atctttccaa ttgcacggat gaccagtgga aacctgaact tccaacaaag aatggtacgg    300

gtcgcagctg agtttaacag agccggccag ttcacccctg cagttttgaa gactctacaa    360

gtttatgaac ggggttgccg ctggtacccc attgttggac ctgtccctgg agtggccgtt    420

ttcgccaact ccctacatgt gagtgataaa cctttcccgg gagcaactca cgtgctaacc    480

aacctgccgc tcccgcagag acccaagcct gaagactttt gccccttga gtgtgctatg     540

gctactgtct atgacattgg tcatgacgcc gtcatgtatg tggccgaggg gaaagtctcc    600

tgggcccctc gtggcggaaa tgaagtgaaa tttgaaactg tccccgagga gttgaaattg    660

attgcggacc ggctccgcac ctccatcccg ccccaccatg tagtggacat gtctaagttc    720

gccttcacgg ctcctgggcg tggtgtttct atgcgggttg aacgccaaca cggctgcctc    780

cccactgaca ctgtccctga aggcaactgc tggtggagct tgtttaactt gctcccactg    840

gaagtccaga acaaagaaat ccgccatgct aaccaatttg gctaccagac caagcatggt    900

gtttctggca agtacctaca gcggaggctg caagttaatg gtctccgagc agtaactgac    960

ccaaatggac ctatcgtcgt acagtacttc tccgttaagg agagttggat ccgccacttg   1020

aaactggcgg gagaacccag ctaccctggg tttgaggacc tcctcagaat aagggttgag   1080

cccaatacgt cgccattggc tgacaaggat gaaaaaattt tccggtttgg cagtcacaag   1140

tggtacggcg ctggaaagag agcaaggaaa gcacgctctt gtgcgactgc cacagtcgct   1200

ggccgcgctt tgtccgttcg tgaaacccgg caggccaagg ggcacgaggt tgccggcgcc   1260

aacaaggctg agcacctcaa acattattcc ccgcctgccg aagggaattg tggttggcac   1320

tgcatttccg ccatcgccaa ccggatggtg aattccaaat ttgaaaccac ccttcccgaa   1380

agagtgagac ctccagatga ctgggctact gacgaggatc ttgtgaatgc cattcaaatc   1440

ctcagacttc ctgcggcctt ggacaggaac ggtgcttgtg ttagcgccaa gtacgtactt   1500

aagctggaag gtgagcattg gactgtcact gtgacccctg ggatgtctcc ttctttgctc   1560

cctcttgaat gtgttcaggg ctgttgtgag cacaagggtg gtcttggttc cccagatgca   1620

gtcgaggtct tcggatttga ccctgcctgc cttgaccggc tggctgaggt gatgcacctg   1680

cctagcagtg ttatcccagc cgccctggcc gaaatgtccg gcgattccga tcgttcggct   1740

tccccggtca ccaccgtgtg gactgtttcg cagttctttg cccgtcacaa cggagggaat   1800

caccctgacc aggcgcgctt agggaaaatt atcagccttt gtcaggtgat tgaggactgc   1860

tgctgttccc agaacaaaac caaccgggtc accccggagg aggtcgcagc aaagattgac   1920
```

-continued

```
ctgtacctcc gtggtgcaac aaatcttgaa gaatgcttgg ccaggcttga gaaagcgcgc   1980

ccgccacgcg taatggac                                                 1998
```

<210> SEQ ID NO 59
<211> LENGTH: 1938
<212> TYPE: DNA
<213> ORGANISM: Porcine reproductive and respiratory syndrome virus

<400> SEQUENCE: 59

```
atgtctggga cgttctcccg gtgcatgtgc accccggctg cccgggtatt ttggaacgcc     60

ggccaagtct tttgcacacg gtgtctcagt gcgcggtctc ttctctctcc agagcttcag    120

gacactgacc tcggtgcagt tggcttgttt tacaagccta gggacaagct tcactggaaa    180

gtccctatcg gcatccctca ggtggaatgt actccatccg ggtgctgttg gctctcagct    240

gttttccctt tggcgcgtat gacctccggc aatcacaact tcctccaacg acttgtgaag    300

gttgctgatg ttttgtaccg tgacggttgc ttggcacctc gacaccttcg tgaactccaa    360

gtttacgagc gcggctgcaa ctggtacccg atcacggggc ccgtgcccgg gatgggtttg    420

tttgcgaact ccatgcacgt atccgaccag ccgttccctg gtgccaccca tgtgttgact    480

aactcgcctt tgcctcaaca ggcttgtcgg cagccgttct gtccatttga ggaggctcat    540

tctagcgtgt acaggtggaa gaaatttgtg gttttcacgg actcctccct caacggtcga    600

tctcgcatga tgtggacgcc ggaatccgat gattcagccg ccctggaggt actaccgcct    660

gagttagaac gtcaggtcga aatcctcatt cggagttttc ctgctcatca ccctgtcgac    720

ctggccgact gggagctcac tgagtcccct gagaacggtt tttccttcaa cacgtctcat    780

tcttgcggtc accttgtcca gaaccccgac gtgtttgatg gcaagtgctg gctctcctgc    840

tttttgggcc agtcggtcga agtgcgctgc catgaggaac atctagctga cgccttcggt    900

taccaaacca agtggggcgt gcatggtaag tacctccagc gcaggcttca agttcgcggc    960

attcgtgctg tagtcgatcc tgatggtccc attcacgttg aagcgctgtc ttgcccccag   1020

tcttggatca ggcacctgac tctggatgat gatgtcaccc caggattcgt tcgcctgaca   1080

tcccttcgca ttgtgccgaa cacagagcct accacttccc ggatctttcg gtttggagcg   1140

cataagtggt atggcgctgc cggcaaacgg gctcgtgcta agcgtgccgc taaaagtgag   1200

aaggattcgg ctcccacccc caaggttgcc ctgccggtcc ccacctgtgg aattaccacc   1260

tactctccac cgacagacgg gtcttgtggt tggcatgtcc ttgccgccat aatgaaccgg   1320

atgataaatg gtgacttcac gtcccctctg actcagtaca acagaccaga ggatgattgg   1380

gcttctgatt atgatcttgt tcaggcgatt caatgtctac gactgcctgc taccgtggtt   1440

cggaatcgcg cctgtcctaa cgccaagtac cttataaaac ttaacggagt tcactgggag   1500

gtagaggtga ggtctggaat ggctcctcgc tccctttctc gtgaatgtgt ggttggcgtt   1560

tgctctgaag gctgtgtcgc accgccttat ccagcagacg ggctacctaa acgtgcactc   1620

gaggccttgg cgtctgctta cagactaccc tccgattgtg ttagctctgg tattgctgac   1680

tttcttgcta atccacctcc tcaggaattc tggaccctcg acaaaaatgt gacctccccg   1740

tcaccagagc ggtccggctt ctctagtttg tataaattac tattagaggt tgttccgcaa   1800

aaatgcggtg ccacggaagg ggctttcatc tatgctgttg agaggatgtt gaaggattgt   1860

ccgagctcca aacaggccat ggcccttctg gcaaaaatta aagttccatc ctcaaaggcc   1920

ccgtctgtgt ccctggac                                                 1938
```

-continued

<210> SEQ ID NO 60
<211> LENGTH: 652
<212> TYPE: DNA
<213> ORGANISM: Porcine reproductive and respiratory syndrome virus

<400> SEQUENCE: 60
aaatttggcg acagcaacgc tgacgtacca ggacgagccc ctagatttgt ctgcatcctc 60
acagactgaa tatgaggctt ttcctccagc accactgcag aacatgggta ttccggaggt 120
ggaagggcaa gaagctgagg aagtcctgag tggaatctcg atatactgga tgacatcaat 180
tctgccctgt atcatcaagc ggttccctgt caagcgtagc gatcacacgc ccaataggtg 240
cggagagtga ccttaccatt ggctcagtcg ccactgaaga tattccacgc atcctcggga 300
aaatagaaga tgccggtgag atgtccaacc agggaccctt ggcattctcc gaggaaaaac 360
cggtagatga ccaacctacc aaagaccccc ggatgtcgtc gcggaggtca gacaagagcg 420
caccagctcg gtccgcaggc acaggtggcg tcggcttgtt tactgatttg ccccttcaga 480
cggtgtggat gcggacgggg ggggcccgtt acggacggta aaaacaaaaa ctgaaaggtt 540
ctttgaccag ctgagccgtc aggtttttaa cctcgtctcc catctccctg ttttcttctc 600
ataccttttc aaacctggca gtggttattc tccgggtgat tggggttttg ca 652

<210> SEQ ID NO 61
<211> LENGTH: 660
<212> TYPE: DNA
<213> ORGANISM: Porcine reproductive and respiratory syndrome virus

<400> SEQUENCE: 61
gaatttgccg aactcaagcg cccgcgtttc tccgcacaag ccttaattga ccgaggcggt 60
ccacttgccg atgtccatgc aaaaataaag aaccgggtat atgaacagtg cctccaagct 120
tgtgagcccg gtagtcgtgc aaccccagcc accagggagt ggctcgacaa aatgtgggat 180
agggtggaca tgaaaacttg gcgctgcacc tcgcagttcc aagctggtcg cattcttgcg 240
tccctcaaat tcctccctga catgattcaa gacacaccgc ctcctgttcc caggaagaac 300
cgagctagtg acaatgccgg cctgaagcaa ctggtggcac agtgggatag gaaattgagt 360
gtgacccccc ccccaaaacc ggttgggcca gtgcttgacc agatcgtccc tccgcctacg 420
gatatccagc aagaagatgt caccccctcc gatgggccac cccatgcgcc ggattttcct 480
agtcgagtga gcacgggcgg gagttggaaa ggccttatgc tttccggcac ccgtctcgcg 540
gggtctatca gccagcgcct tatgacatgg gtttttgaag ttttctccca cctcccagct 600
tttatgctca cacttttctc gccgcggggc tctatggctc caggtgattg gttgtttgca 660

<210> SEQ ID NO 62
<211> LENGTH: 3198
<212> TYPE: DNA
<213> ORGANISM: Porcine reproductive and respiratory syndrome virus

<400> SEQUENCE: 62
gaccccattt ttctcgccac tgggtggcgc gggtgctggg ccggccgaag ccccattgag 60
caaccctctg aaaaacctat cgcgtttgcc cagttggatg aaaagaaaat tacggctagg 120
actgtggtcg cccagcctta tgaccccaac caagccgtaa agtgcttgcg ggtattgcag 180
gcgggtgggg tgatggtggc tgaggcggtc ccaaaagtgg tcaaggtttc cgctgttcca 240
ttccgagccc cctttttccc taccggagtg aaagttgacc ctgaatgtag ggtcgtggtt 300
gaccctgaca ctttcactgc agctctccgg tctggctact ccaccacaaa ccttgtcctt 360

-continued

```
ggtgtagggg actttgccca gctgaatgga ttaaaaatca ggcaaatttc caagccttca    420
ggaggaggcc cacatctcat ggctgccctg catgttgcct gctcgatggt tttggacatg    480
cttgctggga tttatgtgac tgcggtgggt tcttgcggca ccggcaccaa cgatccgtgg    540
tgcgctaacc cgtttggcgt ccctggctac ggacctgcct ccctctgcac gtccagattg    600
tgcatttccc agcatgccct taccctgccc ttgacagcac ttgtggcggg attcggtatc    660
caagaaattg ccttagtcgt tttgattttt gtttccatcg gaggcatggc tcataggttg    720
agttgtaaag ctgatatgct gtgtattttg cttgcaattg ccagcaatgt ttgggtacct    780
cttacctggt tgctttgtgt gtttccttgc tggttgcgct gtttttcttt gcacccccctt   840
accatcctat ggttggtgtt tttcttgatt tctgtgaata tgccttcagg aatcttggcc    900
atggtgttgt tggtttctct ttggcttctt ggtcgtaata ctaatgttgc tggtcttgtc    960
accccctacg acattcatca ttacaccagt ggcccccgcg gtgttgccgc cttggctacc   1020
gcaccagatg ggacttactt agccgctgtc cgccgtgctg cgttgactgg ccgcaccatg   1080
ctgttcaccc cgtcccagct tgggtctctt cttgagggtg ctttcagaac tcgaaagccc   1140
tcactgaaca ccgtcaatgt ggtcgggtcc tccatgggct ctggcggggt gtttaccatc   1200
gacgggaaag tcaagtgcgt aactgccgca catgtcctta cgggtaactc agctagggtt   1260
tccggggtcg gcttcaatca aatgcttgac tttgacgtaa agggggattt cgccatagcc   1320
gattgcccga attggcaagg ggctgccccc aagacccaat tctgcgagga tggatggact   1380
ggccgtgcct attggctaac atcctctggc gtcgaacccg gcgtcattgg aaaaggattc   1440
gccttctgct tcaccgcgtg cggcgattcc gggtccccag tgatcaccga ggccggtgag   1500
cttgtcggcg ttcacacggg atcaaataaa caagggggag gcatcgtcac gcgcccctca   1560
ggccagtttt gtaatgtggc acccatcaag ctaagcgaat taagtgaatt ctttgctggg   1620
cccaaggtcc cgctcggtga tgtggaggtt ggcaaccata taattaaaga cataggcgaa   1680
gtgccttcag atctttgtgc cttgctcgct gccaaacctg aactggaagg aggcctctcc   1740
accgtccaac ttctttgtgt gttttttctc ctgtggagaa tgatgggaca tgcctggacg   1800
cccttggttg ctgtgggttt ctttatcttg aatgaggttc tcccagccgt cctggtccgg   1860
agtattttct cctttggaat gtttgtgcta tcctggctca ctccatggtc tgcgcaagtt   1920
ctaatgatca ggcttctaac agcagctctt aacaggaaca gatggtcact tgccttttc    1980
agccttggtg cggtgaccgg ttttgtcgca gatcttgcgg ccactcaggg gcatccgttg   2040
cagacagtga tgaatttgag tacctatgca ttcctgcctc ggatgatggt tgtgacctca   2100
ccagtcccag tgatcgcgtg cggtgtcgtg cacctacttg ccatcatttt gtacttgttt   2160
aagtaccgtg gcctgcacta tatccttgtt ggcgatggag tgttctctgc ggctttcttc   2220
ctgcggtact ttgccgaggg aaagttgagg gaagggttgt cccaatcctg cggaatgaat   2280
catgagtccc taactgttgc ccttgctatg agactcaatg acgaggactt ggatttcctt   2340
acgaaatgga ctgattttaa gtgctttgtt tctgcgtcca acatgaggaa tgcagcgggt   2400
caatttatcg aggctgccta tgctaaagca cttagagtag aacttgccca gttggtgcag   2460
gttgataaag ttcgaggtac tttggccaaa cttgaagctt ttgctgatac cgtggcaccc   2520
caactctcgc ccggtgacat tgttgtcgct ctcggccata cgcctgttgg cagtatcttc   2580
gacctaaagg ttggtagcac caagcatacc ctccaagcca ttgaaaccag agtccttgca   2640
gggtccaaaa tgaccgtggc gcgcgtcgtc gacccgaccc ctacgccccc acccgcaccc   2700
ctgtccatcc ccctcccacc gaaagtcctg gagaatgccc ccaacgcttg gggggatgag   2760
```

-continued

```
gaccgtttga ataagaagaa gaggcccagg atggaagccc tcggcatcta tgttatgggt   2820

gggaaaaagt accagaaatt ttgggacaag aattccggtg atgtgtttta tgaggaggtc   2880

catgacaaca cagatgagtg ggagtgtctc agagtcggcg accctgccga ctttgaccct   2940

gagaagggaa ctctgtgtgg acatgtcacc attgaagata aggcttacca tgtttacacc   3000

tcctcatctg gtaagaagtt cttggtcccc gtcaacccag agaatggaag agtccagtgg   3060

gaagctgcca agctttccgt ggagcagccc cttggcatga tgaacgtcga cggtgaactg   3120

actgccaaag aactggagaa actgaaaaga ataattgata aactccaggg cctgactaag   3180

gagcagtgtt taaactgc                                                 3198
```

<210> SEQ ID NO 63
<211> LENGTH: 3228
<212> TYPE: DNA
<213> ORGANISM: Porcine reproductive and respiratory syndrome virus

<400> SEQUENCE: 63

```
gatcctgtgc acttggcaac gggttggcgc gggtgctggc gtggtgagag ccccatccat     60

caaccacacc aaaagcccat agcttatgcc aatttggatg aaaagaaaat gtctgcccaa    120

acggtggttg ctgtcccata cgatcccagt caggctatca aatgcctgaa agttctgcag    180

gcgggagggg ccatcgtgga ccagcctaca cctgaggtcg ttcgtgtgtc cgagatcccc    240

ttctcagccc catttttccc aaaagttcca gtcaacccag attgcagggt tgtggtagat    300

tcggacactt ttgtggctgc ggttcgctgc ggttactcga cagcacaact ggttctgggc    360

cggggcaact ttgccaagtt aaatcagacc ccccccagga actctatctc caccaaaacg    420

actggtgggg cctcttacac ccttgctgtg gctcaagtgt ctgcgtggac tcttgttcat    480

ttcatcctcg gtctttggtt cacatcacct caagtgtgtg gccgaggaac cgctgaccca    540

tggtgttcaa atccttttc atatcctacc tatggccccg gagttgtgtg ctcctctcga    600

ctttgtgtgt ctgccgacgg ggtcaccctg ccattgttct cagccgtggc acaactctcc    660

ggtagagagg tggggatttt tattttggtg ctcgtctcct tgactgcttt ggcccaccgc    720

atggctctta aggcagacat gttagtggtc ttttcggctt tttgtgctta cgcctggccc    780

atgagctcct ggttaatctg cttctttcct atactcttga agtgggttac ccttcaccct    840

cttactatgc tttgggtgca ctcattcttg gtgttttgtc tgccagcagc cggcatcctc    900

tcactaggga taactggcct tctttgggca attggccgct ttacccaggt tgccggaatt    960

attacacctt atgacatcca ccagtacacc tctgggccac gtggtgcagc tgctgtggcc   1020

acagccccag aaggcactta tatggccgcc gtccggagag ctgctttaac tgggcgaact   1080

ttaatcttca ccccgtctgc agttggatcc cttctcgaag gtgctttcag gactcataaa   1140

ccctgcctta acaccgtgaa tgttgtaggc tcttcccttg gttccggagg ggttttcacc   1200

attgatggca gaagaactgt cgtcactgct gcccatgtgt tgaacggcga cacagctaga   1260

gtcaccggcg actcctacaa ccgcatgcac actttcaaga ccaatggtga ttatgcctgg   1320

tcccatgctg atgactggca gggcgttgcc cctgtggtca aggttgcgaa ggggtaccgc   1380

ggtcgtgcct actggcaaac atcaactggt gtcgaacccg gtatcattgg ggaagggttc   1440

gccttctgtt ttactaactg cggcgattcg gggtcacccg tcatctcaga atctggtgat   1500

cttattggaa tccacaccgg ttcaaacaaa cttggttctg gtcttgtgac aacccctgaa   1560

ggggagacct gcaccatcaa agaaaccaag ctctctgacc tttccagaca ttttgcaggc   1620
```

-continued

```
ccaagcgttc ctcttgggga cattaaattg agtccggcca tcatccctga tgtaacatcc   1680

attccgagtg acttggcatc gctcctagcc tccgtccctg tagtggaagg cggcctctcg   1740

accgttcaac ttttgtgtgt ctttttcctt ctctggcgca tgatgggcca tgcctggaca   1800

cccattgttg ccgtgggctt ctttttgctg aatgaaattc ttccagcagt tttggtccga   1860

gccgtgtttt cttttgcact ctttgtgctt gcatgggcca ccccctggtc tgcacaggtg   1920

ttgatgatta gactcctcac ggcatctctc aaccgcaaca agctttctct ggcgttctac   1980

gcactcgggg gtgtcgtcgg tttggcagct gaaatcggga cttttgctgg cagattgtct   2040

gaattgtctc aagctctttc gacatactgc ttcttaccta gggtccttgc tatgaccagt   2100

tgtgttccca ccatcatcat tggtggactc cataccctcg gtgtgattct gtggttattc   2160

aaataccggt gcctccacaa catgctggtt ggtgatggga gtttttcaag cgccttcttc   2220

ctacggtatt ttgcagaggg taatctcaga aaaggtgttt cacagtcctg tggcatgaat   2280

aacgagtccc taacggctgc tttagcttgc aagttgtcac aggctgacct tgattttttg   2340

tccagcttaa cgaacttcaa gtgctttgta tctgcttcaa acatgaaaaa tgctgccggc   2400

cagtacattg aagcagcgta tgccaaggcc ctgcgccaag agttggcctc tctagttcag   2460

attgacaaaa tgaaaggagt tttgtccaag ctcgaggcct ttgctgaaac agccaccccg   2520

tcccttgaca taggtgacgt gattgttctg cttgggcaac atcctcacgg atccatcctc   2580

gatattaatg tggggactga aaggaaaact gtgtccgtgc aagagacccg gagcctaggc   2640

ggctccaaat tcagtgtttg tactgtcgtg tccaacacac ccgtggacgc cttgaccggc   2700

atcccactcc agacaccaac ccctcttttt gagaatggtc cgcgtcatcg cagcgaggaa   2760

gacgatctta aagtcgagag gatgaagaaa cactgtgtat ccctcggctt ccacaacatc   2820

aatggcaaag tttactgcaa aatttgggac aagtctaccg gtgacacctt ttacacggat   2880

gattcccggt acacccaaga ccatgctttt caggacaggt cagccgacta cagagacagg   2940

gactatgagg gtgtgcaaac cacccccaa cagggatttg atccaaagtc tgaaacccct   3000

gttggcactg ttgtgatcgg cggtattacg tataacaggt atctgatcaa aggtaaggag   3060

gttctggtcc ccaagcctga caactgcctt gaagctgcca agctgtccct tgagcaagct   3120

ctcgctggga tgggccaaac ttgcgacctt acagctgccg aggtggaaaa gctaaagcgc   3180

atcattagtc aactccaagg tttgaccact gaacaggctt taaactgt               3228
```

<210> SEQ ID NO 64
<211> LENGTH: 2696
<212> TYPE: DNA
<213> ORGANISM: Porcine reproductive and respiratory syndrome virus

<400> SEQUENCE: 64

```
tgtataatag tactttgaat caggtgcttg ctattttccc aacccctggt tcccggccaa     60

agcttcatga ttttcagcaa tggctaatag ctgtacattc ctctatattt tcctctgttg    120

cagcttcttg tactcttttt gttgtgctgt ggttgcgggt tccaatgcta cgtattgctt    180

ttggtttccg ctggttaggg gcaatttttc tttcgaactc acagtgaact acacggtgtg    240

tccaccttgc ctcacccggc aagcagccac agaggcctac gaacctggca ggtctctttg    300

gtgcaggata gggtatgatc gctgtgggga ggacgatcat gacgaactag ggtttgtggt    360

gccgtctggc ctctccagcg aaggccactt gaccagtgtt tacgcctggt tggcgttcct    420

gtctttcagt tacacagccc agttccatcc tgagatattc gggataggga atgtgagtca    480

agtttatgtt gacatcaggc atcaattcat ttgcgccgtt cacgacgggc agaacgccac    540
```

-continued

```
tttgcctcgc catgacaata tttcagccgt gttccagact tattaccaac atcaagtcga    600
cggcggcaat tggtttcacc tagaatggct gcgtcccttc ttttcctctt ggttggtttt    660
aaatgtctct tggtttctca ggcgttcgcc tgcaagccat gtttcagttc gagtcttgca    720
gacattaaga ccaacaccac cgcagcggca ggctttgctg tcctccaaga catcagttgc    780
cttaggtatc gcaactcggc ctctgaggcg tttcgcaaaa tccctcagtg tcgtacggcg    840
atagggacac ccatgtatat tactgtcaca gccaatgtaa ccgatgagaa ttatttgcat    900
tcctctgacc ttctcatgct ttcttcttgc cttttctacg cttctgagat gagtgaaaag    960
ggatttaaag tggtatttgg caatgtgtca ggcatcgtgg ctgtgtgcgt caactttacc   1020
agctacgtcc aacatgtcaa ggaatttacc caacgctcct tggtagtcga ccatgtgcgg   1080
ctgctccatt tcatgacacc tgagaccatg aggtgggcaa ctgttttagc ctgtcttttt   1140
gccattctgt tggccatttg aatgtttaag tatgttgggg aaatgcttga ccgcgggcta   1200
ttgctcgtca ttgctttttt tgtggtgtat cgtgccgtct tggtttgttg cgctcgccag   1260
cgccaacagc agcaacagct ctcatttaca gttgatttat aacttgacgc tatgtgagct   1320
gaatggcaca gattggttag ctggtgaatt tgactgggca gtggagtgtt ttgtcatttt   1380
tcctgtgttg actcacattg tctcctatgg tgccctcacc accagccatt tccttgacac   1440
agtcggtctg gtcactgtgt ctaccgccgg cttttcccac gggcggtatg ttctgagtag   1500
catctacgcg gtctgtgccc tggctgcgtt gatttgcttc gtcattaggt ttacgaagaa   1560
ttgcatgtcc tggcgctact catgtaccag atataccaac tttcttctgg acactaaggg   1620
cagactctat cgttggcggt cgcctgtcat catagagaaa aggggtaaag ttgaggtcga   1680
aggtcatctg atcgacctca agagagttgt gcttgatggt tccgcggcaa cccctataac   1740
caaagtttca gccgagcaat ggggtcgtcc ttagatgact tctgccatga tagcacggct   1800
ccacaaaagg tgcttttggc gttctctatt acctacacgc cagtgatgat atatgcccta   1860
aaagtaagtc gcggccgact gctagggctt ctgcaccttt tgatcttcct aaattgtgct   1920
ttcaccttcg ggtacatgac attcgtgcac tttcagagca caaacaaggt cgcgctcact   1980
atgggagcag tagttgcact cctttggggg gtgtactcag ccatagaaac ctggaaattc   2040
atcacctcca gatgccgttt gtgcttgcta ggccgcaagt acattttggc ccctgcccac   2100
cacgttgaaa gtgccgcagg ctttcatccg atagcggcaa atgataacca cgcatttgtc   2160
gtccggcgtc ccggctccac tacggttaac ggcacattgg tgcccgggtt gaaaagcctc   2220
gtgttgggtg gcagaaaagc tgtcaaacag ggagtggtaa accttgttaa atatgccaaa   2280
taacaacggc aagcagcaga agaaaaagaa gggggatggc cagccagtca atcagctgtg   2340
ccagatgctg ggtaagatca tcgctcagca aaaccagtcc agaggcaagg gaccgggaaa   2400
gaaaaacaag aagaaaaacc cggagaagcc ccattttcct ctagcgactg aagatgatgt   2460
cagacatcac ttcacctctg gtgagcggca attgtgtctg tcgtcaatcc agacagcctt   2520
taatcaaggc gctggaactt gtaccctgtc agattcaggg aggataagtt acactgtgga   2580
gtttagtttg ccgacgcatc atactgtgcg cctgatccgc gtcacagcgt caccctcagc   2640
atgatgagct ggcattcttg aggcatccca gtgtttgaat tggaagaatg cgtggt       2696
```

<210> SEQ ID NO 65
<211> LENGTH: 2696
<212> TYPE: DNA
<213> ORGANISM: Porcine reproductive and respiratory syndrome virus -continued

<400> SEQUENCE: 65
tgtataatag tactttgaat caggtgcttg ctatttttcc aacccctggt tcccggccaa 60
agcttcatga ttttcagcaa tggctaatag ctgtacattc ctctatattt tcctctgttg 120
cagcttcttg tactcttttt gttgtgctgt ggttgcgggt tccaatgcta cgtattgctt 180
ttggtttccg ctggttaggg gcaatttttc cttcgaactc acagtgaact acacggtgtg 240
tccaccttgc ctcacccggc aagcagccat agaggcctac gaacctggca ggtctctttg 300
gtgcaggata gggtatgatc gctgtgggga ggacgatcat gacgaactag ggtttgtggt 360
gccgtctggc ctctccagcg aaggccactt gaccagtgtt tacgcctggt tggcgttcct 420
gtctttcagt tacacagccc agttccatcc tgagatattc gggataggga atgtgagtca 480
agtttatgtt gacatcaggc atcaatccat ttgcgccgtt cacgacgggc agaacgccac 540
tttgcctcgc catgacaata tttcagccgt gttccagact tattaccaac atcaagtcga 600
cggcggcaat tggtttcacc tagaatggct gcgtcccttc ttttcctctt ggttggtttt 660
aaatgtctct tggtttctca ggcgttcgct tgcaagccat gtttcagttc gagtcttgca 720
gacattaaga ccaacaccac cgcagcggca ggctttgctg tcctccaaga catcagttgc 780
cttaggtatc gcaactcggc ctctgaggcg tttcgcaaaa tccctcagtg tcgtacggcg 840
atagggacac ccatgtatat tactgtcaca gccaatgtaa ccgatgagaa ttatttgcat 900
tcctctgacc ttctcatgct ttcttcttgc cttttctacg cttctgagat gagtgaaaag 960
ggatttaaag tggtatttgg caatgtgtca ggcatcgtgg ctgtgtgcgt caactttacc 1020
agctacgtcc aacatgtcaa ggaatttacc caacgctcct tggtagtcga ccatgtgcgg 1080
ctgctccatt tcatgacacc tgagaccatg aggtgggcaa ctgttttagc ctgtcttttt 1140
gccattctgt tggccattta aatgtttgag tatgttgggg aaatgcttga ccgcgggcta 1200
ttgctcgtca ttgctttttt tgtggtgtat cgtgccgtct tggtttgttg cgctcgccag 1260
cgccaacagc atcaacagcc ctcatttaca gttgatttat aacttgacgc tatgtgagct 1320
gaatggcaca gattggttag ctggtgaatt tgactgggca gtggagtgtt ttgtcatttt 1380
tcctgtgttg actcacattg tctcctatgg tgccctcacc accagccatt tccttgacac 1440
agtcggtctg gtcactgtgt ctaccgccgg cttttcccac gggcggtatg ttctgagtag 1500
catctacgcg gtctgtgccc tggctgcgtt gatttgcttc gtcattaggt ttacgaagaa 1560
ttgcatgtcc tggcgctact catgtaccag atataccaac tttcttctgg acactaaggg 1620
cagactctat cgttggcggt cgcctgtcat catagagaaa aggggtaaag ttgaggtcga 1680
aggtcatctg atcgacctca agagagttgt gcttgatggt tccgcggcaa cccctataac 1740
caaaatttca gccgagcaat ggggtcgtcc ttagatgact tctgccatga tagcacggct 1800
ccactaaagg tgcttttggc gttctctatt acctacacgc cagtgatgat atatgcccta 1860
aaagtaagtc gcggccgact gttagggctt ctgcaccttt tgatcttcct aaattgtgct 1920
ttcaccttcg ggtacatgac attcgtgcac tttcagagca caaacaaggt cgcgctcact 1980
atgggagcag tagttgcact cctttggggg gtgtactcag ccatagaaac ctggaaattc 2040
atcacctcca gatgccgttt gtgcttgcta ggccgcaagt acattttggc ccctgcccac 2100
cacgttgaaa gtgccgcagg ctttcatccg atagcggcaa atgataacca cgcatttgtc 2160
gtccggcgtc ccggctccac tacggttaac ggcacattgg tgcccgggtt gaaaagcctc 2220
gtgttgggtg gcagaaaagc tgtcaaacag ggagtggtaa accttgttaa atatgccaaa 2280
taacaacggc aagcagcaga agaaaaagaa gggggatggc cagccagtca atcagctgtg 2340

-continued ccagatgctg ggtaagatca tcgctcagca aaaccagtcc agaggcaagg gaccgggaaa 2400
gaaaaacaag aagaaaaacc cggagaagcc ccattttcct ctagcgactg aagatgatgt 2460
cagacatcac ttcacctctg gtgagcggct attgtgtctg tcgtcaatcc agacagcctt 2520
taatcaaggc gctggaattt gtaccctgtc agattcaggg aggataagtt acactgtgga 2580
gtttagtttg ccgacgcatc atactgtgcg cctgatccgc gtcacagcgt caccctcagc 2640
atgatgagct ggcattcttg aggcatccca gtgtttgaat tggaagaatg tgtggt 2696

<210> SEQ ID NO 66
<211> LENGTH: 1098
<212> TYPE: DNA
<213> ORGANISM: Porcine reproductive and respiratory syndrome virus

<400> SEQUENCE: 66
attccacgca tcctcgggaa aatagaagat gccggtgaga tgtccaacca gggacccttg 60
gcattctccg aggaaaaacc ggtagatgac caacctacca aagacccccg gatgtcgtcg 120
cggaggtcag acaagagcgc accagctcgg tccgcaggca caggtggcgt cggcttgttt 180
actgatttgc cccttcagac ggtgtggatg cggacggggg gggcccgtta cggacggtaa 240
aaacaaaaac tgaaaggttc tttgaccagc tgagccgtca ggtttttaac ctcgtctccc 300
atctccctgt tttcttctca taccttttca aacctggcag tggttattct ccgggtgatt 360
ggggttttgc agcttttact ctattgtgcc tctttttatg ttacagttat ccagcctttg 420
gtattgctcc cctcttgggt gtattttctg ggtcttctcg gcgcgtccga atgggggttt 480
ttggttgctg gttggctttt gctgttggtc tgttcaaatc tgtgcccgac ccagtcggca 540
ctgcttgtga atttgactcg ccagagtgca gaaacatcct tcattctttt gagcttctca 600
aaccttggga ccctgttcgc agccttgttg tgggccccgt cggtctcggc cttgccattc 660
ttggcaggtt actgggcggg gcacgctaca tctggcactt tttgcttagg cttggcattg 720
ttgcagattg tatcttggct ggagcttatg tgctttctca aggtaggtgt aaaaagtgct 780
ggggatcttg tataagaact gctcctaatg aggtcgcttt taacgtgttt cctttcacac 840
gtgcgaccag gtcgtcactt gttgacctgt gtgatcggtt ttgcgcgcca aaaggcatgg 900
accccatttt tctcgccact gggtggcgcg ggtgctgggc cggccgaagc cccattgagc 960
aaccctctga aaaacctatc gcgtttgccc agttggatga aaagaaaatt acggctagga 1020
ctgtggtcgc ccagccttat gaccccaacc aagccgtaaa gtgcttgcgg gtattgcagg 1080
cgggtggggt gatggtgg 1098

<210> SEQ ID NO 67
<211> LENGTH: 1108
<212> TYPE: DNA
<213> ORGANISM: Porcine reproductive and respiratory syndrome virus

<400> SEQUENCE: 67
cctcctgttc ccaggaagaa ccgagctagt gacaatgccg gcctgaagca actggtggca 60
cagtgggata ggaaattgag tgtgaccccc cccccaaaac cggttgggcc agtgcttgac 120
cagatcgtcc ctccgcctac ggatatccag caagaagatg tcaccccctc cgatgggcca 180
ccccatgcgc cggattttcc tagtcgagtg agcacgggcg ggagttggaa aggccttatg 240
ctttccggca cccgtctcgc ggggtctatc agccagcgcc ttatgacatg ggtttttgaa 300
gttttctccc acctcccagc ttttatgctc acacttttct cgccgcgggg ctctatggct 360

-continued

```
ccaggtgatt ggttgtttgc aggtgtcgtt ttacttgctc tcttgctctg tcgttcttac    420

ccgatactcg gatgccttcc cttattgggt gtcttttctg gttctttgcg gcgtgttcgt    480

ctgggtgttt ttggttcttg gatggctttt gctgtatttt tattctcgac tccatccaac    540

ccagtcggtt cttcttgtga ccacgattcg ccggagtgtc atgctgagct tttggctctt    600

gagcagcgcc aactttggga acctgtgcgc ggccttgtgg tcggccccctc aggcctctta    660

tgtgtcattc ttggcaagtt actcggtggg tcacgttatc tctggcatgt tctcctacgt    720

ttatgcatgc ttgcagattt ggccctttct cttgtttatg tggtgtccca ggggcgttgt    780

cacaagtgtt ggggaaagtg tataaggaca gctcctgcgg aggtggctct taatgtattt    840

cctttctcgc gcgccacccg tgtctctctt gtatccttgt gtgatcgatt ccaaacgcca    900

aaaggggttg atcctgtgca cttggcaacg ggttggcgcg ggtgctggcg tggtgagagc    960

cccatccatc aaccacacca aaagcccata gcttatgcca atttggatga aaagaaaatg   1020

tctgcccaaa cggtggttgc tgtcccatac gatcccagtc aggctatcaa atgcctgaaa   1080

gttctgcagg cgggaggggc catcgtgg                                      1108
```

<210> SEQ ID NO 68
<211> LENGTH: 7193
<212> TYPE: DNA
<213> ORGANISM: Porcine reproductive and respiratory syndrome virus

<400> SEQUENCE: 68

```
atgtctggga tgcttgatcg gtgcacgtgt acccccaatg ccagggtgtt tatggcggaa     60

ggccaagtct actgcacacg atgcctcagt gcacggtctc tccttcccct gaatctccaa    120

gcttctgagc ttggggtgct aggcctattc tacaggcccg aagagccact ccggtggacg    180

ttgccacgtg cattccccac tgttgagtgc tcccccgccg gagcctgctg gctttctgca    240

atctttccaa ttgcacggat gaccagtgga aacctgaact tccaacaaag aatggtacgg    300

gtcgcagctg agtttaacag agccggccag ttcacccctg cagttttgaa gactctacaa    360

gtttatgaac ggggttgccg ctggtacccc attgttggac ctgtccctgg agtggccgtt    420

ttcgccaact ccctacatgt gagtgataaa cctttcccgg gagcaactca cgtgctaacc    480

aacctgccgc tcccgcagag acccaagcct gaagactttt gccccctttga gtgtgctatg    540

gctactgtct atgacattgg tcatgacgcc gtcatgtatg tggccgaggg gaaagtctcc    600

tgggccccctc gtggcggaaa tgaagtgaaa tttgaaactg tccccgagga gttgaaattg    660

attgcggacc ggctccgcac ctccatcccg ccccaccatg tagtggacat gtctaagttc    720

gccttcacgg ctcctgggcg tggtgtttct atgcgggttg aacgccaaca cggctgcctc    780

cccactgaca ctgtccctga aggcaactgc tggtggagct tgtttaactt gctcccactg    840

gaagtccaga acaaagaaat ccgccatgct aaccaatttg gctaccagac caagcatggt    900

gtttctggca agtacctaca gcggaggctg caagttaatg gtctccgagc agtaactgac    960

ccaaatggac ctatcgtcgt acagtacttc tccgttaagg agagttggat ccgccacttg   1020

aaactggcgg gagaacccag ctaccctggg tttgaggacc tcctcagaat aagggttgag   1080

cccaatacgt cgccattggc tgacaaggat gaaaaaattt tccggtttgg cagtcacaag   1140

tggtacggcg ctggaaagag agcaaggaaa gcacgctctt gtgcgactgc cacagtcgct   1200

ggccgcgctt tgtccgttcg tgaaacccgg caggccaagg ggcacgaggt tgccggcgcc   1260

aacaaggctg agcacctcaa acattattcc ccgcctgccg aagggaattg tggttggcac   1320

tgcatttccg ccatcgccaa ccggatggtg aattccaaat ttgaaaccac ccttcccgaa   1380
```

-continued

```
agagtgagac ctccagatga ctgggctact gacgaggatc ttgtgaatgc cattcaaatc   1440
ctcagacttc ctgcggcctt ggacaggaac ggtgcttgtg ttagcgccaa gtacgtactt   1500
aagctggaag gtgagcattg gactgtcact gtgacccctg ggatgtctcc ttctttgctc   1560
cctcttgaat gtgttcaggg ctgttgtgag cacaagggtg gtcttggttc cccagatgca   1620
gtcgaggtct tcggatttga ccctgcctgc cttgaccggc tggctgaggt gatgcacctg   1680
cctagcagtg ttatcccagc cgccctggcc gaaatgtccg gcgattccga tcgttcggct   1740
tccccggtca ccaccgtgtg gactgtttcg cagttctttg cccgtcacaa cggagggaat   1800
caccctgacc aggcgcgctt agggaaaatt atcagccttt gtcaggtgat tgaggactgc   1860
tgctgttccc agaacaaaac caaccgggtc accccggagg aggtcgcagc aaagattgac   1920
ctgtacctcc gtggtgcaac aaatcttgaa gaatgcttgg ccaggcttga gaaagcgcgc   1980
ccgccacgcg taatggacac ctcctttgat tgggatgttg tgctccctgg ggttgaggcg   2040
gcaactcaga cgaccgaact gccccgggtc aaccagtgtc gcgctctggt ccctgttgtg   2100
actcaaaagt ctctggacaa taactcggtt cctctgaccg ccttctcgct gtccaattac   2160
tactaccgtg cacaaggtga cgagattcgt caccgtgaca ggctaaacgc cgtactctct   2220
aagttggagg gggctgttcg agaagaatat gggctcatgc cgactggacc tggcccgcga   2280
cccgcactgt cgagcgggct cgatgggctt aaagacagat ggagagatct gctgaaacta   2340
gccaacgccc agacaacctc agaaatgatg gcctgggcag ccgagcaggt tgatctagaa   2400
gcttgggtca aaagctaccc acggtggaca ccaccacccc ctccgccaag agttcagcct   2460
cgaaaagcga agcctgtcag gagcttgcca gagagcaagc ctgtccctgc cccgcgcagg   2520
aaggttagat ccgatcgtgg cagcccggtt ttgttgggcg acaatgttcc taacagttgg   2580
gaagacttga ctgtcggtgg ccccccttgat ctcctgaccc cacccgagtc agtgacacct   2640
ccagtgagct tgcgcttacg tccgcgccgc aacacacttt taggccggtg acacctttgg   2700
gtgaaccggc cccagttccc gcaccgcgca gaactgtgtc ccgaccggtg acatccttga   2760
atgggccgat ccttatgtcc gcaccgcggc acaagtttca gcaggtggaa aaagcaaatt   2820
tggcgacagc aacgctgacg taccaggacg agcccctaga tttgtctgca tcctcacaga   2880
ctgaatatga ggcttttcct ccagcaccac tgcagaacat gggtattccg gaggtggaag   2940
ggcaagaagc tgaggaagtc ctgagtggaa tctcgatata ctggatgaca tcaattctgc   3000
cctgtatcat caagcggttc cctgtcaagc gtagcgatca cacgcccaat aggtgcggag   3060
agtgacctta ccattggctc agtcgccact gaagatattc cacgcatcct cgggaaaata   3120
gaagatgccg gtgagatgtc caaccaggga cccttggcat tctccgagga aaaaccggta   3180
gatgaccaac ctaccaaaga cccccggatg tcgtcgcgga ggtcagacaa gagcgcacca   3240
gctcggtccg caggcacagg tggcgtcggc ttgtttactg atttgcccct tcagacggtg   3300
tggatgcgga cgggggggc ccgttacgga cggtaaaaac aaaaactgaa aggttctttg   3360
accagctgag ccgtcaggtt tttaacctcg tctcccatct ccctgttttc ttctcatacc   3420
ttttcaaacc tggcagtggt tattctccgg gtgattgggg ttttgcagct tttactctat   3480
tgtgcctctt tttatgttac agttatccag cctttggtat tgctcccctc ttgggtgtat   3540
tttctgggtc ttctcggcgc gtccgaatgg gggtttttgg ttgctggttg gcttttgctg   3600
ttggtctgtt caaatctgtg cccgacccag tcggcactgc ttgtgaattt gactcgccag   3660
agtgcagaaa catccttcat tcttttgagc ttctcaaacc ttgggaccct gttcgcagcc   3720
```

-continued

```
ttgttgtggg ccccgtcggt ctcggccttg ccattcttgg caggttactg ggcggggcac   3780
gctacatctg gcacttttg cttaggcttg gcattgttgc agattgtatc ttggctggag   3840
cttatgtgct ttctcaaggt aggtgtaaaa agtgctgggg atcttgtata agaactgctc   3900
ctaatgaggt cgcttttaac gtgtttcctt tcacacgtgc gaccaggtcg tcacttgttg   3960
acctgtgtga tcggttttgc gcgccaaaag gcatggaccc catttttctc gccactgggt   4020
ggcgcgggtg ctgggccggc cgaagcccca ttgagcaacc ctctgaaaaa cctatcgcgt   4080
ttgcccagtt ggatgaaaag aaaattacgg ctaggactgt ggtcgcccag ccttatgacc   4140
ccaaccaagc cgtaaagtgc ttgcgggtat tgcaggcggg tggggtgatg gtggctgagg   4200
cggtcccaaa agtggtcaag gtttccgctg ttccattccg agcccccttt tttcctaccg   4260
gagtgaaagt tgaccctgaa tgtagggtcg tggttgaccc tgacactttc actgcagctc   4320
tccggtctgg ctactccacc acaaaccttg tccttggtgt aggggacttt gcccagctga   4380
atggattaaa aatcaggcaa atttccaagc cttcaggagg aggcccacat ctcatggctg   4440
ccctgcatgt tgcctgctcg atggttttgg acatgcttgc tgggatttat gtgactgcgg   4500
tgggttcttg cggcaccggc accaacgatc cgtggtgcgc taacccgttt ggcgtccctg   4560
gctacggacc tgcctccctc tgcacgtcca gattgtgcat ttcccagcat gcccttaccc   4620
tgcccttgac agcacttgtg gcgggattcg gtatccaaga aattgcctta gtcgttttga   4680
tttttgtttc catcggaggc atggctcata ggttgagttg taaagctgat atgctgtgta   4740
ttttgcttgc aattgccagc aatgtttggg tacctcttac ctggttgctt tgtgtgtttc   4800
cttgctggtt gcgctgtttt tctttgcacc cccttaccat cctatggttg gtgtttttct   4860
tgatttctgt gaatatgcct tcaggaatct tggccatggt gttgttggtt tctctttggc   4920
ttcttggtcg taatactaat gttgctggtc ttgtcacccc ctacgacatt catcattaca   4980
ccagtggccc ccgcggtgtt gccgccttgg ctaccgcacc agatgggact tacttagccg   5040
ctgtccgccg tgctgcgttg actggccgca ccatgctgtt caccccgtcc cagcttgggt   5100
ctcttcttga gggtgctttc agaactcgaa agccctcact gaacaccgtc aatgtggtcg   5160
ggtcctccat gggctctggc ggggtgttta ccatcgacgg gaaagtcaag tgcgtaactg   5220
ccgcacatgt ccttacgggt aactcagcta gggtttccgg ggtcggcttc aatcaaatgc   5280
ttgactttga cgtaaagggg gatttcgcca tagccgattg cccgaattgg caaggggctg   5340
cccccaagac ccaattctgc gaggatggat ggactggccg tgcctattgg ctaacatcct   5400
ctggcgtcga acccggcgtc attggaaaag gattcgcctt ctgcttcacc gcgtgcggcg   5460
attccgggtc cccagtgatc accgaggccg gtgagcttgt cggcgttcac acgggatcaa   5520
ataaacaagg gggaggcatc gtcacgcgcc cctcaggcca gttttgtaat gtggcaccca   5580
tcaagctaag cgaattaagt gaattctttg ctgggcccaa ggtcccgctc ggtgatgtgg   5640
aggttggcaa ccatataatt aaagacatag gcgaagtgcc ttcagatctt tgtgccttgc   5700
tcgctgccaa acctgaactg gaaggaggcc tctccaccgt ccaacttctt tgtgtgtttt   5760
ttctcctgtg gagaatgatg ggacatgcct ggacgccctt ggttgctgtg ggtttcttta   5820
tcttgaatga ggttctccca gccgtcctgg tccggagtat tttctccttt ggaatgtttg   5880
tgctatcctg gctcactcca tggtctgcgc aagttctaat gatcaggctt ctaacagcag   5940
ctcttaacag gaacagatgg tcacttgcct ttttcagcct tggtgcggtg accggttttg   6000
tcgcagatct tgcggccact caggggcatc cgttgcagac agtgatgaat ttgagtacct   6060
atgcattcct gcctcggatg atggttgtga cctcaccagt cccagtgatc gcgtgcggtg   6120
```

-continued

```
tcgtgcacct acttgccatc attttgtact tgtttaagta ccgtggcctg cactatatcc   6180
ttgttggcga tggagtgttc tctgcggctt tcttcctgcg gtactttgcc gagggaaagt   6240
tgagggaagg gttgtcccaa tcctgcggaa tgaatcatga gtccctaact gttgcccttg   6300
ctatgagact caatgacgag gacttggatt tccttacgaa atggactgat tttaagtgct   6360
ttgtttctgc gtccaacatg aggaatgcag cgggtcaatt tatcgaggct gcctatgcta   6420
aagcacttag agtagaactt gcccagttgg tgcaggttga taaagttcga ggtactttgg   6480
ccaaacttga agcttttgct gataccgtgg caccccaact ctcgcccggt gacattgttg   6540
tcgctctcgg ccatacgcct gttggcagta tcttcgacct aaaggttggt agcaccaagc   6600
ataccctcca agccattgaa accagagtcc ttgcagggtc caaaatgacc gtggcgcgcg   6660
tcgtcgaccc gacccctacg cccccacccg cacccctgtc catccccctc ccaccgaaag   6720
tcctggagaa tgcccccaac gcttgggggg atgaggaccg tttgaataag aagaagaggc   6780
ccaggatgga agccctcggc atctatgtta tgggtgggaa aaagtaccag aaattttggg   6840
acaagaattc cggtgatgtg ttttatgagg aggtccatga caacacagat gagtgggagt   6900
gtctcagagt cggcgaccct gccgactttg accctgagaa gggaactctg tgtggacatg   6960
tcaccattga agataaggct taccatgttt acacctcctc atctggtaag aagttcttgg   7020
tccccgtcaa cccagagaat ggaagagtcc agtgggaagc tgccaagctt tccgtggagc   7080
agccccttgg catgatgaac gtcgacggtg aactgactgc caaagaactg gagaaactga   7140
aaagaataat tgataaactc cagggcctga ctaaggagca gtgtttaaac tgc          7193
```

<210> SEQ ID NO 69
<211> LENGTH: 4382
<212> TYPE: DNA
<213> ORGANISM: Porcine reproductive and respiratory syndrome virus

<400> SEQUENCE: 69

```
gtgtttaaac tgctagccgc cagcggcttg acccgctgtg gtcgcggcgg cttagttgtt     60
actgagacag cggtgaagat cgtcaaattt cacaaccgga ccttcacctt gggacctgtg    120
aatttaaaag tggccagtga ggttgagctg aaagacgcgg ttgagcacaa ccagcacccg    180
gttgcaagac cggttgatgg tggtgttgtg ctcctgcgtt ctgcagttcc ttcgcttgtc    240
gacgtcttaa tctccggtgc tgatgcatct cccaagttac ttgcccatca cgggccggga    300
aacactggga tcgatggcac gctctgggat tttgagtccg aagccattaa agaggaagtc    360
gcacttagtg cgcaaataat acaggcttgt gacattaggc gcggtgacgc acctgaaatt    420
ggtctccctt acaaactata ccctgttagg ggcaaccctg agcgggtaaa aggagttttg    480
cagaatacaa ggtttggaga cataccttac aaaaccccca gtgacaccgg aagcccagtg    540
cacgcggctg cctgccttac gcccaacgcc accccggtga ctgatgggcg ctctgtcttg    600
gccacgacca tgccctccgg gttcgagttg tatgtaccca ccattccggc gtctgttctt    660
gattatcttg attctaggcc tgactgccct aaacagttga cagagcacgg ctgtgaagat    720
gccgcattga gagatctctc caagtatgac ttgtccaccc aaggctttgt tttgcctgga    780
gttcttcgcc ttgtgcggaa gtacctgttt gcccacgtgg gtaagtgccc gtccgttcat    840
cggccttcca cttaccccgc caaaaattct atggctggaa taaatgggaa caggtttcca    900
accaaggaca ttcagagcgt ccctgaaatc gacgttctgt gcgcacaggc tgtgcgagaa    960
aactggcaaa ctgttacccc ttgtaccctt aagaaacagt actgcgggaa gaagaagact   1020
```

-continued

```
aggaccatac tcggcaccaa caacttcatt gcgctggccc accgggcagc gttgagtggt   1080
gtcacccaag gcttcatgaa aaaagcattt aactcgccca tcgccctcgg gaaaaacaaa   1140
tttaaagagc tacagactcc ggtcctcggc aggtgccttg aagctgatct tgcatcctgc   1200
gatcgatcca cacctgcaat tgtccgctgg tttgccgcca atcttcttta tgaactttcc   1260
tgtgctgaag agcatctacc gtcgtacgtg ctgaactgct gccacgacct actggtcacg   1320
cagtccggcg cagtgactaa gagaggtggc ctgtcgtctg gtgacccgat cacctctgtg   1380
tccaacacca tttacagctt ggtgatctat gcacagcaca tggtgcttag ttacttcaaa   1440
agtggtcatc cccatggcct tctgttttta caagaccagc taaagtttga ggacatgctc   1500
aaggtccaac ccctgatcgt ctattcggac gaccttgtgc tgtatgccga gtctcccacc   1560
atgccaaact accattggtg ggttgaacat ctgaatctga tgttggggtt tcagacggac   1620
ccaaagaaga caaccataac agactcacca tcatttctag gctgtagaat agtaaatgga   1680
cgccagctag tccccaaccg tgacaggatt ctcgcggccc tcgcctacca catgaaggcg   1740
agtaatgttt ctgaatacta cgcctcagcg gctgcaatac tcatggacag ctgtgcttgt   1800
ttagagtatg atcctgaatg gtttgaagaa cttgtagttg gaatagcgca gtgcgcccgc   1860
aaggacggct acagctttcc cggcacgccg ttcttcatgt ccatgtggga aaaactcagg   1920
tcaaattatg aggggaaaaa gtcgagagtg tgcgggtact gcggggcccc ggccccgtac   1980
gctactgcct gcggccttga cgtctgcatt taccacaccc acttccacca gcattgtcca   2040
gtcacaatct ggtgcggcca tccagcgggt tctggttctt gtaatgagtg caagtccccc   2100
atagggaaag gcacaagccc cctagacgag gtgctagaac aagtcccgta taagccccca   2160
cggaccgtaa ttatgcatgt ggagcagggt cttacccccc ttgacccagg taggtaccag   2220
actcgccgcg gattagtctc cgtcaggcgt ggaatcaagg gaaatgaagt tgaactacca   2280
gacggtgatt atgctagtac cgccttgctc cccacctgta aagagatcaa catggtcgct   2340
gtcgcttcta atgtgttgcg cagcaggttc atcatcggtc cacccggtgc tgggaaaaca   2400
tactggctcc ttcaacaagt ccaggatggt gatgttattt acacaccaac tcaccagacc   2460
atgcttgaca tgatcagagc tttggggacg tgccgattca atgtccctac aggcacaaca   2520
ctgcagttcc ctgtcccctc ccgtaccggt ccgtgggttc gcatcctagc cggtggttgg   2580
tgtcctggca agaattcctt cctggatgaa gcagcgtatt acaatcacct tgatgtcttg   2640
aggcttctta gtaaaactac cctcacctgt ctgggagact ttaaactact ccacccagtg   2700
ggttttgatt cccattgcta tgtttttgac atcatgcctc agactcaatt aaagaccatc   2760
tggagatttg gacagaatat ctgtgatgcc attcaaccag attacaggga caaactcatg   2820
tccatggtca acacaacccg tgtaacttac gtggaaaaac ccgtcaggta tgggcaagtc   2880
cttaccccct accataagga ccgagaggac ggcgccatca ccattgactc cagtcaaggt   2940
gccacgtttg atgtggttac attgcatttg cccactaaag attcactcaa caggcaaaga   3000
gcccttgttg ctatcactag ggcaagacat gcaatttttg tgtatgaccc acacaagcaa   3060
ctgcagagcc tgtttgatct ccctgcaaaa ggcacacccg tcaacctcgc tgtgcaccgc   3120
gacgggcagc ttattgtgct ggatagaaat aacaaggaat gcacggttgc tcaggctcta   3180
ggcaatggag ataaatttag ggccacagac aaacgcgttg tggattctct ccgcgccatt   3240
tgtgctgatc tagaagggtc gagctctccg ctccccaagg tcgcacacaa cttgggattt   3300
tatttctcac ctgatttaac gcagtttgct aaactcccag tagaacttgc accccactgg   3360
cccgtggtga caactcagaa caatgaaaag tggccagatc ggctggttac cagccttcgc   3420
```

-continued

```
cctatccata aatatagccg cgcgtgcatt ggtgccggct atatggtggg tccctcggtg   3480
ttcctgggca ctcctggggt cgtgtcatac tacctcacaa aatttgttaa gggcgaggct   3540
caagtgcttc cggagacgat cttcagcacc ggccgaattg aggtagattg ccgggaatat   3600
cttgatgatc gggagcgaga agttgctgcg tccctcccac atgccttcat tggtgacgtc   3660
aaaggcacta ccgttggggg atgtcaccat gtcacctcca aataccttcc gcgcttcctt   3720
cccaaggaaa cagttgcggt agtcggggtt tcaagccccg gaaaagccgc gaaagcagtg   3780
tgcacactga cagatgtgta cctcccagac cttgaagcct atctccaccc ggagactcag   3840
tccaagtgct ggaaattgat gttggacttc aaggaagttc actgatggtc tggaaagaca   3900
aaacagccta tttccaactt gaaggtcgct acttcacctg gtatcagctt gctagctatg   3960
cctcgtacat ccgtgttcct gtcaactcta cggtgtactt ggacccctgc atgggccccg   4020
ccctttgcaa caggagagtc gtcgggtcca cccactgggg ggctgacctc gcagtcaccc   4080
cttatgatta cggcgctaaa atcatcctgt ctagcgcgta ccatggtgaa atgccccccg   4140
gatacaaaat tctggcgtgc gcggaattct cgttggatga cccagtcagg tataaacata   4200
cctgggggtt tgaatcggat acagcgtatc tatatgagtt caccggaaac ggtgaggact   4260
gggaggatta caatgatgcg ttccgtgcgc gccagaaagg gaaaatttac aaggccactg   4320
ccaccagcat gaagttttat ttccctccgg gccctgtcat tgaaccaact ttaggcctga   4380
at                                                                  4382
```

<210> SEQ ID NO 70
<211> LENGTH: 768
<212> TYPE: DNA
<213> ORGANISM: Porcine reproductive and respiratory syndrome virus

<400> SEQUENCE: 70

```
atgaaatggg gtctatgcaa agcctttttg acaaaattgg ccaacttttt gtggatgctt     60
tcacggagtt cttggtgtcc attgttgata tcattatatt tttggccatt ttgtttggct    120
tcaccatcgc aggttggctg gtggtctttt gcatcagatt ggtttgctcc gcgatactcc    180
gtgcgcgccc tgccattcac tctgagcaat tacagaagat cctatgaggc ctttctctct    240
cagtgccagg tggacattcc cacctgggga actaaacatc ctttggggat gctttggcac    300
cataaggtgt caaccctgat tgatgaaatg gtgtcgcgtc gaatgtaccg catcatggaa    360
aaagcaggac aggctgcctg gaaacaggta gtgagcgagg ctacgctgtc tcgcattagt    420
agtttggatg tggtggctca ttttcagcat cttgccgcca ttgaagccga gacctgtaaa    480
tatctggcct ctcggctgcc catgctacac cacctgcgca tgacagggtc aaatgtaacc    540
atagtgtata atagtacttt gaatcaggtg tttgctgttt tcccaacccc tggttcccgg    600
ccaaagcttc atgatttcca gcaatggcta atagctgtac attcctctat attttcctct    660
gttgcagctt cttgtactct ttttgttgtg ctgtggttgc gggttccaat gctacgtact    720
gtttttggtt tccgctggtt aggggcaatt tttctttcga actcacgg                 768
```

<210> SEQ ID NO 71
<211> LENGTH: 732
<212> TYPE: DNA
<213> ORGANISM: Porcine reproductive and respiratory syndrome virus

<400> SEQUENCE: 71

```
atggctaata gctgtacatt cctctatatt ttcctctgtt gcagcttctt gtactctttt     60
```

-continued

```
tgttgtgctg tggttgcggg ttccaatgct acgtactgtt tttggtttcc gctggttagg    120

ggcaattttt ctttcgaact cacggtgaat tacacggtgt gcccgccttg cctcacccgg    180

caagcagccg cagaggccta cgaacccggc aggtcccttt ggtgcaggat agggcatgat    240

cgatgtgggg aggacgatca tgatgaacta gggtttgtgg tgccgtctgg cctctccagc    300

gaaggccact tgaccagtgc ttacccctgg ttggcgttcc tgtccttcag ctatacggcc    360

cagttccatc ccgagatatt cgggataggg aatgtgagtc gagtctatgt tgacatcaag    420

caccaattca tttgcgctgt tcatgatggg cagaacacca ccttgcccca ccatgacaac    480

atttcagccg tgtttcagac ctattaccag catcaggtcg acgggggcaa ttggtttcac    540

ctagaatggc tgcgtccctt cttttcctct tggttggttt taaatgtctc ttggtttctc    600

aggcgttcgc ctgcaagcca tgtttcagtt cgagtctttc agacatcaag accaacacca    660

ccgcagcggc aggctttgct gtcctccaag acatcagttg ccttaggcat cgcaactcgg    720

cctctgaggc ga                                                        732
```

<210> SEQ ID NO 72
<211> LENGTH: 534
<212> TYPE: DNA
<213> ORGANISM: Porcine reproductive and respiratory syndrome virus

<400> SEQUENCE: 72

```
atggctgcgt cccttctttt cctcttggtt ggttttaaat gtctcttggt ttctcaggcg     60

ttcgcctgca agccatgttt cagttcgagt ctttcagaca tcaagaccaa caccaccgca    120

gcggcaggct ttgctgtcct ccaagacatc agttgcctta ggcatcgcaa ctcggcctct    180

gaggcgattc gcaaagtccc tcagtgccgc acggcgatag ggacacccgt gtatatcact    240

gtcacagcca atgttaccga tgagaattat ttgcattcct ctgatcttct catgctttct    300

tcttgccttt tctatgcttc tgagatgagt gaaaagggat ttaaggtggt atttggcaat    360

gtgtcaggca tcgtggcagt gtgcgtcaac ttcaccagtt acgtccaaca tgtcaaggaa    420

tttacccaac gttccttggt agttgaccat gtgcggctgc tccatttcat gacgcccgag    480

accatgaggt gggcaactgt tttagcctgt ctttttacca ttctgttggc aatt          534
```

<210> SEQ ID NO 73
<211> LENGTH: 600
<212> TYPE: DNA
<213> ORGANISM: Porcine reproductive and respiratory syndrome virus

<400> SEQUENCE: 73

```
atgttgggga aatgcttgac cgcgggctgt tgctcgcaat tgcttttttt atggtgtatc     60

gtgccgtctt gttttgttgc gctcgtcagc gccaacggga acagcggctc aaatttacag    120

ctgatttaca acttgacgct atgtgagctg aatggcacag attggctagc taataaattt    180

gactgggcag tggagtgttt tgtcattttt cctgtgttga ctcacattgt ctcttatggt    240

gccctcacta ctagccattt ccttgacaca gtcggtctgg tcactgtgtc taccgctggg    300

tttgttcacg ggcggtatgt tctgagtagc atgtacgcgg tctgtgccct ggctgcgttg    360

atttgcttcg tcattaggct tgcgaagaat tgcatgtcct ggcgctactc atgtaccaga    420

tataccaact ttcttctgga cactaagggc agactctatc gttggcggtc gcctgtcatc    480

atagagaaaa ggggcaaagt tgaggtcgaa ggtcacctga tcgacctcaa aagagttgtg    540

cttgatggtt ccgcggctac ccctgtaacc agagtttcag cggaacaatg gagtcgtcct    600
```

-continued

<210> SEQ ID NO 74
<211> LENGTH: 519
<212> TYPE: DNA
<213> ORGANISM: Porcine reproductive and respiratory syndrome virus

<400> SEQUENCE: 74
atggagtcgt ccttagatga cttctgtcat gatagcacgg ctccacaaaa ggtgctcttg 60
gcgttttcta ttacctacac gccagtgatg atatatgccc taaaggtgag tcgcggccac 120
tgctagggct tctgcacctt ttggtcttcc tgaattgtgc tttcaccttc gggtacatga 180
cattcgtgca ctttcagagt acaaataagg tcgcgctcac tatgggagca gtagttgcac 240
tcctttgggg ggtgtactca gccatacaaa cctggaaatt catcacctcc agatgccgtt 300
tgtgctgcta ggccgcaagt acattctggc cctgcccac cacgttgaaa gtgccgcagg 360
ctttcatccg attgcggcaa atgataacca cgcatttgtc gtccggcgtc ccggctccac 420
tacggtcaac ggcacattgg tgcccgggtt aaaaagcctc gtgttggtgg cagaaaagct 480
gttaaacagg gagtggtaaa ccttgttaaa tatgccaaa 519

<210> SEQ ID NO 75
<211> LENGTH: 368
<212> TYPE: DNA
<213> ORGANISM: Porcine reproductive and respiratory syndrome virus

<400> SEQUENCE: 75
atgccaaata acaccggcaa gcagcagaag agaaagaagg gggatggcca gccagtcaat 60
cagctgtgcc agatgctggg taagatcatc gctcaccaaa accagtccag aggcaaggga 120
ccgggaaaga aaaataagaa gaaaaacccg gagaagcccc atttccctct agcgactgaa 180
gatgatgtca gacatcactt taccccctagt gagcgtcaat tgtgtctgtc gtcaatccag 240
accgccttta atcaaggcgc tgggacttgc accctgtcag attcagggag gataagttac 300
actgtggagt ttagtttgcc tacgcatcat actgtgcgcc tgatccgcgt cacagcatca 360
ccctcagc 368

<210> SEQ ID NO 76
<211> LENGTH: 7194
<212> TYPE: DNA
<213> ORGANISM: Porcine reproductive and respiratory syndrome virus

<400> SEQUENCE: 76
atgtctggga tacttgatcg gtgtacgtgc acccccaatg ccagggtgtt tatggcggag 60
ggccaggtct actgcacacg atgtctcagt gcacggtctc tccttcctct gaatctccag 120
actcccgagc ttggggtgtt gggtctattc tacaggcccg aagaaccact ccggtggacg 180
ttgccacgtg cattccccac tgttgagtgt tccccgctg gggcctgctg gctttctgca 240
atctttccaa ttgcgcgaat gaccagtgga aacctgaact tccaacaaag aatggtacgg 300
gtcgcagctg agctttacag agccggccag ctcacccctg tcgtcttgaa gactctgcaa 360
gtttacgaac ggggttgccg ctggtacccc attgttggac ctgtccctgg agtggccgtt 420
ttcgccaact ccctacatgt gagtgataaa cctttcccag ggcaactca cgtgttaacc 480 aacctgccgc tcccgcagag acccaagccc gaagacttct gcccctttga atgcgccatg 540
gccaccgtct atgacattgg tcatgacgct gtcatgtaca tggccggagg gaaagtctcc 600
tgggcccctc gtggcgggga tggagtgaaa tttgaaactg tccccaaggg gttggagtta 660
actgcggacc gactccgctc ctccttcccg ccccaccacg tagtggacat gtccaggttt 720

-continued

```
gctttcacaa cccctgagtg tggtgcctct atgcgggtcg gacgccaacg tggctgcctc    780
cccgctggta ctgtccctga aggcaactgt tggtggagct tgtttggctc gctcccactg    840
gaagttctga acaaagaaat tcgctatgcc aaccgatttg gctaccaaac taagcatggt    900
gtctctggca agtacctaca gcggaggctg caagttaatg gtctccgggc agtaactgac    960
acacatggac ctatcgtcat acaatacttc tccgttaagg agagttggat ccgccacttg   1020
agactggcgg aagaacccag cctccctggg tttgaggatc tcctcagaat aagggttgag   1080
cccaacacat cgccattgct tggcaagggt gaaaaaatct tccgttttgg caatcacaaa   1140
tggtacggcg ctggaaagag agcaaggaaa gcacgctcta gtgcgactgc tacggtcgct   1200
gaccgcgctt tgtccgctcg tgaaacccgg ctggccaagg agcacgaggt tgccggcgcc   1260
aataaggctg agcacctcaa gcactactcc ccgcctgccg aagggaattg tggttggcac   1320
tgtatttccg ccatcgtcaa ccggatggtg aactccaaat ttgaaaccac cctccccgag   1380
agagtgagac ctccagatga ctgggctact gacgaggatc ttgcgaacac catccaaatc   1440
ctcaggcttc ctgcggcctt ggacaggggc ggtgcttgtg ttagcgccaa gtatgtactt   1500
aagctggaag gtgaacattg gactgtctct gtgacccctg ggatgtctcc ctctttgctc   1560
ccccttgaat gcgtccaggg ctgttgtgat cataagagcg gtcttggttc cccagatacg   1620
gtcgaagttt ccggatttga ccctgcctgc cttgaccggc tggctgaggt gatgcacctg   1680
cctagcagtg ccatcccagc cgctctggcc gaaatgtccg gcgattccga tcgtccggct   1740
tccccggtca ccactgtgtg gacggtttcg cagttctttg cccgccacac aggagggaat   1800
caccctgacc aggtgtgctt aggaaaaatc attagccttt gtcaagtgct tgagagttgc   1860
tgctgtttcc agaacaaaac caaccgggcc accccggaag aggtcgcggc aaaaattgac   1920
ctgtacctcc gcggagcaac aggtcttgaa gaatgcttgg ccaggcttga gagggctcgc   1980
ccaccgagtg taatggacac ctcctttgat tggaatgttg tgcttcctgg ggtttgaggcg   2040
gcaactcaga caaccaaacc gccccaggtc aaccagtgtc gcgctctggt ccctgttgtg   2100
actcaagagt ctttggacaa tggctcggtt cctctgaccg ccttctcgct gtccaattac   2160
tactaccgcg cgcaaggaga cgaggttcgt caccgtgata ggttaaacgc cgtactctcc   2220
aagttggagg gtgctgttcg agaagaatac gggctcatgc caactggacc tggcccgcga   2280
cccgcactgc cgagtgggct tgacgagctt aaagaccaga tggaggagga tctgctgaaa   2340
ctagccaatg cccagacaac ttcagaaatg atggcctggg cagccgagca ggttgatcta   2400
aaagcttggg ttaaaaacta cccacggtgg acaccaccgc cccctccacc aagagtccag   2460
cctcgaaaaa caaagcctgt caagagtttg ccagagagca agcctgtccc cgccccgcgc   2520
aggaaggtta ggtccgattg tggcagcccg attttattgg gcgacaatgt tcctaacagt   2580
tgggaagatt tgactgttgg tggcccccctt gatctctcga cctcacccga gccggtgaca   2640
cctccgagtg agcttgcgct catgtccgca ccgcaacaca cttttaggtc ggtgataccc   2700
ttgggtgaac cggccccagt tcccgcattg cgcaaaactg tgccccgacc ggtaacaccc   2760
ttgagcgagc cgatccctgt gtccgcaccg caatgcaagt ttcagcaggt ggaaaaagcg   2820
gatctggcgg cagcagcgct ggcgtaccag gacgagcccc tagatttgtc tgcatcctca   2880
caaactgaat atgaggcttc tcccctagaa ccactgcaga gcatgggcgt tctaaaggtg   2940
gaaggacaag aagctgagga agtcctgagt ggaatctcgg acatactgga tgacatcaac   3000
ccggtgcctg tatcatcaaa cggctccctg tcaagcgtga ggatcacacg cccaaaatac   3060
tcagctcaag ccatcatcga ctcgggcggg ccctgcagtg ggcacctcca agggataaag   3120
```

-continued

```
gaaacatgcc tcagtatcat gcgtgaggca tgtgatgcga ctaagcttga tgaccctact   3180
acgcaggaat ggctttctcg catgtgggat agggtggaca tgctgacttg gcgcaacacg   3240
tctgcttacc aggcgcttcg caccttagat agcaggtttg agtttctccc aaaaatgata   3300
ctcgagacac cgccgcccta tccgtgtgag tttgtgatga tgcctcacac gcctgcacct   3360
tctgtaagtg cggagagtga tcttaccatt ggctcagtcg ccactgaaga tgttccacgc   3420
atcctcggga aaatagaaga tgtcggcgag atgaccaacc agggaccctt ggcattctcc   3480
gaggaagaac cggtggatca ccaacctgcc aagggctccc ggtcattgtc gcggaggcct   3540
gacgagagta caccaactct gtccgcaagc gcaggtggca ccgacttacc caccgatttg   3600
ccgctttcag acggtgtgga tgcggacggg ggggggccgt tacggacggt aaaaaacaaa   3660
actcaaaggc tctttgacca actgagccgt caggtttta acctcgtctc ccatctccct   3720
gttttcttct cacgccttct cctacctggc ggtggttatt ctccgggtga ttggggcttt   3780
gcagctttta ctctattgtg cctctttttg tgttatagct acccagcctt tggtattgct   3840
ccccttttgg gtgtattttc tgggtcttct cggcgcgttc gaatgggggt ttttggctgc   3900
tggttggctt ttgctgttgg cctgttcaag cctgtgtccg acccagtcgg cactgcttgt   3960
gagtttgact cgccagagtg tagaaacatc cttctttctt ttgagcttct caaaccttgg   4020
gaccctgttc gcagccttgt tgtgggcccc gtcggtctcg gtcttgccat tcttggcagg   4080
ttactgggcg gggcacgctg tatctggcac tttttgctta ggcttggcat tgttacagat   4140
tgtatcctgg ctggagctta tgtgctttct caaggtaggt gtaaaaagtg ctggggatct   4200
tgtataagaa ctgctcctag tgaggtcgcc tttaacgtgt ttccttttac acgtgcgacc   4260
aggtcgtcac ttaccaactt gtgcgatcgg ttttgtgcgc caaaaggcat ggaccccatt   4320
ttcctcgcca ctgggtggcg cgggtgctgg accggccgaa gccccattga gcaaccctct   4380
gaaaaaccca tcgcgtttgc ccagttggat gaaaagaaga ttacggctaa gactgtggtc   4440
gcccagcctt atgaccccaa ccaagccgta aagtgtttgc gggtgttaca ggcgggcggg   4500
gtgatggtgg ctgaggcagt tccaaaagtg gtcaaggttt ccgctgtccc attccgagcc   4560
cccttctttc ccactggggt gaaagttgat cctgggtgca ggatcgtggt tgaccccgac   4620
accttcactg cagctctccg gtctggttac tccaccacaa acctcgtcct tggtgtaggg   4680
gactttgccc agctgaatgg attaaaaatt aggcaaattt ccaagccttc tggaggaggc   4740
ccacacctca tggctgccct gcatgttgct tgctcgatga ccttgcacat gcttgctggg   4800
atttacgtga ctgcggtggg ttcttgcggc accggcacca acgatccgtg gtgcgctaac   4860
ccgtttgccg tccctggcta tggacctgga tctctctgca cgtccaaatt gtgcatctcc   4920
caacatggcc tcaccctgcc cttaacagca cttgttgcgg gattcggtat tcaggaaatt   4980
gccttggtcg ttttgatttt tgtttccatc gggggcatgg ctcataggtt gagttgtaag   5040
gctgatatgc tgtgtgtttt gcttgcaatc gccagctatg tttgggtacc tctaacctgg   5100
ttgctttgtg tgtttccctg ctggttgcgc tgtttttctt tgcacccact caccatccta   5160
tggttggtgt ttttcttgat ttctgtaaat atgccttcag gaatcttggc catggtgttg   5220
ttggtttctc tttggcttct tggacgttat actaatgtcg ctggtcttgt cacccttat    5280
gatattcacc attacaccag tggcccccgc ggtgttgccg ccttggctac agcaccagat   5340
gggacctact tggccgctgt ccgccgcgct gcgttgactg gccgcaccat gctgtttacc   5400
ccgtctcagc ttgggtccct tcttgagggc gcttttagaa ctcaaaagcc ctcgttgaac   5460
```

-continued accgtcaatg tggtcggtcc tccatgggct ctggcggggt gttcaccatc gacgggaaaa 5520
tcaagtgcgt aactgccgca catgtcctta cgggcaattc agctagggtt tccggggtcg 5580
gtttcaacca aatgcttgac tttgatgtaa aaggagactt cgccatggcc gattgcccgg 5640
attggcaagg ggctgctccc aagacccaat tctgcaagga tggatggact ggccgtgcct 5700
actggctaac atcctctggc gtcgaacccg gtgtcattgg aaaaggattc gccttctgct 5760
tcaccgcgtg cggcattccg ggtccccagt gatcaccgag gccggtgagc ttgtcggtgt 5820
ccacacggga tcaaataaac aaggaggagg catcgtcacg cgcccctcag gccagttttg 5880
taatgtgtca cccgtcaagc taagcgaatt aagtgaattc tttgctgggc ctaaggtccc 5940
gctcggtgat gtgaaggttg gcagccatat aatcaaagat ataggcgagg taccttcaga 6000
tctttgcgcc ttgcttgctg ccaaacctga actggaagga ggcctctcca ccgtccaact 6060
tctgtgtgtg ttttttctcc tgtggaggat gatgggacat gcctggacgc ccttggttgc 6120
tgtggggttc tttatcttga atgaggttct tccagctgtc ctggtccgga gtgtcttctc 6180
ctttggaatg tttgtgctat cctggctcac accatggtct gcgcaagttc tgatgatcag 6240
gcttctaaca gcagctctta acaggaacag aggttcactt gccttttaca ccctcggtgc 6300
aataaccggc tttgtccaga tcttgcggtt actcagggac atccgttgca ggcagtgatg 6360
aatttgagca cctatgcatt cctgcctcgg atgatggttg tgacctcacc agtcccagtg 6420
atcgcgtgtg gtgttgcgca cctgcttgcc atcattttgt acttgtttaa gtaccgcggc 6480
ctgcacaaga tccttgttgg cgatggagcg ttctctgcgg ctttcttcct gcgatacttt 6540
gccgagggaa agttgaggga aggggtgtcg caatcctgcg gaatgaatca tgagtcactg 6600
actggtgccc tcgccatgaa actcaatgac gaggacttgg atttccttac gaaatggact 6660
gattttaagt gctttgtttc tgcatccaac atgaggaatg cagcgggcca atttatcgag 6720
gctgcctatg ctaaagcact tagagtagaa cttgcccagt tggtacaggt tgataaggtt 6780
cgaggcacta tggccaaact agaagctttt gctgacaccg tggcacccca actctcgccc 6840
ggtgacattg ttgtcgctct tggccatacg cctgttggca gtatcttcga cctaaaggtt 6900
ggtagcacta agcacaccct ccaagccatt gagaccagat ttcttgctgg gtccaaaatg 6960
accgtggcgc gtgtcgtcga cccgaccccc acgcccccac ccgcacccgt gcccatcccc 7020
ctcccaccga aagttctgga gaatggtccc aacgcttggg gggatgagga tcgtttgaat 7080
aaaaaaaaaa ggcgcaggat ggaagccctc ggcatctatg ttatgggtgg gaaaaagtac 7140
cagaaatttt gggataagaa ctccggtgat gtgttttatg aggaggtcca taat 7194

<210> SEQ ID NO 77
<211> LENGTH: 4352
<212> TYPE: DNA
<213> ORGANISM: Porcine reproductive and respiratory syndrome virus

<400> SEQUENCE: 77
tgataaactc cagtgcctga ctaaggagca gtgtttaaac tgctagccgc cagcggcttg 60
acccgctgtg gtcgcggcgg cttggttgtc actgagacag cggtaaaaat agtcaaattt 120
cacaaccgga ccttcaccct gggacctgtg aatttaaaag tggccagtga ggttgagtta 180
aaagacgcgg tcgagcacaa ccaacacccg gttgcaagac cggttgatgg tggtgttgtg 240
ctcctgcgtt ctgcagttcc ttcacttata gacgtcctga tctccggtgc cgacgcatct 300
cctaagttgc tcgcccatca cgggccgggg aacactggga tcgatggcac gctttgggat 360
ttcgagtctg aggccactaa agaggaagtc gcacttagtg cgcaaataat acaggcttgt 420

-continued

```
gacatcaggc gcggggacgc acccaaaatt gatctcccct acaagctgta ccctgttagg    480
ggcaaccctg agcgggtgaa aggagttctg aggaatacaa ggtttggaga cataccttac    540
aagaccccca gtgacactgg gagcccggtg cacgcggccg cctgccttac gcctaacgcc    600
actccggtga ctgacgggcg ctccatcttg gccacgacca tgccctctgg gtttgagttg    660
tatgtaccga ccattccagc gtctgtcctt gattaccttg attctaggcc tgactgccct    720
aaacagttga cagagcacgg ctgtgaagat gccgcactga gagacctctc caaatatgac    780
ttgtccaccc aaggctttgt tttacctgga gttcttcgcc tcgtgcggaa atacctgttt    840
gcccatgtag gtaagtgccc acctgttcac cggccttcta cttatcctgc taagaattct    900
atggctggac taaatgggaa caggttcccg accaaggata ttcagagcgt ccctgaaatc    960
gacgttctgt gcgcgcaggc tgtgcggaaa actggcagac tgttacccct tgtaccctta   1020
agaagcagta ttgcgggaag aagaaaacta ggacaatact cggcaccaat aacttcatcg   1080
cgctggctca tcgggcagcg ttgagtggtg tcacccaggg cttcatgaaa aaggcattta   1140
actcgcccat cgccctcgga aaaaacaaat ttaaggagct acaaactccg gtcctaggca   1200
gatgccttga agctgatctt gcatcctgcg accgatccac acctgcaatt gtccgttggt   1260
ttgccgccaa tcttctttat gaacttgcct gtgctgaaga tcacctgcca tcttatgtgc   1320
tgaactgttg ccacgactta ttggtcacgc agtctggcgc agtgactaag agaggtggcc   1380
tgtcatctgg cgacccgatc acctctgtgt ctaacaccat ttacagcttg gtgatctatg   1440
cacagcacat ggtgctcagt tacttcaaaa gtggtcaccc ccacggcctt ctgttcttac   1500
aagaccagct aaagtttgag gacatgctca aggttcaacc cctgatcgtc tattcggacg   1560
acctcgtgct gtatgccgag tctcccacca tgccaaacta ccactggtgg gttgaacatc   1620
tgaatttaat gctggggttt cagacggacc caaagaagac agctataaca gactcgccat   1680
catttctagg ctgcaggata ataaatggac gccagctagt ccctaaccgt gacaggattc   1740
tcgcggccct cgcctaccat atgaaggcga gtaatgtttc tcaatactac gcttcggcgg   1800
ctgcaatact catggacagc tgtgcttgtt tagagtatga tcctgaatgg tttgaagaac   1860
ttatagttgg aatatcgcag tgcgcccgca aggacggcta tagctttccc ggtccgccgt   1920
tcttcttgtc tatgtgggaa aaactcaggt ctaattatga ggggaagaag tcgagagtgt   1980
gcgggtactg cggggccccg gccccgtacg ctactgcctg tggcctcgat gtctgcattt   2040
accacaccca cttccaccag cattgtccgg ttataatttg gtgtggccac ccagcgggtt   2100
ctggttcttg tagtgagtgc aaatcccccg tggggaaagg cacaagccct ctggacgagg   2160
tgttaaaaca agtcccgtat aaacccccac ggaccataat catgcatgtg gaacagggtc   2220
ttacccccct tgacccaggc agataccaga ctcgccgcgg attggtctcc gttaggcgcg   2280
gaatcagggg gaatgaagtt gaactaccag acggtgatta cgctagtacc gccttgctcc   2340
ccacctgtaa agagatcaac atggtcgctg tcgcttctaa tgtgttgcgc agcaggttca   2400
tcatcggtcc gcccggtgct gggaagacat actggcttct acaacaggtc caggatggtg   2460
atgtcattta cacaccaact caccagacca tgcttgacat gattagagct ttggggacgt   2520
gccggttcaa cgtcccagca ggcacaacgc tgcaattccc tgtcccctcc cgtaccggtc   2580
cgtgggttcg catcctagcc ggcggttggt gtcctggcaa gaattccttc ctggatgaag   2640
cagcgtattg caatcacctt gatgtcttga ggcttcttag caaaactacc ctcacctgtc   2700
tgggagattt caaacaactc cacccagtgg gttttgattc tcattgctat gtttttgaca   2760
```

-continued

```
ctatgcctca gactcaactg aagaccatct ggagattcgg acagaatatt tgtgatgcca   2820

tccaaccaga ttacagagac aaactcatgt ccatggtcaa cacaacccgt gtaacctacg   2880

tggagagacc tgtcaggcat gggcaagtcc tcacccccta ccacagggac cgagaggacg   2940

acgccatcac cattgactcc agccaaggcg ccacatttga tgtggttaca ttgcatttgc   3000

ccactaaaga ttcactcaac aggcaaagag cccttgttgc tatcaccagg gcaagacatg   3060

ctatctttgt gtatgaccca cacaggcaac tgcagagcct atttgatctt cctgcgaaaa   3120

gcacccctgt caacctcgca gtgcaccgcg acgggcagct gatcgtgcta gatagaaata   3180

acaaagaatg cacggttgct caggctcttg gcaacggaga taaatttagg gccacagaca   3240

agcgcgttgt agactctctc cgcgccattt gtgctgatct agaagggtct agctctccgc   3300

tccccaaggt cgcccacaac ttgggatttc atttctcacc tgatttgaca cagtttgcca   3360

aactcccagt agaacttgca cctcactggc ccgtggtgac aacccagaac aatgaaaagt   3420

ggccagatcg gctggttgct agccttcgcc ctattcataa atatagccgc gcgtgcattg   3480

gtgccggcta tatggtgggc ccctcggtgt ttctaggcac ccctggggtc gtgtcatact   3540

acctcacaaa atttattaag ggcgaggctc aagtgcttcc ggagacggtc ttcagcaccg   3600

gtcgaattga ggtagattgc cgggaatacc ttgatgatcg ggagccagaa gttgctgcgt   3660

ccctcccaca tgccttcatt ggcgacgtca aaggcactac cgttgggggga tgtcaccatg  3720

tcacttccaa ataccttccg cgcttccttc ctaaggaatc agttgcggta gtcggggttt   3780

cgagccccgg aaaagccgcg aaagcagtgt gcacactgac agatgtgtac ctcccagacc   3840

ttgaagccta cctccacccg gaaacccagt ccaagtgctg gaaattgatg ttggacttca   3900

aggaagtccg actgatggtc tggaaagaca agacggccta tttccaactt gaaggccgct   3960

atttcacctg gtatcagctt gctagctacg cctcgtacat ccgtgttcct gtcaactctg   4020

cggtgtactt agacccctgc atgggccctg ccctttgcaa caggagagtt atcgggtcca   4080

ctcattgggg agctgacctc gcagtcaccc cttatgatta cggtgccaaa attattttgt   4140

ctagtgcgta ccatggtgaa atgcctcccg ggtacaagat tctggcgtgc gcagagttct   4200

cgcttgacga cccagtcaag tacaagcaca cctgggggtt tgaatcggat acagcgtatc   4260

tgtatgagtt caccggaaac ggtgaggact gggaggatta caatgatgcg tttcgtgcgc   4320

gccaggaggg gaaagtctat aaggccactg cc                                 4352
```

<210> SEQ ID NO 78
<211> LENGTH: 768
<212> TYPE: DNA
<213> ORGANISM: Porcine reproductive and respiratory syndrome virus

<400> SEQUENCE: 78

```
atgaaatggg gtctatgcaa agcctttttg acaaaattgg ccaacttttc gtggatgctt     60

tcacggagtt cttggtgtcc attgttgata tcattatatt tttggccatt ttgtttggct    120

tcaccatcgc cggttggctg gtggtctttt gcatcagatt ggtttgctcc gcgctactcc    180

gtgcgcgccc tgccattcac tctgagcaat tacagaagat cctatgaggc ctttctttct    240

cagtgccagg tggacattcc cacctgggga tttaaacatc ctttggggat gttttggcac    300

cataaggtgt caaccctgat tgatgaaatg gtgtcgcgtc gaatgtaccg catcatggat    360

aaagcaggac aggctgcctg gaaacaggtg gtgagcgagg ctacgctgtc tcgcattagt    420

agtttggatg tggtggctca ctttcagcat cttgccgcca ttgaagccga gacctgtaaa    480

tatttggcct ctcggctgcc catgctacac aacctgcgca tgacagggtc aaatgtaacc    540
```

-continued

```
atagtgtata atagtacttt gaatcaggtg cttgctattt ttccaacccc tggttcccgg    600

ccaaagcttc atgattttca gcaatggcta atagctgtac attcctctat attttcctct    660

gttgcagctt cttgtactct tttgttgtg ctgtggttgc gggttccaat gctacgtatt    720

gcttttggtt tccgctggtt aggggcaatt tttccttcga actcacag                 768
```

<210> SEQ ID NO 79
<211> LENGTH: 662
<212> TYPE: DNA
<213> ORGANISM: Porcine reproductive and respiratory syndrome virus

<400> SEQUENCE: 79

```
atggctaata gctgtacatt cctctatatt ttcctctgtt gcagcttctt gtactctttt     60

tgttgtgctg tggttgcggg ttccaatgct acgtattgct tttggtttcc gctggttagg    120

ggcaattttt ccttcgaact cacagtgaac tacacggtgt gtccaccttg cctcacccgg    180

caagcagcca tagaggccta cgaacctggc aggtctcttt ggtgcaggat agggtatgat    240

cgctgtgggg aggacgatca tgacgaacta gggtttgtgg tgccgtctgg cctctccagc    300

gaaggccact tgaccagtgt ttacgcctgg ttggcgttcc tgtctttcag ttacacagcc    360

cagttccatc ctgagatatt cgggataggg aatgtgagtc aagtttatgt tgacatcagg    420

catcaatcca tttgcgccgt tcacgacggg cagaacgcca ctttgcctcg ccatgacaat    480

atttcagccg tgttccagac ttattaccaa catcaagtcg acggcggcaa ttggtttcac    540

ctagaatggc tgcgtccctt cttttcctct tggttggttt taaatgtctc ttggtttctc    600

aggcgttcgc ttgcaagcca tgtttcagtt cgagtcttgc agacattaag accaacacca    660

cc                                                                   662
```

<210> SEQ ID NO 80
<211> LENGTH: 535
<212> TYPE: DNA
<213> ORGANISM: Porcine reproductive and respiratory syndrome virus

<400> SEQUENCE: 80

```
atggctgcgt cccttctttt cctcttggtt ggttttaaat gtctcttggt ttctcaggcg     60

ttcgcttgca agccatgttt cagttcgagt cttgcagaca ttaagaccaa caccaccgca    120

gcggcaggct ttgctgtcct ccaagacatc agttgcctta ggtatcgcaa ctcggcctct    180

gaggcgtttc gcaaaatccc tcagtgtcgt acggcgatag ggacacccat gtatattact    240

gtcacagcca atgtaaccga tgagaattat ttgcattcct ctgaccttct catgcttttct    300

tcttgccttt tctacgcttc tgagatgagt gaaaagggat ttaaagtggt atttggcaat    360

gtgtcaggca tcgtggctgt gtgcgtcaac tttaccagct acgtccaaca tgtcaaggaa    420

tttacccaac gctccttggt agtcgaccat gtgcggctgc tccatttcat gacacctgag    480

accatgaggt gggcaactgt tttagcctgt ctttttgcca ttctgttggc cattt         535
```

<210> SEQ ID NO 81
<211> LENGTH: 600
<212> TYPE: DNA
<213> ORGANISM: Porcine reproductive and respiratory syndrome virus

<400> SEQUENCE: 81

```
atgttgggga aatgcttgac cgcgggctat tgctcgtcat tgcttttttt gtggtgtatc     60

gtgccgtctt ggtttgttgc gctcgccagc gccaacagca tcaacagccc tcatttacag    120
```

-continued

```
ttgatttata acttgacgct atgtgagctg aatggcacag attggttagc tggtgaattt    180

gactgggcag tggagtgttt tgtcattttt cctgtgttga ctcacattgt ctcctatggt    240

gccctcacca ccagccattt ccttgacaca gtcggtctgg tcactgtgtc taccgccggc    300

ttttcccacg ggcggtatgt tctgagtagc atctacgcgg tctgtgccct ggctgcgttg    360

atttgcttcg tcattaggtt tacgaagaat tgcatgtcct ggcgctactc atgtaccaga    420

tataccaact ttcttctgga cactaagggc agactctatc gttggcggtc gcctgtcatc    480

atagagaaaa ggggtaaagt tgaggtcgaa ggtcatctga tcgacctcaa gagagttgtg    540

cttgatggtt ccgcggcaac ccctataacc aaaatttcag ccgagcaatg ggtcgtcct     600
```

<210> SEQ ID NO 82
<211> LENGTH: 522
<212> TYPE: DNA
<213> ORGANISM: Porcine reproductive and respiratory syndrome virus

<400> SEQUENCE: 82

```
atggggtcgt ccttagatga cttctgccat gatagcacgg ctccactaaa ggtgcttttg     60

gcgttctcta ttacctacac gccagtgatg atatatgccc taaaagtaag tcgcggccga    120

ctgttagggc ttctgcacct tttgatcttc ctaaattgtg ctttcacctt cgggtacatg    180

acattcgtgc actttcagag cacaaacaag gtcgcgctca ctatgggagc agtagttgca    240

ctcctttggg gggtgtactc agccatagaa acctggaaat tcatcacctc cagatgccgt    300

ttgtgcttgc taggccgcaa gtacattttg gcccctgccc accacgttga aagtgccgca    360

ggctttcatc cgatagcggc aaatgataac cacgcatttg tcgtccggcg tcccggctcc    420

actacggtta acggcacatt ggtgcccggg ttgaaaagcc tcgtgttggg tggcagaaaa    480

gctgtcaaac agggagtggt aaaccttgtt aaatatgcca aa                      522
```

<210> SEQ ID NO 83
<211> LENGTH: 469
<212> TYPE: DNA
<213> ORGANISM: Porcine reproductive and respiratory syndrome virus

<400> SEQUENCE: 83

```
atgccaaata acaacggcaa gcagcagaag aaaaagaagg gggatggcca gccagtcaat     60

cagctgtgcc agatgctggg taagatcatc gctcagcaaa accagtccag aggcaaggga    120

ccgggaaaga aaaacaagaa gaaaaacccg gagaagcccc atttcctctt agcgactgaa    180

gatgatgtca gacatcactt cacctctggt gagcggctat tgtgtctgtc gtcaatccag    240

acagccttta atcaaggcgc tggaatttgt accctgtcag attcagggag gataagttac    300

actgtggagt ttagtttgcc gacgcatcat actgtgcgcc tgatccgcgt cacagcgtca    360

ccctcagcat gatgagctgg cattcttgag gcatcccagt gtttgaattg gaagaatgtg    420

tggtgaatgg cactgattga cattgtgctt ctaagtcacc tattcaatt               469
```

<210> SEQ ID NO 84
<211> LENGTH: 20
<212> TYPE: DNA
<213> ORGANISM: Porcine reproductive and respiratory syndrome virus
<220> FEATURE:
<223> OTHER INFORMATION: Description of Artificial Sequence:Synthetic
      DNA

<400> SEQUENCE: 84

```
cgtacggcga tagggacacc                                                20
```

-continued

<210> SEQ ID NO 85
<211> LENGTH: 20
<212> TYPE: DNA
<213> ORGANISM: Porcine reproductive and respiratory syndrome virus
<220> FEATURE:
<223> OTHER INFORMATION: Description of Artificial Sequence:Synthetic DNA

<400> SEQUENCE: 85
ggcatatatc atcactggcg 20

<210> SEQ ID NO 86
<211> LENGTH: 7
<212> TYPE: PRT
<213> ORGANISM: Porcine reproductive and respiratory syndrome virus

<400> SEQUENCE: 86

Asn Gly Asn Ser Gly Ser Asn
1 5

<210> SEQ ID NO 87
<211> LENGTH: 7
<212> TYPE: PRT
<213> ORGANISM: Porcine reproductive and respiratory syndrome virus

<400> SEQUENCE: 87

Ser Asn Asp Ser Ser Ser His
1 5

<210> SEQ ID NO 88
<211> LENGTH: 7
<212> TYPE: PRT
<213> ORGANISM: Porcine reproductive and respiratory syndrome virus

<400> SEQUENCE: 88

Ser Ser Ser Asn Ser Ser His
1 5

<210> SEQ ID NO 89
<211> LENGTH: 7
<212> TYPE: PRT
<213> ORGANISM: Porcine reproductive and respiratory syndrome virus

<400> SEQUENCE: 89

Ser Ala Asn Ser Ser Ser His
1 5

<210> SEQ ID NO 90
<211> LENGTH: 7
<212> TYPE: PRT
<213> ORGANISM: Porcine reproductive and respiratory syndrome virus

<400> SEQUENCE: 90

His Ser Asn Ser Ser Ser His
1 5

<210> SEQ ID NO 91
<211> LENGTH: 7
<212> TYPE: PRT
<213> ORGANISM: Porcine reproductive and respiratory syndrome virus

<400> SEQUENCE: 91

Ser Asn Ser Ser Ser Ser His
1 5

-continued

<210> SEQ ID NO 92
<211> LENGTH: 7
<212> TYPE: PRT
<213> ORGANISM: Porcine reproductive and respiratory syndrome virus

<400> SEQUENCE: 92

Asn Asn Ser Ser Ser Ser His
1 5

<210> SEQ ID NO 93
<211> LENGTH: 8
<212> TYPE: PRT
<213> ORGANISM: Porcine reproductive and respiratory syndrome virus

<400> SEQUENCE: 93

Asn Gly Gly Asp Ser Ser Thr Tyr
1 5

<210> SEQ ID NO 94
<211> LENGTH: 10
<212> TYPE: PRT
<213> ORGANISM: Porcine reproductive and respiratory syndrome virus

<400> SEQUENCE: 94

Ala Asn Lys Phe Asp Trp Ala Val Glu Thr
1 5 10

<210> SEQ ID NO 95
<211> LENGTH: 10
<212> TYPE: PRT
<213> ORGANISM: Porcine reproductive and respiratory syndrome virus

<400> SEQUENCE: 95

Ala Asn Lys Phe Asp Trp Ala Val Glu Pro
1 5 10

<210> SEQ ID NO 96
<211> LENGTH: 10
<212> TYPE: PRT
<213> ORGANISM: Porcine reproductive and respiratory syndrome virus

<400> SEQUENCE: 96

Ala Gly Glu Phe Asp Trp Ala Val Glu Thr
1 5 10

<210> SEQ ID NO 97
<211> LENGTH: 10
<212> TYPE: PRT
<213> ORGANISM: Porcine reproductive and respiratory syndrome virus

<400> SEQUENCE: 97

Ala Asp Lys Phe Asp Trp Ala Val Glu Pro
1 5 10

<210> SEQ ID NO 98
<211> LENGTH: 10
<212> TYPE: PRT
<213> ORGANISM: Porcine reproductive and respiratory syndrome virus

<400> SEQUENCE: 98

Ala Asp Arg Phe Asp Trp Ala Val Glu Pro
1 5 10

<210> SEQ ID NO 99

-continued

<211> LENGTH: 10
<212> TYPE: PRT
<213> ORGANISM: Porcine reproductive and respiratory syndrome virus

<400> SEQUENCE: 99

Ser Ser His Phe Gly Trp Ala Val Glu Thr
1 5 10

<210> SEQ ID NO 100
<211> LENGTH: 9
<212> TYPE: PRT
<213> ORGANISM: Porcine reproductive and respiratory syndrome virus

<400> SEQUENCE: 100

Leu Ile Cys Phe Val Ile Arg Leu Ala
1 5

<210> SEQ ID NO 101
<211> LENGTH: 9
<212> TYPE: PRT
<213> ORGANISM: Porcine reproductive and respiratory syndrome virus

<400> SEQUENCE: 101

Leu Thr Cys Phe Val Ile Arg Phe Ala
1 5

<210> SEQ ID NO 102
<211> LENGTH: 9
<212> TYPE: PRT
<213> ORGANISM: Porcine reproductive and respiratory syndrome virus

<400> SEQUENCE: 102

Leu Ile Cys Phe Val Ile Arg Phe Thr
1 5

<210> SEQ ID NO 103
<211> LENGTH: 9
<212> TYPE: PRT
<213> ORGANISM: Porcine reproductive and respiratory syndrome virus

<400> SEQUENCE: 103

Leu Ala Cys Phe Val Ile Arg Phe Ala
1 5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence:Synthetic
DNA

<400> SEQUENCE: 104

Leu Thr Cys Phe Val Ile Arg Phe Val
1 5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence:Synthetic
DNA

<400> SEQUENCE: 105

Leu Thr Cys Phe Ile Ile Arg Phe Ala

-continued

```
  1               5


<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence:Synthetic
      DNA

<400> SEQUENCE: 106

Phe Ile Cys Phe Val Ile Arg Phe Ala
  1               5


<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence:Synthetic
      DNA

<400> SEQUENCE: 107

Phe Val Cys Phe Val Ile Arg Ala Ala
  1               5


<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence:Synthetic
      DNA

<400> SEQUENCE: 108

Leu Gln Leu Ile Tyr Asn Leu Thr Leu Cys Glu Leu Asn Gly Thr Asp
  1               5                  10                  15
Trp Leu


<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 109

gggatccttt tgtggagccg t                                            21


<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 110

ggggaattcg ggatagggaa tgtg                                         24


<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA
```

<400> SEQUENCE: 111
gggggatcct gttggtaata gagtctg 27

<210> SEQ ID NO 112
<211> LENGTH: 28
<212> TYPE: DNA
<213> ORGANISM: Artificial Sequence
<220> FEATURE:
<223> OTHER INFORMATION: Description of Artificial Sequence:Synthetic DNA

<400> SEQUENCE: 112
ggtgaattcg ttttatttcc ctccgggc 28

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 113
gatagagtct gcccttag 18

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 114
ggtttcacct agaatggc 18

<210> SEQ ID NO 115
<211> LENGTH: 17
<212> TYPE: DNA
<213> ORGANISM: Artificial Sequence
<220> FEATURE:
<223> OTHER INFORMATION: Description of Artificial Sequence:Synthetic DNA

<400> SEQUENCE: 115
gcttctgaga tgagtga 17

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 116
caaccaggcg taaacact 18

<210> SEQ ID NO 117
<211> LENGTH: 17
<212> TYPE: DNA
<213> ORGANISM: Artificial Sequence
<220> FEATURE:
<223> OTHER INFORMATION: Description of Artificial Sequence:Synthetic DNA -continued

<400> SEQUENCE: 117
ctgagcaatt acagaag 17

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 118
gactgatggt ctggaaag 18

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 119
ctgtatccga ttcaaacc 18

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 120
aggttggctg gtggtctt 18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 121
tcgctcacta cctgtttc 18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 122
tgtgcccgcc ttgcctca 18

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 123

-continued aaaccaattg cccccgtc 18

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 124
tatatcactg tcacagcc 18

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 125
caaattgcca acagaatg 18

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 126
caacttgacg ctatgtgagc 20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 127
gccgcggaac catcaagcac 20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 128
gactgctagg gcttctgcac 20

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 129

-continued cgttgaccgt agtggagc 18

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 130
ccccatttcc ctctagcgac tg 22

<210> SEQ ID NO 131
<211> LENGTH: 22
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 131
cggccgtgtg gttctcgcca at 22

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 132
ggggaattcg ggatagggaa tgtg 24

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 133
ggggatcctt ttgtggagcc gt 22

<210> SEQ ID NO 134
<211> LENGTH: 28
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 134
ggtgaattcg ttttatttcc ctccgggc 28

<210> SEQ ID NO 135
<211> LENGTH: 27
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 135
gggggatcct gttggtaata gagtctg 27

-continued

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 136
ggtttcacct agaatggc 18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 137
gatagagtct gcccttag 18

<210> SEQ ID NO 138
<211> LENGTH: 17
<212> TYPE: DNA
<213> ORGANISM: Artificial Sequence
<220> FEATURE:
<223> OTHER INFORMATION: Description of Artificial Sequence:Synthetic DNA

<400> SEQUENCE: 138
gcttctgaga tgagtga 17

<210> SEQ ID NO 139
<211> LENGTH: 17
<212> TYPE: DNA
<213> ORGANISM: Artificial Sequence
<220> FEATURE:
<223> OTHER INFORMATION: Description of Artificial Sequence:Synthetic DNA

<400> SEQUENCE: 139
ctgagcaatt acagaag 17

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 140
caaccaggcg taaacact 18

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence:Synthetic DNA

<400> SEQUENCE: 141
gactgcttta cggtctctc 19

-continued

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 142
gatgcctgac acattgcc 18

<210> SEQ ID NO 143
<211> LENGTH: 19
<212> TYPE: DNA
<213> ORGANISM: Artificial Sequence
<220> FEATURE:
<223> OTHER INFORMATION: Description of Artificial Sequence:Synthetic DNA

<400> SEQUENCE: 143
ctgcaagact cgaactgaa 19

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence:Synthetic DNA

<400> SEQUENCE: 144
ccccattgtt ggacctgtcc 20

<210> SEQ ID NO 145
<211> LENGTH: 19
<212> TYPE: DNA
<213> ORGANISM: Artificial Sequence
<220> FEATURE:
<223> OTHER INFORMATION: Description of Artificial Sequence:Synthetic DNA

<400> SEQUENCE: 145
gtcacaacag ggaccgagc 19

<210> SEQ ID NO 146
<211> LENGTH: 27
<212> TYPE: DNA
<213> ORGANISM: Artificial Sequence
<220> FEATURE:
<223> OTHER INFORMATION: Description of Artificial Sequence:Synthetic DNA

<400> SEQUENCE: 146
ccaagctccc ctgaaggagg ctgtcac 27

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence:Synthetic DNA

<400> SEQUENCE: 147
ccaagctccc ctgaaggagg ctgtcac 27

```
<210> SEQ ID NO 148
<211> LENGTH: 25
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 148

agcatcccag acatggttaa agggg                                    25

<210> SEQ ID NO 149
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 149

ccaccccttt aacc                                                14

<210> SEQ ID NO 150
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 150

ccaccccttg aacc                                                14

<210> SEQ ID NO 151
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 151

cctgtcattg aacc                                                14

<210> SEQ ID NO 152
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 152

ccacccctgt aacc                                                14

<210> SEQ ID NO 153
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 153

ccaccccttt aacc                                                14

<210> SEQ ID NO 154
```

```
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 154

ggtcaaatgt aacc                                                        14

<210> SEQ ID NO 155
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 155

ccaccccttt gacc                                                        14

<210> SEQ ID NO 156
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 156

aaggccactt gacc                                                        14

<210> SEQ ID NO 157
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 157

ccaccccttt cacc                                                        14

<210> SEQ ID NO 158
<211> LENGTH: 15
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 158

ccaccccgtt tcacc                                                       15

<210> SEQ ID NO 159
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 159

caattggttt cacc                                                        14

<210> SEQ ID NO 160
<211> LENGTH: 14
```

```
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 160

ccaccccgtc aact                                                        14

<210> SEQ ID NO 161
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 161

agtgtgcgtc aact                                                        14

<210> SEQ ID NO 162
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 162

ccaccccttt agcc                                                        14

<210> SEQ ID NO 163
<211> LENGTH: 15
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 163

ccaccccttt tagcc                                                       15

<210> SEQ ID NO 164
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 164

caactgtttt agcc                                                        14

<210> SEQ ID NO 165
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 165

ccacccctgt aacc                                                        14

<210> SEQ ID NO 166
<211> LENGTH: 14
<212> TYPE: DNA
```

-continued

<213> ORGANISM: Artificial Sequence
<220> FEATURE:
<223> OTHER INFORMATION: Description of Artificial Sequence:Synthetic
      DNA

<400> SEQUENCE: 166
ccaccccttt aacc 14

<210> SEQ ID NO 167
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 167
ctacccctgt aacc 14

<210> SEQ ID NO 168
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 168
ccaccccttt aacc 14

<210> SEQ ID NO 169
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 169
ccacccctat aacc 14

<210> SEQ ID NO 170
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 170
ggcaaatgat aacc 14

<210> SEQ ID NO 171
<211> LENGTH: 15
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 171 ccacccccctt aaacc 15

<210> SEQ ID NO 172
<211> LENGTH: 15
<212> TYPE: DNA
<213> ORGANISM: Artificial Sequence -continued

```
<220> FEATURE:
<223> OTHER INFORMATION: Description of Artificial Sequence:Synthetic
      DNA

<400> SEQUENCE: 172

agggagtggt aaacc                                                    15

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 173

cgtacggcga tagggacacc                                               20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 174

ggcatatatc atcactggcg                                               20

<210> SEQ ID NO 175
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 175

ccaccccttt aacc                                                     14
```